(12) United States Patent
Nishimura et al.

(10) Patent No.: US 12,110,334 B2
(45) Date of Patent: Oct. 8, 2024

(54) NEUTRALIZING ANTIBODIES TO THE αvβ8 INTEGRIN COMPLEX FOR IMMUNOTHERAPY

(71) Applicant: The Regents of the University of California, Oakland, CA (US)

(72) Inventors: Stephen L. Nishimura, San Francisco, CA (US); Jianlong Lou, San Francisco, CA (US); James D. Marks, San Francisco, CA (US); Jody L. Baron, San Francisco, CA (US); Yifan Cheng, San Francisco, CA (US); Shenping Wu, San Francisco, CA (US); Anthony Cormier, San Francisco, CA (US); Naoki Takasaka, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/153,277

(22) Filed: Jan. 11, 2023

(65) Prior Publication Data

US 2023/0331851 A1 Oct. 19, 2023

Related U.S. Application Data

(62) Division of application No. 17/155,784, filed on Jan. 22, 2021, now Pat. No. 11,591,402, which is a division of application No. 16/331,902, filed as application No. PCT/US2017/054306 on Sep. 29, 2017, now Pat. No. 10,954,304.

(60) Provisional application No. 62/529,381, filed on Jul. 6, 2017, provisional application No. 62/401,570, filed on Sep. 29, 2016.

(51) Int. Cl.
| | |
|---|---|
| *G01N 33/53* | (2006.01) |
| *A61P 1/04* | (2006.01) |
| *A61P 31/20* | (2006.01) |
| *A61P 35/04* | (2006.01) |
| *A61P 37/04* | (2006.01) |
| *C07K 14/705* | (2006.01) |
| *C07K 16/00* | (2006.01) |
| *C07K 16/22* | (2006.01) |
| *C07K 16/28* | (2006.01) |
| *C07K 16/46* | (2006.01) |
| *G01N 33/563* | (2006.01) |
| *A61K 39/00* | (2006.01) |

(52) U.S. Cl.
CPC ........... *C07K 16/2839* (2013.01); *A61P 1/04* (2018.01); *A61P 31/20* (2018.01); *A61P 35/04* (2018.01); *A61P 37/04* (2018.01); *C07K 14/705* (2013.01); *C07K 16/22* (2013.01); *G01N 33/563* (2013.01); *A61K 2039/505* (2013.01); *C07K 2317/24* (2013.01); *C07K 2317/34* (2013.01); *C07K 2317/56* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,290,572 B2 | 3/2016 | Nishimura et al. | |
| 9,492,569 B2 | 11/2016 | Nishimura et al. | |
| 9,845,357 B2 | 12/2017 | Nishimura et al. | |
| 10,954,304 B2 | 3/2021 | Nishimura et al. | |
| 2012/0251523 A1 | 10/2012 | Unutmaz et al. | |
| 2013/0064837 A1 | 3/2013 | Nishimura et al. | |
| 2014/0271478 A1 | 9/2014 | Nishimura et al. | |
| 2019/0218298 A1 | 7/2019 | Nishimura et al. | |

FOREIGN PATENT DOCUMENTS

| | | | |
|---|---|---|---|
| CN | 102834412 A | 12/2012 | |
| EP | 1957522 A2 | 8/2008 | |
| WO | 2011103490 A2 | 8/2011 | |
| WO | WO-2013026004 A2 * | 2/2013 | ............ A61K 49/00 |
| WO | 2014165524 A2 | 10/2014 | |
| WO | 2016040839 A1 | 3/2016 | |
| WO | 2018064478 A1 | 4/2018 | |

OTHER PUBLICATIONS

U.S. Appl. No. 16/331,902 , Notice of Allowance, Mailed On Nov. 12, 2020, 9 pages.
U.S. Appl. No. 17/155,784 , Notice of Allowance, Mailed On Oct. 13, 2022, 8 pages.
AU2017335991 , "First Examination Report", Jul. 15, 2022, 4 pages.
Application No. CA3,036,232 , Office Action, Mailed On Aug. 11, 2021, 3 pages.
Application No. CA3,036,232 , Office Action, Mailed On Jul. 28, 2022, 3 pages.
Application No. CA3,036,232 , Office Action, Mailed On Jun. 26, 2020, 3 pages.
Application No. CN201780060796.1 , Office Action, Mailed On Oct. 10, 2022, 13 pages.
Eberlein et al., "A Human Monoclonal Antibody 264RAD Targeting αvβ6 Integrin Reduces Tumour Growth and Metastasis, and Modulates Key Biomarkers in Vivo", Oncogene, vol. 32, No. 37, Oct. 29, 2012, pp. 4406-4416.
Application No. EP17857499.2 , Extended European Search Report, Mailed On Apr. 21, 2020, 11 pages.
Application No. EP17857499.2 , Office Action, Mailed On Apr. 13, 2022, 4 pages.

(Continued)

*Primary Examiner* — Maher M Haddad
(74) *Attorney, Agent, or Firm* — Kilpatrick Townsend & Stockton LLP

(57) ABSTRACT

New antibodies and methods of use are described.

12 Claims, 68 Drawing Sheets
Specification includes a Sequence Listing.

(56) References Cited

OTHER PUBLICATIONS

Application No. EP17857499.2, Office Action, Mailed On Feb. 19, 2021, 7 pages.
Koopman et al., "Antibody-Mediated Blockade of Integrin αvβ6 Inhibits Tumor Progression in Vivo by a Transforming Growth Factor-β-Regulated Mechanism", Cancer Research, American Association for Cancer Research, vol. 68, Issue 2, Jan. 15, 2008, pp. 561-570.
Minagawa et al., "Selective Targeting of TGF-β Activation to Treat Fibroinflammatory Airway Disease", Science Translational Medicine, vol. 6, No. 241, Jun. 18, 2014, 30 pages.
Application No. PCT/US2017/054306, International Preliminary Report on Patentability, Mailed On Apr. 11, 2019, 9 pages.
Application No. PCT/US2017/054306, International Search Report and Written Opinion, Mailed On Mar. 8, 2018, 15 pages.
PCT/US2017/054306, "Invitation to Pay Additional Fees and Partial Search Report", Jan. 9, 2018, 3 pages.
Reszka-Blanco et al., "Inhibition of Integrin αVβ8 in Combination with Low Dose Radiation Induces Antitumor Effect in Advanced Immune Checkpoint Blockade Refractory Tumor Model", Available Online at: https://jitc.bmj.com/content/jitc/9/Suppl_2/A625.full.pdf; Abstract No. 595; The Journal for Immuno Therapy of Cancer, vol. 9, Nov. 10, 2021, p. A625.
Seed et al., "Inhibition of Integrin AVβ8-Mediated TGF-β Activation with C6D4 Provides Improved Potency and Selectivity Vs General TGF-β Inhibitors for Cancer Immunotherapy", Available Online at: https://jitc.bmj.com/content/jitc/8/Suppl_3/A432.full.pdf; Abstract No. 722; The Journal for Immuno Therapy of Cancer, vol. 8, Nov. 9, 2020, pp. A432-A433.
Stockis et al., "Blocking Immunosuppression by Human Tregs in Vivo with Antibodies Targeting Integrin αVβ8", Proceedings of the National Academy of Sciences, vol. 114, No. 47, Nov. 21, 2017, pp. 1-8.
Takasaka et al., "Integrin αvβ8-Expressing Tumor Cells Evade Host Immunity by Regulating TGF-β Activation in Immune Cells", JCI Insight, vol. 3, Issue 20, e122591, Oct. 18, 2018, pp. 1-17.
Worthington et al., "Integrin αVβ8-Mediated Tgf-βActivation by Effector Regulatory T Cells is Essential for Suppression of T-Cell-Mediated Inflammation", Immunity, vol. 42, No. 5, May 19, 2015, pp. 903-915.
Wu, "Fab Assisted CryoEM of Asymmetrical Membrane Proteins", The University of California, San Francisco, Presentation at Yale University, pp. 1-48, Jan. 2017.

* cited by examiner

| VH | Framework 1 | CDR1 | Framework 2 | CDR2 | Framework 3 | CDR3 | Framework 4 |
|---|---|---|---|---|---|---|---|
| (Mouse Hybridoma Name) | | | | | | | |
| B13C4 15-8 | EVQLLQSGPELKKPGETVKISCKASGY | TFTDYSMH | WVKQAPGKGLKWMG | WIKTETGEPTYADDFKG | RFAFSLETSATTAYLQINNLKNEDTAKYFCAI | YYYGRDS | WGQGTTLTVSS |
| B13C4 15-10 | QIQLLQSGPELKKPGETVKISCKASGY | TFTDYSMH | WVKQAPGKGLKWMG | WIKTETGEPTYADDFKG | RFAFSLETSATTAYLQINNLKNEDTAKYFCAI | YYYGRDS | WGQGTTLTVSS |
| B13H3.2 | QIQLLQSGPELKKPGETVKISCKASGY | TFTDYSMH | WVKQAPGKGLKWMG | WIKTETDEPTYADDFKE | RFAFSLETSASTANLQINLNKEDTAKYFCAI | YYYGRDS | WGQGTTLTVSS |
| B13C1231015 | QIQLLQSGPELKKPGETVKISCKASGY | TFTDYSIH | WVKQAPGKGLKWMG | WIKTETGEPTYADDFNG | REAFSLETSASTAYLQINNLKNEDTATYFCAI | YYYGRDS | WGQGTTLTVSS |
| B15B11vh | QIQLLQSGPELKKPGETVKISCKASGY | TFTDYSMH | WVKQAPGKGLKWVA | RINTETGEPTFADDFRG | RFAVSLETSASTAYLQINNLKNEDTATYFCAI | YYYGRDS | WGQGTTLTVSS |
| B2B2 15-9 | QIQLLQSGPELKKPGETVKISCLASGY | TPTDYSMH | WVKQAPGKGLKWVA | RINTETGEPTFADDFGG | RFAVSLETSASTAYLQINNLKNEDTATYFCAI | YYYGRDS | WGQGTTLTVSS |
| R1ID12715.3 | EVQHVESGGGLVQPGGSLKLSCGASGF | TFSSFGMS | WVRQTPDKRLELVA | TINSNGGSTYYPDMKG | RFTISRDMAKNTLVHQMSSLKSEDTAMYYCAS | ACYRYGAFFDY | WGQGTTLTVSS |
| (Produced Rabbit IgG clone name) | | | | | | | |
| RSBLVH-1 | EVQLLESGPELKKPGETVKISCKASGY | TFTDYSIH | WVKQAPGKGLKWMG | WIKTETGEPTYADDFKG | RFAFSLETSASTAYLQINNLKNEDTATYFCAI | YYYGRDS | WGQGTTLTVSS |
| RSBLVH-3 | QVQLMQSGPELKKPGETVKISCKASGY | TFTDYSIH | WVKQAPGKGLKWMG | WIKTETGEPTYADDFNG | RFAFSLETSASTAYLQINNLKNEDTATYFCAI | YYYGRDS | WGQGTTLTVSS |
| RSBLVH-16 | QIQLLQSGPELKKPGETVKISCKASGY | TFTDYSMH | WVKQAPGKGLKWVA | RINTETGEPTFADDFRG | RFAVSLETSASTAYLQINNLKNEDTATYFCAI | YYYGRDS | WGQGTTLTVSS |
| (scFv clone from Yeast Display library) | | | | | | | |
| 29 | QIQLLQSGPELKKPGETVKISCKASGY | TFTDYSMH | WVKQAPGKGLKWVA | RINTETGEPTFADDFRG | RFAVSLETSASTAYLQINNLKNEDTATYFCAI | YYYGRDS | WGQGTTLTVSS |
| 44 | QIQLLQSGPELKKPGETVKISCKASGY | TFTDYSMH | WVKQAPGKGLKWVA | RINTETGEPTFADDFRG | RFAVSLETSASTAYLQINNLKNEDTATYFCAI | YYYGRDS | WGQGTTLTVSS |
| A1=B4=F9 | QIQLLQSGPELKKPGETVKISCKASGY | TFTDYSMH | WVKQAPGKGLKWVA | RINTETGEPTFADDFRG | RFAVSLETSASTAYLQINNLKNEDTATYFCAI | YYYGRDT | WGQGTTLSVSS |
| A5=C6 | QIQLLQSGPELKKPGETVKISCKASGY | TFTDYSMH | WVKQAPGKGLKWVA | RINTETGEPTFADDFRG | RFAVSLETSASTAYLQINNLKNEDTATYFCAI | FYYGRDS | WGQGTAFTVSS |
| D4=E6 | QIQLLQSGPELKKPGETVKISCKASGY | TFTDYSMH | WVKQAPGKGLKWVA | RINTETGEPTFADDFRG | RFAVSLETSASTAYLQINNLKNEDTATYFCAI | YYYGRDS | WGQGTTLTVSS |

| Final clone for in vivo/in vitro functional test in IgG format | | | | | | | |
|---|---|---|---|---|---|---|---|
| C6D4 | QIQLLQSGPELKKPGETVKISCKASGY | TFTDYSMH | WVKQAPGKGLKWVA | RINTETGEPTFADDFRG | RFAVSLETSASTAYLQINNLKNEDTATYFCAI | FYYGRDS | WGQGTTLTVSS |

FIG. 1

| VH | Framework 1 | CDR1 | Framework 2 | CDR2 | Framework 3 | CDR3 | Framework 4 |
|---|---|---|---|---|---|---|---|
| (Mouse Hybridoma Name) | | | | | | | |
| B2B2 35-20 | DIVMSQSPSSMYASLGERVTITC | KASQDINSYLS | WFQQKPGKSPKTLIY | RANRLVD | GVPSRFSGSGSGQDYSLTISSLEYEDMGIYYC | LQYDEFPPLT | FGAGTKLELKA |
| B2B2 35- 26 | QIVLTQSPSSMYASLGERVTITC | KASQDINSYLS | WFQQKPGKSPKTLIY | RANRLVD | GVPSRFSGSGSGSGQDYSLTISSLEYEDMGIYYC | LQYDEFPPLT | FGAGTKLELKA |
| B15B1lvk34-26 | QIVLTQSPAINSASPGEKVTMTC | SASSSVSYMH | WYQQKPGTSPKLWIY | DTSNLAS | GVPARFSGSGSGSGTSYSLTISMEAEDAATYYC | QQWSSNPLT | FGSGTRLEIKA |
| B15B1lvk33-24 | EIVLIQSPAINSASPGEKVTMTC | SASSSVSYMH | WYQKPGSSPKLWIY | DTSNLAS | GVPARFSGSGSGSGTSYSLTISSMEAEDAATYYC | QQWSSNPLT | FGDGTRLEIKA |
| B15B1lvk35-26 | QIVLIQSPAINSASPGEKVTMTC | SASSSVSYMH | WYQKSGTSPKLWIY | DTSNLAS | GVPARFSGSGSGSGTSYSLTISSMEAEDAATYYC | QQWSSNPPT | FGSGTRLEIKA |
| B13C12134-25 | DIKMTQSPAINSASPGEKVTMTC | SASSSVSYMH | WYQKSTSPKRWIY | DTSKLAS | GVPARFSGSGSGSGTSVSLTISSMEAEDAATYYC | QQWSSNPFT | FGDGTRLEIKA |
| B13C12133-26 | QMVLHSPAINSASPGEKVTMTC | SASSSVSYMH | WYQKPGSSPKPWIY | GTSNLAS | GVPARFSGSGSGSGTSVSLTISSMEAEDAATYYC | QQWSSNPPT | FGSGTRLEIKA |
| B13C4 35-20 | DIVMSQSPSSLAVSAGEKVTMSC | KSSQSLLNSRTRKNYLA | WYQQKPGQSPRLLIY | WASTRES | GVPDRFTGSGSGTDFLTISSVQAEDLAVYYC | KQSYNLLT | FGAGTKLEIKA |
| B15B1lvk35-20 | DIKMTQSPSSLAVSAGENVTVSC | KSSQSLLNSRTRKNYLA | WYQQKPGQSPKLLIY | WASTRES | GVPDRFTGSGSGTDFLTISSVQAEDLAVYFC | KQSYNLLT | FGAGTKLEIKA |
| B12C12335-25 | DIKMTQSPSSLAVSPGERVTMSC | KSSQSLLHSRTRKNYLA | WYQQKPGQSPKLLIY | WASTRES | GVPDRFTGSGSGTDFLTISSVQAEDLAVYYC | KQSYNLLT | FGAGTKLEIKA |
| B13C1233520 | DIVMSQSPSSLAVSPGERVTMSC | KSSQSLLHSRTRKNYLA | WYQQKPGQSPKLLIY | WASTRES | GVPDRFTGSGSGTDFLTISSVQAEDLAVYYC | KQSYNLLT | FGAGTKLEIKA |
| (Produced Rabbit IgG clone name) | | | | | | | |
| RSDLVK-1 | DIVMTQSPSSLAVSAGEKVTMSC | KSSQSLLNSRTRKNYLA | WYQQKPGQSPRLLIY | WASTRES | GVPDRFTGSGSGTDFLTISSVQAEDLAVYFC | KQSYNLLT | FGAGTKLEIKA |
| RSDLVK-6 | DIVMTQSPSSLAVSAGEKVTMSC | KSSQSLLNSRTRKNYLA | WYQQKPGQSPRLLIY | WASTRES | GVPDRFTGSGSGTDFLTISSVQAEDLAVYFC | KQSYNLLT | FGAGTKLEIKA |
| RSDLVK-10 | DIVMTQSPSSLAVSPGERVTMSC | KSSQSLLNSRTRKNYLA | WYQQKPGQSPRLLIY | WASTRES | GVPDRFTGSGSGTDFLTISSVQAEDLAVYFC | KQSYNLLT | FGAGTKLEIKA |
| RSDLVK-13 | DIVMSQSPSSLAVSPGERVTMSC | KSSQSLLHSRTRKNYLA | WYQQKPGQSPKLLIY | WASTRES | GVPDRFTGSGSGTDFLTISSVQAEDLAVYYC | KQSYNLLT | FGAGTKLEIKA |
| (scFv clone from Yeast Display library) | | | | | | | |
| 29 | DIVMSQSPSSLAVSAGEKVTMSC | KSSQSLLNSRTRKNYLA | WYQQKPGQSPRLLIY | WASTRES | GVPDRFTGSGSGTDFLTISSVQAEDLAVYYC | KQSYNLLT | FGAGTKLEIKA |
| 44 | DIVMSQSPSSLAVSAGEKVTMSC | KSSQSLLNSRTRKNYLA | WYQQKPGQSPRLLIY | WASTRES | GVPDRFTGSGSGTDFLTISSVQAEDLAVYYC | KQSYNLLT | FGAGTKLEIKA |
| A1=B4=F9 | DIVMSQSPSSLAVSAGEKVTMSC | KSSQSLLNSRTRKNYLA | WYQQKPGQSPRLLIY | WASTRES | GVPDRFTGSGSGTDFLTISSVQAEDLAVYYC | KQSYNLLT | FGAGTKLEIKA |
| A5=C6 | DIVMSQSPSSLAVSAGEKVTMSC | KSSQSLLNSRTRKNYLA | WYQQKPGQSPRLLIY | WASTRES | GVPDRFTGSGSGTDFLTISSVQAEDLAVYYC | KQSYNLLT | FGAGTKLEIKA |
| D4=E6 | DIVMSQSPSSLAVSAGEKVTMSC | KSSQSLLNSRTRKNYLA | WYQQKPGQXPRLLIY | WASTRES | GVPDRFTGSGSGTDFLTISSVQAEDLAVYYC | KQSYNLLT | FGAGTKLEIKA |
| Final clone for in vivo/in vitro functional test in IgG format | | | | | | | |
| C6D4 | DIVMTQSPSSLAVSAGEKVTMSC | KSSQSLLNSRTRKNYLA | WYQQKPGQSPRLLIY | WASTRES | GVPDRFTGSGSGTDFLTISSVQAEDLAVYYC | KQSYNLLS | FGAGTKLEIKR |

FIG. 2

| | | |
|---|---|---|
| Human | αv | FLQDGTKTVEYAPCRSQDI*DADG*QGFCQGGFSIDFTKADRVLLGGPGSF*Y*WQGQ |
| Chimp | αv | FLQDGTKTVEYAPCRSQDI*DADG*QGFCQGGFSIDFTKADRVLLGGPGSF*Y*WQGQ |
| Rhesus | αv | FLQDGTKTVEYAPCRSQDI*DADG*QGFCQGGFSIDFTKADRVLLGGPGSF*Y*WQGQ |
| Cyno | αv | FLQDGTKTVEYAPCRSQDI*DADG*QGFCQGGFSIDFTKADRVLLGGPGSF*Y*WQGQ |
| Cow | αv | FLQDGTKTVEYAPCRSKNI*DADG*QGFCQGGFSIDFTKADRVLLGGPGSF*Y*WQGQ |
| Pig | αv | FLQDGAKTVEYAPCRSKNI*DADG*QGFCQGGFSIDFTKADRVLLGGPGSF*Y*WQGQ |
| Horse | αv | FLQDGTKTVEYAPCRSKNI*DADG*QGFCQGGFSIDFTKADRVLLGGPGSF*Y*WQGQ |
| Mouse | αv | FLQDGTKTVEYAPCRSKNI*DADG*QGFCQGGFSIDFTKADRVLLGGPGSF*Y*WQGQ |
| Rat | αv | FLQDGTKTVEYAPCRSKNI*DADG*QGFCQGGFSIDFTKADRVLLGGPGSF*Y*WQGQ |
| Armadillo | αv | FLQDGTKTVEYAPCRSRSI*DADG*QGFCQGGFSIDFTKADRVLLGGPGSF*Y*WQGQ |
| Platypus | αv | FLQDGTKTVEYAPCRSRSI*DADG*QGFCQGGFSIDFTKADRVLLGGPGSF*Y*WQGQ |

Integrin αv: Epitope for C6D4 in Bold Underlined Italics

| | | |
|---|---|---|
| Human | β8 | SASMHNNIEKLNSVGNDLSRKMAFFSRDFRLGFGSYVDKTVSPYISIHPERIHNQC*SDYNLD*CMPPHGYIHVLSLTENITEFEKAVHRQKIS |
| Chimp | β8 | SASMHNNIEKLNSVGNDLSRKMAFFSRDFRLGFGSYVDKTVSPYISIHPERIHNQC*SDYNLD*CMPPHGYIHVLSLTENITEFEKAVHRQKIS |
| Rhesus | β8 | SASMHNNIEKLNSVGNDLSRKMAFFSRDFRLGFGSYVDKTVSPYISIHPERIHNQC*SDYNLD*CMPPHGYIHVLSLTENITEFEKAVHRQKIS |
| Cyno | β8 | SASMHNNIEKLNSVGNDLSRKMAFFSRDFRLGFGSYVDKTVSPYISIHPERIHNQC*SDYNLD*CMPPHGYIHVLSLTENITEFEKAVHRQKIS |
| Cow | β8 | SASMHNNIEKLNSVGNDLSRKMAFFSRDFRLGFGSYVDKTVSPYISIHPERIHNQC*SDYNLD*CMPPHGYIHVLSLTENITEFEKAVHRQKIS |
| Pig | β8 | SASMHNNIEKLNTVGNDLSRKMAFFSRDFRLGFGSYVDKTVSPYISIHPERIHNQC*SDYNLD*CMPPHGYIHVLSLTENITEFEKAVHRQKIS |
| Horse | β8 | SASMHNNIEKLNSVGNDLSRKMAFFSRDFRLGFGSYVDKTVSPYISIHPERIHNQC*SDYNLD*CMPPHGYIHVLSLTENITEFEKAVHRQKIS |
| Mouse | β8 | SASMHNNIEKLNSVGNDLSKKMAFFSRDFRLGFGSYVDKTVSPYISIHPERIHNQC*SDYNLD*CMPPHGYIHVLSLTENITEFEKAVHRQKIS |
| Rat | β8 | SASMHNNIEKLNSVGNDLSKKMALFSHDERLGFGSYVDKTVSPYISIHPERIHNQC*SDYNLD*CMPPHGYIHVLSLTENITEFAKAVHRQKIS |
| Armadillo | β8 | SASMHNNIEKLNSVGNDLSRKMAFFSLDFRLGFGSYVDKTVSPYISIHPERIHNQC*SDYNLD*CMPPHGYIHVLSLTENITEFEKAVHRQKIS |
| Platypus | β8 | SASMHNNIEKLNSVGNDLSQKMADFTRDFRLGFGSYVDKTVSPYISIHPGRIRNQC*SQYLD*CMPPHGYIHVLPITENVTEFEKAVNKQKIS |

FIG. 4

```
  1  FNLDVDSPAEYSGPEGSYFGFAVDFFVPSASSRMFLLVGAPKANTTQPGI   50
 51  VEGGQVLKCDWSSTRRCQPIEFDATGNRDYAKDDPLEFKSHQWFGASVRS  100
101  KQDKILACAPLYHWRTEMKQEREPVGTCFLQDGTKTVEYAPCRSQDI*DAD*  150
151  *G*QGFCQGGFSIDFTKADRVLLGGPGSF*YW*QGQLISDQVAEIVSKYDPNVY  200
201  SIKYNNQLATRTAQAIFDDSYLGYSVAVGDFNGDIDDFVSGVPRAARTL  250
251  GMVYIYDGKNMSSLYNFTGEQMAAYFGFSVAATDINGDDYADVFIGAPLF  300
301  MDRGSDGKLQEVGQVSVSLQRASGDFQTTKLNGFEVFARFGSAIAPLGDL  350
351  DQDGFNDIAIAAPYGGEDKKGIVYIFNGRSTGLNAVPSQILEGQWAARSM  400
401  PPSFGYSMKGATDIDKNGYPDLIVGAFGVDRAILYRARPVITVNAGLEVY  450
451  PSILNQDNKTCSLPGTALKVSCFNVRFCLKADGKGVLPRKLNFQVELLLD  500
501  KLKQKGAIRRALFLYSRSPSHSKNMTISRGGLMQCEELIAYLRDESEFRD  550
551  KLTPITIFMEYRLDYRTAADTTGLQPILNQFTPANISRQAHILLDCGEDN  600
601  VCKPKLEVSVDSDQKKIYIGDDNPLTLIVKAQNQGEGAYEAELIVSIPLQ  650
651  ADFIGVVRNNEALARLSCAFKTENQTRQVVCDLGNPMKAGTQLLAGLRFS  700
701  VHQQSEMDTSVKFDLQIQSSNLFDKVSPVVSHKVDLAVLAAVEIRGVSSP  750
751  DHVFLPIPNWEHKENPETEEDVGPVVQHIYELRNNGPSSFSKAMLHLQWP  800
801  YKYNNNTLLYILHYDIDGPMNCTSDMEINPLRIKISSLQTTEKNDTVAGQ  850
851  GERDHLITKRDLALSEGDIHTLGCGVAQCLKIVCQVGRLDRGKSAILYVK  900
901  SLLWTETFMNKENQNHSYSLKSSASFNVIEFPYKNLPIEDITNSTLVTTN  950
951  VTWGIQPAPMPVPVWVIILAVLAGLLLLAVLVFVMYRMGFFKRVRPPQEE 1000
1001 QEREQLQPHENGEGNSET                                 1018
```

Integrin AlphaV (Human, No Signal Peptide) –
Epitope for C6D4 in *Bold Underlined Italics*

```
  1  EDNRCASSNAASCARCLALGPECGWCVQEDFISGGSRSERCDIVSNLISK   50
 51  GCSVDSIEYPSVHVIIPTENEINTQVTPGEVSIQLRPGAEANFMLKVHPL  100
101  KKYPVDLYYLVDVSASM*H*NNIEKLNSVGNDLSRKMAFFSRDFRLGFGSYV  150
151  DKTVSPYISIHPERIHNQC*SDYNLD*CMPPHGYIHVLSLTENITEFEKAV*H*  200
201  *R*QKISGNIDTPEGGFDAMLQAAVCESHIGWRKEAKRLLLVMTDQTSHLAL  250
251  DSKLAGIVVPNDGNCHLKNNVYVKSTTMEHPSLGQLSEKLIDNNINVIFA  300
301  VQGKQFHWYKDLLPLLPGTIAGEIESKAANLNNLVVEAYQKLISEVKVQV  350
351  ENQVQGIYFNITAICPDGSRKPGMEGCRNVTSNDEVLFNVTVTMKKCDVT  400
401  GGKNYAIIKPIGFNETAKIHIHRNCSCQCEDNRGPKGKCVDETFLDSKCF  450
451  QCDENKCHFDEDQFSSESCKSHKDQPVCSGRGVCVCGKCSCHKIKLGKVY  500
501  GKYCEKDDFSCPYHHGNLCAGHGECEAGRCQCFSGWEGDRCQCPSAAAQH  550
551  CVNSKGQVCSGRGTCVCGRCECTDPRSIGRFCEHCPTCYTACKENWNCMQ  600
601  CLHPHNLSQAILDQCKTSCALMEQQHYVDQTSECFSSPSYLRIFFIIFIV  650
651  TFLIGLLKVLIIRQVILQWNSNKIKSSSDYRVSASKKDKLILQSVCTRAV  700
701  TYRREKPEEIKMDISKLNAHETFRCNF                        727
```

Integrin Beta8 (Human, No Signal Peptide) –
Epitope for C6D4 in *Bold Underlined Italics*

FIG. 5

| PBS | ALT Day 0 | HBSag ELISA | ALT Day 7 | HBSag ELISA | ALT Day 14 | HBSag ELISA |
|---|---|---|---|---|---|---|
| 1 | 71 | POS | 33 | POS | 68 | POS |
| 2 | 77 | POS | 10 | POS | 27 | POS |
| 3 | 20 | POS | 16 | POS | 38 | POS |
| 4 | 33 | POS | 17 | POS | 51 | POS |
| 5 | 28 | POS | 14 | POS | 31 | POS |
| C6D4 | | | | | | |
| 1 | 38 | POS | 23 | NEG | 26 | NEG |
| 2 | 31 | POS | 24 | NEG | 20 | NEG |
| 3 | 24 | POS | 59 | NEG | 31 | NEG |
| 4 | 28 | POS | 24 | POS | 20 | POS |

FIG. 10

| VH (Mouse Hybridoma clone Name) | Framework 1 | CDR1 | Framework 2 | CDR2 | Framework 3 | CDR3 | Framework 4 |
|---|---|---|---|---|---|---|---|
| 4F1 | QVQLQQSGAELVRPGTSVKVSCKASGY | AFTDYLIE | WVKQRPGQGLEWIG | VINPETGGTNYNAKFKV | KATLTADKSSSTAYMQLGGLTFDDSAVYFCAR | EGNARTYYYAMDY | WGQGTSVTVSS |
| 6B9 | QVQLQQSGAELVRPGTSVKVSCKASGY | AFTDYLIE | WVKQRPGQGLEWIG | VINPETGGTNYNAKFKG | KATLTADKSSSTVYMQLSSLTSGDSAVYFCAR | EAGNIYAMDY | WGQGTSVTVSS |
| (scFv clone Name from yeast display library) | | | | | | | |
| 6B9.1 | QVQLQQSGAELVRPGTSVKVSCKASGY | AFTDYLIE | WVKQRPGQGLEWIG | VINPETGGTNYNAKFRG | KATLTADKSSSAYMQLSSLTSGDSAVYFCAR | EAGNIYAMDY | WGQGTSVTVSS |
| A1 | QVQLQQSGAELVRPGASVKVSCKASGY | AFTDYLIE | WVKQRPGQGLEWIG | VINPETGGTNYNAKFRG | KATLTADKSSSSVYMQLSSLTSGDSAVYFCAR | EAGNIYAMDY | WGQGTSVTVSS |
| A2 | QVQLQQSGAELVRPGTSVKVSCKASGY | AFTDYLIE | WVKQRPGQGLEWIG | VINPETGGTNYNAKFRG | KATLTADKSSSTAYMQLSSLTSGDSAVYFCAR | EAGNIYAMDY | WGQGTSVTVSS |
| A8 | QVQLQQSGAELVRPGTSVKVSCKASGY | AFTDYLIE | WVKQRPGQGLEWIG | VINPETGGTNYNAKFRG | KATLTADKSSSAYMQLSGLTSGDSAVYFCAR | EAGNIYAMDY | WGQGTSVTVSS |
| A11 | QVQLQQSGAELVRPGTSVKVSCKASGY | AFTDNLIE | WVKQRPGQGLEWIG | VINPETGGTNYNAKFRG | KATLTADKSSSAYMQLSSLTSGDSAVYFCAR | EAGNIYAMDY | WGQGTSVTVSS |
| B1 | QVQLQQSGAELVRPGTSVKVSCKASGY | AFTDYLIE | WVKQRPGQGLEWIG | VINPETGGTNYNAKFRG | KATLTADKSSSAYMQLSSLTSGDSAVYFCAR | EAGNIYAMDY | WGQGTSVTVSS |
| B3 | QVQLQQSGAELVRPGTSVKVSCKASGY | AFTDYLIE | WVKQRPGQGLEWIG | VINPETGGTNYNAKFRG | KATLTADKSSSAYMQLSSLTSGDSAVYFCAR | EAGNIYAMDY | WGQGTSVTVSS |
| C4=F10 | QVQLQQSGAELVRPGTSVKVSCKASGY | AFTDYLIE | WVKQRPGQGLEWIG | VINPETGGTNYNAKFRG | RATLTADKSSSAYMQLSSLTSGDSAVYFCAR | EAGNIYAMDY | WGQGTSVTVSS |
| C7=D1 | QVQLQQSGAELVRPGTSVKVSCKASGY | AFTDYLIE | WVKQRPGQGLEWIG | VINPETGGTNYNAKFRG | KATLTADKSSSAYMQLSSLTSGDSAVYFCAR | EAGNIYAMDY | WGQGTSVTVSS |
| D3=F1 | QVQLQQSGAELVRPGTSVKVSCKASGY | AFTDYLIE | WVKQRPGQGLEWIG | VINPETGGTNYNAKFRG | KATLTADKSSSAYMQLSSLTSGDSAVYFCAR | EAGNIYAMDY | WGQGTSVTVSS |
| D10=E5 | QVQLQQSGAELVRPGTSVKVSCKASGY | AFTDYLIE | WVKQRPGQGLEWIG | VINPETGGTNYNAKFRG | KVTLTADKTSSSAYMQLSSLTSGDSAVYFCAR | EAGNIYAMDY | WGQGTSVTVSS |
| G4 | QVQLQQSGAELVRPGTSVKVSCKASGY | AFTDYLIE | WVKQRPGQGLEWIG | VINPETGGTNYNAKFRG | KVTLTADKSSSAYMQINSLTSGDSAVYFCAR | EAGNIYAMDY | WGQGTSVTVSS |
| (Produced Rabbit IgG clone name) | | | | | | | |
| C4 | QVQLQQSGAELVRPGTSVKVSCKASGY | AFTDYLIE | WVKQRPGQGLEWIG | VINPETGGTNYNAKFRG | RATLTADKSSSAYMQLSSLTSGDSAVYFCAR | EAGNIYAMDY | WGQGTSVTVSS |
| D10 | QVQLQQSGAELVRPGTSVKVSCKASGY | AFTDYLIE | WVKQRPGQGLEWIG | VINPETGGTNYNAKFRG | KVTLTADKTSSSAYMQLSSLTSGDSAVYFCAR | EAGNIYAMDY | WGQGTSVTVSS |
| (scFv clone from Phage Display library) | | | | | | | |
| 4F1A11 | QVQLQQSGAELVRPGTSVKVSCKASGY | AFTDYLIE | WVKQRPGQGLEWIG | VINPETGGTNYNAKFRG | RATLTADKSSSAYMQLSSLTSGDSAVYFCAR | EAGNIYAMDY | WGQGTSVTVSS |
| 4F1E1 | QVQLQQSGAELVRPGTSVKVSCKASGY | AFTDYLIQ | WVKQRPGQGLEWIG | VINPETGGTNYNAKFRG | KATLTADKSSSAYMQLSSLTSGDSAVYFCAR | EAGNIYAMDY | WGQGTSVTVSS |
| 4F1G3 | QVQLQQSGAELVRPGTSVRVSCKASGY | AFTDYLIQ | WVKQRPGQGLEWIG | VINPETGGTNYNAKFRG | KATLTAMKSSSAYMQLSSLTSGDSAVYFCAR | EAGNIYAMDY | WGQGTSVTVSS |
| 4F1E10 | QVQLQQSGAELVRPGTSVKVSCKASGY | AFTDYLIQ | WVKQRPGQGLEWIG | VINPETGGTNYNAKFRG | KATLTADKSSSAYMQLSSLTSGDSAVYFCAR | EAGNIYAMDY | WGQGTSVTVSS |
| 4F1E9 | QVQLQQSGAELVRPGTSVKVPCKASGY | AFTDYLIE | WVKQRPGQGLEWIG | VINPETGGTNYNAKFRG | KATLTADKSSSAYMQLSSLTSGDSAVYFCAR | EAGNIYAMDY | WGQGTSVTVSS |
| 4F1H12 | QVQLQQSGAELVRPGTSVKVSCKASGY | AFTDYLIQ | WVKQRPGQGLEWIG | VINPETGGTNYNAKFRG | KATLTADKSSSAYMQLSSLTSGDSAVYFCAR | EAGNIYAMDY | WGQGTSVTVSS |
| Final clone for in vitro functional test in IgG format | | | | | | | |
| F9 | QVQLQQSGAELVRPGTSVKVSCKASGY | AFTDYLIQ | WVKQRPGQGLEWIG | VINPETGGTNYNAKFRG | KATLTADKSSSAYMQLSSLTSGDSAVYFCAR | EAGNIYAMDY | WGQGTSVTVSS |

FIG. 11A

| VL | Framework 1 | CDR1 | Framework2 | CDR2 | Framework3 | CDR3 | Framework 4 |
|---|---|---|---|---|---|---|---|
| (Mouse Hybridoma clone Name) | | | | | | | |
| 4F1 | DIQMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| 689 | DIEMTQTPASLSASVGETVTITC | RASENIYSYLV | WYQQKQGKSPQLVIV | NAKTLAE | GVPSRFSGSGSGTQFSLKINSLQPEDFGSYYC | QHHGTPYT | FGGGTKLEIKA |
| (scFv clone Name from yeast display library) | | | | | | | |
| 6B9.1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| A1 = A2 = C4 = C7 = D1 = D10 = E5 = F1 = E10 = G4 | | | | | | | |
| A6 | DIVMTQSPASLSASVGETVTITC | RASVNIYSYLV | WYQQKQGKSPQLLVH | NAKTLAE | GVPSRFSGSGSGTQFSLKINSVQPEDFGSYYC | QHHHGTPYT | FGGGTKLEIKA |
| A11 | HIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| B1 | DIVMTQSPASLSASVGETVTITC | RASVNIYSYLV | WYQQKQGKSPQLLVH | NAKTLAE | GVPSRFSGSGSGTQFSLKINSLQPEDFGSYYCY | QHHHGTPYT | FGGGTKLEIKA |
| B3 | DIVMTQSPASLSASVGETVTITC | RASVNIYSYLV | WYQQKQGKSPQLLVH | NAKTLAA | GVPSRFSGSGSGTQFSLKINSLQPEDFGSYYC | QHHHGTPYT | FGGGTKLEIKA |
| D10=E5 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| (Produced Rabbit IgG clone name) | | | | | | | |
| C4 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| D10 | DIEMTQTPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| (scFv clone from Phage Display library) | | | | | | | |
| 4F1E1 = 4F1G3 = 4F1B5 = 4F1G1 = 4F1A9 = 4F1F9 = 4F1A9 = 4F1D10 = 4F1E9 = 4F1E10 = 4F1H10 = 4F1H11 = 4F1H12 | | | | | | | |
| 4F1A11 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| Final clone for in vitro functional test in IgG format | | | | | | | |
| F9 | DIVMTQSPAFLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |

FIG. 11B

C6D4 binds integrin αVβ8 at the head domain

Zoom-in onto the integrin αVβ8 head domains and bound Fab C6D4

C6D4, Vk, CDR1: KSSQSLLNSRTRKNYLA
αV, β-propeller domain, blade W3: ...DIDADGQG...SFYWQ...

Interacting residues are in bold

C6D4, Vh, CDR1: DYSMH  CDR3: FYYGRDS
β8, SDL: 153 TVSPYISIHPERIHNQCSDYNLDCMPPH 180
C6D4, Vk, CDR1: KSSQSLLNSRTRKNYLA  CDR2: WASTRES  CDR3: KQSYNLLS
Interacting residues are in bold

This residue is technically outside of the CDR

C6D4, Vk, CDR2: YWASTRES
β8, α1 helix: 114 SASMHNNIEKLNSVGNDLSRKMAFFS 139
Interacting residues are in bold

This residue is technically outside of the CDR

C6D4, Vh, CDR1: YTFTDYSMH

β8, α2 helix: 191 NITEFEKAVHR 201

Interacting residues are in bold

β8 integrin subunit is increased in expression in the crypt epithelial cells of patients infected with H. Pylori
H. Pylori
FIG. 21A  FIG. 21B
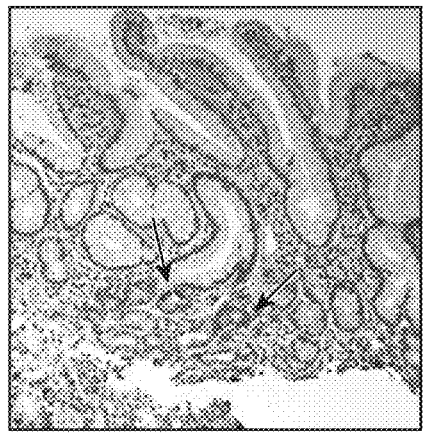
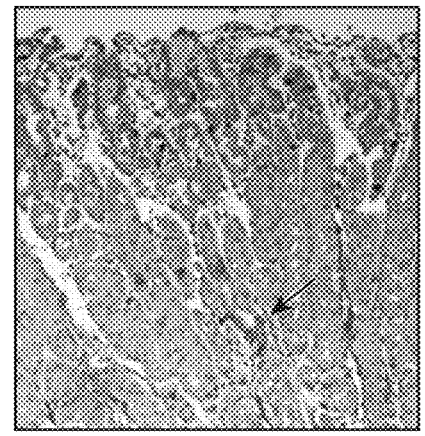
Normal
FIG. 21C  FIG. 21D

Method of LLC-multiple metastasis model

LLC.1 cells s.c.
(1M cells)

Surgery:
Isolate weight and measure primary tumor and perform immune cell analysis Euthanasia when mice lose 20% of body weight or have Local recurrence (> 1 cm).

WT mice
C57BL/6
(n=22)

Day 1    8    15    22    36+
3/24/2017

Surgery at day 15

B5 (does not cross-react with mouse, serves as negative control);
C6D4-Murine IgG2a given 1x/wk IP at 7mg/kg

FIG. 28

Lung Adenocarcinoma: β8 expression inversely correlates with PD-PL1 expression anti-PD-L1 (E1L3N)

anti-β8 (F9)

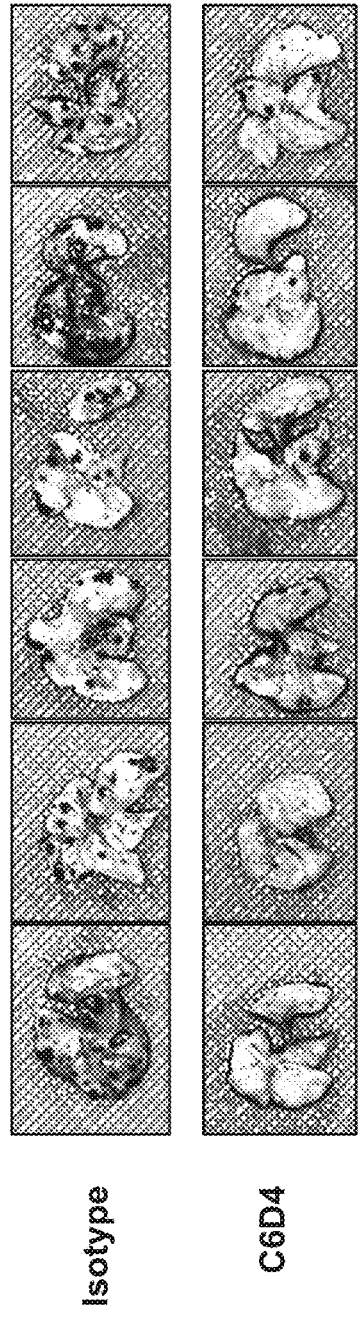
FIG. 34A
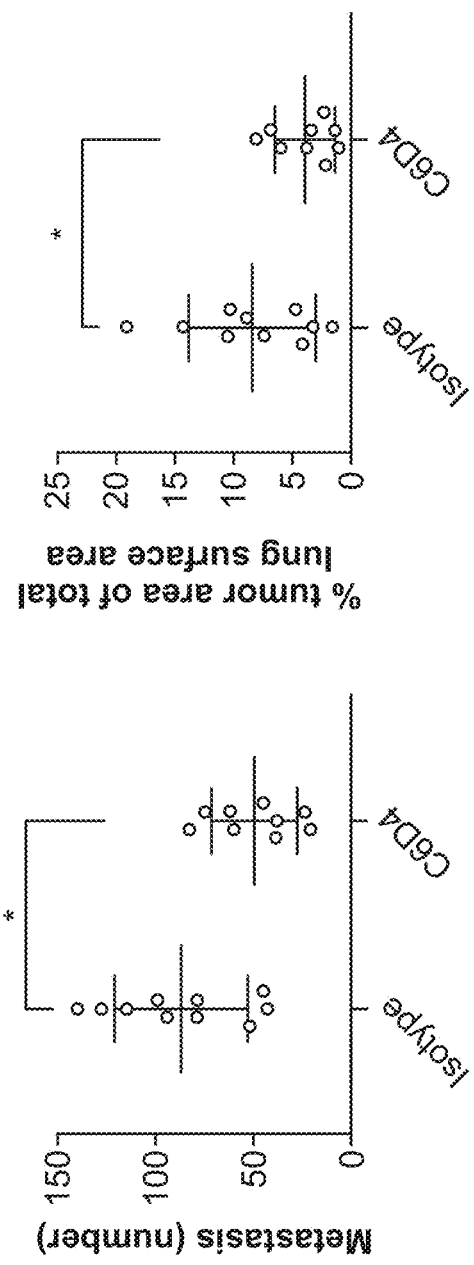
FIG. 34C
FIG. 34B

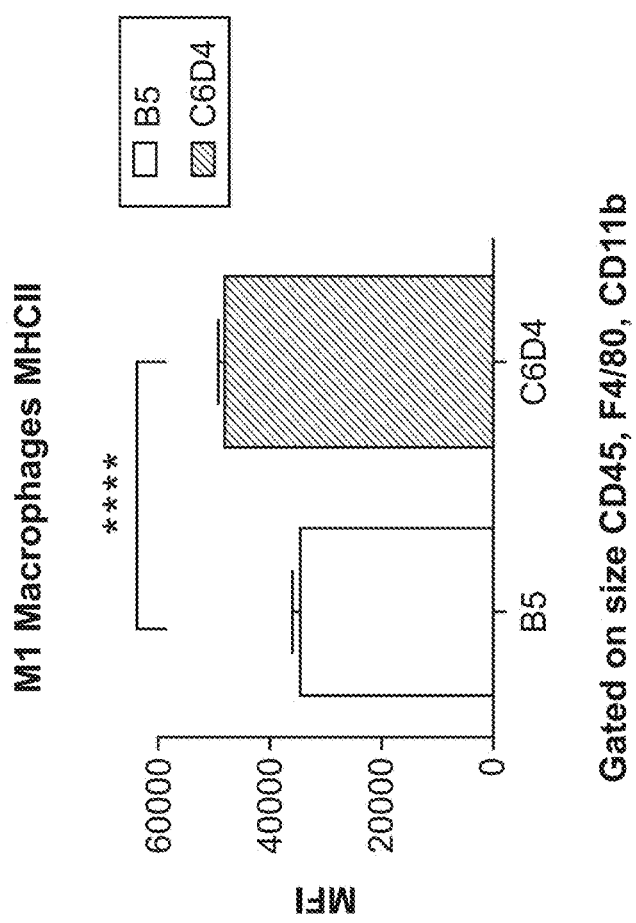
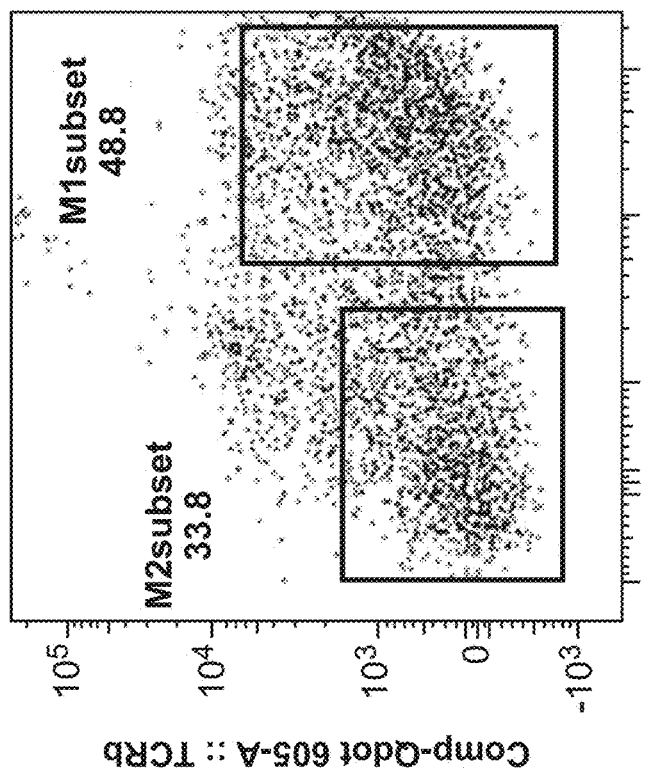
FIG. 35H
FIG. 35G

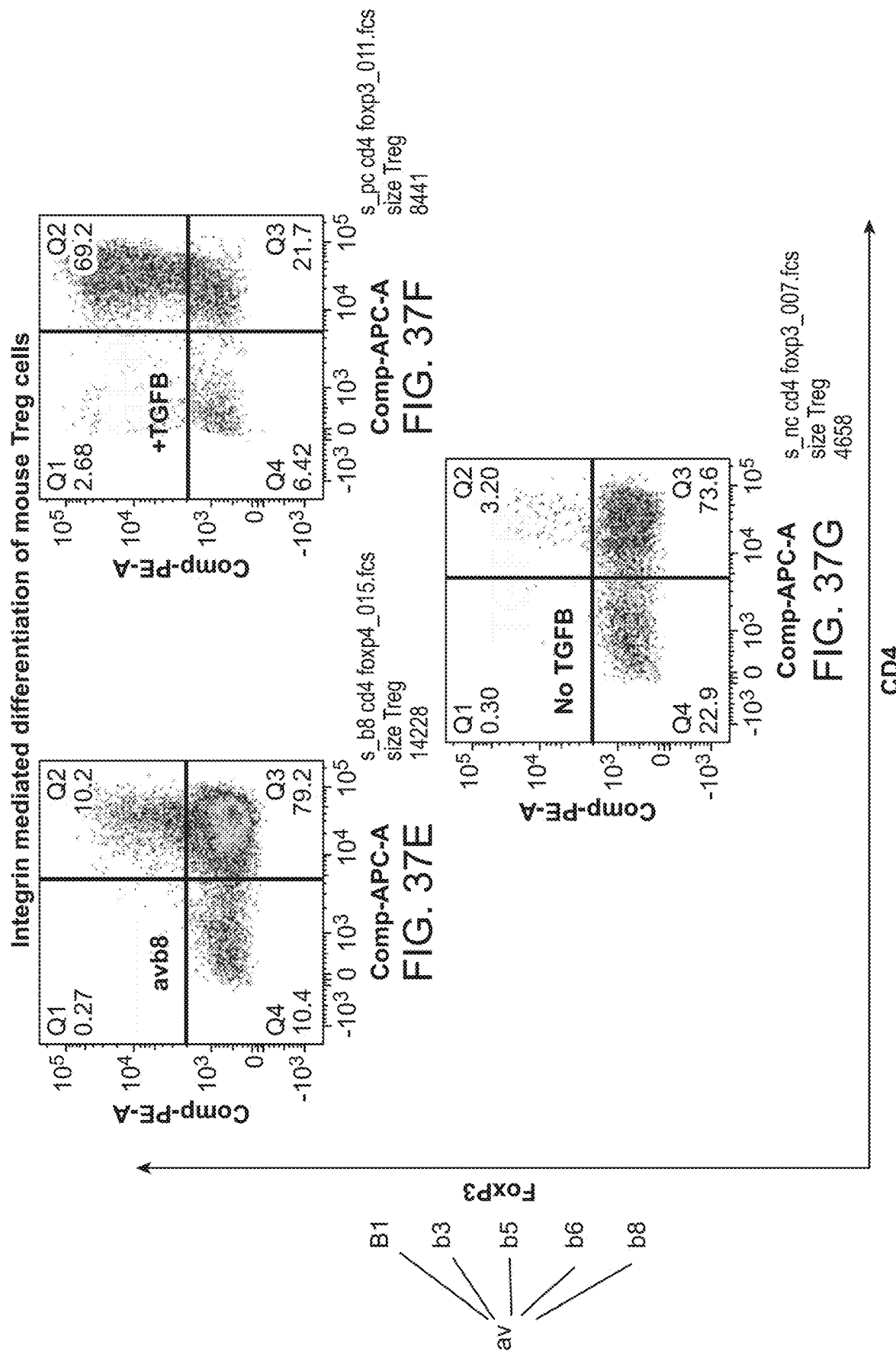

Structure based development of a C6D4 derivative (C6D4-RGD3) that is cross-reactive to both avb6 and avb8

αVβ6: GRGDLGRLKK
αIIbβ3: GRGDSP
αIIbβ3: AKQRGDV

FIG. 38A

Structure based development of a C6D4 derivative (C6D4-RGD3) that is cross-reactive to both avb6 and avb8

TGFB1      MPPSGLRLLLLLLPLLWLLVLTPGRPAAGLSTCKTITMELVKRKRIEAIRGQIISKLRLASPPSQGEVPPGPLPE
TGFB2      MHYCVLSAFL------------ILHLVTVALSLSTCSTLDMDQFMRKRIEAIRGQIISKLKLTSPPEDYPEPEEVPP
TGFB3      MKMHLQRALV------------VLALLNFATVSLSLSTCTTLDFGHIKKKRVEAIRGQIISKLRLTSPPEPTVM---EHPY
cons       *           :           :::  ::* *:  :::  . .* ***:*.::*.:: *      : *

TGFB1      AVLALYNSTRDRVAGESAE-------PEPEPEADYYAKEVTRVLMVE---THNEIYDKFKQSTHSIYMFFNTSELRE
TGFB2      EVISIYNSTRDLLQEKASRRAAACERRSDEEYYAKEVYKIKHKFDMIQGLAEHNELAVCPKGITSKVFRF-DVSAMEK
TGFB3      QVLALYNSTRDLLQEKASRRAAACERRSDEEYYAKEVYKIKHKFDMIQGLAEHNELAVCPKGITSKVFRF-NVSSVEK
cons       *::::****:   *:.                  : ::  :       .      .:  :::: *. **    :

TGFB1      AVFPPVLLSRAELRLLRLKL------KVEQHVELYQKYSN---NSWRYLSNRLLAPSDSPEWLSFDVTGVVRQWL
TGFB2      ----NASNLVKAEFRVRLQNPKARVPEQRIELYQILKSRDLTSPTQRYIDSKVVKTRAEGEWLSFDVTDAVHEWL
TGFB3      ----NRTNLFRAEFRVLRVPNESSKRNEQRIELFQILRPDEH---IAQRYIGGKNLPTRGTAEWLSFDVTDTVREWL
cons       .      *: :**:*: :            ::**: :             : :   .: *  . .****.  :*

TGFB1      SRGGEIEGFRLSAHCSCDSRD-------NTLQ---VDINGFTTGRGDLATIHG---MNRPFLLMAAT
TGFB2      HHKDRNLGFKISLHCPCCTFVPSNNYIIPNKSEELEARFAGIDGTSTYTSGDQKTIKSTRKKNSGKTPHLLLMLL
TGFB3      LRRESNLGLEISIHCPCHTFQPNG-DILENIHEVMEIKFKGVDNEDDHGRGDLGRLKKQK---DHHNPHLILMMI
cons       .    ::*::*  * .:.                              *  .            .:**::*

TGFB1      PLERAQHL-QSSL-RHRRALDTNYCFSSTEKNCCVRQLYIDFRKDLGWKWIHEPKGYHANFCLGPCPYIWSLDTQY
TGFB2      PSYRLESQ-QTNRRKKRALDAAYCFRNVQDNCCLRPLYIDFKRDLGWKWIHEPKGYNANFCAGACPYLWSSDTQH
TGFB3      PPHRLDNPGQGGQRKKRALDTNYCFRNLEENCCVRPLYIDFRQDLGWKWVHEPKGYYANFCSGPCPYLRSADTTH
cons       *  *            :** :*.: :.**:* ***::*:**:   *:  :**

TGFB1      SKVLALYNQHNPGASAAPCCVPQALEPLPIVYYVGRKPKVEQLSNMIVRSCKCS
TGFB2      SRVLSLYNTINPEASASPCCVSQDLEPLTILYYIGKTPKIEQLSNMIVKSCKCS
TGFB3      STVLGLYNTLNPEASASPCCVPQDLEPLTILYYVGRTPKVEQLSNMVVKSCKCS
cons       * .* :.::****.* **.:::*:::***:*:*****

FIG. 38B

Structure based development of a C6D4 derivative (C6D4-RGD3) that is cross-reactive to both avb6 and avb8

C6D4_vk
DIVMTQSPSSLAVSAGEKVTMSCKSSQSLLNSRTRKNYLAWYQQKPGQSPRLLIYWASTRESGVPDRFTGSGSGTDFTLTISSVQAEDLAVYYCKQSYNLLSFGAGTKLE
LKAADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC

C6D4-RGD1 KSSQS

FIG. 39

Vk CDR1/RGD mutant binding to avb8 expressing cells compared to WT C6D4 n=4

C6D4 binding to αvβ8 is not enhanced by cations C6D4-RGD3 binding to αvβ8 is enhanced by cations and cation-dependent to αvβ6

| Mab (5 ug/ml) | Receptor | Binding in EDTA buffer (% compared with binding to anti-av clone 11D12V2) | Binding in Mg buffer relative to clone 68 (% compared with binding to anti-av clone 11D12V2 |
|---|---|---|---|
| C6D4 | avb8 | 105% | 103% |
| C6D4 | avb6 | 0% | 0% |
| RGD3 | avb8 | 11% | 98% |
| RGD3 | avb6 | 0% | 120% |

FIG. 42

Humanization of C6D4

C6D4 Humanization design and FACS Screened based on risk factor and germline (VH1/VK3) picking results with yeast scFv KD data

| VH (Mouse IgG2a) | Framework 1 | CDR1 | Framework 2 | CDR2 | Framework 3 | CDR3 | Framework 4 | scFv KD (nM) |
|---|---|---|---|---|---|---|---|---|
| C6D4 | QIQLVQSGPELKKPGETVKISCKASGYTFT | DYSMH | WVKQAPGKGLKWVA | RINTETGEPTFADDFRG | RFAVSLETSASTAYLQINNLKNEDTATYFCAI | FYYGRDS | WGQGTTLTVSS | 7.2507 |
| HuC6D4 V1 | QIQLVQSGAEVKKPGASVKISCKASGYTFT | DYSMH | WVRQAPGQGLEWVA | RINTETGEPTFADDFRG | RFVTMLDTSTSTAYLEIRSLRSDDTAVYFCAI | FYYGRDS | WGQGTTLTVSS | 15.571 |
| Mutclone A3 | QIQLVQSGAEVKKPGASVKISCKASGYTFT | DYSMH | WVRQAPGQGLEWVA | RINTETGEPTFADDFRG | RFTVTLDTSTSTAYLEIRSLRSDDTAVYFCAI | FYYGRDS | WGQGTTLTVSS | 7.4638 |
| Mutclone B7 | QIQLVQSGAKVKKPGASVKISCKASGYTFT | DYSMH | WVRQAPGQGLEWVA | RINTETGEPTFADDFRG | RFSVTLDTSTSTAYLEIRSLRSDDTAVYFCAI | FYYGRDT | WGQGTAITVSS | 6.9373 |
| Mutclone E5 | QIQLVQSGAEVKKPGASVKISCKASGYTFT | DYSMH | WVRQAPGQGLEWVA | RINTETGEPTFADDFRG | RFTVTLDTSTSTAYLEIRSLRSDDTAVYFCAI | FYYGRDT | WGQGTTLTVSS | 6.5826 |

| VK (Mouse IgG2a) | Framework 1 | CDR1 | Framework 2 | CDR2 | Framework 3 | CDR3 | Framework 4 | scFv KD (nM) |
|---|---|---|---|---|---|---|---|---|
| C6D4 | DIVMTQSPSSLAVSAGEKVTMSC | KSSQSLLNSRTRKNYLA | WYQQKPGQSPRLLIY | WASTRES | GVPDRFTGSGSGTDFTLTISSVQAEDLAVYYC | KQSYNLLS | FGAGTKLELKR | 7.2507 |
| HuC6D4 V1 | EIVMTQSPATLSVSPGERVTMSC | KSSQSLLNSRTRKNYLA | WYQQKPGQAPRLLIY | WASTRES | GVPARFSGSGSGTEFTLTISSVQSEDFAVYYC | KQSYNLLS | FGQGTVLEIKR | 15.571 |
| Mutclone A3 | EIVMTQSPATLSVSPGEIVTMSC | KSSQSLLNSRTRKNYLA | WYQQKPGQAPRLLIY | WASTRES | GVPARFSGSGSGTEFTLTISSVQSEDFAVYYC | KQSYNLIS | FGQGTVLEIKR | 7.4638 |
| Mutclone B7 | EIVMTQSPATLSVSPGERVTMSC | KSSQSLLNSRTRKNYLA | WYQQRPGQAPRLLIY | WASTRES | DVPARFSGSGSGTEFTLTISSVQSEDFAVYYC | KQSSNLIS | FGQGTVLEIKR | 6.9373 |
| Mutclone E5 | EIVMTQTPVTLSVSPGERVTMSC | KSSQSLLNSRSRKNYLA | WYQQKPGQAPRLLIY | WASTRES | GVPARFSGSGSGTEFTLTISSVQSEDFAVYYC | KQSYNLIS | FGQGTVLEIKR | 6.5826 |

FIG. 46

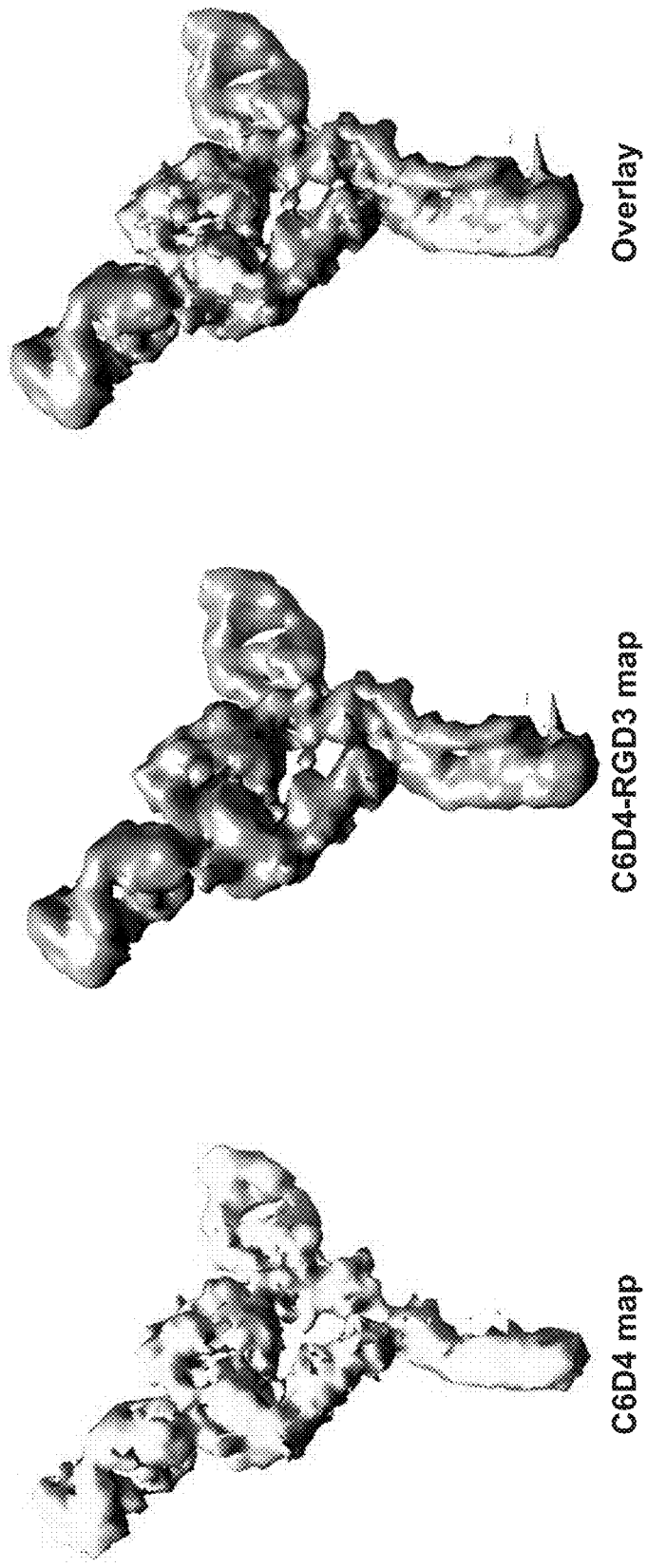

| VH (Mouse Hybridoma Name) | Framework 1 | CDR1 | Framework 2 | CDR2 | Framework 3 | CDR3 | Framework 4 |
|---|---|---|---|---|---|---|---|
| HuC6D4V1 | QIQLVQSGPELKKPGASVKISCKASGYTFT | DYSMH | WVRQAPGQGLEWVA | RINTETGEPTFADDFRG | RFTVTLDTSTSTAYLEIRSLRSDDTAVYFCAI | FYYGRDS | WGQGTTLTVSS |
| HuC6D4A3 | QIQLVQSGAEVKKPGASVKISCKASGYTFT | DYSMH | WVRQAPGQGLEWVA | RINTETGEPTFADDFRG | RFTVTLDTSTSTAYLEIRSLRSDDTAVYFCAI | FYYGRDS | WGQGTTLTVSS |
| HuC6D4B7 | QIQLVQSGAEVKKPGASVKISCKASGYTFT | DYSMH | WVRQAPGQGLEWVA | RINTETGEPTFADDFRG | RFSVTLDTSTSTAYLEITSLRSDDTAVYFCAI | FYYGRDT | WGQGTTLTVSS |
| HuC6D4E5 | QIQLVQSGAEVKKPGASVKISCKASGYTFT | DYSMH | WVRQAPGQGLEWVA | RINTETGEPTFADDFRG | RFTVTLDTSTSTAYLEIRSLRSDDTAVYFCAI | FYYGRDT | WGQGTTLTVSS |

Final clone for in vivo/in vitro Functional test in IgG format

| VH (Mouse Hybridoma Name) | Framework 1 | CDR1 | Framework 2 | CDR2 | Framework 3 | CDR3 | Framework 4 |
|---|---|---|---|---|---|---|---|
| C6D4 | QIQLLQSGPELKKPGETVKISCKASGYTFT | DYSMH | WVKQAPGKGLKWVA | RINTETGEPTFADDFRG | RFAVSLETSASTAYLQINNLKNEDTATYFCAI | FYYGRDS | WGQGTTLTVSS |
| HuC6D4 | QIQLVQSGAEVKKPGASVKISCKASGYTFT | DYSMH | WVRQAPGQGLEWVA | RINTETGEPTFADDFRG | RFAVSLETSASTAYLQINNLKNEDTATYFCAI | FYYGRDS | WGQGTTLTVSS |
| C6D4-RGD3 | QIQLVQSGPELKKPGETVKISCKASGYTFT | DYSMH | WVKQAPGKGLKWVA | RINTETGEPTFADDFRG | RFTVTLDTSTSTAYLEIRSLRSDDTAVYFCAI | FYYGRDT | WGQGTTLTVSS |
| HuC6D4-RGD3 | QIQLVQSGAEVKKPGASVKISCKASGYTFT | DYSMH | WVRQAPGQGLEWVA | RINTETGEPTFADDFRG | RFTVTLDTSTSTAYLEIRSLRSDDTAVYFCAI | FYYGRDT | WGQGTTLTVSS |

Consensus sequence of HuC6D4 related clones:

Consensus VH: QIQL$x_1$QSG$x_2 x_3 x_{34}$KKPG$x_4 x_5$VKISCKASGYTFT DYSMH WV$x_6$QAPG$x_7$G$x_L8$W$x_9 x_{10}$ $x_{11} x_{12}$TET$x_{13}$EPT$x_{14}$ADDF$x_{15} x_{16}$ RF$x_{17} x_{18} x_{19}$L$x_{20}$TS$x_{21} x_{22}$TA$x_{23}$L$x_{24} x_{25} x_{26}$L$x_{27} x_{28} x_{29}$DT$x_{30}$YFCAI $x_{31}$YYGRD$x_{32}$ WGQGT$x_{33}$LVTVSS where $x_1$ = V or L, $x_2$ = A or P, $x_3$ = E or K, $x_4$ = A or E, $x_5$ = S or T, $x_6$ = R or K, $x_7$ = Q or K, $x_8$ = E or K, $x_9$ = V or M, $x_{10}$ = A or G, $x_{11}$ = R or W, $x_{12}$ = N or K, $x_{13}$ = G or D, $x_{14}$ = F or Y, $x_{15}$ = R, N, K or G, $x_{16}$ = G or E, $x_{17}$ = T, A, or S, $x_{18}$ = V or F, $x_{19}$ = T or S, $x_{20}$ = D or E, $x_{21}$ = T or A, $x_{22}$ = S or T, $x_{23}$ = Y or N, $x_{24}$ = E or Q, $x_{25}$ = R, N, I or T, $x_{26}$ = S or N, $x_{27}$ = R or K, $x_{28}$ = S or N, $x_{29}$ = D or E, $x_{30}$ = V, T, or K, $x_{31}$ = F or Y, $x_{32}$ = T or S, $x_{33}$ = T or A, $x_{34}$ = V or L.

FIG. 50

| VL (Mouse Hybridoma Name) | Framework 1 | CDR1 | Framework 2 | CDR2 | Framework 3 | CDR3 | Framework 4 |
|---|---|---|---|---|---|---|---|
| HuC6D4V1 | EIVMTQSPATLSVSPGERVTMSC | KSSQSLLNSRTRKNYLA | WYQQKPGQAPRLLIY | WASTRES | GVPARFSGSGSGTEFTLTISSVQSEDFAVYYC | KQSYNLLS | FGQGTVLEIKR |
| HuC6D4A3 | EIVMTQSPATLSVSPGEIVTMSC | KSSQSLLNSRSRKNYLA | WYQQKPGQAPRLLIY | WASTRES | GVPARFSGSGSGTEFTLTISSVQSEDFAVYYC | KQSYNLLS | FGQGTVLEIKR |
| HuC6D4B7 | EIVMTQTPVTLSVSPGERVTMSC | KSSQSLLNSRTRKNYLA | WYQQKPGQAPRLLIY | WASTRES | DVPARFSGSGSGTEFTLTISSVQSEDFAVYYC | KQSYNLLS | FGQGTVLEIKR |
| HuC6D4E5 | EIVMTQSPATLSVSPGERVTMSC | KSSQSLLNSRSRKNYLA | WYQQKPGQAPRLLIY | WASTRES | GVPARFSGSGSGTEFTLTISSVQSEDFAVYYC | KQSYNLLS | FGQGTVLEIKR |

Final clone for in vivo/in vitro Functional test in IgG format

| VL (Mouse Hybridoma Name) | Framework 1 | CDR1 | Framework 2 | CDR2 | Framework 3 | CDR3 | Framework 4 |
|---|---|---|---|---|---|---|---|
| C6D4 | DIVMTQSPSSLAVSAGEKVTMSC | KSSQSLLNSRSRKVTMSC | WYQQKPGQSPRLLIY | WASTRES | GYPDRFTGSGSGTDFTLTISSVQAEDLAVYYC | KQSYNLLS | FGAGTKLELKR |
| HuC6D4 | DIVMTQSPSSLAVSAGEKVTMSC | KSSQSLLNSRSRKNYLA | WYQQKPGQSPRLLIY | WASTRES | GYPDRFTGSGSGTEFTLTISSVQAEDLAVYYC | KQSYNLLS | FGAGTKLELKR |
| C6D4-RGD3 | DIVMTQSPSSLAVSAGEKVTMSC | KSSQSLLGRDLGRLKKNALA | WYQQKPGQAPRLLIY | WASTRES | GYPDRFTGSGSGTDFTLTISSVQAEDLAVYYC | KQSYNLLS | FGAGTKLELKR |
| HuC6D4-RGD3 | EIVMTQSPATLSVSPGERVTMSC | KSSQSLLGRDLGRLKKNALA | WYQQKPGQAPRLLIY | WASTRES | GYPARFSGSGSGTEFTLTISSVQSEDFAVYYC | KQSYNLLS | FGQGTVLEIKR |

Consensus sequence of HuC6D4 related clones:

Consensus VL: x40IVMx41Qx42Px43x44Lx45VSx46GEx47VTMSC KSSQSLLNSRx48RKNYLA WYQQKPGQx49PRLLIY WASTRES
x50VPx51RFx52SGSGSGTx53FTLTISSVQx54EDx55AVYYC KQSYNLLS FGx56GTx57LEx58KR where x40 = E or D, x41 = T or S, x42 = S or T, x43 = A, S or V, x44 = T, S, x45 = S or A, x46 = P or A, x47 = R, K or I, x48 = S or T, x49 = A or S
x50 = G or D, x51 = A or D, x52 = S or T, x53 = E or D, x54 = S, D or A, x55 = F or L, x56 = Q or A, x57 = V or K, x58 = I or L.

RGD3 loop: GRGDLGRLK inside VL CDR1

FIG. 51

F9 Variants and parents Confirmed sequence

| VH | Framework 1 | CDR1 | Framework 2 | CDR2 | Framework 3 | CDR3 | Framework 4 |
|---|---|---|---|---|---|---|---|
| (Mouse Hybridoma clone Name) | | | | | | | |
| 4F1 | QVQLQQSGAELVRPGTSVKVSCKASGY | AFTNYLIE | WVKQRPGQGLEWIG | VINPGTGGTNYNAKFKV | KATLTADKSSSTAYMQLGSLTSDDSAVYFCAR | EGNARTYYYAMDY | WGQGTSVTVSS |
| 6B9 | QVQLQQSGAELVRPGASVKVSCKASGY | AFTDYLIE | WVKQRPGQGLEWIG | VINPETGGTNYNAKFRG | KATLTADKSSSVYMQLSSLTSGDSAVYFCAR | EAGNYIYAMDY | WGQGTSVTVSS |
| (scFv clone Name from yeast display library) | | | | | | | |
| 6B9.1 | QVQLQQSGAELVRPGTSVKVSCKASGY | AFTDYLIE | WVKQRPGQGLEWIG | VINPETGGTNYNAKFRG | KATLTADKSSSTAYMQLSSLTSGDSAVYFCAR | EAGNYIYAMDY | WGQGTSVTVSS |
| A1 | QVQLQQSGAELVRPGTSVKVSCKASGY | AFTDYLIE | WVKQRPGQGLEWIG | VINPETGGTNYNAKFRG | KATLTADKSSSSAYMQLSSLTSGDSAVYFCAR | EAGNYIYAMDY | WGQGTSVTVSS |
| A2 | QVQLQQSGAELVRPGTSVKVSCKASGY | AFTDYLIE | WVKQRPGQGLEWIG | VINPETGGTNYNAKFRG | KATLTADKSGGSAYMQLSSLTSGDSAVYFCAR | EAGNYIYAMDY | WGQGTSVTVSS |
| A8 | QVQLQQSGAELVRPGTSVKVSCKASGY | AFTDYLIE | WVKQRPGQGLEWIG | VINPETGGTNYNAKFRG | KATLTADKSSSTAYMQLSSLTSGDSAVYFCAR | EAGNYIYAMDY | WGQGTSVTVSS |
| A11 | QVQLQQSGAELVRPGTSVKVSCKASGY | AFTDNLIE | WVKQRPGQGLEWIG | VINPETGGTNYNAKFRG | KATLTADKSSSSAYMQLSSLTSGDSAVYFCAR | EAGNYIYAMDY | WGQGTSVTVSS |
| B1 | QVQLQQSGAELVRPGTSVKVSCKASGY | AFTDYLIE | WVKQRPGQGLEWIG | VINPETGGTNYNAKFRG | KATLTADKSSSSAYMQLSLSSGDSAVYFCAR | EAGNYIYAMDY | WGQGTSVTVSS |
| B3 | QVQLQQSGAELVRPGTSVKVSCKASGY | AFTDYLIE | WVKQRPGQGLEWIG | VINPETGGTNYNAKFRG | KATLTADKSSSSAYMQLSSLTSGDSAVYFCAR | EAGNYIYAMDY | WGQGTSVTVSS |
| C4=E10 | QVQLQQSGAELVRPGTSVKVSCKASGY | AFTDYLIE | WVKQRPGQGLEWIG | VINPETGGTNYNAKFRG | KATLTADKSSSSAYMQLSSLTSGDSAVYFCAR | EAGNYIYAMDY | WGQGTSVTVSS |
| C7=D1 | QVQLQQSGAELVRPGTSVKVSCKASGY | AFTDYLIE | WVKQRPGQGLEWIG | VINPETGGTNYNAKFRG | KATLTADKSGGSAYMQLSSLTSGDSAVYFCAR | EAGNYIYAMDY | WGQGTSVTVSS |
| D3=F1 | QVQLQQSGAELVRPGTSVKVSCKASGY | AFTDYLIE | WVKQRPGQGLEWIG | VINPETGGTNYNAKFRG | KATLTADKSSSSAYMQLSLTSDDSAVYFCAR | EAGNYIYAMDY | WGQGTSVTVSS |
| D10=E5 | QVQLQQSGAELVRPGTSVKVSCKASGY | AFTDYLIE | WVKQRPGQGLEWIG | VINPETGGTNYNAKFRG | KVTLTADKTSSSAYMQLSSLTSGDSAVYFCAR | EAGNYIYAMDY | WGQGTSVTVSS |
| E6 | QVQLQQSGAELVRPGTSVKVSCKASGY | AFTDYLIE | WVKQRPGQGLEWIG | VINPETGGTNYNAKFRG | KATLTADKSSSSAYMQLSSLTSGDSAVYFCAR | EAGNYIYAMDY | WGQGTSVTVSS |
| F2 | QVQLQQSGAELVRPGTSVKVSCKASGY | AFTDYLIE | WVKQRPGQGLEWIG | VINPETGGTNYNAKFRG | KATLTADKSSSSAYMQLSSLTSGDSAVYFCAR | EAGNYIYAMDY | WGQGTSVTVSS |
| G4 | QVQLQQSGAELVRPGTSVKVSCKASGY | AFTDYLIE | WVKQRPGQGLEWIG | VINPETGGTNYNAKFRG | KVTLTADKSSSSAYMQLNSLTSGDSAVYFCAR | EAGNYIYAMDY | WGQGTSVTVSS |

FIG. 52

(Produced Rabbit IgG clone name)

| Clone | Sequence |
|---|---|
| C4 | QVQLQQSGAELVRPGTSVKVSCKASGY AFTDYLIE WVKQRPGQGLEWIG VINPETGGTNYNAKFRG RATLTADKSSSSAYMQLSSLTSGDSAVYFCAR EAGNYIYAMDY WGQGTSVTVSS |
| D10 | QVQLQQSGAELVRPGTSVKVSCKASGY AFTDYLIE WVKQRPGQGLEWIG VINPETGGTNYNAKFRG KVTLTADKTSSSAYMQLSSLTSGDSAVYFCAR EAGNYIYAMDY WGQGTSVTVSS |

(scFv clone from Phage Display library)

| Clone | Sequence |
|---|---|
| 4F1E1 | QVQLQQSGAELVRPGTSVKVSCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1G3 | QVQLQQSGAELVRPGTSVKVSCKASGY AFTDYLI* WVKQRPGQGLEWIG VINPETGGTNYNAKFRG KATLTANKSSSSAYMQLSSLTSGDSAVYFCAR EAGNYIYAMDY WGQGTSVTVSS |
| 4F1B5 | QVQLQQSGAELVRPGTSVKVSCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1G11 | QVQLQQSGAELVRPGTSVKVSCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1A9 | QVQLQQSGAELVRPGTSVKVSCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1H9 | QVQLQQSGAELVRPGTSVKVSCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1F9 | QVQLQQSGAELVRPGTSVKVSCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1H9 | QVQLQQSGAELVRPGTSVKVSCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1D10 | QVQLQQSGAELVRPGTSVKVSCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1E10 | QVQLQQSGAELVRPGTSVKVPCKASGY AFTDYLI* WVKQRPGQGLEWIG VINPETGGTNYNAKFRG KATLTADKSSSSAYMQLSSLTSGDSAVYFCAR EAGNYIYAMDY WGQGTSVTVSS |
| 4F1F10 | QVQLQQSGAELVRPGTSVKVSCKASGY AFTDYLI* WVKQRPGQGLEWIG VINPETGGTNYNAKFRG KATLTADKSSSSAVLQLSSLTSGDSAVYFCAR EAGNYIYAMDY WGQGTSVTVSS |
| 4F1H12 | QVQLQQSGAELVRPGTSVKVSCKASGY AFTDYLIE WVKQRPGQGLEWIG VINPETGGTNYNAKFRG KATLTADKSSSSAYMQLSSLTSGDSAVYFCAR EAGNYIYAMDY WGQGTSVTVSS |
| 4F1E9 | QVQLQQSGAELVRPGTSVKVSCKASGY AFTDYLIE WVKQRPGQGLEWIG VINPETGGTNYNAKFRG RATLTADKSSSSAYMQLSSLTSGDSAVYFCAR EAGNYIYAMDY WGQGTSVTVSS |
| 4FA11 | QVQLQQSGAELVRPGTSVKVSCKASGY AFTDYLIE WVKQRPGQGLEWIG VINPETGGTNYNAKFRG KATLTADKSSSSAYMQLSSLTSGDSAVYFCAR EAGNYIYAMDY WGQGTSVTVSS |
| 4FH11 | QVQLQQSGAELVRPGTSVKVSCKASGY AFTDYLIE WVKQRPGQGLEWIG VINPETGGTNYNAKFRG KATLTADKSSSSAYMQLSSLTSGDSAVYFCAR EAGNYIYAMDY WGQGTSVTVSS |

Final clone for in vitro Functional test in IgG format

| Clone | Sequence |
|---|---|
| F9 | QVQLQQSGAELVRPGTSVKVSCKASGY AFTDYLIQ WVKQRPGQGLEWIG VINPETGGTNYNAKFRG KATLTADKSSSSAYMQLSSLTSGDSAVYFCAR EAGNYIYAMDY WGQGTSVTVSS |

FIG. 52 (Cont.)

F9 Variants and parents Confirmed sequence

| VH (Mouse Hybridoma clone Name) | Framework 1 | CDR1 | Framework 2 | CDR2 | Framework 3 | CDR3 | Framework 4 |
|---|---|---|---|---|---|---|---|
| 4F1 | DIQMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKA |
| 6B9 | DIEMTQTPASLSASVGETVTITC | RASENIYSYLV | WYQQKQGKSPQLLVY | NAKTLAE | GVPSRFSGSGSGTQFSLKINSLQPEDFGSYYC | QHHHGTPYT | FGGGTKLEIKA |

(scFv clone Name from yeast display library)

| | Framework 1 | CDR1 | Framework 2 | CDR2 | Framework 3 | CDR3 | Framework 4 |
|---|---|---|---|---|---|---|---|
| 6B9.1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| A1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| A2 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| A8 | DIVMTQSPASLSASVGETVTITC | RASVNIYSYLV | WYQQKQGKSPQLLVH | NAKTLAE | GVPSRFSGSGSGTQFSLKINSVQPEDFGSYYC | QHHHGTPYT | FGGGTKLEIKR |
| A11 | HIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| B1 | DIVMTQSPASLSASVGETVTITC | RASVNIYSYLV | WYQQKQGKSPQLLVH | NAKTLAE | GVPSRFSGSGSGTQFSLKINSLQPEDVGSYYC | QHHHGTPYT | FGGGTKLEIKR |
| B3 | DIVMTQSPASLSASVGETVTITC | RASVNIYSYLV | WYQQKQGKSPQLLVH | NAKTLAA | GVPSRFSGSGSGTQFSLKINSLQPEDFGSYYC | QHHHGTPYT | FGGGTKLEIKR |
| C4=F10 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| C7=D1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| D3=F1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| D10=E5 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |
| E8 | DIVMTQSPASLSASVGETVTITC | RASVNIYSYLV | WYQQKQGKSPQLLVH | NAKTLAE | GVPSRFSGSGSGTRFSLKINSLQPEDFGSYYC | QHHHGTPYT | FGGGTKLEIKR |
| F2 | DIVMTQSPASLSASVGETVTITC | RASVNIYSYLV | WYQQKQGKSPQLLVH | NAKTLAE | GVPSRFSGSGSGTQFSLKTSSLQPEDFGSYYC | QHHHGTPYT | FGGGTKLEIKR |
| G4 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHHGTPYT | FGGGTKLEIKR |

FIG. 53

| Clone | | | | | | | |
|---|---|---|---|---|---|---|---|
| (Produced Rabbit IgG clone name) | | | | | | | |
| C4 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIKR |
| D10 | DIEMTQTPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| (scFv clone from Phage Display library) | | | | | | | |
| 4F1E1 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1G3 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1B5 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1G11 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1A9 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1B9 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1F9 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1H9 | DIVMTQSPASLSASVGETVTITC | RASVNIYSYLV | WYQQKQGKSPQLLVH | NAKTLAE | GVPSRFSGSGSXTQFSLKINSLQPEDFGSYYC | QHHGTPYT | FGGGTKLEIK |
| 4F1D10 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1E10 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1F10 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1H12 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1E9 | DIVMTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1A11 | DIVVTQSPASLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |
| 4F1H11 | DIVMTQSPAFLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIK |

| Final clone for in vitro Functional test in IgG format | | | | | | | |
|---|---|---|---|---|---|---|---|
| F9 | DIVMTQSPAFLSASVGETVTITC | RASVNIYSYLV | WYQQKQGKSPQLLVH | NAKTLAE | GVPSRFSGSGSGTQFSLKINSLQPEDFGSYYC | QHHGTPYT | FGGGTKLEIKR |

FIG. 53 (Cont.)

NEUTRALIZING ANTIBODIES TO THE αvβ8 INTEGRIN COMPLEX FOR IMMUNOTHERAPY

CROSS-REFERENCE TO RELATED PATENT APPLICATIONS

This application is a divisional of Ser. No. 17/155,784 filed Jan. 22, 2021, which is a divisional of Ser. No. 16/331,902, filed Mar. 8, 2019, which is a US National Stage entry of International Application No. PCT/US2017/054306, filed Sep. 29, 2017, which claims benefit of priority to U.S. Provisional Patent Application No. 62/401,570, filed Sep. 29, 2016 and U.S. Provisional Patent Application No. 62/529,381, filed Jul. 6, 2017, all of which are incorporated by reference in their entirety for all purposes.

REFERENCE TO A "SEQUENCE LISTING" SUBMITTED AS ASCII TEXT FILES VIA EFS-WEB

The Sequence Listing written in file 081906-1369766-224040US_SL.xml created on May 18, 2023 bytes, is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under grant no. U54 HL119893, awarded by the National Institutes of Health. The government has certain rights in the invention.

BACKGROUND OF THE INVENTION

Transforming growth factor β (TGFβ) was originally characterized as an oncogene capable of inducing a transformed phenotype in non-neoplastic cells. A number of TGFβ family members have since been characterized, based on the presence of similar amino acid domains.

Some TGF-β isoforms are expressed ubiquitously in mammals (TGF-β 1-3), but are maintained in an inactive form by non-covalent interaction with a propeptide, the latency associated domain of TGF-β (LAP). For TGFβ to signal, it must be released from its inactive complex by a process called TGFβ activation. The latent TGF complex includes 3 components: the active (mature) TGFβ dimmer, LAP (latency associated peptide) and LTBP (latent TGFβ binding protein). LAP is a dimer, linked by a disulfide bond, that represents the N-terminal end of the TGFβ precursor protein. The mature TGFβ protein represents the C terminal end (about 25 kD) of the precursor. The bond between the TGFβs and LAP is proteolytically cleaved within the Golgi, but the TGF-β propeptide remains bound to TGFβ by non-covalent interactions. The complex of TGFβ and LAP is called the small latent complex (SLC). It is the association of LAP and TGFβ that confers latency. LAP-TGFβ binding is reversible and the isolated purified components can recombine to form an inactive SLC. Both the SLC and the larger complex are referred to herein as latent TGFβ, as both are inactive.

In general, integrins are adhesion molecules and mediate the attachment of cells to extracellular matrix proteins. Integrin αvβ8 binds to the LAP of TGF-β and mediates the activation of TGF-β1 and 3 (Mu et al. (2002) *J. Cell Biol.* 159:493). Integrin αvβ8-mediated activation of TGF-β is required for in vivo activation of TGF-β (i.e., release of the mature TGF-β polypeptide), thus αvβ8 is a gatekeeper of TGF-β function. Integrin αvβ8 is expressed in normal epithelia (e.g., airway epithelia), mesenchymal cells, and neuronal tissues.

The integrin β8 (Itgb8) has been associated with forkhead box P3 (Foxp3)-positive T cells and T-regulatory-specific epigenetic remodeling. See, e.g., Vandenbon, et al., *Proc. Natl. Acad. Sci. USA* vol. 113 no. 17 pp. E2393-E2402 (2016). FoxP3 is a transcription factor involved in the development of T-regulatory (Treg) cells. Human and mouse effector Treg cells express functional TGF-β-activating integrin αvβ8. See, Worthington, Immunity Volume 42, Issue 5, pp. 903-915 (May 2015). Treg cell integrin αvβ8-mediated TGF-β activation is not needed for T cell homeostasis and integrin αvβ8 expression by Treg cells suppresses active inflammation.

DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

The terms "anti-αvβ8 antibody," "αvβ8 specific antibody," "αvβ8 antibody," and "anti-αvβ8" are used synonymously herein to refer to an antibody that specifically binds to αvβ8. Similarly, an anti-β8 antibody (and like terms) refer to an antibody that specifically binds to β8. The anti-αvβ8 antibodies and anti-β8 antibodies described herein bind to the protein expressed on αvβ8 expressing cells.

An αvβ8-associated disorder is a condition characterized by the presence of αvβ8-expressing cells, either cells expressing an increased level of αvβ8, or increased number of αvβ8-expressing cells relative to a normal, non-diseased control. TGFβ-associated disorders (disorders characterized by higher than normal TGFβ activity) include αvβ8-associated disorders, as αvβ8 is involved in activating TGFβ in certain circumstances, as described herein.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. As described below, the algorithms can account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "antibody" refers to a polypeptide comprising a framework region encoded by an immunoglobulin gene, or fragments thereof, that specifically bind and recognize an antigen, e.g., human $\alpha v \beta 8$, a particular cell surface marker, or any desired target. Typically, the "variable region" contains the antigen-binding region of the antibody (or its functional equivalent) and is most critical in specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Antibodies described herein can be of any isotype of isotype class. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'2, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., supra; Marks et al., *Biotechnology*, 10:779-783, (1992)).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhocyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some complementary determining region ("CDR") residues and possibly some framework ("FR") residues are substituted by residues from analogous sites in rodent antibodies.

Antibodies or antigen-binding molecules of the invention further includes one or more immunoglobulin chains that are chemically conjugated to, or expressed as, fusion proteins with other proteins. It also includes bispecific antibody. A bispecific or bifunctional antibody is an artificial hybrid antibody having two different heavy/light chain pairs and two different binding sites. Other antigen-binding fragments or antibody portions of the invention include bivalent scFv (diabody), bispecific scFv antibodies where the antibody molecule recognizes two different epitopes, single binding domains (dAbs), and minibodies.

The various antibodies or antigen-binding fragments described herein can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources.

A "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities.

As used herein, "V-region" refers to an antibody variable region domain comprising the segments of Framework 1, CDR1, Framework 2, CDR2, Framework 3, CDR3, and Framework 4. These segments are included in the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson and Wu, *Nucleic Acids Res.* 2000 Jan. 1; 28(1): 214-218 and Johnson et al., Nucleic Acids Res., 29:205-206 (2001); Chothia & Lesk, (1987) *J. Mol. Biol.* 196, 901-917; Chothia et al. (1989) Nature 342, 877-883; Chothia et al. (1992) J. Mol. Biol. 227, 799-817; A1-Lazikani et al., *J. Mol. Biol* 1997, 273(4)). Unless otherwise indicated, CDRs are determined according to Kabat. Definitions of antigen combining sites are also described in the following: Ruiz et al. *Nucleic Acids Res.*, 28, 219-221 (2000); and Lefranc *Nucleic Acids Res.* January 1; 29(1):207-9 (2001); MacCallum et al., *J. Mol. Biol.*, 262: 732-745 (1996); and Martin et al, *Proc. Natl Acad. Sci. USA*, 86, 9268-9272 (1989); Martin, et al, *Meth-ods Enzymol.*, 203: 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *Proc. Natl. Acad. Sci. USA*, 81:6851-6855 (1984); Morrison and Oi, Adv. *Immunol.*, 44:65-92 (1988); Verhocyen et al., *Science*, 239:1534-1536 (1988); Padlan, *Molec. Immun.*, 28:489-498 (1991); Padlan, *Molec. Immun.*, 31(3):169-217 (1994).

The antibody binds to an "epitope" on the antigen. The epitope is the specific antibody binding interaction site on the antigen, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The term "specifically bind" refers to a molecule (e.g., antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, an antibody that specifically binds β8 will typically bind to β8 with at least a 2-fold greater affinity than a non-β8 target (e.g., a different integrin subunit, e.g., β6).

The term "binds" with respect to a cell type (e.g., an antibody that binds fibrotic cells, hepatocytes, chondrocytes, etc.), typically indicates that an agent binds a majority of the cells in a pure population of those cells. For example, an antibody that binds a given cell type typically binds to at least ⅔ of the cells in a population of the indicated cells (e.g., 75, 80, 85, 90, 91, 92, 93, 94, 95, 96, 97, 98, 99, or 100%). One of skill will recognize that some variability will arise depending on the method and/or threshold of determining binding.

As used herein, a first antibody, or an antigen-binding portion thereof, "competes" for binding to a target with a second antibody, or an antigen-binding portion thereof, when binding of the second antibody with the target is detectably decreased in the presence of the first antibody compared to the binding of the second antibody in the absence of the first antibody. The alternative, where the binding of the first antibody to the target is also detectably decreased in the presence of the second antibody, can, but need not be the case. That is, a second antibody can inhibit the binding of a first antibody to the target without that first antibody inhibiting the binding of the second antibody to the target. However, where each antibody detectably inhibits the binding of the other antibody to its cognate epitope or ligand, whether to the same, greater, or lesser extent, the antibodies are said to "cross-compete" with each other for binding of their respective epitope(s). Both competing and cross-competing antibodies are encompassed by the present invention. The term "competitor" antibody can be applied to the first or second antibody as can be determined by one of skill in the art. In some cases, the presence of the competitor antibody (e.g., the first antibody) reduces binding of the second antibody to the target by at least 10%, e.g., 20%, 30%, 40%, 50%, 60%, 70%, 80%, or more, e.g., so that binding of the second antibody to target is undetectable in the presence of the first (competitor) antibody.

The term "differentially expressed" or "differentially regulated" refers generally to a protein or nucleic acid biomarker that is overexpressed (upregulated) or underexpressed (downregulated) in one sample compared to at least one other sample. In the context of the present invention, the term generally refers to overexpression of a biomarker (e.g., αvβ8) on a diseased cell compared to a normal cell.

For example, the terms "overexpressed" or "upregulated" interchangeably refer to a protein or nucleic acid, generally a biomarker, that is transcribed or translated at a detectably greater than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be 10%, 20%, 30%, 40%, 50%, 60%, 70%, 80%, 90% or more in comparison to a normal cell.

The terms "agonist," "activator," "inducer" and like terms refer to molecules that increase activity or expression as compared to a control. Agonists are agents that, e.g., bind to, stimulate, increase, activate, enhance activation, sensitize or upregulate the activity of the target. The expression or activity can be increased 10%, 20%, 30%, 40%, 50%, 60%, 70%, 80%, 90% 100% or more than that in a control. In certain instances, the activation is 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "diagnosis" refers to a relative probability that a disorder such as cancer or an inflammatory condition is present in the subject. Similarly, the term "prognosis" refers to a relative probability that a certain future outcome may occur in the subject. For example, prognosis can refer to the likelihood that an individual will develop a TGFβ or αvβ8 associated disorder, have recurrence, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, a TGFβ or αvβ8 associated disorder. In some embodiments, the sample may be a tissue biopsy, such as needle biopsy, fine needle biopsy, surgical biopsy, etc. The sample can also be a blood sample or blood fraction, e.g., white blood cell fraction, serum, or plasma. The sample can comprise a tissue sample harboring a lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

The terms "therapy," "treatment," and "amelioration" refer to any reduction in the severity of symptoms. In the case of treating an inflammatory condition, the treatment can refer to reducing, e.g., blood levels of inflammatory cytokines, blood levels of active mature TGFβ, pain, swelling, recruitment of immune cells, etc. In the case of treating cancer, treatment can refer to reducing, e.g., tumor size, number of cancer cells, growth rate, metastatic activity, cell death of non-cancer cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (no detectable symptoms remaining) or partial, such that symptoms are less frequent of severe than in a patient without the treatment described herein. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

An "inflammatory condition" refers to any inflammation in an individual, and can be transient (e.g., in response to exposure to a pathogen or allergen) or chronic. Inflammation is characterized by inflammatory cytokines such as IFN-gamma, IL-6, and TNF-alpha that recruit and activate macrophages and other leukocytes. In some cases, inflammation can develop into a chronic, harmful condition or autoimmune condition (e.g., MS, lupus, rheumatoid arthritis, Crohn's disease). Inflammation can be evident locally (e.g., at a localized site of infection or exposure) or systemically (e.g., atherosclerosis, high blood pressure). In some embodiments, the antibody compositions and methods described herein can be used to treat inflammatory conditions.

"Cancer", "tumor," "transformed" and like terms include precancerous, neoplastic, transformed, and cancerous cells, and can refer to a solid tumor, or a non-solid cancer (see, e.g., Edge et al. AJCC Cancer Staging Manual ($7^{th}$ ed. 2009); Cibas and Ducatman Cytology: Diagnostic principles and clinical correlates ($3^{rd}$ ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique ($3^{rd}$ ed. 1994)). Although transformation can arise from infection with a transforming virus and incorporation of new genomic DNA, or uptake of exogenous DNA, it can also arise spontaneously or following exposure to a carcinogen.

The term "cancer" can refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia (AML), chronic myeloid leukemia (CML), and multiple myeloma. In some embodiments, the antibody compositions and methods described herein can be used for treating cancer.

The term "co-administer" refers to the simultaneous presence of two active agents in the blood of an individual. Active agents that are co-administered can be concurrently or sequentially delivered.

BRIEF SUMMARY OF THE INVENTION

In some aspects, an antibody is provided that specifically binds human αvβ8 and blocks binding of TGFβ peptide to αvβ8, wherein the antibody binds to an epitope on human αvβ8 comprising amino acids D148, A149, D150, G151, and Y178 of human αv as occurs in SEQ ID NO:393 and amino acids H118, S170, D171, Y172, N173 L174, D175, H200, and R201 of human β8 as occurs in SEQ ID NO:394.

In some embodiments, an antibody (optionally a chimeric or humanized antibody) is provided that comprises heavy chain CDRs SEQ ID NO:562, SEQ ID NO: 563, and SEQ ID NO; 564 and light chain CDRs SEQ ID NO:569, SEQ ID NO: 570, and SEQ ID NO: 571.

In some embodiments, an antibody (optionally a chimeric or humanized antibody) is provided that comprises:
heavy chain CDRs SEQ ID NO:313, SEQ ID NO:314, and SEQ ID NO:315; and light chain CDRs SEQ ID NO:334, SEQ ID NO:335, and SEQ ID NO:336; or
heavy chain CDRs SEQ ID NO:319, SEQ ID NO:320, and SEQ ID NO:321; and light chain CDRs SEQ ID NO:340, SEQ ID NO:341, and SEQ ID NO:342; or
heavy chain CDRs SEQ ID NO:316, SEQ ID NO:317, and SEQ ID NO:318; and light chain CDRs SEQ ID NO:337, SEQ ID NO:338, and SEQ ID NO:339; or
heavy chain CDRs SEQ ID NO:322, SEQ ID NO:323, and SEQ ID NO:324; and light chain CDRs SEQ ID NO:343, SEQ ID NO:344, and SEQ ID NO:345; or
heavy chain CDRs SEQ ID NO:322, SEQ ID NO:323, and SEQ ID NO:324; and light chain CDRs SEQ ID NO:346, SEQ ID NO:347, and SEQ ID NO:348; or
heavy chain CDRs SEQ ID NO:322, SEQ ID NO:323, and SEQ ID NO:324; and light chain CDRs SEQ ID NO:349, SEQ ID NO:350, and SEQ ID NO:351; or
heavy chain CDRs SEQ ID NO:325, SEQ ID NO:326, and SEQ ID NO:327; and light chain CDRs SEQ ID NO:352, SEQ ID NO:353, and SEQ ID NO:354; or
heavy chain CDRs SEQ ID NO:325, SEQ ID NO:326, and SEQ ID NO:327; and light chain CDRs SEQ ID NO:355, SEQ ID NO:356, and SEQ ID NO:357; or
heavy chain CDRs SEQ ID NO:325, SEQ ID NO:326, and SEQ ID NO:327; and light chain CDRs SEQ ID NO:358, SEQ ID NO:359, and SEQ ID NO:360; or
heavy chain CDRs SEQ ID NO:367, SEQ ID NO:368, and SEQ ID NO:369; and light chain CDRs SEQ ID NO:373, SEQ ID NO:374, and SEQ ID NO:375; or heavy chain CDRs SEQ ID NO:364, SEQ ID NO:365, and SEQ ID NO:366; and light chain CDRs SEQ ID NO:373, SEQ ID NO:374, and SEQ ID NO:375; or
heavy chain CDRs SEQ ID NO:367, SEQ ID NO:368, and SEQ ID NO:369; and light chain CDRs SEQ ID NO:376, SEQ ID NO:377, and SEQ ID NO:378; or
heavy chain CDRs SEQ ID NO:370, SEQ ID NO:371, and SEQ ID NO:372; and light chain CDRs SEQ ID NO:373, SEQ ID NO:374, and SEQ ID NO:375; or
heavy chain CDRs SEQ ID NO:331, SEQ ID NO:332, and SEQ ID NO:333; and light chain CDRs SEQ ID NO:382, SEQ ID NO:383, and SEQ ID NO:384; or
heavy chain CDRs SEQ ID NO:379, SEQ ID NO:380, and SEQ ID NO:381; and light chain CDRs SEQ ID NO:361, SEQ ID NO:362, and SEQ ID NO:363; or
heavy chain CDRs SEQ ID NO:331, SEQ ID NO:332, and SEQ ID NO:333; and light chain CDRs SEQ ID NO:361, SEQ ID NO:362, and SEQ ID NO:363; or
heavy chain CDRs SEQ ID NO:508, SEQ ID NO:509, and SEQ ID NO:510; and light chain CDRs SEQ ID NO:529, SEQ ID NO:530, and SEQ ID NO:531; or
heavy chain CDRs SEQ ID NO:511, SEQ ID NO:512, and SEQ ID NO:513; and light chain CDRs SEQ ID NO:532, SEQ ID NO:533, and SEQ ID NO:534; or
heavy chain CDRs SEQ ID NO:514, SEQ ID NO:515, and SEQ ID NO:516; and light chain CDRs SEQ ID NO:535, SEQ ID NO:536, and SEQ ID NO:537; or
heavy chain CDRs SEQ ID NO:517, SEQ ID NO:518, and SEQ ID NO:519; and light chain CDRs SEQ ID NO:538, SEQ ID NO:539, and SEQ ID NO:540; or
heavy chain CDRs SEQ ID NO:520, SEQ ID NO:521, and SEQ ID NO:522; and light chain CDRs SEQ ID NO:541, SEQ ID NO:542, and SEQ ID NO:543; or
heavy chain CDRs SEQ ID NO:523, SEQ ID NO:524, and SEQ ID NO:525; and light chain CDRs SEQ ID NO:544, SEQ ID NO:545, and SEQ ID NO:546; or
heavy chain CDRs SEQ ID NO:526, SEQ ID NO:527, and SEQ ID NO:528; and light chain CDRs SEQ ID NO:547, SEQ ID NO:548, and SEQ ID NO:549; or other antibodies described herein.

In some embodiments, the antibody is linked to a detectable label.

In some embodiments, the antibody further comprises heavy chain framework sequences FR1, FR2, FR3, and FR4 as SEQ ID NO: 558, SEQ ID NO: 559, SEQ ID NO: 560, and SEQ ID NO: 561, respectively, and light chain framework sequences FR1, FR2, FR3, and FR4 as SEQ ID NO: 565, SEQ ID NO: 566, SEQ ID NO: 567, and SEQ ID NO: 568, respectively.

In some embodiments, the antibody further comprises heavy chain framework sequences FR1, FR2, FR3, and FR4 as SEQ ID NO: 550, SEQ ID NO: 551, SEQ ID NO: 552, and SEQ ID NO: 553, respectively, and light chain framework sequences FR1, FR2, FR3, and FR4 as SEQ ID NO: 554, SEQ ID NO: 555, SEQ ID NO: 556, and SEQ ID NO: 557, respectively.

In some embodiments, the antibody is humanized. In some embodiments, the humanized antibody comprises SEQ ID NO:395, SEQ ID NO:403, SEQ ID NO:411; SEQ ID NO:419, SEQ ID NO:427, SEQ ID NO:443, SEQ ID NO:451, SEQ ID NO:459, SEQ ID NO:467; SEQ ID NO:475, SEQ ID NO:484, or SEQ ID NO:500.

Also provided is an antibody that binds to αvβ8 and αvβ6 and comprising a light chain CDR1 comprising the sequence RGDL. In some embodiments, the antibody comprises variable regions comprising heavy chain CDRs SEQ ID NO:523, SEQ ID NO:524, and SEQ ID NO:525; and light chain CDRs SEQ ID NO:544, SEQ ID NO:545, and SEQ ID NO:546; or heavy chain CDRs SEQ ID NO:526, SEQ ID NO:527, and SEQ ID NO:528; and light chain CDRs SEQ ID NO:547, SEQ ID NO:548, and SEQ ID NO:549.

In some embodiments, the antibody further comprises heavy chain framework sequences FR1, FR2, FR3, and FR4 as SEQ ID NO: 558, SEQ ID NO: 559, SEQ ID NO: 560, and SEQ ID NO: 561, respectively, and light chain framework sequences FR1, FR2, FR3, and FR4 as SEQ ID NO: 565, SEQ ID NO: 566, SEQ ID NO: 567, and SEQ ID NO: 568, respectively.

In some embodiments, the antibody further comprises heavy chain framework sequences FR1, FR2, FR3, and FR4 as SEQ ID NO: 550, SEQ ID NO: 551, SEQ ID NO: 552, and SEQ ID NO: 553, respectively, and light chain framework sequences FR1, FR2, FR3, and FR4 as SEQ ID NO: 554, SEQ ID NO: 555, SEQ ID NO: 556, and SEQ ID NO: 557, respectively.

In some embodiments, the antibody is humanized.

In some embodiments, the antibody is linked to a detectable label.

Also provided is an antibody that specifically binds human αvβ8 and blocks binding of TGFβ peptide to αvβ8, wherein the antibody binds to the specificity determining loop (SDL) of human β8. In some embodiments, the antibody further binds to one, two, or all three of the human αv-head domain, the α1 helix of human β8, or the α2 helix of human β8. In some embodiments, the antibody is humanized or chimeric. In some embodiments, the antibody is linked to a detectable label.

Also provided is a pharmaceutical composition comprising an antibody as described above or elsewhere herein in a pharmaceutically acceptable excipient.

Also provided is a method of enhancing an immune response to a viral infection in a human individual. In some embodiments, the method comprises administering a sufficient amount of an antibody as described above or elsewhere herein to the individual, thereby enhancing an immune response to the viral infection.

In some embodiments, the viral infection is a hepatitis infection. In some embodiments, the viral infection is a hepatitis B infection.

Also provided is a method of enhancing an immune response to a viral infection in a human individual, the method comprising administering a sufficient amount of the antibody to the individual, wherein the antibody specifically binds to human αvβ8 and blocks binding of TGFβ peptide to αvβ8 or blocks activation of αvβ8 by binding of TGFβ human αvβ8, thereby enhancing an immune response to the viral infection.

Also provided is a method of enhancing an immune response to cancer in a human individual, the method comprising administering a sufficient amount of an antibody as described above or elsewhere herein to the individual, thereby enhancing an immune response to the cancer.

In some embodiments, the cancer is lung cancer. In some embodiments, the cancer is a metastatic cancer. In some embodiments, the cancer is a primary cancer.

Also provided is a method of enhancing an immune response to *H. pyroli* in a human individual, the method comprising administering a sufficient amount of an antibody as described above or elsewhere herein to the individual, thereby enhancing an immune response to *H. pyroli*.

In some embodiments, the human individual has a peptide ulcer, gastric carcinoma or MALT lymphoma.

Also provided is an antibody that specifically binds to human αvβ8 and that comprises human heavy chain CDRs SEQ ID NO:299, SEQ ID NO:301, and SEQ ID NO:303; and light chain CDRs SEQ ID NO:307, SEQ ID NO:309, and SEQ ID NO:311. Alternatively, any antibodies having heavy chain CDRs or a heavy chain variable region as set forth in FIG. 53 and light chain CDRs or a light chain variable region from a corresponding sequence as set forth in FIG. 54 can be used In some embodiments, the antibody is linked to a detectable label.

Also provided is a method of detecting the presence, absence, or quantity of human in a sample, the method comprising, contacting to the sample an antibody that specifically binds to human αvβ8 and that comprises human heavy chain CDRs SEQ ID NO:299, SEQ ID NO:301, and SEQ ID NO:303; and light chain CDRs SEQ ID NO:307, SEQ ID NO:309, and SEQ ID NO:311, and detecting or quantifying binding of the antibody to the sample.

In some embodiments, the sample is a formalin-fixed sample.

BRIEF DESCRIPTION OF THE DRAWINGS

FIG. 1 illustrates heavy chain amino acid sequences for clones used in the construction of the composite antibody C6D4. B13C4 15-8: all sequences (SEQ ID NO:1), Framework 1 (SEQ ID NO:2), CDR1 (SEQ ID NO:3), Framework 2 (SEQ ID NO:4), CDR2 (SEQ ID NO:5), Framework 3 (SEQ ID NO:6), CRD3 (SEQ ID NO:7), and Framework 4 (SEQ ID NO:8); B13C4 15-10: all sequences (SEQ ID NO:9), Framework 1 (SEQ ID NO:10), CDR1 (SEQ ID NO:11), Framework 2 (SEQ ID NO:12), CDR2 (SEQ ID NO:13), Framework 3 (SEQ ID NO:14), CRD3 (SEQ ID NO:15), and Framework 4 (SEQ ID NO:16); B13H3.2: all sequences (SEQ ID NO:17), Framework 1 (SEQ ID NO:18), CDR1 (SEQ ID NO:19), Framework 2 (SEQ ID NO:20), CDR2 (SEQ ID NO:21), Framework 3 (SEQ ID NO:22), CRD3 (SEQ ID NO:23), and Framework 4 (SEQ ID NO:24); B13C1231015: all sequences (SEQ ID NO:25), Framework 1 (SEQ ID NO:26), CDR1 (SEQ ID NO:27), Framework 2 (SEQ ID NO:28), CDR2 (SEQ ID NO:29), Framework 3 (SEQ ID NO:30), CRD3 (SEQ ID NO:31), and Framework 4 (SEQ ID NO:32); B15B11VH: all sequences (SEQ ID NO:33), Framework 1 (SEQ ID NO:34), CDR1 (SEQ ID NO:35), Framework 2 (SEQ ID NO:36), CDR2 (SEQ ID NO:37), Framework 3 (SEQ ID NO:38), CRD3 (SEQ ID NO:39), and Framework 4 (SEQ ID NO:40); B2B2 15-9: all sequences (SEQ ID NO:41), Framework 1 (SEQ ID NO:42), CDR1 (SEQ ID NO:43), Framework 2 (SEQ ID NO:44), CDR2 (SEQ ID NO:45), Framework 3 (SEQ ID NO:46), CRD3 (SEQ ID NO:47), and Framework 4 (SEQ ID NO:48); R11D12715.3: all sequences (SEQ ID NO:49), Framework 1 (SEQ ID NO:50), CDR1 (SEQ ID NO:51), Framework 2 (SEQ ID NO:52), CDR2 (SEQ ID NO:53), Framework 3 (SEQ ID NO:54), CRD3 (SEQ ID NO:55), and Framework 4 (SEQ ID NO:56); RSDLVH-1: all sequences (SEQ ID NO:57 and SEQ ID NO:65), Framework 1 (SEQ ID NO:58 and SEQ ID NO:66), CDR1 (SEQ ID NO:59 and SEQ ID NO:67), Framework 2 (SEQ ID NO:60 and SEQ ID NO:68), CDR2 (SEQ ID NO:61 and SEQ ID NO:69), Framework 3 (SEQ ID NO:62 and SEQ ID NO:70), CRD3 (SEQ ID NO:63 and SEQ ID NO:71), and Framework 4 (SEQ ID NO:64 and SEQ ID NO:72); RSDLVH-3: all sequences (SEQ ID NO:73), Framework 1 (SEQ ID NO:74), CDR1 (SEQ ID NO:75), Framework 2 (SEQ ID NO:76), CDR2 (SEQ ID NO:77), Framework 3 (SEQ ID NO:78), CRD3 (SEQ ID NO:79), and Framework 4 (SEQ ID NO:80); RSDLVH-16: all sequences (SEQ ID NO:81), Framework 1 (SEQ ID NO:82), CDR1 (SEQ ID NO:83), Framework 2 (SEQ ID NO:84), CDR2 (SEQ ID NO:85), Framework 3 (SEQ ID NO:86), CRD3 (SEQ ID NO:87), and Framework 4 (SEQ ID NO:88); both 29 and 44: all sequences (SEQ ID NO:89), Framework 1 (SEQ ID NO:90), CDR1 (SEQ ID NO:91), Framework 2 (SEQ ID NO:92), CDR2 (SEQ ID NO:93), Framework 3 (SEQ ID NO:94), CRD3 (SEQ ID NO:95), and Framework 4 (SEQ ID NO:96); A1=B4=F9: all sequences (SEQ ID NO:97), Framework 1 (SEQ ID NO:98), CDR1 (SEQ ID NO:99), Framework 2 (SEQ ID NO:100), CDR2 (SEQ ID NO:101), Framework 3 (SEQ ID NO:102), CRD3 (SEQ ID NO:103), and Framework 4 (SEQ ID NO:104); A5=C6: all sequences (SEQ ID NO:105), Framework 1 (SEQ ID NO:106), CDR1 (SEQ ID NO:107), Framework 2 (SEQ ID NO:108), CDR2 (SEQ ID NO:109), Framework 3 (SEQ ID NO:110), CRD3 (SEQ ID NO:111), and Framework 4 (SEQ ID NO:112); D4=E6: all sequences (SEQ ID NO:113), Framework 1 (SEQ ID NO:114), CDR1 (SEQ ID NO:115), Framework 2 (SEQ ID NO:116), CDR2 (SEQ ID NO:117), Framework 3 (SEQ ID NO:118), CRD3 (SEQ ID NO:119), and Framework 4 (SEQ ID NO:120); and C6D4: all sequences (SEQ ID NO:121), Framework 1 (SEQ ID NO:122), CDR1 (SEQ ID NO:123), Framework 2 (SEQ ID NO:124), CDR2 (SEQ ID NO:125), Framework 3 (SEQ ID NO: 126), CRD3 (SEQ ID NO:127), and Framework 4 (SEQ ID NO:128).

FIG. 2 illustrates light chain amino acid sequences for clones used in the construction of the composite antibody C6D4. B2B2 35-20: all sequences (SEQ ID NO:129), Framework 1 (SEQ ID NO:130), CDR1 (SEQ ID NO:131), Framework 2 (SEQ ID NO:132), CDR2 (SEQ ID NO:133), Framework 3 (SEQ ID NO:134), CRD3 (SEQ ID NO:135), and Framework 4 (SEQ ID NO:136); B2B2 35-26: all sequences (SEQ ID NO:137), Framework 1 (SEQ ID NO:138), CDR1 (SEQ ID NO:139), Framework 2 (SEQ ID NO:140), CDR2 (SEQ ID NO:141), Framework 3 (SEQ ID NO:142), CRD3 (SEQ ID NO:143), and Framework 4 (SEQ ID NO:144); B15B11vk34-26: all sequences (SEQ ID NO:145), Framework 1 (SEQ ID NO:146), CDR1 (SEQ ID NO:147), Framework 2 (SEQ ID NO:148), CDR2 (SEQ ID NO:149), Framework 3 (SEQ ID NO:150), CRD3 (SEQ ID NO:151), and Framework 4 (SEQ ID NO:152); B15B11vk33-24: all sequences (SEQ ID NO:153), Framework 1 (SEQ ID NO:154), CDR1 (SEQ ID NO:155), Framework 2 (SEQ ID NO:156), CDR2 (SEQ ID NO:157), Framework 3 (SEQ ID NO:158), CRD3 (SEQ ID NO:159), and Framework 4 (SEQ ID NO:160); B15B11vk35-26: all sequences (SEQ ID NO: 161), Framework 1 (SEQ ID NO:162), CDR1 (SEQ ID NO: 163), Framework 2 (SEQ ID NO:164), CDR2 (SEQ ID NO:165), Framework 3 (SEQ ID NO:166), CRD3 (SEQ ID NO:167), and Framework 4 (SEQ ID NO:168); B13C12134-25: all sequences (SEQ ID NO:169), Framework 1 (SEQ ID NO:170), CDR1 (SEQ ID NO:171), Framework 2 (SEQ ID NO:172), CDR2 (SEQ ID NO:173), Framework 3 (SEQ ID NO:174), CRD3 (SEQ ID NO:175), and Framework 4 (SEQ ID NO:176); B13C12133-26: all sequences (SEQ ID NO:177), Framework 1 (SEQ ID NO:178), CDR1 (SEQ ID NO:179), Framework 2 (SEQ ID NO:180), CDR2 (SEQ ID NO:181), Framework 3 (SEQ ID NO:182), CRD3 (SEQ ID NO:183), and Framework 4 (SEQ ID NO:184); B13C4 35-20: all sequences (SEQ ID NO:185), Framework 1 (SEQ ID NO:186), CDR1 (SEQ ID NO:187), Framework 2 (SEQ ID NO:188), CDR2 (SEQ ID NO:189), Framework 3 (SEQ ID NO:190), CRD3 (SEQ ID NO:191), and Framework 4 (SEQ ID NO:192); B15B11vk35-20: all sequences (SEQ ID NO:193), Framework 1 (SEQ ID NO:194), CDR1 (SEQ ID NO:195), Framework 2 (SEQ ID NO:196), CDR2 (SEQ ID NO:197), Framework 3 (SEQ ID NO: 198), CRD3 (SEQ ID NO: 199), and Framework 4 (SEQ ID NO:200); B13C12335-25: all sequences (SEQ ID NO:201), Framework 1 (SEQ ID NO:202), CDR1 (SEQ ID NO:203), Framework 2 (SEQ ID NO:204), CDR2 (SEQ ID NO:205), Framework 3 (SEQ ID NO:206), CRD3 (SEQ ID NO:207), and Framework 4 (SEQ ID NO:208); B13C1233520: all sequences (SEQ ID NO:209), Framework 1 (SEQ ID NO:210), CDR1 (SEQ ID NO:211), Framework 2 (SEQ ID NO:212), CDR2 (SEQ ID NO:213), Framework 3 (SEQ ID NO:214), CRD3 (SEQ ID NO:215), and Framework 4 (SEQ ID NO:216); RSDLVK-1: all sequences (SEQ ID NO:217), Framework 1 (SEQ ID NO:218), CDR1 (SEQ ID NO:219), Framework 2 (SEQ ID NO:220), CDR2 (SEQ ID NO:221), Framework 3 (SEQ ID NO:222), CRD3 (SEQ ID NO:223), and Framework 4 (SEQ ID NO:224); RSDLVK-6: all sequences (SEQ ID NO:225), Framework 1 (SEQ ID NO:226), CDR1 (SEQ ID NO:227), Framework 2 (SEQ ID NO:228), CDR2 (SEQ ID NO:229), Framework 3 (SEQ ID NO:230), CRD3 (SEQ ID NO:231), and Framework 4 (SEQ ID NO:232); RSDLVK-10: all sequences (SEQ ID NO:233), Framework 1 (SEQ ID NO:234), CDR1 (SEQ ID NO:235), Framework 2 (SEQ ID NO:236), CDR2 (SEQ ID NO:237), Framework 3 (SEQ ID NO:238), CRD3 (SEQ ID NO:239), and Framework 4 (SEQ ID NO:240); RSDLVK-13: all sequences (SEQ ID NO:241), Framework 1 (SEQ ID NO:242), CDR1 (SEQ ID NO:243), Framework 2 (SEQ ID NO:244), CDR2 (SEQ ID NO:245), Framework 3 (SEQ ID NO:246), CRD3 (SEQ ID NO:247), and Framework 4 (SEQ ID NO:248); 29: all sequences (SEQ ID NO:249), Framework 1 (SEQ ID NO:250), CDR1 (SEQ ID NO:251), Framework 2 (SEQ ID NO:252), CDR2 (SEQ ID NO:253), Framework 3 (SEQ ID NO:254), CRD3 (SEQ ID NO:255), and Framework 4 (SEQ ID NO:256); 44: all sequences (SEQ ID NO:257), Framework 1 (SEQ ID NO:258), CDR1 (SEQ ID NO:259), Framework 2 (SEQ ID NO:260), CDR2 (SEQ ID NO:261), Framework 3 (SEQ ID NO:262), CRD3 (SEQ ID NO:263), and Framework 4 (SEQ ID NO:264); A1=B4=F9: all sequences (SEQ ID NO:265), Framework 1 (SEQ ID NO:266), CDR1 (SEQ ID NO:267), Framework 2 (SEQ ID NO:268), CDR2 (SEQ ID NO:269), Framework 3 (SEQ ID NO:270), CRD3 (SEQ ID NO:271), and Framework 4 (SEQ ID NO:272); A5-C6: all sequences (SEQ ID NO:273), Framework 1 (SEQ ID NO:274), CDR1 (SEQ ID NO:275), Framework 2 (SEQ ID NO:276), CDR2 (SEQ ID NO:277), Framework 3 (SEQ ID NO:278), CRD3 (SEQ ID NO:279), and Framework 4 (SEQ ID NO:280); D4=E6: all sequences (SEQ ID NO:281), Framework 1 (SEQ ID NO:282), CDR1 (SEQ ID NO:283), Framework 2 (SEQ ID NO:284), CDR2 (SEQ ID NO:285), Framework 3 (SEQ ID NO:286), CRD3 (SEQ ID NO:287), and Framework 4 (SEQ ID NO:288); and C6D4: all sequences (SEQ ID NO:289), Framework 1 (SEQ ID NO:290), CDR1 (SEQ ID NO:291), Framework 2 (SEQ ID NO:292), CDR2 (SEQ ID NO:293), Framework 3 (SEQ ID NO:294), CRD3 (SEQ ID NO:295), and Framework 4 (SEQ ID NO:296).

FIG. 4 illustrates conservation of epitope among mammals, indicating the antibodies can be useful in multiple preclinical animal models and have broad utility, including in veterinary applications. Human αv (SEQ ID NO:591); Chimp αv (SEQ ID NO:592); Rhesus αv (SEQ ID NO:593); Cyno αv (SEQ ID NO:594); Cow αv (SEQ ID NO:595); Pig αv (SEQ ID NO:596); Horse αv (SEQ ID NO:597); Mouse αv (SEQ ID NO:598); Rat αv (SEQ ID NO:599); Armadillo αv (SEQ ID NO:600); Platypus αv (SEQ ID NO:601); Human β8 (SEQ ID NO:602); Chimp β8 (SEQ ID NO:603); Rhesus β8 (SEQ ID NO:604); Cyno β8 (SEQ ID NO:605); Cow β8 (SEQ ID NO:606); Pig β8(SEQ ID NO:607); Horse β8 (SEQ ID NO:608); Mouse β8 (SEQ ID NO:609); Rat 8 (SEQ ID NO:610); Armadillo β8 (SEQ ID NO:611); and Platypus β8 (SEQ ID NO:612).

FIG. 5 illustrates integrin alphaV (SEQ ID NO:394) and beta8 (SEQ ID NO:395) sequences. The epitope for C6D4 is in bold underlined italics.

FIG. 10 is a table of HepB surface antigen (HBSag) clearance from a chronic infection mouse model as a result of treatment with C6D4.

FIG. 11A-B illustrate amino acid sequences for clones used in the construction of the engineered antibody 4F1F9, an antibody used for detection of αvβ8 in human tissues. FIG. 11A Sequences-4F1: all sequences (SEQ ID NO:624), Framework 1 (SEQ ID NO:625), CDR1 (SEQ ID NO:628), Framework 2 (SEQ ID NO:632), CDR2 (SEQ ID NO:634), Framework 3 (SEQ ID NO:637), CDR3 (SEQ ID NO:651), Framework 4 (SEQ ID NO:655), 6B9: all sequences (SEQ ID NO:656), Framework 1 (SEQ ID NO:625), CDR1 (SEQ ID NO:629), Framework 2 (SEQ ID NO:632), CDR2 (SEQ ID NO:635), Framework 3 (SEQ ID NO:638), CDR3 (SEQ ID NO:652), Framework 4 (SEQ ID NO:655), 6B9.1: all sequences (SEQ ID NO:657), Framework 1 (SEQ ID NO:625), CDR1 (SEQ ID NO:629), Framework 2 (SEQ ID NO:632), CDR2 (SEQ ID NO:636), Framework 3 (SEQ ID NO:638), CDR3 (SEQ ID NO:653), Framework 4 (SEQ ID NO:655), A1: all sequences (SEQ ID NO:658), Framework 1 (SEQ ID NO:626), CDR1 (SEQ ID NO:629), Framework 2 (SEQ ID NO:633), CDR2 (SEQ ID NO:636), Framework 3 (SEQ ID NO:639), CDR3 (SEQ ID NO:654), Framework 4 (SEQ ID NO:655), A2: all sequences (SEQ ID NO:659), Framework 1 (SEQ ID NO:625), CDR1 (SEQ ID NO:629), Framework 2 (SEQ ID NO:633), CDR2 (SEQ ID NO:636), Framework 3 (SEQ ID NO:640), CDR3 (SEQ ID NO:654), Framework 4 (SEQ ID NO:655), A8: all sequences (SEQ ID NO:660), Framework 1 (SEQ ID NO:625), CDR1 (SEQ ID NO:629), Framework 2 (SEQ ID NO:633), CDR2 (SEQ ID NO:636), Framework 3 (SEQ ID NO:641), CDR3 (SEQ ID NO:654), Framework 4 (SEQ ID NO:655), A11: all sequences (SEQ ID NO:661), Framework 1 (SEQ ID NO:625), CDR1 (SEQ ID NO:630), Framework 2 (SEQ ID NO:633), CDR2 (SEQ ID NO:636), Framework 3 (SEQ ID NO:638), CDR3 (SEQ ID NO:654), Framework 4 (SEQ ID NO:655), B1: all sequences (SEQ ID NO:662), Framework 1 (SEQ ID NO:625), CDR1 (SEQ ID NO:629), Framework 2 (SEQ ID NO:632), CDR2 (SEQ ID NO:636), Framework 3 (SEQ ID NO:642), CDR3 (SEQ ID NO:654), Framework 4 (SEQ ID NO:655), B3: all sequences (SEQ ID NO:663), Framework 1 (SEQ ID NO:625), CDR1 (SEQ ID NO:629), Framework 2 (SEQ ID NO:633), CDR2 (SEQ ID NO:636), Framework 3 (SEQ ID NO:643), CDR3 (SEQ ID NO:654), Framework 4 (SEQ ID NO:655), C4=F10: all sequences (SEQ ID NO:664), Framework 1 (SEQ ID NO:625), CDR1 (SEQ ID NO:629), Framework 2 (SEQ ID NO:633), CDR2 (SEQ ID NO:636), Framework 3 (SEQ ID NO:644), CDR3 (SEQ ID NO:654), Framework 4 (SEQ ID NO:655), C7=D1: all sequences (SEQ ID NO:665), Framework 1 (SEQ ID NO:625), CDR1 (SEQ ID NO:629), Framework 2 (SEQ ID NO:633), CDR2 (SEQ ID NO:636), Framework 3 (SEQ ID NO:644), CDR3 (SEQ ID NO:654), Framework 4 (SEQ ID NO:655), D3=F1: all sequences (SEQ ID NO:666), Framework 1 (SEQ ID NO:625), CDR1 (SEQ ID NO:629), Framework 2 (SEQ ID NO:633), CDR2 (SEQ ID NO:636), Framework 3 (SEQ ID NO:645), CDR3 (SEQ ID NO:654), Framework 4 (SEQ ID NO:655), D10=E5: all sequences (SEQ ID NO:667), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), G4: all sequences (SEQ ID NO:668), Framework 1 (SEQ ID NO:625), CDR1 (SEQ ID NO:629), Framework 2 (SEQ ID NO:633), CDR2 (SEQ ID NO:636), Framework 3 (SEQ ID NO:647), CDR3 (SEQ ID NO:654), Framework 4 (SEQ ID NO:655), C4: all sequences (SEQ ID NO:669), Framework 1 (SEQ ID NO:625), CDR1 (SEQ ID NO:629), Framework 2 (SEQ ID NO:633), CDR2 (SEQ ID NO:636), Framework 3 (SEQ ID NO:650), CDR3 (SEQ ID NO:654), Framework 4 (SEQ ID NO:655), D10: all sequences (SEQ ID NO:670), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), 4F1A11: all sequences (SEQ ID NO:671), Framework 1 (SEQ ID NO:625), CDR1 (SEQ ID NO:629), Framework 2 (SEQ ID NO:632), CDR2 (SEQ ID NO:636), Framework 3 (SEQ ID NO:650), CDR3 (SEQ ID NO:654), Framework 4 (SEQ ID NO:655), 4F1E1: all sequences (SEQ ID NO:672), Framework 1 (SEQ ID NO:625), CDR1 (SEQ ID NO:631), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1G3: all sequences (SEQ ID NO:673), Framework 1 (SEQ ID NO:625), CDR1 (SEQ ID NO:631), Framework 2 (SEQ ID NO:632), CDR2 (SEQ ID NO:636), Framework 3 (SEQ ID NO:648), CDR3 (SEQ ID NO:654), Framework 4 (SEQ ID NO:655), 4F1E10: all sequences (SEQ ID NO:674), Framework 1 (SEQ ID NO:627), CDR1 (SEQ ID NO:631), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1E9: all sequences (SEQ ID NO:675), Framework 1 (SEQ ID NO:625), CDR1 (SEQ ID NO:629), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1H12: all sequences (SEQ ID NO:676), Framework 1 (SEQ ID NO:625), CDR1 (SEQ ID NO:631), Framework 2 (SEQ ID NO:632), CDR2 (SEQ ID NO:636), Framework 3 (SEQ ID NO:649), CDR3 (SEQ ID NO:654), Framework 4 (SEQ ID NO:655), F9: all sequences (SEQ ID NO:677), Framework 1 (SEQ ID NO:625), CDR1 (SEQ ID NO:631), Framework 2 (SEQ ID NO:632), CDR2 (SEQ ID NO:636), Framework 3 (SEQ ID NO:638), CDR3 (SEQ ID NO:654), and Framework 4 (SEQ ID NO:655). FIG. 11B Sequences-4F1: all sequences (SEQ ID NO:678), Framework 1 (SEQ ID NO:692), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), 6B9: all sequences (SEQ ID NO:679), Framework 1 (SEQ ID NO:699), CDR1 (SEQ ID NO:700), Framework 2 (SEQ ID NO:701), CDR2 (SEQ ID NO:695), Framework 3 (SEQ ID NO:696), CDR3 (SEQ ID NO:702), Framework 4 (SEQ ID NO:698), 6B9.1: all sequences (SEQ ID NO:680), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A1=A2=C4=C7=D1=D10=E5=F1=F10=G4: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A8: all sequences (SEQ ID NO:682), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A11: all sequences (SEQ ID NO:683), Framework 1 (SEQ ID NO:704), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), B1: all sequences (SEQ ID NO:684), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), B3: all sequences (SEQ ID NO:685), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), D10-E5: all sequences (SEQ ID NO:686), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), C4: all sequences (SEQ ID NO:687), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:706), D10: all sequences (SEQ ID NO:688), Framework 1 (SEQ ID NO:699), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:706), 4F1E1=1F1G3-4F1B5=4F1G11=4F1A9=4F1B9=4F1H9-4F1D10-4F1E9=4F1F10=4F1H11=4F1H12: all sequences (SEQ ID NO:689), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), 4FA11: all sequences (SEQ ID NO:690), Framework 1 (SEQ ID NO:705), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), F9: all sequences (SEQ ID NO:691), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), and Framework 4 (SEQ ID NO:706).

FIGS. 21A-D show immunodetection of the integrin b8 subunit in formalin fixed paraffin embedded sections from patient infected with *H. pylori* (A,B) or showing normal histology (C,D). The sections were stained with clone F9 in rabbit IgG format and detected using TSA signal amplification (Perkin Elmer). The brown precipitate indicates positive staining and the nuclei are counterstained with hematoxylin. The arrows indicate examples of positive crypts with stained crypt epithelial cells. The results show that the b8 integrin subunit is increased in expression in the stomachs of patients with *H. pylori*.

FIG. 28 shows a mouse model for evaluating lung metastasis using the LLC tumor cell line which does not express integrins αvβ6 or αvβ8. The LLC tumor cell line is syngenic to the host C57B/6 strain. The LLC.1 cell line has been passed though mice one time and regrown from lung metastasis. After two weeks, subcutaneously injected tumor (1×10$^6$) LLC.1 cells form large tumor nodules (~1 cm). The tumors are removed surgically and when animals lose 20% body weight they are euthanized.

FIG. 29B shows the survival curve when animals removed for local recurrence are excluded. At autopsy, the animals with 20% weight loss all have metastatic implants in their lungs. Here, C6D4 antibodies have been injected for up to 90 days in surviving animals. This experiment was performed eleven times, each time providing similar results (data not shown). Additionally, post-mortem examination did not reveal any abnormal inflammatory response in the tissues examined.

FIGS. 34A-C shows the inhibition of B16 lung metastases as compared to an isotype sample. FIG. 34A are photographs of representative lungs in anterior and posterior views and visible lung metastases were counted and the total lung surface area involved with metastases was assessed. FIG. 34B shows the effect of C6D4 on total number of lung metastases. The B16-F10 highly metastatic tumor cell line is syngenic to the host C57B/6 strain and does not express integrins αvβ6 or αvβ8. The B16-F10 tumor cells were transfected with murine itgb8. After selection in G418 and two rounds of sorting a pool of high expressing αvβ8 cells was injected intravenously via the tail vein. After three injections (i.p.) of isotype control (SV5) or C6D4, both at 7 mg/kg at days 0, 7 and 14, the mice were euthanized at day 18. FIG. 34C shows the effect of C6D4 as measured by percentage of total lung surface area involved by metastatic melanoma.

FIGS. 35A-H show that C6D4 effects macrophage polarization to a proinflammatory phenotype. Increases in MHCII expression by tumor associated macrophages and dendritic cells is important in host immune responses to tumor antigens.

FIGS. 37A-G are scatterplots showing integrin mediated differentiation of mouse Treg cells. Tumor associated CD4+T regulatory cells play an important role in suppressing the host immune response and help tumors escape immune surveillance. The differentiation of Treg requires TGF-beta. It is thought that TGF-beta provided by mechanisms such as integrin αvβ8 mediated activation are important for Treg differentiation and function. Here, we immobilized the ectodomains of various integrins (2 mg/ml) on ELISA plates (co-coated with anti-CD3) and plate naïve murine splenic CD4+ cells with hIL-2 and retinoic acid. After 5 days the cells were fixed, permeabilized and stained with anti-CD4 and FoxP3. As a positive and negative control, cells were plated on wells with only anti-CD3 (no integrin) in the presence (+) or absence (−) of rTGF-b. The percentage of FoxP3 expressing cells are shown in each of the scatterplots (Q2).

FIGS. 38A-D shows structural representations of a C6D4 derivative (termed "RGD3" or "CD64-RGD3") that is cross-reactive to αvβ6 and αvβ8 but not αvβ1, αvβ3, or αvβ5. FIG. 38A shows a close-up view of C6D4-RGD3 (gold) in complex with αvβ8 derived from cryoEM maps. Green is the αv subunit and blue is the β8 subunit. Shown in red is the LTGF-B1 peptide derived from structures of Latent-TGFB1 in complex with the integrin αvβ6. (αvβ6 (SEQ ID NO:709), αIIbβ3 (SEQ ID NO:710 (GRGDSP) and SEQ ID NO:711 (AKQRGDV). FIG. 38B shows sequence alignments of hTGFβ1-3 and the position of the RGD domains in TGFβ1 (SEQ ID NO:714) and TGFB3 (SEQ ID NO:715). TGFB2 (SEQ ID NO:716) does not have an RGD sequence. FIG. 38C shows the sequence of three mutant D4 Vk CDR1 loops containing portions of the hTGFB3 RGD sequence (in red) developed herein (C6D4 vk (SEQ ID NO:717); C6D4-RDG1 (SEQ ID NO:718); C6D4-RDG2 (SEQ ID NO:719); and C6D4-RDG3 (SEQ ID NO:720). FIG. 38D shows a zoomed image of the D4 loop (shown in gold) and the clash with the position of the bound RGD sequence of TGFB1 in complex with integrin αvβ6.

FIG. 39 shows cell surface staining experiments of C6VH expressed with either RGD1, RGD2 or RGD3 mutants (as set forth in FIG. 38) as rabbit IgG. Binding to human Cho cells expressing αvβ8 was expressed as a percentage of binding of C6D4.

FIG. 40 shows cell surface staining experiments of C6VH expressed with either D4 Vk or RGD1, RGD2 or RGD3 mutants as rabbit IgG. Binding to Cho cells expressing human αvβ8 or SW480 cells expressing αvβ6 are shown. Relative binding is defined as staining compared to staining of non-transfected Cho or SW480 cells.

FIG. 41 shows binding experiments of C6VH expressed with either D4 Vk or RGD1, RGD2 or RGD3 mutants as rabbit IgG, to various av-integrins. All integrins were coated on ELISA plates at 2 mg/ml, blocked with BSA, and antibodies were allowed to bind. Binding of C6D4 and C6D4-RGD3 were detected with anti-rabbit HRP. The results are shown relative to control wells coated with anti-av (clone 8B8) where av-integrins were detected with another av-antibody recognizing an non-overlapping epitope (L230-biotin), followed by SA-HRP.

FIG. 42 shows the effect of cations on the binding of C6D4 and C6D4-RGD3 to various receptors. Binding in EDTA containing buffer defines cation-dependence because EDTA binds to $Ca^{++}$ and $Mg^{++}$. Magnesium cation buffers contains 1 mM $Ca^{++}$ and 1 mM $Mg^{++}$. Here, the results are relative to anti-av, clone 11D12V2. All antibodies were coated on ELISA plates at 5 μg/ml. The αvβ8 or αvβ6 receptors (0.5 μg/ml) were bound for 1 hour and were then detected with biotinylated anti-av clone 8B8. The small amount of αvβ8 binding to C6D4-RGD3 in EDTA buffer (compared with no αvβ6 binding to C6D4-RGD3 in EDTA buffer) suggests that the binding to αvB6 is more dependent on the RGD binding loop of Vk CDR1 than the binding to αvβ8.

FIGS. 43A and 43B show inhibition of αvβ8 adhesion and TGF-beta activation. Cho 3.2.8.1 cells transfected with b8 were used in adhesion assays to wells coated with branched GRGDLGRLK peptide (SEQ ID NO:721) (10 μg/ml). Cho-b8 cells were allowed to bind in adhesion assays (FIG. 43A) in the presence of C6D4, RGD3 or control Mab at various concentrations. Cho-b8 cells were allowed to attach to wells with TMLC TGF-β reporter cells in the presence of C6D4, RGD3 or control Mab at various concentrations (FIG. 43B). The values are shown as a proportion of control Mab (SV5) control. The results indicate that C6D4-RGD3 and C6D4 block αvβ8 function similarly.

FIGS. 44A-B show adhesion assays and FIGS. 44C-D show TGF-beta activation. Here, Cho3.2.8.1 cells were transfected with GARP and LTGFB1. GARP (LRRC32) is a cell surface scaffolding molecule present on the surface of Treg cells and binds LTGF-b to the cell surface. Upper panels (FIGS. 44A and 44B) show adhesion assays of Cho cells expressing GARP/LTGFβ adhering to immobilized αvβ8 (FIG. 44A) or αvβ6 (FIG. 44B) performed in the presence of anti-β8 (C6D4), 3G9 (anti-β6) or the bispecific antibody RGD3 (anti-β6 and anti-38). In the lower panels (FIGS. 44C and 44D), the TGF-beta reporters cells TMLC, were added to each well to determine the amount of TGF-β activation in response to αvβ8 (FIG. 44C) or αvβ6 (FIG. 44D) performed in the presence of anti-β8 (C6D4), 3G9 (anti-β6) or the bispecific antibody RGD3 (anti-β6 and anti-β8). The results are reported as relative luciferase activity to wells treated with isotype control antibody (SV5). Below each graph is the EC50 of each inhibitory antibody.

FIG. 45 shows binding assay of αvβ6 to TGFβ3 peptide. Mab 3G9 is a potent inhibitor of αvβ6-mediated TGF-b activation. C6D4-RGD3 shows cross-competition with 3G9 binding suggesting that they have overlapping binding footprints or allosterically influence each other's binding. However, these antibodies have different modes of action as 3G9 binding to αvβ6 is not cation-dependent while C6D4-RGD3 binding is cation dependent.

FIG. 46 illustrates heavy and light chain amino acid sequences for clones used in the construction of the composite humanized antibody C6D4. VH sequences-C6D4: all sequences (SEQ ID NO:722), Framework 1 (SEQ ID NO:732), CDR1 (SEQ ID NO:733), Framework 2 (SEQ ID NO:734), CDR2 (SEQ ID NO:735), Framework 3 (SEQ ID NO:736), CDR3 (SEQ ID NO:737), Framework 4 (SEQ ID NO:738); HuC6D4 V1: all sequences (SEQ ID NO:723), Framework 1 (SEQ ID NO:739), CDR1 (SEQ ID NO:733), Framework 2 (SEQ ID NO:740), CDR2 (SEQ ID NO:735), Framework 3 (SEQ ID NO:741), CDR3 (SEQ ID NO:737), Framework 4 (SEQ ID NO:738); Mutclone A3: all sequences (SEQ ID NO:724), Framework 1 (SEQ ID NO:739), CDR1 (SEQ ID NO:733), Framework 2 (SEQ ID NO:740), CDR2 (SEQ ID NO:735), Framework 3 (SEQ ID NO:741), CDR3 (SEQ ID NO:737), Framework 4 (SEQ ID NO:738); Mutclone B7: all sequences (SEQ ID NO:725), Framework 1 (SEQ ID NO:742), CDR1 (SEQ ID NO:733), Framework 2 (SEQ ID NO:740), CDR2 (SEQ ID NO:735), Framework 3 (SEQ ID) NO:743), CDR3 (SEQ ID NO:744), Framework 4 (SEQ ID NO:738); Mutclone E5: all sequences (SEQ ID NO:726), Framework 1 (SEQ ID NO:739), CDR1 (SEQ ID NO:733), Framework 2 (SEQ ID NO:740), CDR2 (SEQ ID NO:735), Framework 3 (SEQ ID NO:741), CDR3 (SEQ ID NO:744), and Framework 4 (SEQ ID NO:738). VK sequences —C6D4: all sequences (SEQ ID NO:727), Framework 1 (SEQ ID NO:745), CDR1 (SEQ ID NO:746), Framework 2 (SEQ ID NO:747), CDR2 (SEQ ID NO:748), Framework 3 (SEQ ID NO:749), CDR3 (SEQ ID NO:750), Framework 4 (SEQ ID NO:751); HuC6D4 V1: all sequences (SEQ ID NO:728), Framework 1 (SEQ ID NO:752), CDR1 (SEQ ID NO:746), Framework 2 (SEQ ID NO:747), CDR2 (SEQ ID NO:748), Framework 3 (SEQ ID NO:753), CDR3 (SEQ ID NO:750), Framework 4 (SEQ ID NO:754); Mutclone A3: all sequences (SEQ ID NO:729), Framework 1 (SEQ ID NO:755), CDR1 (SEQ ID NO:756), Framework 2 (SEQ ID NO:747), CDR2 (SEQ ID NO:748), Framework 3 (SEQ ID NO:753), CDR3 (SEQ ID NO:750), Framework 4 (SEQ ID NO:754); Mutclone B7: all sequences (SEQ ID NO:730), Framework 1 (SEQ ID NO:757), CDR1 (SEQ ID NO:746), Framework 2 (SEQ ID NO:747), CDR2 (SEQ ID NO:748), Framework 3 (SEQ ID NO:758), CDR3 (SEQ ID NO:750), Framework 4 (SEQ ID NO:754); Mutclone E5: all sequences (SEQ ID NO:731), Framework 1 (SEQ ID NO:752), CDR1 (SEQ ID NO:756), Framework 2 (SEQ ID NO:747), CDR2 (SEQ ID NO:748), Framework 3 (SEQ ID NO:753), CDR3 (SEQ ID NO:750), and Framework 4 (SEQ ID NO:754).

FIGS. 49A-C shows CryoEM maps of C6D4 and C6D4-RGD αvβ8 complexes having similar positioning. Here, C6D4 Fab-αvβ8 (FIG. 49A) is compared with RGD3-αvβ8 map (FIG. 49B), or in overlay (FIG. 49C), based on cryoEM derived density maps. The anti-av 11D12V2 Fab was used to increase molecular mass of the complex and to assist in particle orientation.

FIG. 50 illustrates heavy chain amino acid sequences for clones used in the construction of the composite humanized antibodies C6D4 and C6D4-RGD3. Consensus sequences for the humanized version of C6D4 and C6D4-RGD3 are provided. VH sequences —HuC6D4VI: all (SEQ ID NO:395), Framework 1 (SEQ ID NO:396), CDR1 (SEQ ID NO:397), Framework 2 (SEQ ID NO:398), CDR2 (SEQ ID NO:399), Framework 3 (SEQ ID NO:400), CDR3 (SEQ ID NO:401), and Framework 4 (SEQ ID NO:402); HuC6D4A3: all (SEQ ID NO:403), Framework 1 (SEQ ID NO:404), CDR1 (SEQ ID NO:405), Framework 2 (SEQ ID NO:406), CDR2 (SEQ ID NO:407), Framework 3 (SEQ ID NO:408), CDR3 (SEQ ID NO:409), and Framework 4 (SEQ ID NO:410); HuC6D4B7: all (SEQ ID NO:411), Framework 1 (SEQ ID NO:412), CDR1 (SEQ ID NO:413), Framework 2 (SEQ ID NO:414), CDR2 (SEQ ID NO:415), Framework 3 (SEQ ID NO:416), CDR3 (SEQ ID NO:417), and Framework 4 (SEQ ID NO:418); HuC6D4E5: all (SEQ ID NO:419), Framework 1 (SEQ ID NO:420), CDR1 (SEQ ID NO:421), Framework 2 (SEQ ID NO:422), CDR2 (SEQ ID NO:423), Framework 3 (SEQ ID NO:424), CDR3 (SEQ ID NO:425), and Framework 4 (SEQ ID NO:426); C6D4: all sequences (SEQ ID NO:722), Framework 1 (SEQ ID NO:732), CDR1 (SEQ ID NO:733), Framework 2 (SEQ ID NO:734), CDR2 (SEQ ID NO:735), Framework 3 (SEQ ID NO:736), CDR3 (SEQ ID NO:737), and Framework 4 (SEQ ID NO:738); HuC6D4: all (SEQ ID NO:427), Framework 1 (SEQ ID NO:428), CDR1 (SEQ ID NO:429), Framework 2 (SEQ ID NO:430), CDR2 (SEQ ID NO:431), Framework 3 (SEQ ID NO:432), CDR3 (SEQ ID NO:433), and Framework 4 (SEQ ID NO:434); C6D4-RGD3: all (SEQ ID NO:435), Framework 1 (SEQ ID NO:436), CDR1 (SEQ ID NO:437), Framework 2 (SEQ ID NO:438), CDR2 (SEQ ID NO:439), Framework 3 (SEQ ID NO:440), CDR3 (SEQ ID NO:441), and Framework 4 (SEQ ID NO:442); HuC6D4-RGD3: all (SEQ ID NO:443), Framework 1 (SEQ ID NO:444), CDR1 (SEQ ID NO:445), Framework 2 (SEQ ID NO:446), CDR2 (SEQ ID NO:447), Framework 3 (SEQ ID NO:448), CDR3 (SEQ ID NO:449), and Framework 4 (SEQ ID NO:450); and Consensus VH: Framework 1 (SEQ ID NO:558), CDR1 (SEQ ID NO:563), Framework 2 (SEQ ID NO:559), CDR2 (SEQ ID NO:563), Framework 3 (SEQ ID NO:560), CDR3 (SEQ ID NO:564), and Framework 4 (SEQ ID NO:561).

FIG. 51 illustrates light chain amino acid sequences for clones used in the construction of the composite humanized antibodies C6D4 and C6D4-RGD3. Consensus sequences for the humanized version of C6D4 and C6D4-RGD3 are provided. VL sequences-HuC6D4V1: all (SEQ ID NO:451), Framework 1 (SEQ ID NO:452), CDR1 (SEQ ID NO:453), Framework 2 (SEQ ID NO:454), CDR2 (SEQ ID NO:455), Framework 3 (SEQ ID NO:456), CDR3 (SEQ ID NO:457), and Framework 4 (SEQ ID NO:458); HuC6D4A3: all (SEQ ID NO:459), Framework 1 (SEQ ID NO:460), CDR1 (SEQ ID NO:461), Framework 2 (SEQ ID NO:462), CDR2 (SEQ ID NO:463), Framework 3 (SEQ ID NO:464), CDR3 (SEQ ID NO:465), and Framework 4 (SEQ ID NO:466); HuC6D4B7: all (SEQ ID NO:467), Framework 1 (SEQ ID NO:468), CDR1 (SEQ ID NO:469), Framework 2 (SEQ ID NO:470), CDR2 (SEQ ID NO:471), Framework 3 (SEQ ID NO:472), CDR3 (SEQ ID NO:473), and Framework 4 (SEQ ID NO:474); HuC6D4E5: all (SEQ ID NO:475), Framework 1 (SEQ ID NO:476), CDR1 (SEQ ID NO:478), Framework 2 (SEQ ID NO:479), CDR2 (SEQ ID NO:480), Framework 3 (SEQ ID NO:481), CDR3 (SEQ ID NO:482), and Framework 4 (SEQ ID NO:483); C6D4: all sequences (SEQ ID NO:727), Framework 1 (SEQ ID NO:745), CDR1 (SEQ ID NO:746), Framework 2 (SEQ ID NO:747), CDR2 (SEQ ID NO:748), Framework 3 (SEQ ID NO:749), CDR3 (SEQ ID NO: 750), and Framework 4 (SEQ ID NO:751); HuC6D4: all sequences (SEQ ID NO:484), Framework 1 (SEQ ID NO:485), CDR1 (SEQ ID NO:486), Framework 2 (SEQ ID NO:487), CDR2 (SEQ ID NO:488), Framework 3 (SEQ ID NO:489), CDR3 (SEQ ID NO:490), and Framework 4 (SEQ ID NO:491); C6D4-RGD3: all (SEQ ID NO:492), Framework 1 (SEQ ID NO:493), CDR1 (SEQ ID NO:494), Framework 2 (SEQ ID NO:495), CDR2 (SEQ ID NO:496), Framework 3 (SEQ ID NO:497), CDR3 (SEQ ID NO:498), and Framework 4 (SEQ ID NO:499); HuC6D4-RGD3: all (SEQ ID NO:500), Framework 1 (SEQ ID NO:501), CDR1 (SEQ ID NO:502), Framework 2 (SEQ ID NO:503), CDR2 (SEQ ID NO:504), Framework 3 (SEQ ID NO:505), CDR3 (SEQ ID NO:506), and Framework 4 (SEQ ID NO:507); and Consensus VL: Framework 1 (SEQ ID NO:565), CDR1 (SEQ ID NO:569), Framework 2 (SEQ ID NO:566), CDR2 (SEQ ID NO:570), Framework 3 (SEQ ID NO:567), CDR3 (SEQ ID NO:571), and Framework 4 (SEQ ID NO:568). RDG3 loop (SEQ ID NO:721).

FIG. 52 illustrates heavy chain amino acid sequences for clones used in the construction of the composite antibody F9. Sequences-4F1: all sequences (SEQ ID NO:624), Framework 1 (SEQ ID NO:625), CDR1 (SEQ ID NO:628), Framework 2 (SEQ ID NO:632), CDR2 (SEQ ID NO:634), Framework 3 (SEQ ID NO:637), CDR3 (SEQ ID NO:651), Framework 4 (SEQ ID NO:655), 6B9: all sequences (SEQ ID NO:656), Framework 1 (SEQ ID NO:625), CDR1 (SEQ ID NO:629), Framework 2 (SEQ ID NO:632), CDR2 (SEQ ID NO:635), Framework 3 (SEQ ID NO:638), CDR3 (SEQ ID NO:652), Framework 4 (SEQ ID NO:655), 6B9.1: all sequences (SEQ ID NO:657), Framework 1 (SEQ ID NO:625), CDR1 (SEQ ID NO:629), Framework 2 (SEQ ID NO:632), CDR2 (SEQ ID NO:636), Framework 3 (SEQ ID NO:638), CDR3 (SEQ ID NO:653), Framework 4 (SEQ ID NO:655), A1: all sequences (SEQ ID NO:658), Framework 1 (SEQ ID NO:626), CDR1 (SEQ ID NO:629), Framework 2 (SEQ ID NO:633), CDR2 (SEQ ID NO:636), Framework 3 (SEQ ID NO:639), CDR3 (SEQ ID NO:654), Framework 4 (SEQ ID NO:655), A2: all sequences (SEQ ID NO:659), Framework 1 (SEQ ID NO:625), CDR1 (SEQ ID NO:629), Framework 2 (SEQ ID NO:633), CDR2 (SEQ ID NO:636), Framework 3 (SEQ ID NO:640), CDR3 (SEQ ID NO:654), Framework 4 (SEQ ID NO:655), A8: all sequences (SEQ ID NO:660), Framework 1 (SEQ ID NO:625), CDR1 (SEQ ID NO:629), Framework 2 (SEQ ID NO:633), CDR2 (SEQ ID NO:636), Framework 3 (SEQ ID NO:641), CDR3 (SEQ ID NO:654), Framework 4 (SEQ ID NO:655), A11: all sequences (SEQ ID NO:661), Framework 1 (SEQ ID NO:625), CDR1 (SEQ ID NO:630), Framework 2 (SEQ ID NO:633), CDR2 (SEQ ID NO:636), Framework 3 (SEQ ID NO:638), CDR3 (SEQ ID NO:654), Framework 4 (SEQ ID NO:655), B1: all sequences (SEQ ID NO:662), Framework 1 (SEQ ID NO:625), CDR1 (SEQ ID NO:629), Framework 2 (SEQ ID NO:632), CDR2 (SEQ ID NO:636), Framework 3 (SEQ ID NO:642), CDR3 (SEQ ID NO:654), Framework 4 (SEQ ID NO:655), B3: all sequences (SEQ ID NO:663), Framework 1 (SEQ ID NO:625), CDR1 (SEQ ID NO:629), Framework 2 (SEQ ID NO:633), CDR2 (SEQ ID NO:636), Framework 3 (SEQ ID NO:643), CDR3 (SEQ ID NO:654), Framework 4 (SEQ ID NO:655), C4=F10: all sequences (SEQ ID NO:664), Framework 1 (SEQ ID NO:625), CDR1 (SEQ ID NO:629), Framework 2 (SEQ ID NO:633), CDR2 (SEQ ID NO:636), Framework 3 (SEQ ID NO:644), CDR3 (SEQ ID NO:654), Framework 4 (SEQ ID NO:655), C7=D1: all sequences (SEQ ID NO:665), Framework 1 (SEQ ID NO:625), CDR1 (SEQ ID NO:629), Framework 2 (SEQ ID NO:633), CDR2 (SEQ ID NO:636), Framework 3 (SEQ ID NO:644), CDR3 (SEQ ID NO:654), Framework 4 (SEQ ID NO:655), D3=F1: all sequences (SEQ ID NO:666), Framework 1 (SEQ ID NO:625), CDR1 (SEQ ID NO:629), Framework 2 (SEQ ID NO:633), CDR2 (SEQ ID NO:636), Framework 3 (SEQ ID NO:645), CDR3 (SEQ ID NO:654), Framework 4 (SEQ ID NO:655), D10=E5: all sequences (SEQ ID NO:667), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), E8: all sequences (SEQ ID NO:667), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), F2: all sequences (SEQ ID NO:667), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), G4: all sequences (SEQ ID NO:668), Framework 1 (SEQ ID NO:625), CDR1 (SEQ ID NO:629), Framework 2 (SEQ ID NO:633), CDR2 (SEQ ID NO:636), Framework 3 (SEQ ID NO:647), CDR3 (SEQ ID NO:654), Framework 4 (SEQ ID NO:655), C4: all sequences (SEQ ID NO:669), Framework 1 (SEQ ID NO:625), CDR1 (SEQ ID NO:629), Framework 2 (SEQ ID NO:633), CDR2 (SEQ ID NO:636), Framework 3 (SEQ ID NO:650), CDR3 (SEQ ID NO:654), Framework 4 (SEQ ID NO:655), D10: all sequences (SEQ ID NO:670), Framework 1 (SEQ ID NO:625), CDR1 (SEQ ID NO:629), Framework 2 (SEQ ID NO:633), CDR2 (SEQ ID NO:636), Framework 3 (SEQ ID NO:646), CDR3 (SEQ ID NO:654), Framework 4 (SEQ ID NO:655), 4F1A11: all sequences (SEQ ID NO:671), Framework 1 (SEQ ID NO:625), CDR1 (SEQ ID NO:629), Framework 2 (SEQ ID NO:632), CDR2 (SEQ ID NO:636), Framework 3 (SEQ ID NO:650), CDR3 (SEQ ID NO:654), Framework 4 (SEQ ID NO:655), 4F1E1: all sequences (SEQ ID NO:672), Framework 1 (SEQ ID NO:625), CDR1 (SEQ ID NO:631), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1G3: all sequences (SEQ ID NO:673), Framework 1 (SEQ ID NO:625), CDR1 (SEQ ID NO:631), Framework 2 (SEQ ID NO:632), CDR2 (SEQ ID NO:636), Framework 3 (SEQ ID NO:648), CDR3 (SEQ ID NO:654), Framework 4 (SEQ ID NO:655), 4F1E10: all sequences (SEQ ID NO:674), Framework 1 (SEQ ID NO:627), CDR1 (SEQ ID NO:631), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1E9: all sequences (SEQ ID NO:675), Framework 1 (SEQ ID NO:625), CDR1 (SEQ ID NO:629), Framework 2 (SEQ ID NO:632), CDR2 (SEQ ID NO:636), Framework 3 (SEQ ID NO:638), CDR3 (SEQ ID NO:654), Framework 4 (SEQ ID NO:655), 4F1H12: all sequences (SEQ ID NO:676), Framework 1 (SEQ ID NO:625), CDR1 (SEQ ID NO:631), Framework 2 (SEQ ID NO:632), CDR2 (SEQ ID NO:636), Framework 3 (SEQ ID NO:649), CDR3 (SEQ ID NO:654), Framework 4 (SEQ ID NO:655), F9: all sequences (SEQ ID NO:677), Framework 1 (SEQ ID NO:625), CDR1 (SEQ ID NO:631), Framework 2 (SEQ ID NO:632), CDR2 (SEQ ID NO:636), Framework 3 (SEQ ID NO:638), CDR3 (SEQ ID NO:654), and Framework 4 (SEQ ID NO:655).

FIG. 53 illustrates light chain amino acid sequences for clones used in the construction of the composite antibody F9. VL Sequences-4F1: all sequences (SEQ ID NO:678), Framework 1 (SEQ ID NO:692), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), 6B9: all sequences (SEQ ID NO:679), Framework 1 (SEQ ID NO:699), CDR1 (SEQ ID NO:700), Framework 2 (SEQ ID NO:701), CDR2 (SEQ ID NO:695), Framework 3 (SEQ ID NO:696), CDR3 (SEQ ID NO:702), Framework 4 (SEQ ID NO:698), 6B9.1: all sequences (SEQ ID NO:680), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A1: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A2: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A8: all sequences (SEQ ID NO:682), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), A11: all sequences (SEQ ID NO:683), Framework 1 (SEQ ID NO:704), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), B1: all sequences (SEQ ID NO:684), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), B3: all sequences (SEQ ID NO:685), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), C4=F10: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), C7=D1: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), D3=F1: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), D10=E5: all sequences (SEQ ID NO:686), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), E8: all sequences (SEQ ID NO:686), Framework 1 (SEQ ID NO:703), CDR1 (SEQ ID NO:693), Framework 2 (SEQ ID NO:694), CDR2 (SEQ ID NO:695), Framework 3 (SEQ ID NO:755), CDR3 (SEQ ID NO:697), Framework 4 (SEQ ID NO:698), F2: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), G4: all sequences (SEQ ID NO:681), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), C4: all sequences (SEQ ID NO:687), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:706), D10: all sequences (SEQ ID NO:688), Framework 1 (SEQ ID NO:699), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:706), 4F1E1=1F1G3-4F1B5=4F1G11-4F1A9=4F1B9-4F1H9=4F1D10-4F1E9=4F1F10=4F1H11=4F1H12: all sequences (SEQ ID NO:689), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), 4FA11: all sequences (SEQ ID NO:690), Framework 1 (SEQ ID NO:705), CDR1 (SEQ ID NO:693), Framework 2 (SEQ ID NO:694), CDR2 (SEQ ID NO:695), Framework 3 (SEQ ID NO:696), CDR3 (SEQ ID NO:697), Framework 4 (SEQ ID NO:698), F9: all sequences (SEQ ID NO:691), Framework 1 (SEQ ID NO:703), CDR1 (SEQ ID NO:693), Framework 2 (SEQ ID NO:694), CDR2 (SEQ ID NO:695), Framework 3 (SEQ ID NO:696), CDR3 (SEQ ID NO:697), and Framework 4 (SEQ ID NO:706).

DETAILED DESCRIPTION OF THE INVENTION

I. Introduction

The inventors have discovered certain antibodies that bind to human integrin αvβ8 and cause at least partial reduction in ligand binding function. Based on that discovery, they have developed detailed structural models to aid in the discovery of antibodies that bind to integrin αvβ8 at particular epitopes that optimally block the ligand binding site of integrin αvβ8. Some of the antibodies identified bind to both the av-integrin subunit head domain and the β8-integrin subunit head domain to effectively cover the ligand binding site of the integrin αvβ8 without engaging to the ligand binding site itself (i.e. acting as a ligand-mimetic).

Further, the inventors have discovered that blocking ligand binding to integrin αvβ8 is effective in inhibiting cancer (including but not limited to metastatic cancer) and also is effective in treating viral infections. Without intending to limit the scope of the described invention, it is believed that integrin αvβ8 plays a role in blocking regulatory T cells (Tregs) function and/or development and thus that the antibodies described herein stimulate immunity to tumor cells and viruses. Accordingly, antibodies and methods of their use, among other aspects, are provided herein.

The inventors have also identified introduced an "RGDL" sequence (SEQ ID NO:756) into a CDR of the anti-αvβ8 antibody and have shown that such an introduction renders the antibody able to bind αvβ6 while maintaining substantially the same binding activity for αvβ8.

II. Antibodies

Provided herein are antibodies that bind human (and in some embodiments other mammalian, e.g., such as mouse, guinea pig, pig, and rabbit) integrin αvβ8. In some embodiments, the antibodies are isolated, are chimeric (comprising at least some heterologous amino acid sequence), are labeled or covalently linked to another molecule such a cytotoxic agent or a combination thereof. In some embodiments, the antibodies specifically bind human integrin αvβ8 and block binding of a ligand to human integrin αvβ8. Exemplary ligands can include, for example, TGFβ and LAP. In some embodiments, the antibodies bind in a cation-dependent manner or have enhanced binding in the presence of cations.

Figure 7:
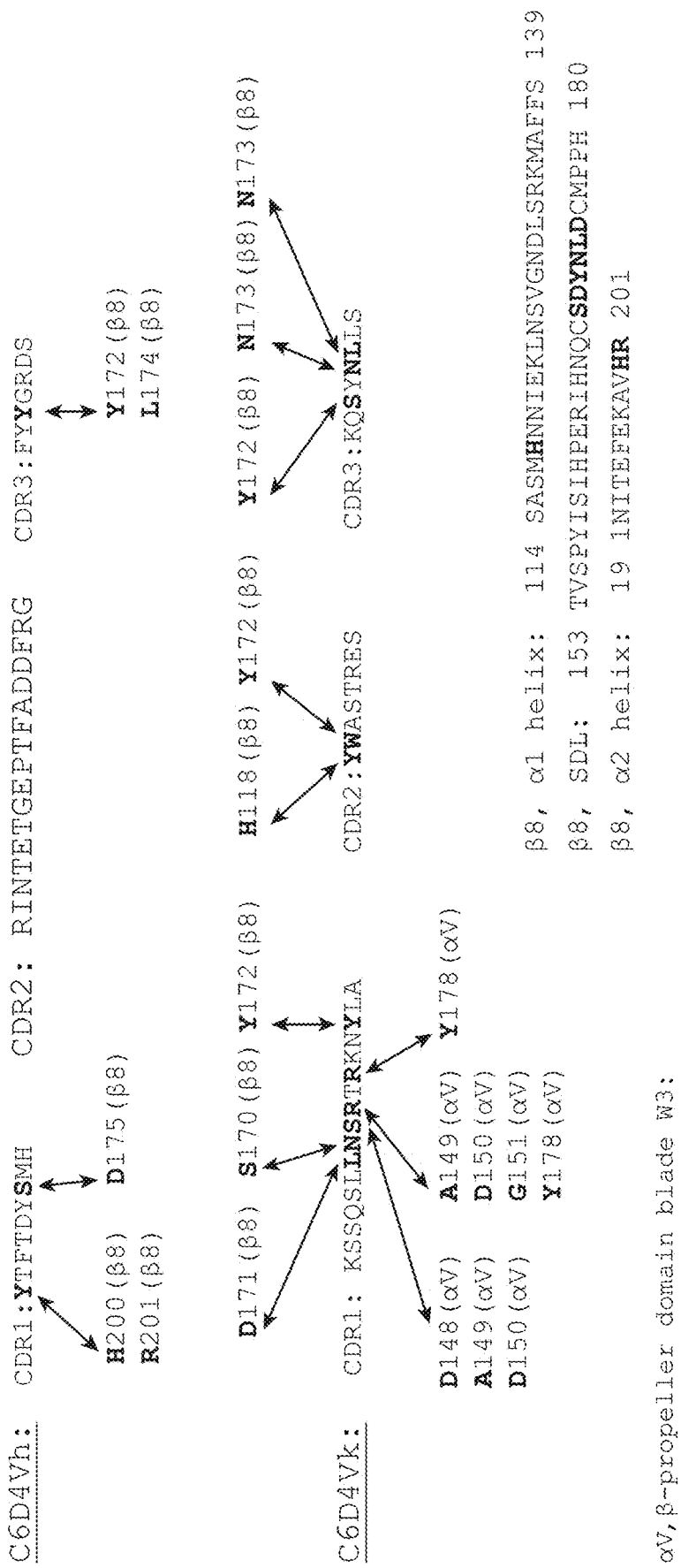
FIG. 7 illustrates the residues of the SDL and β8α1 and α2 helices and αv head of integrin αvβ8 that directly interact with C6D4 upon binding. The head sequence of integrin αv is FNLDVDSPAEYSGPEGSYFGFAVDFFVP-SASSRMFLLVGAPKANTTQPGIVEGGQVLKC DWSSTRRCQPIEFDATGNRDYAKDDPLEFKSHQWF-GASVRSKQDKILACAPLYHWRTE MKQEREPVGTCFLQDGTKTVEYAPCRSQDI-DADGQGFCQGGFSIDFTKADRVLLGGPGS FYWQGQLISDQVAEIVSKYDPNVYSIKYNNQLATR-TAQAIFDDSYLGYSVAVGDFNGD GIDDFVSGVPRAARTLGMVYIYDGKNMSSLYNFT-GEQMAAYFGFSVAATDINGDDYAD VFI-GAPLFMDRGSDGKLQEVGQVSVSLQRASGDFQTTKL NGFEVFARFGSAIAPLGDLD QDGFNDIAIAAPY-GGEDKKGIVYIFNGRSTGLNAVPSQI-LEGQWAARSMPPSFGYSMKG ATDIDKNGYPDLIVGAFGVDRAILYRARP (SEQ ID NO:623). Sequences C6D4 VH CDR1 (SEQ ID NO:613); C6D4 VH CDR2 (SEQ ID NO:614); C6D4 VH CDR3 (SEQ ID NO:615); C6D4 Vk CDR1 (SEQ ID NO:616); C6D4 Vk CDR2 (SEQ ID NO:617); C6D4 Vk CDR3 (SEQ ID NO:618); β8, al helix (SEQ ID NO:619); β8, SDL (SEQ ID NO:620); β8, α2 helix (SEQ ID NO:621); and αV, β-propeller domain blade W3 (SEQ ID NO:622).

In some embodiments the epitope bound by the antibodies described herein on human integrin αvβ8 comprise amino acids in (1) the specificity determining loop (SDL) of the integrin β8 protein (e.g., TVSPYISIHPERIHNQCSDYNLDCMPPH (SEQ ID NO:620)), (2) in the a1 (e.g., SASMHNNIEKLNSVGNDLSRKMAFFS (SEQ ID NO:619)) or a2 (e.g., NITEFEKAVHR (SEQ ID NO:621)) helices of the β8 integrin protein, (3) the head of the av protein (e.g., DADGQ (SEQ ID NO:757); SFYWQ (SEQ ID NO:758); FDDSY (SEQ ID NO:759)) or other portions of KQDKILACAPLYHWR-TEMKQEREPVGTCFLQDGTKTVEYAPCRSQDI-DADGQGFCQGG FSIDFTKADRVLLGGPGSFYWQGQLISDQVAEIVSKY-DPNVYSIKYNNQLATRTAQAIFD (SEQ ID NO:760) or (4) a combination thereof (e.g., 1 and 2, 2 and 3, 1 and 3, or 1, 2, and 3) as they occur in the native human integrin αvβ8 protein, including for example to all of the listed portions of human integrin αvβ8. In some embodiments, the antibody binds to one or more or all amino acid in the SDL selected from: D175 (e.g., in NLDCM (SEQ ID NO:761)), L174 (e.g., in YNLDC (SEQ ID NO:762)), or S170, D171, or Y172 (e.g., in QCSDYNL (SEQ ID NO:763)), or combinations thereof, wherein the numbering is based on the human integrin β8 protein (SEQ ID NO:394). See, e.g., FIG. 7. In some embodiments, the antibody binds to the amino acid H118 (e.g., in SMHNN) (SEQ ID NO:764) in the α1 helix of the β8 integrin protein), wherein the numbering is based on the human integrin β8 protein (SEQ ID NO:394). In some embodiments, the antibody binds to the amino acid H200 or R201 (e.g., in AVHRQ) in the α2 helix of the β8 integrin protein, or combinations thereof, wherein the numbering is based on the human integrin β8 protein (SEQ ID NO:394). In some embodiments, the antibody binds to one or more or all amino acid (underlined) in the head of the αv protein selected from: D148, A149, D150, G151, or Y178 (e.g., in SFYWQ (SEQ ID NO:758)) or combinations thereof, wherein the numbering is based on the human integrin αv protein (SEQ ID NO:393). In some embodiments, the antibody binds to each of the above indicated (underlined) amino acids described in this paragraph. As can be seen from FIGS. 12-18, interaction with the above-described domains of integrin αvβ8 is beneficial.

As noted above, in some embodiments, the antibodies specifically bind human integrin αvβ8 and block binding of a ligand to human integrin αvβ8. The ability of an antibody to block αvβ8 integrin binding of a ligand can be determined by inhibition of binding of a soluble form of αvβ8 or a full-length form of αvβ8 expressed on the surface of cells to immobilized latent-TGF-beta or a portion thereof containing the sequence RGDL See, e.g., Ozawa, A, et al. J Biol Chem. 291(22):11551-65 (2016).

In some embodiments, the antibodies comprise one or more CDR (or all of the heavy chain CDRs of a clone, or all of the light chain CDRs of a clone) as follows:

| Heavy Chains | Clone name | CDR1 VH (SEQ ID:) | CDR2 VH (SEQ ID:) | CDR3 VH (SEQ ID:) |
|---|---|---|---|---|
| Heavy | B2B2 | TFTDYSMH (313) | RINTETGEP TFADDFGG (314) | YYYGRDS (315) |
| Heavy | B13C4 | TFTDYSMH (316) | WIKTETGEP TYADDFKG (317) | YYYGRDS (318) |
| Heavy | B13H3 | TFTDYSMH (319) | WIKTETDEP TYADDFKE (320) | YYYGRDS (321) |
| Heavy | B15B11 | TFTDYSMH (322) | RINTETGEP TFADDFRG (323) | YYYGRDS (324) |
| Heavy | B13C12 | TFTDYSIH (325) | WIKTETGEP TYADDFNG (326) | YYYGRDS (327) |
| Heavy | A1 | TFTDYSMH (328) | RINTETGEP TFADDFRG (329) | YYYGRDT (330) |
| Heavy | C6 | TFTDYSMH (331) | RINTETGEP TFADDFRG (332) | FYYGRDS (333) |

| Light Chains | Clone name | CDR1 Vk | CDR2 Vk | CDR3 Vk |
|---|---|---|---|---|
| Light | B2B2 | KASQDINSYLS (334) | RANRLVD (335) | LQYDEFP PLT (336) |
| Light | B13C4 | KSSQSLLNSRT RKNYLA (337) | WASTRES (338) | KQSYNLL T (339) |
| Light | B13H3 | KSSQSLLNSRI RKNYLA (340) | WASTRES (341) | KQSYNLL T (342) |
| Light | B15B11.1 | SASSSVSYMH (343) | DTSNLAS (344) | QQWSSNP LT (345) |
| Light | B15B11.2 | SASSSVSYMH (346) | DTSNLAS (347) | QQWSSNP PT (348) |
| Light | B15B11.3 | KSSQSLLNSRT RKNYLA (349) | WASTRES (350) | KQSYNLL T (351) |
| Light | B13C12.1 | SASSSVSYMH (352) | DTSKLAS (353) | QQWSSNP FT (354) |
| Light | B13C12.2 | SASSSVSYMH (355) | GTSNLAS (356) | QQWSSNP PT (357) |
| Light | B13C12.3 | KSSQSLLHSRT RKNYLA (358) | WASTRES (359) | KQSYNLL T (360) |
| Light | D4 | KSSQSLLNSRT RKNYLA (361) | WASTRES (362) | KQSYNLL S (363) |

In some embodiments, the antibodies comprise one or more CDR (or all of the heavy chain CDRs of a clone, or all of the light chain CDRs of a clone) as follows:

| Heavy Chains | Clone name | CDR1L VH (SEQ ID:) | CDR2 VH (SEQ ID:) | CDR3 VH (SEQ ID:) |
|---|---|---|---|---|
| Heavy | HuC6D4V1 | DYSMH (397) | RINTETGEP TFADDFRG (399) | FYYGRDS (401) |
| Heavy | HuC6D4A3 | DYSMH (405) | RINTETGEP TFADDFRG (407) | FYYGRDS (409) |
| Heavy | HuC6D4B7 | DYSMH (413) | RINTETGEP TFADDFRG (415) | FYYGRDT (417) |
| Heavy | HuC6D4E5 | DYSMH (421) | RINTETGEP TFADDFRG (423) | FYYGRDT (425) |
| Heavy | HuC6D4 | DYSMH (429) | RINTETGEP TFADDFRG (431) | FYYGRDT (433) |
| Heavy | C6D4-RGD3 | DYSMH (437) | RINTETGEP TFADDFRG (439) | FYYGRDS (441) |
| Heavy | HuC6D4-RGD3 | DYSMH (445) | RINTETGEP TFADDFRG (447) | FYYGRDT (449) |

| Light Chains | Clone name | CDR1 Vk (SEQ ID:) | CDR2 Vk (SEQ ID:) | CDR3 Vk (SEQ ID:) |
|---|---|---|---|---|
| Light | HuC6D4V1 | KSSQSLLNSRT RKNYLA (529) | WASTRES (530) | KQSYNLLS (531) |
| Light | HuC6D4A3 | KSSQSLLNSRS RKNYLA (532) | WASTRES (533) | KQSYNLLS (534) |
| Light | HuC6D4B7 | KSSQSLLNSRT (RKNYLA 535) | WASTRES (536) | KQSSNLIS (537) |

-continued

| Chain | Clone | CDR1 (SEQ ID:) | CDR2 (SEQ ID:) | CDR3 (SEQ ID:) |
|---|---|---|---|---|
| Light | HuC6D4E5 | KSSQSLLNSRS RKNYLA (538) | WASTRES (539) | KQSYNLLS (540) |
| Light | HuC6D4 | KSSQSLLNSRS RKNYLA (541) | WASTRES (542) | KQSYNLLS (543) |
| Light | C6D4-RGD3 | KSSQSLLGRGD LGRLKKNALA (544) | WASTRES (545) | KQSYNLLS (546) |
| Light | HuC6D4-RGD3 | KSSQSLLGRGD LGRLKKNALA (547) | WASTRES (548) | KQSYNLLS (549) |

In some embodiments, an antibody described herein comprises heavy and light chain CDRs as paired in the following table:

| Combinations (H + L) | Clone name | CDR1 (SEQ ID:) | CDR2 (SEQ ID:) | CDR3 (SEQ ID:) |
|---|---|---|---|---|
| H | B2B2 | TFTDYSMH (313) | RINTETGEPTFADDFGG (314) | YYYGRDS (315) |
| L | B2B2 | KASQDINSYLS (334) | RANRLVD (335) | LQYDEFPPLT (336) |
| H | B13H3 | TFTDYSMH (319) | WIKTETDEPTYADDFKE (320) | YYYGRDS (321) |
| L | B13H3 | KSSQSLLNSRIRKNYLA (340) | WASTRES (341) | KQSYNLLT (342) |
| H | B13C4 | TFTDYSMH (316) | WIKTETGEPTYADDFKG (317) | YYYGRDS (318) |
| L | B13C4 | KSSQSLLNSRTRKNYLA (337) | WASTRES (338) | KQSYNLLT (339) |
| H | B15B11 | TFTDYSMH (322) | RINTETGEPTFADDFRG (323) | YYYGRDS (324) |
| H | B15B11.1 | SASSSVSYMH (343) | DTSNLAS (344) | QQWSSNPLT (345) |
| H | B15B11 | TFTDYSMH (322) | RINTETGEPTFADDFRG (323) | YYYGRDS (324) |
| L | B15B11.2 | SASSSVSYMH (346) | DTSNLAS (347) | QQWSSNPPT (348) |
| H | B15B11 | TFTDYSMH (322) | RINTETGEPTFADDFRG (323) | YYYGRDS (324) |
| L | B15B11.3 | KSSQSLLNSRTRKNYLA (358) | WASTRES (359) | KQSYNLLT (360) |
| H | B13C12 | TFTDYSIH (325) | WIKTETGEPTYADDFNG (326) | YYYGRDS (327) |
| L | B13C12.1 | SASSSVSYMH (352) | DTSKLAS (353) | QQWSSNPFT (354) |
| H | B13C12 | TFTDYSIH (325) | WIKTETGEPTYADDENG (326) | YYYGRDS (327) |
| L | B13C12.2 | SASSSVSYMH (355) | GTSNLAS (356) | QQWSSNPPT (357) |
| H | B13C12 | TFTDYSIH (325) | WIKTETGEPTYADDFNG (326) | YYYGRDS (327) |
| L | B13C12.3 | KSSQSLLHSRTRKNYLA (358) | WASTRES (359) | KQSYNLLT (360) |
| H | RSDLVH-3 | TFTDYSIH (367) | WIKTETGEPTYADDFNG (368) | YYYGRDS (369) |

-continued

| Combinations (H + L) | Clone name | CDR1 (SEQ ID:) | CDR2 (SEQ ID:) | CDR3 (SEQ ID:) |
|---|---|---|---|---|
| L | RSDLVK-10 | KSSQSLLNSRTRKNYLA (373) | WASTRES (374) | KQSYNLLT (375) |
| H | RSDLVH-1 | TFTDYSIH (364) | WIKTETGEPTYADDFKG (365) | YYYGRDS (366) |
| L | RSDLVK-10 | KSSQSLLNSRTRKNYLA (373) | WASTRES (374) | KQSYNLLT (375) |
| H | RSDLVH-3 | TFTDYSIH (367) | WIKTETGEPTYADDFNG (368) | YYYGRDS (369) |
| L | RSDLVK-13 | KSSQSLLHSRTRKNYLA (376) | WASTRES (377) | KQSYNLLT (378) |
| H | RSDLVH-16 | TFTDYSMH (370) | RINTETGEPTFADDFRG (371) | YYYGRDS (372) |
| L | RSDLVK-10 | KSSQSLLNSRTRKNYLA (373) | WASTRES (374) | KQSYNLLT (375) |
| H | C6H | TFTDYSMH (766) | RINTETGEPTFADDFRG (767) | FYYGRDS (768) |
| L | C6K | KSSQSLLNSRTRKNYLA (382) | WASTRES (383) | KQSYNLLT (384) |
| H | D4H | TFTDYSMH (379) | RINTETGEPTFADDFRG (380) | YYYGRDS (381) |
| L | D4K | KSSQSLLNSRTRKNYLA (361) | WASTRES (362) | KQSYNLLS (363) |
| H | C6H | TFTDYSMH (766) | RINTETGEPTFADDFRG (767) | FYYGRDS (768) |
| L | D4K | KSSQSLLNSRTRKNYLA (361) | WASTRES (362) | KQSYNLLS (363) |

In some embodiments, an antibody described herein comprises heavy and light chain CDRs as paired in the following table:

| Combinations (H + L) | Clone name | CDR1 (SEQ ID:) | CDR2 (SEQ ID:) | CDR3 (SEQ ID:) |
|---|---|---|---|---|
| H | HuC6D4V1 | DYSMH (397) | RINTETGEPTFADDFRG (398) | FYYGRDS (399) |
| L | HuC6D4V1 | KSSQSLLNSRTRKNYLA (529) | WASTRES (530) | KQSYNLLS (531) |
| H | HuC6D4A3 | DYSMH (405) | RINTETGEPTFADDFRG (407) | FYYGRDS (409) |
| L | HuC6D4A3 | KSSQSLLNSRSRKNYLA (532) | WASTRES (533) | KQSYNLLS (534) |
| H | HuC6D4B7 | DYSMH (413) | RINTETGEPTFADDFRG (415) | FYYGRDT (417) |
| L | HuC6D4B7 | KSSQSLLNSRTRKNYLA (535) | WASTRES (536) | KQSSNLIS (537) |
| H | HuC6D4E5 | DYSMH (421) | RINTETGEPTFADDFRG (423) | FYYGRDT (425) |
| L | HuC6D4E5 | KSSQSLLNSRSRKNYLA (538) | WASTRES (539) | KQSYNLLS (540) |

-continued

| Combinations (H + L) | Clone name | CDR1 (SEQ ID:) | CDR2 (SEQ ID:) | CDR3 (SEQ ID |
|---|---|---|---|---|
| H | HuC6D4 | DYSMH (429) | RINTETGEPTFADDFRG (431) | FYYGRDT (433) |
| L | HuC6D4 | KSSQSLLNSRSRKNYLA (541) | WASTRES (542) | KQSYNLLS (543) |
| H | C6D4-RGD3 | DYSMH (437) | RINTETGEPTFADDFRG (439) | FYYGRDS (441) |
| L | C6D4-RGD3 | KSSQSLLGRGDLGRLKKNALA (544) | WASTRES (545) | KQSYNLLS (546) |
| H | HuC6D4-RGD3 | DYSMH (445) | RINTETGEPTFADDFRG (447) | FYYGRDT (449) |
| L | HuC6D4-RGD3 | KSSQSLLGRGDLGRLKKNALA (547) | WASTRES (548) | KQSYNLLS (549) |
| H | C6D4 | DYSMH (123) | RINTETGEPTFADDFRG (125) | FYYGRDS (127) |
| L | C6D4 | KSSQSLLNSRSRKNYLA (291) | WASTRES (293) | KQSYNLLS (295) |
| H | C6RGD2 | DYSMH (769) | RINTETGEPTFADDFRG (770) | FYYGRDS (771) |
| L | C6RGD2 | KSSQSLLNSGRGDLGNALA (772) | WASTRES (773) | KQSYNLIS (774) |
| H | C6RGD3-1 | DYSMH (775) | RINTETGEPTFADDFRG (776) | FYYGRDT (777) |
| L | C6RGD3-1 | KSSQSLLGRGDLGRLKKQKDHNALA (778) | WASTRES (779) | KQSSNLIS (780) |
| H | C6RGD3-2 | DYSMH (781) | RINTETGEPTFADDFRG (782) | FYYGRDY (783) |
| L | C6RGD3-2 | KSSQSLLGRGDLGRLKKQKDNALA (784) | WASTRES (785) | KQSYNLLS (786) |
| H | C6RGD3-3 | DYSMH (787) | RINTETGEPTFADDFRG (788) | FYYGRDT (789) |
| L | C6RGD3-3 | KSSQSLLGRGDLGRLKKQKNALA (790) | WASTRES (791) | KQSYNLLS (792) |
| H | C6RGD3-4 | DYSMH (793) | RINTETGEPTFADDFRG (794) | FYYGRDS (795) |
| L | C6RGD3-4 | KSSQSLLGRGDLGRLKKQNALA (796) | WASTRES (797) | KQSYNLLS (798) |
| H | C6RGD3 | DYSMH (799) | RINTETGEPTFADDFRG (800) | FYYGRDT (801) |
| L | C6RGD3 | KSSQSLLGRGDLGRLKKNALA (802) | WASTRES (803) | KQSYNLLS (804) |
| H | C6RGD3-6 | DYSMH (805) | RINTETGEPTFADDFRG (806) | FYYGRDS (807 |
| L | C6RGD3-6 | KSSQSLLGRGDLGRLKNALA (808) | WASTRES (809) | KQSYNLLS (810) |
| H | C6RDG3-7 | DYSMH (811) | RINTETGEPTFADDFRG (812) | FYYGRDS (813) |
| L | C6RGD3-7 | KSSQSLLGRGDLGRLNALA (814) | WASTRES (815) | KQSYNLLS (816) |
| H | C6RGD3-8 | DYSMH (817) | RINTETGEPTFADDFRG (818) | FYYGRDT (819) |

-continued

| Combinations (H + L) | Clone name | CDR1 (SEQ ID:) | CDR2 (SEQ ID:) | CDR3 (SEQ ID) |
|---|---|---|---|---|
| L | C6RGD3-8 | KSSQSLLGRGDLGRNALA (820) | WASTRES (821) | KQSSNLIS (822) |
| H | C6RGD1 | DYSMH (823) | RINTETGEPTFADDFRG (824) | FYYGRDY (825) |
| L | C6RGD1 | KSSQSLLGRGDLGNALA (826) | WASTRES (827) | KQSYNLLS (828) |
| H | C6RGD3-9 | DYSMH (829) | RINTETGEPTFADDFRG (830) | FYYGRDT (831) |
| L | C6RGD3-9 | KSSQSLLGRGDLGRLKKQKDHH (832) | WASTRES (833) | KQSYNLLS (834) |
| H | C6RGD3-10 | DYSMH (835) | RINTETGEPTFADDFRG (836) | FYYGRDS (837) |
| L | C6RGD3-10 | KSSQSLLGRGDLGRLKKQKDH (838) | WASTRES (839) | KQSYNLLS (840) |
| H | C6RGD3-11 | DYSMH (841) | RINTETGEPTFADDFRG (842) | FYYGRDT (843) |
| L | C6RGD3-11 | KSSQSLLGRGDLGRLKKQKD (844) | WASTRES (845) | KQSYNLLS (846) |
| H | C6RGD3-12 | DYSMH (847) | RINTETGEPTFADDFRG (848) | FYYGRDT (849) |
| L | C6RGD3-12 | KSSQSLLGRGDLGRLKKQK (850) | WASTRES (851) | KQSSNLIS (852) |
| H | C6RGD3-13 | DYSMH (853) | RINTETGEPTFADDFRG (854) | FYYGRDY (855) |
| L | C6RGD3-13 | KSSQSLLGRGDLGRLKKQ (856) | WASTRES (857) | KQSYNLLS (858) |
| H | C6RGD3-14 | DYSMH (859) | RINTETGEPTFADDFRG (860) | FYYGRDT (861) |
| L | C6RGD3-14 | KSSQSLLGRGDLGRLKK (862) | WASTRES (863) | KQSYNLLS (864) |
| H | C6RGD3-15 | DYSMH (865) | RINTETGEPTFADDFRG (866) | FYYGRDS (867) |
| L | C6RGD3-15 | KSSQSLLGRGDLGRLK (868) | WASTRES (869) | KQSYNLLS (870) |
| H | C6RGD3-16 | DYSMH (871) | RINTETGEPTFADDFRG (872) | FYYGRDT (873) |
| L | C6RGD3-16 | KSSQSLLGRGDLGRL (874) | WASTRES (875) | KQSYNLLS (876) |

In some embodiments, an antibody as described herein comprises one, two, three or all four of the framework sequences as provided here:

| Frameworks | Fr1 (SEQ ID NO:) | Fr2 (SEQ ID NO:) |
|---|---|---|
| H | (Q)IQL(L)(Q)SGPELKKPGETVKISCKASGY (385)<br> E    M E | WVKQAPGKGLKW(V)A (386)<br>                      M |
| | Where (X) can be specified AA | |
| L | (D)IVM(T)QSPSSLAV(S)AGE(K)VT(M)SC (389)<br> E      S          P     N   V | WYQQKPGQSP(R)LLIY (390)<br>                  K |
| | Where (X) can be specified AA all alternatives listed under | |

| Frameworks | Fr3 (SEQ ID NO:) | Fr4 (SEQ ID NO:) |
|---|---|---|
| H | RFA(V)SLETSASTAYLQINNLKNEDTATYFCAI (387)<br>   F | WGQGTT(L)TVSS (388)<br>       V |
| L | GVPDRFTGSGSGTDFTLTISSVQAEDLAVY(Y)C (391)<br>                              F | FGAGT(K)LE(L)K (392)<br>       R     I |

In some embodiments, an antibody as described herein comprises one, two, three or all four of the framework sequences as provided here:

| Frameworks | Fr1 (SEQ ID NO:) | Fr2 (SEQ ID NO:) |
|---|---|---|
| H | QIQLVQSG(P)(E)(L)KKPG(E)(T)VKISCKASGYTFT (550)<br>         A  K  V      A  S | WV(K)QAPG(K)GL(K)WVA (551)<br>    R        Q      E |
| | Where (X) can be specified AA | |
| L | (D)IVMTQ(S)P(S)(S)L(A)VS(A)GE(K)VTMSC (554)<br> E       T   A T  S    P     R<br>                V             I | WYQQKPGQSPRLLIY (555)<br>             A |

| Frameworks | | |
|---|---|---|
| | Fr3 (SEQ ID NO:) | |
| H | RF(A)V(S)L(E)TS(A)STAYL(Q)I(N)(N)L(K)(N)(E)DTA(T)YFCAI (552)<br>    T   T   D    T          E   R  S  R S D   V<br>    S                           T | |
| | Where (X) can be specified AA all alternatives listed under | |
| L | (G)VP(D)RF(T)GSGSGT(D)FTLTISSVQ(A)ED(L)AVYYC (556)<br> D      A     S           E          S    F | |
| | Fr4 (SEQ ID NO:) | |
| H | WGQGT(T)LTVSS (553)<br>       A | |
| L | FG(A)GT(K)LE(L)KR (557)<br>   Q    V    I | |

In some embodiments, an antibody as described herein comprises one, two, three or all four of the framework sequences as provided here:

| Frameworks | Fr1 (SEQ ID NO:) | Fr2 (SEQ ID NO:) |
|---|---|---|
| H | QIQL(V)QSG(P)(E)(L)KKPG(E)(T)VKISCKASGYTFT (550)<br>     L      A K V     A S | WV(K)QAPG(K)GL(K)W(V)(A)  (877)<br>   R     Q    E  M G |
|  | Where (X) can be specified AA |  |
| L | (D)IVM(T)Q(S)P(S)(S)L(A)VS(A)GE(K)VTMSC (880)<br> E     S    T    A T  S     P     R<br>                      V               I | WYQQKPGQ(S)PRLLIY (881)<br>           A |

| Frameworks |  |
|---|---|
|  | Fr3 (SEQ ID NO:) |
| H | RF(A)(V)(S)L(E)TS(A)(S)TA(Y)L(Q)I(N)(N)L(K)(N)(E)DTA(T)YFCAI (878)<br>   T  F  T    D    T T     N   E     R     S   R  S   D      V<br>   S                                      I                                K<br>                                 T |
|  | Where (X) can be specified AA all alternatives listed under |
| L | (G)VP(D)RF(T)GSGSGT(D)FTLTISSVQ(A)ED(L)AVYYC (882)<br>     D     A    S        E                 S      F<br>                                                   D |
|  | Fr4 (SEQ ID NO:) |
| H | WGQGT(T)LTVSS (879)<br>      A |
| L | FG(A)GT(K)LE(I)KR (883)<br>   Q     V    L |

In some embodiments, the antibodies comprise the CDR1, CDR2, and CDR3 heavy chain sequences as provided herein, including but not limited to, e.g.,
SEQ ID NO:3, SEQ ID NO:5, and SEQ ID NO:7;
SEQ ID NO:11, SEQ ID NO:13, and SEQ ID NO:15;
SEQ ID NO:19, SEQ ID NO:21, and SEQ ID NO:23;
SEQ ID NO:27, SEQ ID NO:29, and SEQ ID NO:31;
SEQ ID NO:35, SEQ ID NO:37, and SEQ ID NO:39;
SEQ ID NO:43, SEQ ID NO:45, and SEQ ID NO:47;
SEQ ID NO:51, SEQ ID NO:53, and SEQ ID NO:55;
SEQ ID NO:59, SEQ ID NO:61, and SEQ ID NO:63;
SEQ ID NO:67, SEQ ID NO:69, and SEQ ID NO:71;
SEQ ID NO:75, SEQ ID NO:77, and SEQ ID NO:79;
SEQ ID NO:83, SEQ ID NO:85, and SEQ ID NO:87;
SEQ ID NO:91, SEQ ID NO:93, and SEQ ID NO:95;
SEQ ID NO:99, SEQ ID NO:101, and SEQ ID NO:103;
SEQ ID NO: 107, SEQ ID NO: 109, and SEQ ID NO:111;
SEQ ID NO:115, SEQ ID NO: 117, and SEQ ID NO:119;
SEQ ID NO:123, SEQ ID NO:125, and SEQ ID NO:127;
SEQ ID NO:291, SEQ ID NO:293, and SEQ ID NO:295;
SEQ ID NO:313, SEQ ID NO:314, and SEQ ID NO:315;
SEQ ID NO:316, SEQ ID NO:317, and SEQ ID NO:318;
SEQ ID NO:319, SEQ ID NO:320, and SEQ ID NO:321;
SEQ ID NO:322, SEQ ID NO:323, and SEQ ID NO:324;
SEQ ID NO:325, SEQ ID NO:326, and SEQ ID NO:327;
SEQ ID NO:328, SEQ ID NO:329, and SEQ ID NO:330;
SEQ ID NO:331, SEQ ID NO:332, and SEQ ID NO:333;
SEQ ID NO:367, SEQ ID NO:368, and SEQ ID NO:369;
SEQ ID NO:364, SEQ ID NO:365, and SEQ ID NO:366;
SEQ ID NO:370, SEQ ID NO:371, and SEQ ID NO:372;
SEQ ID NO:379, SEQ ID NO:380, and SEQ ID NO:381;
SEQ ID NO:397, SEQ ID NO:399, and SEQ ID NO:401;
SEQ ID NO:405, SEQ ID NO:407, and SEQ ID NO:409;
SEQ ID NO:413, SEQ ID NO:415, and SEQ ID NO:417;
SEQ ID NO:421, SEQ ID NO:423, and SEQ ID NO:425; or
SEQ ID NO:429, SEQ ID NO:431, and SEQ ID NO:433.

In some embodiments, the antibodies comprise the heavy chain CDR1, CDR2, and CDR3 sequences described above but contain 1, 2, or 3 conservative amino acid substitutions in one, two or more CDR sequences compared to those listed above.

In some embodiments, the antibodies comprise the light chain CDR1, CDR2, and CDR3 sequences as provided herein, including but not limited to, e.g.,
SEQ ID NO:131, SEQ ID NO:133, and SEQ ID NO:135;
SEQ ID NO:139, SEQ ID NO:141, and SEQ ID NO:143;
SEQ ID NO:147, SEQ ID NO:149, and SEQ ID NO:151;
SEQ ID NO:155, SEQ ID NO:157, and SEQ ID NO:159;
SEQ ID NO:163, SEQ ID NO: 165, and SEQ ID NO:167;
SEQ ID NO:171, SEQ ID NO:173, and SEQ ID NO:175;
SEQ ID NO:179, SEQ ID NO:181, and SEQ ID NO:183;
SEQ ID NO: 187, SEQ ID NO: 189, and SEQ ID NO: 191;
SEQ ID NO:195, SEQ ID NO:197, and SEQ ID NO:199;
SEQ ID NO:203, SEQ ID NO:205, and SEQ ID NO:207;
SEQ ID NO:211, SEQ ID NO:213, and SEQ ID NO:215;
SEQ ID NO:219, SEQ ID NO:221, and SEQ ID NO:223;
SEQ ID NO:227, SEQ ID NO:229, and SEQ ID NO:231;
SEQ ID NO:243, SEQ ID NO:245, and SEQ ID NO:247;
SEQ ID NO:251, SEQ ID NO:253, and SEQ ID NO:255;
SEQ ID NO:259, SEQ ID NO:261, and SEQ ID NO:263;
SEQ ID NO:267, SEQ ID NO:269, and SEQ ID NO:271;
SEQ ID NO:275, SEQ ID NO:277, and SEQ ID NO:279;
SEQ ID NO:283, SEQ ID NO:285, and SEQ ID NO:287;
SEQ ID NO:291, SEQ ID NO:293, and SEQ ID NO:295;

SEQ ID NO:307, SEQ ID NO:309, and SEQ ID NO:311;
SEQ ID NO:334, SEQ ID NO:335, and SEQ ID NO:336;
SEQ ID NO:337, SEQ ID NO:338, and SEQ ID NO:339;
SEQ ID NO:340, SEQ ID NO:341, and SEQ ID NO:342;
SEQ ID NO:343, SEQ ID NO:344, and SEQ ID NO:345;
SEQ ID NO:346, SEQ ID NO:347, and SEQ ID NO:348;
SEQ ID NO:349, SEQ ID NO:350, and SEQ ID NO:351;
SEQ ID NO:352, SEQ ID NO:353, and SEQ ID NO:354;
SEQ ID NO:355, SEQ ID NO:356, and SEQ ID NO:357;
SEQ ID NO:358, SEQ ID NO:359, and SEQ ID NO:360;
SEQ ID NO:361, SEQ ID NO:362, and SEQ ID NO:363;
SEQ ID NO:373, SEQ ID NO:374, and SEQ ID NO:375;
SEQ ID NO:376, SEQ ID NO:377, and SEQ ID NO:378;
SEQ ID NO:382, SEQ ID NO:383, and SEQ ID NO:384;
SEQ ID NO:453, SEQ ID NO:455, and SEQ ID NO:457;
SEQ ID NO:461, SEQ ID NO:463, and SEQ ID NO:465;
SEQ ID NO:469, SEQ ID NO:471, and SEQ ID NO:473;
SEQ ID NO:478, SEQ ID NO:480, and SEQ ID NO:482; or
SEQ ID NO:486, SEQ ID NO:488, and SEQ ID NO:490.

In some embodiments, the antibodies comprise the light chain CDR1, CDR2, and CDR3 sequences described above but contain 1, 2, or 3 conservative amino acid substitutions in one, two or more CDR sequences compared to those listed above. In some embodiments, the light chain CDR1 sequence is 12-18 amino acids long, , e.g., 14-17, e.g., 12, 13, 14, 15, 16, 17, or 18 amino acids long.

In some embodiments, the antibodies comprise the heavy and light chain CDR1, CDR2, and CDR3 sequences as provided herein, including but not limited to, e.g., heavy chain CDRs SEQ ID NO:313, SEQ ID NO:314, and SEQ ID NO:315; and light chain CDRs SEQ ID NO:334, SEQ ID NO:335, and SEQ ID NO:336; or heavy chain CDRs SEQ ID NO:319, SEQ ID NO:320, and SEQ ID NO:321; and light chain CDRs SEQ ID NO:340, SEQ ID NO:341, and SEQ ID NO:342; or
heavy chain CDRs SEQ ID NO:316, SEQ ID NO:317, and SEQ ID NO:318; and light chain CDRs SEQ ID NO:337, SEQ ID NO:338, and SEQ ID NO:339; or
heavy chain CDRs SEQ ID NO:322, SEQ ID NO:323, and SEQ ID NO:324; and light chain CDRs SEQ ID NO:343, SEQ ID NO:344, and SEQ ID NO:345; or
heavy chain CDRs SEQ ID NO:322, SEQ ID NO:323, and SEQ ID NO:324; and light chain CDRs SEQ ID NO:346, SEQ ID NO:347, and SEQ ID NO:348; or
heavy chain CDRs SEQ ID NO:322, SEQ ID NO:323, and SEQ ID NO:324; and light chain CDRs SEQ ID NO:349, SEQ ID NO:350, and SEQ ID NO:351; or
heavy chain CDRs SEQ ID NO:325, SEQ ID NO:326, and SEQ ID NO:327; and light chain CDRs SEQ ID NO:352, SEQ ID NO:353, and SEQ ID NO:354; or
heavy chain CDRs SEQ ID NO:325, SEQ ID NO:326, and SEQ ID NO:327; and light chain CDRs SEQ ID NO:355, SEQ ID NO:356, and SEQ ID NO:357; or
heavy chain CDRs SEQ ID NO:325, SEQ ID NO:326, and SEQ ID NO:327; and light chain CDRs SEQ ID NO:358, SEQ ID NO:359, and SEQ ID NO:360; or
heavy chain CDRs SEQ ID NO:367, SEQ ID NO:368, and SEQ ID NO:369; and light chain CDRs SEQ ID NO:373, SEQ ID NO:374, and SEQ ID NO:375; or
heavy chain CDRs SEQ ID NO:364, SEQ ID NO:365, and SEQ ID NO:366; and light chain CDRs SEQ ID NO:373, SEQ ID NO:374, and SEQ ID NO:375; or
heavy chain CDRs SEQ ID NO:367, SEQ ID NO:368, and SEQ ID NO:369; and light chain CDRs SEQ ID NO:376, SEQ ID NO:377, and SEQ ID NO:378; or
heavy chain CDRs SEQ ID NO:370, SEQ ID NO:371, and SEQ ID NO:372; and light chain CDRs SEQ ID NO:373, SEQ ID NO:374, and SEQ ID NO:375; or
heavy chain CDRs SEQ ID NO:331, SEQ ID NO:332, and SEQ ID NO:333; and light chain CDRs SEQ ID NO:382, SEQ ID NO:383, and SEQ ID NO:384; or
heavy chain CDRs SEQ ID NO:379, SEQ ID NO:380, and SEQ ID NO:381; and light chain CDRs SEQ ID NO:361, SEQ ID NO:362, and SEQ ID NO:363; or
heavy chain CDRs SEQ ID NO:331, SEQ ID NO:332, and SEQ ID NO:333; and light chain CDRs SEQ ID NO:361, SEQ ID NO:362, and SEQ ID NO:363; or
heavy chain CDRs SEQ ID NO:508, SEQ ID NO:509, and SEQ ID NO:510; and light chain CDRs SEQ ID NO:529, SEQ ID NO:530, and SEQ ID NO:531; or
heavy chain CDRs SEQ ID NO:511, SEQ ID NO:512, and SEQ ID NO:513; and light chain CDRs SEQ ID NO:532, SEQ ID NO:533, and SEQ ID NO:534; or
heavy chain CDRs SEQ ID NO:514, SEQ ID NO:515, and SEQ ID NO:516; and light chain CDRs SEQ ID NO:535, SEQ ID NO:536, and SEQ ID NO:537; or
heavy chain CDRs SEQ ID NO:517, SEQ ID NO:518, and SEQ ID NO:519; and light chain CDRs SEQ ID NO:538, SEQ ID NO:539, and SEQ ID NO:540; or
heavy chain CDRs SEQ ID NO:520, SEQ ID NO:521, and SEQ ID NO:522; and light chain CDRs SEQ ID NO:541, SEQ ID NO:542, and SEQ ID NO:543; or
heavy chain CDRs SEQ ID NO:523, SEQ ID NO:524, and SEQ ID NO:525; and light chain CDRs SEQ ID NO:544, SEQ ID NO:545, and SEQ ID NO:546; or
heavy chain CDRs SEQ ID NO:526, SEQ ID NO:527, and SEQ ID NO:528; and light chain CDRs SEQ ID NO:547, SEQ ID NO:548, and SEQ ID NO:549.

In some embodiments, the antibodies comprise the heavy and light chain CDR1, CDR2, and CDR3 sequences described above but contain 1, 2, or 3 conservative amino acid substitutions in one, two or more CDR sequences compared to those listed above.

In some embodiments, any antibody described herein can comprise a light chain CDR1 comprising a RGD sequence, e.g., as provided in the following table:

| $CDR_{L1}$ | Vk |
|---|---|
| KSSQSLLNSRSRKNYLA (SEQ ID NO: 572) | D4 |
| KSSQSLLNSGRGDLGNALA (SEQ ID NO: 574) | RGD2 |
| KSSQSLLGRGDLGRLKKQKDHNALA (SEQ ID NO: 576) | RGD3-1 |
| KSSQSLLGRGDLGRLKKQKDNALA (SEQ ID NO: 577) | RGD3-2 |
| KSSQSLLGRGDLGRLKKQKNALA (SEQ ID NO: 578) | RGD3-3 |
| KSSQSLLGRGDLGRLKKQNALA (SEQ ID NO: 579) | RGD3-4 |
| KSSQSLLGRGDLGRLKKNALA (SEQ ID NO: 575) | RGD3 |
| KSSQSLLGRGDLGRLKNALA (SEQ ID NO: 580) | RGD3-6 |
| KSSQSLLGRGDLGRLNALA (SEQ ID NO: 581) | RGD3-7 |
| KSSQSLLGRGDLGRNALA (SEQ ID NO: 582) | RGD3-8 |
| KSSQSLLGRGDLGNALA (SEQ ID NO: 573) | RGD1 |
| KSSQSLLGRGDLGRLKKQKDHH (SEQ ID NO: 583) | RGD3-9 |
| KSSQSLLGRGDLGRLKKQKDH (SEQ ID NO: 584) | RGD3-10 |

| CDR$_{L1}$ | Vk |
|---|---|
| KSSQSLLGRGDLGRLKKQKD (SEQ ID NO: 585) | RGD3-11 |
| KSSQSLLGRGDLGRLKKQK (SEQ ID NO: 586) | RGD3-12 |
| KSSQSLLGRGDLGRLKKQ (SEQ ID NO: 587) | RGD3-13 |
| KSSQSLLGRGDLGRLKK (SEQ ID NO: 588) | RGD3-14 |
| KSSQSLLGRGDLGRLK (SEQ ID NO: 589) | RGD3-15 |
| KSSQSLLGRGDLGRL (SEQ ID NO: 590) | RGD3-16 |

In some embodiments, any of the antibodies described herein can comprise as CDR1 one of the CDRs selected from SEQ ID NO:572, SEQ ID NO:573, SEQ ID NO:574, SEQ ID NO:575, SEQ ID NO:576, SEQ ID NO:577, SEQ ID NO:578, SEQ ID NO:579, SEQ ID NO:580, SEQ ID NO:581, SEQ ID NO:582, SEQ ID NO:583, SEQ ID NO:584, SEQ ID NO:585, SEQ ID NO:586, SEQ ID NO:587, SEQ ID NO:588, SEQ ID NO:589, and SEQ ID NO:590.

In some embodiments, the antibody can comprise heavy and light chain CDR1, CDR2, and CDR3 sequences as provided below, including but not limited to, e.g., heavy chain CDRs SEQ ID NO:523, SEQ ID NO:524, and SEQ ID NO:525; and light chain CDRs SEQ ID NO:572, SEQ ID NO:545, and SEQ ID NO:546; or heavy chain CDRs SEQ ID NO:523, SEQ ID NO:524, and SEQ ID NO:525; and light chain CDRs SEQ ID NO:573, SEQ ID NO:545, and SEQ ID NO:546; or heavy chain CDRs SEQ ID NO:523, SEQ ID NO:524, and SEQ ID NO:525; and light chain CDRs SEQ ID NO:574, SEQ ID NO:545, and SEQ ID NO:546; or heavy chain CDRs SEQ ID NO:523, SEQ ID NO:524, and SEQ ID NO:525; and light chain CDRs SEQ ID NO:575, SEQ ID NO:545, and SEQ ID NO:546; or heavy chain CDRs SEQ ID NO:523, SEQ ID NO:524, and SEQ ID NO:525; and light chain CDRs SEQ ID NO:576, SEQ ID NO:545, and SEQ ID NO:546; or heavy chain CDRs SEQ ID NO:523, SEQ ID NO:524, and SEQ ID NO:525; and light chain CDRs SEQ ID NO:577, SEQ ID NO:545, and SEQ ID NO:546; or heavy chain CDRs SEQ ID NO:523, SEQ ID NO:524, and SEQ ID NO:525; and light chain CDRs SEQ ID NO:578, SEQ ID NO:545, and SEQ ID NO:546; or heavy chain CDRs SEQ ID NO:523, SEQ ID NO:524, and SEQ ID NO:525; and light chain CDRs SEQ ID NO:579, SEQ ID NO:545, and SEQ ID NO:546; or heavy chain CDRs SEQ ID NO:523, SEQ ID NO:524, and SEQ ID NO:525; and light chain CDRs SEQ ID NO:580, SEQ ID NO:545, and SEQ ID NO:546; or heavy chain CDRs SEQ ID NO:523, SEQ ID NO:524, and SEQ ID NO:525; and light chain CDRs SEQ ID NO:581, SEQ ID NO:545, and SEQ ID NO:546; or heavy chain CDRs SEQ ID NO:523, SEQ ID NO:524, and SEQ ID NO:525; and light chain CDRs SEQ ID NO:582, SEQ ID NO:545, and SEQ ID NO:546; or heavy chain CDRs SEQ ID NO:523, SEQ ID NO:524, and SEQ ID NO:525; and light chain CDRs SEQ ID NO:583, SEQ ID NO:545, and SEQ ID NO:546; or heavy chain CDRs SEQ ID NO:523, SEQ ID NO:524, and SEQ ID NO:525; and light chain CDRs SEQ ID NO:584, SEQ ID NO:545, and SEQ ID NO:546; or heavy chain CDRs SEQ ID NO:523, SEQ ID NO:524, and SEQ ID NO:525; and light chain CDRs SEQ ID NO:585, SEQ ID NO:545, and SEQ ID NO:546; or heavy chain CDRs SEQ ID NO:523, SEQ ID NO:524, and SEQ ID NO:525; and light chain CDRs SEQ ID NO:586, SEQ ID NO:545, and SEQ ID NO:546; or heavy chain CDRs SEQ ID NO:523, SEQ ID NO:524, and SEQ ID NO:525; and light chain CDRs SEQ ID NO:587, SEQ ID NO:545, and SEQ ID NO:546; or heavy chain CDRs SEQ ID NO:523, SEQ ID NO:524, and SEQ ID NO:525; and light chain CDRs SEQ ID NO:589, SEQ ID NO:545, and SEQ ID NO:546; or heavy chain CDRs SEQ ID NO:523, SEQ ID NO:524, and SEQ ID NO:525; and light chain CDRs SEQ ID NO:590, SEQ ID NO:545, and SEQ ID NO:546; or heavy chain CDRs SEQ ID NO:523, SEQ ID NO:524, and SEQ ID NO:525; and light chain CDRs SEQ ID NO:572, SEQ ID NO:545, and SEQ ID NO:534; or heavy chain CDRs SEQ ID NO:523, SEQ ID NO:524, and SEQ ID NO:525; and light chain CDRs SEQ ID NO:573, SEQ ID NO:545, and SEQ ID NO:534; or heavy chain CDRs SEQ ID NO:523, SEQ ID NO:524, and SEQ ID NO:525; and light chain CDRs SEQ ID NO:574, SEQ ID NO:545, and SEQ ID NO:534; or heavy chain CDRs SEQ ID NO:523, SEQ ID NO:524, and SEQ ID NO:525; and light chain CDRs SEQ ID NO:575, SEQ ID NO:545, and SEQ ID NO:534; or heavy chain CDRs SEQ ID NO:523, SEQ ID NO:524, and SEQ ID NO:525; and light chain CDRs SEQ ID NO:576, SEQ ID NO:545, and SEQ ID NO:534; or heavy chain CDRs SEQ ID NO:523, SEQ ID NO:524, and SEQ ID NO:525; and light chain CDRs SEQ ID NO:577, SEQ ID NO:545, and SEQ ID NO:534; or heavy chain CDRs SEQ ID NO:523, SEQ ID NO:524, and SEQ ID NO:525; and light chain CDRs SEQ ID NO:578, SEQ ID NO:545, and SEQ ID NO:534; or heavy chain CDRs SEQ ID NO:523, SEQ ID NO:524, and SEQ ID NO:525; and light chain CDRs SEQ ID NO:579, SEQ ID NO:545, and SEQ ID NO:534; or heavy chain CDRs SEQ ID NO:523, SEQ ID NO:524, and SEQ ID NO:525; and light chain CDRs SEQ ID NO:580, SEQ ID NO:545, and SEQ ID NO:534; or heavy chain CDRs SEQ ID NO:523, SEQ ID NO:524, and SEQ ID NO:525; and light chain CDRs SEQ ID NO:581, SEQ ID NO:545, and SEQ ID NO:534; or heavy chain CDRs SEQ ID NO:523, SEQ ID NO:524, and SEQ ID NO:525; and light chain CDRs SEQ ID NO:582, SEQ ID NO:545, and SEQ ID NO:534; or heavy chain CDRs SEQ ID NO:523, SEQ ID NO:524, and SEQ ID NO:525; and light chain CDRs SEQ ID NO:583, SEQ ID NO:545, and SEQ ID NO:534; or heavy chain CDRs SEQ ID NO:523, SEQ ID NO:524, and SEQ ID NO:525; and light chain CDRs SEQ ID NO:584, SEQ ID NO:545, and SEQ ID NO:534; or heavy chain CDRs SEQ ID NO:523, SEQ ID NO:524, and SEQ ID NO:525; and light chain CDRs SEQ ID NO:585, SEQ ID NO:545, and SEQ ID NO:534; or heavy chain CDRs SEQ ID NO:523, SEQ ID NO:524, and SEQ ID NO:525; and light chain CDRs SEQ ID NO:586, SEQ ID NO:545, and SEQ ID NO:534; or heavy chain CDRs SEQ ID NO:523, SEQ ID NO:524, and SEQ ID NO:525; and light chain CDRs SEQ ID NO:587, SEQ ID NO:545, and SEQ ID NO:534; or heavy chain CDRs SEQ ID NO:523, SEQ ID NO:524, and SEQ ID NO:525; and light chain CDRs SEQ ID NO:588, SEQ ID NO:545, and SEQ ID NO:534; or heavy chain CDRs SEQ ID NO:523, SEQ ID NO:524, and SEQ ID NO:525; and light chain CDRs SEQ ID NO:589, SEQ ID NO:545, and SEQ ID NO:534; or
heavy chain CDRs SEQ ID NO:523, SEQ ID NO:524, and SEQ ID NO:525; and light chain CDRs SEQ ID NO:590, SEQ ID NO:545, and SEQ ID NO:534; or
heavy chain CDRs SEQ ID NO:523, SEQ ID NO:524, and SEQ ID NO:525; and light chain CDRs SEQ ID NO:572, SEQ ID NO:545, and SEQ ID NO:537; or
heavy chain CDRs SEQ ID NO:523, SEQ ID NO:524, and SEQ ID NO:525; and light chain CDRs SEQ ID NO:573, SEQ ID NO:545, and SEQ ID NO:537; or
heavy chain CDRs SEQ ID NO:523, SEQ ID NO:524, and SEQ ID NO:525; and light chain CDRs SEQ ID NO:574, SEQ ID NO:545, and SEQ ID NO:537; or
heavy chain CDRs SEQ ID NO:523, SEQ ID NO:524, and SEQ ID NO:525; and light chain CDRs SEQ ID NO:575, SEQ ID NO:545, and SEQ ID NO:537; or
heavy chain CDRs SEQ ID NO:523, SEQ ID NO:524, and SEQ ID NO:525; and light chain CDRs SEQ ID NO:576, SEQ ID NO:545, and SEQ ID NO:537; or
heavy chain CDRs SEQ ID NO:523, SEQ ID NO:524, and SEQ ID NO:525; and light chain CDRs SEQ ID NO:577, SEQ ID NO:545, and SEQ ID NO:537; or
heavy chain CDRs SEQ ID NO:523, SEQ ID NO:524, and SEQ ID NO:525; and light chain CDRs SEQ ID NO:578, SEQ ID NO:545, and SEQ ID NO:537; or
heavy chain CDRs SEQ ID NO:523, SEQ ID NO:524, and SEQ ID NO:525; and light chain CDRs SEQ ID NO:579, SEQ ID NO:545, and SEQ ID NO:537; or
heavy chain CDRs SEQ ID NO:523, SEQ ID NO:524, and SEQ ID NO:525; and light chain CDRs SEQ ID NO:580, SEQ ID NO:545, and SEQ ID NO:537; or
heavy chain CDRs SEQ ID NO:523, SEQ ID NO:524, and SEQ ID NO:525; and light chain CDRs SEQ ID NO:581, SEQ ID NO:545, and SEQ ID NO:537; or
heavy chain CDRs SEQ ID NO:523, SEQ ID NO:524, and SEQ ID NO:525; and light chain CDRs SEQ ID NO:582, SEQ ID NO:545, and SEQ ID NO:537; or
heavy chain CDRs SEQ ID NO:523, SEQ ID NO:524, and SEQ ID NO:525; and light chain CDRs SEQ ID NO:583, SEQ ID NO:545, and SEQ ID NO:537; or
heavy chain CDRs SEQ ID NO:523, SEQ ID NO:524, and SEQ ID NO:525; and light chain CDRs SEQ ID NO:584, SEQ ID NO:545, and SEQ ID NO:537; or
heavy chain CDRs SEQ ID NO:523, SEQ ID NO:524, and SEQ ID NO:525; and light chain CDRs SEQ ID NO:585, SEQ ID NO:545, and SEQ ID NO:537; or
heavy chain CDRs SEQ ID NO:523, SEQ ID NO:524, and SEQ ID NO:525; and light chain CDRs SEQ ID NO:586, SEQ ID NO:545, and SEQ ID NO:537; or
heavy chain CDRs SEQ ID NO:523, SEQ ID NO:524, and SEQ ID NO:525; and light chain CDRs SEQ ID NO:587, SEQ ID NO:545, and SEQ ID NO:537; or
heavy chain CDRs SEQ ID NO:523, SEQ ID NO:524, and SEQ ID NO:525; and light chain CDRs SEQ ID NO:588, SEQ ID NO:545, and SEQ ID NO:537; or
heavy chain CDRs SEQ ID NO:523, SEQ ID NO:524, and SEQ ID NO:525; and light chain CDRs SEQ ID NO:589, SEQ ID NO:545, and SEQ ID NO:537; or
heavy chain CDRs SEQ ID NO:523, SEQ ID NO:524, and SEQ ID NO:525; and light chain CDRs SEQ ID NO:590, SEQ ID NO:545, and SEQ ID NO:537.

In some embodiments, the antibodies comprise the heavy and light chain CDR1, CDR2, and CDR3 sequences described above but contain 1, 2, or 3 conservative amino acid substitutions in one, two or more CDR sequences compared to those listed above.

In some embodiments, any of the antibodies disclosed herein can comprise one of the heavy chain variable regions selected from SEQ ID NO:1, SEQ ID NO:9, SEQ ID NO:17, SEQ ID NO:25, SEQ ID NO:33, SEQ ID NO:41, SEQ ID NO:49, SEQ ID NO:57, SEQ ID NO:65, SEQ ID NO: 73, SEQ ID NO:81, SEQ ID NO:89, SEQ ID NO:97, SEQ ID NO: 105, SEQ ID NO:113, SEQ ID NO: 121, or SEQ ID NO:297, or SEQ ID NO:395, SEQ ID NO:403, SEQ ID NO:411, SEQ ID NO:419, SEQ ID NO:427, SEQ ID NO:435, or SEQ ID NO:443.

In some embodiments, any of the antibodies disclosed herein can comprise one of the light chain variable regions selected from SEQ ID NO:129, SEQ ID NO:137, SEQ ID NO:145, SEQ ID NO: 153, SEQ ID NO:161, SEQ ID NO: 169, SEQ ID NO:177, SEQ ID NO:185, SEQ ID NO:193, SEQ ID NO:201, SEQ ID NO:209, SEQ ID NO:217, SEQ ID NO:225, SEQ ID NO:233, SEQ ID NO:241, SEQ ID NO:249, SEQ ID NO:257, SEQ ID NO:265, SEQ ID NO:273, SEQ ID NO:281, SEQ ID NO:289, SEQ ID NO:305, or SEQ ID NO:451, SEQ ID NO:459, SEQ ID NO:467, SEQ ID NO:475, SEQ ID NO:484, SEQ ID NO:492, or SEQ ID NO:500.

In some embodiments, the antibodies disclosed here can comprise one or more or all of the light chain variable regions (CDRs or framework regions) selected from SEQ ID NO:565, SEQ ID NO:566, SEQ ID NO:567, SEQ ID NO:568, SEQ ID NO:569, SEQ ID NO:570, or SEQ ID NO:571.

In some embodiments, any of the antibodies disclosed herein can comprise one or more or all of the heavy chain variable regions (CDRs or framework regions) selected from SEQ ID NO:558, SEQ ID NO:559, SEQ ID NO:560, SEQ ID NO:561, SEQ ID NO:562, SEQ ID NO:563, or SEQ ID NO:564.

Heavy chain variable regions can be paired with light chain regions as desired, including or not limited to for variable regions comprising the paired CDRs as set forth above.

In addition, as noted above, the inventors have discovered that an RGDL sequence (SEQ ID NO:756) can be inserted into a light chain CDR1 sequence in an αvβ8-binding antibody to obtain an antibody that has six CDRs in total and that binds both αvβ8 and αvβ6. The antibodies at least partially block ligand binding function. Sec, e.g., FIGS. 38A-D. Thus in some embodiments, antibodies are provided that bind to αvβ8 and αvβ6 and comprise an RGDL sequence (SEQ ID NO:756) in the light chain CDR1 sequence. For instance, in some embodiments the light chain CDR1 is between 20-22 amino acids (e.g., 21 amino acids) an optionally comprises KSSQSLLGRGDLGRLKK (SEQ ID NO:765) or a sequence containing 1, 2, or 3 conservative amino acid substitutions.

Additionally, the inventors have discovered that an RGDL sequence (SEQ ID NO:756) can be inserted into a light chain CDR1 sequence in an αvβ8-binding antibody to obtain an antibody that has six CDRs and that binds αvβ8, αvβ6 and αvβ3 (i.e., is tri-specific). See, Example 12.

In some embodiments, any antibody described herein can comprise a light chain CDR1 sequence selected from, but not limited to, SEQ ID NO:572, SEQ ID NO:573, SEQ ID NO:574, SEQ ID NO:575, SEQ ID NO:576, SEQ ID NO:577, SEQ ID NO:578, SEQ ID NO: 579, SEQ ID NO:580, SEQ ID NO:581, SEQ ID NO:582, SEQ ID NO:583, SEQ ID NO:584, SEQ ID NO:585, SEQ ID NO:586, SEQ ID NO:587, SEQ ID NO:588, SEQ ID NO:589, and SEQ ID NO:590. In some embodiments, any of the light chain CDR1 sequences set forth in this paragraph can be combined with any light chain CDR2, light chain CDR3, heavy chain CDR1, heavy chain CDR2 and heavy chain CDR3, set forth herein.

In some embodiments, antibodies comprising the light chain CDR1 sequences described in the preceding paragraph can contain 1, 2, or 3 conservative amino acid substitutions in the CDR1 sequence compared to those listed above (i.e., SEQ ID NO:572-590).

In some embodiments, the antibodies can comprise the heavy chain CDR1, CDR2, and CDR3 sequences as provided herein, including but not limited to, e.g., SEQ ID NO:437, SEQ ID NO:439, and SEQ ID NO:441; or
SEQ ID NO:445, SEQ ID NO:447, and SEQ ID NO:449.

In some embodiments, the antibodies can comprise the heavy chain CDR1, CDR2, and CDR3 sequences described above but contain 1, 2, or 3 conservative amino acid substitutions in one, two or more CDR sequences compared to those listed above.

In some embodiments, the antibodies can comprise the light chain CDR1, CDR2, and CDR3 sequences as provided herein, including but not limited to, e.g., SEQ ID NO:494, SEQ ID NO:496, and SEQ ID NO:498; or
SEQ ID NO:502, SEQ ID NO:504, and SEQ ID NO:506.

In some embodiments, the antibodies can comprise the light chain CDR1, CDR2, and CDR3 sequences described above but contain 1, 2, or 3 conservative amino acid substitutions in one, two or more CDR sequences compared to those listed above.

Heavy chain variable regions can be paired with light chain regions as desired, including or not limited to for variable regions comprising the paired CDRs as set forth above.

For preparation and use of suitable antibodies as described herein, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody as described herein can also be produced in various formats, including as a Fab, a Fab', a F(ab')$_2$, a scFv, or a dAB. The antibody fragments can be obtained by a variety of methods, including, digestion of an intact antibody with an enzyme, such as pepsin (to generate (Fab')$_2$ fragments) or papain (to generate Fab fragments); or de novo synthesis. Antibody fragments can also be synthesized using recombinant DNA methodology. In some embodiments, an anti-β8 antibody comprises F(ab')2 fragments that specifically bind β8. An antibody of the invention can also include a human constant region. See, e.g., Fundamental Immunology (Paul ed., 4d ed. 1999); Bird, et al., *Science* 242:423 (1988); and Huston, et al., *Proc. Natl. Acad. Sci. USA* 85:5879 (1988).

Methods for humanizing or primatizing non-human antibodies are also known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20:

227,2007). The antibody or antibody fragment can also be labeled, or conjugated to a therapeutic agent as described below.

The specificity of antibody binding can be defined in terms of the comparative dissociation constants (Kd) of the antibody for the target (e.g., β8) as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target.

The desired affinity for an antibody, e.g., high (pM to low nM), medium (low nM to 100 nM), or low (about 100 nM or higher), may differ depending upon whether it is being used as a diagnostic or therapeutic. For example, an antibody with medium affinity may be more successful in localizing to desired tissue as compared to one with a high affinity. Thus, antibodies having different affinities can be used for diagnostic and therapeutic applications.

A targeting moiety will typically bind with a Kd of less than about 1000 nM, e.g., less than 250, 100, 50, 20 or lower nM. In some embodiments, the Kd of the affinity agent is less than 15, 10, 5, or 1 nM. In some embodiments, the Kd is 1-100 nM, 0.1-50 nM, 0.1-10 nM, or 1-20 nM. The value of the dissociation constant (Kd) can be determined by well-known methods, and can be computed even for complex mixtures by methods as disclosed, e.g., in Caceci et al., Byte (1984) 9:340-362.

Affinity of an antibody, or any targeting agent, for a target can be determined according to methods known in the art, e.g., as reviewed in Ernst et al. Determination of Equilibrium Dissociation Constants, Therapeutic Monoclonal Antibodies (Wiley & Sons ed. 2009).

Quantitative ELISA, and similar array-based affinity methods can be used. ELISA (Enzyme linked immunosorbent signaling assay) is an antibody-based method. In some cases, an antibody specific for target of interest is affixed to a substrate, and contacted with a sample suspected of containing the target. The surface is then washed to remove unbound substances. Target binding can be detected in a variety of ways, e.g., using a second step with a labeled antibody, direct labeling of the target, or labeling of the primary antibody with a label that is detectable upon antigen binding. In some cases, the antigen is affixed to the substrate (e.g., using a substrate with high affinity for proteins, or a Strepavidin-biotin interaction) and detected using a labeled antibody (or other targeting moiety). Several permutations of the original ELISA methods have been developed and are known in the art (see Lequin (2005) Clin. Chem. 51:2415-18 for a review).

The Kd, Kon, and Koff can also be determined using surface plasmon resonance (SPR), e.g., as measured by using a Biacore T100 system or using kinetic exclusion assays (e.g., KinExA®). SPR techniques are reviewed, e.g., in Hahnfeld et al. Determination of Kinetic Data Using SPR Biosensors, Molecular Diagnosis of Infectious Diseases (2004). In a typical SPR experiment, one interactant (target or targeting agent) is immobilized on an SPR-active, gold-coated glass slide in a flow cell, and a sample containing the other interactant is introduced to flow across the surface. When light of a given frequency is shined on the surface, the changes to the optical reflectivity of the gold indicate binding, and the kinetics of binding. Kinetic exclusion assays is the preferred method to determine affinity unless indicated otherwise. This technique is described in, e.g. Darling et al., *Assay and Drug Development Technologies* Vol. 2, number 6 647-657 (2004).

Binding affinity can also be determined by anchoring a biotinylated interactant to a streptavidin (SA) sensor chip. The other interactant is then contacted with the chip and detected, e.g., as described in Abdessamad et al. (2002) *Nuc. Acids Res.* 30: c45.

Also provided are polynucleotides encoding the antibodies described herein, or binding fragments thereof comprising at least heavy chain or light chain CDRs or both, e.g., polynucleotides, expression cassettes (e.g., a promoter linked to a coding sequence), or expression vectors encoding heavy or light chain variable regions or segments comprising the complementary determining regions as described herein. In some embodiments, the polynucleotide sequence is optimized for expression, e.g., optimized for mammalian expression or optimized for expression in a particular cell type.

III. Methods of Treatment

The anti-αvβ8 antibodies described herein (including αvβ8 binding fragments thereof, labeled antibodies, immunoconjugates, pharmaceutical compositions, etc.) as well as antibodies that bind both αvβ8 and αvβ6 as described herein or binding fragments thereof can be used to detect, treat, ameliorate, or prevent chronic obstructive pulmonary disease (COPD) and asthma, inflammatory bowel disease, inflammatory brain autoimmune disease, multiple sclerosis, a demylinating disease (e.g., transverse myelitis, Devic's disease, Guillain-Barré syndrome), neuroinflammation, kidney disease, or glioma, arthritis, fibrotic disorders, such as airway fibrosis, idiopathic pulmonary fibrosis, non-specific interstitial pneumonia, post-infectious lung fibrosis, diffuse alveolar damage, collagen-vascular disease associated lung fibrosis, drug-induced lung fibrosis, silicosis, asbestos-related lung fibrosis, respiratory bronchiolitis, respiratory bronchiolitis interstitial lung disease, desquamative interstitial fibrosis, cryptogenic organizing pneumonia, chronic hypersensitivity pneumonia, drug-related lung or hepatic fibrosis, renal fibrosis, and liver fibrosis (e.g., induced by alcohol, drug use, steatohepatitis, viral infection (e.g., hepatitis B or C), choleostasis, etc., and cancer, including but not limited to adenocarcinoma, squamous carcinoma, breast carcinoma, and cancer growth and metastasis. Accordingly, the antibodies and pharmaceutical compositions described herein can be administered to a human having or suspected of having one of the above-listed diseases in an appropriate dosage to ameliorate or treat one of the disease or at least one symptom thereof.

Without intending to limit the scope of the invention, in some embodiments it is believed that antibodies described herein function in part by triggering an increase in MHCII expression in antigen presenting cells. See, e.g., FIG. 36A-F.

Moreover, the anti-αvβ8 antibodies described herein (including αvβ8 binding fragments thereof, labeled antibodies, immunoconjugates, pharmaceutical compositions, etc.) can be used to treat, ameliorate, or prevent viral infections (e.g., by stimulating an immune response). Other antibodies that specifically bind to αvβ8 and that block binding of one or more αvβ8 ligand, for example such as described in WO2011/103490 or WO2015/026004 can also be used to treat, ameliorate, or prevent viral infections. Exemplary viral infections include but are not limited to hepatitis A, B (HBV), and C (HCV), herpes simplex virus (e.g., HISVI, HSVII), HIV, and influenza infections, all of which are enhanced by Treg-mediated immune suppression (Keynan, Y, et al., *Clin Infect Dis.* 2008 Apr. 1;46(7):1046-52.

Also provided are pharmaceutical compositions comprising the present anti-xvβ8 antibodies or antigen-binding molecules as well as antibodies that bind both αvβ8 and αvβ6 as described herein or binding fragments thereof, either of which can be formulated together with a pharmaceutically acceptable carrier. The compositions can additionally contain other therapeutic agents that are suitable for treating or preventing a given disorder. Pharmaceutically carriers can enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition as described herein can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, intranasal, inhalational, spinal or epidermal administration (e.g., by injection or infusion). Depending on the route of administration, the active compound, i.e., antibody, may be coated in a material to protect the compound from the action of acids and other natural conditions that may inactivate the compound.

The antibodies, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions of the present invention. Applicable methods for formulating the antibodies and determining appropriate dosing and scheduling can be found, for example, in *Remington: The Science and Practice of Pharmacy*, 21$^{st}$ Ed., University of the Sciences in Philadelphia, Eds., Lippincott Williams & Wilkins (2005); and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of the anti-αvβ8 antibody is employed in the pharmaceutical compositions of the invention. The anti-αvβ8 antibodies are formulated into pharmaceutically acceptable dosage forms by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

In some embodiments, the pharmacological compositions comprise a mixture of the anti-αvβ8 antibody or antigen binding molecule (e.g. that blocks ligand binding or blocks activation by ligand binding) and a second pharmacological agent. Without intending to limit the invention, it is noted that the inventors have found that thymic stromal lymphopoietin (TSLP) is an inducer of viral clearance in a mouse model of acute and chronic HBV and thus is useful to combine TSLP with an antbody as described herein for anti-viral treatments. Moreover, the inventors have found that OX40 agonists are effective in stimulating an immune response to HBV in combination with an antbody as described herein.

As an alternative to mixing the anti-αvβ8 antibody and second pharmacological agent in a pharmacological composition, the anti-αvβ8 antibody and second pharmacological agent can be separately administered to the human in need thereof within a time frame (e.g., within 3, 2, o 1 day or within 24, 13, 6, or 3 hours of each other).

IV. Diagnostic Compositions and Applications

Integrin αvβ8 is expressed on fibroblasts, stellate cells, chondrocytes, activated macrophages and subsets of T and B-cells. Integrin αvβ8 is increased in expression in fibroblasts in COPD and pulmonary fibrosis, and can be used as a surrogate marker for increased fibroblast cell mass. Thus the presently disclosed antibodies can be broadly applicable to bioimaging strategies to detect fibroinflammatory processes. The presently described therapeutic and diagnostic antibodies can be applied to: inflammatory bowel disease (IBD), chronic obstructive pulmonary disease (COPD), asthma, arthritis, a hepatic fibroinflammatory disorder, alcohol induced liver injury, non-alcoholic steatohepatitis (NASH), viral hepatitis, and primary biliary cirrhosis (PBC), graft rejection after liver transplantation, autoimmune hepatitis, an autoimmune disorder, lupus erythematosus, scleroderma, dermatomyositis, bullous pemphigoid, pemphigus vulgaris, a pulmonary fibrotic disorder, an inflammatory brain autoimmune disease, multiple sclerosis, a demyelinating disease, neuroinflammation, kidney disease, glomerulonephritis, hepatocellular carcinoma (HCC), adenocarcinoma, squamous carcinoma, glioma, melanoma, prostate, ovarian, uterine and breast carcinoma.

The inventors have found that β8 and PD-LI expression inversely correlate. Thus, anti-αvβ8 antibodies described herein can be used as a marker for PD-L1 expression and optionally for selecting invenniduals most likely to benefit from anti-αvβ8 treatment.

Anti-αvβ8 antibodies described herein (including αvβ8 binding fragments thereof, affinity matured variants, or scFvs) can be used for diagnosis, either in vivo or in vitro (e.g., using a biological sample obtained from an individual). In addition to the above-described antibodies, antibodies having the following CDRs can be used for diagnosis and prognosis: heavy chain CDRs SEQ ID NO:299, SEQ ID NO:301, and SEQ ID NO:303; and light chain CDRs SEQ ID NO:307, SEQ ID NO:309, and SEQ ID NO:311. In some embodiments, the antibodies have a heavy chain variable region comprising SEQ ID NO:297 and a light chain variable region of SEQ ID NO:305. Alternatively, any antibodies having heavy chain CDRs or a heavy chain variable region as set forth in FIG. 53 and light chain CDRs or a light chain variable region from a corresponding sequence as set forth in FIG. 54 can be used. The antibodies are particularly useful in detecting αvβ8 in samples that have been fixed, for example in formalin-fixed samples, including for example formalin-fixed paraffin-embedded (FFPE) biological (e.g., tissue or cell) samples.

When used for detection or diagnosis, the antibody is typically conjugated or otherwise associated with a detectable label. The association can be direct e.g., a covalent bond, or indirect, e.g., using a secondary binding agent, chelator, or linker.

A labeled antibody can be provided to an individual to determine the applicability of an intended therapy. For example, a labeled antibody may be used to detect the integrin β8 density within a diseased area. For therapies intended to target TGFβ or αvβ8 activity (to reduce TGFβ or αvβ8 activity), the density of 38 is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MRI, PET scanning, etc.). Such in vivo methods can be carried out using any of the presently disclosed antibodies.

Any of the presently disclosed antibodies can also be used for in vitro diagnostic or monitoring methods, e.g., using cells or tissue from a patient sample. In some embodiments, labeled F9 (or a 8 binding fragment or affinity-matured variant) is used, as it can bind fixed cells as well as non-fixed cells.

In some embodiments, the diagnostic antibody is a single-chain variable fragment (scFv). Intact antibodies (e.g., IgG) can be used for radioimmunotherapy or targeted delivery of therapeutic agents because they exhibit high uptake and retention. In some cases, the persistence in circulation of intact mAbs can result in high background (Olafsen et al. (2012) *Tumour Biol.* 33:669-77; Cai et al. (2007) *J Nucl Med.* 48:304-10). ScFvs, typically with a molecular mass of ~25 kD, are rapidly excreted by the kidneys, but are monovalent and can have lower affinity. The issues of monovalency can be overcome with advanced antibody engineering (as shown herein), where affinities can be improved to the low nM to pM range. Such antibodies have short enough half-lives to be useful as imaging agents and have suitable binding characteristics for tissue targeting (Cortez-Retamozo et al. (2004) *Cancer Res.* 64:2853-7). As shown herein, we have created a very high affinity scFV antibody derivatives of 4F1, 6B9, called F9, that can be converted to humanized scFV platforms. These improved antibodies are not function blocking, and thus can be used in combination with a therapeutic agent that targets β8.

A diagnostic agent comprising an antibody described herein can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). The terms "detectable agent," "detectable moiety," "label," "imaging agent," and like terms are used synonymously herein. A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. PET is particularly sensitive and quantitative, and thus valuable for characterizing fibrotic processes in vivo (Olafsen et al. (2012) *Tumour Biol.* 33:669-77; Cai et al. (2007) *J Nucl Med.* 48:304-10). This is useful beyond a companion diagnostic and would be generally useful to diagnose, clinically stage and follow fibrotic patients during any treatment regimen.

A radioisotope can be incorporated into the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes* 2nd Ed.: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8, 11-tetraazacyclotetradec-1-yl)methyl] benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7, 10-tetraazacyclododecane-1,4,7,10-tetra(methylene phosphonic acid) (DOTP), 1,4,8,11-tetraazacyclotetradecane-1,4,8,11-tetraacetic acid (TETA), 1,4,7,10-tetraazacyclododecane-1,4,7,10-tetraacetic acid (DOTA), N1,N1-bis(pyridin-2-ylmethyl)ethane-1,2-diamine (ENPy2) and derivatives thereof.

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives.

EXAMPLES

The following examples are offered to illustrate, but not to limit the claimed invention.

Example 1. Construction of Composite Antibody C6D4

ITGB-8 knockout mice were immunized with recombinant Human Integrin alpha V beta 8 (αvβ8) protein. Approximately 5000 hybridomas were generated and screened for their ability to bind to αvβ8 in an enzyme-linked immunosorbent assay (ELISA). Results were confirmed by cell staining, and function blocking was determined with the use of a transforming growth factor-beta (TGF-β) bioassay. Blocking antibodies were screened against a recombinant form of αvβ8 engineered to lack the specificity determining loop (SDL) of the β8 head domain. Antibodies not binding this engineered αvβ8 were then selected.

Variable (V) genes from eight hybridomas were next isolated, sequenced, and found to comprise seven $V_H$ and eleven $V_K$ genes that were unique but related. FIG. 1 and FIG. 2 provide sequence information for the products of these $V_H$ and $V_K$ genes. Sequence information is using the Kabat numbering scheme. Each V gene was amplified under mutagenic conditions, and a single-chain variable fragment (scFV) library was constructed by mixing the amplified cDNA and using splice overlap. The library served as an amplification template using primers designed to complement rabbit IgG expressing dual $V_H$ and $V_L$ vectors. Eleven distinct $V_H$ genes and sixteen distinct $V_K$ genes were identified after sequencing >100 random clones and transfected in 165 different combinations into 293 cells. The eight pairs that produced the best binders were determined by cell staining and FACS analysis, and by measuring binding affinity for CHO cells expressing αvβ8. The eight pairs each comprised a $V_H$ domain selected from RSDLVH-1, RSDLVH-3, and RSDLVH-16; and a $V_K$ domain selected from RSDLVK-1, RSDLVK-6, RSDLVK-10, and RSDLVK-13; the sequences of which are shown in FIG. 1 and FIG. 2.

These eight rabbit IgG $V_H/V_K$ pairs were then used to create a new mutagenic scFV yeast display library that was inserted into a yeast expression library vector. Two high-affinity binders from this selection and affinity maturation step were identified and designated clone 29 and clone 44. Random mutation mutagenic libraries were next made from genes of clones 29 and 44, and from these libraries the higher-affinity binding clones C6 and D4 were selected and determined (FIG. 1 and FIG. 2). Mutations in the complementarity-determining regions (CDRs) of C6 $V_H$ and D4 $V_K$ were identified, and the two chains were combined to create the composite antibody C6D4 (FIG. 1 and FIG. 2).

Example 2. Characterization of C6D4 Binding Affinity

A Kinetic Exclusion Assay (KINEXA®) was used to measure the binding affinity of C6D4. The affinity as a murine IgG2a was measured as 832 pM. As a recombinant IgG, C6D4 was found to result in substantially complete blockage of αvβ8-mediated TGF-β activation. This result implies blockage that is better than with B5, an allosteric inhibitor of αvβ8-mediated TGF-β activation. (Minagawa, et al, *Sci Trans Med.* 2014 Jun. 18;6(241):241ra79)

Figure 19:
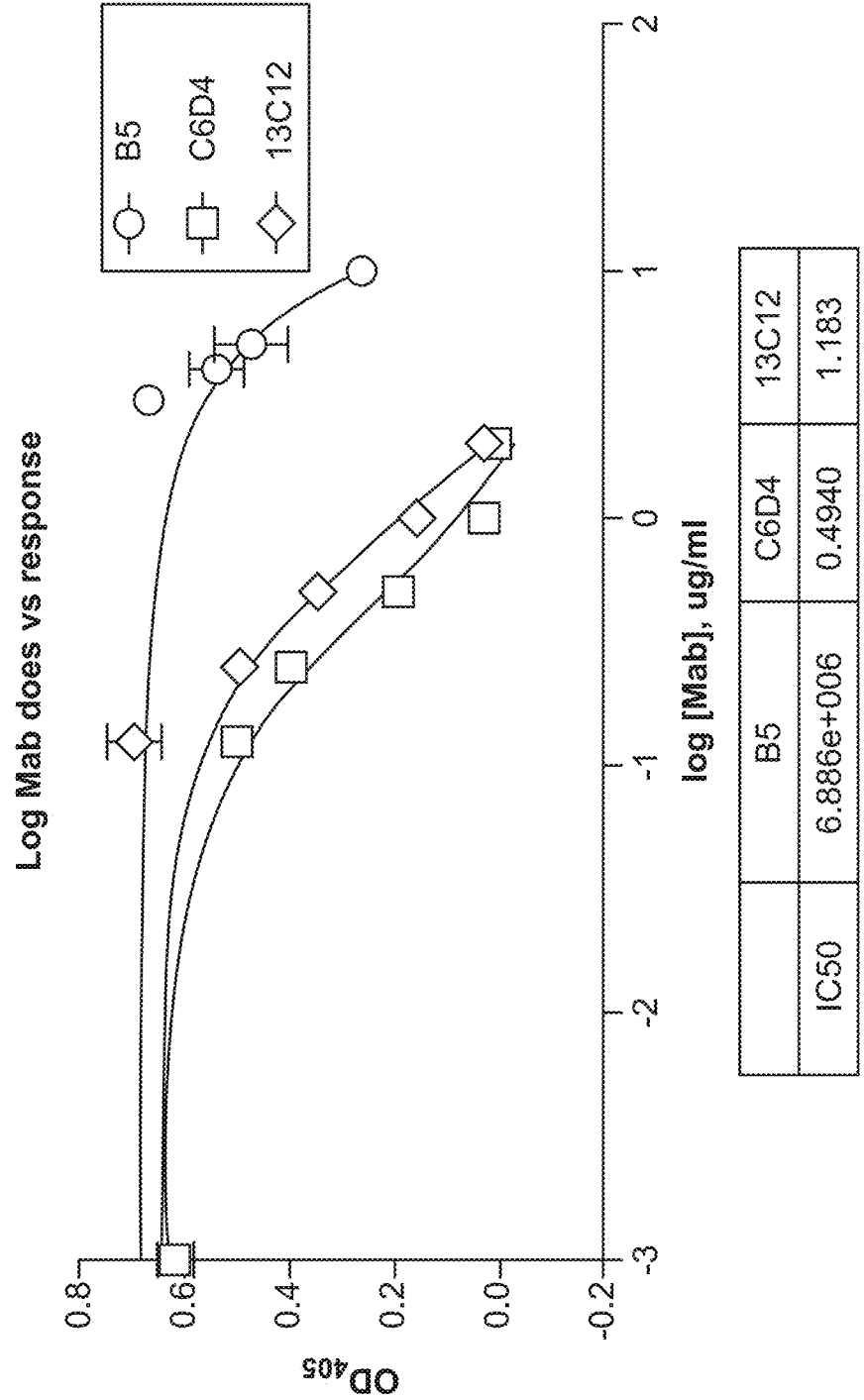
FIG. 19 shows that C6D4 is a potent inhibitor of binding of secreted αvβ8 to L-TGF-b3 peptide.

C6D4 was also shown to block adhesion of cells to immobilized latent TGF-β. A peptide with the sequence DDHGRGDLGRLK (SEQ ID NO:713), which corresponds to aa 257-268 of human TGF-β3 (NP_003230) was synthesized on an 8 lysine core (Multiple antigen presenting peptide, BioSyn) and used at 1 µg/ml to coat a 96 well ELISA plate. A truncated secreted form of αvβ8 which was fused in frame to alkaline phosphatase (Gline S E, et al. *J Biol Chem.* 2004 Dec. 24; 279(52):54567-72) was added with Mab at the indicated concentrations. The results (FIG. 19) show the superiority of C6D4 over B5 and the improvement of C6D4 compared to Clone 13C12. The table gives the IC50 values in µg/ml.

Figure 20:
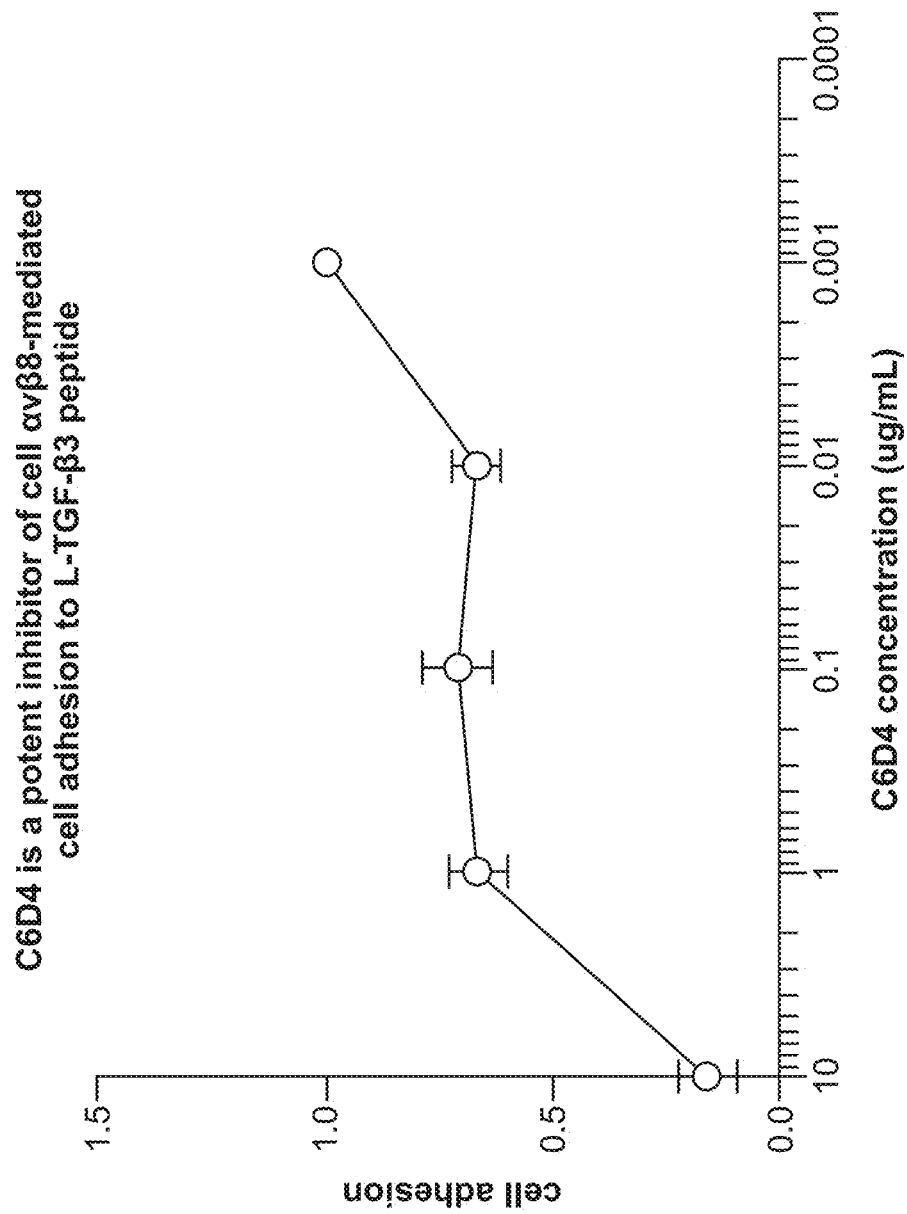
FIG. 20 shows that C6D4 is a potent inhibitor of cell αvβ8-mediated cell adhesion to L-TGF-b3 peptide.

Further, a peptide with the sequence DDHIGRGDLGRLK (SEQ ID NO:713), which corresponds to aa 257-268 of human TGF-β3 (NP_003230) was synthesized on an 8 lysine core (Multiple antigen presenting peptide, BioSyn) and used at 0.51 µg/ml to coat a 96 well ELISA plate. CHO lec cells stably transfected with αvβ8 were allowed to bind to the peptide coated wells for 30 min at RT. Unbound cells were washed off with PBS. The Mab C6D4 was added at the indicated concentrations. Results were presented as stained cells detected after staining with crystal violet (OD590). The results (FIG. 20) show that C6D4 almost completely blocks cell adhesion to the peptide.

Example 3. Characterization of C6D4 Binding Structure

The current understanding of integrin structure is faced with the hurdle of having to reconcile two polar opposite views of integrin conformation. One camp proposes that integrins are always bent. The other believes that integrins must undergo a significant conformational "switchblade" change from a bent conformation to an extended conformation upon activation, opening the "headpieces" of the integrins to be fully functional. This model of integrin extension proposes one of the largest tertiary and quaternary structural rearrangements in biology.

Proof of such conformational extremes has been hampered by compromises and shortcomings associated with techniques routinely used in structural biology. Traditional crystallography produces crystal structures with atomic resolution but is reliant on the conformations and conditions under which crystals can be formed. In the case of integrins, only compact, closed conformations have been seen by crystallography. Alternatively, size exclusion chromatography (SEC) of integrins under activating conditions have demonstrated large shifts in size consistent with integrin extension. Such changes in conformation have been directly visualized using negative stain electron microscopy (EM) studies but at low resolution. Thus, the atomic details of the integrin ligand binding and the integrin activation mechanism remains unresolved.

Single-particle cryo-electron microscopy (cryoEM) can be used to determine the structure of biological macromolecules without crystals, thus offering an alternative that circumvents the obstacles of crystalizing integrins in the extended form. Recent hardware and software developments demonstrate that single-particle cryoEM has the power to provide atomic-level structural understanding of molecules that are traditionally challenging to study. Because single-particle cryoEM does not require the formation of crystals, and allows examination in the native functional conformations unaffected by crystal packing forces or high-salt crystallization buffers, this method is uniquely suited to understanding structures of proteins or integrin-ligand or integrin-Fab complexes that are difficult to crystallize. Here, we have used single particle cryoEM to address some of the biggest mysteries in structural biology, the structural mechanisms of integrin activation and conversely the mechanism of action of integrin inhibitors.

Previously published crystal structures of the latent TGF-β arginine-glycyine-aspartic acid (RGD) peptide of αvβ6 show the positioning of the TGF-β RGD in the αvβ6 binding pocket, as well as the positioning of the R of the TGF-β RGD proximate to the αv head. Cryo-electron microscopy of the new composite antibody C6D4 structure have now produced a ~4-5-angstrom-resolution structure of the C6D4 Fab binding to αvβ8. To generate the structures of αvβ8 in complex with C6D4, purified recombinant αvβ8 and C6D4 Fab complexes were isolated by size exclusion chromatography and then plunge frozen on grids in liquid nitrogen. Images of ~61,000 individual particle images captured by electron microscopy were selected to produce a 3D electron density map which was used to build model of αvβ8 in complex with C6D4 Fab using existing Protein Data Bank (PDB) entries for the integrin αvβ3, αIIbβ3, and Fabs with similar CDRs.

Figure 3:
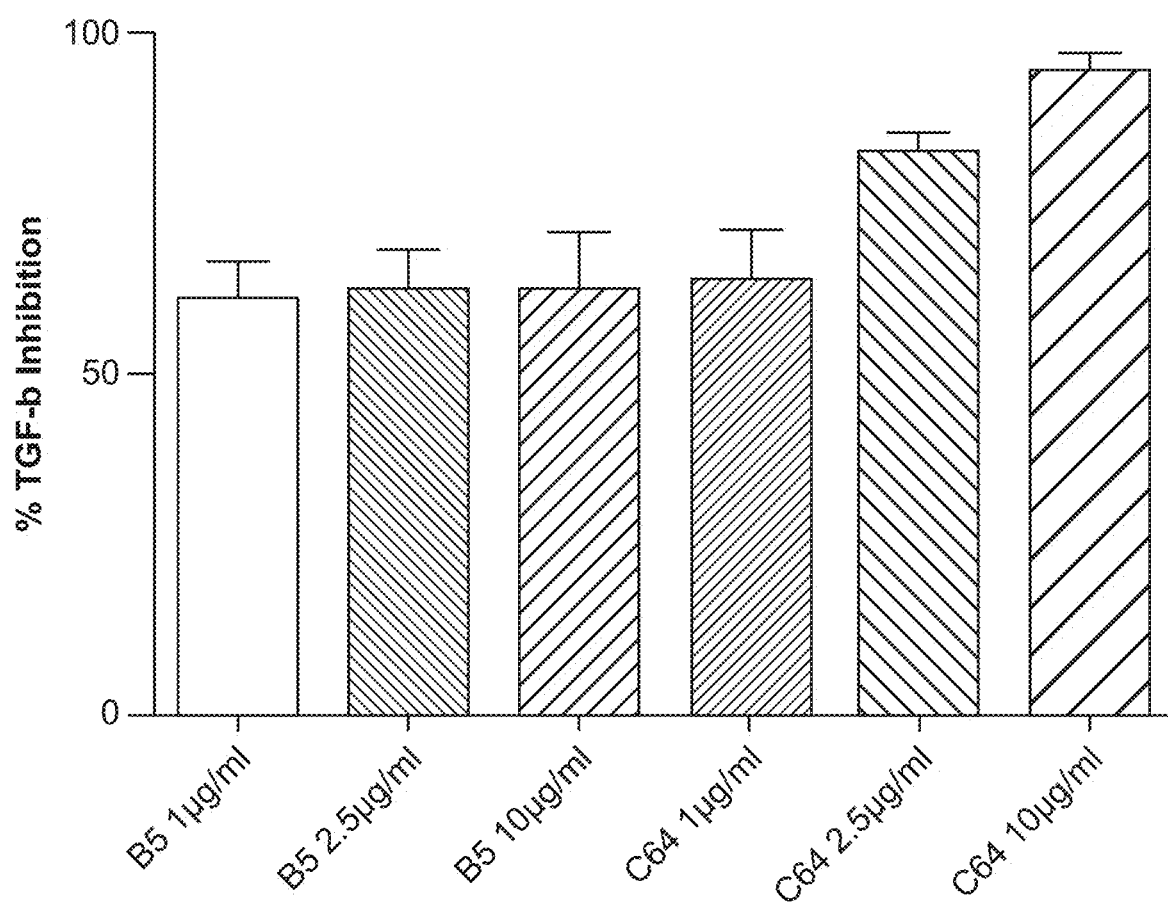
FIG. 3 is a plot of transforming growth factor-beta (TGF-β) binding inhibition percentages for different concentrations of the allosteric inhibitor B5 and the composite antibody C6D4.
Figure 6:
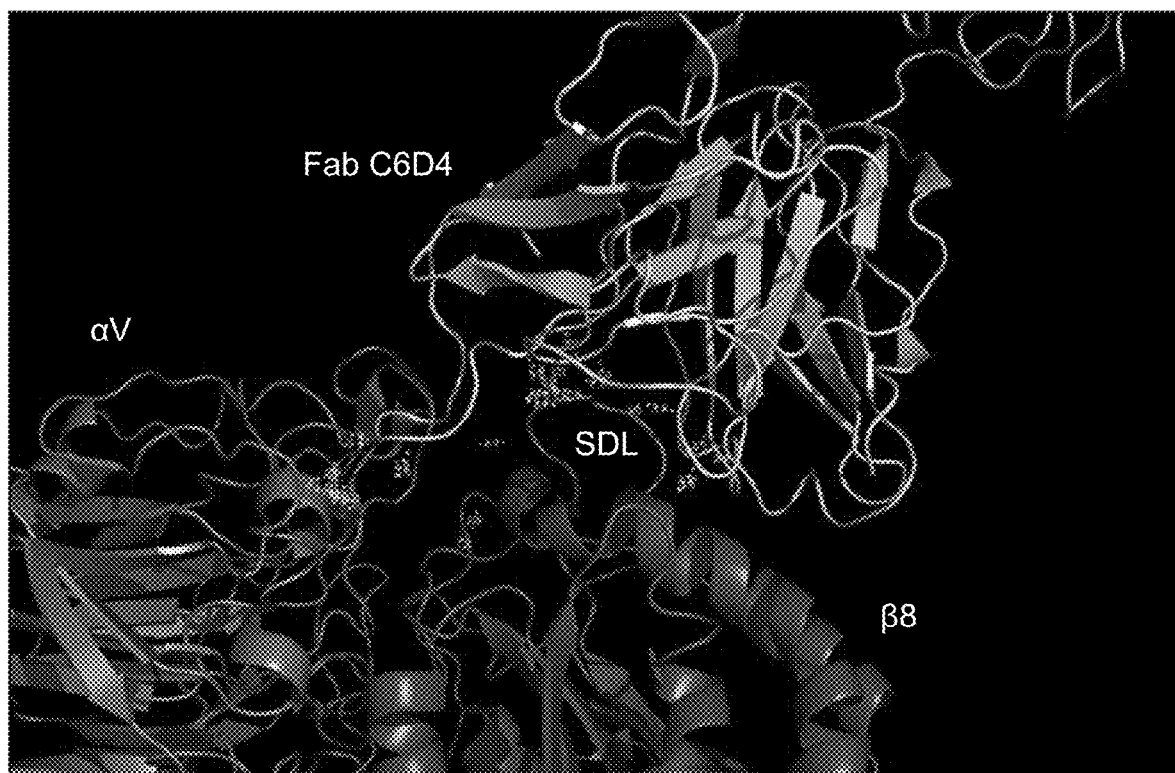
FIG. 6 illustrates cryoEM results, highlighting the interactions between C6D4 and the (SDL) loop of β8, the α1 and α2 helices of β8, and the head of αv.
Figure 13A:
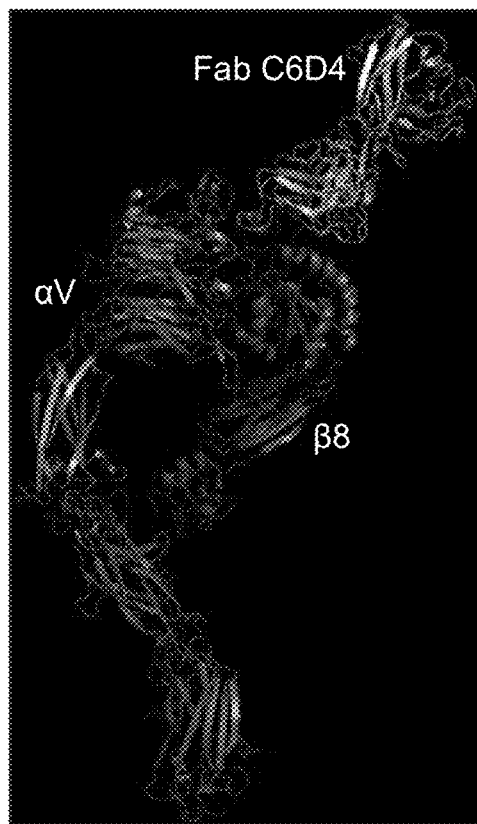
FIGS. 13A-B illustrate a model of how the complex is generated from the crystal structure of αVβ3 (PDB ID: 3IJE), with the β8 model based on β3 using CHIMERA and MODELLER (Yang et al., *J Struct Biol.* 2012 September; 179(3):269-78). Refinement of the model to the cryo-electron microscopy map is done in rigid body in COOT (Emsley P, et al., *Acta Crystallographica Section D—Biological Crystallography.* 2010, 66:486-501), followed by complete refinement in PHENIX (Adams et al., *Acta Cryst.* 2010; D66:213-221).
Figure 13B:
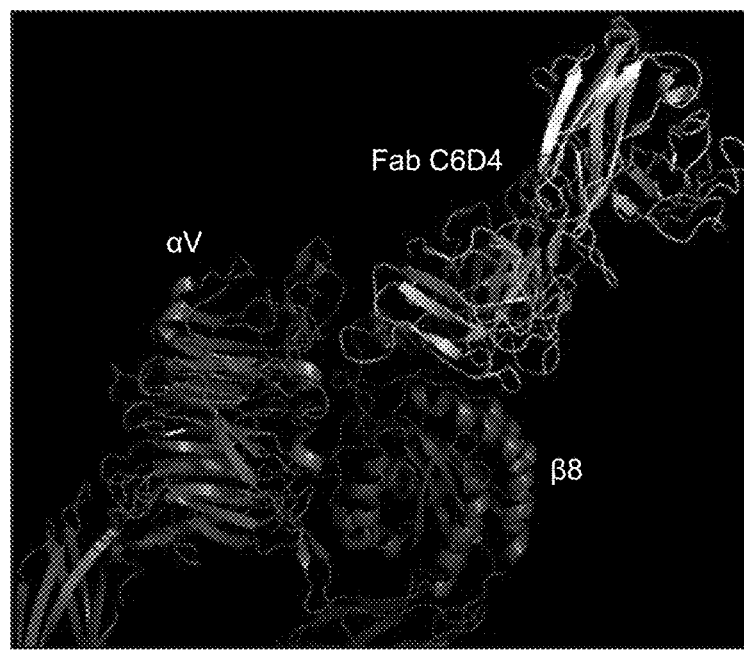
Figure 14:
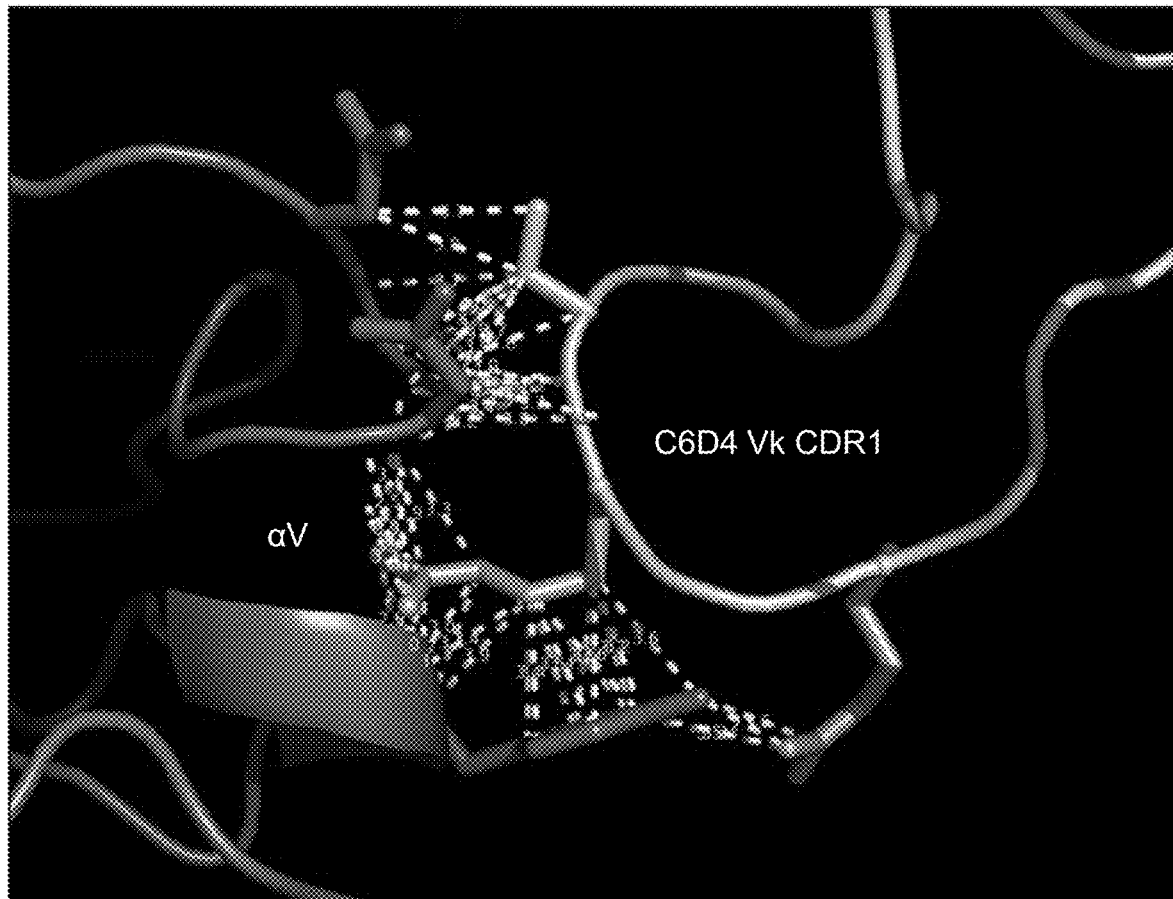
FIG. 14 illustrates interaction of C6D4 Vk CDR1 (SEQ ID NO:616) with integrin αV (SEQ ID NO:622, positions 46-52 and 75-79): Model of the αVβ8/C6D4 Fab complex. Interacting residues are represented as sticks. The dashed lines represent inter-atom distances comprised between 2.5 and 4.0 Å indicating potential interactions.
Figure 15:
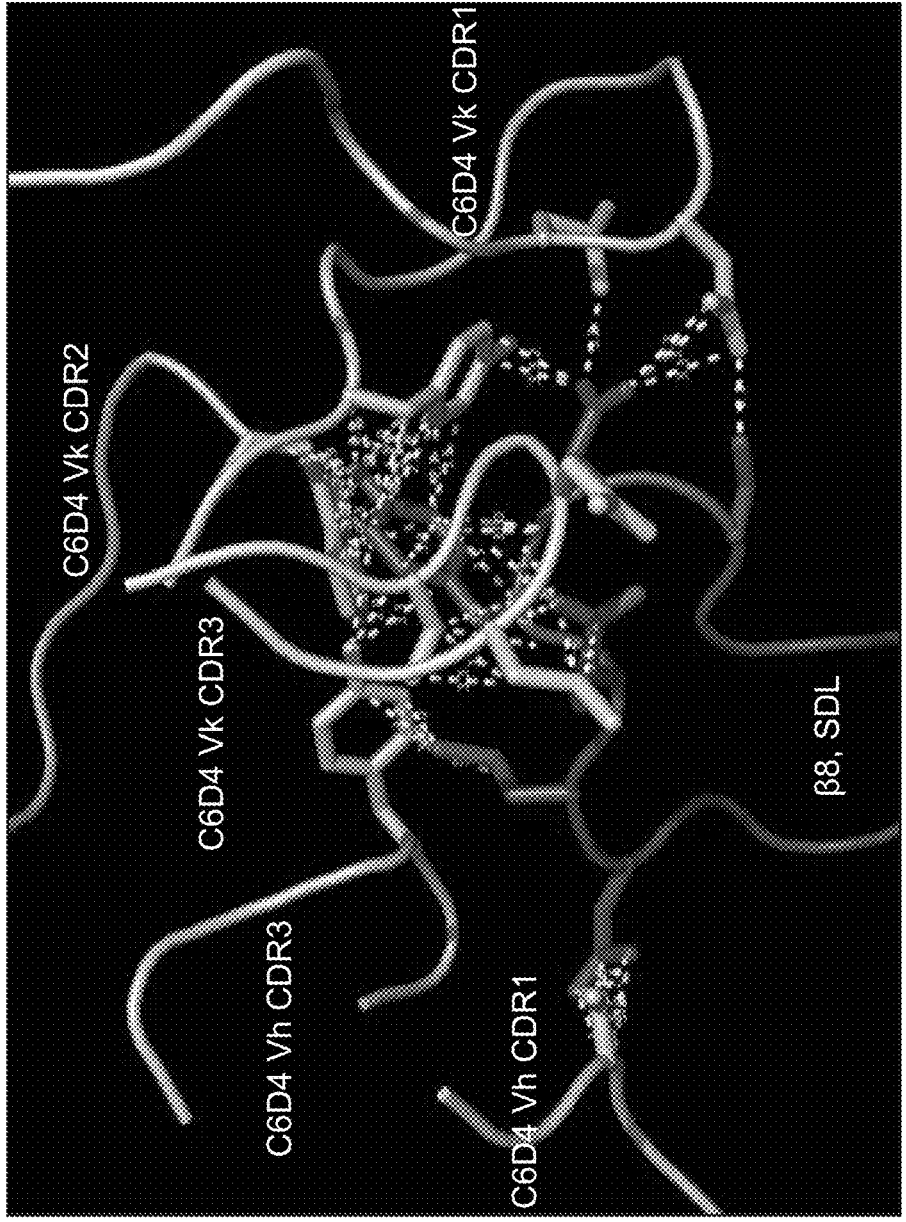
FIG. 15 illustrates interaction of C6D4 with the SDL region of integrin β8: Model of the αVβ8/C6D4 Fab complex. Interacting residues are represented as sticks. The dashed lines represent inter-atom distances comprised between 2.5 and 4.0 Å indicating potential interactions. C6D4 VH CDR1 (SEQ ID NO:707), C6D4 VH CDR3 (SEQ ID NO:615), β8, SDL (SEQ ID NO:620), C6D4 Vk CDR1 (SEQ ID NO:616), C6D4 Vk CDR2 (SEQ ID NO:708), and C6D4 Vk CDR3 (SEQ ID NO:618).
Figure 16:
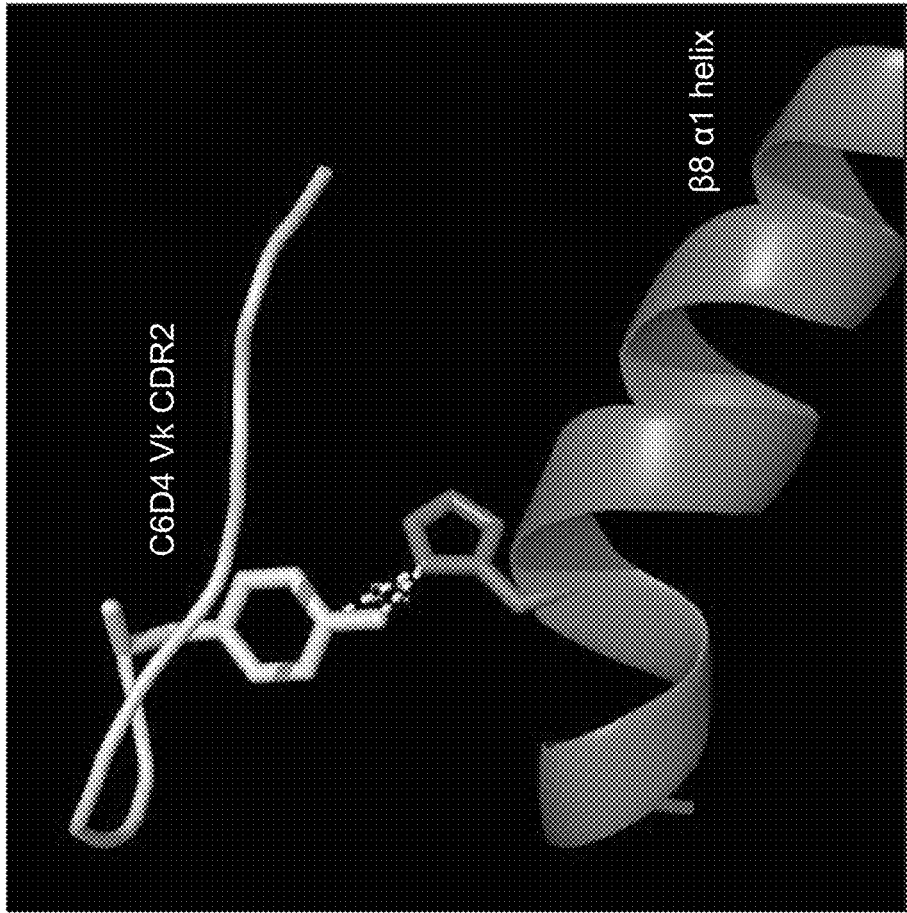
FIG. 16 illustrates interaction of C6D4 Vk CDR2 (SEQ ID NO:617) with the al helix of integrin β8 (SEQ ID NO:619): Model of the αVβ8/C6D4 Fab complex. Interacting residues are represented as sticks. The dashed lines represent inter-atom distances comprised between 2.5 and 4.0 Å indicating potential interactions.
Figure 17:
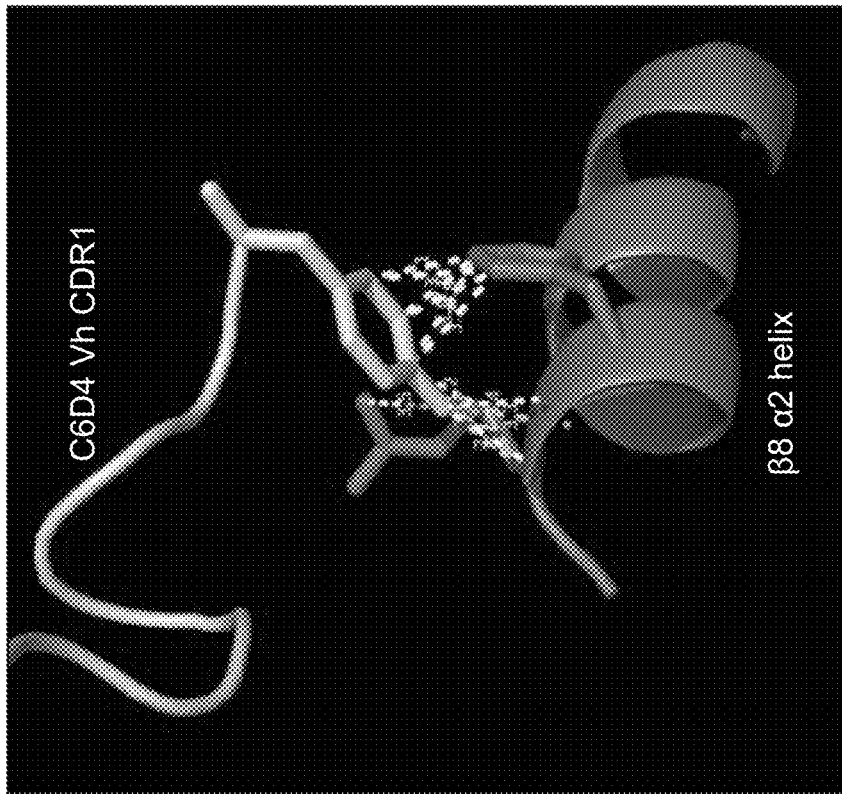
FIG. 17 illustrates interaction of C6D4 Vk CDR1 (SEQ ID NO:613) with the α2 helix of integrin β8 (SEQ ID NO:621): Model of the αVβ8/C6D4 Fab complex. Interacting residues are represented as sticks. The dashed lines represent inter-atom distances comprised between 2.5 and 4.0 Å indicating potential interactions.
Figure 18:
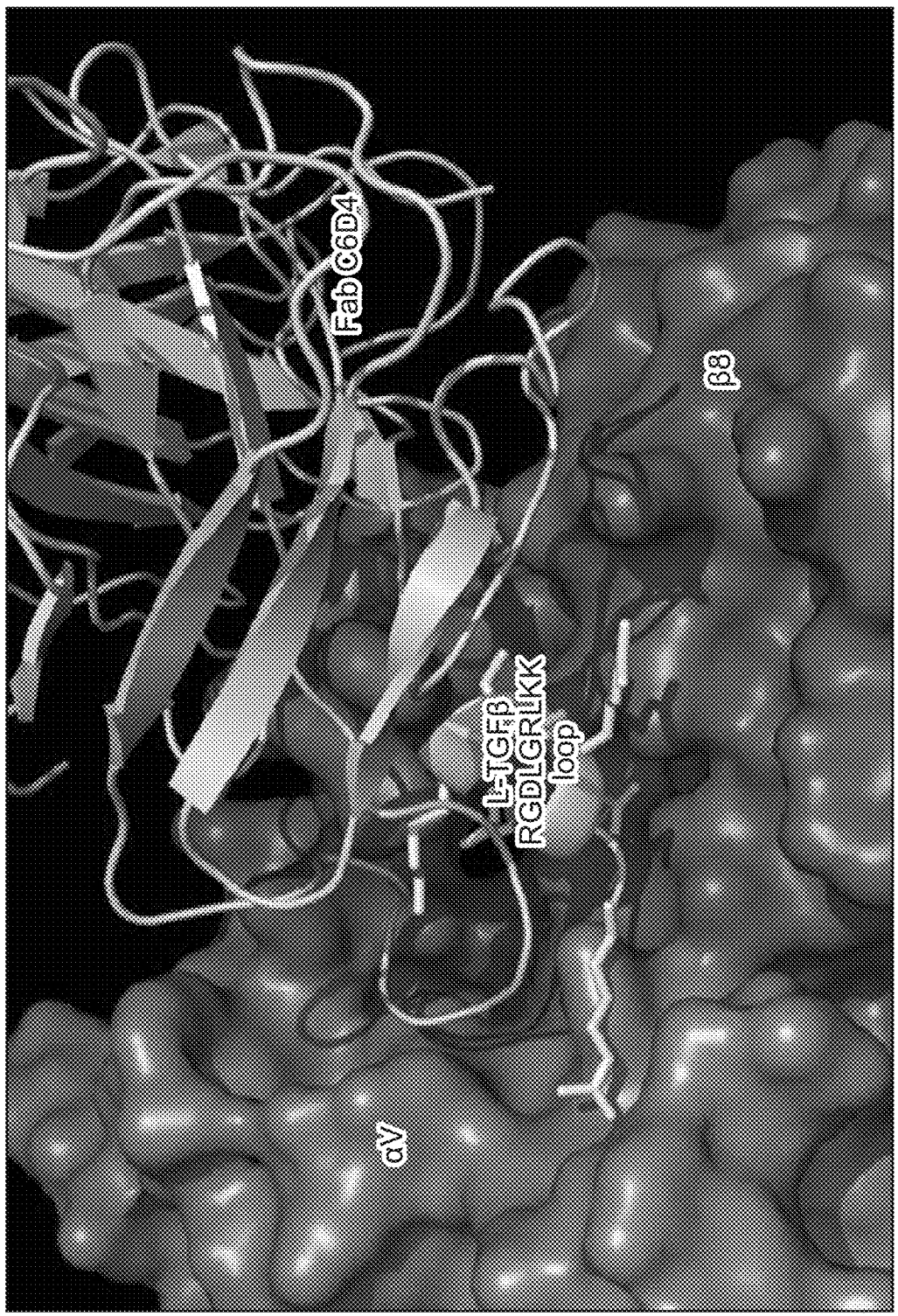
FIG. 18 illustrates that C6D4 blocks the access of L-TGFβ to the ligand binding pocket of integrin β8 and C6D4 bound to integrin αVβ8 directly clashes with the position of the RGDLGRLKK loop of L-TGFβ (SEQ ID NO:712). The surface of the αVβ8/C6D4 Fab complex is shown. The surface is αVβ8, while the cartoon is C6D4. In sticks are superimposed the residues RGDLGRLKK (SEQ ID NO:712) from the integrin binding loop of L-TGFβ as found when bound to integrin αVβ6 (PDB 4UM9) ((4) Structural determinants of integrin β-subunit specificity for latent TGF-β. Dong X, et al. *Nat. Struct. Mol. Biol.* 2014 December; 21(12):1091-6).

FIGS. 13A and 13B presents cryoEM results showing binding of the C6D4 Fab to the integrin αvβ8 at the head domain. FIGS. 13A and 13B illustrate this binding between C6D4 and αvβ8 in closer detail. From the C6D4 antibody footprint of FIG. 6, it can be seen that C6D4 binds primarily to the SDL loop of 38, making additional contacts with other secondary structures on the β8 a1 and a2 helices and on the head of αv. Together, these components of the binding configuration result in the almost complete occlusion of the ligand binding pocket. The residues of the β8 a1 and a2 helices and αv head that directly interact with C6D4 are further detailed in FIG. 7.

Figure 8:
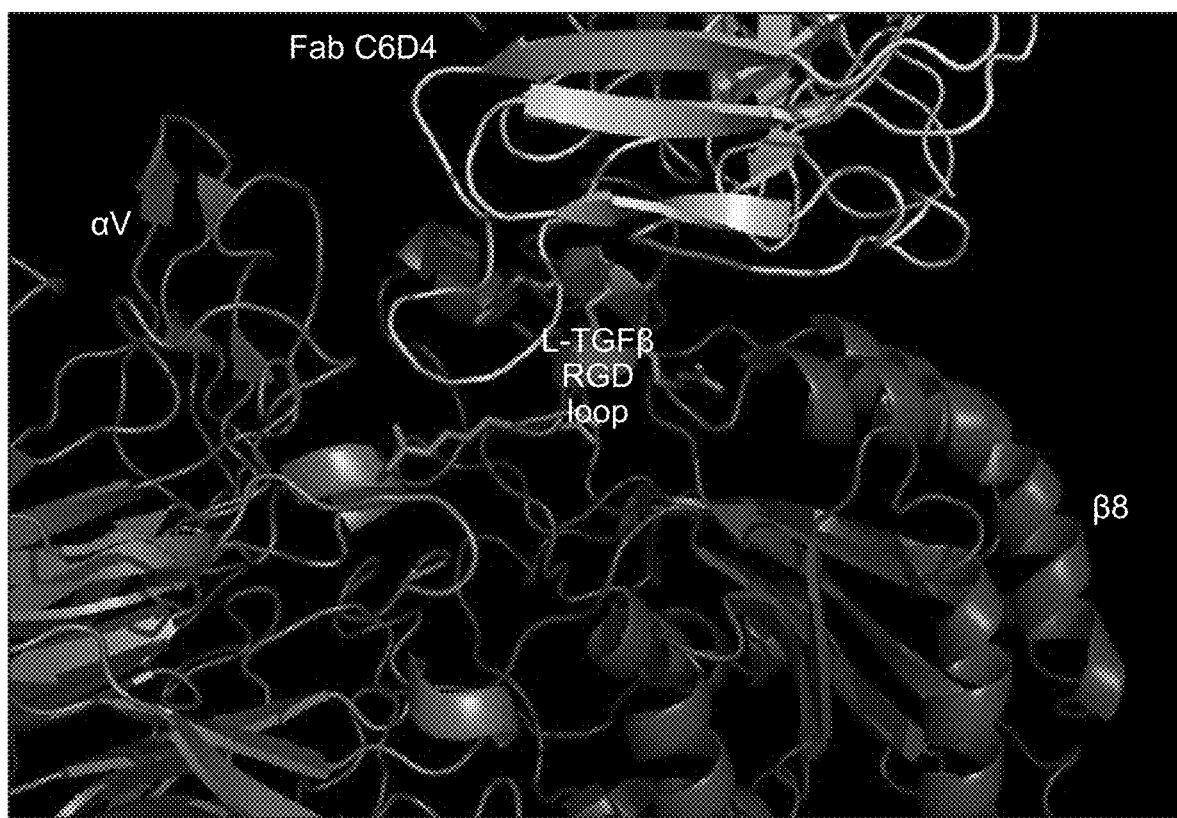
FIG. 8 illustrates the overlapping of the C6D4 epitope with the ligand binding pocket of integrin αvβ8, in relation to the association of the integrin with latent TGF-β.

The elucidated structure shows that the CDR1 domain of the D4 $V_L$ binds close to the contact site for the R of RGD in the previously published αvβ6-RGD crystal structure. Because the αv subunit is shared by both αvβ6 and αvβ8, this finding suggests that the CDR1 loop of D4 $V_L$ is optimally positioned to sterically inhibit the binding of the R of RGD of latent TGF-β to αvβ8. On the other side of the SDL is a hydrophobic binding pocket having an L that immediately follows the RGD, forming an RGDL peptide. This hydrophobic pocket has been shown to be essential as a secondary binding site for the binding of the latent TGF-β RGD peptide to αvβ6. See, e.g., Shi M, et al., Nature 474(7351):343-9 (2011). The L or RGDL has also been shown to be essential for the binding of the latent TGF-β RGD peptide to αvβ8. (See, e.g., Ozawa, A, et al. J Biol Chem. 291(22):11551-65 (2016). The CDR3 loop of C6 $V_H$ has now been shown to bind in such a way as to substantially cover the hydrophobic binding pocket located on the β8 subunit head domain. Additionally, C6D4 was found to interact extensively with the SDL of B8. FIG. 8 illustrates the overlapping of the C6D4 epitope with the ligand binding pocket of integrin αvβ8, showing how it can prevent the association of the integrin with latent TGF-β, and thus the activation of latent TGF-β. Importantly, all contact residues with C6D4 are believed to be conserved in αvβ8 across all mammalian species. This is in contrast to the allosteric inhibitor B5, which only reacts significantly against human αvβ8.

Example 4. Modeling of C6D4 Effects on Lung Cancer Survival

Syngeneic models for the study of lung cancer are very limited. The Lewis lung carcinoma (LLC) model is the only reproducible syngeneic lung cancer model currently widely in use. LLC is a cell line established from the lung of a C57BL mouse bearing a primary Lewis lung carcinoma. This line is highly tumorigenic and is used to model pulmonary metastasis that results after resection of the primary tumor. In this way the model mimics the clinical scenario closely. It is a useful model for evaluating the efficacy of chemotherapeutic agents in vivo. An advantage of the LLC model is that tumor cells are immunologically compatible, unlike the immunodeficient strains used in most other xenograft models. The LLC model was used as a preclinical model to evaluate vinorelbine prior to its use in clinical trials. The LLC cell line is injected subcutaneously into the subcutis of C57B6 mice, and within two weeks primary tumors reproducibly reach sizes of 10 mm. After resection of the primary tumor, lung metastasis appears in 2-4 weeks. The primary endpoints in this model are weight loss and lung metastasis number.

Figure 9:
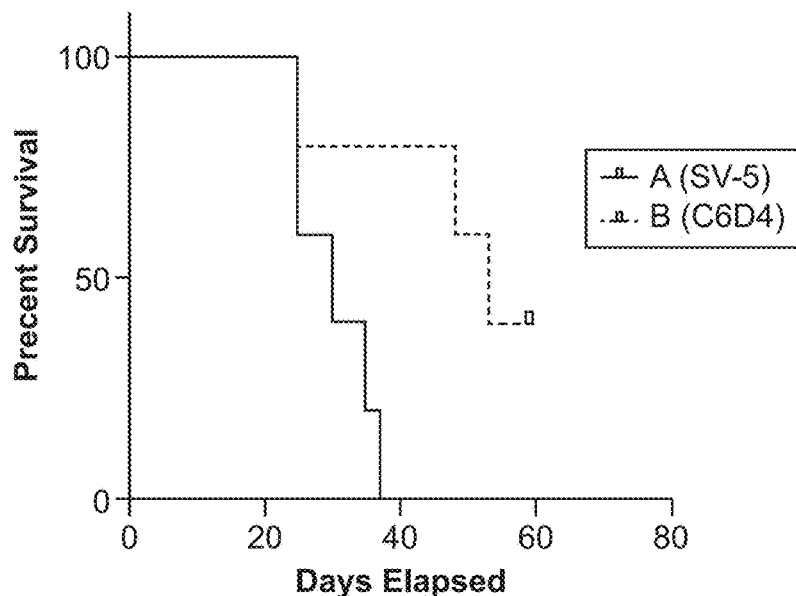
FIG. 9 is a plot of percent survival of mice injected with Lewis lung carcinoma (LLC) cells. The primary tumors were removed and the animals treated with C6D4 murine IgG2a or SV5 isotype control at a dosage of 7 mg/kg once per week. In this model, mice are euthanized after losing 20% body weight due to recurrence of the primary tumor or due to metastasis.
Figure 12:
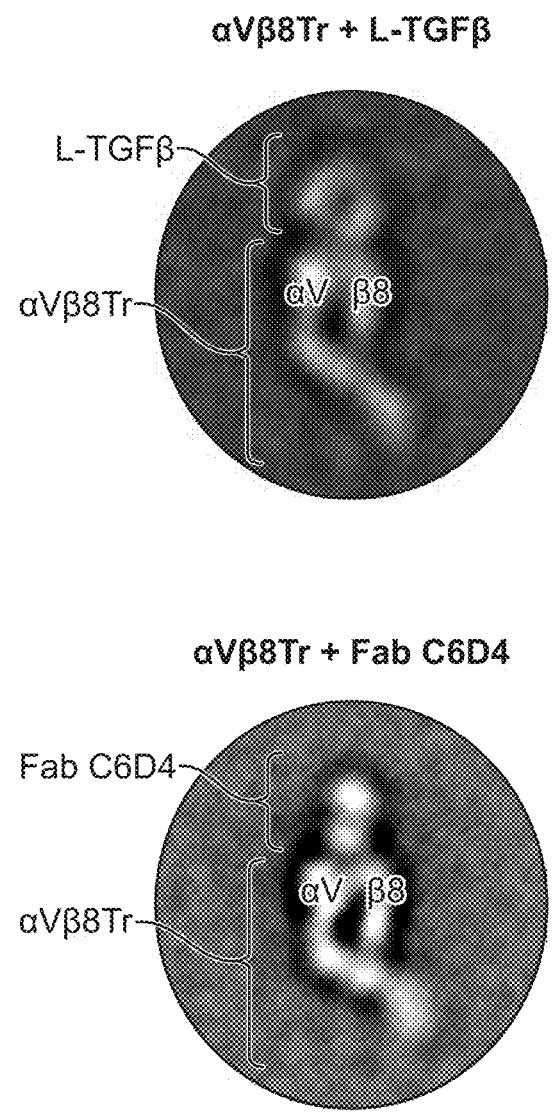
FIG. 12 demonstrates how the C6D4 epitope overlaps directly with the ligand binding pocket of integrin αVβ8, preventing association of integrin αVβ8 with L-TGFβ and thus activation of L-TGFβ. Representative class averages of integrin complexes observed by negative staining electron microscopy.

FIG. 9 presents result indicating that C6D4 increases survival in the LLC model. Mice received intraperitoneal injections of either C6D4 murine IgG2a or SV5 isotype control (7 mg/kg) at the time of primary tumor removal (day 0), and then once every week until weight loss exceeded 20%. The positive results indicate the first demonstration of an anti-β8 antibody inhibiting lung cancer metastasis. The fact that C6D4 inhibits lung cancer metastasis in this model indicates its potential as a treatment to prevent lung cancer metastasis. Because the mechanism of this antibody in cancer likely involves inhibiting the function or development of immunosuppressive Treg cells, C6D4 can have broad applications to any number of cancers where Treg cells play an immunosuppressive role.

FIG. 28 provides a schematic of the LLC model used herein to evaluate lung metastasis. The LLC tumor cell line is syngeneic to the host C57B/6 strain. This cell line does not express the integrins αvβ6 or αvβ8. The LLC.1 cell line has been passed though mice one time and regrown from lung metastasis. After two weeks, subcutaneously injected tumor (1×10⁶) LLC.1 cells form large tumor nodules (~1 cm). The tumors are removed surgically and when animals lose 20% of their body weight they are euthanized.

Figure 29A:
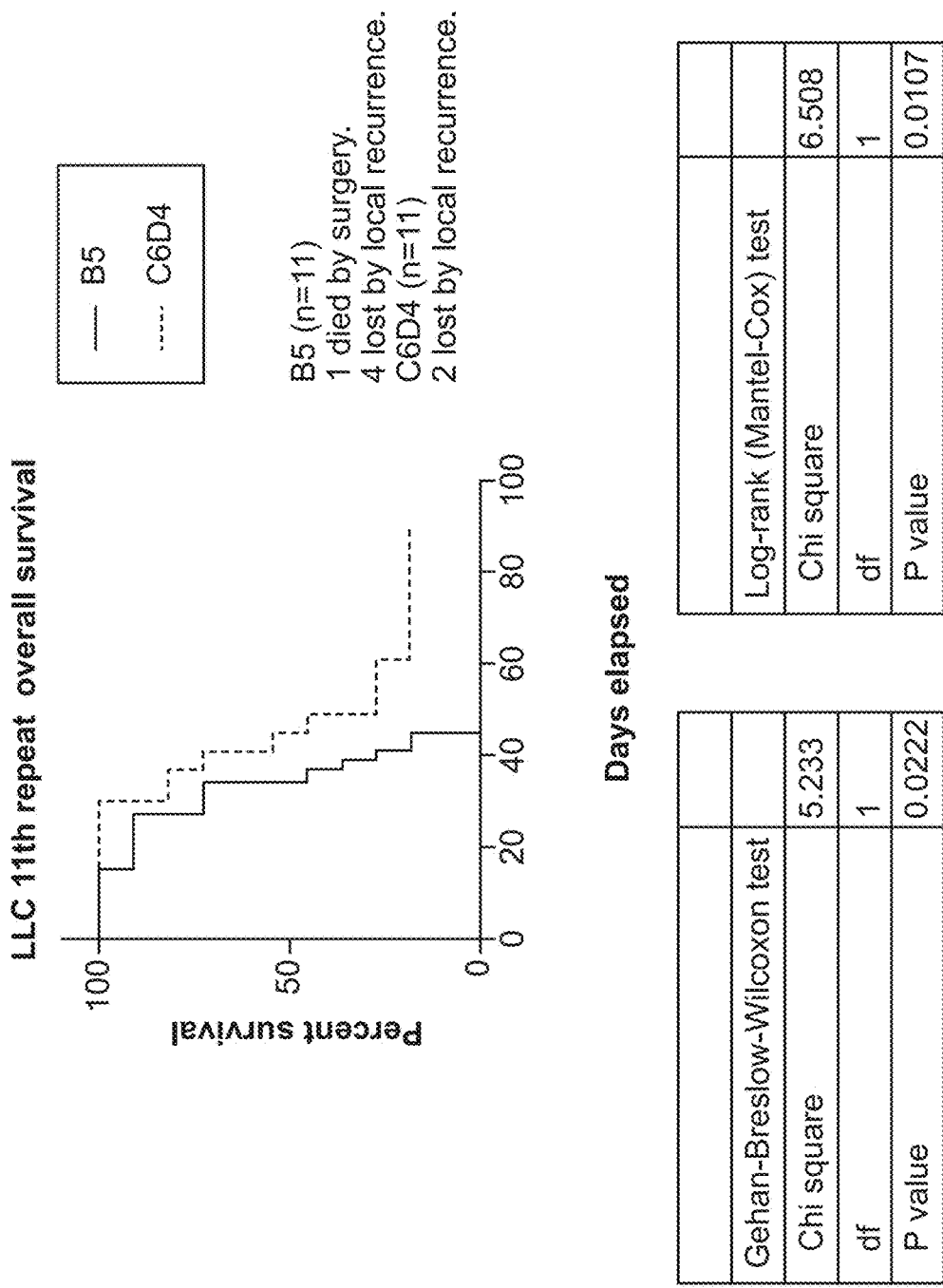
FIGS. 29A and 29B show the effect of C6D4 on mouse survival using the LLC tumor cell line model set forth in FIG. 28. Survival curves (FIG. 29A) represent mice euthanized for reasons of local recurrence or weight loss.
Figure 29B:
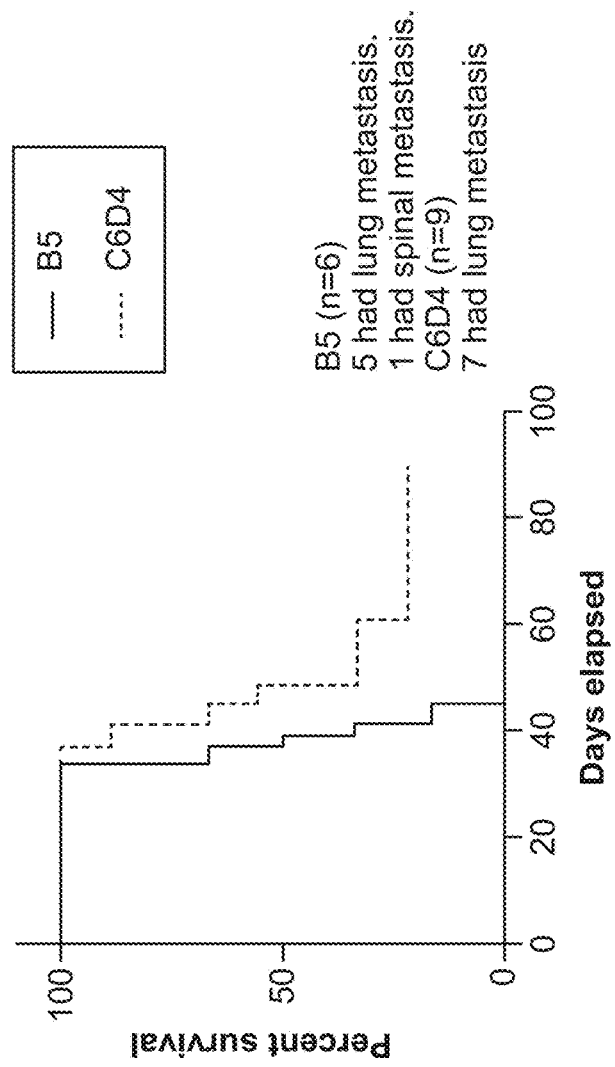
Figure 30A:
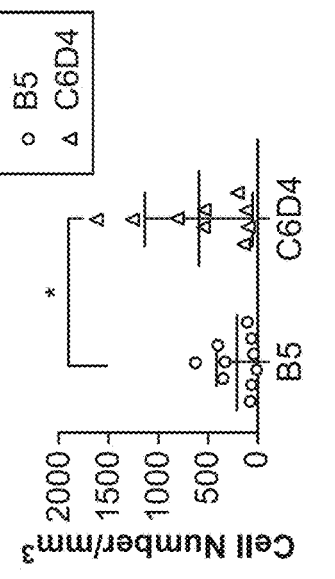
FIGS. 30A-F show the effect of CD64 on tumor growth and tumor immune response using the LLC tumor cell line model set forth in FIG. 28. Here, resected LLC.1 primary tumors in mice that received two injections of isotype control (B5, which only reacts with human and not mouse b8) or C6D4 (which cross reacts with mouse and human), the primary tumor weights are recorded, dimensions are measured, and tumors are enzymatically disaggregated and immune cells isolated and counted. Flow cytometry was performed on the tumor infiltrating immune cells, and the tumor infiltrating immune cells are separated from tumor cells using Percoll gradient centrifugation. Shown here is one of three experiments each providing similar results. In each group n is equal to or greater than 10.
Figure 30B:
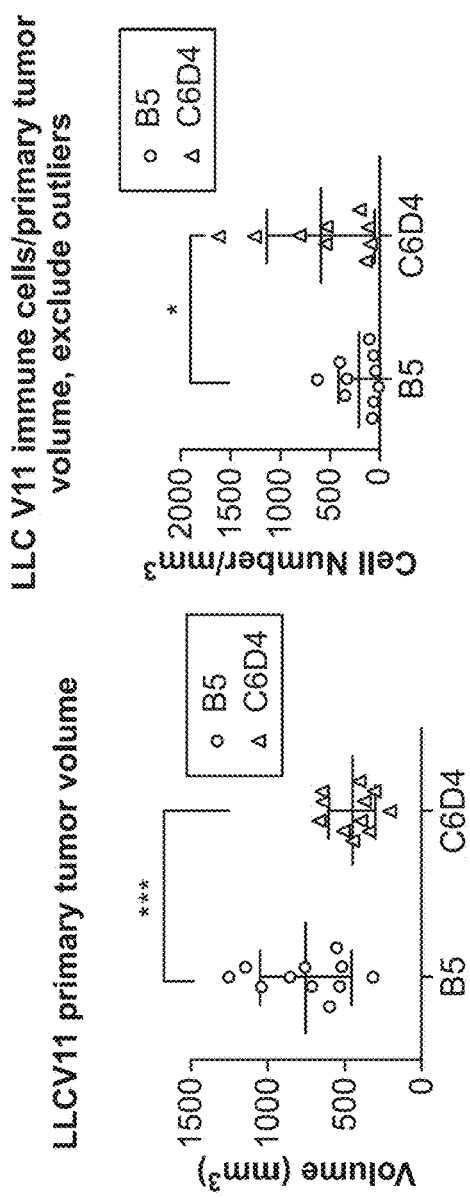
Figure 30C:
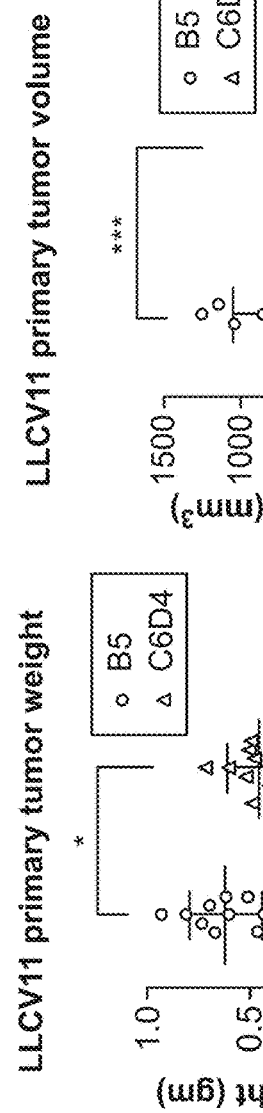
Figures 30D, 30E, 30F:
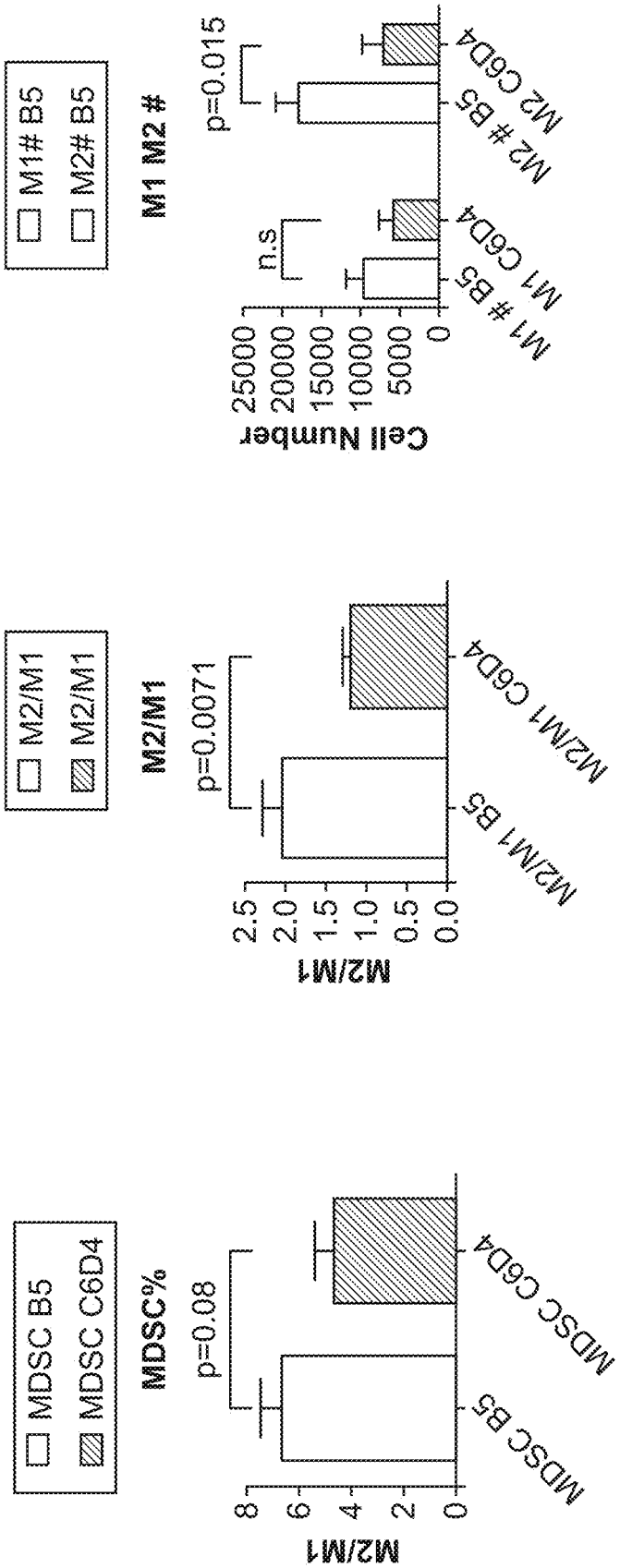

The LLC model lung metastasis experiment described in the preceding paragraph was repeated eleven (11) times and the results in each of the eleven experiments were found to be similar (data not shown). FIGS. 29A and 29B present data from the eleventh experiment indicating that C6D4 increases survival in the LLC model. In each instance, mice received intraperitoneal injections of either C6D4 murine IgG2a or SV5 isotype control (7 mg/kg) at the time of primary tumor removal (day 0), and then once every week until weight loss exceeded 20%. The results indicate the anti-8 antibody (C6D4) inhibits lung cancer metastasis. Survival curves in FIG. 29A represent mice euthanized for reasons of local recurrence or weight loss. In FIG. 29B, the animals removed for local recurrence are excluded. At autopsy, the animals with 20% weight loss all have metastatic implants in their lungs. The C6D4 antibodies were injected for up to 90 days in surviving animals. Interestingly, post-mortem examination did not reveal any abnormal inflammatory response in the tissues examined. The fact that C6D4 inhibits lung cancer metastasis in this model indicates its potential as a treatment to prevent lung cancer metastasis. Because the mechanism of this antibody in cancer likely involves inhibiting the function or development of immunosuppressive Treg cells, C6D4 can have broad applications to any number of cancers where Treg cells play an immunosuppressive role.

The effect of C6D4 was also evaluated with respect to tumor growth and tumor immune response. From the resected LLC.1 primary tumors in mice that received two injections of isotype control (B5, which only cross reacts with human and not mouse b8) or C6D4 (which cross-reacts with mouse and human), the primary tumor weights were recorded and dimensions measured. The tumors were enzymatically disaggregated and immune cells isolated and counted. Flow cytometry was performed and tumor infiltrating immune cells separated from tumor cells using Percoll gradient centrifugation. FIGS. 30A-F is one of three experiments with similar results (remaining data not shown). In each experiment, n was greater than, or equal to, 10 in each test group.

Example 5. C6D4 Effects on Metastatic Disease Using a Melanoma Disease Model

Figure 31:
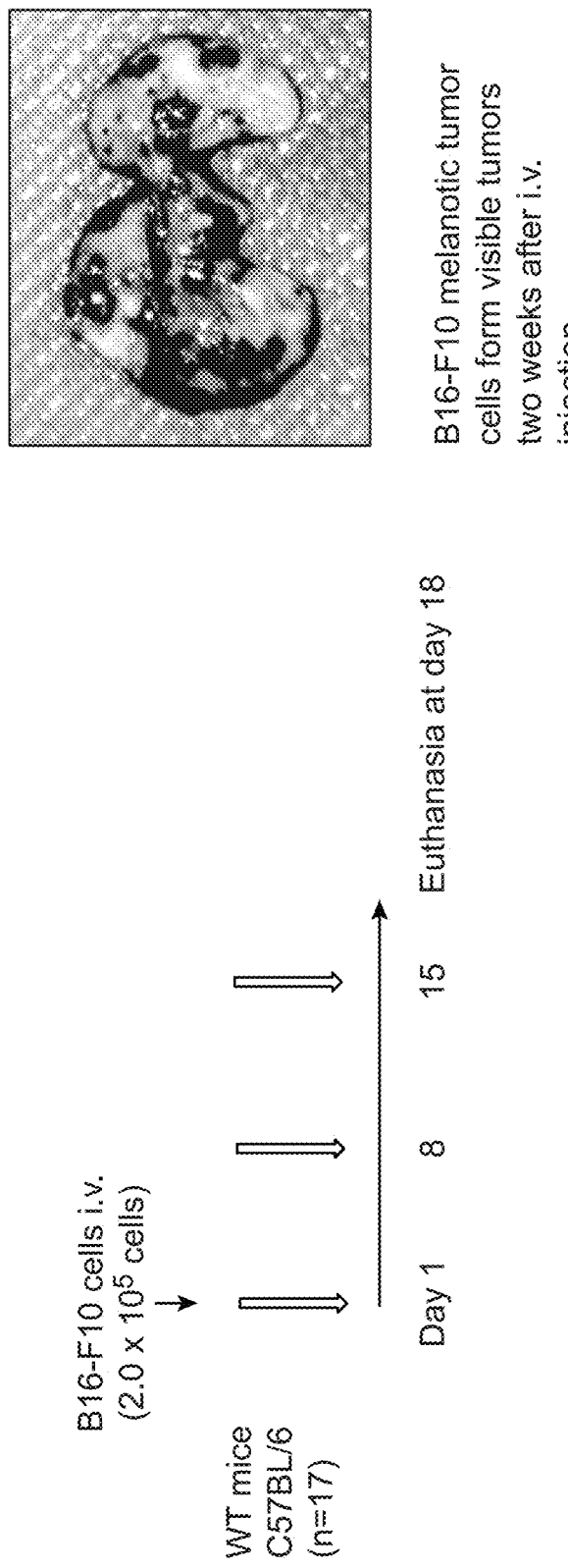
FIG. 31 shows a mouse model for evaluating metastatic disease using B16-F10 tumor cells. The B16-F10 highly metastatic tumor cell line is syngenic to the host C57B/6 strain. This line does not express integrins αvβ6 or αvβ8. The B16-F10 was transfected with murine itgb8 and after selection and sorting expresses surface αvβ8 at high levels. When injected intravenously via the tail vein, visible lung metastases appear by 14 days.
Figure 32A:
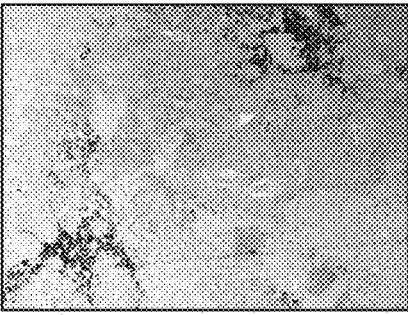
FIGS. 32A-H are lung adenocarcinoma samples stained with anti-b8 (FIGS. 32E-H) or anti-PD-L1 (E1L3N, Cell signaling) FIG. 32A-D. Here, it was observed that beta 8 expression inversely correlated with PD-L1 expression.
Figure 32B:
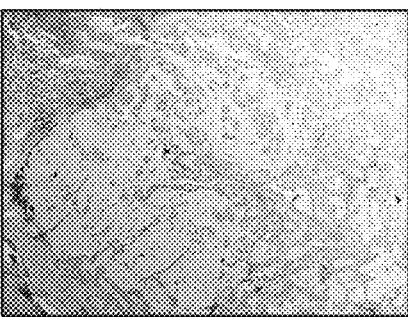
Figure 32C:
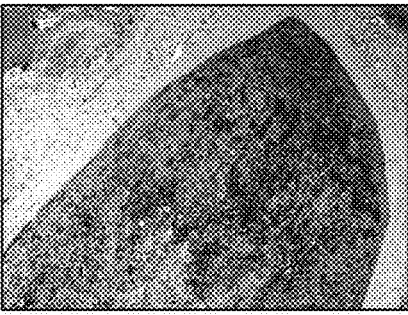
Figure 32D:
Figure 32E:
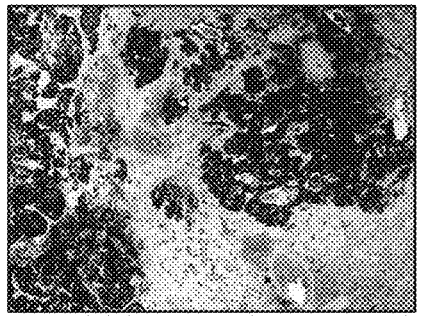
Figure 32F:
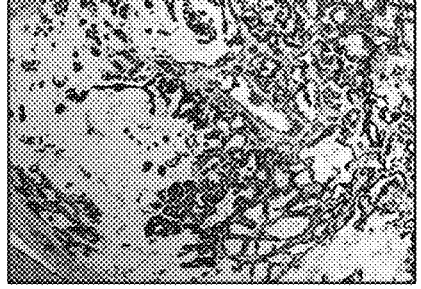
Figure 32G:
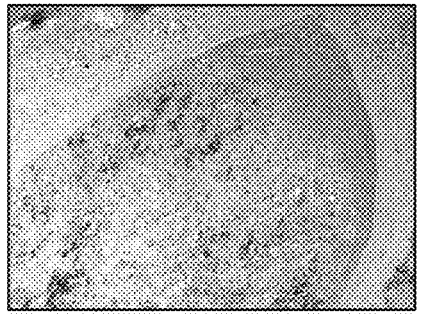
Figure 32H:
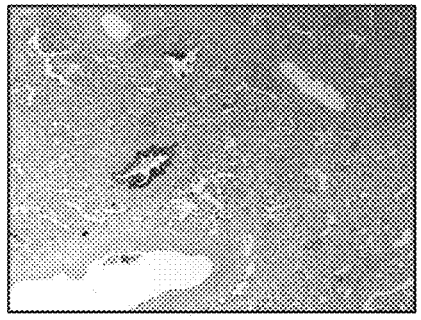
Figure 33B:
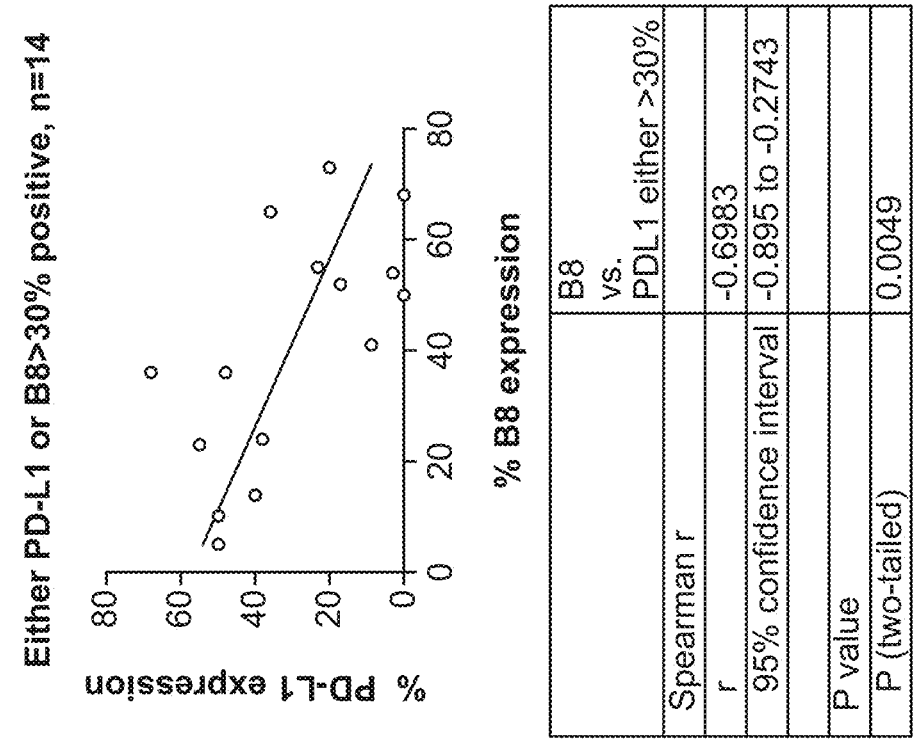
FIG. 33B shows in all cases that stained at least 30% for beta 8 or PD-L1 were grouped together and the staining proportions were correlated.
Figure 33A:
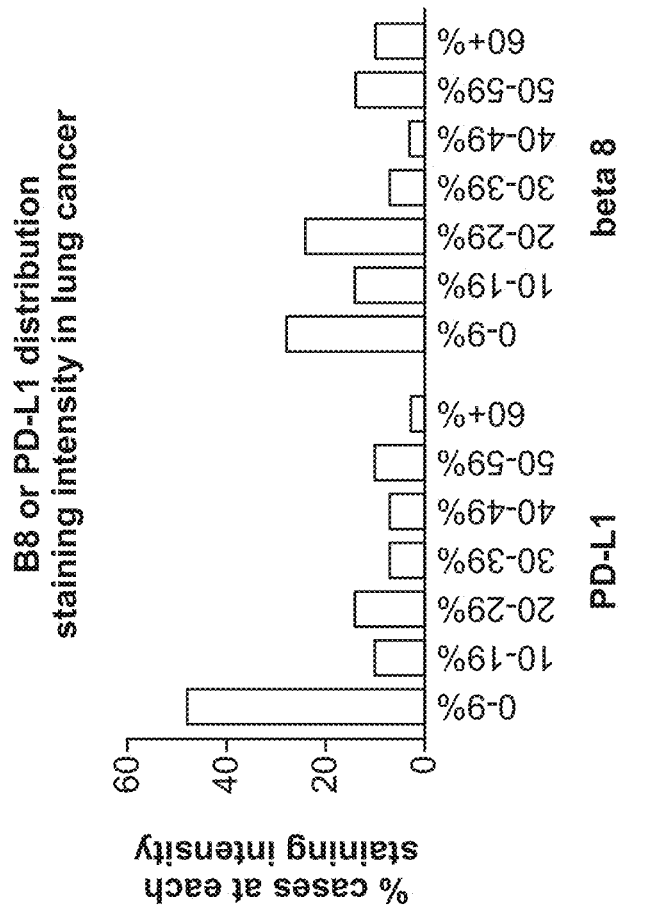
FIG. 33A shows distribution of lung adenocarcinoma samples of FIG. 32 (n=29) with staining for either PD-L1 or beta 8.
Figures 35A, 35B:
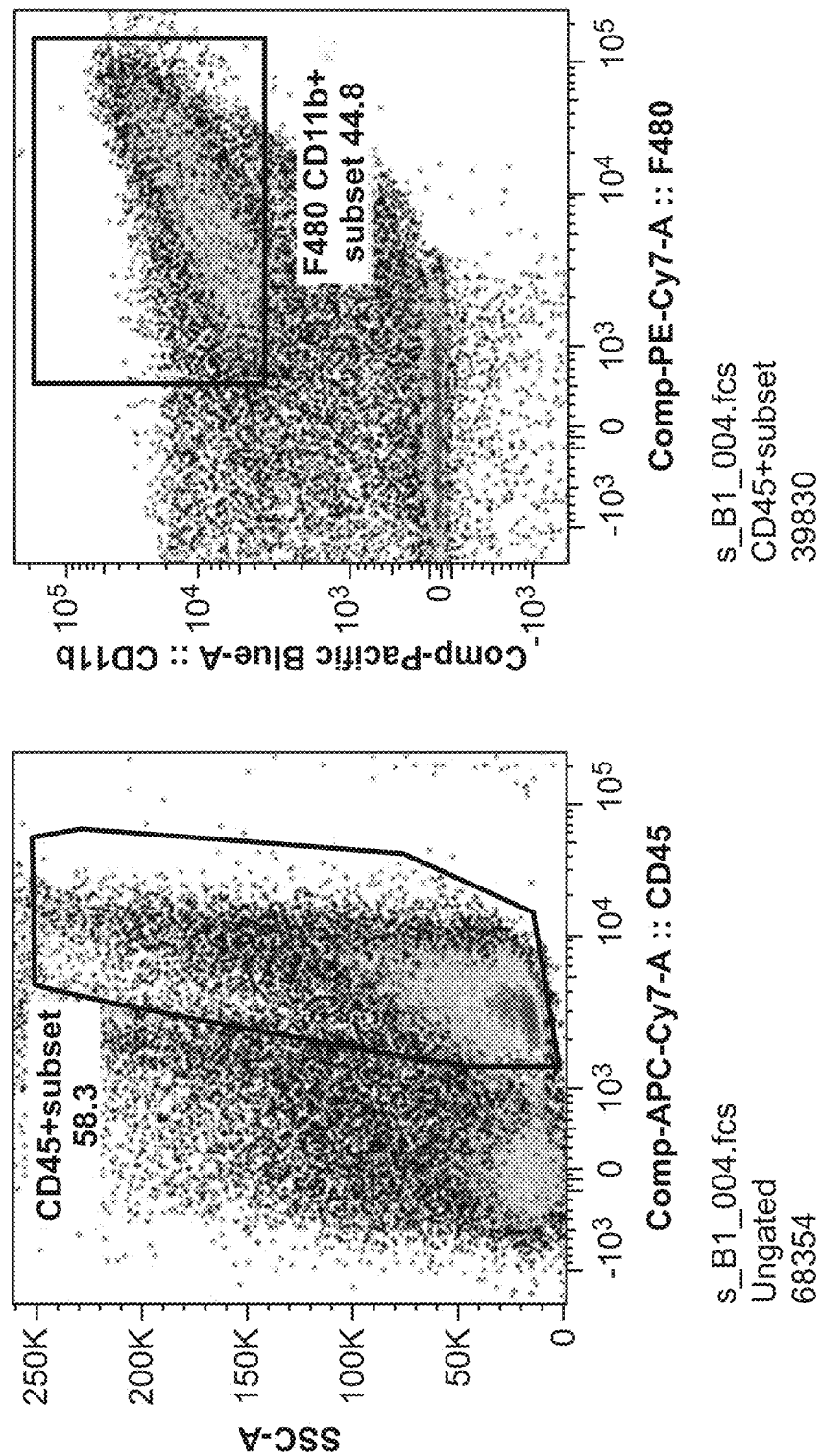
Figure 35D:
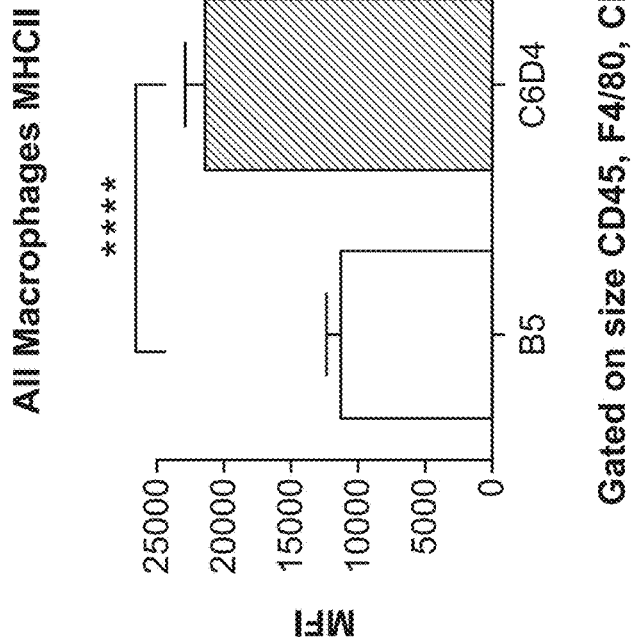
Figure 35C:
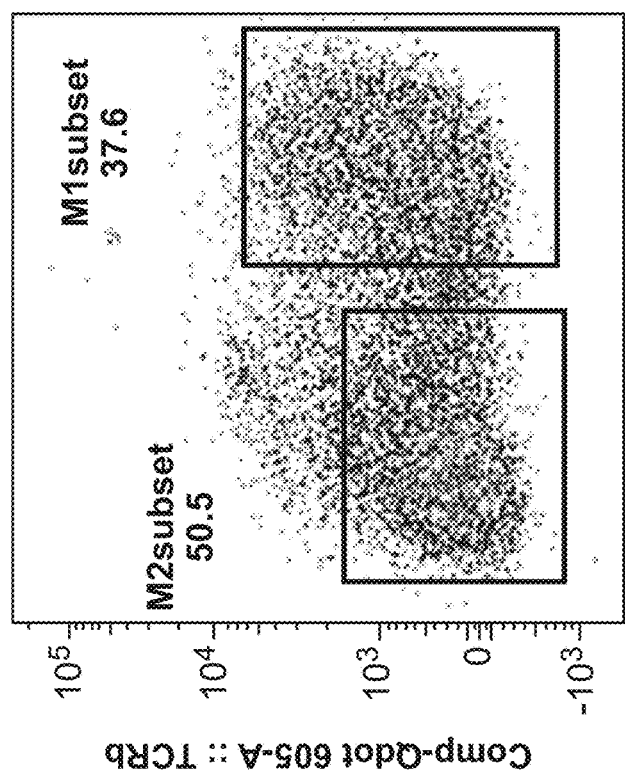
Figures 35E, 35F:
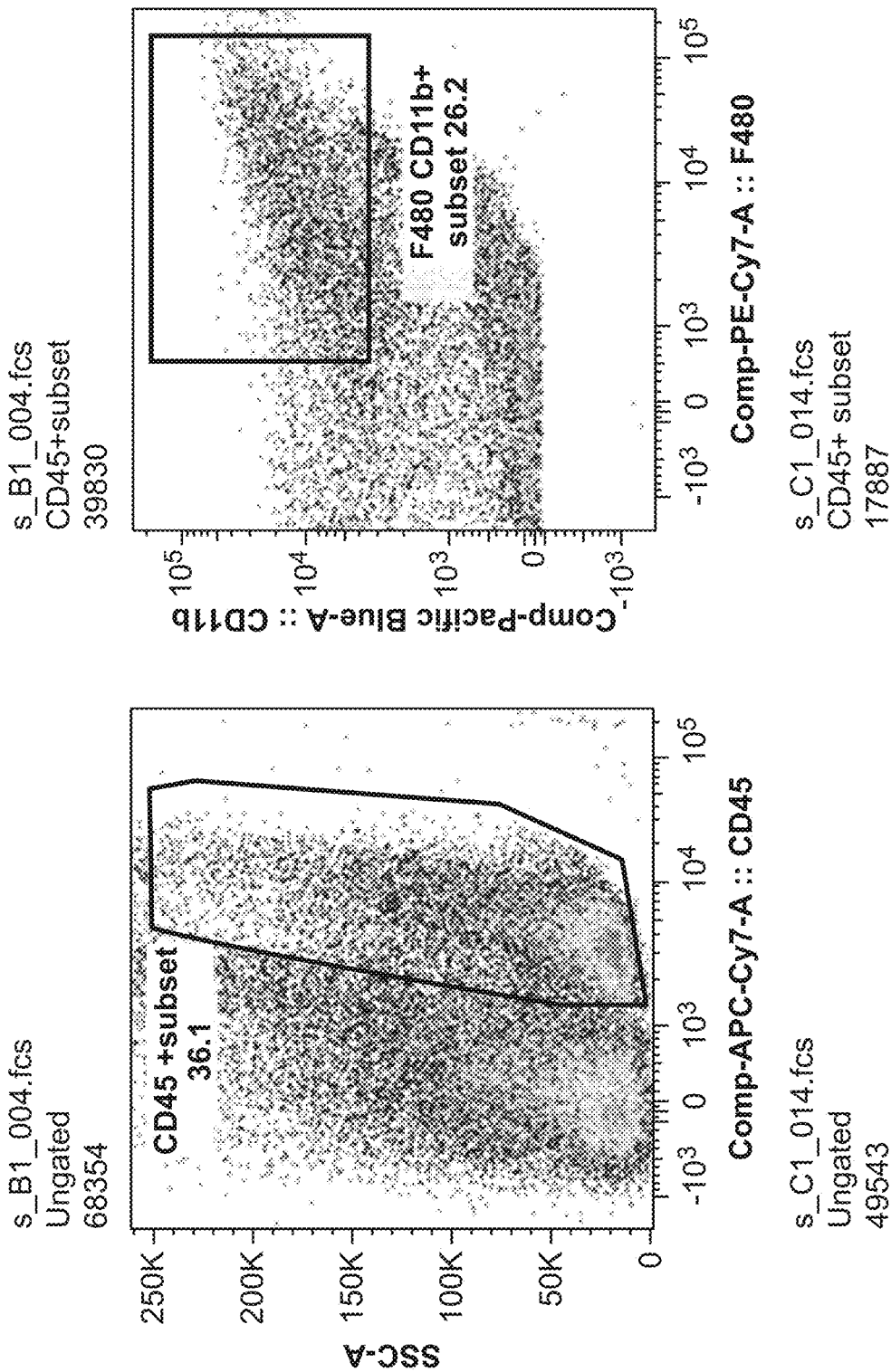
Figures 36A, 36B:
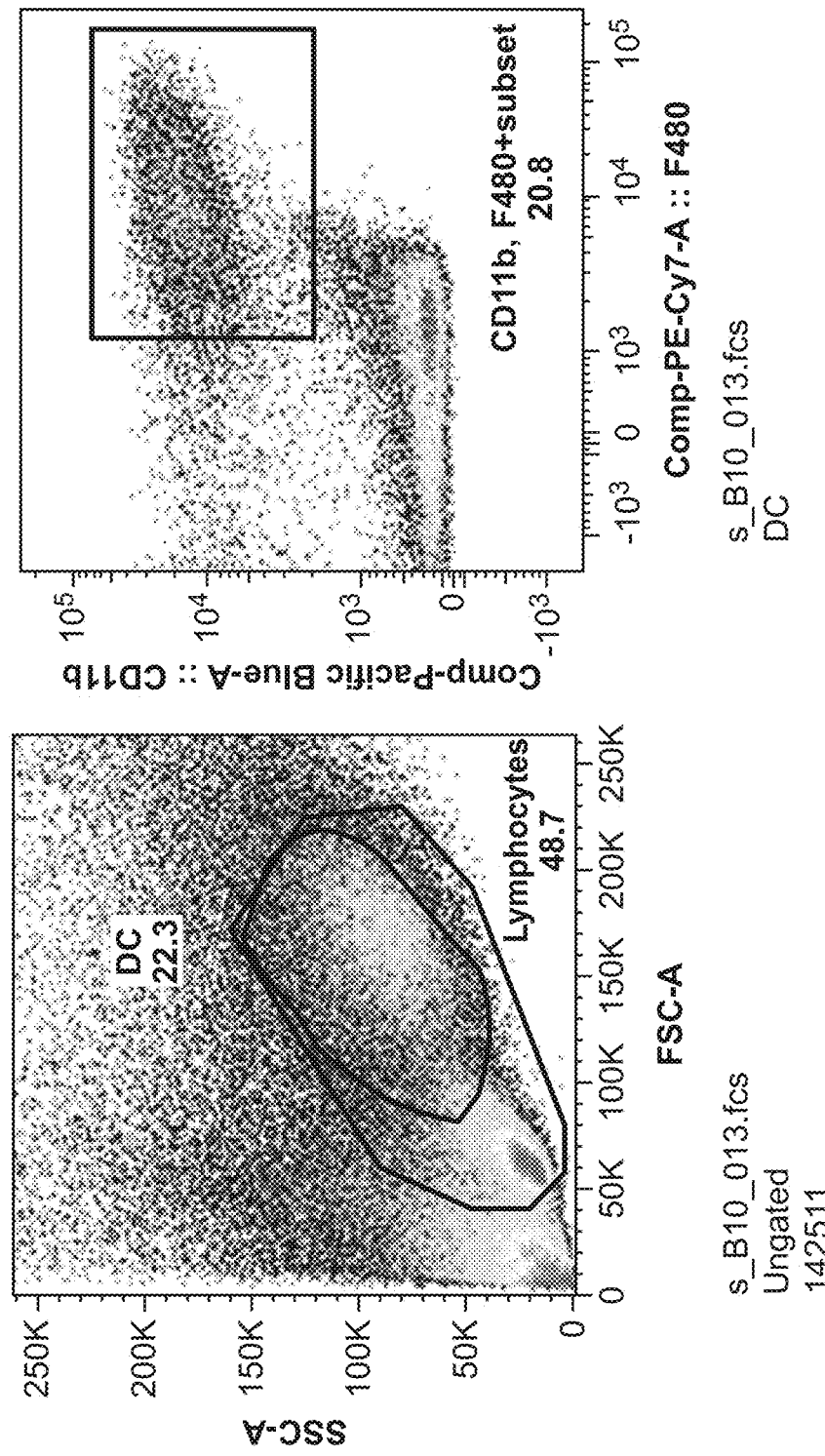
FIGS. 36A-F shows that C6D4 increases MIICII expression by tumor associated dendritic cells. Increases in MHCII by antigen presenting cells will increase antigen presentation.
Figures 36C, 36D:
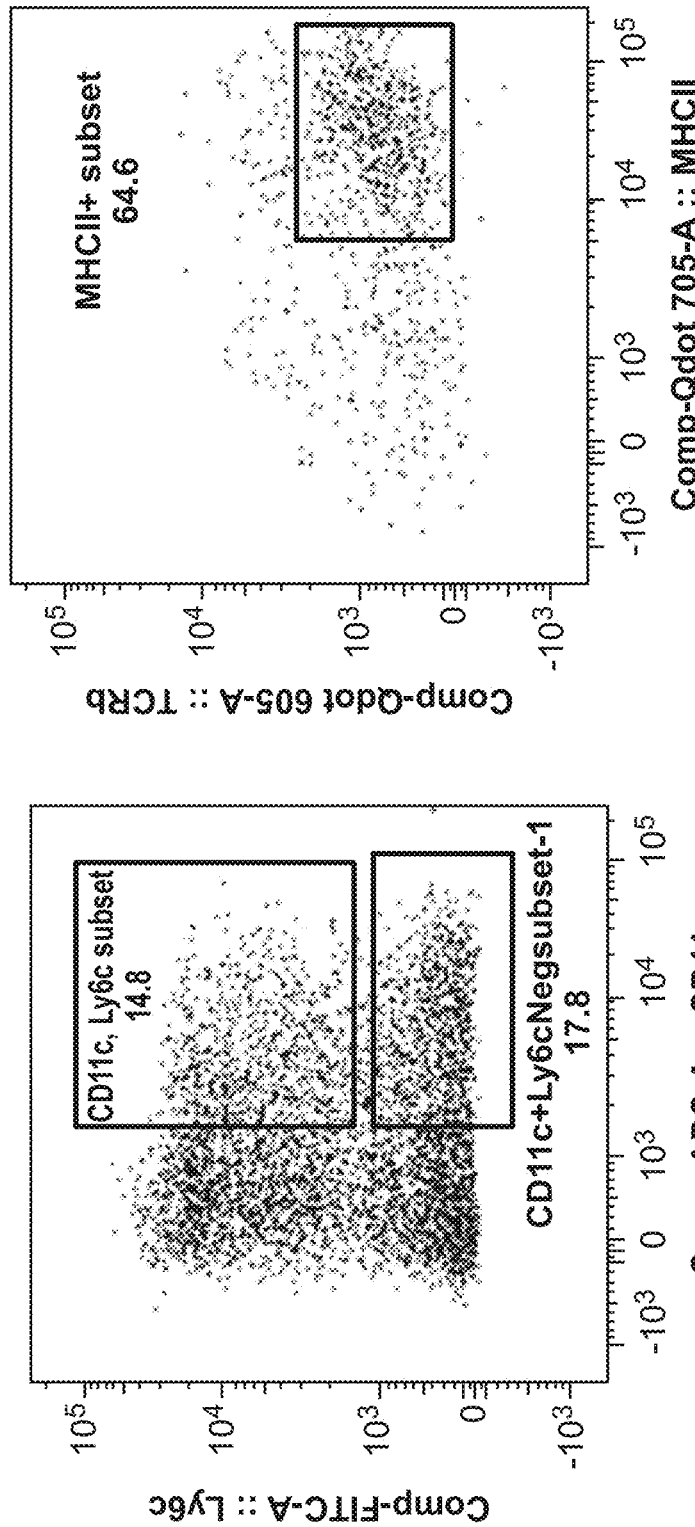
Figures 36E, 36F:
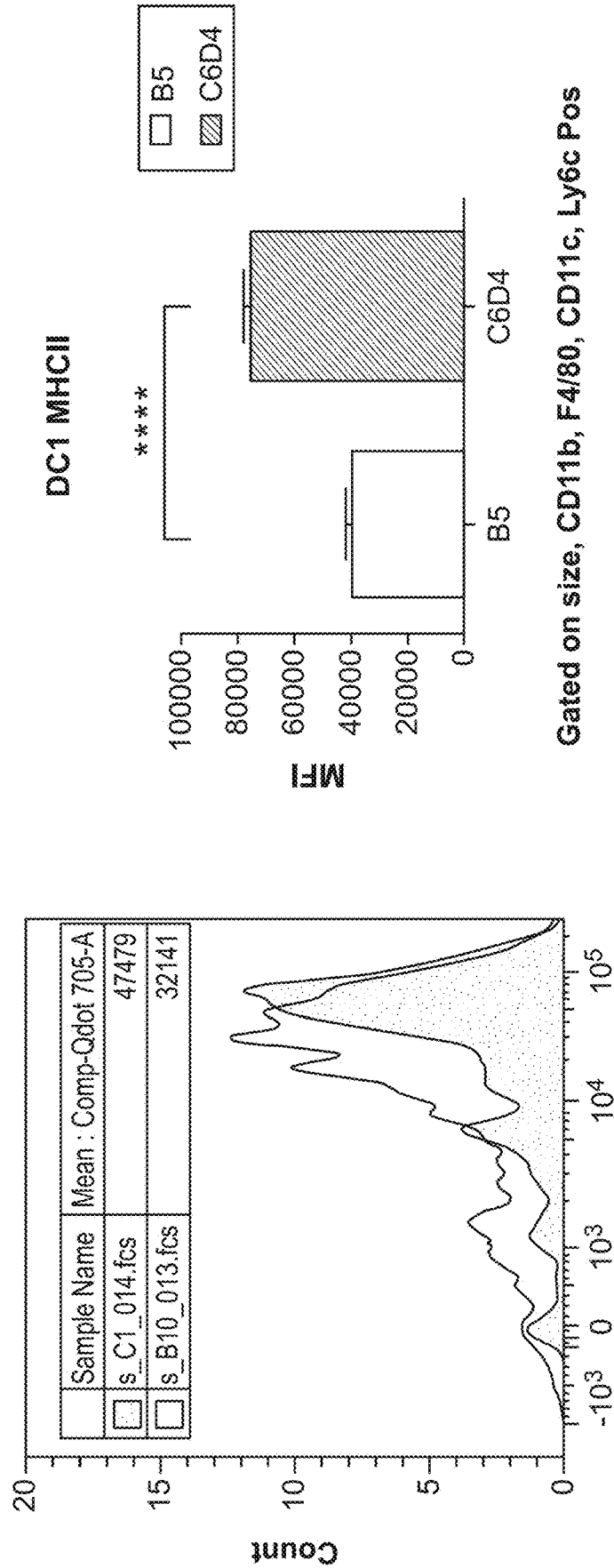
Figures 37A, 37B, 37C, 37D:
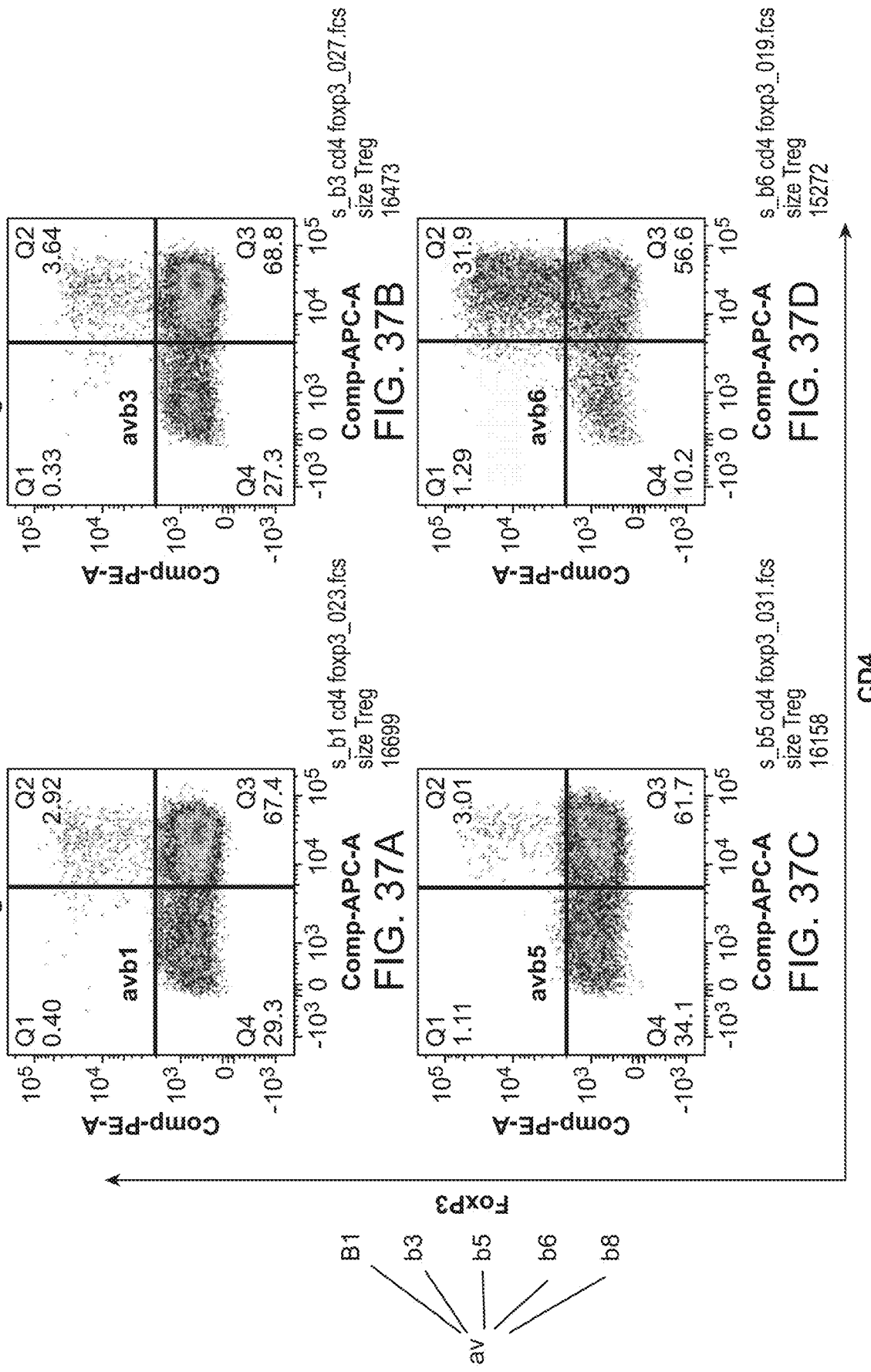

A model for the study of metastasis was tested herein that utilized the B16-F10 tumor cell line. The B16-F10 highly metastatic tumor cell line is syngenic to the host C57B/6 strain. This line does not express the integrins αvβ6 or αvβ8. The B16-F10 cell line was transfected with murine ITGb8 and after selection in G418 and two rounds of sorting, a pool of high expressing αvβ8 cells were identified. When injected intravenously via the tail vein, visible lung metastases appeared within 14 days. A schematic of the metastatic disease melanoma model described in this paragraph is provided in FIG. 31. After three injections (i.p.) of isotype control (SV5) or C6D4, both at 7 mg/kg, at days 0, 7 and 14, the mice were euthanized at day 18. FIG. 34A shows photographs of representative lungs in anterior and posterior views; visible lung metastases were counted and the total lung surface area involved with metastases was assessed. FIG. 34B shows the total number of metastases and FIG. 34C shows the percentage of total lung surface area involved in metastatic melanoma.

Example 6. Modeling of C6D4 Effects on Hepatitis B Infection and Disease Outcome Because the hepatitis B virus (HBV) does not infect mice, research has typically focused on using transgenic and knockout mouse models to study HBV immunity. In this model, viral antigens in the liver are exposed to an immune system that is not immunologically tolerant, and that has not been previously exposed to HBV. The goal is to mimic the immunologic events that would normally occur during primary HBV infection. In addition, this model permits manipulation of the immune system that is exposed to the virus, to be able to identify and dissect the cells, cytokines, and chemokines contributing to chronic hepatitis or disease resolution.

To generate the model, the resident (tolerized) immune system of the HBV-transgenic mice is ablated by backcrossing to immune-deficient strains (Mombaerts et al. (1992) *Nature* 360:225 and Mombaerts et al. (1992) *Cell* 68:869). This breeding strategy generates animals expressing high levels of viral antigen (HBV-Env) or virus (HBV-replication) in the liver, in the absence of a tolerant immune system (Baron et al. (2002) *Immunity* 16:583). Into these mice, HBV-naive syngeneic splenocytes (the equivalent of a whole spleen) are transferred from wild-type mice to reconstitute the immune system, mimic the point of primary infection, and test the importance of cellular and soluble mediators in HBV pathogenesis. Careful monitoring of immune responses and pathologic outcomes has revealed the utility of this model in mimicking or modifying acute and chronic HBV infection (Publicover et al. (2011) J. Clin. *Investigation* 2011:1154 and Publicover et al. (2013) J. Clin. *Investigation* 123:3728). In this way, the mouse model provides an experimental system to examine the reversibility of the altered immune priming that facilitates HBV persistence, and to test immune-modulatory therapeutics.

Results shown in FIG. 10 indicate that C6D4 induces HBV viral clearance in the chronic infection mouse model without causing hepatitis. In the figure, HepB surface antigen (HBSag) is a surrogate for intact HBV. Clearance of HBSag is a marker of HBV clearance. ALT is the liver enzyme monitored to measure liver inflammation and damage. The normal range of ALT in mice is 15-40. It can be seen from the data that the C6D4 antibody promoted HBsAg clearance in three of four chronic HBV model mice.

Example 7. Construction and Characterization of Composite Antibody 4F1F9

A yeast display scFV library was created using V-genes from hybridoma clones 6B9 and 4F1, a new clone 6B9.1 was selected from this library, then another yeast display scFV library was created using the V-gene of 6B9.1 and random mutagenesis, sixteen affinity-matured variant from this second library were characterized in terms of binding affinity and two clones C4 and D10 were transformed in to rabbit IgG format, both reacts weakly with human β8 in formalin-fixed paraffin-embedded tissue. A third mutagenic scFV library was then created from the variable regions of these two antibodies and inserted in a phage display vector and displayed as scFv on the phage surface (FIG. 11A-B). The induced phage library was screened against immobilized paraffin-embedded human αvβ8. Multiple rounds of selection were carried out, and fifteen phage clones were characterized in detail before the final clone F9 (FIG. 11A-B) was picked and transformed into IgG format for in vitro characterization.

Clone F9 in the IgG format was found to work efficiently in formalin-fixed paraffin-embedded tissues. The clone can be suitable for use as a companion diagnostic, for example to determine tumors expressing αvβ8 or infiltrated by immune cells expressing αvβ8 (i.e. dendritic cells, Treg cells), as a bioimaging reagent for measuring β8-specific tumor uptake and for informing C6D4 treatment decisions. The F9 antibody can also be used to detect αvβ8 in fluid or tissue lysate samples using ELISA.

Example 8. Methods to Inhibit and/or Treat H. pylori Pathogenicity

Figure 22:
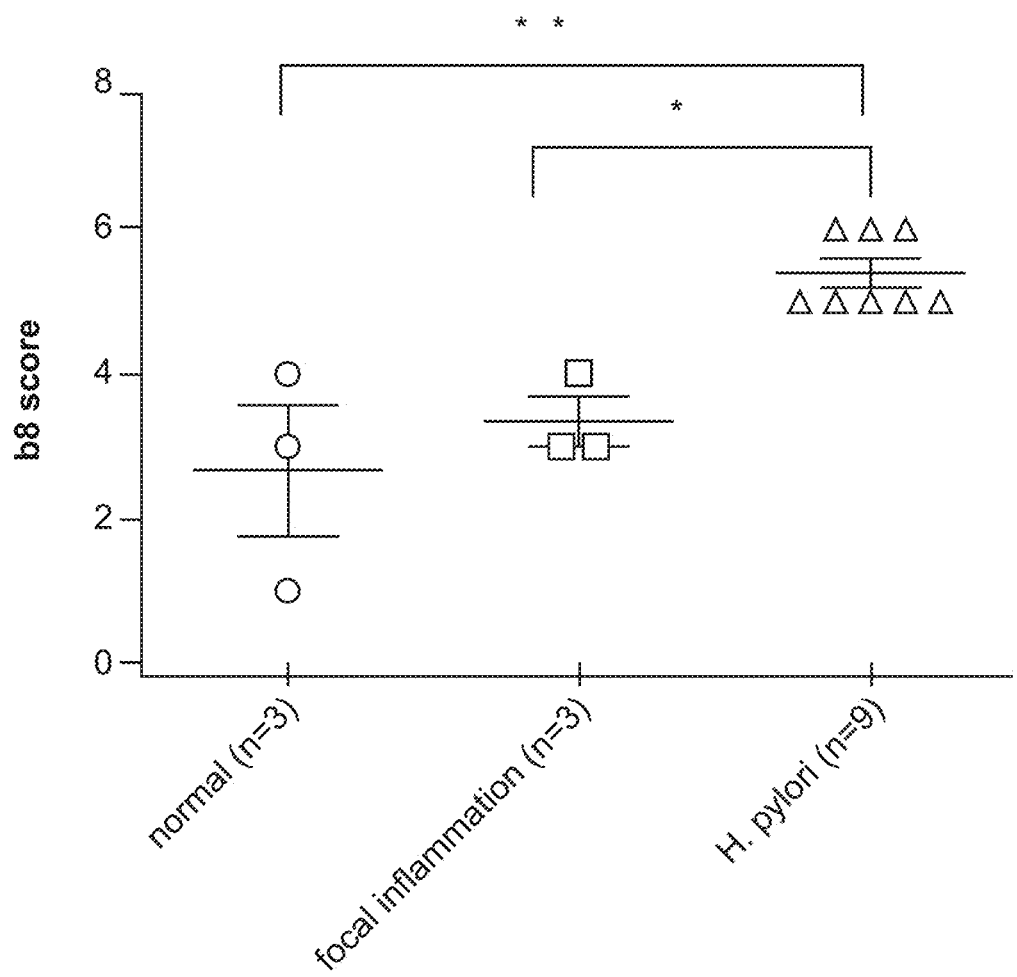
FIG. 22 shows quantification of Immunodetection of the integrin b8 subunit in formalin fixed paraffin embedded sections from patient infected with *H. pylori*, showing normal histology or mild chronic inflammation. The sections were stained with clone F9 in rabbit IgG format and detected using TSA signal amplification (Perkin Elmer). The following scoring system was devised to capture the crypto-epithelial staining, 0=no stain, 1=just contrast+, 2=scattered, 3=diffuse and stromal staining, 0=no stain, 1-just contrast+, 2-scattered, 3=diffuse. Shown is a combined score and the n is shown. ANOVA with Sidak's multiple comparisons test. ** p<0.01, * p<0.05
Figure 23:
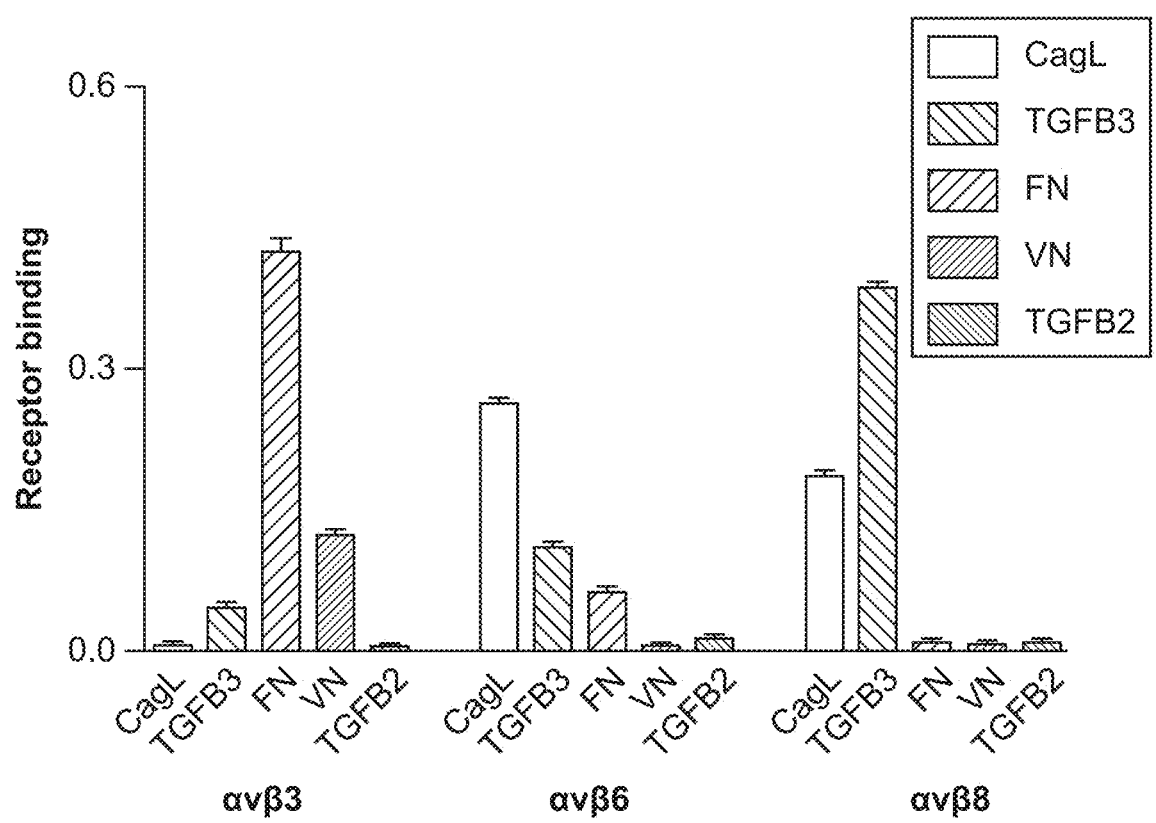
FIG. 23 shows binding assay of alkaline phosphatase (AP) αvβ3, αvβ6 and αvβ8 fusion proteins to CagL, the MAP RGD peptide derived from the TGFB3 sequence DDHGRGDLGRLK (SEQ ID NO:713), Fibronectin, Vitronectin or a MAP peptide derived from the TGFB2 sequence that corresponds to the RGD containing sequence of TGFB1 and TGFB3. All proteins are coated on ELISA plates at 5 µg/ml and input of AP receptors are normalized to AP activity. Results shown represent signal above BSA coated wells. The results show that αvβ8 (and αvβ6) binds to CagL as well as to TGFb3 peptide, whereas αvβ3 binds to FN and VN, poorly to TGFB3 and not at all to CagL. αvβ3 and αvβ8 show no binding and αvβ6 shows very weak binding to the control TGFb2 peptide. Shown are S.E.M.
Figure 24:
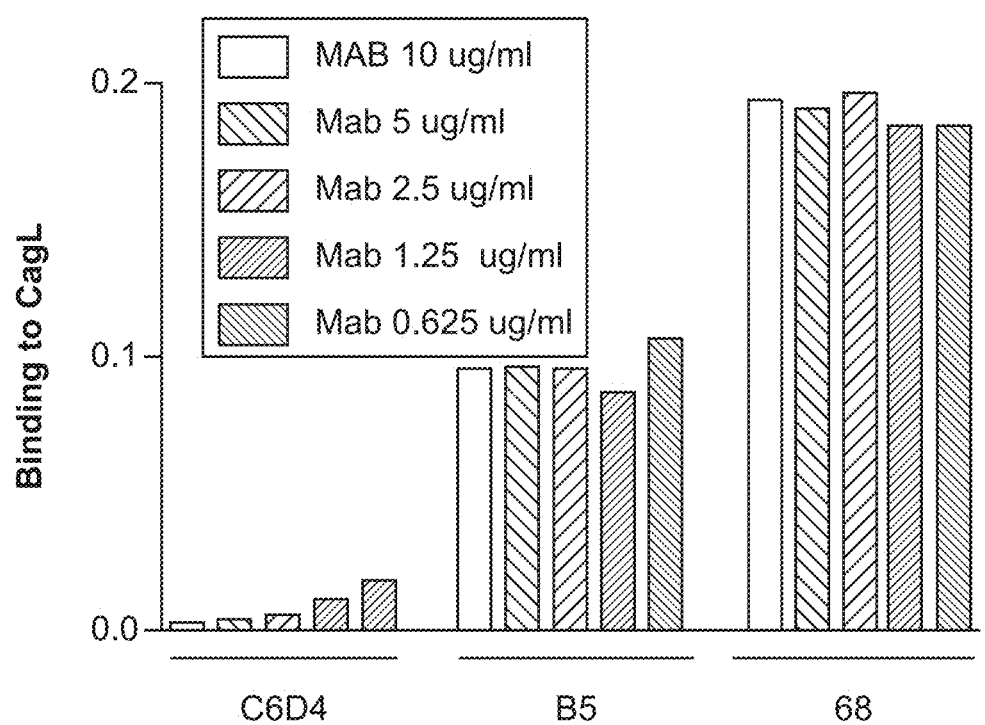
FIG. 24 shows binding assay of alkaline phosphatase (AP) αvβ8 fusion protein to CagL in the presence of C6D4, an allosteric inhibitor, B5, or a non-blocking antibody to the same epitope as B5, clone 68 which serves as a negative control. CagL is coated on ELISA plates at 5 µg/ml. Results shown represent signal above BSA coated wells. The results show that αvβ8 binding to CagL is completely inhibited by C6D4 and are partially inhibited by B5.
Figure 25:
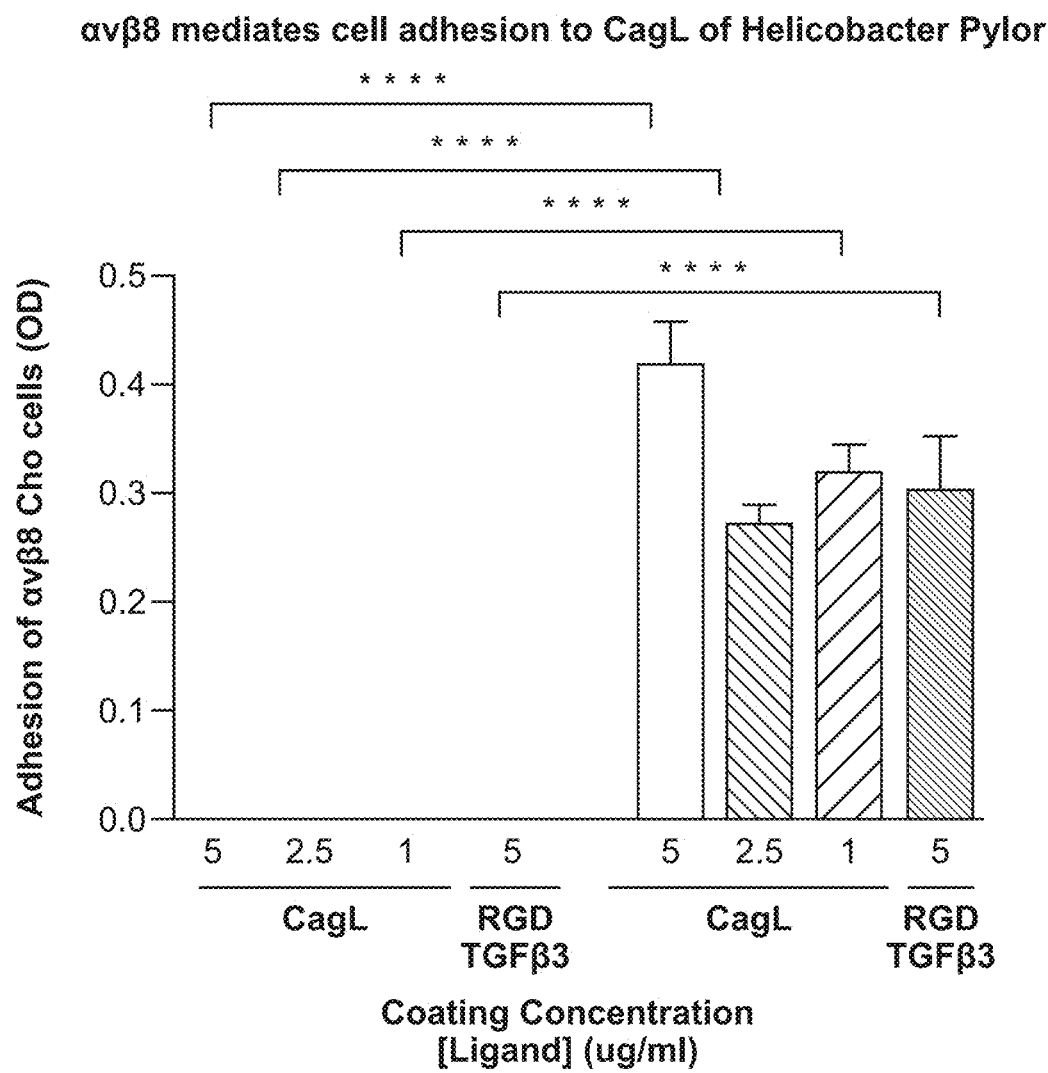
FIG. 25 shows adhesion assay of CHO Lec cells stably expressing human ITGAV and ITGB8 to recombinant CagL protein at the indicated concentrations (gift of Eric. Sundberg, University of Maryland, MD). Binding is compared to wells coated with a multiple antigen presenting peptide containing the RGD peptide derived from the TGFB3 sequence DDHGRGDLGRLK (SEQ ID NO:713), which corresponds to aa 257-268 of human TGF-b3 (NP_003230). 50×10^3 cells were allowed to attach to the wells for 30 min at RT. Unbound cells were washed off with PBS. Results were presented as stained cells detected after staining with crystal violet (OD590). Results shown represent signal above the nominal binding of mock transfected CHO Lec cells to CagL or TGFB3 peptide coated wells (5 µg.ml). The results show that αvβ8 mediates cell adhesion to CagL as well as to TGFb3 peptide. Shown are S.E.M. Significance was determined by ANOVA and Sidak's multiple comparison test. ****=p<0.00001
Figure 26:
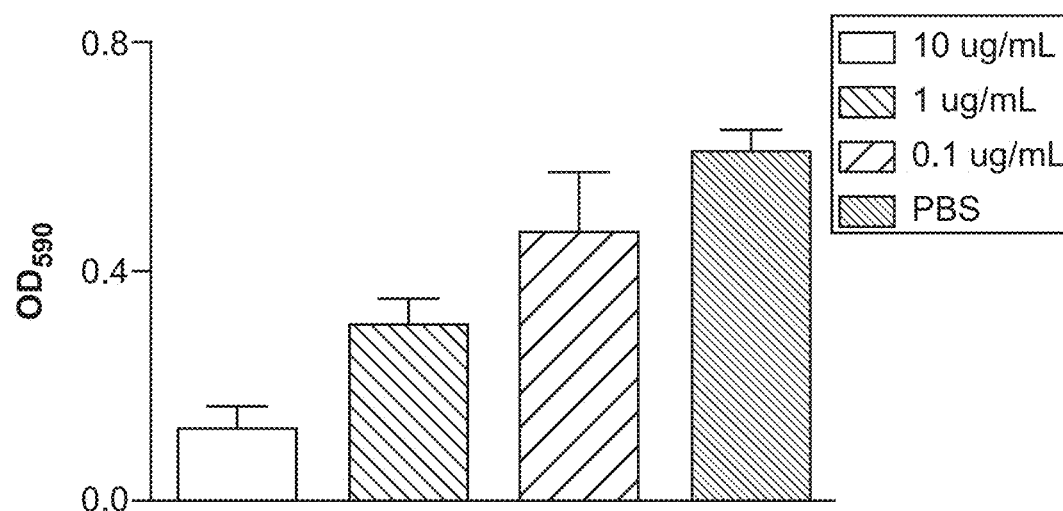
FIG. 26 shows adhesion assay of CHO Lec cells stably expressing human ITGAV and ITGB8 to the TGF-b3 RGD MAP peptide (DDHGRGDLGRLK (SEQ ID NO:713)) (coating concentration 5 µg/ml). 50×10/\3 cells were pre-incubated with cagL at the indicated concentrations of CagL vs PBS control for 15 min at RT and then the cells allowed to attach to the wells for 30 min at RT. Unbound cells were washed off with PBS. Results were presented as stained cells detected after staining with crystal violet (OD590). Results shown represent signal above the nominal binding of mock transfected CHO Lec cells to TGFB3 peptide coated wells (5 µg/ml). The results show that αvβ8 mediates cell adhesion to CagL is RGD dependent. Shown are S.E.M. N=3
Figure 27:
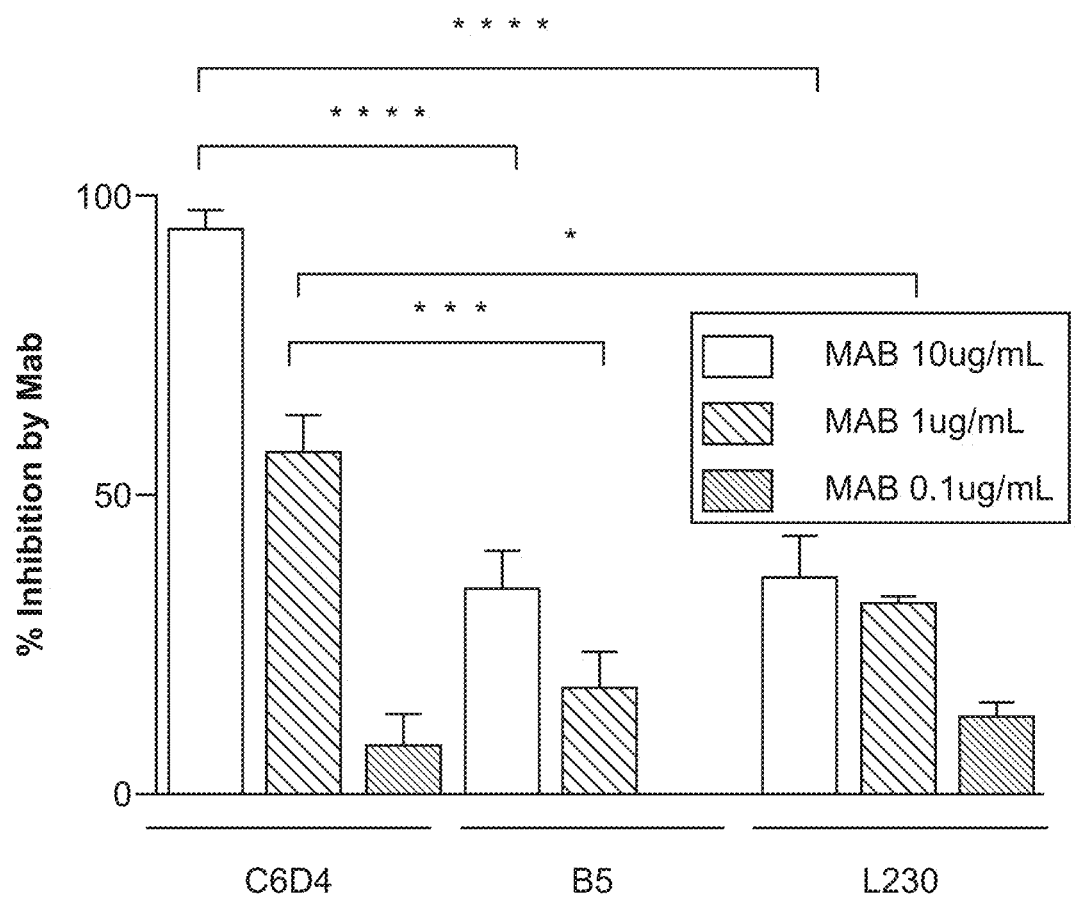
FIG. 27 shows adhesion assay of modified Chinese Hamster Ovary Cells (CHO Lec) cells stably expressing human ITGAV and ITGB8 to recombinant CagL protein at 5 µg/ml coating concentration, 50×10/\3 cells were mixed with the Mabs at the indicated concentrations and allowed to attach to the wells for 30 min at RT. B5 is a previously described allosteric inhibitor of αvβ8-binidng to TGF-β and L230 is a previously described anti-av blocking antibody. Unbound cells were washed off with PBS. Results are presented as stained cells detected after staining with crystal violet (OD590). Results shown represent % inhibition relative to the control binding defined by binding in presence of an isotype control antibody (anti-SV5) at the same concentration. Shown are S.E.M. Significance was determined by ANOVA and Sidak's multiple comparison test. **=p<0.00001, * p<0.001, *<0.05. The results show that C6D4 more efficiently blocks αvβ8 mediates cell adhesion to CagL than B5 or L230.

The bacterium Helicobacter pylori (H. pylori) infects the stomachs of approximately half of the world's population and is associated with peptic ulcer disease, gastric carcinoma and gastric lymphoma (MALToma). The pathogenicity of Helicobacter pylori is linked to a type IV secretion system and the cytotoxicity-associated gene pathogenicity island cagPAI. The cagPAI proteins are transcribed from a 40 kb stretch of H. pylori DNA encoding ~31 genes of which one, cagL, contains an RGDL integrin binding motif. This RGDL motif is thought to act as a receptor for integrins so that the H. pylori pilus can interact with gastric epithelial cells and then penetrate the cell membrane and the oncogenic toxin cagA can be injected into the cell (see Kwok, et al, Nature, 2007449, 862-866, and Barden, et al, Journal of Molecular Biology, 2015, 427 (6) Part B, 1304-1315). We have used the anti-β8 clone F9 to stain human stomach biopsies and have found that the integrin αvβ8 is expressed by gastric crypt epithelial cells and this expression is increased in patients with chronic active gastritis due to H. pylori infection (see FIGS. 21 and 22). The ectodomain of integrins αvβ6 and αvβ8, but not other RGD-binding integrins (αvβ1, αvβ3, αvβ5 and a5β1) have been shown to preferentially bind to CagL via an RGDL dependent mechanism (see Barden, et al, Gastroenterology, 2010, 138(3). Previously, it was thought that the a51 integrin was the main CagL receptor on gastric epithelial cells (see Kwok, et al, Nature, 2007, 449 (7164): 862-6. We have found that the integrins αvβ6 and αvβ8 bind with similar efficiency to CagL while the αvβ3 integrin does not bind to CagL (See FIG. 23). The αvβ8-mediated binding to CagL can be efficiently blocked by C6D4 (See FIG. 24). The αvβ8 integrin also mediates strong cell adhesion to CagL (see FIG. 25) and CagL can compete for αvβ8-mediated cell adhesion to the TGF-β3 RGD peptide, indicating that αvβ8 binds to the RGD site of CagL (See FIG. 26). C6D4 can efficiently block cell adhesion to CagL (See FIG. 27).

Blocking αvβ8-mediated binding of CagL with C6D4 or its derivatives (i.e. IgA, monomeric or dimeric) can be used as a method to inhibit H. pylori pathogenicity (i.e. peptic ulcer disease, gastric carcinoma or MALToma) by blocking entry of the oncogenic toxin CagA. In addition, C6D4 could provide protection against H. pylori itself or from its indirect oncogenic and toxic effects by inhibiting Treg function and increasing more effective immunity against H. pylori, gastric carcinoma, and MALToma. Such effects can be predicted by findings in murine models where H. pylori immune escape has been shown to be mediated by dendritic cell-induced Treg skewing and Th17 suppression (see Kao, et al, Gastroenterology, 2010 138(3):1046-54). Because the integrin αvβ8-mediated TGF-β activation has been shown to be required for Treg development and function (see Worthington, et al, Immunity, 2015, Volume 42, Issue 5, pp. 903-915), inhibiting αvβ8-mediated TGF-β activation using C6D4 or its derivatives will protect against the oncogenic effects of H. pylori infection by enhancing immunity to H. pylori itself while simultaneously increasing anti-tumoral immunity. Another possible mechanism by which blocking αvβ8-mediated TGF-β activation with C6D4 or its derivatives could block Treg function is by inhibiting migration of Tregs to the H. pylori infected gastric mucosa. The chemokine CCL20 is a potent chemokine for Tregs and dendritic cells, which are required for Treg differentiation, and αvβ8-mediated TGF-β activation provides a major contribution to CCL20 production and function (see Cook, et al, Gut (2014), 63(10):1550-9; Brand, et al, J Biol Chem, 2015, 290(23): 14717-28, Hashimoto, et al, J Immunol 195(3):1182-90.). Therefore, treating patients with C6D4 or another anti-αvβ8 antibody alone, in combination with antibodies to other CagL binding integrins (a51, Act-1, or αvβ6, 3G9) or in combination with standard H. pylori therapy (i.e. bismuth salts, proton pump inhibitors, macrolides, amoxicillin, metronidazole) would treat not only the pathogenic mechanism of H. pylori but would enhance immunity to more efficiently eliminate H. pylori, while at the same time protecting and/or treating the malignant complications of chronic H. pylori infection.

Example 9. Construction of Composite Humanized Antibody C6D4

FIG. 46, FIG. 50, and FIG. 51, show sequence alignment of various C6D4 humanized clones. FIGS. 50 and 51 also provide heavy chain and light chain amino acid consensus sequences for the humanized C6D4 related clones. The C6D4 antibody humanization focused on the V domain framework region of both the heavy and light chain. The humanization process was performed to include three criteria:
 (1) The humanized version of antibody(HuC6D4) should have similar or improved affinity and specificity for αvβ8 as the murine version C6D4;
 (2) The final amino acid in the HuC6D4 antibody framework region should be as close as possible to the translated antibody framework region of the human germline version that was selected as the target gene family ($V_H1/V_K3$);
 (3) Production levels of the final humanized version (HuC6D4) in IgG or other format should be scalable for industry application.

We designed a potential humanized lead version of the murine C6D4 based on the chosen germline of human antibody($V_H1/V_K3$), and the humanization algorithm developed at UCSF, and other published information for antibody human drug development, with main consideration on IgG general structure, $V_H$-$V_L$ interface, IgG folding packing, surface accessibility, vernier zone impact, humanization hotspots and other risk factors.

These designed lead versions were synthesized and expressed as scFV using yeast display. The measured Kd showed an approximate 2-fold decrease from the parent murine C6D4 scFv.

Next, a random mutation based yeast scFv display library was created using the humanized lead version as the starting point, and FACS sorting performed to pick the best binders to αvβ from the displayed yeast library. Three mutant candidates (C6D4-RGD1, C6D4-RGD2 and C6D4-RGD3) were chosen for further testing in IgG format (See, for example FIG. 38C and FIG. 39).

Example 10. Characterization of Humanized C6D4 and CD64-RGD3 Binding Affinity Shown in FIG. 39 is cell surface staining experiments of $C6V_H$ expressed with either RGD1, RGD2, or RGD3 mutants (as disclosed in Example 8) as rabbit IgG. Binding to human Cho cells expressing αvβ8 was expressed as a percentage of binding of C6D4. The results show that RGD3 mutant has substantially higher relative binding to αvβ8 as compared to wildtype C6D4, RGD1 mutant or RDG2 mutant.

Figure 40:
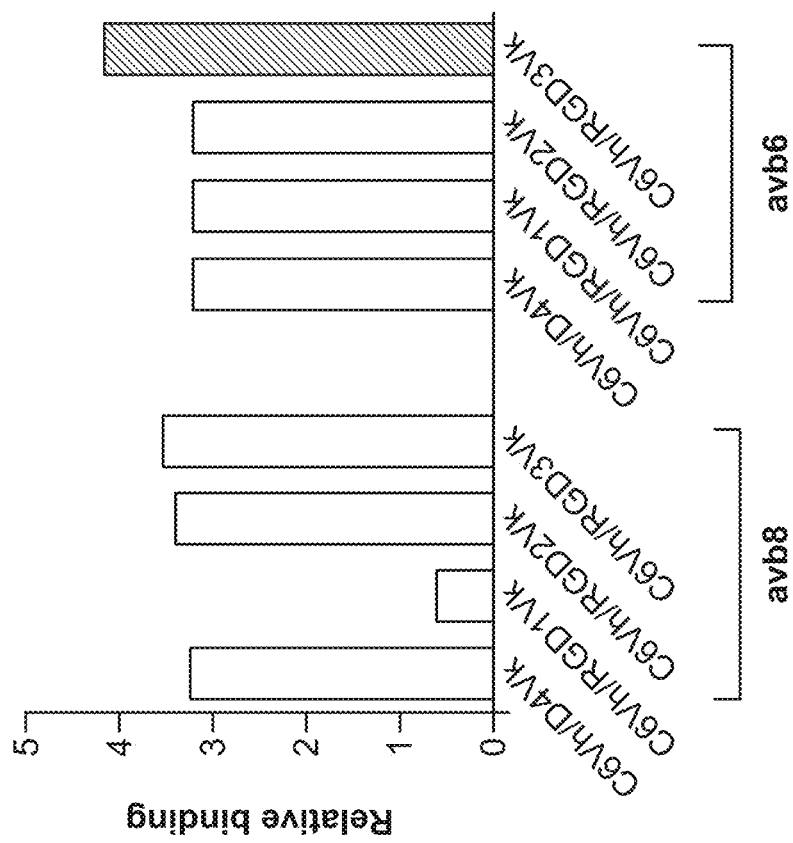

FIG. 40 shows cell surface staining experiments of $C6V_H$ expressed with either D4 Vk or RGD1, RGD2 or RGD3 mutants (as disclosed in Example 8) as rabbit IgG. Binding to Cho cells expressing human αvβ8 or SW480 cells expressing αvβ6 are shown. Relative binding is defined as staining compared to staining of non-transfected Cho or SW480 cells. The results show that the C6D4-RGD3 mutant has substantially higher relative binding to αvβ6 as compared to wildtype C6D4, RGD1 mutant, or RDG2 mutant.

Figure 41:
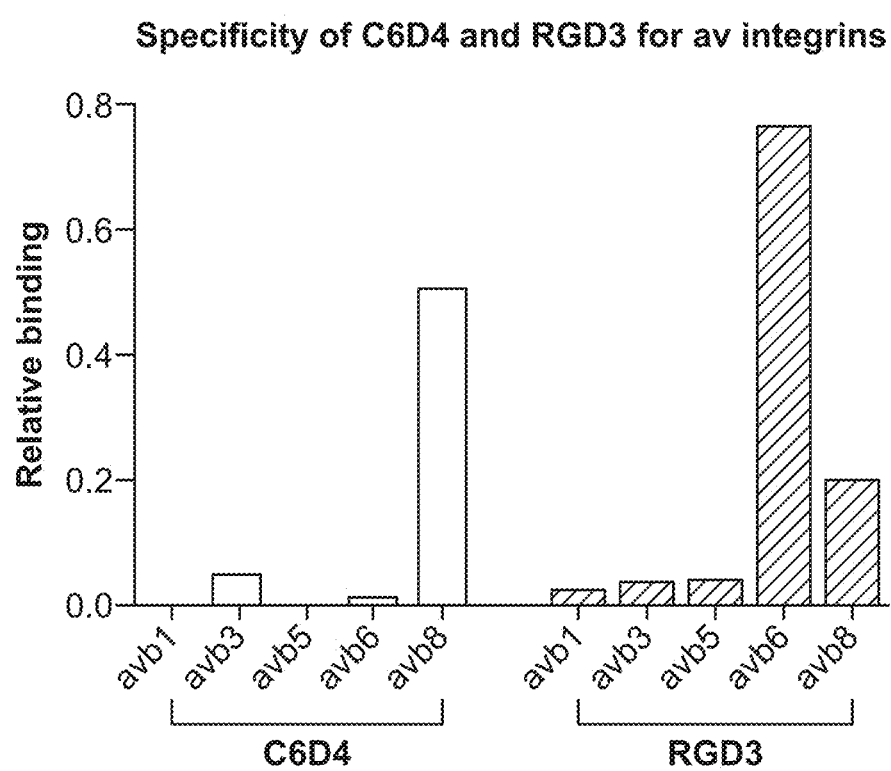
Figure 43A:
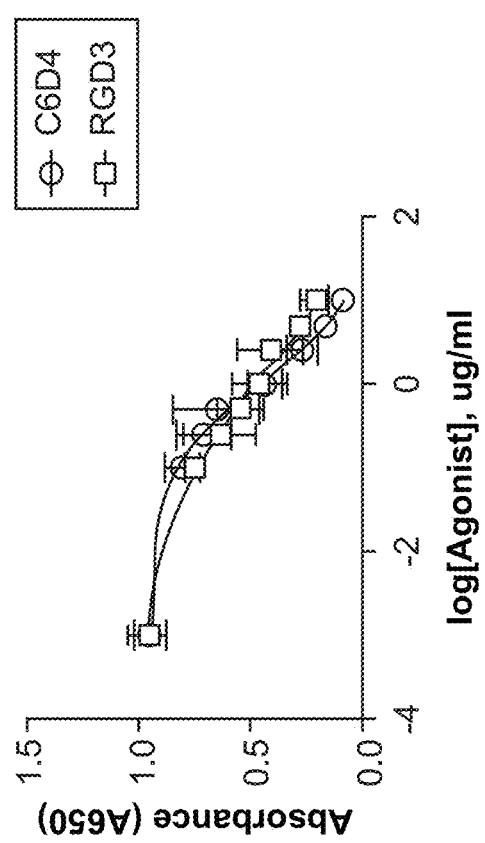
Figure 43B:
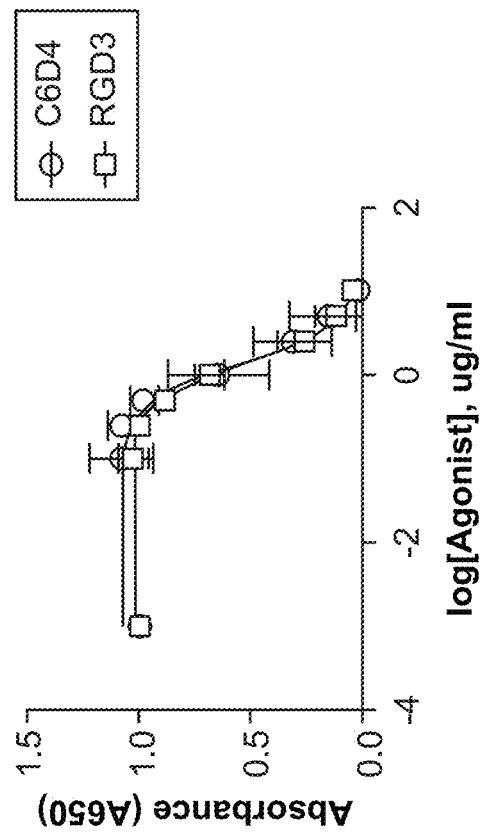
Figure 44A:
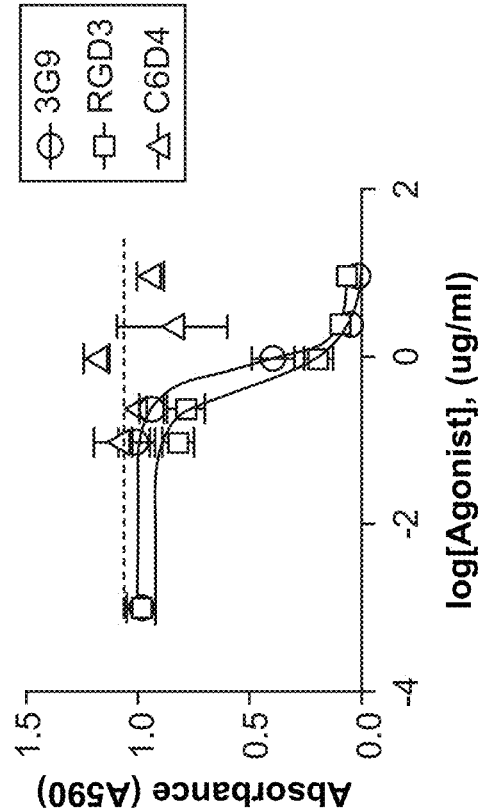
Figure 44B:
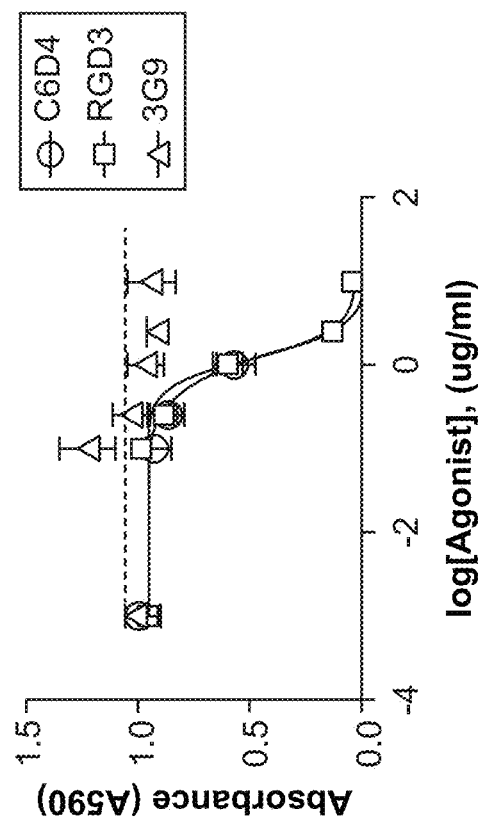
Figure 44D:
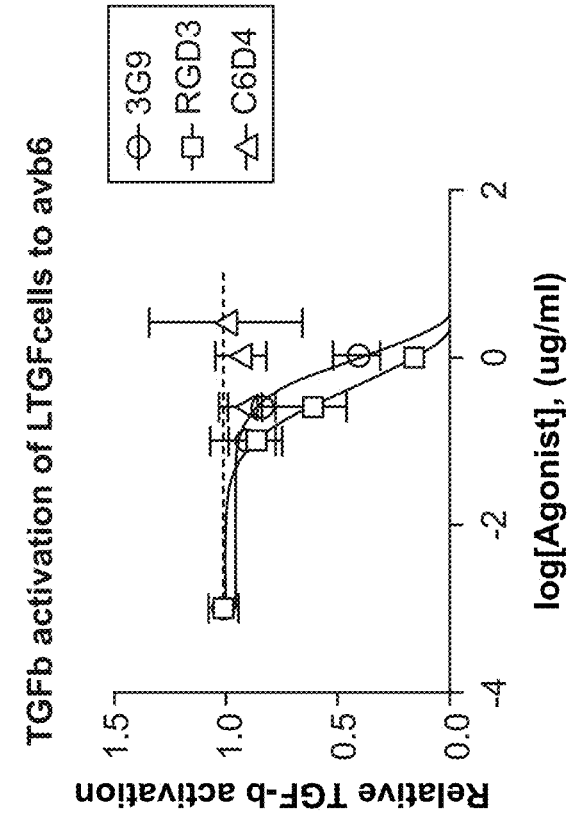
Figure 44C:
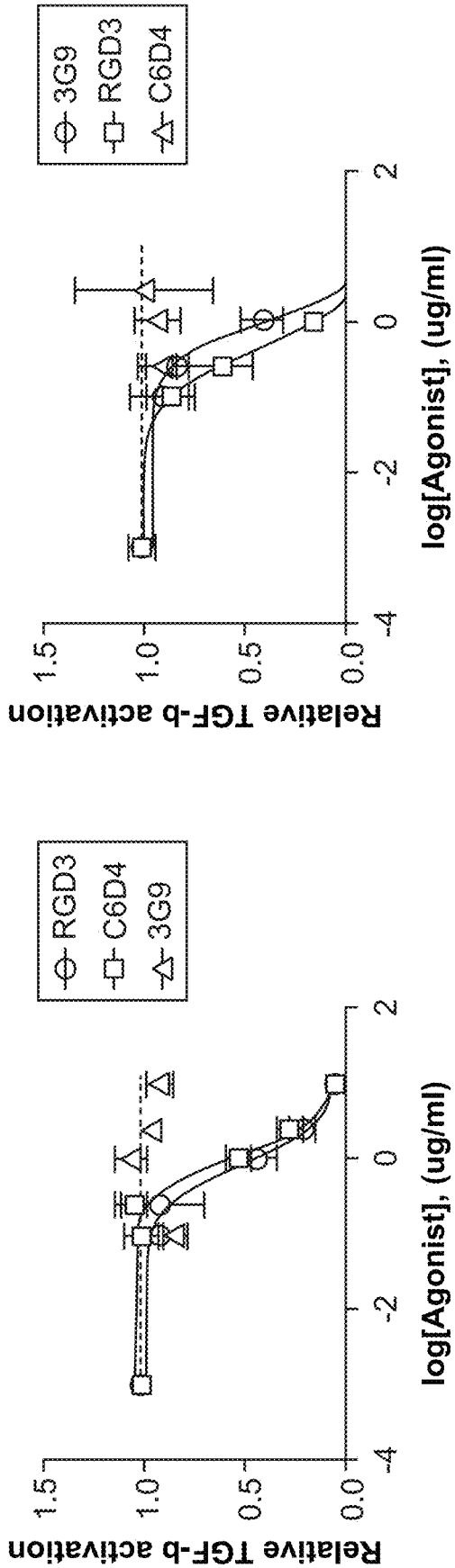
Figure 45:
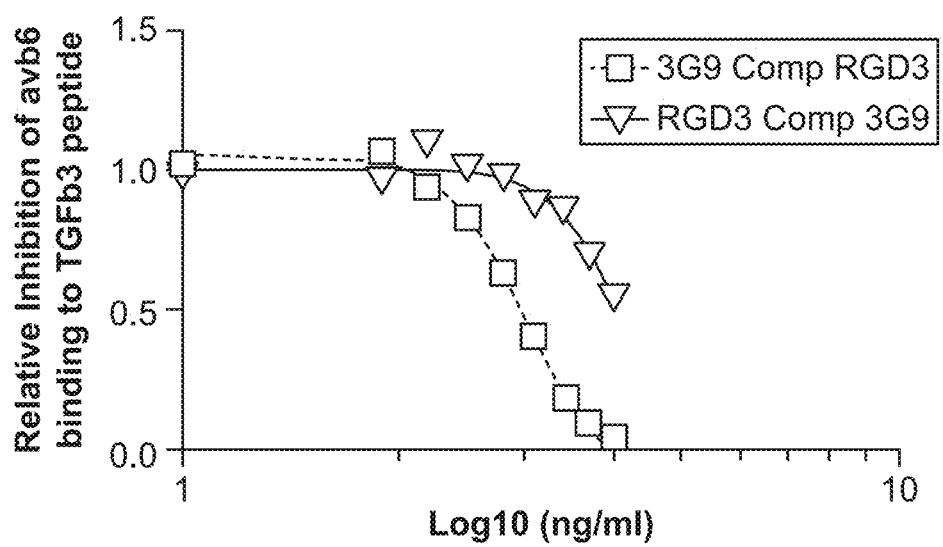

Shown in FIG. 41 is a binding experiment of $C6V_H$ expressed with either D4 Vk or RGD1, RGD2 or RGD3 mutants (as disclosed in Example 8) as rabbit IgG to various av-integrins. The integrins αvβ1, αvβ3, αvβ5, αvβ6 and αvβ8 were purchased from R&D systems. All integrins were coated on ELISA plates at 2 mg/ml, blocked with BSA, and antibodies were allowed to bind. Binding of C6D4 and RGD3 was detected with anti-rabbit HRP. The results shown are relative to control wells coated with anti-av (clone 8B8) where av-integrins were detected with another av-antibody recognizing an non-overlapping epitope (L230-biotin), followed by SA-HRP. The results show that RGD3 mutant has substantially higher binding to αvβ6, while C6D4 has higher relative binding to αvβ8.

Figure 47:
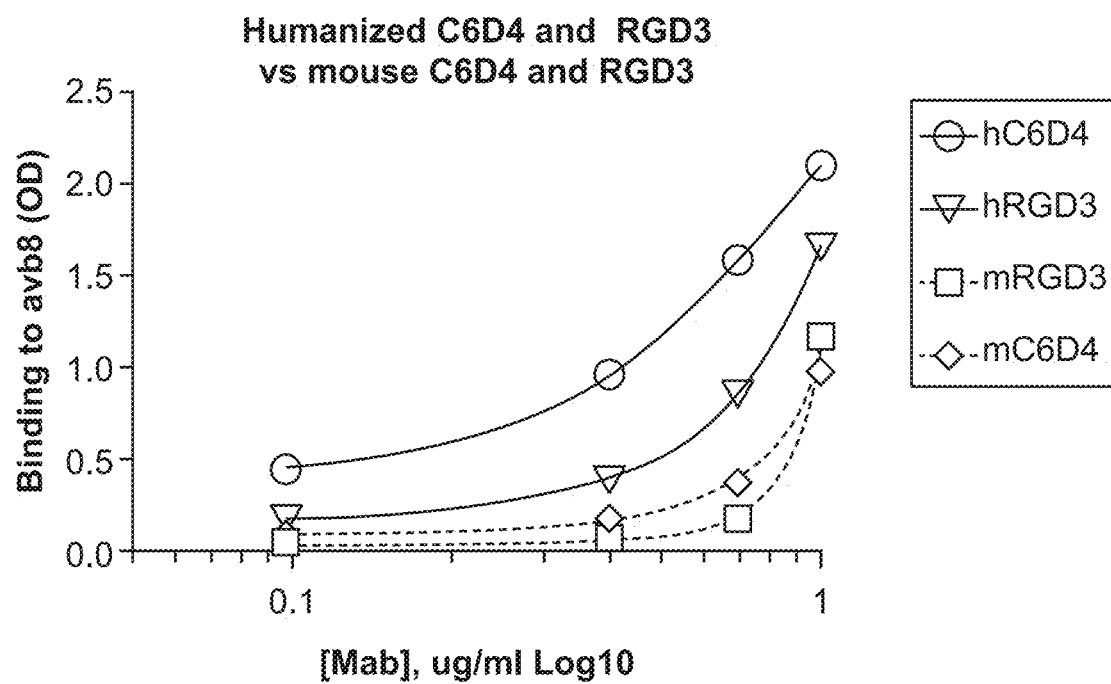
FIG. 47 shows binding assay of humanized C6D4 or RDG3 to recombinant αvβ8. Humanized C6D4 or RDG3 (Frameworks and CHI are human; hinge and CH2-3 are mouse) were immobilized on ELISA plates at the indicated concentrations. As a negative control, some wells were coated with anti-SV5 at the same concentrations. Non-specific binding sites were blocked with BSA. Recombinant αvβ8 ectodomain (0.5 μg/ml) was added to each well and after binding and washing in binding buffer (1 mM Ca and Mg), the bound αvβ8 was detected with biotinylated anti-av (8b8) and detected with SA-HRP. Results are shown as specific binding (minus SV5 control).
Figure 48A:
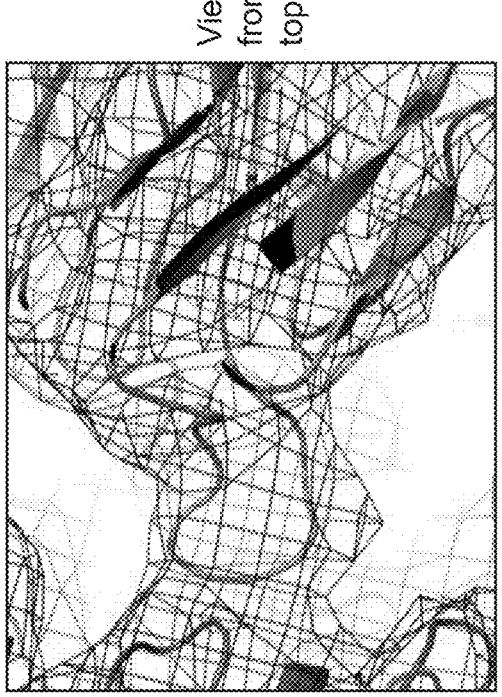
FIG. 48A-D shows superposition of C6D4/αvβ8 cartoon model with wire map of C6D4/αvβ8 (FIGS. 48A and 48C) compared to a superposition of the same C6D4/αvβ8 cartoon model with wire map of C6D4-RGD3/αvβ8 (FIG. 48B and D). The comparison of the two maps shows a different orientation of the CDR1 Vk loop of C6D4-RGD3 towards the beta8 subunit ligand binding site.
Figure 48B:
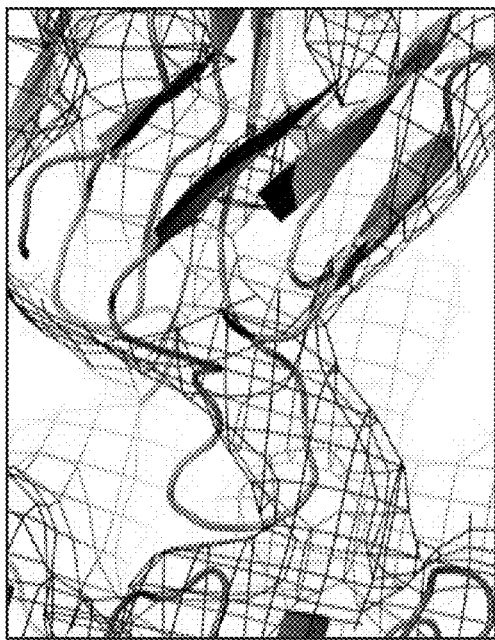
Figure 48C:
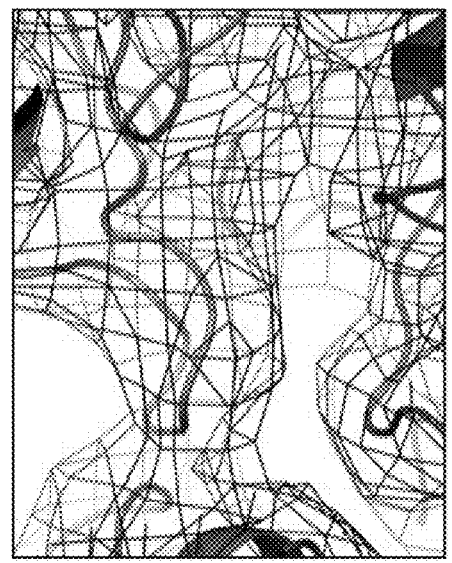
Figure 48D:
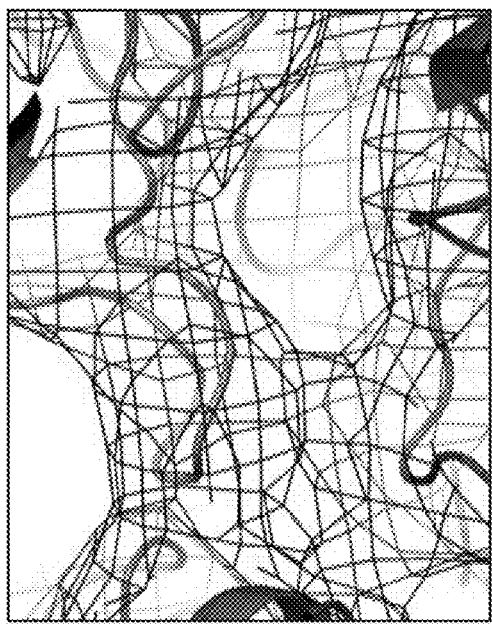
Figure 54A:
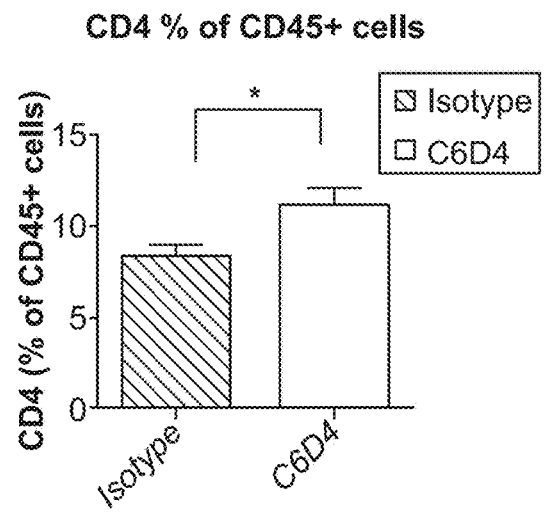
FIG. 54A-54D are graphs showing percentage of cells staining positive for various cell surface markers. Mice were injected with Lewis lung carcinoma (LLC) cells and SV5 (isotype control) or C6D4 at a dosage of 7 mg/kg once per week.
Figure 54B:
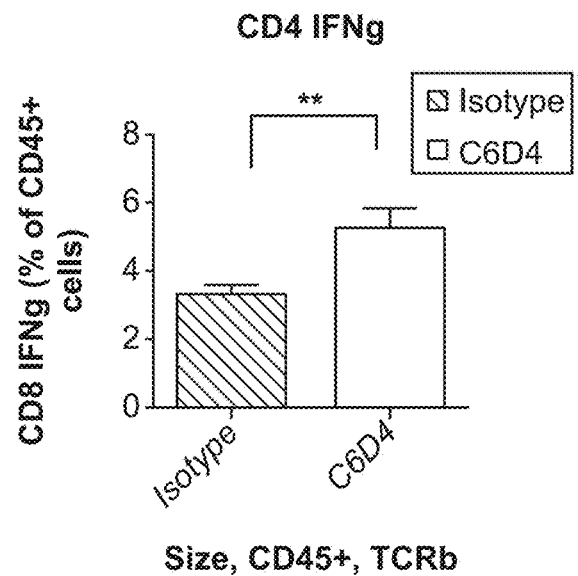
Figure 54C:
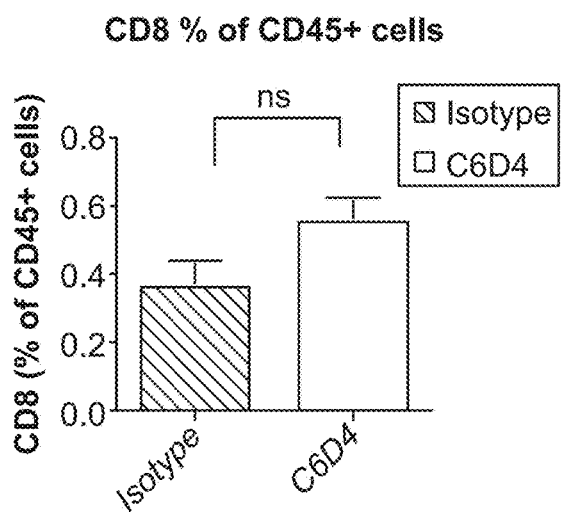
Figure 54D:
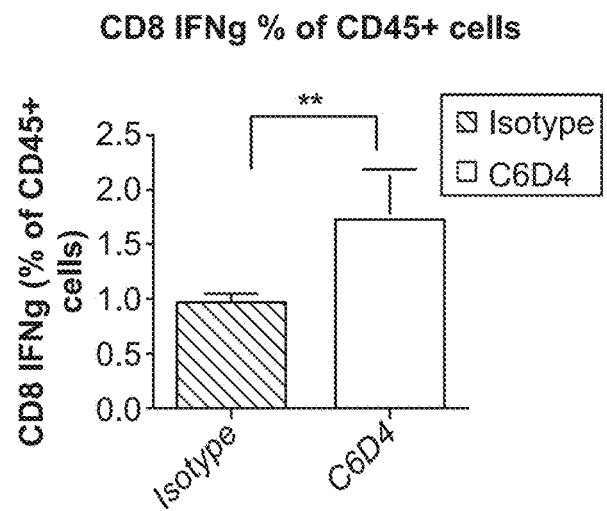

C6D4 and C6D4-RGD3 were also shown to bind avidly to αvβ8. Humanized C6D4 or C6D4-RGD3 (Frameworks and CHI are human; hinge and CH2-3 are mouse) were immobilized on ELISA plates at the indicated concentrations. As a negative control, some wells were coated with anti-SV5 at the same concentrations. Non-specific binding sites were blocked with BSA. Recombinant αvβ8 ectodomain (0.5 µg/ml) was added to each well and after binding and washing in binding buffer (1 mM Ca$^{++}$ and Mg$^{++}$), the bound αvβ8 was detected with biotinylated anti-av (8b8) and detected with SA-HRP. The results of this experiment are shown as specific binding (minus SV5 control)(FIG. 47). The results show that C6D4 and C6D4-RGD3 outperform murine C6D4 and C6D4-RGD3 antibodies by avidly binding αvβ8.

Example 11. Characterization of Humanized C6D4-RGD3 Binding Structure

As set forth in Example 3, modeling and CryoEM maps can be used to provide structural information with respect to antibody binding. FIG. 48A-D presents a map of RGD3 binding to the ligand pocket of αvβ8. The map is derived from C6D4 in complex with αvβ8 and is compared to C6D4-RGD3 in complex with αvβ8. The density map when compared with the headpiece of αvβ6 in complex with LTGFB1 shows the similarity of the position of the RGD residues of LTGFB1 with the RGD residues of C6D4-RGD3. Magenta wire represent s RGD3+αvβ8 density map, Black represents C6D4+αvβ8 density map; Gold represents C6D4 Fab; Green represents the αv subunit; Blue represents the β8 subunit.

FIG. 49 is a cryoEM map showing the CDR Vk1 loop of C6D4-RGD3 occupies the ligand binding pocket of αvβ8. Here, models of C6D4 Fab-αvβ8 (FIG. 49A) are compared with RGD3-αvβ8 map (FIG. 49B) or in overlay (FIG. 49C) based on cryoEM derived density maps. The anti-av 11D12V2 Fab was used to increase molecular mass of the complex and to assist in particle orientation. The results show that the C6D4 and C6D4-RGD3 complexes possess highly similar positioning.

Example 12. Characterization of D4-RGD3 Mutants Having Various Loop Length of the RGD and Flanking Sequence of Pro-TGF-Beta 3

There is an amphipathic alpha-helix following the R-G-D sequence of Latent-TGF-beta1 and Latent-TGF-beta3. Of the 3 engineered versions (RGD1, RGD2, RGD3) of D4 only RGD3 contained the amphipathic helix. Therefore, we engineered various loops containing portions of the RGD and flanking sequences of Pro-TGF-beta 3 to determine if loop length altered affinity, specificity or production of each clone. Because the $V_H$ was not altered, we cloned all new constructs into the CDRL1 region of the C6D4 murine IgG expression vector and transfected the various new D4-RGD3-mutants into 293 cells. After 10 days, protein expression was compared using an murine IgG ELISA (shown as relative expression levels in the Table provided below). Integrins αvβ1, αvβ3, αvβ5, αvβ6 or αvβ8 (R&D systems) were coated on Immulon 4HBX ELISA plates (Thermo Scientific) for 1 hour at room temperature followed by blocking with a 5% bovine serum albumin solution (Sigma-Aldrich) overnight at 4° C. Supernatants with various RGD3 mutant antibodies were applied at 1/10 dilutions onto the wells for 1 hour at room temperature. Antibodies bound to the integrins were detected with an anti-mouse IgG-HRP antibody (GE Healthcare) and revealed with TMB substrate (Pierce). Binding was quantified by intensity as 0-4 (0 representing no apparent binding; 4 representing robust binding) and results normalized to expression. As can be seen from the data provided in the table below, different CDRL1 swaps into Vk D4 show distinct binding specificities. As a result, we identified several mutants having bi-specific (e.g., RGD3-2 and RGD3-3) or tri-specific (e.g., RGD3-7 and RGD3-8) binding specificities.

| Inserted Vk CDR$_{L1}$ domain swap into D4 | Murine IgG H + L Vector | | IgG ELISA Expression Level | Binding to recombinant human integrins | | | | |
|---|---|---|---|---|---|---|---|---|
| CDR$_{L1}$ | VH | Vk | | αvβ1 | αvβ3 | αvβ5 | αvβ6 | αvβ8 |
| KSSQSLLNSRSRKNYLA (SEQ ID NO: 572) | C6 | D4 | 4 | 0 | 0 | 0 | 0 | 4 |
| KSSQSLLNSGRGDLGNALA (SEQ ID NO: 574) | C6 | RGD2 | 4 | 0 | 0 | 0 | 0 | 2 |
| KSSQSLLGRGDLGRLKKQKDHNALA (SEQ ID NO: 576) | C6 | RGD3-1 | 3 | 0 | 0 | 0 | 4 | 1 |
| KSSQSLLGRGDLGRLKKQKDNALA (SEQ ID NO: 577) | C6 | RGD3-2 | 3 | 0 | 0 | 0 | 4 | 4 |
| KSSQSLLGRGDLGRLKKQKNALA (SEQ ID NO: 578) | C6 | RGD3-3 | 3 | 0 | 0 | 0 | 4 | 4 |
| KSSQSLLGRGDLGRLKKQNALA (SEQ ID NO: 579) | C6 | RGD3-4 | 3 | 0 | 0 | 0 | 4 | 4 |
| KSSQSLLGRGDLGRLKKNALA (SEQ ID NO: 575) | C6 | RGD3 | 3 | 0 | 0 | 0 | 4 | 4 |
| KSSQSLLGRGDLGRLKNALA (SEQ ID NO: 580) | C6 | RGD3-6 | 3 | 0 | 0 | 0 | 4 | 4 |
| KSSQSLLGRGDLGRLNALA (SEQ ID NO: 581) | C6 | RGD3-7 | 3 | 0 | 4 | 0 | 2 | 2 |
| KSSQSLLGRGDLGRNALA (SEQ ID NO: 582) | C6 | RGD3-8 | 3 | 0 | 3 | 0 | 3 | 3 |
| KSSQSLLGRGDLGNALA (SEQ ID NO: 573) | C6 | RGD1 | 2 | 0 | 0 | 0 | 0 | 1 |
| KSSQSLLGRGDLGRLKKQKDHH (SEQ ID NO: 583) | C6 | RGD3-9 | 1 | 0 | 0 | 0 | 3 | 0 |
| KSSQSLLGRGDLGRLKKQKDH (SEQ ID NO: 584) | C6 | RGD3-10 | 2 | 0 | 0 | 0 | 1 | 0 |
| KSSQSLLGRGDLGRLKKQKD (SEQ ID NO: 585) | C6 | RGD3-11 | 2 | 0 | 0 | 0 | 2 | 1 |
| KSSQSLLGRGDLGRLKKQK (SEQ ID NO: 586) | C6 | RGD3-12 | 2 | 0 | 1 | 0 | 2 | 0 |
| KSSQSLLGRGDLGRLKKQ (SEQ ID NO: 587) | C6 | RGD3-13 | 2 | 0 | 0 | 0 | 2 | 0 |
| KSSQSLLGRGDLGRLKK (SEQ ID NO: 588) | C6 | RGD3-14 | 3 | 0 | 0 | 0 | 1 | 1 |
| KSSQSLLGRGDLGRLK (SEQ ID NO: 589) | C6 | RGD3-15 | 3 | 0 | 0 | 0 | 0 | 0 |
| KSSQSLLGRGDLGRL (SEQ ID NO: 590) | C6 | RGD3-16 | 3 | 0 | 0 | 0 | 0 | 0 |

Example 13. C6D4 Induces Th1 Bias and Increases CD8 IFN-γ Producing Cells

Seventeen C57B/7 mice were injected with 10⁶ Lewis lung carcinoma (LLC) tumor cells and 8 were injected IP with anti-SV5 (isotype control) or 9 mice with C6D4 (both groups at 7 mg/kg). Mab injections were repeated at day 7 and tumors were harvested at day 11. Tumor infiltrating lymphoid cells were isolated from tumors by enzyme digestion and Percoll gradient centrifugation and stained for CD45, TCRb, CD4, CD8 and surface capture assay for IFNg. Live CD45+ cells were gated and B220, Ly6g, CD11c, CD11b negative, TCRb positive cells were segregated in CD4, CD8, IFN-g positive subsets. The results from this experiment are shown in FIG. 54A-54D. Shown are percentages. * p<0.05, ** p<0.01.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

Informal Sequence Listing

```
B13C4 15-8
                                                          SEQ ID NO: 1
EVQLQQSGPELKKPGETVKISCKASGY TFTDYSMH WVKQAPGKGLKWMG WIKTETGEPTYADDFKG

RFAFSLETSATTAYLQINNLKNEDTAKYFCAI YYYGRDS WGQGTTLTVSS

VH Framework 1
                                                          SEQ ID NO: 2
EVQLQQSGPELKKPGETVKISCKASGY VH CDR1
                                                          SEQ ID NO: 3
TFTDYSMH VH Framework 2
                                                          SEQ ID NO: 4
WVKQAPGKGLKWMG VH CDR2
                                                          SEQ ID NO: 5
WIKTETGEPTYADDFKG VH Framework 3
                                                          SEQ ID NO: 6
RFAFSLETSATTAYLQINNLKNEDTAKYFCAI VH CDR 3
                                                          SEQ ID NO: 7
YYYGRDS VH Framework 4
                                                          SEQ ID NO: 8
WGQGTTLTVSS B13C4 15-10
                                                          SEQ ID NO: 9
QIQLLQSGPELKKPGETVKISCKASGY TFTDYSMH WVKQAPGKGLKWMG WIKTETGEPTYADDFKG

RFAFSLETSATTAYLQINNLKNEDTAKYFCAI YYYGRDS WGQGTTLTVSS

VH Framework 1
                                                          SEQ ID NO: 10
QIQLLQSGPELKKPGETVKISCKASGY VH CDR1
                                                          SEQ ID NO: 11
TFTDYSMH VH Framework 2
                                                          SEQ ID NO: 12
WVKQAPGKGLKWMG VH CDR2
                                                          SEQ ID NO: 13
WIKTETGEPTYADDFKG VH Framework 3
                                                          SEQ ID NO: 14
RFAFSLETSATTAYLQINNLKNEDTAKYFCAI VH CDR 3
                                                          SEQ ID NO: 15
YYYGRDS VH Framework 4
                                                          SEQ ID NO: 16
WGQGTTLTVSS B13H3.2
                                                          SEQ ID NO: 17
QIQLLQSGPELKKPGETVKISCKASGY TFTDYSMH WVKQAPGKGLKWMG WIKTETDEPTYADDFKE

RFAFSLETSASTANLQIINLKNEDTATYFCAI YYYGRDS WGQGTTLTVSSSEQ
```

-continued

VH Framework 1                                           SEQ ID NO: 18
QIQLLQSGPELKKPGETVKISCKASGY

VH CDR1                                                  SEQ ID NO: 19
TFTDYSMH

VH Framework 2                                           SEQ ID NO: 20
WVKQAPGKGLKWMG VH CDR2                                                  SEQ ID NO: 21
WIKTETDEPTYADDFKE VH Framework 3                                           SEQ ID NO: 22
RFAFSLETSASTANLQIINLKNEDTATYFCAI

VH CDR 3                                                 SEQ ID NO: 23
YYYGRDS

VH Framework 4                                           SEQ ID NO: 24
WGQGTTLTVSSSEQ B13C1231015                                              SEQ ID NO: 25
QIQLLQSGPELKKPGETVKISCKASGY TFTDYSIH WVKQAPGKGLKWMG WIKTETGEPTYADDFNG
RFAFSLETSASTAYLQINNLKNEDTATYFCAI YYYGRDS WGQGTTLTVSS VH Framework 1                                           SEQ ID NO: 26
QIQLLQSGPELKKPGETVKISCKASGY

VH CDR1                                                  SEQ ID NO: 27
TFTDYSIH

VH Framework 2                                           SEQ ID NO: 28
WVKQAPGKGLKWMG VH CDR2                                                  SEQ ID NO: 29
WIKTETGEPTYADDFNG VH Framework 3                                           SEQ ID NO: 30
RFAFSLETSASTAYLQINNLKNEDTATYFCAI

VH CDR 3                                                 SEQ ID NO: 31
YYYGRDS

VH Framework 4                                           SEQ ID NO: 32
WGQGTTLTVSS B15B11VH                                                 SEQ ID NO: 33
QIQLLQSGPELKKPGETVKISCKASGY TFTDYSMH WVKQAPGKGLKWVA RINTETGEPTFADDFRG
RFAVSLETSASTAYLQINNLKNEDTATYFCAI YYYGRDS WGQGTTLTVSS VH Framework 1                                           SEQ ID NO: 34
QIQLLQSGPELKKPGETVKISCKASGY

VH CDR1                                                  SEQ ID NO: 35
TFTDYSMH

VH Framework 2                                           SEQ ID NO: 36
WVKQAPGKGLKWVA

```
VH CDR2
                                                  SEQ ID NO: 37
RINTETGEPTFADDFRG

VH Framework 3
                                                  SEQ ID NO: 38
RFAVSLETSASTAYLQINNLKNEDTATYFCAI

VH CDR 3
                                                  SEQ ID NO: 39
YYYGRDS

VH Framework 4
                                                  SEQ ID NO: 40
WGQGTTLTVSS B2B2 15-9
                                                  SEQ ID NO: 41
QIQLLQSGPELKKPGETVKISCLASGY TFTDYSMH WVKQAPGKGLKWVA RINTETGEPTFADDFGG

RFAVSLETSASTAYLQINNLKNEDTATYFCAI YYYGRDS WGQGTTLTVSS

VH Framework 1
                                                  SEQ ID NO: 42
QIQLLQSGPELKKPGETVKISCLASGY

VH CDR1
                                                  SEQ ID NO: 43
TFTDYSMH

VH Framework 2
                                                  SEQ ID NO: 44
WVKQAPGKGLKWVA VH CDR2
                                                  SEQ ID NO: 45
RINTETGEPTFADDFGG VH Framework 3
                                                  SEQ ID NO: 46
RFAVSLETSASTAYLQINNLKNEDTATYFCAI

VH CDR 3
                                                  SEQ ID NO: 47
YYYGRDS

VH Framework 4
                                                  SEQ ID NO: 48
WGQGTTLTVSS R11D12715.3
                                                  SEQ ID NO: 49
EVQLVESGGGLVQPGGSLKLSCAASGF TFSSFGMS WVRQTPDKRLELVA TINSNGGSTYYPDNMKG

RFTISRDNAKNTLYLQMSSLKSEDTAMYYCAS ACYRYGAFFDY WGQGTTLTVSS

VH Framework 1
                                                  SEQ ID NO: 50
EVQLVESGGGLVQPGGSLKLSCAASGF

VH CDR1
                                                  SEQ ID NO: 51
TFSSFGMS

VH Framework 2
                                                  SEQ ID NO: 52
WVRQTPDKRLELVA VH CDR2
                                                  SEQ ID NO: 53
TINSNGGSTYYPDNMKG VH Framework 3
                                                  SEQ ID NO: 54
RFTISRDNAKNTLYLQMSSLKSEDTAMYYCAS VH CDR 3
                                                  SEQ ID NO: 55
ACYRYGAFFDY
```

-continued

VH Framework 4
SEQ ID NO: 56
WGQGTTLTVSS

RSDLVH-1
SEQ ID NO: 57
EVQLLESGPELKKPGETVKISCKASGY TFTDYSIH WVKQAPGKGLKWMG WIKTETGEPTYADDFKG

RFAFSLETSASTAYLQINNLKNEDTATYFCAI YYYGRDS WGQGTTVTVSS

VH Framework 1
SEQ ID NO: 58
EVQLLESGPELKKPGETVKISCKASGY

VH CDR1
SEQ ID NO: 59
TFTDYSIH

VH Framework 2
SEQ ID NO: 60
WVKQAPGKGLKWMG

VH CDR2
SEQ ID NO: 61
WIKTETGEPTYADDFKG

VH Framework 3
SEQ ID NO: 62
RFAFSLETSASTAYLQINNLKNEDTATYFCAI

VH CDR 3
SEQ ID NO: 63
YYYGRDS

VH Framework 4
SEQ ID NO: 64
WGQGTTVTVSS

RSDLVH-1
SEQ ID NO: 65
EVQLLESGPELKKPGETVKISCKASGY TFTDYSIH WVKQAPGKGLKWMG WIKTETGEPTYADDFKG

RFAFSLETSASTAYLQINNLKNEDTATYFCAI YYYGRDS WGQGTTVTVSS

VH Framework 1
SEQ ID NO: 66
EVQLLESGPELKKPGETVKISCKASGY

VH CDR1
SEQ ID NO: 67
TFTDYSIH

VH Framework 2
SEQ ID NO: 68
WVKQAPGKGLKWMG

VH CDR2
SEQ ID NO: 69
WIKTETGEPTYADDFKG

VH Framework 3
SEQ ID NO: 70
RFAFSLETSASTAYLQINNLKNEDTATYFCAI

VH CDR 3
SEQ ID NO: 71
YYYGRDS

VH Framework 4
SEQ ID NO: 72
WGQGTTVTVSS

RSDLVH-3
SEQ ID NO: 73
QVQLMQSGPELKKPGETVKISCKASGY TFTDYSIH WVKQAPGKGLKWMG WIKTETGEPTYADDFNG

RFAFSLETSASTAYLQINNLKNEDTATYFCAI YYYGRDS WGQGTTLTVSS

```
VH Framework 1
                                                  SEQ ID NO: 74
QVQLMQSGPELKKPGETVKISCKASGY

VH CDR1
                                                  SEQ ID NO: 75
TFTDYSIH

VH Framework 2
                                                  SEQ ID NO: 76
WVKQAPGKGLKWMG VH CDR2
                                                  SEQ ID NO: 77
WIKTETGEPTYADDFNG VH Framework 3
                                                  SEQ ID NO: 78
RFAFSLETSASTAYLQINNLKNEDTATYFCAI

VH CDR 3
                                                  SEQ ID NO: 79
YYYGRDS

VH Framework 4
                                                  SEQ ID NO: 80
WGQGTTLTVSS RSDLVH-16
                                                  SEQ ID NO: 81
QIQLQQSGPELKKPGETVKISCKASGY TFTDYSMH WVKQAPGKGLKWVA RINTETGEPTFADDFRG

RFAVSLETSASTAYLQINNLKNEDTATYFCAI YYYGRDS WGQGTTLTVSS

VH Framework 1
                                                  SEQ ID NO: 82
QIQLQQSGPELKKPGETVKISCKASGY

VH CDR1
                                                  SEQ ID NO: 83
TFTDYSMH

VH Framework 2
                                                  SEQ ID NO: 84
WVKQAPGKGLKWVA VH CDR2
                                                  SEQ ID NO: 85
RINTETGEPTFADDFRG VH Framework 3
                                                  SEQ ID NO: 86
RFAVSLETSASTAYLINNLKNEDTATYFCAI

VH CDR 3
                                                  SEQ ID NO: 87
YYYGRDS

VH Framework 4
                                                  SEQ ID NO: 88
WGQGTTLTVSS 29 and 44
                                                  SEQ ID NO: 89
QIQLLQSGPELKKPGETVKISCKASGY TFTDYSMH WVKQAPGKGLKWVA RINTETGEPTFADDFRG

RFAVSLETSASTAYLQINNLKNEDTATYFCAI YYYGRDS WGQGTTLTVSS

VH Framework 1
                                                  SEQ ID NO: 90
QIQLLQSGPELKKPGETVKISCKASGY

VH CDR1
                                                  SEQ ID NO: 91
TFTDYSMH

VH Framework 2
                                                  SEQ ID NO: 92
WVKQAPGKGLKWVA
```

```
VH CDR2
                                                           SEQ ID NO: 93
RINTETGEPTFADDFRG

VH Framework 3
                                                           SEQ ID NO: 94
RFAVSLETSASTAYLQINNLKNEDTATYFCAI VH CDR 3
                                                           SEQ ID NO: 95
YYYGRDS VH Framework 4
                                                           SEQ ID NO: 96
WGQGTTLTVSS A1 = B4 = F9
                                                           SEQ ID NO: 97
QIQLLQSGPELKKPGETVKISCKASGY TFTDYSMH WVKQAPGKGLKWVA RINTETGEPTFADDFRG

RFAVSLETSASTAYLQINNLKNEDTATYFCAI YYYGRDT WGQGTTLSVSS

VH Framework 1
                                                           SEQ ID NO: 98
QIQLLQSGPELKKPGETVKISCKASGY VH CDR1
                                                           SEQ ID NO: 99
TFTDYSMH VH Framework 2
                                                           SEQ ID NO: 100
WVKQAPGKGLKWVA VH CDR2
                                                           SEQ ID NO: 101
RINTETGEPTFADDFRG VH Framework 3
                                                           SEQ ID NO: 102
RFAVSLETSASTAYLQINNLKNEDTATYFCAI VH CDR 3
                                                           SEQ ID NO: 103
YYYGRDT VH Framework 4
                                                           SEQ ID NO: 104
WGQGTTLSVSS A5 = C6
                                                           SEQ ID NO: 105
QIQLLQSGPELKKPGETVKISCKASGY TFTDYSMH WVKQAPGKGLKWVA RINTETGEPTFADDFRG

RFAVSLETSASTAYLQINNLKNEDTATYFCAI FYYGRDS WGQGTALTVSS

VH Framework 1
                                                           SEQ ID NO: 106
QIQLLQSGPELKKPGETVKISCKASGY VH CDR1
                                                           SEQ ID NO: 107
TFTDYSMH VH Framework 2
                                                           SEQ ID NO: 108
WVKQAPGKGLKWVA VH CDR2
                                                           SEQ ID NO: 109
RINTETGEPTFADDFRG VH Framework 3
                                                           SEQ ID NO: 110
RFAVSLETSASTAYLQINNLKNEDTATYFCAI VH CDR 3
                                                           SEQ ID NO: 111
FYYGRDS
```

-continued

VH Framework 4
SEQ ID NO: 112
WGQGTALTVSS

D4 = E6
SEQ ID NO: 113
QIQLLQSGPELKKPGETVKISCKASGY TFTDYSMH WVKQAPGKGLKWVA RINTETGEPTFADDFRG

RFAVSLETSASTAYLQINNLKNEDTATYFCAI YYYGRDS WGQGTTLTVSS

VH Framework 1
SEQ ID NO: 114
QIQLLQSGPELKKPGETVKISCKASGY

VH CDR1
SEQ ID NO: 115
TFTDYSMH

VH Framework 2
SEQ ID NO: 116
WVKQAPGKGLKWVA

VH CDR2
SEQ ID NO: 117
RINTETGEPTFADDFRG

VH Framework 3
SEQ ID NO: 118
RFAVSLETSASTAYLQINNLKNEDTATYFCAI

VH CDR 3
SEQ ID NO: 119
YYYGRDS

VH Framework 4
SEQ ID NO: 120
WGQGTTLTVSS

C6D4
SEQ ID NO: 121
QIQLLQSGPELKKPGETVKISCKASGY TFTDYSMH WVKQAPGKGLKWVA RINTETGEPTFADDFRG

RFAVSLETSASTAYLQINNLKNEDTATYFCAI FYYGRDS WGQGTTLTVSS

VH Framework 1
SEQ ID NO: 122
QIQLLQSGPELKKPGETVKISCKASGY

VH CDR1
SEQ ID NO: 123
TFTDYSMH

VH Framework 2
SEQ ID NO: 124
WVKQAPGKGLKWVA

VH CDR2
SEQ ID NO: 125
RINTETGEPTFADDFRG

VH Framework 3
SEQ ID NO: 126
RFAVSLETSASTAYLQINNLKNEDTATYFCAI

VH CDR 3
SEQ ID NO: 127
FYYGRDS

VH Framework 4
SEQ ID NO: 128
WGQGTTLTVSS

B2B2 35-20
SEQ ID NO: 129
DIVMSQSPSSMYASLGERVTITC KASQDINSYLS WFQQKPGKSPKTLIY RANRLVD

GVPSRFSGSGSGQDYSLTISSLEYEDMGIYYC LQYDEFPPLT FGAGTKLELKA

```
VL Framework 1                                              SEQ ID NO: 130
DIVMSQSPSSMYASLGERVTITC VL CDR1                                                     SEQ ID NO: 131
KASQDINSYLS VL Framework 2                                              SEQ ID NO: 132
WFQQKPGKSPKTLIY VL CDR2                                                     SEQ ID NO: 133
RANRLVD VL Framework 3                                              SEQ ID NO: 134
GVPSRFSGSGSGQDYSLTISSLEYEDMGIYYC VL CDR 3                                                    SEQ ID NO: 135
LQYDEFPPLT VL Framework 4                                              SEQ ID NO: 136
FGAGTKLELKA B2B2 35-26                                                  SEQ ID NO: 137
QIVLTQSPSSMYASLGERVTITC KASQDINSYLS WFQQKPGKSPKTLIY RANRLVD

GVPSRFSGSGSGQDYSLTISSLEYEDMGIYYC LQYDEFPPLT FGAGTKLELKA

VL Framework 1                                              SEQ ID NO: 138
QIVLTQSPSSMYASLGERVTITC VL CDR1                                                     SEQ ID NO: 139
KASQDINSYLS VL Framework 2                                              SEQ ID NO: 140
WFQQKPGKSPKTLIY VL CDR2                                                     SEQ ID NO: 141
RANRLVD VL Framework 3                                              SEQ ID NO: 142
GVPSRFSGSGSGQDYSLTISSLEYEDMGIYYC VL CDR 3                                                    SEQ ID NO: 143
LQYDEFPPLT VL Framework 4                                              SEQ ID NO: 144
FGAGTKLELKA B15B11vk34-26                                               SEQ ID NO: 145
QIVLTQSPAIMSASPGEKVTMTC SASSSVSYMH WYQQKPGTSPKLWIY DTSNLAS

GVPARFSGSGSGTSYSLTISSMEAEDAATYYC QQWSSNPLT FGSGTKLEIKA

VL Framework 1                                              SEQ ID NO: 146
QIVLTQSPAIMSASPGEKVTMTC VL CDR1                                                     SEQ ID NO: 147
SASSSVSYMH
```

```
VL Framework 2                                          SEQ ID NO: 148
WYQQKPGTSPKLWIY

VL CDR2                                                 SEQ ID NO: 149
DTSNLAS

VL Framework 3                                          SEQ ID NO: 150
GVPARFSGSGSGTSYSLTISSMEAEDAATYYC

VL CDR 3                                                SEQ ID NO: 151
QQWSSNPLT

VL Framework 4                                          SEQ ID NO: 152
FGSGTKLEIKA B15B11vk33-24                                           SEQ ID NO: 153
EIVLTQSPAIMSASPGEKVTMTC SASSSVSYMH WYQQKPGSSPKLWIY DTSNLAS

GVPARFSGSGSGTSYSLTISSMEAEDAATYYC QQWSSNPLT FGDGTRLEIKA

VL Framework 1                                          SEQ ID NO: 154
EIVLTQSPAIMSASPGEKVTMTC VL CDR1                                                 SEQ ID NO: 155
SASSSVSYMH VL Framework 2                                          SEQ ID NO: 156
WYQQKPGSSPKLWIY

VL CDR2                                                 SEQ ID NO: 157
DTSNLAS

VL Framework 3                                          SEQ ID NO: 158
GVPARFSGSGSGTSYSLTISSMEAEDAATYYC

VL CDR 3                                                SEQ ID NO: 159
QQWSSNPLT

VL Framework 4                                          SEQ ID NO: 160
FGDGTRLEIKA B15B11vk35-26                                           SEQ ID NO: 161
QIVLTQSPAIMSASPGEKVTMTC SASSSVSYMH WYQQKSGTSPKLWIY DTSNLAS

GVPARFSGSGSGTSYSLTISSMEAEDAATYYC QQWSSNPPT FGAGTKLELKA

VL Framework 1                                          SEQ ID NO: 162
QIVLTQSPAIMSASPGEKVTMTC VL CDR1                                                 SEQ ID NO: 163
SASSSVSYMH VL Framework 2                                          SEQ ID NO: 164
WYQQKSGTSPKLWIY VL CDR2                                                 SEQ ID NO: 165
DTSNLAS
```

```
VL Framework 3                                           SEQ ID NO: 166
GVPARFSGSGSGTSYSLTISSMEAEDAATYYC VL CDR 3                                                 SEQ ID NO: 167
QQWSSNPPT VL Framework 4                                           SEQ ID NO: 168
FGAGTKLELKA B13C12134-25                                             SEQ ID NO: 169
DIKMTQSPAIMSASPGEKVTMTC SASSSVSYMH WYQQKSGTSPKRWIY DTSKLAS
GVPARFSGSGSGTSYSLTISSMEAEDAATYYC QQWSSNPFT FGSGTKLEIKA VL Framework 1                                           SEQ ID NO: 170
DIKMTQSPAIMSASPGEKVTMTC VL CDR1                                                  SEQ ID NO: 171
SASSSVSYMH VL Framework 2                                           SEQ ID NO: 172
WYQQKSGTSPKRWIY

VL CDR2                                                  SEQ ID NO: 173
DTSKLAS

VL Framework 3                                           SEQ ID NO: 174
GVPARFSGSGSGTSYSLTISSMEAEDAATYYC VL CDR 3                                                 SEQ ID NO: 175
QQWSSNPFT VL Framework 4                                           SEQ ID NO: 176
FGSGTKLEIKA B13C12133-26                                             SEQ ID NO: 177
QMVLTHSPAIMSASPGEKVTMTC SASSSVSYMH WYQQKPGSSPKPWIY GTSNLAS
GVPARFSGSGSGTSYSLTISRMEAEDAATYYC QQWSSNPPT FGDGTRLEIKA VL Framework 1                                           SEQ ID NO: 178
QMVLTHSPAIMSASPGEKVTMTC VL CDR1                                                  SEQ ID NO: 179
SASSSVSYMH VL Framework 2                                           SEQ ID NO: 180
WYQQKPGSSPKPWIY

VL CDR2                                                  SEQ ID NO: 181
GTSNLAS

VL Framework 3                                           SEQ ID NO: 182
GVPARFSGSGSGTSYSLTISRMEAEDAATYYC VL CDR 3                                                 SEQ ID NO: 183
QQWSSNPPT
```

```
VL Framework 4
                                                         SEQ ID NO: 184
FGDGTRLEIKA B13C4 35-20
                                                         SEQ ID NO: 185
DIVMSQSPSSLAVSAGEKVTMSC KSSQSLLNSRTRKNYLA WYQQKPGQSPRLLIY WASTRES

GVPDRFTGSGSGTDFTLTISSVQAEDLAVYYC KQSYNLLT FGAGTKLELKA

VL Framework 1
                                                         SEQ ID NO: 186
DIVMSQSPSSLAVSAGEKVTMSC VL CDR1
                                                         SEQ ID NO: 187
KSSQSLLNSRTRKNYLA VL Framework 2
                                                         SEQ ID NO: 188
WYQQKPGQSPRLLIY VL CDR2
                                                         SEQ ID NO: 189
WASTRES VL Framework 3
                                                         SEQ ID NO: 190
GVPDRFTGSGSGTDFTLTISSVQAEDLAVYYC VL CDR 3
                                                         SEQ ID NO: 191
KQSYNLLT VL Framework 4
                                                         SEQ ID NO: 192
FGAGTKLELKA B15B11vk35-20
                                                         SEQ ID NO: 193
DIVMSQSPSSLAVSAGENVTVSC KSSQSLLNSRTRKNYLA WYQQKPGQSPKLLIY WASTRES

GVPDRFTGSGSGTDFTLTISSVQAEDLAVYFC KQSYNLLT FGAGTKLELKA

VL Framework 1
                                                         SEQ ID NO: 194
DIVMSQSPSSLAVSAGENVTVSC VL CDR1
                                                         SEQ ID NO: 195
DIVMSQSPSSLAVSAGENVTVSC VL Framework 2
                                                         SEQ ID NO: 196
WYQQKPGQSPKLLIY VL CDR2
                                                         SEQ ID NO: 197
WASTRES VL Framework 3
                                                         SEQ ID NO: 198
GVPDRFTGSGSGTDFTLTISSVQAEDLAVYFC VL CDR 3
                                                         SEQ ID NO: 199
KQSYNLLT VL Framework 4
                                                         SEQ ID NO: 200
FGAGTKLELKA B13C12335-25
                                                         SEQ ID NO: 201
DIKMTQSPSSLAVSPGEKVTMSC KSSQSLLHSRTRKNYLA WYQQKPGQSPKLLIY WASTRES

GVPDRFTGSGSGTDFTLTISSVQAEDLAVYYC KQSYNLLT FGAGTKLELKA
```

```
VL Framework 1                                      SEQ ID NO: 202
DIKMTQSPSSLAVSPGEKVTMSC VL CDR1                                             SEQ ID NO: 203
KSSQSLLHSRTRKNYLA VL Framework 2                                      SEQ ID NO: 204
WYQQKPGQSPKLLIY

VL CDR2                                             SEQ ID NO: 205
WASTRES

VL Framework 3                                      SEQ ID NO: 206
GVPDRFTGSGSGTDFTLTISSVQAEDLAVYYC

VL CDR 3                                            SEQ ID NO: 207
KQSYNLLT

VL Framework 4                                      SEQ ID NO: 208
FGAGTKLELKA

B13C1233520                                         SEQ ID NO: 209
DIVMSQSPSSLAVSPGEKVTMSC KSSQSLLHSRTRKNYLA WYQQKPGQSPKLLIY WASTRES

GVPDRFTGSGSGTDFTLTISSVQAEDLAVYYC KQSYNLLT FGAGTKLELKA

VL Framework 1                                      SEQ ID NO: 210
DIVMSQSPSSLAVSPGEKVTMSC VL CDR1                                             SEQ ID NO: 211
KSSQSLLHSRTRKNYLA VL Framework 2                                      SEQ ID NO: 212
WYQQKPGQSPKLLIY

VL CDR2                                             SEQ ID NO: 213
WASTRES

VL Framework 3                                      SEQ ID NO: 214
GVPDRFTGSGSGTDFTLTISSVQAEDLAVYYC

VL CDR 3                                            SEQ ID NO: 215
KQSYNLLT

VL Framework 4                                      SEQ ID NO: 216
FGAGTKLELKA

RSDLVK-1                                            SEQ ID NO: 217
DIVMTQSPSSLAVSAGEKVTMSC KSSQSLLNSRTRKNYLA WYQQKPGQSPRLLIY WASTRES

GVPDRFTGSGSGTDFTLTISSVQAEDLAVYYC KQSYNLLT FGAGTKLELKR

VL Framework 1                                      SEQ ID NO: 218
DIVMTQSPSSLAVSAGEKVTMSC VL CDR1                                             SEQ ID NO: 219
KSSQSLLNSRTRKNYLA
```

```
VL Framework 2
                                                   SEQ ID NO: 220
WYQQKPGQSPRLLIY VL CDR2
                                                   SEQ ID NO: 221
WASTRES VL Framework 3
                                                   SEQ ID NO: 222
GVPDRFTGSGSGTDFTLTISSVQAEDLAVYYC VL CDR 3
                                                   SEQ ID NO: 223
KQSYNLLT VL Framework 4
                                                   SEQ ID NO: 224
FGAGTKLELKR RSDLVK-6
                                                   SEQ ID NO: 225
DIVMTQSPSSLAVSAGEKVTMSC KSSQSLLNSRTRKNYLA WYQQKPGQSPRLLIY WASTRES

GVPDRFTGSGSGTDFTLTISSVQAEDLAVYYC KQSYNLLT FGAGTRLEIKR

VL Framework 1
                                                   SEQ ID NO: 226
DIVMTQSPSSLAVSAGEKVTMSC VL CDR1
                                                   SEQ ID NO: 227
KSSQSLLNSRTRKNYLA VL Framework 2
                                                   SEQ ID NO: 228
WYQQKPGQSPRLLIY VL CDR2
                                                   SEQ ID NO: 229
WASTRES VL Framework 3
                                                   SEQ ID NO: 230
GVPDRFTGSGSGTDFTLTISSVQAEDLAVYYC VL CDR 3
                                                   SEQ ID NO: 231
KQSYNLLT VL Framework 4
                                                   SEQ ID NO: 232
FGAGTRLEIKR RSDLVK-10
                                                   SEQ ID NO: 233
DIVMTQSPSSLAVSAGENVTVSC KSSQSLLNSRTRKNYLA WYQQKPGQSPKLLIY WASTRES

GVPDRFTGSGSGTGFTLTISSVQAEDLAVYFC KQSYNLLT FGAGTRLEIKR

VL Framework 1
                                                   SEQ ID NO: 234
DIVMTQSPSSLAVSAGENVTVSC VL CDR1
                                                   SEQ ID NO: 235
KSSQSLLNSRTRKNYLA VL Framework 2
                                                   SEQ ID NO: 236
WYQQKPGQSPKLLIY VL CDR2
                                                   SEQ ID NO: 237
WASTRES
```

```
VL Framework 3                                          SEQ ID NO: 238
GVPDRFTGSGSGTGFTLTISSVQAEDLAVYFC

VL CDR 3                                                SEQ ID NO: 239
KQSYNLLT

VL Framework 4                                          SEQ ID NO: 240
FGAGTRLEIKR RSDLVK-13                                               SEQ ID NO: 241
DIVMSQSPSSLAVSPGEKVTMSC KSSQSLLHSRTRKNYLA WYQQKPGQSPKLLIY WASTRES

GVPDRFTGSGSGTDFTLTISSVQAEDLAVYYC KQSYNLLT FGAGTKLELKR

VL Framework 1                                          SEQ ID NO: 242
DIVMSQSPSSLAVSPGEKVTMSC VL CDR1                                                 SEQ ID NO: 243
KSSQSLLHSRTRKNYLA VL Framework 2                                          SEQ ID NO: 244
WYQQKPGQSPKLLIY

VL CDR2                                                 SEQ ID NO: 245
WASTRES

VL Framework 3                                          SEQ ID NO: 246
GVPDRFTGSGSGTDFTLTISSVQAEDLAVYYC

VL CDR 3                                                SEQ ID NO: 247
KQSYNLLT

VL Framework 4                                          SEQ ID NO: 248
FGAGTKLELKR 29                                                      SEQ ID NO: 249
DIVMSQSPSSLAVSAGEKVTMSC KSSQSLLNSRTRKNYLA WYQQKPGQSPRLLIY WASTRES

GVPDRFTGSGSGTDFTLTISSVQAEDLAVYYC KQSYNLLT FGAGTKLELKA

VL Framework 1                                          SEQ ID NO: 250
DIVMSQSPSSLAVSAGEKVTMSC VL CDR1                                                 SEQ ID NO: 251
KSSQSLLNSRTRKNYLA VL Framework 2                                          SEQ ID NO: 252
WYQQKPGQSPRLLIY

VL CDR2                                                 SEQ ID NO: 253
WASTRES

VL Framework 3                                          SEQ ID NO: 254
GVPDRFTGSGSGTDFTLTISSVQAEDLAVYYC VL CDR 3                                                SEQ ID NO: 255
KQSYNLLT
```

-continued

```
VL Framework 4
                                                 SEQ ID NO: 256
FGAGTKLELKA 44
                                                 SEQ ID NO: 257
DIVMSQSPSSLAVSAGEKVTMSC KSSQSLLNSRTRKNYLA WYQQKPGQSPRLLIY WASTRES

GVPDRFTGSGSGTDFTLTISSVQDEDLAVYYC KQSYNLLT FGAGTKLELKA

VL Framework 1
                                                 SEQ ID NO: 258
DIVMSQSPSSLAVSAGEKVTMSC VL CDR1
                                                 SEQ ID NO: 259
KSSQSLLNSRTRKNYLA VL Framework 2
                                                 SEQ ID NO: 260
WYQQKPGQSPRLLIY

VL CDR2
                                                 SEQ ID NO: 261
WASTRES

VL Framework 3
                                                 SEQ ID NO: 262
GVPDRFTGSGSGTDFTLTISSVQDEDLAVYYC VL CDR 3
                                                 SEQ ID NO: 263
KQSYNLLT VL Framework 4
                                                 SEQ ID NO: 264
FGAGTKLELKA A1 = B4 = F9
                                                 SEQ ID NO: 265
DIVMSQSPSSLAVSAGEKVTMSC KSSQSLLNSRTRKNYLA WYQQKPGQSPRLLIY WASTRES

GVPDRFTGSGSGTDFTLTISSVQAEDLAVYYC KQSYNLLT FGAGTKLELKA

VL Framework 1
                                                 SEQ ID NO: 266
DIVMSQSPSSLAVSAGEKVTMSC VL CDR1
                                                 SEQ ID NO: 267
KSSQSLLNSRTRKNYLA VL Framework 2
                                                 SEQ ID NO: 268
WYQQKPGQSPRLLIY

VL CDR2
                                                 SEQ ID NO: 269
WASTRES

VL Framework 3
                                                 SEQ ID NO: 270
GVPDRFTGSGSGTDFTLTISSVQAEDLAVYYC VL CDR 3
                                                 SEQ ID NO: 271
KQSYNLLT VL Framework 4
                                                 SEQ ID NO: 272
FGAGTKLELKA A5 = C6
                                                 SEQ ID NO: 273
DIVMSQSPSSLAVSAGEKVTMSC KSSQSLLNSRTRKNYLA WYQQKPGQSPRLLIY WASTRES

GVPDRFTGSGSGTDFTLTISSVQAEDLAVYYC KQSYNLLT FGAGTKLELKA
```

```
VL Framework 1                                          SEQ ID NO: 274
DIVMSQSPSSLAVSAGEKVTMSC VL CDR1                                                 SEQ ID NO: 275
KSSQSLLNSRTRKNYLA VL Framework 2                                          SEQ ID NO: 276
WYQQKPGQSPRLLIY

VL CDR2                                                 SEQ ID NO: 277
WASTRES

VL Framework 3                                          SEQ ID NO: 278
GVPDRFTGSGSGTDFTLTISSVQAEDLAVYYC

VL CDR 3                                                SEQ ID NO: 279
KQSYNLLT

VL Framework 4                                          SEQ ID NO: 280
FGAGTKLELKA D4 = E6                                                 SEQ ID NO: 281
DIVMSQSPSSLAVSAGEKVTMSC KSSQSLLNSRTRKNYLA WYQQKPGQXPRLLIY WASTRES

GVPDRFTGSGSGTDFTLTISSVQDEDLAVYYC KQSYNLLS FGAGTKLELKA

VL Framework 1                                          SEQ ID NO: 282
DIVMSQSPSSLAVSAGEKVTMSC VL CDR1                                                 SEQ ID NO: 283
KSSQSLLNSRTRKNYLA VL Framework 2                                          SEQ ID NO: 284
WYQQKPGQXPRLLIY

VL CDR2                                                 SEQ ID NO: 285
WASTRES

VL Framework 3                                          SEQ ID NO: 286
GVPDRFTGSGSGTDFTLTISSVQDEDLAVYYC

VL CDR3                                                 SEQ ID NO: 287
KQSYNLLS

VL Framework 4                                          SEQ ID NO: 288
FGAGTKLELKA C6D4                                                    SEQ ID NO: 289
DIVMTQSPSSLAVSAGEKVTMSC KSSQSLLNSRTRKNYLA WYQQKPGQSPRLLIY WASTRES

GVPDRFTGSGSGTDFTLTISSVQAEDLAVYYC KQSYNLLS FGAGTKLELKR

VL Framework 1                                          SEQ ID NO: 290
DIVMTQSPSSLAVSAGEKVTMSC VL CDR1                                                 SEQ ID NO: 291
KSSQSLLNSRTRKNYLA
```

-continued

VL Framework 2

WYQQKPGQSPRLLIY
SEQ ID NO: 292

VL CDR2

WASTRES
SEQ ID NO: 293

VL Framework 3

GVPDRFTGSGSGTDFTLTISSVQAEDLAVYYC
SEQ ID NO: 294

VL CDR3

KQSYNLLS
SEQ ID NO: 295

VL Framework 4

FGAGTKLELKR
SEQ ID NO: 296

F9 VH

QVQLQQSGAELVRPGTSVKVSCKASGY AFTDYLIQ WVKQRPGQGLEWIG VINPETGGTNYNAKFRG

KATLTADKSSSSAYMQLSSLTSGDSAVYFCAR EAGNYIYAMDY WGQGTSVTVSS
SEQ ID NO: 297

VH Framework 1

QVQLQQSGAELVRPGTSVKVSCKASGY
SEQ ID NO: 298

VH CDR1

AFTDYLIQ
SEQ ID NO: 299

VH Framework 2

WVKQRPGQGLEWIG
SEQ ID NO: 300

VH CDR2

VINPETGGTNYNAKFRG
SEQ ID NO: 301

VH Framework 3

KATLTADKSSSSAYMQLSSLTSGDSAVYFCAR
SEQ ID NO: 302

VH CDR3

EAGNYIYAMDY
SEQ ID NO: 303

VH Framework 4

WGQGTSVTVSS
SEQ ID NO: 304

F9 VL

DIVMTQSPAFLSASVGETVTITC RASVNIYSYLV WYQQKQGKSPQLLVH NAKTLAE

GVPSRFSGSGSGTQFSLKINSLQPEDFGSYYC QHHHGTPYT FGGGTKLEIKR
SEQ ID NO: 305

VL Framework 1

DIVMTQSPAFLSASVGETVTITC
SEQ ID NO: 306

VL CDR1

RASVNIYSYLV
SEQ ID NO: 307

VL Framework 2

WYQQKQGKSPQLLVH
SEQ ID NO: 308

VL CDR2

NAKTLAE
SEQ ID NO: 309

-continued

| | |
|---|---|
| VL Framework 3<br>GVPSRFSGSGSGTQFSLKINSLQPEDFGSYYC | SEQ ID NO: 310 |
| VL CDR3<br>QHHHGTPYT | SEQ ID NO: 311 |
| VL Framework 4<br>FGGGTKLEIKR | SEQ ID NO: 312 |
| B2B2 VH CDR1<br>TFTDYSMH | SEQ ID NO: 313 |
| B2B2 VH CDR2<br>RINTETGEPTFADDFGG | SEQ ID NO: 314 |
| B2B2 VH CDR3<br>YYYGRDS | SEQ ID NO: 315 |
| B13C4 VH CDR1<br>TFTDYSMH | SEQ ID NO: 316 |
| B13C4 VH CDR2<br>WIKTETGEPTYADDFKG | SEQ ID NO: 317 |
| B13C4 VH CDR3<br>YYYGRDS | SEQ ID NO: 318 |
| B13H3 VH CDR1<br>TFTDYSMH | SEQ ID NO: 319 |
| B13H3 VH CDR2<br>WIKTETDEPTYADDFKE | SEQ ID NO: 320 |
| B13H3 VH CDR3<br>YYYGRDS | SEQ ID NO: 321 |
| B15B11 VH CDR1<br>TFTDYSMH | SEQ ID NO: 322 |
| B15B11 VH CDR2<br>RINTETGEPTFADDFRG | SEQ ID NO: 323 |
| B15B11 VH CDR3<br>YYYGRDS | SEQ ID NO: 324 |
| B13C12 VH CDR1<br>TFTDYSIH | SEQ ID NO: 325 |
| B13C12 VH CDR2<br>WIKTETGEPTYADDFNG | SEQ ID NO: 326 |
| B13C12 VH CDR3<br>YYYGRDS | SEQ ID NO: 327 |
| A1 VH CDR1<br>TFTDYSMH | SEQ ID NO: 328 |
| A1 VH CDR2 | |

```
                                                  SEQ ID NO: 329
RINTETGEPTFADDFRG

A1 VH CDR3
                                                  SEQ ID NO: 330
YYYGRDT

C6 VH CDR1
                                                  SEQ ID NO: 331
TFTDYSMH

C6 VH CDR2
                                                  SEQ ID NO: 332
RINTETGEPTFADDFRG

C6 VH CDR3
                                                  SEQ ID NO: 333
FYYGRDS

B2B2 CDR1
                                                  SEQ ID NO: 334
KASQDINSYLS

B2B2 Vk CDR2
                                                  SEQ ID NO: 335
RANRLVD

B2B2 Vk CDR3
                                                  SEQ ID NO: 336
LQYDEFPPLT

B13C4 Vk CDR1
                                                  SEQ ID NO: 337
KSSQSLLNSRTRKNYLA

B13C4 Vk CDR2
                                                  SEQ ID NO: 338
WASTRES

B13C4 Vk CDR3
                                                  SEQ ID NO: 339
KQSYNLLT

B13H3 Vk CDR1
                                                  SEQ ID NO: 340
KSSQSLLNSRIRKNYLA

B13H3 Vk CDR2
                                                  SEQ ID NO: 341
WASTRES

B13H3 Vk CDR3
                                                  SEQ ID NO: 342
KQSYNLLT

B15B11.1 Vk CDR1
                                                  SEQ ID NO: 343
SASSSVSYMH

B15B11.1 Vk CDR2
                                                  SEQ ID NO: 344
DTSNLAS

B15B11.1 Vk CDR3
                                                  SEQ ID NO: 345
QQWSSNPLT

B15B11.2 Vk CDR1
                                                  SEQ ID NO: 346
SASSSVSYMH

B15B11.2 Vk CDR2
                                                  SEQ ID NO: 347
DTSNLAS

B15B11.2 Vk CDR3
                                                  SEQ ID NO: 348
QQWSSNPPT
```

| | |
|---|---|
| B15B11.3 Vk CDR1<br>KSSQSLLNSRTRKNYLA | SEQ ID NO: 349 |
| B15B11.3 Vk CDR2<br>WASTRES | SEQ ID NO: 350 |
| B15B11.3 Vk CDR3<br>KQSYNLLT | SEQ ID NO: 351 |
| B13C12.1 Vk CDR1<br>SASSSVSYMH | SEQ ID NO: 352 |
| B13C12.1 Vk CDR2<br>DTSKLAS | SEQ ID NO: 353 |
| B13C12.1 Vk CDR3<br>QQWSSNPFT | SEQ ID NO: 354 |
| B13C12.2 Vk CDR1<br>SASSSVSYMH | SEQ ID NO: 355 |
| B13C12.2 Vk CDR2<br>GTSNLAS | SEQ ID NO: 356 |
| B13C12.2 Vk CDR3<br>QQWSSNPPT | SEQ ID NO: 357 |
| B13C12.3 Vk CDR1<br>KSSQSLLHSRTRKNYLA | SEQ ID NO: 358 |
| B13C12.3 Vk CDR2<br>WASTRES | SEQ ID NO: 359 |
| B13C12.3 Vk CDR3<br>KQSYNLLT | SEQ ID NO: 360 |
| D4 Vk CDR1<br>KSSQSLLNSRTRKNYLA | SEQ ID NO: 361 |
| D4 Vk CDR2<br>WASTRES | SEQ ID NO: 362 |
| D4 Vk CDR3<br>KQSYNLLS | SEQ ID NO: 363 |
| RSDL VH-1 VH CDR1<br>TFTDYSIH | SEQ ID NO: 364 |
| RSDL VH-1 VH CDR2<br>WIKTETGEPTYADDFKG | SEQ ID NO: 365 |
| RSDLVH-1 VH CDR3<br>YYYGRDS | SEQ ID NO: 366 |
| RSDLVH-3 VH CDR1<br>TFTDYSIH | SEQ ID NO: 367 |
| RSDLVH-3 VH CDR2<br>WIKTETGEPTYADDFNG | SEQ ID NO: 368 |

-continued

| | |
|---|---|
| RSDLVH-3 VH CDR3<br>YYYGRDS | SEQ ID NO: 369 |
| RSDLVH-16 VH CDR1<br>TFTDYSMH | SEQ ID NO: 370 |
| RSDLVH-16 VH CDR2<br>RINTETGEPTFADDFRG | SEQ ID NO: 371 |
| RSDLVH-16 VH CDR3<br>YYYGRDS | SEQ ID NO: 372 |
| RSDLVK-10 Vk CDR1<br>KSSQSLLNSRTRKNYLA | SEQ ID NO: 373 |
| RSDLVK-10 Vk CDR2<br>WASTRES | SEQ ID NO: 374 |
| RSDLVK-10 Vk CDR3<br>KQSYNLLT | SEQ ID NO: 375 |
| RSDLVK-13 Vk CDR1<br>KSSQSLLHSRTRKNYLA | SEQ ID NO: 376 |
| RSDLVK-13 Vk CDR2<br>WASTRES | SEQ ID NO: 377 |
| RSDLVK-13 Vk CDR3<br>KQSYNLLT | SEQ ID NO: 378 |
| D4H VH CDR1<br>TFTDYSMH | SEQ ID NO: 379 |
| D4H VH CDR2<br>RINTETGEPTFADDFRG | SEQ ID NO: 380 |
| D4H VH CDR3<br>YYYGRDS | SEQ ID NO: 381 |
| C6k Vk CDR1<br>KSSQSLLNSRTRKNYLA | SEQ ID NO: 382 |
| C6k Vk CDR2<br>WASTRES | SEQ ID NO: 383 |
| C6k Vk CDR3<br>KQSYNLLT | SEQ ID NO: 384 |
| heavy chain FR1<br>(Q/E)IQL(L/M)(Q/E)SGPELKKPGETVKISCKASGY | SEQ ID NO: 385 |
| heavy chain FR2<br>WVKQAPGKGLKW(V/M)A | SEQ ID NO: 386 |
| heavy chain FR3<br>RFA(V/F)SLETSASTAYLQINNLKNEDTATYFCAI | SEQ ID NO: 387 |
| heavy chain FR4<br>WYQQKPGQSP(K/R)LLIY | SEQ ID NO: 388 |

-continued light chain FR1  
(D/E)IVM(T/S)QSPSSLAV(/PS)AGE(K/N)VT(M/V)SC                    SEQ ID NO: 389 light chain FR2  
WYQQKPGQSP(K/R)LLIY                                            SEQ ID NO: 390 light chain FR3  
GVPDRFTGSGSGTDFTLTISSVQAEDLAVY(Y/F)C                           SEQ ID NO: 391 light chain FR4  
FGAGT(R/K)LE(L/I)K                                             SEQ ID NO: 392

Human αv
                                                               SEQ ID NO: 393
```
   1  FNLDVDSPAEYSGPEGSYFGFAVDFFVPSASSRMFLLVGAPKANTTQPGI    50
  51  VEGGQVLKCDWSSTRRCQPIEFDATGNRDYAKDDPLEFKSHQWFGASVRS   100
 101  KQDKILACAPLYHWRTEMKQEREPVGTCFLQDGTKTVEYAPCRSQDIDAD   150
 151  GQGFCQGGFSIDFTKADRVLLGGPGSFYWQGQLISDQVAEIVSKYDPNVY   200
 201  SIKYNNQLATRTAQAIFDDSYLGYSVAVGDFNGDGIDDFVSGVPRAARTL   250
 251  GMVYIYDGKNMSSLYNFTGEQMAAYFGFSVAATDINGDDYADVFIGAPLF   300
 301  MDRGSDGKLQEVGQVSVSLQRASGDFQTTKLNGFEVFARFGSAIAPLGDL   350
 351  DQDGFNDIAIAAPYGGEDKKGIVYIFNGRSTGLNAVPSQILEGQWAARSM   400
 401  PPSFGYSMKGATDIDKNGYPDLIVGAFGVDRAILYRARPVITVNAGLEVY   450
 451  PSILNQDNKTCSLPGTALKVSCFNVRFCLKADGKGVLPRKLNFQVELLLD   500
 501  KLKQKGAIRRALFLYSRSPSHSKNMTISRGGLMQCEELIAYLRDESEFRD   550
 551  KLTPITIFMEYRLDYRTAADTTGLQPILNQFTPANISRQAHILLDCGEDN   600
 601  VCKPKLEVSVDSDQKKIYIGDDNPLTLIVKAQNQGEGAYEAELIVSIPLQ   650
 651  ADFIGVVRNNEALARLSCAFKTENQTRQVVCDLGNPMKAGTQLLAGLRFS   700
 701  VHQQSEMDTSVKFDLQIQSSNLFDKVSPVVSHKVDLAVLAAVEIRGVSSP   750
 751  DHVFLPIPNWEHKENPETEEDVGPVVQHIYELRNNGPSSFSKAMLHLQWP   800
 801  YKYNNNTLLYILHYDIDGPMNCTSDMEINPLRIKISSLQTTEKNDTVAGQ   850
 851  GERDHLITKRDLALSEGDIHTLGCGVAQCLKIVCQVGRLDRGKSAILYVK   900
 901  SLLWTETFMNKENQNHSYSLKSSASFNVIEFPYKNLPIEDITNSTLVTTN   950
 951  VTWGIQPAPMPVPVWVIILAVLAGLLLLAVLVFVMYRMGFFKRVRPPQEE  1000
1001  QEREQLQPHENGEGNSET                                   1018
```

Human β8
                                                               SEQ ID NO: 394
```
   1  EDNRCASSNAASCARCLALGPECGWCVQEDFISGGSRSERCDIVSNLISK    50
  51  GCSVDSIEYPSVHVIIPTENEINTQVTPGEVSIQLRPGAEANFMLKVHPL   100
 101  KKYPVDLYYLVDVSASMHNNIEKLNSVGNDLSRKMAFFSRDFRLGFGSYV   150
 151  DKTVSPYISIHPERIHNQCSDYNLDCMPPHGYIHVLSLTENITEFEKAVH   200
 201  RQKISGNIDTPEGGFDAMLQAAVCESHIGWRKEAKRLLLVMTDQTSHLAL   250
 251  DSKLAGIVVPNDGNCHLKNNVYVKSTTMEHPSLGQLSEKLIDNNINVIFA   300
 301  VQGKQFHWYKDLLPLLPGTIAGEIESKAANLNNLVVEAYQKLISEVKVQV   350
 351  ENQVQGIYFNITAICPDGSRKPGMEGCRNVTSNDEVLFNVTVTMKKCDVT   400
 401  GGKNYAIIKPIGFNETAKIHIHRNCSCQCEDNRGPKGKCVDETFLDSKCF   450
```

```
451  QCDENKCHFDEDQFSSESCKSHKDQPVCSGRGVCVCGKCSCHKIKLGKVY        500

501  GKYCEKDDFSCPYHHGNLCAGHGECEAGRCQCFSGWEGDRCQCPSAAAQH        550

551  CVNSKGQVCSGRGTCVCGRCECTDPRSIGRFCEHCPTCYTACKENWNCMQ        600

601  CLHPHNLSQAILDQCKTSCALMEQQHYVDQTSECFSSPSYLRIFFIIFIV        650

651  TFLIGLLKVLIIRQVILQWNSNKIKSSSDYRVSASKKDKLILQSVCTRAV        700

701  TYRREKPEEIKMDISKLNAHETFRCNF                              727
```

HuC6D4V1
SEQ ID NO: 395
QIQLVQSGAEVKKPGASVKISCKASGYTFT DYSMH WVRQAPGQGLEWVA RINTETGEPTFADDFRG

RFTVTLDTSTSTAYLEIRSLRSDDTAVYFCAI FYYGRDS WGQGTTLTVSS

VH Framework 1
SEQ ID NO: 396
QIQLVQSGAEVKKPGASVKISCKASGYTFT

VH CDR1
SEQ ID NO: 397
DYSMH

VH Framework 2
SEQ ID NO: 398
WVRQAPGQGLEWVA

VH CDR2
SEQ ID NO: 399
RINTETGEPTFADDFRG

VH Framework 3
SEQ ID NO: 400
RFTVILDTSTSTAYLEIRSLRSDDTAVYFCAI

VH CDR 3
SEQ ID NO: 401
FYYGRDS

VH Framework 4
SEQ ID NO: 402
WGQGTTLTVSS

HuC6D4A3
SEQ ID NO: 403
QIQLVQSGAEVKKPGASVKISCKASGYTFT DYSMH WVRQAPGQGLEWVA RINTETGEPTFADDFRG

RFTVTLDTSTSTAYLEIRSLRSDDTAVYFCAI FYYGRDS WGQGTTLTVSS

VH Framework 1
SEQ ID NO: 404
QIQLVQSGAEVKKPGASVKISCKASGYTFT

VH CDR1
SEQ ID NO: 405
DYSMH

VH Framework 2
SEQ ID NO: 406
WVRQAPGQGLEWVA

VH CDR2
SEQ ID NO: 407
RINTETGEPTFADDFRG

VH Framework 3
SEQ ID NO: 408
RFTVILDTSTSTAYLEIRSLRSDDTAVYFCAI

VH CDR 3
SEQ ID NO: 409
FYYGRDS

VH Framework 4
SEQ ID NO: 410
WGQGTTLTVSS

-continued

HuC6D4B7
SEQ ID NO: 411
QIQLVQSGAKVKKPGASVKISCKASGYTFT DYSMH WVRQAPGQGLEWVA RINTETGEPTFADDFRG
RFSVTLDTSTSTAYLEITSLRSDDTAVYFCAI FYYGRDT WGQGTALTVSS

VH Framework 1
SEQ ID NO: 412
QIQLVQSGAKVKKPGASVKISCKASGYTFT

VH CDR1
SEQ ID NO: 413
DYSMH

VH Framework 2
SEQ ID NO: 414
WVRQAPGQGLEWVA

VH CDR2
SEQ ID NO: 415
RINTETGEPTFADDFRG

VH Framework 3
SEQ ID NO: 416
RFSVTLDTSTSTAYLEITSLRSDDTAVYFCAI

VH CDR 3
SEQ ID NO: 417
FYYGRDT

VH Framework 4
SEQ ID NO: 418
WGQGTALTVSS

HuC6D4E5
SEQ ID NO: 419
QIQLVQSGAEVKKPGASVKISCKASGYTFT DYSMH WVRQAPGQGLEWVA RINTETGEPTFADDFRG
RFTVTLDTSTSTAYLEIRSLRSDDTAVYFCAI FYYGRDT WGQGTTLTVSS

VH Framework 1
SEQ ID NO: 420
QIQLVQSGAEVKKPGASVKISCKASGYTFT

VH CDR1
SEQ ID NO: 421
DYSMH

VH Framework 2
SEQ ID NO: 422
WVRQAPGQGLEWVA

VH CDR2
SEQ ID NO: 423
RINTETGEPTFADDFRG

VH Framework 3
SEQ ID NO: 424
RFTVILDTSTSTAYLEIRSLRSDDTAVYFCAI

VH CDR 3
SEQ ID NO: 425
FYYGRDT

VH Framework 4
SEQ ID NO: 426
WGQGTTLTVSS

HuC6D4
SEQ ID NO: 427
QIQLVQSGAEVKKPGASVKISCKASGYTFT DYSMH WVRQAPGQGLEWVA RINTETGEPTFADDFRG
RFTVTLDTSTSTAYLEIRSLRSDDTAVYFCAI FYYGRDT WGQGTTLTVSS

VH Framework 1
SEQ ID NO: 428
QIQLVQSGAEVKKPGASVKISCKASGYTFT

-continued

VH CDR1  
SEQ ID NO: 429  
DYSMH

VH Framework 2  
SEQ ID NO: 430  
WVRQAPGQGLEWVA

VH CDR2  
SEQ ID NO: 431  
RINTETGEPTFADDFRG

VH Framework 3  
SEQ ID NO: 432  
RFTVILDTSTSTAYLEIRSLRSDDTAVYFCAI

VH CDR 3  
SEQ ID NO: 433  
FYYGRDT

VH Framework 4  
SEQ ID NO: 434  
WGQGTTLTVSS

C6D4-RGD3  
SEQ ID NO: 435  
QIQLLQSGPELKKPGETVKISCKASGYTFT DYSMH WVKQAPGKGLKWVA RINTETGEPTFADDFRG

RFAVSLETSASTAYLQINNLKNEDTATYFCAI FYYGRDS WGQGTTLTVSS

VH Framework 1  
SEQ ID NO: 436  
QIQLLQSGPELKKPGETVKISCKASGYTFT

VH CDR1  
SEQ ID NO: 437  
DYSMH

VH Framework 2  
SEQ ID NO: 438  
WVKQAPGKGLKWVA

VH CDR2  
SEQ ID NO: 439  
RINTETGEPTFADDFRG

VH Framework 3  
SEQ ID NO: 440  
RFAVSLETSASTAYLQINNLKNEDTATYFCAI

VH CDR 3  
SEQ ID NO: 441  
FYYGRDS

VH Framework 4  
SEQ ID NO: 442  
WGQGTTLTVSS

HuC6D4-RGD3  
SEQ ID NO: 443  
QIQLVQSGAEVKKPGASVKISCKASGYTFT DYSMH WVRQAPGQGLEWVA RINTETGEPTFADDFRG

RFTVTLDTSTSTAYLEIRSLRSDDTAVYFCAI FYYGRDT WGQGTTLTVSS

VH Framework 1  
SEQ ID NO: 444  
QIQLVQSGAEVKKPGASVKISCKASGYTFT

VH CDR1  
SEQ ID NO: 445  
DYSMH

VH Framework 2  
SEQ ID NO: 446  
WVRQAPGQGLEWVA

VH CDR2  
SEQ ID NO: 447  
RINTETGEPTFADDFRG

-continued

VH Framework 3

SEQ ID NO: 448

RFTVILDTSTSTAYLEIRSLRSDDTAVYFCAI

VH CDR 3

SEQ ID NO: 449

FYYGRDT

VH Framework 4

SEQ ID NO: 450

WGQGTTLTVSS

HuC6D4V1

SEQ ID NO: 451

EIVMTQSPATLSVSPGERVTMSC KSSQSLLNSRTRKNYLA WYQQKPGQAPRLLIY WASTRES

GVPARFSGSGSGTEFTLTISSVQSEDFAVYYC KQSYNLLS FGQGTVLEIKR

Vk Framework 1

SEQ ID NO: 452

EIVMTQSPATLSVSPGERVTMSC

Vk CDR1

SEQ ID NO: 453

KSSQSLLNSRTRKNYLA

Vk Framework 2

SEQ ID NO: 454

WYQQKPGQAPRLLIY

Vk CDR2

SEQ ID NO: 455

WASTRES

Vk Framework 3

SEQ ID NO: 456

GVPARFSGSGSGTEFTLTISSVQSEDFAVYYC

Vk CDR 3

SEQ ID NO: 457

KQSYNLLS

Vk Framework 4

SEQ ID NO: 458

FGQGTVLEIKR

HuC6D4A3

SEQ ID NO: 459

EIVMTQSPATLSVSPGEIVTMSC KSSQSLLNSRSRKNYLA WYQQKPGQAPRLLIY WASTRES

GVPARFSGSGSGTEFTLTISSVQSEDFAVYYC KQSYNLLS FGQGTVLEIKR

Vk Framework 1

SEQ ID NO: 460

EIVMTQSPATLSVSPGEIVTMSC

Vk CDR1

SEQ ID NO: 461

KSSQSLLNSRSRKNYLA

Vk Framework 2

SEQ ID NO: 462

WYQQKPGQAPRLLIY

Vk CDR2

SEQ ID NO: 463

WASTRES

Vk Framework 3

SEQ ID NO: 464

GVPARFSGSGSGTEFTLTISSVQSEDFAVYYC

Vk CDR 3

SEQ ID NO: 465

KQSYNLIS

Vk Framework 4

SEQ ID NO: 466

FGQGTVLEIKR

```
HuC6D4B7
                                                       SEQ ID NO: 467
EIVMTQTPVTLSVSPGERVTMSC KSSQSLLNSRTRKNYLA WYQQKPGQAPRLLIY WASTRES

DVPARFSGSGSGTEFTLTISSVQSEDFAVYYC KQSSNLIS FGQGTVLEIKR

Vk Framework 1
                                                       SEQ ID NO: 468
EIVMTQTPVTLSVSPGERVTMSC Vk CDR1
                                                       SEQ ID NO: 469
KSSQSLLNSRTRKNYLA Vk Framework 2
                                                       SEQ ID NO: 470
WYQQKPGQAPRLLIY Vk CDR2
                                                       SEQ ID NO: 471
WASTRES Vk Framework 3
                                                       SEQ ID NO: 472
DVPARFSGSGSGTEFTLTISSVQSEDFAVYYC Vk CDR 3
                                                       SEQ ID NO: 473
KQSSNLIS Vk Framework 4
                                                       SEQ ID NO: 474
FGQGTVLEIKR HuC6D4E5
                                                       SEQ ID NO: 475
EIVMTQSPATLSVSPGERVTMSC KSSQSLLNSRSRKNYLA WYQQKPGQAPRLLIY WASTRES

GVPARFSGSGSGTEFTLTISSVQSEDFAVYYC KQSYNLLS FGQGTVLEIKR

Vk Framework 1
                                                       SEQ ID NO: 476
EIVMTQSPATLSVSPGERVTMSC Vk CDR1
                                                       SEQ ID NO: 478
KSSQSLLNSRSRKNYLA Vk Framework 2
                                                       SEQ ID NO: 479
WYQQKPGQAPRLLIY Vk CDR2
                                                       SEQ ID NO: 480
WASTRES Vk Framework 3
                                                       SEQ ID NO: 481
GVPARFSGSGSGTEFTLTISSVQSEDFAVYYC Vk CDR 3
                                                       SEQ ID NO: 482
KQSYNLLS Vk Framework 4
                                                       SEQ ID NO: 483
FGQGTVLEIKR HuC6D4
                                                       SEQ ID NO: 484
EIVMTQSPATLSVSPGERVTMSC KSSQSLLNSRSRKNYLA WYQQKPGQAPRLLIY WASTRES

GVPARFSGSGSGTEFTLTISSVQSEDFAVYYC KQSYNLLS FGQGTVLEIKR

Vk Framework 1
                                                       SEQ ID NO: 485
EIVMTQSPATLSVSPGERVTMSC
```

Vk CDR1
KSSQSLLNSRSRKNYLA
SEQ ID NO: 486

Vk Framework 2
WYQQKPGQAPRLLIY
SEQ ID NO: 487

Vk CDR2
WASTRES
SEQ ID NO: 488

Vk Framework 3
GVPARFSGSGSGTEFTLTISSVQSEDFAVYYC
SEQ ID NO: 489

Vk CDR 3
KQSYNLLS
SEQ ID NO: 490

Vk Framework 4
FGQGTVLEIKR
SEQ ID NO: 491

C6D4-RGD3
DIVMTQSPSSLAVSAGEKVTMSC KSSQSLLGRGDLGRLKKNALA WYQQKPGQSPRLLIY WASTRES
GVPDRFTGSGSGTDFTLTISSVQAEDLAVYYC KQSYNLLS FGAGTKLELKR
SEQ ID NO: 492

Vk Framework 1
DIVMTQSPSSLAVSAGEKVTMSC
SEQ ID NO: 493

Vk CDR1
KSSQSLLGRGDLGRLKKNALA
SEQ ID NO: 494

Vk Framework 2
WYQQKPGQSPRLLIY
SEQ ID NO: 495

Vk CDR2
WASTRES
SEQ ID NO: 496

Vk Framework 3
GVPDRFTGSGSGTDFTLTISSVQAEDLAVYYC
SEQ ID NO: 497

Vk CDR 3
KQSYNLLS
SEQ ID NO: 498

Vk Framework 4
FGAGTKLELKR
SEQ ID NO: 499

HuC6D4-RGD3
EIVMTQSPATLSVSPGERVTMSC KSSQSLLGRGDLGRLKKNALA WYQQKPGQAPRLLIY WASTRES
GVPARFSGSGSGTEFTLTISSVQSEDFAVYYC KQSYNLLS FGQGTVLEIKR
SEQ ID NO: 500

Vk Framework 1
EIVMTQSPATLSVSPGERVTMSC
SEQ ID NO: 501

Vk CDR1
KSSQSLLGRGDLGRLKKNALA
SEQ ID NO: 502

Vk Framework 2
WYQQKPGQAPRLLIY
SEQ ID NO: 503

Vk CDR2
WASTRES
SEQ ID NO: 504

| | |
|---|---|
| Vk Framework 3<br>GVPARFSGSGSGTEFTLTISSVQSEDFAVYYC | SEQ ID NO: 505 |
| Vk CDR 3<br>KQSYNLLS | SEQ ID NO: 506 |
| Vk Framework 4<br>FGQGTVLEIKR | SEQ ID NO: 507 |
| Huc6D4V1 VH CDR1<br>DYSMH | SEQ ID NO: 508 |
| Huc6D4V1 VH CDR2<br>RINTETGEPTFADDFRG | SEQ ID NO: 509 |
| Huc6D4V1 VH CDR3<br>FYYGRDS | SEQ ID NO: 510 |
| HuC6D4A3 VH CDR1<br>DYSMH | SEQ ID NO: 511 |
| HuC6D4A3 VH CDR2<br>RINTETGEPTFADDFRG | SEQ ID NO: 512 |
| HuC6D4A3 VH CDR3<br>FYYGRDS | SEQ ID NO: 513 |
| HuC6D4B7 VH CDR1<br>DYSMH | SEQ ID NO: 514 |
| HuC6D4B7 VH CDR2<br>RINTETGEPTFADDFRG | SEQ ID NO: 515 |
| HuC6D4B7 VH CDR3<br>FYYGRDT | SEQ ID NO: 516 |
| HuC6D4E5 VH CDR1<br>DYSMH | SEQ ID NO: 517 |
| HuC6D4E5 VH CDR2<br>RINTETGEPTFADDFRG | SEQ ID NO: 518 |
| HuC6D4E5 VH CDR3<br>FYYGRDT | SEQ ID NO: 519 |
| HuC6D4 VH CDR1<br>DYSMH | SEQ ID NO: 520 |
| HuC6D4 VH CDR2<br>RINTETGEPTFADDFRG | SEQ ID NO: 521 |
| HuC6D4 VH CDR3<br>FYYGRDT | SEQ ID NO: 522 |
| C6D4-RGD3 VH CDR1<br>DYSMH | SEQ ID NO: 523 |
| C6D4-RGD3 VH CDR2<br>RINTETGEPTFADDFRG | SEQ ID NO: 524 |
| C6D4-RGD3 VH CDR3 | |

-continued

```
FYYGRDS                                       SEQ ID NO: 525

HuC6D4-RGD3 VH CDR1
DYSMH                                         SEQ ID NO: 526

HuC6D4-RGD3 VH CDR2
RINTETGEPTFADDFRG                             SEQ ID NO: 527

HuC6D4-RGD3 VH CDR3
FYYGRDT                                       SEQ ID NO: 528

HuC6D4V1 Vk CDR1
KSSQSLLNSRTRKNYLA                             SEQ ID NO: 529

HuC6D4V1 Vk CDR2
WASTRES                                       SEQ ID NO: 530

HuC6D4V1 Vk CDR3
KQSYNLLS                                      SEQ ID NO: 531

HuC6D4A3 Vk CDR1
KSSQSLLNSRSRKNYLA                             SEQ ID NO: 532

HuC6D4A3 Vk CDR2
WASTRES                                       SEQ ID NO: 533

HuC6D4A3 Vk CDR3
KQSYNLIS                                      SEQ ID NO: 534

HuC6D4B7 Vk CDR1
KSSQSLLNSRTRKNYLA                             SEQ ID NO: 535

HuC6D4B7 Vk CDR2
WASTRES                                       SEQ ID NO: 536

HuC6D4B7 Vk CDR3
KQSSNLIS                                      SEQ ID NO: 537

HuC6D4E5 Vk CDR1
KSSQSLLNSRSRKNYLA                             SEQ ID NO: 538

HuC6D4E5 Vk CDR2
WASTRES                                       SEQ ID NO: 539

HuC6D4E5 Vk CDR3
KQSYNLLS                                      SEQ ID NO: 540

HuC6D4 Vk CDR1
KSSQSLLNSRSRKNYLA                             SEQ ID NO: 541

HuC6D4 Vk CDR2
WASTRES                                       SEQ ID NO: 542

HuC6D4 Vk CDR3
KQSYNLLS                                      SEQ ID NO: 543

C6D4-RGD3 Vk CDR1
KSSQSLLGRGDLGRLKKNALA                         SEQ ID NO: 544
```

-continued

```
C6D4-RGD3 Vk CDR2
                                         SEQ ID NO: 545
WASTRES

C6D4-RGD3 Vk CDR3
                                         SEQ ID NO: 546
KQSYNLLS

HuC6D4-RGD3 Vk CDR1
                                         SEQ ID NO: 547
KSSQSLLGRGDLGRLKKNALA

HuC6D4-RGD3 Vk CDR2
                                         SEQ ID NO: 548
WASTRES

HuC6D4-RGD3 Vk CDR3
                                         SEQ ID NO: 549
KQSYNLLS heavy chain FR1
                                         SEQ ID NO: 550
QIQLVQSG(P/A)(E/K)(L/V)KKPG(E/A)(T/S)VKISCKASGYTFT heavy chain FR2
                                         SEQ ID NO: 551
WV(K/R)QAPG(K/Q)GL(K/E)WVA heavy chain FR3
                                         SEQ ID NO: 552
RF(A/T/S)V(S/T)L(E/D)TS(A/T)STAYL(Q/E)I(N/R/T)
(N/S)L(K/R)(N/S)(E/D)DTA(T/V)YFCAI heavy chain FR4
                                         SEQ ID NO: 553
WGQGT(T/A)LTVSS light chain FR1
                                         SEQ ID NO: 554
(D/E)IVMTQ(S/T)P(S/A/V)(S/T)L(A/S)VS(A/P)GE(K/R/I)VTMSC light chain FR2
                                         SEQ ID NO: 555
WYQQKPGQ(S/A)PRLLIY light chain FR3
                                         SEQ ID NO: 556
(G/D)VP(D/A)RF(T/S)GSGSGT(D/E)FTLTISSVQ(A/S)ED(L/F)AVYYC light chain FR4
                                         SEQ ID NO: 557
FG(A/Q)GT(K/V)LE(L/I)KR heavy chain FR1
                                         SEQ ID NO: 558
QIQLx1QSGx2x3x34KKPGx4x5VKISCKASGYTFT heavy chain FR2
                                         SEQ ID NO: 559
WVx6QAPGx7GLx8Wx9x10 heavy chain FR3
                                         SEQ ID NO: 560
RFx17x18x19Lx20TSx21x22TAx23Lx24Ix25x26Lx27x28x29DTAx30YFCAI heavy chain FR4
                                         SEQ ID NO: 561
WGQGTx33LVTVSS heavy chain CDR1
                                         SEQ ID NO: 562
DYSMH heavy chain CDR2
                                         SEQ ID NO: 563
x11Ix12TETx13EPTx14ADDFx15x16
```

```
heavy chain CDR3                                          SEQ ID NO: 564
x31YYGRDx32
```
where x1 = V or L, x2 = A or P, x3 = E or K, x4 = A or E, x5 = S or T, x6 = R or K, x7 = Q or K, x8 = E or K, x9 = V or M, x10 = A or G, x11 = R or W, x12 = N or K, x13 = G or D, x14 = F or Y, x15 = R, N, K or G, x16 = G or E, x17 = T, A, or S, x18 = V or F, x19 = T or S, x20 = D or E, x21 = T or A, x22 = S or T, x23 = Y or N, x24 = E or Q, x25 = R, N, I or T, x26 = S or N, x27 = R or K, x28 = S or N, x29 = D or E, x30 = V, T, or K, x31 = F or Y, x32 = T or S, x33 = T or A, x34 = V or L.

```
light chain FR1                                           SEQ ID NO: 565
x40IVMx41Qx42Px43x44Lx45VSx46GEx47VTMSC light chain FR2                                           SEQ ID NO: 566
WYQQKPGQx49PRLLIY light chain FR3                                           SEQ ID NO: 567
x50VPx51RFx52GSGSGTx53FTLTISSVQx54EDx55AVYYC light chain FR4                                           SEQ ID NO: 568
FGx56GTx57LEx58KR light chain CDR1                                          SEQ ID NO: 569
KSSQSLLNSRx48RKNYLA light chain CDR2                                          SEQ ID NO: 570
WASTRES light chain CDR3                                          SEQ ID NO: 571
KQSYNLLS
```
where x40 = E or D, x41 = T or S, x42 = S or T, x43 = A, S or V, x44 = T, S, x45 = S or A, x46 = P or A, x47 = R, K or I, x48 = S or T, x49 = A or S, x50 = G or D, x51 = A or D, x52 = S or T, x53 = E or D, x54 = S, D or A, x55 = F or L, x56 = Q or A, x57 = V or K, x58 = I or L.

```
(C6D4)                                                    SEQ ID NO: 572
KSSQSLLNSRSRKNYLA (RGD1)                                                    SEQ ID NO: 573
KSSQSLLGRGDLGNALA (RGD2)                                                    SEQ ID NO: 574
KSSQSLLNSGRGDLGNALA (RGD3)                                                    SEQ ID NO: 575
KSSQSLLGRGDLGRLKKNALA (RGD3-1)                                                  SEQ ID NO: 576
KSSQSLLGRGDLGRLKKQKDHNALA (RGD3-2)                                                  SEQ ID NO: 577
KSSQSLLGRGDLGRLKKQKDNALA
```

-continued (RGD3-3)　　　　　　　　　　　　　　　　　　　　　　　　　　　　　　SEQ ID NO: 578

KSSQSLLGRGDLGRLKKQKNALA (RGD3-4)　　　　　　　　　　　　　　　　　　　　　　　　　　　　　　SEQ ID NO: 579

KSSQSLLGRGDLGRLKKQNALA (RGD3-6)　　　　　　　　　　　　　　　　　　　　　　　　　　　　　　SEQ ID NO: 580

KSSQSLLGRGDLGRLKNALA (RGD3-7)　　　　　　　　　　　　　　　　　　　　　　　　　　　　　　SEQ ID NO: 581

KSSQSLLGRGDLGRLNALA (RGD3-8)　　　　　　　　　　　　　　　　　　　　　　　　　　　　　　SEQ ID NO: 582

KSSQSLLGRGDLGRNALA (RGD3-9)　　　　　　　　　　　　　　　　　　　　　　　　　　　　　　SEQ ID NO: 583

KSSQSLLGRGDLGRLKKQKDHH (RGD3-10)　　　　　　　　　　　　　　　　　　　　　　　　　　　　　 SEQ ID NO: 584

KSSQSLLGRGDLGRLKKQKDH (RGD3-11)　　　　　　　　　　　　　　　　　　　　　　　　　　　　　 SEQ ID NO: 585

KSSQSLLGRGDLGRLKKQKD (RGD3-12)　　　　　　　　　　　　　　　　　　　　　　　　　　　　　 SEQ ID NO: 586

KSSQSLLGRGDLGRLKKQK (RGD3-13)　　　　　　　　　　　　　　　　　　　　　　　　　　　　　 SEQ ID NO: 587

KSSQSLLGRGDLGRLKKQ (RGD3-14)　　　　　　　　　　　　　　　　　　　　　　　　　　　　　 SEQ ID NO: 588

KSSQSLLGRGDLGRLKK (RGD3-15)　　　　　　　　　　　　　　　　　　　　　　　　　　　　　 SEQ ID NO: 589

KSSQSLLGRGDLGRLK (RGD3-16)　　　　　　　　　　　　　　　　　　　　　　　　　　　　　 SEQ ID NO: 590

KSSQSLLGRGDLGRL

Human αv　　　　　　　　　　　　　　　　　　　　　　　　　　　　　 SEQ ID NO: 591

FLQDGTKTVEYAPCRSQDI_DADG_QGFCQGGFSIDFTKADRVLLGGPGSF_Y_WQGQ

Chimp αv　　　　　　　　　　　　　　　　　　　　　　　　　　　　　 SEQ ID NO: 592

FLQDGTKTVEYAPCRSQDI_DADG_QGFCQGGFSIDFTKADRVLLGGPGSF_Y_WQGQ

Rhesus αv　　　　　　　　　　　　　　　　　　　　　　　　　　　　　SEQ ID NO: 593

FLQDGTKTVEYAPCRSQDI_DADG_QGFCQGGFSIDFTKADRVLLGGPGSF_Y_WQGQ

Cyno αv　　　　　　　　　　　　　　　　　　　　　　　　　　　　　　SEQ ID NO: 594

FLQDGTKTVEYAPCRSQDI_DADG_QGFCQGGFSIDFTKADRVLLGGPGSF_Y_WQGQ

Cow αv　　　　　　　　　　　　　　　　　　　　　　　　　　　　　　 SEQ ID NO: 595

FLQDGTKTVEYAPCRSKNI_DADG_QGFCQGGFSIDFTKADRVLLGGPGSF_Y_WQGQ

Pig αv　　　　　　　　　　　　　　　　　　　　　　　　　　　　　　 SEQ ID NO: 596

FLQDGTKTVEYAPCRSKNI_DADG_QGFCQGGFSIDFTKADRVLLGGPGSF_Y_WQGQ

Horse αv　　　　　　　　　　　　　　　　　　　　　　　　　　　　　 SEQ ID NO: 597

FLQDGAKTVEYAPCRSKNI_DADG_QGFCQGGFSIDFTKADRVLLGGPGSF_Y_WQGQ

```
Mouse αv
                                                       SEQ ID NO: 598
FLQDGTKTVEYAPCRSKNIDADGQGFCQGGFSIDFTKADRVLLGGPGSFYWQGQ Rat αv
                                                       SEQ ID NO: 599
FLQDGTKTVEYAPCRSKNIDADGQGFCQGGFSIDFTKADRVLLGGPGSFYWQGQ Armadillo αv
                                                       SEQ ID NO: 600
FLQDGTKTVEYAPCRSKNIDADGQGFCQGGFSIDFTKADRVLLGGPGSFYWQGQ Platypus αv
                                                       SEQ ID NO: 601
FLQDGTKTVEYAPCRSRSIDADGQGFCQGGFSIDFTKADRVLLGGPGSFYWQGQ Human β8
                                                       SEQ ID NO: 602
SASMHNNIEKLNSVGNDLSRKMAFFSRDFRLGFGSYVDKTVSPYISIHPERIHNQCSDYNLDCMPPHGYI

HVLSLTENITEFEKAVHRQKIS

Chimp β8
                                                       SEQ ID NO: 603
SASMHNNIEKLNSVGNDLSRKMAFFSRDFRLGFGSYVDKTVSPYISIHPERIHNQCSDYNLDCMPPHGYI

HVLSLTENITEFERAVHRQKIS

Rhesus β8
                                                       SEQ ID NO: 604
SASMHNNIEKLNSVGNDLSRKMAFFSRDFRLGFGSYVDKTVSPYISIHPERIHNQCSDYNLDCMPPHGYI

HVLSLTENITEFEKAVHRQKIS

Cyno β8
                                                       SEQ ID NO: 605
SASMHNNIEKLNSVGNDLSRKMAFFSRDFRLGFGSYVDKTVSPYISIHPERIHNQCSDYNLDCMPPHGYI

HVLSLTENITEFEKAVHRQKIS

Cow β8
                                                       SEQ ID NO: 606
SASMHNNIEKLNSVGNDLSRKMAFFSRDFRLGFGSYVDKTVSPYISIHPERIHNQCSDYNLDCMPPHGYI

HVLSLTENITEFEKAVHRQKIS

Pig β8
                                                       SEQ ID NO: 607
SASMHNNIEKLNTVGNDLSRKMAFFSRDFRLGFGSYVDKTVSPYISIHPERIHNQCSDYNLDCMPPHGYI

HVLSLTENITEFEKAVHRQKIS

Horse β8
                                                       SEQ ID NO: 608
SASMHNNIEKLNSVGNDLSRKMAFFSRDFRLGFGSYVDKTVSPYISIHPERIHNQCSDYNLDCMPPHGYI

HVLSLTENITEFEKAVHRQKIS

Mouse β8
                                                       SEQ ID NO: 609
SASMHNNIEKLNSVGNDLSKKMALYSRDFRLGFGSYVDKTVSPYISIHPERIHNQCSDYNLDCMPPHGYI

HVLSLTENITEFEKAVHRQKIS

Rat β8
                                                       SEQ ID NO: 610
SASMHNNIEKLNSVGNDLSKKMALFSHDFRLGFGSYVDKTVSPYISIHPERIHNQCSDYNLDCMPPHGYI

HVLSLTENITEFEKAVHRQKIS

Armadillo β8
                                                       SEQ ID NO: 611
SASMHNNIEKLNSVGNDLSRKMAFFSLDFRLGFGSYVDKTVSPYISIHPERIHNQCSDYNLDCMPPHGYI

HVLSLTENITEFAKAVHRQKIS
```

Platypus β8
SEQ ID NO: 612
SASMHNNIEKLNSVGNDLSQKMADFTRDFRLGFGSYVDKTVSPYISIHPGRIRNQC*SQYDLD*CMPPHGYI

HVLPLTENVTEFEKAVNKQKIS

C6D4 VH CDR1
SEQ ID NO: 613
YTFTDYSMH

C6D4 VH CDR2
SEQ ID NO: 614
RINTETGEPTFADDFRG

C6D4 VH CDR3
SEQ ID NO: 615
FYYGRDS

C6D4 Vk CDR1
SEQ ID NO: 616
KSSQSLLNSRTRKNYLA

C6D4 Vk CDR2
SEQ ID NO: 617
YWASTRES

C6D4 Vk CDR3
SEQ ID NO: 618
KQSYNLLS

β8, α1 helix
SEQ ID NO: 619
SASMHNNIEKLNSVGNDLSRKMAFFS

β8, SDL
SEQ ID NO: 620
TVSPYISIHPERIHNQCSDYNLDCMPPH

β8, α2 helix
SEQ ID NO: 621
NITEFEKAVHR

αV, β-propeller domain blade W3
SEQ ID NO: 622
KQDKILACAPLYHWRTEMKQEREPVGTCFLQDGTKTVEYAPCRSQDIDADGQGFCQGGFSIDFTKADRVL

LGGPGSFYWQGQLISDQVAEIVSKYDPNVYSIKYNNQLATRTAQAIFD head sequence of integrin αv:
SEQ ID NO: 623
FNLDVDSPAEYSGPEGSYFGFAVDFFVPSASSRMFLLVGAPKANTTQPGIVEGGQVLKCDWSSTRRCQPI

EFDATGNRDYAKDDPLEFKSHQWFGASVRSKQDKILACAPLYHWRTEMKQEREPVGTCFLQDGTKTVEYA

PCRSQDIDADGQGFCQGGFSIDFTKADRVLLGGPGSFYWQGQLISDQVAEIVSKYDPNVYSIKYNNQLAT

RTAQAIFDDSYLGYSVAVGDFNGDGIDDFVSGVPRAARTLGMVYIYDGKNMSSLYNFTGEQMAAYFGFSV

AATDINGDDYADVFIGAPLFMDRGSDGKLQEVGQVSVSLQRASGDFQTTKLNGFEVFARFGSAIAPLGDL

DQDGFNDIAIAAPYGGEDKKGIVYIFNGRSTGLNAVPSQILEGQWAARSMPPSFGYSMKGATDIDKNGYP

DLIVGAFGVDRAILYRARP

4F1 VH
SEQ ID NO: 624
QVQLQQSGAELVRPGTSVKVSCKASGY AFTNYLIE WVKQRPGQGLEWIG VINPGTGGTNYNKKFKV

KATLTADKSSSTAYMQLGGLTFDDSAVYFCAR EGNARTYYYAMDY WGQGTSVTVSS

VH Framework 1
SEQ ID NO: 625
QVQLQQSGAELVRPGTSVKVSCKASGY

VH CDR1
SEQ ID NO: 628
AFTNYLIE

```
VH Framework 2                                          SEQ ID NO: 632
WVKQRPGQGLEWIG VH CDR2                                                 SEQ ID NO: 634
VINPGTGGTNYNKKFKV VH Framework 3                                          SEQ ID NO: 637
KATLTADKSSSTAYMQLGGLTFDDSAVYFCAR VH CDR3                                                 SEQ ID NO: 651
EGNARTYYYAMDY VH Framework 4                                          SEQ ID NO: 655
WGQGTSVTVSS 6B9 VH                                                  SEQ ID NO: 656
QVQLQQSGAELVRPGTSVKVSCKASGY AFTDYLIE WVKQRPGQGLEWIG VINPETGGTNYNAKFKG

KATLTADKSSSAYMQLSSLTSGDSAVYFCAR EAGNYIYAMDY WGQGTSVTVSS

VH Framework 1                                          SEQ ID NO: 625
QVQLQQSGAELVRPGTSVKVSCKASGY

VH CDR1                                                 SEQ ID NO: 629
AFTDYLIE

VH Framework 2                                          SEQ ID NO: 632
WVKQRPGQGLEWIG VH CDR2                                                 SEQ ID NO: 635
VINPETGGTNYNAKFKG VH Framework 3                                          SEQ ID NO: 638
KATLTADKSSSAYMQLSSLTSGDSAVYFCAR VH CDR3                                                 SEQ ID NO: 652
EAGNYIYAMDY VH Framework 4                                          SEQ ID NO: 655
WGQGTSVTVSS 6B9.1 VH                                                SEQ ID NO: 657
QVQLQQSGAELVRPGTSVKVSCKASGY AFTDYLIE WVKQRPGQGLEWIG VINPETGGTNYNAKFRG

KATLTADKSSSAYMQLSSLTSGDSAVYFCAR AGNYIYAMDY WGQGTSVTVSS

VH Framework 1                                          SEQ ID NO: 625
QVQLQQSGAELVRPGTSVKVSCKASGY

VH CDR1                                                 SEQ ID NO: 629
AFTDYLIE

VH Framework 2                                          SEQ ID NO: 632
WVKQRPGQGLEWIG VH CDR2                                                 SEQ ID NO: 636
VINPETGGTNYNAKFRG VH Framework 3                                          SEQ ID NO: 638
KATLTADKSSSAYMQLSSLTSGDSAVYFCAR
```

-continued

VH CDR3  
SEQ ID NO: 653  
AGNYIYAMDY

VH Framework 4  
SEQ ID NO: 655  
WGQGTSVTVSS

A1 VH  
SEQ ID NO: 658  
QVQLQQSGAELVRPGASVKVSCKASGY AFTDYLIE WVRQRPGQGLEWIG VINPETGGTNYNAKFRG

KATLTADKSSSSVYMQLSSLTSGDSAVYFCAR EAGNYIYAMDY WGQGTSVTVSS

VH Framework 1  
SEQ ID NO: 626  
QVQLQQSGAELVRPGASVKVSCKASGY

VH CDR1  
SEQ ID NO: 629  
AFTDYLIE

VH Framework 2  
SEQ ID NO: 633  
WVRQRPGQGLEWIG

VH CDR2  
SEQ ID NO: 636  
VINPETGGTNYNAKFRG

VH Framework 3  
SEQ ID NO: 639  
KATLTADKSSSSVYMQLSSLTSGDSAVYFCAR

VH CDR3  
SEQ ID NO: 654  
EAGNYIYAMDY

VH Framework 4  
SEQ ID NO: 655  
WGQGTSVTVSS

A2 VH  
SEQ ID NO: 659  
QVQLQQSGAELVRPGTSVKVSCKASGY AFTDYLIE WVRQRPGQGLEWIG VINPETGGTNYNAKFRG

KATLTADKSSSTAYMQLSSLTSGDSAVYFCAR EAGNYIYAMDY WGQGTSVTVSS

VH Framework 1  
SEQ ID NO: 625  
QVQLQQSGAELVRPGTSVKVSCKASGY

VH CDR1  
SEQ ID NO: 629  
AFTDYLIE

VH Framework 2  
SEQ ID NO: 633  
WVRQRPGQGLEWIG

VH CDR2  
SEQ ID NO: 636  
VINPETGGTNYNAKFRG

VH Framework 3  
SEQ ID NO: 640  
KATLTADKSSSTAYMQLSSLTSGDSAVYFCAR

VH CDR3  
SEQ ID NO: 654  
EAGNYIYAMDY

VH Framework 4  
SEQ ID NO: 655  
WGQGTSVTVSS

A8 VH  
SEQ ID NO: 660  
QVQLQQSGAELVRPGTSVKVSCKASGY AFTDYLIE WVRQRPGQGLEWIG VINPETGGTNYNAKFRG

KATLTADKSSSSAYMQLSGLTSGDSAVYFCAR EAGNYIYAMDY WGQGTSVTVSS

-continued

```
VH Framework 1
                                           SEQ ID NO: 625
QVQLQQSGAELVRPGTSVKVSCKASGY

VH CDR1
                                           SEQ ID NO: 629
AFTDYLIE

VH Framework 2
                                           SEQ ID NO: 633
WVRQRPGQGLEWIG VH CDR2
                                           SEQ ID NO: 636
VINPETGGTNYNAKFRG VH Framework 3
                                           SEQ ID NO: 641
KATLTADKSSSSAYMQLSGLTSGDSAVYFCAR

VH CDR3
                                           SEQ ID NO: 654
EAGNYIYAMDY

VH Framework 4
                                           SEQ ID NO: 655
WGQGTSVTVSS A11 VH
                                           SEQ ID NO: 661
QVQLQQSGAELVRPGTSVKVSCKASGY AFTDNLIE WVRQRPGQGLEWIG VINPETGGTNYNAKFRG

KATLTADKSSSSAYMQLSSLTSGDSAVYFCAR EAGNYIYAMDY WGQGTSVTVSS

VH Framework 1
                                           SEQ ID NO: 625
QVQLQQSGAELVRPGTSVKVSCKASGY

VH CDR1
                                           SEQ ID NO: 630
AFTDNLIE

VH Framework 2
                                           SEQ ID NO: 633
WVRQRPGQGLEWIG VH CDR2
                                           SEQ ID NO: 636
VINPETGGTNYNAKFRG VH Framework 3
                                           SEQ ID NO: 638
KATLTADKSSSSAYMQLSSLTSGDSAVYFCAR

VH CDR3
                                           SEQ ID NO: 654
EAGNYIYAMDY

VH Framework 4
                                           SEQ ID NO: 655
WGQGTSVTVSS B1 VH
                                           SEQ ID NO: 662
QVQLQQSGAELVRPGTSVKVSCKASGY AFTDYLIE WVKQRPGQGLEWIG VINPETGGTNYNAKFRG

KATLTADKSSSSAYMQLSSLSSGDSAVYFCAR EAGNYIYAMDY WGQGTSVTVSS

VH Framework 1
                                           SEQ ID NO: 625
QVQLQQSGAELVRPGTSVKVSCKASGY

VH CDR1
                                           SEQ ID NO: 629
AFTDYLIE

VH Framework 2
                                           SEQ ID NO: 632
WVKQRPGQGLEWIG
```

-continued

VH CDR2  
SEQ ID NO: 636  
VINPETGGTNYNAKFRG

VH Framework 3  
SEQ ID NO: 642  
KATLTADKSSSSAYMQLSSLSSGDSAVYFCAR

VH CDR3  
SEQ ID NO: 654  
EAGNYIYAMDY

VH Framework 4  
SEQ ID NO: 655  
WGQGTSVTVSS

B3 VH  
SEQ ID NO: 663  
QVQLQQSGAELVRPGTSVKVSCKASGY AFTDYLIE WVRQRPGQGLEWIG VINPETGGTNYNAKFRG

KATLTADKSSSSAYMQLSGLTSGDSAVYFCAR EAGNYIYAMDY WGQGTSVTVSS

VH Framework 1  
SEQ ID NO: 625  
QVQLQQSGAELVRPGTSVKVSCKASGY

VH CDR1  
SEQ ID NO: 629  
AFTDYLIE

VH Framework 2  
SEQ ID NO: 633  
WVRQRPGQGLEWIG

VH CDR2  
SEQ ID NO: 636  
VINPETGGTNYNAKFRG

VH Framework 3  
SEQ ID NO: 643  
KATLTADKSSSSAYMQLSGLTSGDSAVYFCAR

VH CDR3  
SEQ ID NO: 654  
EAGNYIYAMDY

VH Framework 4  
SEQ ID NO: 655  
WGQGTSVTVSS

C4 = F10 VH  
SEQ ID NO: 664  
QVQLQQSGAELVRPGTSVKVSCKASGY AFTDYLIE WVRQRPGQGLEWIG VINPETGGTNYNAKFRG

RATLTADKSSSSAYMQLSSLTSGDSAVYFCAR EAGNYIYAMDY WGQGTSVTVSS

VH Framework 1  
SEQ ID NO: 625  
QVQLQQSGAELVRPGTSVKVSCKASGY

VH CDR1  
SEQ ID NO: 629  
AFTDYLIE

VH Framework 2  
SEQ ID NO: 633  
WVRQRPGQGLEWIG

VH CDR2  
SEQ ID NO: 636  
VINPETGGTNYNAKFRG

VH Framework 3  
SEQ ID NO: 644  
RATLTADKSSSSAYMQLSSLTSGDSAVYFCAR

VH CDR3  
SEQ ID NO: 654  
EAGNYIYAMDY

-continued

VH Framework 4
SEQ ID NO: 655
WGQGTSVTVSS

C7 = D1 VH
SEQ ID NO: 665
QVQLQQSGAELVRPGTSVKVSCKASGY AFTDYLIE WVRQRPGQGLEWIG VINPETGGTNYNAKFRG

KATLTADKSSGSAYMQLSSLTSGDSAVYFCAR EAGNYIYAMDY WGQGTSVTVSS

VH Framework 1
SEQ ID NO: 625
QVQLQQSGAELVRPGTSVKVSCKASGY

VH CDR1
SEQ ID NO: 629
AFTDYLIE

VH Framework 2
SEQ ID NO: 633
WVRQRPGQGLEWIG

VH CDR2
SEQ ID NO: 636
VINPETGGTNYNAKFRG

VH Framework 3
SEQ ID NO: 644
RATLTADKSSSSAYMQLSSLTSGDSAVYFCAR

VH CDR3
SEQ ID NO: 654
EAGNYIYAMDY

VH Framework 4
SEQ ID NO: 655
WGQGTSVTVSS

D3 = F1 VH
SEQ ID NO: 666
QVQLQQSGAELVRPGTSVKVSCKASGY AFTDYLIE WVRQRPGQGLEWIG VINPETGGTNYNAKFRG

KATLTADKSSSSAYMQLSSLTSDDSAVYFCAR EAGNYIYAMDY WGQGTSVTVSS

VH Framework 1
SEQ ID NO: 625
QVQLQQSGAELVRPGTSVKVSCKASGY

VH CDR1
SEQ ID NO: 629
AFTDYLIE

VH Framework 2
SEQ ID NO: 633
WVRQRPGQGLEWIG

VH CDR2
SEQ ID NO: 636
VINPETGGTNYNAKFRG

VH Framework 3
SEQ ID NO: 645
KATLTADKSSSSAYMQLSSLTSDDSAVYFCAR

VH CDR3
SEQ ID NO: 654
EAGNYIYAMDY

VH Framework 4
SEQ ID NO: 655
WGQGTSVTVSS

D10 = E5 VH
SEQ ID NO: 667
QVQLQQSGAELVRPGTSVKVSCKASGY AFTDYLIE WVRQRPGQGLEWIG VINPETGGTNYNAKFRG

KVTLTADKTSSSAYMQLSSLTSGDSAVYFCAR EAGNYIYAMDY WGQGTSVTVSS

```
VH Framework 1                                          SEQ ID NO: 625
QVQLQQSGAELVRPGTSVKVSCKASGY

VH CDR1                                                 SEQ ID NO: 629
AFTDYLIE

VH Framework 2                                          SEQ ID NO: 633
WVRQRPGQGLEWIG VH CDR2                                                 SEQ ID NO: 636
VINPETGGTNYNAKFRG VH Framework 3                                          SEQ ID NO: 646
KVTLTADKTSSSAYMQLSSLTSGDSAVYFCAR VH CDR3                                                 SEQ ID NO: 654
EAGNYIYAMDY VH Framework 4                                          SEQ ID NO: 655
WGQGTSVTVSS G4 VH                                                   SEQ ID NO: 668
QVQLQQSGAELVRPGTSVKVSCKASGY AFTDYLIE WVRQRPGQGLEWIG VINPETGGTNYNAKFRG

KVTLTADKSSSSAYMQLNSLTSGDSAVYFCAR EAGNYIYAMDY WGQGTSVTVSS

VH Framework 1                                          SEQ ID NO: 625
QVQLQQSGAELVRPGTSVKVSCKASGY

VH CDR1                                                 SEQ ID NO: 629
AFTDYLIE

VH Framework 2                                          SEQ ID NO: 633
WVRQRPGQGLEWIG VH CDR2                                                 SEQ ID NO: 636
VINPETGGTNYNAKFRG VH Framework 3                                          SEQ ID NO: 647
KVTLTADKSSSSAYMQLNSLTSGDSAVYFCAR VH CDR3                                                 SEQ ID NO: 654
EAGNYIYAMDY VH Framework 4                                          SEQ ID NO: 655
WGQGTSVTVSS C4 VH                                                   SEQ ID NO: 669
QVQLQQSGAELVRPGTSVKVSCKASGY AFTDYLIE WVRQRPGQGLEWIGVINPETGGTNYNAKFRG

RATLTADKSSSSAYMQLSSLTSGDSAVYFCAR EAGNYIYAMDY WGQGTSVTVSS

VH Framework 1                                          SEQ ID NO: 625
QVQLQQSGAELVRPGTSVKVSCKASGY VH CDR1                                                 SEQ ID NO: 629
AFTDYLIE
```

-continued

```
VH Framework 2                                       SEQ ID NO: 633
WVRQRPGQGLEWIG VH CDR2                                              SEQ ID NO: 636
VINPETGGTNYNAKFRG VH Framework 3                                       SEQ ID NO: 650
RATLTADKSSSSAYMQLSSLTSGDSAVYFCAR

VH CDR3                                              SEQ ID NO: 654
EAGNYIYAMDY

VH Framework 4                                       SEQ ID NO: 655
WGQGTSVTVSS

D10 VH                                               SEQ ID NO: 670
QVQLQQSGAELVRPGTSVKVSCKASGY AFTDYLIE WVRQRPGQGLEWIG VINPETGGTNYNAKFRG

KVTLTADKTSSSAYMQLSSLTSGDSAVYFCAR EAGNYIYAMDY WGQGTSVTVSS

VH Framework 1                                       SEQ ID NO: 625
QVQLQQSGAELVRPGTSVKVSCKASGY

VH CDR1                                              SEQ ID NO: 629
AFTDYLIE

VH Framework 2                                       SEQ ID NO: 633
WVRQRPGQGLEWIG VH CDR2                                              SEQ ID NO: 636
VINPETGGTNYNAKFRG VH Framework 3                                       SEQ ID NO: 646
KVTLTADKTSSSAYMQLSSLTSGDSAVYFCAR

VH CDR3                                              SEQ ID NO: 654
EAGNYIYAMDY

VH Framework 4                                       SEQ ID NO: 655
WGQGTSVTVSS

4F1A11 VH                                            SEQ ID NO: 671
QVQLQQSGAELVRPGTSVKVSCKASGY AFTDYLIE WVKQRPGQGLEWIG VINPETGGTNYNAKFRG

RATLTADKSSSSAYMQLSSLTSGDSAVYFCAR EAGNYIYAMDY WGQGTSVTVSS

VH Framework 1                                       SEQ ID NO: 625
QVQLQQSGAELVRPGTSVKVSCKASGY

VH CDR1                                              SEQ ID NO: 629
AFTDYLIE

VH Framework 2                                       SEQ ID NO: 632
WVKQRPGQGLEWIG VH CDR2                                              SEQ ID NO: 636
VINPETGGTNYNAKFRG
```

```
VH Framework 3                                           SEQ ID NO: 650
RATLTADKSSSSAYMQLSSLTSGDSAVYFCAR VH CDR3                                                  SEQ ID NO: 654
EAGNYIYAMDY VH Framework 4                                           SEQ ID NO: 655
WGQGTSVTVSS 4F1E1 VH                                                 SEQ ID NO: 672
QVQLQQSGAELVRPGTSVKVSCKASGY AFTDYLIQ WVKQRPGQGLEWIG VINPETGGTNYNAKFRG

KATLTADKSSSSAYMQLSSLTSGDSAVYFCAR EAGNYIYAMDY WGQGTSVTVSS

VH Framework 1                                           SEQ ID NO: 625
QVQLQQSGAELVRPGTSVKVSCKASGY

VH CDR1                                                  SEQ ID NO: 631
AFTDYLIQ

VH Framework 2                                           SEQ ID NO: 632
WVKQRPGQGLEWIG VH CDR2                                                  SEQ ID NO: 636
VINPETGGTNYNAKFRG VH Framework 3                                           SEQ ID NO: 638
KATLTADKSSSSAYMQLSSLTSGDSAVYFCAR VH CDR3                                                  SEQ ID NO: 654
EAGNYIYAMDY VH Framework 4                                           SEQ ID NO: 655
WGQGTSVTVSS 4F1G3 VH                                                 SEQ ID NO: 673
QVQLQQSGAELVRPGTSVRVSCKASGY AFTDYLIQ WVKQRPGQGLEWIG VINPETGGTNYNAKFRG

KATLTANKSSSSAYMQLSSLTSGDSAVYFCAR EAGNYIYAMDY WGQGTSVTVSS

VH Framework 1                                           SEQ ID NO: 625
QVQLQQSGAELVRPGTSVKVSCKASGY

VH CDR1                                                  SEQ ID NO: 631
AFTDYLIQ

VH Framework 2                                           SEQ ID NO: 632
WVKQRPGQGLEWIG VH CDR2                                                  SEQ ID NO: 636
VINPETGGTNYNAKFRG VH Framework 3                                           SEQ ID NO: 648
KATLTANKSSSSAYMQLSSLTSGDSAVYFCAR VH CDR3                                                  SEQ ID NO: 654
EAGNYIYAMDY
```

-continued

VH Framework 4  
SEQ ID NO: 655  
WGQGTSVTVSS

4F1E10 VH  
SEQ ID NO: 674  
QVQLQQSGAELVRPGTSVKVPCKASGY AFTDYLIQ WVKQRPGQGLEWIG VINPETGGTNYNAKFRG

KATLTADKSSSSAYMQLSSLTSGDSAVYFCAR EAGNYIYAMDY WGQGTSVTVSS

VH Framework 1  
SEQ ID NO: 627  
QVQLQQSGAELVRPGTSVKVPCKASGY

VH CDR1  
SEQ ID NO: 631  
AFTDYLIQ

VH Framework 2  
SEQ ID NO: 632  
WVKQRPGQGLEWIG

VH CDR2  
SEQ ID NO: 636  
VINPETGGTNYNAKFRG

VH Framework 3  
SEQ ID NO: 638  
KATLTADKSSSSAYMQLSSLTSGDSAVYFCAR

VH CDR3  
SEQ ID NO: 654  
EAGNYIYAMDY

VH Framework 4  
SEQ ID NO: 655  
WGQGTSVTVSS

4F1E9 VH  
SEQ ID NO: 675  
QVQLQQSGAELVRPGTSVKVSCKASGY AFTDYLIE WVKQRPGQGLEWIG VINPETGGTNYNAKFRG

KATLTADKSSSSAYMQLSSLTSGDSAVYFCAR EAGNYIYAMDY WGQGTSVTVSS

VH Framework 1  
SEQ ID NO: 625  
QVQLQQSGAELVRPGTSVKVSCKASGY

VH CDR1  
SEQ ID NO: 629  
AFTDYLIE

VH Framework 2  
SEQ ID NO: 632  
WVKQRPGQGLEWIG

VH CDR2  
SEQ ID NO: 636  
VINPETGGTNYNAKFRG

VH Framework 3  
SEQ ID NO: 638  
KATLTADKSSSSAYMQLSSLTSGDSAVYFCAR

VH CDR3  
SEQ ID NO: 654  
EAGNYIYAMDY

VH Framework 4  
SEQ ID NO: 655  
WGQGTSVTVSS

4F1H12 VH  
SEQ ID NO: 676  
QVQLQQSGAELVRPGTSVKVSCKASGY AFTDYLIQ WVKQRPGQGLEWIG VINPETGGTNYNAKFRG

KATLTADKSSSSAYLQLSSLTSGDSAVYFCAR EAGNYIYAMDY WGQGTSVTVSS

```
VH Framework 1                                          SEQ ID NO: 625
QVQLQQSGAELVRPGTSVKVSCKASGY

VH CDR1                                                 SEQ ID NO: 631
AFTDYLIQ

VH Framework 2                                          SEQ ID NO: 632
WVKQRPGQGLEWIG VH CDR2                                                 SEQ ID NO: 636
VINPETGGTNYNAKFRG VH Framework 3                                          SEQ ID NO: 649
KATLTADKSSSSAYLQLSSLTSGDSAVYFCAR VH CDR3                                                 SEQ ID NO: 654
EAGNYIYAMDY VH Framework 4                                          SEQ ID NO: 655
WGQGTSVTVSS F9 VH                                                   SEQ ID NO: 677
QVQLQQSGAELVRPGTSVKVSCKASGY AFTDYLIQ WVKQRPGQGLEWIG VINPETGGTNYNAKFRG

KATLTADKSSSSAYMQLSSLTSGDSAVYFCAR EAGNYIYAMDY WGQGTSVTVSS

VH Framework 1                                          SEQ ID NO: 625
QVQLQQSGAELVRPGTSVKVSCKASGY

VH CDR1                                                 SEQ ID NO: 631
AFTDYLIQ

VH Framework 2                                          SEQ ID NO: 632
WVKQRPGQGLEWIG VH CDR2                                                 SEQ ID NO: 636
VINPETGGTNYNAKFRG VH Framework 3                                          SEQ ID NO: 638
KATLTADKSSSSAYMQLSSLTSGDSAVYFCAR VH CDR3                                                 SEQ ID NO: 654
EAGNYIYAMDY VH Framework 4                                          SEQ ID NO: 655
WGQGTSVTVSS 4F1 VL                                                  SEQ ID NO: 678
DIQMTQSPASLSASVGETVTITC RASVNIYSYLV WYQQKQGKSPQLLVH NAKTLAE

GVPSRFSGSGSGTQFSLKINSLQPEDFGSYYC QHHHGTPYT FGGGTKLEIKA

VL Framework 1                                          SEQ ID NO: 692
DIQMTQSPASLSASVGETVTITC VL CDR1                                                 SEQ ID NO: 693
RASVNIYSYLV
```

-continued

```
VL Framework 2                                    SEQ ID NO: 694
WYQQKQGKSPQLLVH

VL CDR2                                           SEQ ID NO: 695
NAKTLAE

VL Framework 3                                    SEQ ID NO: 696
GVPSRFSGSGSGTQFSLKINSLQPEDFGSYYC

VL CDR3                                           SEQ ID NO: 697
QHHHGTPYT

VL Framework 4                                    SEQ ID NO: 698
FGGGTKLEIKA

6B9 VL                                            SEQ ID NO: 679
DIEMTQTPASLSASVGETVTITC RASENIYSYLV WYQQKQGKSPQVLVY NAKTLAE
GVPSRFSGSGSGTQFSLKINSLQPEDFGSYYC QHHNGTPYT FGGGTKLEIKA

VL Framework 1                                    SEQ ID NO: 699
DIEMTQTPASLSASVGETVTITC

VL CDR1                                           SEQ ID NO: 700
RASENIYSYLV

VL Framework 2                                    SEQ ID NO: 701
WYQQKQGKSPQVLVY

VL CDR2                                           SEQ ID NO: 695
NAKTLAE

VL Framework 3                                    SEQ ID NO: 696
GVPSRFSGSGSGTQFSLKINSLQPEDFGSYYC

VL CDR3                                           SEQ ID NO: 702
QHHNGTPYT

VL Framework 4                                    SEQ ID NO: 698
FGGGTKLEIKA

6B9.1 VL                                          SEQ ID NO: 680
DIVMTQSPASLSASVGETVTITC RASVNIYSYLV WYQQKQGKSPQLLVH NAKTLAE
GVPSRFSGSGSGTQFSLKINSLQPEDFGSYYC QHHHGTPYT FGGGTKLEIKA

VL Framework 1                                    SEQ ID NO: 703
DIVMTQSPASLSASVGETVTITC

VL CDR1                                           SEQ ID NO: 693
RASVNIYSYLV

VL Framework 2                                    SEQ ID NO: 694
WYQQKQGKSPQLLVH

VL CDR2                                           SEQ ID NO: 695
NAKTLAE
```

```
VL Framework 3                                          SEQ ID NO: 696
GVPSRFSGSGSGTQFSLKINSLQPEDFGSYYC

VL CDR3                                                 SEQ ID NO: 697
QHHHGTPYT

VL Framework 4                                          SEQ ID NO: 698
FGGGTKLEIKA A1 = A2 = C4 = C7 = D1 = D10 = E5 = F1 = F10 = G4 VL    SEQ ID NO: 681
DIVMTQSPASLSASVGETVTITC RASVNIYSYLV WYQQKQGKSPQLLVH NAKTLAE
GVPSRFSGSGSGTQFSLKINSLQPEDFGSYYC QHHHGTPYT FGGGTKLEIKA VL Framework 1                                          SEQ ID NO: 703
DIVMTQSPASLSASVGETVTITC VL CDR1                                                 SEQ ID NO: 693
RASVNIYSYLV VL Framework 2                                          SEQ ID NO: 694
WYQQKQGKSPQLLVH

VL CDR2                                                 SEQ ID NO: 695
NAKTLAE

VL Framework 3                                          SEQ ID NO: 696
GVPSRFSGSGSGTQFSLKINSLQPEDFGSYYC

VL CDR3                                                 SEQ ID NO: 697
QHHHGTPYT

VL Framework 4                                          SEQ ID NO: 698
FGGGTKLEIKA A8 VL                                                   SEQ ID NO: 682
DIVMTQSPASLSASVGETVTITC RASVNIYSYLV WYQQKQGKSPQLLVH NAKTLAE
GVPSRFSGSGSGTQFSLKINSVQPEDFGSYYC QHHHGTPYT FGGGTKLEIKA VL Framework 1                                          SEQ ID NO: 703
DIVMTQSPASLSASVGETVTITC VL CDR1                                                 SEQ ID NO: 693
RASVNIYSYLV VL Framework 2                                          SEQ ID NO: 694
WYQQKQGKSPQLLVH

VL CDR2                                                 SEQ ID NO: 695
NAKTLAE

VL Framework 3                                          SEQ ID NO: 696
GVPSRFSGSGSGTQFSLKINSLQPEDFGSYYC VL CDR3                                                 SEQ ID NO: 697
QHHHGTPYT
```

```
VL Framework 4
                                                    SEQ ID NO: 698
FGGGTKLEIKA A11 VL
                                                    SEQ ID NO: 683
HIVMTQSPASLSASVGETVTITC RASVNIYSYLV WYQQKQGKSPQLLVH NAKTLAE

GVPSRFSGSGSGTQFSLKINSLQPEDFGSYYC QHHHGTPYT FGGGTKLEIKA

VL Framework 1
                                                    SEQ ID NO: 704
HIVMTQSPASLSASVGETVTITC VL CDR1
                                                    SEQ ID NO: 693
RASVNIYSYLV VL Framework 2
                                                    SEQ ID NO: 694
WYQQKQGKSPQLLVH VL CDR2
                                                    SEQ ID NO: 695
NAKTLAE VL Framework 3
                                                    SEQ ID NO: 696
GVPSRFSGSGSGTQFSLKINSLQPEDFGSYYC VL CDR3
                                                    SEQ ID NO: 697
QHHHGTPYT VL Framework 4
                                                    SEQ ID NO: 698
FGGGTKLEIKA B1 VL
                                                    SEQ ID NO: 684
DIVMTQSPASLSASVGETVTITC RASVNIYSYLV WYQQKQGKSPQLLVH NAKTLAE

GVPSRFSGSGSGTQFSLKINSLQPEDVGSYYC QHHHGTPYT FGGGTKLEIKA

VL Framework 1
                                                    SEQ ID NO: 703
DIVMTQSPASLSASVGETVTITC VL CDR1
                                                    SEQ ID NO: 693
RASVNIYSYLV VL Framework 2
                                                    SEQ ID NO: 694
WYQQKQGKSPQLLVH VL CDR2
                                                    SEQ ID NO: 695
NAKTLAE VL Framework 3
                                                    SEQ ID NO: 696
GVPSRFSGSGSGTQFSLKINSLQPEDFGSYYC VL CDR3
                                                    SEQ ID NO: 697
QHHHGTPYT VL Framework 4
                                                    SEQ ID NO: 698
FGGGTKLEIKA B3 VL
                                                    SEQ ID NO: 685
DIVMTQSPASLSASVGETVTITC RASVNIYSYLV WYQQKQGKSPQLLVH NAKTLAE

GVPSRFSGSGSGTQFSLKINSLQPEDFGSYYC QHHHGTPYT FGGGTKLEIKA
```

```
VL Framework 1                                   SEQ ID NO: 703
DIVMTQSPASLSASVGETVTITC

VL CDR1                                          SEQ ID NO: 693
RASVNIYSYLV

VL Framework 2                                   SEQ ID NO: 694
WYQQKQGKSPQLLVH

VL CDR2                                          SEQ ID NO: 695
NAKTLAE

VL Framework 3                                   SEQ ID NO: 696
GVPSRFSGSGSGTQFSLKINSLQPEDFGSYYC

VL CDR3                                          SEQ ID NO: 697
QHHHGTPYT

VL Framework 4                                   SEQ ID NO: 698
FGGGTKLEIKA

D10 = E5 VL                                      SEQ ID NO: 686
DIVMTQSPASLSASVGETVTITC RASVNIYSYLV WYQQKQGKSPQLLVH NAKTLAE

GVPSRFSGSGSGTQFSLKINSLQPEDFGSYYC QHHHGTPYT FGGGTKLEIKA

VL Framework 1                                   SEQ ID NO: 703
DIVMTQSPASLSASVGETVTITC

VL CDR1                                          SEQ ID NO: 693
RASVNIYSYLV

VL Framework 2                                   SEQ ID NO: 694
WYQQKQGKSPQLLVH

VL CDR2                                          SEQ ID NO: 695
NAKTLAE

VL Framework 3                                   SEQ ID NO: 696
GVPSRFSGSGSGTQFSLKINSLQPEDFGSYYC

VL CDR3                                          SEQ ID NO: 697
QHHHGTPYT

VL Framework 4                                   SEQ ID NO: 698
FGGGTKLEIKA

C4 VL                                            SEQ ID NO: 687
DIVMTQSPASLSASVGETVTITC RASVNIYSYLV WYQQKQGKSPQLLVH NAKTLAE

GVPSRFSGSGSGTQFSLKINSLQPEDFGSYYC QHHHGTPYT FGGGTKLEIKR

VL Framework 1                                   SEQ ID NO: 703
DIVMTQSPASLSASVGETVTITC

VL CDR1                                          SEQ ID NO: 693
RASVNIYSYLV
```

```
VL Framework 2                                          SEQ ID NO: 694
WYQQKQGKSPQLLVH

VL CDR2                                                 SEQ ID NO: 695
NAKTLAE

VL Framework 3                                          SEQ ID NO: 696
GVPSRFSGSGSGTQFSLKINSLQPEDFGSYYC

VL CDR3                                                 SEQ ID NO: 697
QHHHGTPYT

VL Framework 4                                          SEQ ID NO: 706
FGGGTKLEIKR D10 VL                                                  SEQ ID NO: 688
DIEMTQTPASLSASVGETVTITC RASVNIYSYLV WYQQKQGKSPQLLVH NAKTLAE
GVPSRFSGSGSGTQFSLKINSLQPEDFGSYYC QHHHGTPYT FGGGTKLEIKR VL Framework 1                                          SEQ ID NO: 699
DIEMTQTPASLSASVGETVTITC VL CDR1                                                 SEQ ID NO: 693
RASVNIYSYLV VL Framework 2                                          SEQ ID NO: 694
WYQQKQGKSPQLLVH

VL CDR2                                                 SEQ ID NO: 695
NAKTLAE

VL Framework 3                                          SEQ ID NO: 696
GVPSRFSGSGSGTQFSLKINSLQPEDFGSYYC

VL CDR3                                                 SEQ ID NO: 697
QHHHGTPYT

VL Framework 4                                          SEQ ID NO: 706
FGGGTKLEIKR 4F1E1 = 1F1G3 = 4F1B5 = 4F1G11 = 4F1A9 = 4F1B9 = 4F1H9 =
4F1D10 = 4F1E9 = 4F1F10 = 4F1H11 = 4F1H12 VL
                                                        SEQ ID NO: 689
DIVMTQSPASLSASVGETVTITC RASVNIYSYLV WYQQKQGKSPQLLVH NAKTLAE
GVPSRFSGSGSGTQFSLKINSLQPEDFGSYYC QHHHGTPYT FGGGTKLEIKA VL Framework 1                                          SEQ ID NO: 703
DIVMTQSPASLSASVGETVTITC VL CDR1                                                 SEQ ID NO: 693
RASVNIYSYLV VL Framework 2                                          SEQ ID NO: 694
WYQQKQGKSPQLLVH VL CDR2                                                 SEQ ID NO: 695
NAKTLAE
```

-continued

```
VL Framework 3                                      SEQ ID NO: 696
GVPSRFSGSGSGTQFSLKINSLQPEDFGSYYC

VL CDR3                                             SEQ ID NO: 697
QHHHGTPYT

VL Framework 4                                      SEQ ID NO: 698
FGGGTKLEIKA

4FA11 VL                                            SEQ ID NO: 690
DIVVTQSPASLSASVGETVTITC RASVNIYSYLV WYQQKQGKSPQLLVH NAKTLAE

GVPSRFSGSGSGTQFSLKINSLQPEDFGSYYC QHHHGTPYT FGGGTKLEIKA

VL Framework 1                                      SEQ ID NO: 705
DIVVTQSPASLSASVGETVTITC

VL CDR1                                             SEQ ID NO: 693
RASVNIYSYLV

VL Framework 2                                      SEQ ID NO: 694
WYQQKQGKSPQLLVH

VL CDR2                                             SEQ ID NO: 695
NAKTLAE

VL Framework 3                                      SEQ ID NO: 696
GVPSRFSGSGSGTQFSLKINSLQPEDFGSYYC

VL CDR3                                             SEQ ID NO: 697
QHHHGTPYT

VL Framework 4                                      SEQ ID NO: 698
FGGGTKLEIKA

F9 VL                                               SEQ ID NO: 691
DIVMTQSPAFLSASVGETVTITC RASVNIYSYLV WYQQKQGKSPQLLVH NAKTLAE

GVPSRFSGSGSGTQFSLKINSLQPEDFGSYYC QHHHGTPYT FGGGTKLEIKR

VL Framework 1                                      SEQ ID NO: 703
DIVMTQSPASLSASVGETVTITC

VL CDR1                                             SEQ ID NO: 693
RASVNIYSYLV

VL Framework 2                                      SEQ ID NO: 694
WYQQKQGKSPQLLVH

VL CDR2                                             SEQ ID NO: 695
NAKTLAE

VL Framework 3                                      SEQ ID NO: 696
GVPSRFSGSGSGTQFSLKINSLQPEDFGSYYC

VL CDR3                                             SEQ ID NO: 697
QHHHGTPYT
```

VL Framework 4                                            SEQ ID NO: 706
FGGGTKLEIKR

C6D4 VH CDR1                                              SEQ ID NO: 707
DYSMH

C6D4 VH CDR3                                              SEQ ID NO: 615
FYYGRDS

β8, SDL                                                   SEQ ID NO: 620
TVSPYISIHPERIHNQCSDYNLDCMPPH

C6D4 Vk CDR1                                              SEQ ID NO: 616
KSSQSLLNSRTRKNYLA

C6D4 Vk CDR2                                              SEQ ID NO: 708
WASTRES

C6D4 Vk CDR3                                              SEQ ID NO: 618
KQSYNLLS

αVβ6:                                                     SEQ ID NO: 709
GRGDLGRLKK

αIIbβ3:                                                   SEQ ID NO: 710
GRGDSP

αIIbβ3:                                                   SEQ ID NO: 711
AKQRGDV loop of L-TGFβ:                                           SEQ ID NO: 712
RGDLGRLKK (TGFB3 sequence):                                         SEQ ID NO: 713
DDHGRGDLGRLK TGBF1                                                     SEQ ID NO: 714
MPPSGLRLLLLLLPLLWLLVLTPGRPAAGLSTCKTIDMELVKRKRIEAIRGQILSKLRLASPPSQGEVPP
GPLPEAVLALYNSTRDRVAGESAEPEPEPEADYYAKEVTRVLMVETHNEIYDKFKQSTHSIYMFFNTSEL
REAVPEPVLLSRAELRLLRLKLKVEQHVELYQKYSNNSWRYLSNRLLAPSDSPEWLSFDVTGVVRQWLSR
GGEIEGFRLSAHCSCDSRDNTLQVDINGFTTGRRGDLATIHGMNRPFLLLMATPLERAQHLQSSRHRRAL
DTNYCFSSTEKNCCVRQLYIDFRKDLGWKWIHEPKGYHANFCLGPCPYIWSLDTQYSKVLALYNQHNPGA
SAAPCCVPQALEPLPIVYYVGRKPKVEQLSNMIVRSCKCS TGFB2                                                     SEQ ID NO: 715
MHYCVLSAFLILHLVTVALSLSTCSTLDMDQFMRKRIEAIRGQILSKLKLTSPPEDYPEPEEVPPEVISI
YNSTRDLLQEKASRRAAACERERSDEEYYAKEVYKIDMPPFFPSENAIPPTFYRPYFRIVRFDVSAMEKN
ASNLVKAEFRVFRLQNPKARVPEQRIELYQILKSKDLTSPTQRYIDSKVVKTRAEGEWLSFDVTDAVHEW
LPSYRLESQQTNRRKKRALDAAYCFRVQDNCCLRPLYIDFKRDLGWKWIHEPKGYNANFCAGACPYLWSS
DTQHSRVLSLYNTINPEASASPCCVSQDLEPLTILYYIGKTPKIEQLSNMIVKSCKCS TGFB3                                                     SEQ ID NO: 716
MKMHLQRALVVLALLNFATVSLSLSTCTTLDFGHIKKKRVEAIRGQILSKLRLTSPPEPTVHVPYQVLA
LYNSTRELLEEMHGEREEGCTQENTESEYYAKEIHKFDMIQGLAEHNELAVCPKGITSKVFRFNVSSVEK

NRTNLFRAEFRVLRVPNPSSKRNEQRIELFQILRPDEHIAKQRYIGGKNLPTRGTAEWLSFDVTDTVREW

LLRRESNLGLEISIHCPCHTFQPNGDILENIHEVMEIKFKGVDNEDDHGRGDLGRLKKQKQHHNPHLILM

MIPPHRLDNPGQGGQRKKRALDTNYCFRNLEENCCVRPLYIDFRQDLGWKWVHEPKGYYANFCSGPCPYL

RSADTTHSTVLGLYNTLNPEASASPCCVPQDLEPLTILYYVGRTPKVEQLSNMVVKSCKCS

C6D4 vk
SEQ ID NO: 717

DIVMTQSPSSLAVSAGEKVTMSCKSSQSLLNSRTRKNYLAWYQQKPGQSPRLLIYWASTRESGVPDRFTG

SGSGTDFTLTISSVQAEDLAVYYCKQSYNLLSFGAGTKLELKAADAAPTVSIFPPSSEQLTSGGASVVCF

LNNFYPKDINVKWKIDGSERQNGVLNSWTDQDSKDSTYSMSSTLTLTKDEYERHNSYTCEATHKTSTSPI

VKSFNRNEC

C6D4-RDG1
SEQ ID NO: 718

KSSQSLLGRGDLGNALA

C6D4-RDG2
SEQ ID NO: 719

KSSQSLLNSGRGDLGNALA

C6D4-RDG3
SEQ ID NO: 720

KSSQSLLGRGDLGRLKKNALA

SEQ ID NO: 721

GRGDLGRLK

C6D4 VH
SEQ ID NO: 722

QIQLVQSGPELKKPGETVKISCKASGYTFT DYSMH WVKQAPGKGLKWVA RINTETGEPTFADDFRG

RFAVSLETSASTAYLQINNLKNEDTATYFCAI FYYGRDS WGQGTTLTVSS

VH Framework 1
SEQ ID NO: 732

QIQLVQSGPELKKPGETVKISCKASGYTFT

VH CDR1
SEQ ID NO: 733

DYSMH

VH Framework 2
SEQ ID NO: 734

WVKQAPGKGLKWVA

VH CDR2
SEQ ID NO: 735

RINTETGEPTFADDFRG

VH Framework 3
SEQ ID NO: 736

RFAVSLETSASTAYLQINNLKNEDTATYFCAI

VH CDR3
SEQ ID NO: 737

FYYGRDS

VH Framework 4
SEQ ID NO: 738

WGQGTTLTVSS

HuC6D4 V1 VH
SEQ ID NO: 723

QIQLVQSGAEVKKPGASVKISCKASGYTFT DYSMH WVRQAPGQGLEWVA RINTETGEPTFADDFRG

RFTVTLDTSTSTAYLEIRSLRSDDAVYFCAI FYYGRDS WGQGTTLTVSS

VH Framework 1
SEQ ID NO: 739

QIQLVQSGAEVKKPGASVKISCKASGYTFT

VH CDR1
SEQ ID NO: 733

DYSMH

```
VH Framework 2                                          SEQ ID NO: 740
WVRQAPGQGLEWVA VH CDR2                                                 SEQ ID NO: 735
RINTETGEPTFADDFRG VH Framework 3                                          SEQ ID NO: 741
RFTVTLDTSTSTAYLEIRSLRSDDTAVYFCAI

VH CDR3                                                 SEQ ID NO: 737
FYYGRDS

VH Framework 4                                          SEQ ID NO: 738
WGQGTTLTVSS Mutclone A3 VH                                          SEQ ID NO: 724
QIQLVQSGAEVKKPGASVKISCKASGYTFT DYSMH WVRQAPGQGLEWVA RINTETGEPTFADDFRG
RFSVTLDTSTSTAYLEITSLRSDDTAVYFCAI FYYGRDT WGQGTTLTVSS VH Framework 1                                          SEQ ID NO: 739
QIQLVQSGAKVKKPGASVKISCKASGYTFT

VH CDR1                                                 SEQ ID NO: 733
DYSMH

VH Framework 2                                          SEQ ID NO: 740
WVRQAPGQGLEWVA VH CDR2                                                 SEQ ID NO: 735
RINTETGEPTFADDFRG VH Framework 3                                          SEQ ID NO: 741
RFTVTLDTSTSTAYLEIRSLRSDDTAVYFCAI

VH CDR3                                                 SEQ ID NO: 737
FYYGRDS

VH Framework 4                                          SEQ ID NO: 738
WGQGTTLTVSS Mutclone B7 VH                                          SEQ ID NO: 725
QIQLVQSGAKVKKPGASVKISCKASGYTFT DYSMH WVRQAPGQGLEWVA RINTETGEPTFADDFRG
RFSVTLDTSTSTAYLEITSLRSDDTAVYFCAI FYYGRDS WGQGTTLTVSS VH Framework 1                                          SEQ ID NO: 742
QIQLVQSGAEVKKPGASVKISCKASGYTFT

VH CDR1                                                 SEQ ID NO: 733
DYSMH

VH Framework 2                                          SEQ ID NO: 740
WVRQAPGQGLEWVA VH CDR2                                                 SEQ ID NO: 735
RINTETGEPTFADDFRG
```

-continued

```
VH Framework 3                                          SEQ ID NO: 743
RFTVTLDTSTSTAYLEIRSLRSDDTAVYFCAI

VH CDR3                                                 SEQ ID NO: 744
FYYGRDT

VH Framework 4                                          SEQ ID NO: 738
WGQGTTLTVSS Mutclone E5 VH                                          SEQ ID NO: 726
QIQLVQSGAEVKKPGASVKISCKASGYTFT DYSMH WVRQAPGQGLEWVA RINTETGEPTFADDFRG

RFTVTLDTSTSTAYLEIRSLRSDDTAVYFCAI FYYGRDT WGQGTTLTVSS

VH Framework 1                                          SEQ ID NO: 739
QIQLVQSGAEVKKPGASVKISCKASGYTFT

VH CDR1                                                 SEQ ID NO: 733
DYSMH

VH Framework 2                                          SEQ ID NO: 740
WVRQAPGQGLEWVA VH CDR2                                                 SEQ ID NO: 735
RINTETGEPTFADDFRG VH Framework 3                                          SEQ ID NO: 743
RFTVTLDTSTSTAYLEIRSLRSDDTAVYFCAI

VH CDR3                                                 SEQ ID NO: 744
FYYGRDT

VH Framework 4                                          SEQ ID NO: 738
WGQGTTLTVSS C6D4 VK                                                 SEQ ID NO: 727
DIVMTQSPSSLAVSAGEKVTMSC KSSQSLLNSRTRKNYLA WYQQKPGQSPRLLIY WASTRES

GVPDRFTGSGSGTDFTLTISSVQAEDLAVYYC KQSYNLLS FGAGTKLELKR

VK Framework 1                                          SEQ ID NO: 745
DIVMTQSPSSLAVSAGEKVTMSC VK CDR1                                                 SEQ ID NO: 746
KSSQSLLNSRTRKNYLA VK Framework 2                                          SEQ ID NO: 747
WYQQKPGQSPRLLIY

VK CDR2                                                 SEQ ID NO: 748
WASTRES

VK Framework 3                                          SEQ ID NO: 749
GVPDRFTGSGSGTDFTLTISSVQAEDLAVYYC VK CDR3                                                 SEQ ID NO: 750
KQSYNLLS
```

```
VK Framework 4
                                                          SEQ ID NO: 751
FGAGTKLELKR HuC6D4 V1 VK
                                                          SEQ ID NO: 728
EIVMTQSPATLSVSPGERVTMSC KSSQSLLNSRTRKNYLA WYQQKPGQAPRLLIY WASTRES

GVPARFSGSGSGTEFTLTISSVQSEDFAVYYC KQSYNLLS FGQGTVLEIKR

VK Framework 1
                                                          SEQ ID NO: 752
EIVMTQSPATLSVSPGERVTMSC VK CDR1
                                                          SEQ ID NO: 746
KSSQSLLNSRTRKNYLA VK Framework 2
                                                          SEQ ID NO: 747
WYQQKPGQSPRLLIY VK CDR2
                                                          SEQ ID NO: 748
WASTRES VK Framework 3
                                                          SEQ ID NO: 753
GVPARFSGSGSGTEFTLTISSVQSEDFAVYYC VK CDR3
                                                          SEQ ID NO: 750
KQSYNLLS VK Framework 4
                                                          SEQ ID NO: 754
FGQGTVLEIKR Mutclone A3 VK
                                                          SEQ ID NO: 729
EIVMTQSPATLSVSPGEIVTMSC KSSQSLLNSRSRKNYLA WYQQKPGQAPRLLIY WASTRES

GVPARFSGSGSGTEFTLTISSVQSEDFAVYYC KQSYNLLS FGQGTVLEIKR

VK Framework 1
                                                          SEQ ID NO: 755
EIVMTQSPATLSVSPGEIVTMSC VK CDR1
                                                          SEQ ID NO: 756
KSSQSLLNSRSRKNYLA VK Framework 2
                                                          SEQ ID NO: 747
WYQQKPGQSPRLLIY VK CDR2
                                                          SEQ ID NO: 748
WASTRES VK Framework 3
                                                          SEQ ID NO: 753
GVPARFSGSGSGTEFTLTISSVQSEDFAVYYC VK CDR3
                                                          SEQ ID NO: 750
KQSYNLLS VK Framework 4
                                                          SEQ ID NO: 754
FGQGTVLEIKR Mutclone B7 VK
                                                          SEQ ID NO: 730
EIVMTQTPVTLSVSPGERVTMSC KSSQSLLNSRTRKNYLA WYQQKPGQAPRLLIY WASTRES

DVPARFSGSGSGTEFTLTISSVQSEDFAVYYC KQSSNLLS FGQGTVLEIKR
```

```
VK Framework 1                                              SEQ ID NO: 757
EIVMTQTPVTLSVSPGERVTMSC VK CDR1                                                     SEQ ID NO: 746
KSSQSLLNSRTRKNYLA VK Framework 2                                              SEQ ID NO: 747
WYQQKPGQSPRLLIY VK CDR2                                                     SEQ ID NO: 748
WASTRES VK Framework 3                                              SEQ ID NO: 758
DVPARFSGSGSGTEFTLTISSVQSEDFAVYYC VK CDR3                                                     SEQ ID NO: 750
KQSYNLLS VK Framework 4                                              SEQ ID NO: 754
FGQGTVLEIKR Mutclone E5 VK                                              SEQ ID NO: 731
EIVMTQSPATLSVSPGERVTMSC KSSQSLLNSRSRKNYLA WYQQKPGQAPRLLIY WASTRES

GVPARFSGSGSGTEFTLTISSVQSEDFAVYYC KQSYNLLS FGQGTVLEIKR

VK Framework 1                                              SEQ ID NO: 752
EIVMTQSPATLSVSPGERVTMSC VK CDR1                                                     SEQ ID NO: 756
KSSQSLLNSRSRKNYLA VK Framework 2                                              SEQ ID NO: 747
WYQQKPGQSPRLLIY VK CDR2                                                     SEQ ID NO: 748
WASTRES VK Framework 3                                              SEQ ID NO: 753
GVPARFSGSGSGTEFTLTISSVQSEDFAVYYC VK CDR3                                                     SEQ ID NO: 750
KQSYNLLS VK Framework 4                                              SEQ ID NO: 754
FGQGTVLEIKR E8 - VL Framework 3                                         SEQ ID NO: 755
GVPSRFSGSGSGTRFSLKINSLQPEDFGSYYC

SEQ ID NO: 756
RGDL

αv
                                                            SEQ ID NO: 757
DADGQ

αv
                                                            SEQ ID NO: 758
SFYWQ
```

αv

FDDSY                                                              SEQ ID NO: 759

KQDKILACAPLYHWRTEMKQEREPVGTCFLQDGTKTVEYAPCRSQDIDADGQGFCQGGFSIDFTKADRVL   SEQ ID NO: 760
LGGPGSFYWQGQLISDQVAEIVSKYDPNVYSIKYNNQLATRTAQAIFD

β8

YNLDC                                                              SEQ ID NO: 761

β8

QCSDYNL                                                            SEQ ID NO: 762

β8

SMHNN                                                              SEQ ID NO: 763

β8

AVHRQ                                                              SEQ ID NO: 764

KSSQSLLGRGDLGRLKK                                                  SEQ ID NO: 765

C6H - VH CDR1

TFTDYSMH                                                           SEQ ID NO: 766

C6H - VH CDR2

RINTETGEPTFADDFRG                                                  SEQ ID NO: 767

C6H - VH CDR3

FYYGRDS                                                            SEQ ID NO: 768 heavy chain FR2

WV(K/R)QAPG(K/Q)GL(K/E)W(V/M)(A/G)                                 SEQ ID NO: 877 heavy chain FR3

RF(A/T/S)(V/F)(S/T)L(E/D)TS(A/T)(S/T)TA(Y/N)L(Q/E)I(N/R/I/T)(N/S)L   SEQ ID NO: 878
(K/R)(N/S)(E/D)DTA(T/V/K)YFCAI heavy chain FR4

WGQGT(T/A)LTVSS                                                    SEQ ID NO: 879 light chain FR1

(D/E)IVM(T/S)Q(S/T)P(S/A/V)(S/T)L(A/S)VS(A/P)GE(K/R/I)VTMSC        SEQ ID NO: 880 light chain FR2

WYQQKPGQ(S/A)PRLLIY                                                SEQ ID NO: 881 light chain FR3

(G/D)VP(D/A)RF(T/S)GSGSGT(D/E)FTLTISSVQ(A/S/D)ED(L/F)AVYC          SEQ ID NO: 882 light chain FR4

FG(A/Q)GT(K/V)LE(i/LI)KR                                           SEQ ID NO: 883

---

SEQUENCE LISTING

Sequence total quantity: 887
SEQ ID NO: 1         moltype = AA   length = 116
FEATURE              Location/Qualifiers
source               1..116

```
                            mol_type = protein
                            organism = Mus musculus
SEQUENCE: 1
EVQLQQSGPE LKKPGETVKI SCKASGYTFT DYSMHWVKQA PGKGLKWMGW IKTETGEPTY    60
ADDFKGRFAF SLETSATTAY LQINNLKNED TAKYFCAIYY YGRDSWGQGT TLTVSS       116

SEQ ID NO: 2            moltype = AA  length = 27
FEATURE                 Location/Qualifiers
REGION                  1..27
                        note = Human (Homo sapiens), chimeric or humanized antibody
                         peptide sequence
source                  1..27
                        mol_type = protein
                        organism = unidentified
SEQUENCE: 2
EVQLQQSGPE LKKPGETVKI SCKASGY                                        27

SEQ ID NO: 3            moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 3
TFTDYSMH                                                              8

SEQ ID NO: 4            moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 4
WVKQAPGKGL KWMG                                                      14

SEQ ID NO: 5            moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 5
WIKTETGEPT YADDFKG                                                   17

SEQ ID NO: 6            moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 6
RFAFSLETSA TTAYLQINNL KNEDTAKYFC AI                                  32

SEQ ID NO: 7            moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 7
YYYGRDS                                                               7

SEQ ID NO: 8            moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
```

```
                        organism = unidentified
SEQUENCE: 8
WGQGTTLTVS S                                                          11

SEQ ID NO: 9            moltype = AA  length = 116
FEATURE                 Location/Qualifiers
source                  1..116
                        mol_type = protein
                        organism = Mus musculus
SEQUENCE: 9
QIQLLQSGPE LKKPGETVKI SCKASGYTFT DYSMHWVKQA PGKGLKWMGW IKTETGEPTY      60
ADDFKGRFAF SLETSATTAY LQINNLKNED TAKYFCAIYY YGRDSWGQGT TLTVSS         116

SEQ ID NO: 10           moltype = AA  length = 27
FEATURE                 Location/Qualifiers
REGION                  1..27
                        note = Human (Homo sapiens), chimeric or humanized antibody
                         peptide sequence
source                  1..27
                        mol_type = protein
                        organism = unidentified
SEQUENCE: 10
QIQLLQSGPE LKKPGETVKI SCKASGY                                         27

SEQ ID NO: 11           moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 11
TFTDYSMH                                                               8

SEQ ID NO: 12           moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 12
WVKQAPGKGL KWMG                                                       14

SEQ ID NO: 13           moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 13
WIKTETGEPT YADDFKG                                                    17

SEQ ID NO: 14           moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 14
RFAFSLETSA TTAYLQINNL KNEDTAKYFC AI                                   32

SEQ ID NO: 15           moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 15
YYYGRDS                                                                7
```

-continued

| | |
|---|---|
| SEQ ID NO: 16 | moltype = AA length = 11 |
| FEATURE | Location/Qualifiers |
| REGION | 1..11 |
| | note = Human (Homo sapiens), chimeric or humanized antibody peptide sequence |
| source | 1..11 |
| | mol_type = protein |
| | organism = unidentified |

SEQUENCE: 16
WGQGTTLTVS S    11

| | |
|---|---|
| SEQ ID NO: 17 | moltype = AA length = 119 |
| FEATURE | Location/Qualifiers |
| REGION | 1..119 |
| | note = Human (Homo sapiens), chimeric or humanized antibody peptide sequence |
| source | 1..119 |
| | mol_type = protein |
| | organism = unidentified |

SEQUENCE: 17
QIQLLQSGPE LKKPGETVKI SCKASGYTFT DYSMHWVKQA PGKGLKWMGW IKTETDEPTY    60
ADDFKERFAF SLETSASTAN LQIINLKNED TATYFCAIYY YGRDSWGQGT TLTVSSSEQ    119

| | |
|---|---|
| SEQ ID NO: 18 | moltype = AA length = 27 |
| FEATURE | Location/Qualifiers |
| REGION | 1..27 |
| | note = Human (Homo sapiens), chimeric or humanized antibody peptide sequence |
| source | 1..27 |
| | mol_type = protein |
| | organism = unidentified |

SEQUENCE: 18
QIQLLQSGPE LKKPGETVKI SCKASGY    27

| | |
|---|---|
| SEQ ID NO: 19 | moltype = AA length = 8 |
| FEATURE | Location/Qualifiers |
| REGION | 1..8 |
| | note = Human (Homo sapiens), chimeric or humanized antibody peptide sequence |
| source | 1..8 |
| | mol_type = protein |
| | organism = unidentified |

SEQUENCE: 19
TFTDYSMH    8

| | |
|---|---|
| SEQ ID NO: 20 | moltype = AA length = 14 |
| FEATURE | Location/Qualifiers |
| REGION | 1..14 |
| | note = Human (Homo sapiens), chimeric or humanized antibody peptide sequence |
| source | 1..14 |
| | mol_type = protein |
| | organism = unidentified |

SEQUENCE: 20
WVKQAPGKGL KWMG    14

| | |
|---|---|
| SEQ ID NO: 21 | moltype = AA length = 17 |
| FEATURE | Location/Qualifiers |
| REGION | 1..17 |
| | note = Human (Homo sapiens), chimeric or humanized antibody peptide sequence |
| source | 1..17 |
| | mol_type = protein |
| | organism = unidentified |

SEQUENCE: 21
WIKTETDEPT YADDFKE    17

| | |
|---|---|
| SEQ ID NO: 22 | moltype = AA length = 32 |
| FEATURE | Location/Qualifiers |
| REGION | 1..32 |
| | note = Human (Homo sapiens), chimeric or humanized antibody peptide sequence |
| source | 1..32 |
| | mol_type = protein |
| | organism = unidentified |

SEQUENCE: 22
RFAFSLETSA STANLQIINL KNEDTATYFC AI    32

| | |
|---|---|
| SEQ ID NO: 23 | moltype = AA length = 7 |

```
FEATURE              Location/Qualifiers
REGION               1..7
                     note = Human (Homo sapiens), chimeric or humanized antibody
                       peptide sequence
source               1..7
                     mol_type = protein
                     organism = unidentified
SEQUENCE: 23
YYYGRDS                                                                    7

SEQ ID NO: 24        moltype = AA  length = 14
FEATURE              Location/Qualifiers
REGION               1..14
                     note = Human (Homo sapiens), chimeric or humanized antibody
                       peptide sequence
source               1..14
                     mol_type = protein
                     organism = unidentified
SEQUENCE: 24
WGQGTTLTVS SSEQ                                                           14

SEQ ID NO: 25        moltype = AA  length = 116
FEATURE              Location/Qualifiers
REGION               1..116
                     note = Human (Homo sapiens), chimeric or humanized antibody
                       peptide sequence
source               1..116
                     mol_type = protein
                     organism = unidentified
SEQUENCE: 25
QIQLLQSGPE LKKPGETVKI SCKASGYTFT DYSIHWVKQA PGKGLKWMGW IKTETGEPTY    60
ADDFNGRFAF SLETSASTAY LQINNLKNED TATYFCAIYY YGRDSWGQGT TLTVSS       116

SEQ ID NO: 26        moltype = AA  length = 27
FEATURE              Location/Qualifiers
REGION               1..27
                     note = Human (Homo sapiens), chimeric or humanized antibody
                       peptide sequence
source               1..27
                     mol_type = protein
                     organism = unidentified
SEQUENCE: 26
QIQLLQSGPE LKKPGETVKI SCKASGY                                             27

SEQ ID NO: 27        moltype = AA  length = 8
FEATURE              Location/Qualifiers
REGION               1..8
                     note = Human (Homo sapiens), chimeric or humanized antibody
                       peptide sequence
source               1..8
                     mol_type = protein
                     organism = unidentified
SEQUENCE: 27
TFTDYSIH                                                                   8

SEQ ID NO: 28        moltype = AA  length = 14
FEATURE              Location/Qualifiers
REGION               1..14
                     note = Human (Homo sapiens), chimeric or humanized antibody
                       peptide sequence
source               1..14
                     mol_type = protein
                     organism = unidentified
SEQUENCE: 28
WVKQAPGKGL KWMG                                                           14

SEQ ID NO: 29        moltype = AA  length = 17
FEATURE              Location/Qualifiers
REGION               1..17
                     note = Human (Homo sapiens), chimeric or humanized antibody
                       peptide sequence
source               1..17
                     mol_type = protein
                     organism = unidentified
SEQUENCE: 29
WIKTETGEPT YADDFNG                                                        17

SEQ ID NO: 30        moltype = AA  length = 32
FEATURE              Location/Qualifiers
```

```
REGION                      1..32
                            note = Human (Homo sapiens), chimeric or humanized antibody
                             peptide sequence
source                      1..32
                            mol_type = protein
                            organism = unidentified
SEQUENCE: 30
RFAFSLETSA STAYLQINNL KNEDTATYFC AI                                    32

SEQ ID NO: 31               moltype = AA  length = 7
FEATURE                     Location/Qualifiers
REGION                      1..7
                            note = Human (Homo sapiens), chimeric or humanized antibody
                             peptide sequence
source                      1..7
                            mol_type = protein
                            organism = unidentified
SEQUENCE: 31
YYYGRDS                                                                 7

SEQ ID NO: 32               moltype = AA  length = 11
FEATURE                     Location/Qualifiers
REGION                      1..11
                            note = Human (Homo sapiens), chimeric or humanized antibody
                             peptide sequence
source                      1..11
                            mol_type = protein
                            organism = unidentified
SEQUENCE: 32
WGQGTTLTVS S                                                           11

SEQ ID NO: 33               moltype = AA  length = 116
FEATURE                     Location/Qualifiers
REGION                      1..116
                            note = Human (Homo sapiens), chimeric or humanized antibody
                             peptide sequence
source                      1..116
                            mol_type = protein
                            organism = unidentified
SEQUENCE: 33
QIQLLQSGPE LKKPGETVKI SCKASGYTFT DYSMHWVKQA PGKGLKWVAR INTETGEPTF      60
ADDFRGRFAV SLETSASTAY LQINNLKNED TATYFCAIYY YGRDSWGQGT TLTVSS         116

SEQ ID NO: 34               moltype = AA  length = 27
FEATURE                     Location/Qualifiers
REGION                      1..27
                            note = Human (Homo sapiens), chimeric or humanized antibody
                             peptide sequence
source                      1..27
                            mol_type = protein
                            organism = unidentified
SEQUENCE: 34
QIQLLQSGPE LKKPGETVKI SCKASGY                                          27

SEQ ID NO: 35               moltype = AA  length = 8
FEATURE                     Location/Qualifiers
REGION                      1..8
                            note = Human (Homo sapiens), chimeric or humanized antibody
                             peptide sequence
source                      1..8
                            mol_type = protein
                            organism = unidentified
SEQUENCE: 35
TFTDYSMH                                                                8

SEQ ID NO: 36               moltype = AA  length = 14
FEATURE                     Location/Qualifiers
REGION                      1..14
                            note = Human (Homo sapiens), chimeric or humanized antibody
                             peptide sequence
source                      1..14
                            mol_type = protein
                            organism = unidentified
SEQUENCE: 36
WVKQAPGKGL KWVA                                                        14

SEQ ID NO: 37               moltype = AA  length = 17
FEATURE                     Location/Qualifiers
REGION                      1..17
```

```
                    note = Human (Homo sapiens), chimeric or humanized antibody
                     peptide sequence
source              1..17
                    mol_type = protein
                    organism = unidentified
SEQUENCE: 37
RINTETGEPT FADDFRG                                                         17

SEQ ID NO: 38       moltype = AA  length = 32
FEATURE             Location/Qualifiers
REGION              1..32
                    note = Human (Homo sapiens), chimeric or humanized antibody
                     peptide sequence
source              1..32
                    mol_type = protein
                    organism = unidentified
SEQUENCE: 38
RFAVSLETSA STAYLQINNL KNEDTATYFC AI                                        32

SEQ ID NO: 39       moltype = AA  length = 7
FEATURE             Location/Qualifiers
REGION              1..7
                    note = Human (Homo sapiens), chimeric or humanized antibody
                     peptide sequence
source              1..7
                    mol_type = protein
                    organism = unidentified
SEQUENCE: 39
YYYGRDS                                                                    7

SEQ ID NO: 40       moltype = AA  length = 11
FEATURE             Location/Qualifiers
REGION              1..11
                    note = Human (Homo sapiens), chimeric or humanized antibody
                     peptide sequence
source              1..11
                    mol_type = protein
                    organism = unidentified
SEQUENCE: 40
WGQGTTLTVS S                                                               11

SEQ ID NO: 41       moltype = AA  length = 116
FEATURE             Location/Qualifiers
REGION              1..116
                    note = Human (Homo sapiens), chimeric or humanized antibody
                     peptide sequence
source              1..116
                    mol_type = protein
                    organism = unidentified
SEQUENCE: 41
QIQLLQSGPE LKKPGETVKI SCLASGYTFT DYSMHWVKQA PGKGLKWVAR INTETGEPTF          60
ADDFGGRFAV SLETSASTAY LQINNLKNED TATYFCAIYY YGRDSWGQGT TLTVSS             116

SEQ ID NO: 42       moltype = AA  length = 27
FEATURE             Location/Qualifiers
REGION              1..27
                    note = Human (Homo sapiens), chimeric or humanized antibody
                     peptide sequence
source              1..27
                    mol_type = protein
                    organism = unidentified
SEQUENCE: 42
QIQLLQSGPE LKKPGETVKI SCLASGY                                              27

SEQ ID NO: 43       moltype = AA  length = 8
FEATURE             Location/Qualifiers
REGION              1..8
                    note = Human (Homo sapiens), chimeric or humanized antibody
                     peptide sequence
source              1..8
                    mol_type = protein
                    organism = unidentified
SEQUENCE: 43
TFTDYSMH                                                                   8

SEQ ID NO: 44       moltype = AA  length = 14
FEATURE             Location/Qualifiers
REGION              1..14
                    note = Human (Homo sapiens), chimeric or humanized antibody
```

```
                            peptide sequence
source                      1..14
                            mol_type = protein
                            organism = unidentified
SEQUENCE: 44
WVKQAPGKGL KWVA                                                              14

SEQ ID NO: 45               moltype = AA  length = 17
FEATURE                     Location/Qualifiers
REGION                      1..17
                            note = Human (Homo sapiens), chimeric or humanized antibody
                             peptide sequence
source                      1..17
                            mol_type = protein
                            organism = unidentified
SEQUENCE: 45
RINTETGEPT FADDFGG                                                           17

SEQ ID NO: 46               moltype = AA  length = 32
FEATURE                     Location/Qualifiers
REGION                      1..32
                            note = Human (Homo sapiens), chimeric or humanized antibody
                             peptide sequence
source                      1..32
                            mol_type = protein
                            organism = unidentified
SEQUENCE: 46
RFAVSLETSA STAYLQINNL KNEDTATYFC AI                                          32

SEQ ID NO: 47               moltype = AA  length = 7
FEATURE                     Location/Qualifiers
REGION                      1..7
                            note = Human (Homo sapiens), chimeric or humanized antibody
                             peptide sequence
source                      1..7
                            mol_type = protein
                            organism = unidentified
SEQUENCE: 47
YYYGRDS                                                                      7

SEQ ID NO: 48               moltype = AA  length = 11
FEATURE                     Location/Qualifiers
REGION                      1..11
                            note = Human (Homo sapiens), chimeric or humanized antibody
                             peptide sequence
source                      1..11
                            mol_type = protein
                            organism = unidentified
SEQUENCE: 48
WGQGTTLTVS S                                                                 11

SEQ ID NO: 49               moltype = AA  length = 120
FEATURE                     Location/Qualifiers
REGION                      1..120
                            note = Human (Homo sapiens), chimeric or humanized antibody
                             peptide sequence
source                      1..120
                            mol_type = protein
                            organism = unidentified
SEQUENCE: 49
EVQLVESGGG LVQPGGSLKL SCAASGFTFS SFGMSWVRQT PDKRLELVAT INSNGGSTYY            60
PDNMKGRFTI SRDNAKNTLY LQMSSLKSED TAMYYCASAC YRYGAFFDYW GQGTTLTVSS            120

SEQ ID NO: 50               moltype = AA  length = 27
FEATURE                     Location/Qualifiers
REGION                      1..27
                            note = Human (Homo sapiens), chimeric or humanized antibody
                             peptide sequence
source                      1..27
                            mol_type = protein
                            organism = unidentified
SEQUENCE: 50
EVQLVESGGG LVQPGGSLKL SCAASGF                                                27

SEQ ID NO: 51               moltype = AA  length = 8
FEATURE                     Location/Qualifiers
REGION                      1..8
                            note = Human (Homo sapiens), chimeric or humanized antibody
                             peptide sequence
```

```
source                  1..8
                        mol_type = protein
                        organism = unidentified
SEQUENCE: 51
TFSSFGMS                                                                    8

SEQ ID NO: 52           moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 52
WVRQTPDKRL ELVA                                                            14

SEQ ID NO: 53           moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 53
TINSNGGSTY YPDNMKG                                                         17

SEQ ID NO: 54           moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 54
RFTISRDNAK NTLYLQMSSL KSEDTAMYYC AS                                        32

SEQ ID NO: 55           moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 55
ACYRGAFFD Y                                                                11

SEQ ID NO: 56           moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 56
WGQGTTLTVS S                                                               11

SEQ ID NO: 57           moltype = AA  length = 116
FEATURE                 Location/Qualifiers
REGION                  1..116
                        note = Human (Homo sapiens), chimeric or humanized antibody
                         peptide sequence
source                  1..116
                        mol_type = protein
                        organism = unidentified
SEQUENCE: 57
EVQLLESGPE LKKPGETVKI SCKASGYTFT DYSIHWVKQA PGKGLKWMGW IKTETGEPTY           60
ADDFKGRFAF SLETSASTAY LQINNLKNED TATYFCAIYY YGRDSWGQGT TVTVSS              116

SEQ ID NO: 58           moltype = AA  length = 27
FEATURE                 Location/Qualifiers
REGION                  1..27
                        note = Human (Homo sapiens), chimeric or humanized antibody
                         peptide sequence
source                  1..27
```

```
                              mol_type = protein
                              organism = unidentified
SEQUENCE: 58
EVQLLESGPE LKKPGETVKI SCKASGY                                              27

SEQ ID NO: 59         moltype = AA   length = 8
FEATURE               Location/Qualifiers
REGION                1..8
                      note = Human (Homo sapiens), chimeric or humanized antibody
                       peptide sequence
source                1..8
                      mol_type = protein
                      organism = unidentified
SEQUENCE: 59
TFTDYSIH                                                                   8

SEQ ID NO: 60         moltype = AA   length = 14
FEATURE               Location/Qualifiers
REGION                1..14
                      note = Human (Homo sapiens), chimeric or humanized antibody
                       peptide sequence
source                1..14
                      mol_type = protein
                      organism = unidentified
SEQUENCE: 60
WVKQAPGKGL KWMG                                                            14

SEQ ID NO: 61         moltype = AA   length = 17
FEATURE               Location/Qualifiers
REGION                1..17
                      note = Human (Homo sapiens), chimeric or humanized antibody
                       peptide sequence
source                1..17
                      mol_type = protein
                      organism = unidentified
SEQUENCE: 61
WIKTETGEPT YADDFKG                                                         17

SEQ ID NO: 62         moltype = AA   length = 32
FEATURE               Location/Qualifiers
REGION                1..32
                      note = Human (Homo sapiens), chimeric or humanized antibody
                       peptide sequence
source                1..32
                      mol_type = protein
                      organism = unidentified
SEQUENCE: 62
RFAFSLETSA STAYLQINNL KNEDTATYFC AI                                        32

SEQ ID NO: 63         moltype = AA   length = 7
FEATURE               Location/Qualifiers
REGION                1..7
                      note = Human (Homo sapiens), chimeric or humanized antibody
                       peptide sequence
source                1..7
                      mol_type = protein
                      organism = unidentified
SEQUENCE: 63
YYYGRDS                                                                    7

SEQ ID NO: 64         moltype = AA   length = 11
FEATURE               Location/Qualifiers
REGION                1..11
                      note = Human (Homo sapiens), chimeric or humanized antibody
                       peptide sequence
source                1..11
                      mol_type = protein
                      organism = unidentified
SEQUENCE: 64
WGQGTTVTVS S                                                               11

SEQ ID NO: 65         moltype = AA   length = 116
FEATURE               Location/Qualifiers
REGION                1..116
                      note = Human (Homo sapiens), chimeric or humanized antibody
                       peptide sequence
source                1..116
                      mol_type = protein
                      organism = unidentified
```

```
SEQUENCE: 65
EVQLLESGPE LKKPGETVKI SCKASGYTFT DYSIHWVKQA PGKGLKWMGW IKTETGEPTY    60
ADDFKGRFAF SLETSASTAY LQINNLKNED TATYFCAIYY YGRDSWGQGT TVTVSS       116

SEQ ID NO: 66           moltype = AA  length = 27
FEATURE                 Location/Qualifiers
REGION                  1..27
                        note = Human (Homo sapiens), chimeric or humanized antibody
                         peptide sequence
source                  1..27
                        mol_type = protein
                        organism = unidentified
SEQUENCE: 66
EVQLLESGPE LKKPGETVKI SCKASGY                                       27

SEQ ID NO: 67           moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 67
TFTDYSIH                                                            8

SEQ ID NO: 68           moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 68
WVKQAPGKGL KWMG                                                     14

SEQ ID NO: 69           moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 69
WIKTETGEPT YADDFKG                                                  17

SEQ ID NO: 70           moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 70
RFAFSLETSA STAYLQINNL KNEDTATYFC AI                                 32

SEQ ID NO: 71           moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 71
YYYGRDS                                                             7

SEQ ID NO: 72           moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 72
```

```
WGQGTTVTVS S                                                           11

SEQ ID NO: 73            moltype = AA  length = 116
FEATURE                  Location/Qualifiers
REGION                   1..116
                         note = Human (Homo sapiens), chimeric or humanized antibody
                           peptide sequence
source                   1..116
                         mol_type = protein
                         organism = unidentified
SEQUENCE: 73
QVQLMQSGPE LKKPGETVKI SCKASGYTFT DYSIHWVKQA PGKGLKWMGW IKTETGEPTY        60
ADDFNGRFAF SLETSASTAY LQINNLKNED TATYFCAIYY YGRDSWGQGT TLTVSS           116

SEQ ID NO: 74            moltype = AA  length = 27
FEATURE                  Location/Qualifiers
REGION                   1..27
                         note = Human (Homo sapiens), chimeric or humanized antibody
                           peptide sequence
source                   1..27
                         mol_type = protein
                         organism = unidentified
SEQUENCE: 74
QVQLMQSGPE LKKPGETVKI SCKASGY                                           27

SEQ ID NO: 75            moltype = AA  length = 8
FEATURE                  Location/Qualifiers
REGION                   1..8
                         note = Human (Homo sapiens), chimeric or humanized antibody
                           peptide sequence
source                   1..8
                         mol_type = protein
                         organism = unidentified
SEQUENCE: 75
TFTDYSIH                                                                 8

SEQ ID NO: 76            moltype = AA  length = 14
FEATURE                  Location/Qualifiers
REGION                   1..14
                         note = Human (Homo sapiens), chimeric or humanized antibody
                           peptide sequence
source                   1..14
                         mol_type = protein
                         organism = unidentified
SEQUENCE: 76
WVKQAPGKGL KWMG                                                         14

SEQ ID NO: 77            moltype = AA  length = 17
FEATURE                  Location/Qualifiers
REGION                   1..17
                         note = Human (Homo sapiens), chimeric or humanized antibody
                           peptide sequence
source                   1..17
                         mol_type = protein
                         organism = unidentified
SEQUENCE: 77
WIKTETGEPT YADDFNG                                                      17

SEQ ID NO: 78            moltype = AA  length = 32
FEATURE                  Location/Qualifiers
REGION                   1..32
                         note = Human (Homo sapiens), chimeric or humanized antibody
                           peptide sequence
source                   1..32
                         mol_type = protein
                         organism = unidentified
SEQUENCE: 78
RFAFSLETSA STAYLQINNL KNEDTATYFC AI                                     32

SEQ ID NO: 79            moltype = AA  length = 7
FEATURE                  Location/Qualifiers
REGION                   1..7
                         note = Human (Homo sapiens), chimeric or humanized antibody
                           peptide sequence
source                   1..7
                         mol_type = protein
                         organism = unidentified
SEQUENCE: 79
YYYGRDS                                                                  7
```

```
SEQ ID NO: 80            moltype = AA  length = 11
FEATURE                  Location/Qualifiers
REGION                   1..11
                         note = Human (Homo sapiens), chimeric or humanized antibody
                          peptide sequence
source                   1..11
                         mol_type = protein
                         organism = unidentified
SEQUENCE: 80
WGQGTTLTVS S                                                                    11

SEQ ID NO: 81            moltype = AA  length = 116
FEATURE                  Location/Qualifiers
REGION                   1..116
                         note = Human (Homo sapiens), chimeric or humanized antibody
                          peptide sequence
source                   1..116
                         mol_type = protein
                         organism = unidentified
SEQUENCE: 81
QIQLQQSGPE LKKPGETVKI SCKASGYTFT DYSMHWVKQA PGKGLKWVAR INTETGEPTF   60
ADDFRGRFAV SLETSASTAY LQINNLKNED TATYFCAIYY YGRDSWGQGT TLTVSS      116

SEQ ID NO: 82            moltype = AA  length = 27
FEATURE                  Location/Qualifiers
REGION                   1..27
                         note = Human (Homo sapiens), chimeric or humanized antibody
                          peptide sequence
source                   1..27
                         mol_type = protein
                         organism = unidentified
SEQUENCE: 82
QIQLQQSGPE LKKPGETVKI SCKASGY                                                   27

SEQ ID NO: 83            moltype = AA  length = 8
FEATURE                  Location/Qualifiers
REGION                   1..8
                         note = Human (Homo sapiens), chimeric or humanized antibody
                          peptide sequence
source                   1..8
                         mol_type = protein
                         organism = unidentified
SEQUENCE: 83
TFTDYSMH                                                                         8

SEQ ID NO: 84            moltype = AA  length = 14
FEATURE                  Location/Qualifiers
REGION                   1..14
                         note = Human (Homo sapiens), chimeric or humanized antibody
                          peptide sequence
source                   1..14
                         mol_type = protein
                         organism = unidentified
SEQUENCE: 84
WVKQAPGKGL KWVA                                                                 14

SEQ ID NO: 85            moltype = AA  length = 17
FEATURE                  Location/Qualifiers
REGION                   1..17
                         note = Human (Homo sapiens), chimeric or humanized antibody
                          peptide sequence
source                   1..17
                         mol_type = protein
                         organism = unidentified
SEQUENCE: 85
RINTETGEPT FADDFRG                                                              17

SEQ ID NO: 86            moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 86
RFAVSLETSA STAYLQINNL KNEDTATYFC AI                                             32
```

```
SEQ ID NO: 87              moltype = AA   length = 7
FEATURE                    Location/Qualifiers
REGION                     1..7
                           note = Human (Homo sapiens), chimeric or humanized antibody
                            peptide sequence
source                     1..7
                           mol_type = protein
                           organism = unidentified
SEQUENCE: 87
YYYGRDS                                                                    7

SEQ ID NO: 88              moltype = AA   length = 11
FEATURE                    Location/Qualifiers
REGION                     1..11
                           note = Human (Homo sapiens), chimeric or humanized antibody
                            peptide sequence
source                     1..11
                           mol_type = protein
                           organism = unidentified
SEQUENCE: 88
WGQGTTLTVS S                                                              11

SEQ ID NO: 89              moltype = AA   length = 116
FEATURE                    Location/Qualifiers
REGION                     1..116
                           note = Human (Homo sapiens), chimeric or humanized antibody
                            peptide sequence
source                     1..116
                           mol_type = protein
                           organism = unidentified
SEQUENCE: 89
QIQLLQSGPE LKKPGETVKI SCKASGYTFT DYSMHWVKQA PGKGLKWVAR INTETGEPTF          60
ADDFRGRFAV SLETSASTAY LQINNLKNED TATYFCAIYY YGRDSWGQGT TLTVSS             116

SEQ ID NO: 90              moltype = AA   length = 27
FEATURE                    Location/Qualifiers
REGION                     1..27
                           note = Human (Homo sapiens), chimeric or humanized antibody
                            peptide sequence
source                     1..27
                           mol_type = protein
                           organism = unidentified
SEQUENCE: 90
QIQLLQSGPE LKKPGETVKI SCKASGY                                             27

SEQ ID NO: 91              moltype = AA   length = 8
FEATURE                    Location/Qualifiers
REGION                     1..8
                           note = Human (Homo sapiens), chimeric or humanized antibody
                            peptide sequence
source                     1..8
                           mol_type = protein
                           organism = unidentified
SEQUENCE: 91
TFTDYSMH                                                                   8

SEQ ID NO: 92              moltype = AA   length = 14
FEATURE                    Location/Qualifiers
REGION                     1..14
                           note = Human (Homo sapiens), chimeric or humanized antibody
                            peptide sequence
source                     1..14
                           mol_type = protein
                           organism = unidentified
SEQUENCE: 92
WVKQAPGKGL KWVA                                                           14

SEQ ID NO: 93              moltype = AA   length = 17
FEATURE                    Location/Qualifiers
REGION                     1..17
                           note = Human (Homo sapiens), chimeric or humanized antibody
                            peptide sequence
source                     1..17
                           mol_type = protein
                           organism = unidentified
SEQUENCE: 93
RINTETGEPT FADDFRG                                                        17

SEQ ID NO: 94              moltype = AA   length = 32
```

```
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 94
RFAVSLETSA STAYLQINNL KNEDTATYFC AI                                 32

SEQ ID NO: 95           moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 95
YYYGRDS                                                             7

SEQ ID NO: 96           moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 96
WGQGTTLTVS S                                                        11

SEQ ID NO: 97           moltype = AA  length = 116
FEATURE                 Location/Qualifiers
REGION                  1..116
                        note = Human (Homo sapiens), chimeric or humanized antibody
                         peptide sequence
source                  1..116
                        mol_type = protein
                        organism = unidentified
SEQUENCE: 97
QIQLLQSGPE LKKPGETVKI SCKASGYTFT DYSMHWVKQA PGKGLKWVAR INTETGEPTF   60
ADDFRGRFAV SLETSASTAY LQINNLKNED TATYFCAIYY YGRDTWGQGT TLSVSS       116

SEQ ID NO: 98           moltype = AA  length = 27
FEATURE                 Location/Qualifiers
REGION                  1..27
                        note = Human (Homo sapiens), chimeric or humanized antibody
                         peptide sequence
source                  1..27
                        mol_type = protein
                        organism = unidentified
SEQUENCE: 98
QIQLLQSGPE LKKPGETVKI SCKASGY                                       27

SEQ ID NO: 99           moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 99
TFTDYSMH                                                            8

SEQ ID NO: 100          moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 100
WVKQAPGKGL KWVA                                                     14

SEQ ID NO: 101          moltype = AA  length = 17
FEATURE                 Location/Qualifiers
```

```
REGION                     1..17
                           note = Human (Homo sapiens), chimeric or humanized antibody
                             peptide sequence
source                     1..17
                           mol_type = protein
                           organism = unidentified
SEQUENCE: 101
RINTETGEPT FADDFRG                                                          17

SEQ ID NO: 102             moltype = AA  length = 32
FEATURE                    Location/Qualifiers
REGION                     1..32
                           note = Human (Homo sapiens), chimeric or humanized antibody
                             peptide sequence
source                     1..32
                           mol_type = protein
                           organism = unidentified
SEQUENCE: 102
RFAVSLETSA STAYLQINNL KNEDTATYFC AI                                         32

SEQ ID NO: 103             moltype = AA  length = 7
FEATURE                    Location/Qualifiers
REGION                     1..7
                           note = Human (Homo sapiens), chimeric or humanized antibody
                             peptide sequence
source                     1..7
                           mol_type = protein
                           organism = unidentified
SEQUENCE: 103
YYYGRDT                                                                     7

SEQ ID NO: 104             moltype = AA  length = 11
FEATURE                    Location/Qualifiers
REGION                     1..11
                           note = Human (Homo sapiens), chimeric or humanized antibody
                             peptide sequence
source                     1..11
                           mol_type = protein
                           organism = unidentified
SEQUENCE: 104
WGQGTTLSVS S                                                                11

SEQ ID NO: 105             moltype = AA  length = 116
FEATURE                    Location/Qualifiers
REGION                     1..116
                           note = Human (Homo sapiens), chimeric or humanized antibody
                             peptide sequence
source                     1..116
                           mol_type = protein
                           organism = unidentified
SEQUENCE: 105
QIQLLQSGPE LKKPGETVKI SCKASGYTFT DYSMHWVKQA PGKGLKWVAR INTETGEPTF            60
ADDFRGRFAV SLETSASTAY LQINNLKNED TATYFCAIFY YGRDSWGQGT ALTVSS               116

SEQ ID NO: 106             moltype = AA  length = 27
FEATURE                    Location/Qualifiers
REGION                     1..27
                           note = Human (Homo sapiens), chimeric or humanized antibody
                             peptide sequence
source                     1..27
                           mol_type = protein
                           organism = unidentified
SEQUENCE: 106
QIQLLQSGPE LKKPGETVKI SCKASGY                                               27

SEQ ID NO: 107             moltype = AA  length = 8
FEATURE                    Location/Qualifiers
REGION                     1..8
                           note = Human (Homo sapiens), chimeric or humanized antibody
                             peptide sequence
source                     1..8
                           mol_type = protein
                           organism = unidentified
SEQUENCE: 107
TFTDYSMH                                                                    8

SEQ ID NO: 108             moltype = AA  length = 14
FEATURE                    Location/Qualifiers
REGION                     1..14
```

```
                          -continued source              1..14
                    mol_type = protein
                    organism = unidentified
SEQUENCE: 108
WVKQAPGKGL KWVA                                                      14

SEQ ID NO: 109      moltype = AA   length = 17
FEATURE             Location/Qualifiers
REGION              1..17
                    note = Human (Homo sapiens), chimeric or humanized antibody
                     peptide sequence
source              1..17
                    mol_type = protein
                    organism = unidentified
SEQUENCE: 109
RINTETGEPT FADDFRG                                                   17

SEQ ID NO: 110      moltype = AA   length = 32
FEATURE             Location/Qualifiers
REGION              1..32
                    note = Human (Homo sapiens), chimeric or humanized antibody
                     peptide sequence
source              1..32
                    mol_type = protein
                    organism = unidentified
SEQUENCE: 110
RFAVSLETSA STAYLQINNL KNEDTATYFC AI                                  32

SEQ ID NO: 111      moltype = AA   length = 7
FEATURE             Location/Qualifiers
REGION              1..7
                    note = Human (Homo sapiens), chimeric or humanized antibody
                     peptide sequence
source              1..7
                    mol_type = protein
                    organism = unidentified
SEQUENCE: 111
FYYGRDS                                                               7

SEQ ID NO: 112      moltype = AA   length = 11
FEATURE             Location/Qualifiers
REGION              1..11
                    note = Human (Homo sapiens), chimeric or humanized antibody
                     peptide sequence
source              1..11
                    mol_type = protein
                    organism = unidentified
SEQUENCE: 112
WGQGTALTVS S                                                         11

SEQ ID NO: 113      moltype = AA   length = 116
FEATURE             Location/Qualifiers
REGION              1..116
                    note = Human (Homo sapiens), chimeric or humanized antibody
                     peptide sequence
source              1..116
                    mol_type = protein
                    organism = unidentified
SEQUENCE: 113
QIQLLQSGPE LKKPGETVKI SCKASGYTFT DYSMHWVKQA PGKGLKWVAR INTETGEPTF    60
ADDFRGRFAV SLETSASTAY LQINNLKNED TATYFCAIYY YGRDSWGQGT TLTVSS       116

SEQ ID NO: 114      moltype = AA   length = 27
FEATURE             Location/Qualifiers
REGION              1..27
                    note = Human (Homo sapiens), chimeric or humanized antibody
                     peptide sequence
source              1..27
                    mol_type = protein
                    organism = unidentified
SEQUENCE: 114
QIQLLQSGPE LKKPGETVKI SCKASGY                                        27

SEQ ID NO: 115      moltype = AA   length = 8
FEATURE             Location/Qualifiers
REGION              1..8
                    note = Human (Homo sapiens), chimeric or humanized antibody
```

```
                            peptide sequence
source                      1..8
                            mol_type = protein
                            organism = unidentified
SEQUENCE: 115
TFTDYSMH                                                                    8

SEQ ID NO: 116              moltype = AA   length = 14
FEATURE                     Location/Qualifiers
REGION                      1..14
                            note = Human (Homo sapiens), chimeric or humanized antibody
                             peptide sequence
source                      1..14
                            mol_type = protein
                            organism = unidentified
SEQUENCE: 116
WVKQAPGKGL KWVA                                                            14

SEQ ID NO: 117              moltype = AA   length = 17
FEATURE                     Location/Qualifiers
REGION                      1..17
                            note = Human (Homo sapiens), chimeric or humanized antibody
                             peptide sequence
source                      1..17
                            mol_type = protein
                            organism = unidentified
SEQUENCE: 117
RINTETGEPT FADDFRG                                                         17

SEQ ID NO: 118              moltype = AA   length = 32
FEATURE                     Location/Qualifiers
REGION                      1..32
                            note = Human (Homo sapiens), chimeric or humanized antibody
                             peptide sequence
source                      1..32
                            mol_type = protein
                            organism = unidentified
SEQUENCE: 118
RFAVSLETSA STAYLQINNL KNEDTATYFC AI                                        32

SEQ ID NO: 119              moltype = AA   length = 7
FEATURE                     Location/Qualifiers
REGION                      1..7
                            note = Human (Homo sapiens), chimeric or humanized antibody
                             peptide sequence
source                      1..7
                            mol_type = protein
                            organism = unidentified
SEQUENCE: 119
YYYGRDS                                                                     7

SEQ ID NO: 120              moltype = AA   length = 11
FEATURE                     Location/Qualifiers
REGION                      1..11
                            note = Human (Homo sapiens), chimeric or humanized antibody
                             peptide sequence
source                      1..11
                            mol_type = protein
                            organism = unidentified
SEQUENCE: 120
WGQGTTLTVS S                                                               11

SEQ ID NO: 121              moltype = AA   length = 116
FEATURE                     Location/Qualifiers
REGION                      1..116
                            note = Human (Homo sapiens), chimeric or humanized antibody
                             peptide sequence
source                      1..116
                            mol_type = protein
                            organism = unidentified
SEQUENCE: 121
QIQLLQSGPE LKKPGETVKI SCKASGYTFT DYSMHWVKQA PGKGLKWVAR INTETGEPTF          60
ADDFRGRFAV SLETSASTAY LQINNLKNED TATYFCAIFY YGRDSWGQGT TLTVSS             116

SEQ ID NO: 122              moltype = AA   length = 27
FEATURE                     Location/Qualifiers
REGION                      1..27
                            note = Human (Homo sapiens), chimeric or humanized antibody
                             peptide sequence
```

```
source                  1..27
                        mol_type = protein
                        organism = unidentified
SEQUENCE: 122
QIQLLQSGPE LKKPGETVKI SCKASGY                                      27

SEQ ID NO: 123          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 123
TFTDYSMH                                                            8

SEQ ID NO: 124          moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 124
WVKQAPGKGL KWVA                                                     14

SEQ ID NO: 125          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 125
RINTETGEPT FADDFRG                                                  17

SEQ ID NO: 126          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 126
RFAVSLETSA STAYLQINNL KNEDTATYFC AI                                 32

SEQ ID NO: 127          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 127
FYYGRDS                                                             7

SEQ ID NO: 128          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 128
WGQGTTLTVS S                                                        11

SEQ ID NO: 129          moltype = AA  length = 109
FEATURE                 Location/Qualifiers
REGION                  1..109
                        note = Human (Homo sapiens), chimeric or humanized antibody
                         peptide sequence
source                  1..109
                        mol_type = protein
```

```
                             organism = unidentified
SEQUENCE: 129
DIVMSQSPSS MYASLGERVT ITCKASQDIN SYLSWFQQKP GKSPKTLIYR ANRLVDGVPS    60
RFSGSGSGQD YSLTISSLEY EDMGIYYCLQ YDEFPPLTFG AGTKLELKA              109

SEQ ID NO: 130           moltype = AA  length = 23
FEATURE                  Location/Qualifiers
REGION                   1..23
                         note = Human (Homo sapiens), chimeric or humanized antibody
                          peptide sequence
source                   1..23
                         mol_type = protein
                         organism = unidentified
SEQUENCE: 130
DIVMSQSPSS MYASLGERVT ITC                                           23

SEQ ID NO: 131           moltype = AA  length = 11
FEATURE                  Location/Qualifiers
REGION                   1..11
                         note = Human (Homo sapiens), chimeric or humanized antibody
                          peptide sequence
source                   1..11
                         mol_type = protein
                         organism = unidentified
SEQUENCE: 131
KASQDINSYL S                                                        11

SEQ ID NO: 132           moltype = AA  length = 15
FEATURE                  Location/Qualifiers
REGION                   1..15
                         note = Human (Homo sapiens), chimeric or humanized antibody
                          peptide sequence
source                   1..15
                         mol_type = protein
                         organism = unidentified
SEQUENCE: 132
WFQQKPGKSP KTLIY                                                    15

SEQ ID NO: 133           moltype = AA  length = 7
FEATURE                  Location/Qualifiers
REGION                   1..7
                         note = Human (Homo sapiens), chimeric or humanized antibody
                          peptide sequence
source                   1..7
                         mol_type = protein
                         organism = unidentified
SEQUENCE: 133
RANRLVD                                                              7

SEQ ID NO: 134           moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 134
GVPSRFSGSG SGQDYSLTIS SLEYEDMGIY YC                                 32

SEQ ID NO: 135           moltype = AA  length = 10
FEATURE                  Location/Qualifiers
REGION                   1..10
                         note = Human (Homo sapiens), chimeric or humanized antibody
                          peptide sequence
source                   1..10
                         mol_type = protein
                         organism = unidentified
SEQUENCE: 135
LQYDEFPPLT                                                          10

SEQ ID NO: 136           moltype = AA  length = 11
FEATURE                  Location/Qualifiers
REGION                   1..11
                         note = Human (Homo sapiens), chimeric or humanized antibody
                          peptide sequence
source                   1..11
                         mol_type = protein
                         organism = unidentified
```

```
SEQUENCE: 136
FGAGTKLELK A                                                            11

SEQ ID NO: 137         moltype = AA  length = 109
FEATURE                Location/Qualifiers
REGION                 1..109
                       note = Human (Homo sapiens), chimeric or humanized antibody
                         peptide sequence
source                 1..109
                       mol_type = protein
                       organism = unidentified
SEQUENCE: 137
QIVLTQSPSS MYASLGERVT ITCKASQDIN SYLSWFQQKP GKSPKTLIYR ANRLVDGVPS        60
RFSGSGSGQD YSLTISSLEY EDMGIYYCLQ YDEFPPLTFG AGTKLELKA                    109

SEQ ID NO: 138         moltype = AA  length = 23
FEATURE                Location/Qualifiers
REGION                 1..23
                       note = Human (Homo sapiens), chimeric or humanized antibody
                         peptide sequence
source                 1..23
                       mol_type = protein
                       organism = unidentified
SEQUENCE: 138
QIVLTQSPSS MYASLGERVT ITC                                                23

SEQ ID NO: 139         moltype = AA  length = 11
FEATURE                Location/Qualifiers
REGION                 1..11
                       note = Human (Homo sapiens), chimeric or humanized antibody
                         peptide sequence
source                 1..11
                       mol_type = protein
                       organism = unidentified
SEQUENCE: 139
KASQDINSYL S                                                             11

SEQ ID NO: 140         moltype = AA  length = 15
FEATURE                Location/Qualifiers
REGION                 1..15
                       note = Human (Homo sapiens), chimeric or humanized antibody
                         peptide sequence
source                 1..15
                       mol_type = protein
                       organism = unidentified
SEQUENCE: 140
WFQQKPGKSP KTLIY                                                         15

SEQ ID NO: 141         moltype = AA  length = 7
FEATURE                Location/Qualifiers
REGION                 1..7
                       note = Human (Homo sapiens), chimeric or humanized antibody
                         peptide sequence
source                 1..7
                       mol_type = protein
                       organism = unidentified
SEQUENCE: 141
RANRLVD                                                                  7

SEQ ID NO: 142         moltype = AA  length = 32
FEATURE                Location/Qualifiers
REGION                 1..32
                       note = Human (Homo sapiens), chimeric or humanized antibody
                         peptide sequence
source                 1..32
                       mol_type = protein
                       organism = unidentified
SEQUENCE: 142
GVPSRFSGSG SGQDYSLTIS SLEYEDMGIY YC                                      32

SEQ ID NO: 143         moltype = AA  length = 10
FEATURE                Location/Qualifiers
REGION                 1..10
                       note = Human (Homo sapiens), chimeric or humanized antibody
                         peptide sequence
source                 1..10
                       mol_type = protein
                       organism = unidentified
SEQUENCE: 143
```

```
LQYDEFPPLT                                                                10

SEQ ID NO: 144          moltype = AA  length = 11
FEATURE                 Location/Qualifiers
REGION                  1..11
                        note = Human (Homo sapiens), chimeric or humanized antibody
                          peptide sequence
source                  1..11
                        mol_type = protein
                        organism = unidentified
SEQUENCE: 144
FGAGTKLELK A                                                              11

SEQ ID NO: 145          moltype = AA  length = 107
FEATURE                 Location/Qualifiers
REGION                  1..107
                        note = Human (Homo sapiens), chimeric or humanized antibody
                          peptide sequence
source                  1..107
                        mol_type = protein
                        organism = unidentified
SEQUENCE: 145
QIVLTQSPAI MSASPGEKVT MTCSASSSVS YMHWYQQKPG TSPKLWIYDT SNLASGVPAR          60
FSGSGSGTSY SLTISSMEAE DAATYYCQQW SSNPLTFGSG TKLEIKA                       107

SEQ ID NO: 146          moltype = AA  length = 23
FEATURE                 Location/Qualifiers
REGION                  1..23
                        note = Human (Homo sapiens), chimeric or humanized antibody
                          peptide sequence
source                  1..23
                        mol_type = protein
                        organism = unidentified
SEQUENCE: 146
QIVLTQSPAI MSASPGEKVT MTC                                                 23

SEQ ID NO: 147          moltype = AA  length = 10
FEATURE                 Location/Qualifiers
REGION                  1..10
                        note = Human (Homo sapiens), chimeric or humanized antibody
                          peptide sequence
source                  1..10
                        mol_type = protein
                        organism = unidentified
SEQUENCE: 147
SASSSVSYMH                                                                10

SEQ ID NO: 148          moltype = AA  length = 15
FEATURE                 Location/Qualifiers
REGION                  1..15
                        note = Human (Homo sapiens), chimeric or humanized antibody
                          peptide sequence
source                  1..15
                        mol_type = protein
                        organism = unidentified
SEQUENCE: 148
WYQQKPGTSP KLWIY                                                          15

SEQ ID NO: 149          moltype = AA  length = 7
FEATURE                 Location/Qualifiers
REGION                  1..7
                        note = Human (Homo sapiens), chimeric or humanized antibody
                          peptide sequence
source                  1..7
                        mol_type = protein
                        organism = unidentified
SEQUENCE: 149
DTSNLAS                                                                   7

SEQ ID NO: 150          moltype = AA  length = 32
FEATURE                 Location/Qualifiers
REGION                  1..32
                        note = Human (Homo sapiens), chimeric or humanized antibody
                          peptide sequence
source                  1..32
                        mol_type = protein
                        organism = unidentified
SEQUENCE: 150
GVPARFSGSG SGTSYSLTIS SMEAEDAATY YC                                       32
```

```
SEQ ID NO: 151         moltype = AA  length = 9
FEATURE                Location/Qualifiers
REGION                 1..9
                       note = Human (Homo sapiens), chimeric or humanized antibody
                        peptide sequence
source                 1..9
                       mol_type = protein
                       organism = unidentified
SEQUENCE: 151
QQWSSNPLT                                                                  9

SEQ ID NO: 152         moltype = AA  length = 11
FEATURE                Location/Qualifiers
REGION                 1..11
                       note = Human (Homo sapiens), chimeric or humanized antibody
                        peptide sequence
source                 1..11
                       mol_type = protein
                       organism = unidentified
SEQUENCE: 152
FGSGTKLEIK A                                                              11

SEQ ID NO: 153         moltype = AA  length = 107
FEATURE                Location/Qualifiers
REGION                 1..107
                       note = Human (Homo sapiens), chimeric or humanized antibody
                        peptide sequence
source                 1..107
                       mol_type = protein
                       organism = unidentified
SEQUENCE: 153
EIVLTQSPAI MSASPGEKVT MTCSASSSVS YMHWYQQKPG SSPKLWIYDT SNLASGVPAR          60
FSGSGSGTSY SLTISSMEAE DAATYYCQQW SSNPLTFGDG TRLEIKA                      107

SEQ ID NO: 154         moltype = AA  length = 23
FEATURE                Location/Qualifiers
REGION                 1..23
                       note = Human (Homo sapiens), chimeric or humanized antibody
                        peptide sequence
source                 1..23
                       mol_type = protein
                       organism = unidentified
SEQUENCE: 154
EIVLTQSPAI MSASPGEKVT MTC                                                 23

SEQ ID NO: 155         moltype = AA  length = 10
FEATURE                Location/Qualifiers
REGION                 1..10
                       note = Human (Homo sapiens), chimeric or humanized antibody
                        peptide sequence
source                 1..10
                       mol_type = protein
                       organism = unidentified
SEQUENCE: 155
SASSSVSYMH                                                                10

SEQ ID NO: 156         moltype = AA  length = 15
FEATURE                Location/Qualifiers
REGION                 1..15
                       note = Human (Homo sapiens), chimeric or humanized antibody
                        peptide sequence
source                 1..15
                       mol_type = protein
                       organism = unidentified
SEQUENCE: 156
WYQQKPGSSP KLWIY                                                          15

SEQ ID NO: 157         moltype = AA  length = 7
FEATURE                Location/Qualifiers
REGION                 1..7
                       note = Human (Homo sapiens), chimeric or humanized antibody
                        peptide sequence
source                 1..7
                       mol_type = protein
                       organism = unidentified
SEQUENCE: 157
DTSNLAS                                                                    7
```

```
SEQ ID NO: 158            moltype = AA   length = 32
FEATURE                   Location/Qualifiers
REGION                    1..32
                          note = Human (Homo sapiens), chimeric or humanized antibody
                            peptide sequence
source                    1..32
                          mol_type = protein
                          organism = unidentified
SEQUENCE: 158
GVPARFSGSG SGTSYSLTIS SMEAEDAATY YC                                    32

SEQ ID NO: 159            moltype = AA   length = 9
FEATURE                   Location/Qualifiers
REGION                    1..9
                          note = Human (Homo sapiens), chimeric or humanized antibody
                            peptide sequence
source                    1..9
                          mol_type = protein
                          organism = unidentified
SEQUENCE: 159
QQWSSNPLT                                                               9

SEQ ID NO: 160            moltype = AA   length = 11
FEATURE                   Location/Qualifiers
REGION                    1..11
                          note = Human (Homo sapiens), chimeric or humanized antibody
                            peptide sequence
source                    1..11
                          mol_type = protein
                          organism = unidentified
SEQUENCE: 160
FGDGTRLEIK A                                                           11

SEQ ID NO: 161            moltype = AA   length = 107
FEATURE                   Location/Qualifiers
REGION                    1..107
                          note = Human (Homo sapiens), chimeric or humanized antibody
                            peptide sequence
source                    1..107
                          mol_type = protein
                          organism = unidentified
SEQUENCE: 161
QIVLTQSPAI MSASPGEKVT MTCSASSSVS YMHWYQQKSG TSPKLWIYDT SNLASGVPAR       60
FSGSGSGTSY SLTISSMEAE DAATYYCQQW SSNPPTFGAG TKLELKA                    107

SEQ ID NO: 162            moltype = AA   length = 23
FEATURE                   Location/Qualifiers
REGION                    1..23
                          note = Human (Homo sapiens), chimeric or humanized antibody
                            peptide sequence
source                    1..23
                          mol_type = protein
                          organism = unidentified
SEQUENCE: 162
QIVLTQSPAI MSASPGEKVT MTC                                              23

SEQ ID NO: 163            moltype = AA   length = 10
FEATURE                   Location/Qualifiers
REGION                    1..10
                          note = Human (Homo sapiens), chimeric or humanized antibody
                            peptide sequence
source                    1..10
                          mol_type = protein
                          organism = unidentified
SEQUENCE: 163
SASSSVSYMH                                                             10

SEQ ID NO: 164            moltype = AA   length = 15
FEATURE                   Location/Qualifiers
REGION                    1..15
                          note = Human (Homo sapiens), chimeric or humanized antibody
                            peptide sequence
source                    1..15
                          mol_type = protein
                          organism = unidentified
SEQUENCE: 164
WYQQKSGTSP KLWIY                                                       15

SEQ ID NO: 165            moltype = AA   length = 7
```

```
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 165
DTSNLAS                                                                          7

SEQ ID NO: 166          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 166
GVPARFSGSG SGTSYSLTIS SMEAEDAATY YC                                              32

SEQ ID NO: 167          moltype = AA  length = 9
FEATURE                 Location/Qualifiers
REGION                  1..9
                        note = Human (Homo sapiens), chimeric or humanized antibody
                         peptide sequence
source                  1..9
                        mol_type = protein
                        organism = unidentified
SEQUENCE: 167
QQWSSNPPT                                                                        9

SEQ ID NO: 168          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 168
FGAGTKLELK A                                                                     11

SEQ ID NO: 169          moltype = AA  length = 107
FEATURE                 Location/Qualifiers
REGION                  1..107
                        note = Human (Homo sapiens), chimeric or humanized antibody
                         peptide sequence
source                  1..107
                        mol_type = protein
                        organism = unidentified
SEQUENCE: 169
DIKMTQSPAI MSASPGEKVT MTCSASSSVS YMHWYQQKSG TSPKRWIYDT SKLASGVPAR                 60
FSGSGSGTSY SLTISSMEAE DAATYYCQQW SSNPFTFGSG TKLEIKA                              107

SEQ ID NO: 170          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 170
DIKMTQSPAI MSASPGEKVT MTC                                                        23

SEQ ID NO: 171          moltype = AA  length = 10
FEATURE                 Location/Qualifiers
REGION                  1..10
                        note = Human (Homo sapiens), chimeric or humanized antibody
                         peptide sequence
source                  1..10
                        mol_type = protein
                        organism = unidentified
SEQUENCE: 171
SASSSVSYMH                                                                       10

SEQ ID NO: 172          moltype = AA  length = 15
FEATURE                 Location/Qualifiers
```

```
REGION                   1..15
                         note = Human (Homo sapiens), chimeric or humanized antibody
                           peptide sequence
source                   1..15
                         mol_type = protein
                         organism = unidentified
SEQUENCE: 172
WYQQKSGTSP KRWIY                                                         15

SEQ ID NO: 173           moltype = AA  length = 7
FEATURE                  Location/Qualifiers
REGION                   1..7
                         note = Human (Homo sapiens), chimeric or humanized antibody
                           peptide sequence
source                   1..7
                         mol_type = protein
                         organism = unidentified
SEQUENCE: 173
DTSKLAS                                                                  7

SEQ ID NO: 174           moltype = AA  length = 32
FEATURE                  Location/Qualifiers
REGION                   1..32
                         note = Human (Homo sapiens), chimeric or humanized antibody
                           peptide sequence
source                   1..32
                         mol_type = protein
                         organism = unidentified
SEQUENCE: 174
GVPARFSGSG SGTSYSLTIS SMEAEDAATY YC                                      32

SEQ ID NO: 175           moltype = AA  length = 9
FEATURE                  Location/Qualifiers
REGION                   1..9
                         note = Human (Homo sapiens), chimeric or humanized antibody
                           peptide sequence
source                   1..9
                         mol_type = protein
                         organism = unidentified
SEQUENCE: 175
QQWSSNPFT                                                                9

SEQ ID NO: 176           moltype = AA  length = 11
FEATURE                  Location/Qualifiers
REGION                   1..11
                         note = Human (Homo sapiens), chimeric or humanized antibody
                           peptide sequence
source                   1..11
                         mol_type = protein
                         organism = unidentified
SEQUENCE: 176
FGSGTKLEIK A                                                             11

SEQ ID NO: 177           moltype = AA  length = 107
FEATURE                  Location/Qualifiers
REGION                   1..107
                         note = Human (Homo sapiens), chimeric or humanized antibody
                           peptide sequence
source                   1..107
                         mol_type = protein
                         organism = unidentified
SEQUENCE: 177
QMVLTHSPAI MSASPGEKVT MTCSASSSVS YMHWYQQKPG SSPKPWIYGT SNLASGVPAR         60
FSGSGSGTSY SLTISRMEAE DAATYYCQQW SSNPPTFGDG TRLEIKA                      107

SEQ ID NO: 178           moltype = AA  length = 23
FEATURE                  Location/Qualifiers
REGION                   1..23
                         note = Human (Homo sapiens), chimeric or humanized antibody
                           peptide sequence
source                   1..23
                         mol_type = protein
                         organism = unidentified
SEQUENCE: 178
QMVLTHSPAI MSASPGEKVT MTC                                                23

SEQ ID NO: 179           moltype = AA  length = 10
FEATURE                  Location/Qualifiers
REGION                   1..10
```

```
                    note = Human (Homo sapiens), chimeric or humanized antibody
                     peptide sequence
source              1..10
                    mol_type = protein
                    organism = unidentified
SEQUENCE: 179
SASSSVSYMH                                                                10

SEQ ID NO: 180      moltype = AA  length = 15
FEATURE             Location/Qualifiers
REGION              1..15
                    note = Human (Homo sapiens), chimeric or humanized antibody
                     peptide sequence
source              1..15
                    mol_type = protein
                    organism = unidentified
SEQUENCE: 180
WYQQKPGSSP KPWIY                                                          15

SEQ ID NO: 181      moltype = AA  length = 7
FEATURE             Location/Qualifiers
REGION              1..7
                    note = Human (Homo sapiens), chimeric or humanized antibody
                     peptide sequence
source              1..7
                    mol_type = protein
                    organism = unidentified
SEQUENCE: 181
GTSNLAS                                                                    7

SEQ ID NO: 182      moltype = AA  length = 32
FEATURE             Location/Qualifiers
REGION              1..32
                    note = Human (Homo sapiens), chimeric or humanized antibody
                     peptide sequence
source              1..32
                    mol_type = protein
                    organism = unidentified
SEQUENCE: 182
GVPARFSGSG SGTSYSLTIS RMEAEDAATY YC                                        32

SEQ ID NO: 183      moltype = AA  length = 9
FEATURE             Location/Qualifiers
REGION              1..9
                    note = Human (Homo sapiens), chimeric or humanized antibody
                     peptide sequence
source              1..9
                    mol_type = protein
                    organism = unidentified
SEQUENCE: 183
QQWSSNPPT                                                                  9

SEQ ID NO: 184      moltype = AA  length = 11
FEATURE             Location/Qualifiers
REGION              1..11
                    note = Human (Homo sapiens), chimeric or humanized antibody
                     peptide sequence
source              1..11
                    mol_type = protein
                    organism = unidentified
SEQUENCE: 184
FGDGTRLEIK A                                                              11

SEQ ID NO: 185      moltype = AA  length = 113
FEATURE             Location/Qualifiers
REGION              1..113
                    note = Human (Homo sapiens), chimeric or humanized antibody
                     peptide sequence
source              1..113
                    mol_type = protein
                    organism = unidentified
SEQUENCE: 185
DIVMSQSPSS LAVSAGEKVT MSCKSSQSLL NSRTRKNYLA WYQQKPGQSP RLLIYWASTR          60
ESGVPDRFTG SGSGTDFTLT ISSVQAEDLA VYYCKQSYNL LTFGAGTKLE LKA                113

SEQ ID NO: 186      moltype = AA  length = 23
FEATURE             Location/Qualifiers
REGION              1..23
                    note = Human (Homo sapiens), chimeric or humanized antibody
```

```
                                peptide sequence
source                          1..23
                                mol_type = protein
                                organism = unidentified
SEQUENCE: 186
DIVMSQSPSS LAVSAGEKVT MSC                                              23

SEQ ID NO: 187                  moltype = AA  length = 17
FEATURE                         Location/Qualifiers
REGION                          1..17
                                note = Human (Homo sapiens), chimeric or humanized antibody
                                peptide sequence
source                          1..17
                                mol_type = protein
                                organism = unidentified
SEQUENCE: 187
KSSQSLLNSR TRKNYLA                                                     17

SEQ ID NO: 188                  moltype = AA  length = 15
FEATURE                         Location/Qualifiers
REGION                          1..15
                                note = Human (Homo sapiens), chimeric or humanized antibody
                                peptide sequence
source                          1..15
                                mol_type = protein
                                organism = unidentified
SEQUENCE: 188
WYQQKPGQSP RLLIY                                                       15

SEQ ID NO: 189                  moltype = AA  length = 7
FEATURE                         Location/Qualifiers
REGION                          1..7
                                note = Human (Homo sapiens), chimeric or humanized antibody
                                peptide sequence
source                          1..7
                                mol_type = protein
                                organism = unidentified
SEQUENCE: 189
WASTRES                                                                7

SEQ ID NO: 190                  moltype = AA  length = 32
FEATURE                         Location/Qualifiers
REGION                          1..32
                                note = Human (Homo sapiens), chimeric or humanized antibody
                                peptide sequence
source                          1..32
                                mol_type = protein
                                organism = unidentified
SEQUENCE: 190
GVPDRFTGSG SGTDFTLTIS SVQAEDLAVY YC                                    32

SEQ ID NO: 191                  moltype = AA  length = 8
FEATURE                         Location/Qualifiers
REGION                          1..8
                                note = Human (Homo sapiens), chimeric or humanized antibody
                                peptide sequence
source                          1..8
                                mol_type = protein
                                organism = unidentified
SEQUENCE: 191
KQSYNLLT                                                               8

SEQ ID NO: 192                  moltype = AA  length = 11
FEATURE                         Location/Qualifiers
REGION                          1..11
                                note = Human (Homo sapiens), chimeric or humanized antibody
                                peptide sequence
source                          1..11
                                mol_type = protein
                                organism = unidentified
SEQUENCE: 192
FGAGTKLELK A                                                           11

SEQ ID NO: 193                  moltype = AA  length = 113
FEATURE                         Location/Qualifiers
REGION                          1..113
                                note = Human (Homo sapiens), chimeric or humanized antibody
                                peptide sequence
source                          1..113
```

```
                        mol_type = protein
                        organism = unidentified
SEQUENCE: 193
DIVMSQSPSS LAVSAGENVT VSCKSSQSLL NSRTRKNYLA WYQQKPGQSP KLLIYWASTR    60
ESGVPDRFTG SGSGTDFTLT ISSVQAEDLA VYFCKQSYNL LTFGAGTKLE LKA          113

SEQ ID NO: 194          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 194
DIVMSQSPSS LAVSAGENVT VSC                                            23

SEQ ID NO: 195          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 195
DIVMSQSPSS LAVSAGENVT VSC                                            23

SEQ ID NO: 196          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 196
WYQQKPGQSP KLLIY                                                     15

SEQ ID NO: 197          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 197
WASTRES                                                               7

SEQ ID NO: 198          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 198
GVPDRFTGSG SGTDFTLTIS SVQAEDLAVY FC                                  32

SEQ ID NO: 199          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 199
KQSYNLLT                                                              8

SEQ ID NO: 200          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
```

```
                              organism = unidentified
SEQUENCE: 200
FGAGTKLELK A                                                                    11

SEQ ID NO: 201          moltype = AA   length = 113
FEATURE                 Location/Qualifiers
REGION                  1..113
                        note = Human (Homo sapiens), chimeric or humanized antibody
                          peptide sequence
source                  1..113
                        mol_type = protein
                        organism = unidentified
SEQUENCE: 201
DIKMTQSPSS LAVSPGEKVT MSCKSSQSLL HSRTRKNYLA WYQQKPGQSP KLLIYWASTR   60
ESGVPDRFTG SGSGTDFTLT ISSVQAEDLA VYYCKQSYNL LTFGAGTKLE LKA         113

SEQ ID NO: 202          moltype = AA   length = 23
FEATURE                 Location/Qualifiers
REGION                  1..23
                        note = Human (Homo sapiens), chimeric or humanized antibody
                          peptide sequence
source                  1..23
                        mol_type = protein
                        organism = unidentified
SEQUENCE: 202
DIKMTQSPSS LAVSPGEKVT MSC                                                       23

SEQ ID NO: 203          moltype = AA   length = 17
FEATURE                 Location/Qualifiers
REGION                  1..17
                        note = Human (Homo sapiens), chimeric or humanized antibody
                          peptide sequence
source                  1..17
                        mol_type = protein
                        organism = unidentified
SEQUENCE: 203
KSSQSLLHSR TRKNYLA                                                              17

SEQ ID NO: 204          moltype = AA   length = 15
FEATURE                 Location/Qualifiers
REGION                  1..15
                        note = Human (Homo sapiens), chimeric or humanized antibody
                          peptide sequence
source                  1..15
                        mol_type = protein
                        organism = unidentified
SEQUENCE: 204
WYQQKPGQSP KLLIY                                                                15

SEQ ID NO: 205          moltype = AA   length = 7
FEATURE                 Location/Qualifiers
REGION                  1..7
                        note = Human (Homo sapiens), chimeric or humanized antibody
                          peptide sequence
source                  1..7
                        mol_type = protein
                        organism = unidentified
SEQUENCE: 205
WASTRES                                                                          7

SEQ ID NO: 206          moltype = AA   length = 32
FEATURE                 Location/Qualifiers
REGION                  1..32
                        note = Human (Homo sapiens), chimeric or humanized antibody
                          peptide sequence
source                  1..32
                        mol_type = protein
                        organism = unidentified
SEQUENCE: 206
GVPDRFTGSG SGTDFTLTIS SVQAEDLAVY YC                                              32

SEQ ID NO: 207          moltype = AA   length = 8
FEATURE                 Location/Qualifiers
REGION                  1..8
                        note = Human (Homo sapiens), chimeric or humanized antibody
                          peptide sequence
source                  1..8
                        mol_type = protein
                        organism = unidentified
```

```
SEQUENCE: 207
KQSYNLLT                                                                    8

SEQ ID NO: 208         moltype = AA  length = 11
FEATURE                Location/Qualifiers
REGION                 1..11
                       note = Human (Homo sapiens), chimeric or humanized antibody
                         peptide sequence
source                 1..11
                       mol_type = protein
                       organism = unidentified
SEQUENCE: 208
FGAGTKLELK A                                                                11

SEQ ID NO: 209         moltype = AA  length = 113
FEATURE                Location/Qualifiers
REGION                 1..113
                       note = Human (Homo sapiens), chimeric or humanized antibody
                         peptide sequence
source                 1..113
                       mol_type = protein
                       organism = unidentified
SEQUENCE: 209
DIVMSQSPSS LAVSPGEKVT MSCKSSQSLL HSRTRKNYLA WYQQKPGQSP KLLIYWASTR           60
ESGVPDRFTG SGSGTDFTLT ISSVQAEDLA VYYCKQSYNL LTFGAGTKLE LKA                 113

SEQ ID NO: 210         moltype = AA  length = 23
FEATURE                Location/Qualifiers
REGION                 1..23
                       note = Human (Homo sapiens), chimeric or humanized antibody
                         peptide sequence
source                 1..23
                       mol_type = protein
                       organism = unidentified
SEQUENCE: 210
DIVMSQSPSS LAVSPGEKVT MSC                                                   23

SEQ ID NO: 211         moltype = AA  length = 17
FEATURE                Location/Qualifiers
REGION                 1..17
                       note = Human (Homo sapiens), chimeric or humanized antibody
                         peptide sequence
source                 1..17
                       mol_type = protein
                       organism = unidentified
SEQUENCE: 211
KSSQSLLHSR TRKNYLA                                                          17

SEQ ID NO: 212         moltype = AA  length = 15
FEATURE                Location/Qualifiers
REGION                 1..15
                       note = Human (Homo sapiens), chimeric or humanized antibody
                         peptide sequence
source                 1..15
                       mol_type = protein
                       organism = unidentified
SEQUENCE: 212
WYQQKPGQSP KLLIY                                                            15

SEQ ID NO: 213         moltype = AA  length = 7
FEATURE                Location/Qualifiers
REGION                 1..7
                       note = Human (Homo sapiens), chimeric or humanized antibody
                         peptide sequence
source                 1..7
                       mol_type = protein
                       organism = unidentified
SEQUENCE: 213
WASTRES                                                                     7

SEQ ID NO: 214         moltype = AA  length = 32
FEATURE                Location/Qualifiers
REGION                 1..32
                       note = Human (Homo sapiens), chimeric or humanized antibody
                         peptide sequence
source                 1..32
                       mol_type = protein
                       organism = unidentified
SEQUENCE: 214
```

```
GVPDRFTGSG SGTDFTLTIS SVQAEDLAVY YC                                     32

SEQ ID NO: 215           moltype = AA  length = 8
FEATURE                  Location/Qualifiers
REGION                   1..8
                         note = Human (Homo sapiens), chimeric or humanized antibody
                           peptide sequence
source                   1..8
                         mol_type = protein
                         organism = unidentified
SEQUENCE: 215
KQSYNLLT                                                                 8

SEQ ID NO: 216           moltype = AA  length = 11
FEATURE                  Location/Qualifiers
REGION                   1..11
                         note = Human (Homo sapiens), chimeric or humanized antibody
                           peptide sequence
source                   1..11
                         mol_type = protein
                         organism = unidentified
SEQUENCE: 216
FGAGTKLELK A                                                            11

SEQ ID NO: 217           moltype = AA  length = 113
FEATURE                  Location/Qualifiers
REGION                   1..113
                         note = Human (Homo sapiens), chimeric or humanized antibody
                           peptide sequence
source                   1..113
                         mol_type = protein
                         organism = unidentified
SEQUENCE: 217
DIVMTQSPSS LAVSAGEKVT MSCKSSQSLL NSRTRKNYLA WYQQKPGQSP RLLIYWASTR        60
ESGVPDRFTG SGSGTDFTLT ISSVQAEDLA VYYCKQSYNL LTFGAGTKLE LKR              113

SEQ ID NO: 218           moltype = AA  length = 23
FEATURE                  Location/Qualifiers
REGION                   1..23
                         note = Human (Homo sapiens), chimeric or humanized antibody
                           peptide sequence
source                   1..23
                         mol_type = protein
                         organism = unidentified
SEQUENCE: 218
DIVMTQSPSS LAVSAGEKVT MSC                                               23

SEQ ID NO: 219           moltype = AA  length = 17
FEATURE                  Location/Qualifiers
REGION                   1..17
                         note = Human (Homo sapiens), chimeric or humanized antibody
                           peptide sequence
source                   1..17
                         mol_type = protein
                         organism = unidentified
SEQUENCE: 219
KSSQSLLNSR TRKNYLA                                                      17

SEQ ID NO: 220           moltype = AA  length = 15
FEATURE                  Location/Qualifiers
REGION                   1..15
                         note = Human (Homo sapiens), chimeric or humanized antibody
                           peptide sequence
source                   1..15
                         mol_type = protein
                         organism = unidentified
SEQUENCE: 220
WYQQKPGQSP RLLIY                                                        15

SEQ ID NO: 221           moltype = AA  length = 7
FEATURE                  Location/Qualifiers
REGION                   1..7
                         note = Human (Homo sapiens), chimeric or humanized antibody
                           peptide sequence
source                   1..7
                         mol_type = protein
                         organism = unidentified
SEQUENCE: 221
WASTRES                                                                  7
```

```
SEQ ID NO: 222         moltype = AA   length = 32
FEATURE                Location/Qualifiers
REGION                 1..32
                       note = Human (Homo sapiens), chimeric or humanized antibody
                         peptide sequence
source                 1..32
                       mol_type = protein
                       organism = unidentified
SEQUENCE: 222
GVPDRFTGSG SGTDFTLTIS SVQAEDLAVY YC                                        32

SEQ ID NO: 223         moltype = AA   length = 8
FEATURE                Location/Qualifiers
REGION                 1..8
                       note = Human (Homo sapiens), chimeric or humanized antibody
                         peptide sequence
source                 1..8
                       mol_type = protein
                       organism = unidentified
SEQUENCE: 223
KQSYNLLT                                                                   8

SEQ ID NO: 224         moltype = AA   length = 11
FEATURE                Location/Qualifiers
REGION                 1..11
                       note = Human (Homo sapiens), chimeric or humanized antibody
                         peptide sequence
source                 1..11
                       mol_type = protein
                       organism = unidentified
SEQUENCE: 224
FGAGTKLELK R                                                               11

SEQ ID NO: 225         moltype = AA   length = 113
FEATURE                Location/Qualifiers
REGION                 1..113
                       note = Human (Homo sapiens), chimeric or humanized antibody
                         peptide sequence
source                 1..113
                       mol_type = protein
                       organism = unidentified
SEQUENCE: 225
DIVMTQSPSS LAVSAGEKVT MSCKSSQSLL NSRTRKNYLA WYQQKPGQSP RLLIYWASTR          60
ESGVPDRFTG SGSGTDFTLT ISSVQAEDLA VYYCKQSYNL LTFGAGTRLE IKR                 113

SEQ ID NO: 226         moltype = AA   length = 23
FEATURE                Location/Qualifiers
REGION                 1..23
                       note = Human (Homo sapiens), chimeric or humanized antibody
                         peptide sequence
source                 1..23
                       mol_type = protein
                       organism = unidentified
SEQUENCE: 226
DIVMTQSPSS LAVSAGEKVT MSC                                                  23

SEQ ID NO: 227         moltype = AA   length = 17
FEATURE                Location/Qualifiers
REGION                 1..17
                       note = Human (Homo sapiens), chimeric or humanized antibody
                         peptide sequence
source                 1..17
                       mol_type = protein
                       organism = unidentified
SEQUENCE: 227
KSSQSLLNSR TRKNYLA                                                         17

SEQ ID NO: 228         moltype = AA   length = 15
FEATURE                Location/Qualifiers
REGION                 1..15
                       note = Human (Homo sapiens), chimeric or humanized antibody
                         peptide sequence
source                 1..15
                       mol_type = protein
                       organism = unidentified
SEQUENCE: 228
WYQQKPGQSP RLLIY                                                           15
```

-continued

```
SEQ ID NO: 229          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 229
WASTRES                                                                     7

SEQ ID NO: 230          moltype = AA   length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 230
GVPDRFTGSG SGTDFTLTIS SVQAEDLAVY YC                                         32

SEQ ID NO: 231          moltype = AA   length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 231
KQSYNLLT                                                                    8

SEQ ID NO: 232          moltype = AA   length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 232
FGAGTRLEIK R                                                                11

SEQ ID NO: 233          moltype = AA   length = 113
FEATURE                 Location/Qualifiers
REGION                  1..113
                        note = Human (Homo sapiens), chimeric or humanized antibody
                         peptide sequence
source                  1..113
                        mol_type = protein
                        organism = unidentified
SEQUENCE: 233
DIVMTQSPSS LAVSAGENVT VSCKSSQSLL NSRTRKNYLA WYQQKPGQSP KLLIYWASTR           60
ESGVPDRFTG SGSGTGFTLT ISSVQAEDLA VYFCKQSYNL LTFGAGTRLE IKR                 113

SEQ ID NO: 234          moltype = AA   length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 234
DIVMTQSPSS LAVSAGENVT VSC                                                   23

SEQ ID NO: 235          moltype = AA   length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 235
KSSQSLLNSR TRKNYLA                                                          17

SEQ ID NO: 236          moltype = AA   length = 15
```

```
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 236
WYQQKPGQSP KLLIY                                                              15

SEQ ID NO: 237          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 237
WASTRES                                                                        7

SEQ ID NO: 238          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 238
GVPDRFTGSG SGTGFTLTIS SVQAEDLAVY FC                                            32

SEQ ID NO: 239          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 239
KQSYNLLT                                                                       8

SEQ ID NO: 240          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 240
FGAGTRLEIK R                                                                  11

SEQ ID NO: 241          moltype = AA  length = 113
FEATURE                 Location/Qualifiers
REGION                  1..113
                        note = Human (Homo sapiens), chimeric or humanized antibody
                         peptide sequence
source                  1..113
                        mol_type = protein
                        organism = unidentified
SEQUENCE: 241
DIVMSQSPSS LAVSPGEKVT MSCKSSQSLL HSRTRKNYLA WYQQKPGQSP KLLIYWASTR  60
ESGVPDRFTG SGSGTDFTLT ISSVQAEDLA VYYCKQSYNL LTFGAGTKLE LKR        113

SEQ ID NO: 242          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 242
DIVMSQSPSS LAVSPGEKVT MSC                                                     23

SEQ ID NO: 243          moltype = AA  length = 17
FEATURE                 Location/Qualifiers
```

```
REGION                    1..17
                          note = Human (Homo sapiens), chimeric or humanized antibody
                             peptide sequence
source                    1..17
                          mol_type = protein
                          organism = unidentified
SEQUENCE: 243
KSSQSLLHSR TRKNYLA                                                           17

SEQ ID NO: 244            moltype = AA  length = 15
FEATURE                   Location/Qualifiers
REGION                    1..15
                          note = Human (Homo sapiens), chimeric or humanized antibody
                             peptide sequence
source                    1..15
                          mol_type = protein
                          organism = unidentified
SEQUENCE: 244
WYQQKPGQSP KLLIY                                                             15

SEQ ID NO: 245            moltype = AA  length = 7
FEATURE                   Location/Qualifiers
REGION                    1..7
                          note = Human (Homo sapiens), chimeric or humanized antibody
                             peptide sequence
source                    1..7
                          mol_type = protein
                          organism = unidentified
SEQUENCE: 245
WASTRES                                                                       7

SEQ ID NO: 246            moltype = AA  length = 32
FEATURE                   Location/Qualifiers
REGION                    1..32
                          note = Human (Homo sapiens), chimeric or humanized antibody
                             peptide sequence
source                    1..32
                          mol_type = protein
                          organism = unidentified
SEQUENCE: 246
GVPDRFTGSG SGTDFTLTIS SVQAEDLAVY YC                                           32

SEQ ID NO: 247            moltype = AA  length = 8
FEATURE                   Location/Qualifiers
REGION                    1..8
                          note = Human (Homo sapiens), chimeric or humanized antibody
                             peptide sequence
source                    1..8
                          mol_type = protein
                          organism = unidentified
SEQUENCE: 247
KQSYNLLT                                                                      8

SEQ ID NO: 248            moltype = AA  length = 11
FEATURE                   Location/Qualifiers
REGION                    1..11
                          note = Human (Homo sapiens), chimeric or humanized antibody
                             peptide sequence
source                    1..11
                          mol_type = protein
                          organism = unidentified
SEQUENCE: 248
FGAGTKLELK R                                                                 11

SEQ ID NO: 249            moltype = AA  length = 113
FEATURE                   Location/Qualifiers
REGION                    1..113
                          note = Human (Homo sapiens), chimeric or humanized antibody
                             peptide sequence
source                    1..113
                          mol_type = protein
                          organism = unidentified
SEQUENCE: 249
DIVMSQSPSS LAVSAGEKVT MSCKSSQSLL NSRTRKNYLA WYQQKPGQSP RLLIYWASTR             60
ESGVPDRFTG SGSGTDFTLT ISSVQAEDLA VYYCKQSYNL LTFGAGTKLE LKA                   113

SEQ ID NO: 250            moltype = AA  length = 23
FEATURE                   Location/Qualifiers
REGION                    1..23
```

```
                            note = Human (Homo sapiens), chimeric or humanized antibody
                             peptide sequence
source                      1..23
                            mol_type = protein
                            organism = unidentified
SEQUENCE: 250
DIVMSQSPSS LAVSAGEKVT MSC                                                    23

SEQ ID NO: 251              moltype = AA   length = 17
FEATURE                     Location/Qualifiers
REGION                      1..17
                            note = Human (Homo sapiens), chimeric or humanized antibody
                             peptide sequence
source                      1..17
                            mol_type = protein
                            organism = unidentified
SEQUENCE: 251
KSSQSLLNSR TRKNYLA                                                           17

SEQ ID NO: 252              moltype = AA   length = 15
FEATURE                     Location/Qualifiers
REGION                      1..15
                            note = Human (Homo sapiens), chimeric or humanized antibody
                             peptide sequence
source                      1..15
                            mol_type = protein
                            organism = unidentified
SEQUENCE: 252
WYQQKPGQSP RLLIY                                                             15

SEQ ID NO: 253              moltype = AA   length = 7
FEATURE                     Location/Qualifiers
REGION                      1..7
                            note = Human (Homo sapiens), chimeric or humanized antibody
                             peptide sequence
source                      1..7
                            mol_type = protein
                            organism = unidentified
SEQUENCE: 253
WASTRES                                                                       7

SEQ ID NO: 254              moltype = AA   length = 32
FEATURE                     Location/Qualifiers
REGION                      1..32
                            note = Human (Homo sapiens), chimeric or humanized antibody
                             peptide sequence
source                      1..32
                            mol_type = protein
                            organism = unidentified
SEQUENCE: 254
GVPDRFTGSG SGTDFTLTIS SVQAEDLAVY YC                                           32

SEQ ID NO: 255              moltype = AA   length = 8
FEATURE                     Location/Qualifiers
REGION                      1..8
                            note = Human (Homo sapiens), chimeric or humanized antibody
                             peptide sequence
source                      1..8
                            mol_type = protein
                            organism = unidentified
SEQUENCE: 255
KQSYNLLT                                                                      8

SEQ ID NO: 256              moltype = AA   length = 11
FEATURE                     Location/Qualifiers
REGION                      1..11
                            note = Human (Homo sapiens), chimeric or humanized antibody
                             peptide sequence
source                      1..11
                            mol_type = protein
                            organism = unidentified
SEQUENCE: 256
FGAGTKLELK A                                                                 11

SEQ ID NO: 257              moltype = AA   length = 113
FEATURE                     Location/Qualifiers
REGION                      1..113
                            note = Human (Homo sapiens), chimeric or humanized antibody
                             peptide sequence
```

| | |
|---|---|
| source | 1..113<br>mol_type = protein<br>organism = unidentified |

SEQUENCE: 257
DIVMSQSPSS LAVSAGEKVT MSCKSSQSLL NSRTRKNYLA WYQQKPGQSP RLLIYWASTR 60
ESGVPDRFTG SGSGTDFTLT ISSVQDEDLA VYYCKQSYNL LTFGAGTKLE LKA        113

| | |
|---|---|
| SEQ ID NO: 258 | moltype = AA  length = 23 |
| FEATURE | Location/Qualifiers |
| REGION | 1..23<br>note = Human (Homo sapiens), chimeric or humanized antibody peptide sequence |
| source | 1..23<br>mol_type = protein<br>organism = unidentified |

SEQUENCE: 258
DIVMSQSPSS LAVSAGEKVT MSC                                         23

| | |
|---|---|
| SEQ ID NO: 259 | moltype = AA  length = 17 |
| FEATURE | Location/Qualifiers |
| REGION | 1..17<br>note = Human (Homo sapiens), chimeric or humanized antibody peptide sequence |
| source | 1..17<br>mol_type = protein<br>organism = unidentified |

SEQUENCE: 259
KSSQSLLNSR TRKNYLA                                                17

| | |
|---|---|
| SEQ ID NO: 260 | moltype = AA  length = 15 |
| FEATURE | Location/Qualifiers |
| REGION | 1..15<br>note = Human (Homo sapiens), chimeric or humanized antibody peptide sequence |
| source | 1..15<br>mol_type = protein<br>organism = unidentified |

SEQUENCE: 260
WYQQKPGQSP RLLIY                                                  15

| | |
|---|---|
| SEQ ID NO: 261 | moltype = AA  length = 7 |
| FEATURE | Location/Qualifiers |
| REGION | 1..7<br>note = Human (Homo sapiens), chimeric or humanized antibody peptide sequence |
| source | 1..7<br>mol_type = protein<br>organism = unidentified |

SEQUENCE: 261
WASTRES                                                           7

| | |
|---|---|
| SEQ ID NO: 262 | moltype = AA  length = 32 |
| FEATURE | Location/Qualifiers |
| REGION | 1..32<br>note = Human (Homo sapiens), chimeric or humanized antibody peptide sequence |
| source | 1..32<br>mol_type = protein<br>organism = unidentified |

SEQUENCE: 262
GVPDRFTGSG SGTDFTLTIS SVQDEDLAVY YC                               32

| | |
|---|---|
| SEQ ID NO: 263 | moltype = AA  length = 8 |
| FEATURE | Location/Qualifiers |
| REGION | 1..8<br>note = Human (Homo sapiens), chimeric or humanized antibody peptide sequence |
| source | 1..8<br>mol_type = protein<br>organism = unidentified |

SEQUENCE: 263
KQSYNLLT                                                          8

| | |
|---|---|
| SEQ ID NO: 264 | moltype = AA  length = 11 |
| FEATURE | Location/Qualifiers |
| REGION | 1..11<br>note = Human (Homo sapiens), chimeric or humanized antibody peptide sequence |
| source | 1..11 |

```
                        mol_type = protein
                        organism = unidentified
SEQUENCE: 264
FGAGTKLELK A                                                        11

SEQ ID NO: 265          moltype = AA  length = 113
FEATURE                 Location/Qualifiers
REGION                  1..113
                        note = Human (Homo sapiens), chimeric or humanized antibody
                         peptide sequence
source                  1..113
                        mol_type = protein
                        organism = unidentified
SEQUENCE: 265
DIVMSQSPSS LAVSAGEKVT MSCKSSQSLL NSRTKNYLA WYQQKPGQSP RLLIYWASTR    60
ESGVPDRFTG SGSGTDFTLT ISSVQAEDLA VYYCKQSYNL LTFGAGTKLE LKA          113

SEQ ID NO: 266          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 266
DIVMSQSPSS LAVSAGEKVT MSC                                           23

SEQ ID NO: 267          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 267
KSSQSLLNSR TRKNYLA                                                  17

SEQ ID NO: 268          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 268
WYQQKPGQSP RLLIY                                                    15

SEQ ID NO: 269          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 269
WASTRES                                                             7

SEQ ID NO: 270          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 270
GVPDRFTGSG SGTDFTLTIS SVQAEDLAVY YC                                 32

SEQ ID NO: 271          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
```

```
                                organism = unidentified
SEQUENCE: 271
KQSYNLLT                                                                8

SEQ ID NO: 272          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 272
FGAGTKLELK A                                                           11

SEQ ID NO: 273          moltype = AA  length = 113
FEATURE                 Location/Qualifiers
REGION                  1..113
                        note = Human (Homo sapiens), chimeric or humanized antibody
                         peptide sequence
source                  1..113
                        mol_type = protein
                        organism = unidentified
SEQUENCE: 273
DIVMSQSPSS LAVSAGEKVT MSCKSSQSLL NSRTRKNYLA WYQQKPGQSP RLLIYWASTR      60
ESGVPDRFTG SGSGTDFTLT ISSVQAEDLA VYYCKQSYNL LTFGAGTKLE LKA            113

SEQ ID NO: 274          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 274
DIVMSQSPSS LAVSAGEKVT MSC                                              23

SEQ ID NO: 275          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 275
KSSQSLLNSR TRKNYLA                                                     17

SEQ ID NO: 276          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 276
WYQQKPGQSP RLLIY                                                       15

SEQ ID NO: 277          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 277
WASTRES                                                                 7

SEQ ID NO: 278          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
```

```
SEQUENCE: 278
GVPDRFTGSG SGTDFTLTIS SVQAEDLAVY YC                                      32

SEQ ID NO: 279          moltype = AA  length = 8
FEATURE                 Location/Qualifiers
REGION                  1..8
                        note = Human (Homo sapiens), chimeric or humanized antibody
                          peptide sequence
source                  1..8
                        mol_type = protein
                        organism = unidentified
SEQUENCE: 279
KQSYNLLT                                                                 8

SEQ ID NO: 280          moltype = AA  length = 11
FEATURE                 Location/Qualifiers
REGION                  1..11
                        note = Human (Homo sapiens), chimeric or humanized antibody
                          peptide sequence
source                  1..11
                        mol_type = protein
                        organism = unidentified
SEQUENCE: 280
FGAGTKLELK A                                                             11

SEQ ID NO: 281          moltype = AA  length = 113
FEATURE                 Location/Qualifiers
REGION                  1..113
                        note = Human (Homo sapiens), chimeric or humanized antibody
                          peptide sequence
VARIANT                 49
                        note = misc_feature - Xaa can be any naturally occurring
                          amino acid
source                  1..113
                        mol_type = protein
                        organism = unidentified
SEQUENCE: 281
DIVMSQSPSS LAVSAGEKVT MSCKSSQSLL NSRTRKNYLA WYQQKPGQXP RLLIYWASTR        60
ESGVPDRFTG SGSGTDFTLT ISSVQDEDLA VYYCKQSYNL LSFGAGTKLE LKA              113

SEQ ID NO: 282          moltype = AA  length = 23
FEATURE                 Location/Qualifiers
REGION                  1..23
                        note = Human (Homo sapiens), chimeric or humanized antibody
                          peptide sequence
source                  1..23
                        mol_type = protein
                        organism = unidentified
SEQUENCE: 282
DIVMSQSPSS LAVSAGEKVT MSC                                                23

SEQ ID NO: 283          moltype = AA  length = 17
FEATURE                 Location/Qualifiers
REGION                  1..17
                        note = Human (Homo sapiens), chimeric or humanized antibody
                          peptide sequence
source                  1..17
                        mol_type = protein
                        organism = unidentified
SEQUENCE: 283
KSSQSLLNSR TRKNYLA                                                       17

SEQ ID NO: 284          moltype = AA  length = 15
FEATURE                 Location/Qualifiers
REGION                  1..15
                        note = Human (Homo sapiens), chimeric or humanized antibody
                          peptide sequence
VARIANT                 9
                        note = misc_feature - Xaa can be any naturally occurring
                          amino acid
source                  1..15
                        mol_type = protein
                        organism = unidentified
SEQUENCE: 284
WYQQKPGQXP RLLIY                                                         15

SEQ ID NO: 285          moltype = AA  length = 7
FEATURE                 Location/Qualifiers
REGION                  1..7
```

```
                        note = Human (Homo sapiens), chimeric or humanized antibody
                         peptide sequence
source                  1..7
                        mol_type = protein
                        organism = unidentified
SEQUENCE: 285
WASTRES                                                                     7

SEQ ID NO: 286          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 286
GVPDRFTGSG SGTDFTLTIS SVQDEDLAVY YC                                         32

SEQ ID NO: 287          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 287
KQSYNLLS                                                                    8

SEQ ID NO: 288          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 288
FGAGTKLELK A                                                                11

SEQ ID NO: 289          moltype = AA  length = 113
FEATURE                 Location/Qualifiers
REGION                  1..113
                        note = Human (Homo sapiens), chimeric or humanized antibody
                         peptide sequence
source                  1..113
                        mol_type = protein
                        organism = unidentified
SEQUENCE: 289
DIVMTQSPSS LAVSAGEKVT MSCKSSQSLL NSRTRKNYLA WYQQKPGQSP RLLIYWASTR           60
ESGVPDRFTG SGSGTDFTLT ISSVQAEDLA VYYCKQSYNL LSFGAGTKLE LKR                  113

SEQ ID NO: 290          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 290
DIVMTQSPSS LAVSAGEKVT MSC                                                   23

SEQ ID NO: 291          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 291
KSSQSLLNSR TRKNYLA                                                          17

SEQ ID NO: 292          moltype = AA  length = 15
FEATURE                 Location/Qualifiers
REGION                  1..15
                        note = Human (Homo sapiens), chimeric or humanized antibody
```

```
                            peptide sequence
source                      1..15
                            mol_type = protein
                            organism = unidentified
SEQUENCE: 292
WYQQKPGQSP RLLIY                                                            15

SEQ ID NO: 293              moltype = AA  length = 7
FEATURE                     Location/Qualifiers
REGION                      1..7
                            note = Human (Homo sapiens), chimeric or humanized antibody
                             peptide sequence
source                      1..7
                            mol_type = protein
                            organism = unidentified
SEQUENCE: 293
WASTRES                                                                      7

SEQ ID NO: 294              moltype = AA  length = 32
FEATURE                     Location/Qualifiers
REGION                      1..32
                            note = Human (Homo sapiens), chimeric or humanized antibody
                             peptide sequence
source                      1..32
                            mol_type = protein
                            organism = unidentified
SEQUENCE: 294
GVPDRFTGSG SGTDFTLTIS SVQAEDLAVY YC                                          32

SEQ ID NO: 295              moltype = AA  length = 8
FEATURE                     Location/Qualifiers
REGION                      1..8
                            note = Human (Homo sapiens), chimeric or humanized antibody
                             peptide sequence
source                      1..8
                            mol_type = protein
                            organism = unidentified
SEQUENCE: 295
KQSYNLLS                                                                     8

SEQ ID NO: 296              moltype = AA  length = 11
FEATURE                     Location/Qualifiers
REGION                      1..11
                            note = Human (Homo sapiens), chimeric or humanized antibody
                             peptide sequence
source                      1..11
                            mol_type = protein
                            organism = unidentified
SEQUENCE: 296
FGAGTKLELK R                                                                11

SEQ ID NO: 297              moltype = AA  length = 120
FEATURE                     Location/Qualifiers
REGION                      1..120
                            note = Human (Homo sapiens), chimeric or humanized antibody
                             peptide sequence
source                      1..120
                            mol_type = protein
                            organism = unidentified
SEQUENCE: 297
QVQLQQSGAE LVRPGTSVKV SCKASGYAFT DYLIQWVKQR PGQGLEWIGV INPETGGTNY            60
NAKFRGKATL TADKSSSSAY MQLSSLTSGD SAVYFCAREA GNYIYAMDYW GQGTSVTVSS           120

SEQ ID NO: 298              moltype = AA  length = 27
FEATURE                     Location/Qualifiers
REGION                      1..27
                            note = Human (Homo sapiens), chimeric or humanized antibody
                             peptide sequence
source                      1..27
                            mol_type = protein
                            organism = unidentified
SEQUENCE: 298
QVQLQQSGAE LVRPGTSVKV SCKASGY                                               27

SEQ ID NO: 299              moltype = AA  length = 8
FEATURE                     Location/Qualifiers
REGION                      1..8
                            note = Human (Homo sapiens), chimeric or humanized antibody
                             peptide sequence
```

```
source                  1..8
                        mol_type = protein
                        organism = unidentified
SEQUENCE: 299
AFTDYLIQ                                                                    8

SEQ ID NO: 300          moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 300
WVKQRPGQGL EWIG                                                             14

SEQ ID NO: 301          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 301
VINPETGGTN YNAKFRG                                                          17

SEQ ID NO: 302          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 302
KATLTADKSS SSAYMQLSSL TSGDSAVYFC AR                                         32

SEQ ID NO: 303          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 303
EAGNYIYAMD Y                                                                11

SEQ ID NO: 304          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 304
WGQGTSVTVS S                                                                11

SEQ ID NO: 305          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 305
DIVMTQSPAF LSASVGETVT ITCRASVNIY SYLVWYQQKQ GKSPQLLVHN AKTLAEGVPS           60
RFSGSGSGTQ FSLKINSLQP EDFGSYYCQH HHGTPYTFGG GTKLEIKR                        108

SEQ ID NO: 306          moltype = AA  length = 23
FEATURE                 Location/Qualifiers
REGION                  1..23
                        note = Human (Homo sapiens), chimeric or humanized antibody
                         peptide sequence
source                  1..23
```

```
                          mol_type = protein
                          organism = unidentified
SEQUENCE: 306
DIVMTQSPAF LSASVGETVT ITC                                                23

SEQ ID NO: 307            moltype = AA  length = 11
FEATURE                   Location/Qualifiers
REGION                    1..11
                          note = Human (Homo sapiens), chimeric or humanized antibody
                           peptide sequence
source                    1..11
                          mol_type = protein
                          organism = unidentified
SEQUENCE: 307
RASVNIYSYL V                                                             11

SEQ ID NO: 308            moltype = AA  length = 15
FEATURE                   Location/Qualifiers
REGION                    1..15
                          note = Human (Homo sapiens), chimeric or humanized antibody
                           peptide sequence
source                    1..15
                          mol_type = protein
                          organism = unidentified
SEQUENCE: 308
WYQQKQGKSP QLLVH                                                         15

SEQ ID NO: 309            moltype = AA  length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 309
NAKTLAE                                                                  7

SEQ ID NO: 310            moltype = AA  length = 32
FEATURE                   Location/Qualifiers
REGION                    1..32
                          note = Human (Homo sapiens), chimeric or humanized antibody
                           peptide sequence
source                    1..32
                          mol_type = protein
                          organism = unidentified
SEQUENCE: 310
GVPSRFSGSG SGTQFSLKIN SLQPEDFGSY YC                                      32

SEQ ID NO: 311            moltype = AA  length = 9
FEATURE                   Location/Qualifiers
REGION                    1..9
                          note = Human (Homo sapiens), chimeric or humanized antibody
                           peptide sequence
source                    1..9
                          mol_type = protein
                          organism = unidentified
SEQUENCE: 311
QHHHGTPYT                                                                9

SEQ ID NO: 312            moltype = AA  length = 11
FEATURE                   Location/Qualifiers
REGION                    1..11
                          note = Human (Homo sapiens), chimeric or humanized antibody
                           peptide sequence
source                    1..11
                          mol_type = protein
                          organism = unidentified
SEQUENCE: 312
FGGGTKLEIK R                                                             11

SEQ ID NO: 313            moltype = AA  length = 8
FEATURE                   Location/Qualifiers
REGION                    1..8
                          note = Human (Homo sapiens), chimeric or humanized antibody
                           peptide sequence
source                    1..8
                          mol_type = protein
                          organism = unidentified
```

```
SEQUENCE: 313
TFTDYSMH                                                                    8

SEQ ID NO: 314          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 314
RINTETGEPT FADDFGG                                                         17

SEQ ID NO: 315          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 315
YYYGRDS                                                                     7

SEQ ID NO: 316          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 316
TFTDYSMH                                                                    8

SEQ ID NO: 317          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 317
WIKTETGEPT YADDFKG                                                         17

SEQ ID NO: 318          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 318
YYYGRDS                                                                     7

SEQ ID NO: 319          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 319
TFTDYSMH                                                                    8

SEQ ID NO: 320          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 320
WIKTETDEPT YADDFKE                                                         17
```

```
SEQ ID NO: 321          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 321
YYYGRDS                                                                   7

SEQ ID NO: 322          moltype = AA   length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 322
TFTDYSMH                                                                  8

SEQ ID NO: 323          moltype = AA   length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 323
RINTETGEPT FADDFRG                                                       17

SEQ ID NO: 324          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 324
YYYGRDS                                                                   7

SEQ ID NO: 325          moltype = AA   length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 325
TFTDYSIH                                                                  8

SEQ ID NO: 326          moltype = AA   length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 326
WIKTETGEPT YADDFNG                                                       17

SEQ ID NO: 327          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 327
YYYGRDS                                                                   7

SEQ ID NO: 328          moltype = AA   length = 8
```

```
FEATURE                 Location/Qualifiers
REGION                  1..8
                        note = Human (Homo sapiens), chimeric or humanized antibody
                         peptide sequence
source                  1..8
                        mol_type = protein
                        organism = unidentified SEQUENCE: 328
TFTDYSMH                                                                8

SEQ ID NO: 329          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified SEQUENCE: 329
RINTETGEPT FADDFRG                                                     17

SEQ ID NO: 330          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified SEQUENCE: 330
YYYGRDT                                                                 7

SEQ ID NO: 331          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified SEQUENCE: 331
TFTDYSMH                                                                8

SEQ ID NO: 332          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified SEQUENCE: 332
RINTETGEPT FADDFRG                                                     17

SEQ ID NO: 333          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified SEQUENCE: 333
FYYGRDS                                                                 7

SEQ ID NO: 334          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified SEQUENCE: 334
KASQDINSYL S                                                           11

SEQ ID NO: 335          moltype = AA  length = 7
FEATURE                 Location/Qualifiers
REGION                  1..7
```

```
                    note = Human (Homo sapiens), chimeric or humanized antibody
                     peptide sequence
source              1..7
                    mol_type = protein
                    organism = unidentified
SEQUENCE: 335
RANRLVD                                                                          7

SEQ ID NO: 336      moltype = AA  length = 10
FEATURE             Location/Qualifiers
REGION              1..10
                    note = Human (Homo sapiens), chimeric or humanized antibody
                     peptide sequence
source              1..10
                    mol_type = protein
                    organism = unidentified
SEQUENCE: 336
LQYDEFPPLT                                                                      10

SEQ ID NO: 337      moltype = AA  length = 17
FEATURE             Location/Qualifiers
REGION              1..17
                    note = Human (Homo sapiens), chimeric or humanized antibody
                     peptide sequence
source              1..17
                    mol_type = protein
                    organism = unidentified
SEQUENCE: 337
KSSQSLLNSR TRKNYLA                                                              17

SEQ ID NO: 338      moltype = AA  length = 7
FEATURE             Location/Qualifiers
REGION              1..7
                    note = Human (Homo sapiens), chimeric or humanized antibody
                     peptide sequence
source              1..7
                    mol_type = protein
                    organism = unidentified
SEQUENCE: 338
WASTRES                                                                          7

SEQ ID NO: 339      moltype = AA  length = 8
FEATURE             Location/Qualifiers
REGION              1..8
                    note = Human (Homo sapiens), chimeric or humanized antibody
                     peptide sequence
source              1..8
                    mol_type = protein
                    organism = unidentified
SEQUENCE: 339
KQSYNLLT                                                                         8

SEQ ID NO: 340      moltype = AA  length = 17
FEATURE             Location/Qualifiers
REGION              1..17
                    note = Human (Homo sapiens), chimeric or humanized antibody
                     peptide sequence
source              1..17
                    mol_type = protein
                    organism = unidentified
SEQUENCE: 340
KSSQSLLNSR IRKNYLA                                                              17

SEQ ID NO: 341      moltype = AA  length = 7
FEATURE             Location/Qualifiers
REGION              1..7
                    note = Human (Homo sapiens), chimeric or humanized antibody
                     peptide sequence
source              1..7
                    mol_type = protein
                    organism = unidentified
SEQUENCE: 341
WASTRES                                                                          7

SEQ ID NO: 342      moltype = AA  length = 8
FEATURE             Location/Qualifiers
REGION              1..8
                    note = Human (Homo sapiens), chimeric or humanized antibody
                     peptide sequence
```

```
source                    1..8
                          mol_type = protein
                          organism = unidentified
SEQUENCE: 342
KQSYNLLT                                                                      8

SEQ ID NO: 343            moltype = AA   length = 10
FEATURE                   Location/Qualifiers
REGION                    1..10
                          note = Human (Homo sapiens), chimeric or humanized antibody
                           peptide sequence
source                    1..10
                          mol_type = protein
                          organism = unidentified
SEQUENCE: 343
SASSSVSYMH                                                                   10

SEQ ID NO: 344            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 344
DTSNLAS                                                                       7

SEQ ID NO: 345            moltype = AA   length = 9
FEATURE                   Location/Qualifiers
REGION                    1..9
                          note = Human (Homo sapiens), chimeric or humanized antibody
                           peptide sequence
source                    1..9
                          mol_type = protein
                          organism = unidentified
SEQUENCE: 345
QQWSSNPLT                                                                     9

SEQ ID NO: 346            moltype = AA   length = 10
FEATURE                   Location/Qualifiers
REGION                    1..10
                          note = Human (Homo sapiens), chimeric or humanized antibody
                           peptide sequence
source                    1..10
                          mol_type = protein
                          organism = unidentified
SEQUENCE: 346
SASSSVSYMH                                                                   10

SEQ ID NO: 347            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 347
DTSNLAS                                                                       7

SEQ ID NO: 348            moltype = AA   length = 9
FEATURE                   Location/Qualifiers
REGION                    1..9
                          note = Human (Homo sapiens), chimeric or humanized antibody
                           peptide sequence
source                    1..9
                          mol_type = protein
                          organism = unidentified
SEQUENCE: 348
QQWSSNPPT                                                                     9

SEQ ID NO: 349            moltype = AA   length = 17
FEATURE                   Location/Qualifiers
REGION                    1..17
                          note = Human (Homo sapiens), chimeric or humanized antibody
                           peptide sequence
source                    1..17
                          mol_type = protein
```

```
                              -continued

SEQUENCE: 349
KSSQSLLNSR TRKNYLA                                              17

SEQ ID NO: 350          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 350
WASTRES                                                          7

SEQ ID NO: 351          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 351
KQSYNLLT                                                         8

SEQ ID NO: 352          moltype = AA  length = 10
FEATURE                 Location/Qualifiers
REGION                  1..10
                        note = Human (Homo sapiens), chimeric or humanized antibody
                         peptide sequence
source                  1..10
                        mol_type = protein
                        organism = unidentified
SEQUENCE: 352
SASSSVSYMH                                                      10

SEQ ID NO: 353          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 353
DTSKLAS                                                          7

SEQ ID NO: 354          moltype = AA  length = 9
FEATURE                 Location/Qualifiers
REGION                  1..9
                        note = Human (Homo sapiens), chimeric or humanized antibody
                         peptide sequence
source                  1..9
                        mol_type = protein
                        organism = unidentified
SEQUENCE: 354
QQWSSNPFT                                                        9

SEQ ID NO: 355          moltype = AA  length = 10
FEATURE                 Location/Qualifiers
REGION                  1..10
                        note = Human (Homo sapiens), chimeric or humanized antibody
                         peptide sequence
source                  1..10
                        mol_type = protein
                        organism = unidentified
SEQUENCE: 355
SASSSVSYMH                                                      10

SEQ ID NO: 356          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 356
```

```
GTSNLAS                                                                                 7

SEQ ID NO: 357           moltype = AA  length = 9
FEATURE                  Location/Qualifiers
REGION                   1..9
                         note = Human (Homo sapiens), chimeric or humanized antibody
                          peptide sequence
source                   1..9
                         mol_type = protein
                         organism = unidentified
SEQUENCE: 357
QQWSSNPPT                                                                               9

SEQ ID NO: 358           moltype = AA  length = 17
FEATURE                  Location/Qualifiers
REGION                   1..17
                         note = Human (Homo sapiens), chimeric or humanized antibody
                          peptide sequence
source                   1..17
                         mol_type = protein
                         organism = unidentified
SEQUENCE: 358
KSSQSLLHSR TRKNYLA                                                                     17

SEQ ID NO: 359           moltype = AA  length = 7
FEATURE                  Location/Qualifiers
REGION                   1..7
                         note = Human (Homo sapiens), chimeric or humanized antibody
                          peptide sequence
source                   1..7
                         mol_type = protein
                         organism = unidentified
SEQUENCE: 359
WASTRES                                                                                 7

SEQ ID NO: 360           moltype = AA  length = 8
FEATURE                  Location/Qualifiers
REGION                   1..8
                         note = Human (Homo sapiens), chimeric or humanized antibody
                          peptide sequence
source                   1..8
                         mol_type = protein
                         organism = unidentified
SEQUENCE: 360
KQSYNLLT                                                                                8

SEQ ID NO: 361           moltype = AA  length = 18
FEATURE                  Location/Qualifiers
REGION                   1..18
                         note = Human (Homo sapiens), chimeric or humanized antibody
                          peptide sequence
source                   1..18
                         mol_type = protein
                         organism = unidentified
SEQUENCE: 361
DKSSQSLLNS RTRKNYLA                                                                    18

SEQ ID NO: 362           moltype = AA  length = 8
FEATURE                  Location/Qualifiers
REGION                   1..8
                         note = Human (Homo sapiens), chimeric or humanized antibody
                          peptide sequence
source                   1..8
                         mol_type = protein
                         organism = unidentified
SEQUENCE: 362
DWASTRES                                                                                8

SEQ ID NO: 363           moltype = AA  length = 9
FEATURE                  Location/Qualifiers
REGION                   1..9
                         note = Human (Homo sapiens), chimeric or humanized antibody
                          peptide sequence
source                   1..9
                         mol_type = protein
                         organism = unidentified
SEQUENCE: 363
DKQSYNLLS                                                                               9
```

```
SEQ ID NO: 364          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 364
TFTDYSIH                                                                        8

SEQ ID NO: 365          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 365
WIKTETGEPT YADDFKG                                                             17

SEQ ID NO: 366          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 366
YYYGRDS                                                                         7

SEQ ID NO: 367          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 367
TFTDYSIH                                                                        8

SEQ ID NO: 368          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 368
WIKTETGEPT YADDFNG                                                             17

SEQ ID NO: 369          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 369
YYYGRDS                                                                         7

SEQ ID NO: 370          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 370
TFTDYSMH                                                                        8

SEQ ID NO: 371          moltype = AA  length = 17
FEATURE                 Location/Qualifiers
```

```
REGION                  1..17
                        note = Human (Homo sapiens), chimeric or humanized antibody
                         peptide sequence
source                  1..17
                        mol_type = protein
                        organism = unidentified
SEQUENCE: 371
RINTETGEPT FADDFRG                                                         17

SEQ ID NO: 372          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 372
YYYGRDS                                                                     7

SEQ ID NO: 373          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 373
KSSQSLLNSR TRKNYLA                                                         17

SEQ ID NO: 374          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 374
WASTRES                                                                     7

SEQ ID NO: 375          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 375
KQSYNLLT                                                                    8

SEQ ID NO: 376          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 376
KSSQSLLHSR TRKNYLA                                                         17

SEQ ID NO: 377          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 377
WASTRES                                                                     7

SEQ ID NO: 378          moltype = AA  length = 8
FEATURE                 Location/Qualifiers
REGION                  1..8
                        note = Human (Homo sapiens), chimeric or humanized antibody
```

```
                              peptide sequence
source                        1..8
                              mol_type = protein
                              organism = unidentified
SEQUENCE: 378
KQSYNLLT                                                                  8

SEQ ID NO: 379                moltype = AA  length = 8
FEATURE                       Location/Qualifiers
REGION                        1..8
                              note = Human (Homo sapiens), chimeric or humanized antibody
                               peptide sequence
source                        1..8
                              mol_type = protein
                              organism = unidentified
SEQUENCE: 379
TFTDYSMH                                                                  8

SEQ ID NO: 380                moltype = AA  length = 17
FEATURE                       Location/Qualifiers
REGION                        1..17
                              note = Human (Homo sapiens), chimeric or humanized antibody
                               peptide sequence
source                        1..17
                              mol_type = protein
                              organism = unidentified
SEQUENCE: 380
RINTETGEPT FADDFRG                                                       17

SEQ ID NO: 381                moltype = AA  length = 7
FEATURE                       Location/Qualifiers
REGION                        1..7
                              note = Human (Homo sapiens), chimeric or humanized antibody
                               peptide sequence
source                        1..7
                              mol_type = protein
                              organism = unidentified
SEQUENCE: 381
YYYGRDS                                                                   7

SEQ ID NO: 382                moltype = AA  length = 17
FEATURE                       Location/Qualifiers
REGION                        1..17
                              note = Human (Homo sapiens), chimeric or humanized antibody
                               peptide sequence
source                        1..17
                              mol_type = protein
                              organism = unidentified
SEQUENCE: 382
KSSQSLLNSR TRKNYLA                                                       17

SEQ ID NO: 383                moltype = AA  length = 7
FEATURE                       Location/Qualifiers
REGION                        1..7
                              note = Human (Homo sapiens), chimeric or humanized antibody
                               peptide sequence
source                        1..7
                              mol_type = protein
                              organism = unidentified
SEQUENCE: 383
WASTRES                                                                   7

SEQ ID NO: 384                moltype = AA  length = 8
FEATURE                       Location/Qualifiers
REGION                        1..8
                              note = Human (Homo sapiens), chimeric or humanized antibody
                               peptide sequence
source                        1..8
                              mol_type = protein
                              organism = unidentified
SEQUENCE: 384
KQSYNLLT                                                                  8

SEQ ID NO: 385                moltype = AA  length = 27
FEATURE                       Location/Qualifiers
REGION                        1..27
                              note = Human (Homo sapiens), chimeric or humanized antibody
                               peptide sequence
VARIANT                       5
```

```
                        note = MISC_FEATURE - Xaa is Leu or Met
source                  1..27
                        mol_type = protein
                        organism = unidentified
SEQUENCE: 385
ZIQLXZSGPE LKKPGETVKI SCKASGY                                              27

SEQ ID NO: 386          moltype = AA  length = 14
FEATURE                 Location/Qualifiers
REGION                  1..14
                        note = Human (Homo sapiens), chimeric or humanized antibody
                         peptide sequence
VARIANT                 13
                        note = MISC_FEATURE - Xaa is Val or Met
source                  1..14
                        mol_type = protein
                        organism = unidentified
SEQUENCE: 386
WVKQAPGKGL KWXA                                                            14

SEQ ID NO: 387          moltype = AA  length = 32
FEATURE                 Location/Qualifiers
REGION                  1..32
                        note = Human (Homo sapiens), chimeric or humanized antibody
                         peptide sequence
VARIANT                 4
                        note = MISC_FEATURE - Xaa is Val or Phe
source                  1..32
                        mol_type = protein
                        organism = unidentified
SEQUENCE: 387
RFAXSLETSA STAYLQINNL KNEDTATYFC AI                                        32

SEQ ID NO: 388          moltype = AA  length = 15
FEATURE                 Location/Qualifiers
REGION                  1..15
                        note = Human (Homo sapiens), chimeric or humanized antibody
                         peptide sequence
VARIANT                 11
                        note = MISC_FEATURE - Xaa is Lys or Arg
source                  1..15
                        mol_type = protein
                        organism = unidentified
SEQUENCE: 388
WYQQKPGQSP XLLIY                                                           15

SEQ ID NO: 389          moltype = AA  length = 23
FEATURE                 Location/Qualifiers
REGION                  1..23
                        note = Human (Homo sapiens), chimeric or humanized antibody
                         peptide sequence
VARIANT                 1
                        note = MISC_FEATURE - Xaa is Asp or Glu
VARIANT                 5
                        note = MISC_FEATURE - Xaa is Thr or Ser
VARIANT                 14
                        note = MISC_FEATURE - Xaa is Pro or Ser
VARIANT                 18
                        note = MISC_FEATURE - Xaa is Lys or Asn
VARIANT                 21
                        note = MISC_FEATURE - Xaa is Met or Val
source                  1..23
                        mol_type = protein
                        organism = unidentified
SEQUENCE: 389
XIVMXQSPSS LAVXAGEXVT XSC                                                  23

SEQ ID NO: 390          moltype = AA  length = 15
FEATURE                 Location/Qualifiers
REGION                  1..15
                        note = Human (Homo sapiens), chimeric or humanized antibody
                         peptide sequence
VARIANT                 11
                        note = MISC_FEATURE - Xaa is Lys or Arg
source                  1..15
                        mol_type = protein
                        organism = unidentified
SEQUENCE: 390
WYQQKPGQSP XLLIY                                                           15
```

```
SEQ ID NO: 391              moltype = AA   length = 32
FEATURE                     Location/Qualifiers
REGION                      1..32
                            note = Human (Homo sapiens), chimeric or humanized antibody
                             peptide sequence
VARIANT                     31
                            note = MISC_FEATURE - Xaa is Tyr or Phe
source                      1..32
                            mol_type = protein
                            organism = unidentified
SEQUENCE: 391
GVPDRFTGSG SGTDFTLTIS SVQAEDLAVY XC                                         32

SEQ ID NO: 392              moltype = AA   length = 10
FEATURE                     Location/Qualifiers
REGION                      1..10
                            note = Human (Homo sapiens), chimeric or humanized antibody
                             peptide sequence
VARIANT                     6
                            note = MISC_FEATURE - Xaa is Lys or Arg
VARIANT                     9
                            note = MISC_FEATURE - Xaa is Leu or Ile
source                      1..10
                            mol_type = protein
                            organism = unidentified
SEQUENCE: 392
FGAGTXLEXK                                                                  10

SEQ ID NO: 393              moltype = AA   length = 1018
FEATURE                     Location/Qualifiers
source                      1..1018
                            mol_type = protein
                            organism = Homo sapiens
SEQUENCE: 393
FNLDVDSPAE YSGPEGSYFG FAVDFFVPSA SSRMFLLVGA PKANTTQPGI VEGGQVLKCD           60
WSSTRRCQPI EFDATGNRDY AKDDPLEFKS HQWFGASVRS KQDKILACAP LYHWRTEMKQ          120
EREPVGTCFL QDGTKTVEYA PCRSQDIDAD GQGFCQGGFS IDFTKADRVL LGGPGSFYWQ          180
GQLISDQVAE IVSKYDPNVY SIKYNNQLAT RTAQAIFDDS YLGYSVAVGD FNGDGIDDFV          240
SGVPRAARTL GMVYIYDGKN MSSLYNFTGE QMAAYFGFSV AATDINGDDY ADVFIGAPLF          300
MDRGSDGKLQ EVGQVSVSLQ RASGDFQTTK LNGFEVFARF GSAIAPLGDL DQDGFNDIAI          360
AAPYGGEDKK GIVYIFNGRS TGLNAVPSQI LEGQWAARSM PPSFGYSMKG ATDIDKNGYP          420
DLIVGAFGVD RAILYRARPV ITVNAGLEVY PSILNQDNKT CSLPGTALKV SCFNVRFCLK          480
ADGKGVLPRK LNFQVELLLD KLKQKGAIRR ALFLYSRSPS HSKNMTISRG GLMQCEELIA          540
YLRDESEFRD KLTPITIFME YRLDYRTAAD TTGLQPILNQ FTPANISRQA HILLDCGEDN          600
VCKPKLEVSV DSDQKKIYIG DDNPLTLIVK AQNQGEGAYE AELIVSIPLQ ADFIGVVRNN          660
EALARLSCAF KTENQTRQVV CDLGNPMKAG TQLLAGLRFS VHQQSEMDTS VKFDLQIQSS          720
NLFDKVSPVV SHKVDLAVLA AVEIRGVSSP DHVFLPIPNW EHKENPETEE DVGPVVQHIY          780
ELRNNGPSSF SKAMLHLQWP YKYNNNTLLY ILHYDIDGPM NCTSDMEINP LRIKISSLQT          840
TEKNDTVAGQ GERDHLITKR DLALSEGDIH TLGCGVAQCL KIVCQVGRLD RGKSAILYVK          900
SLLWTETFMN KENQNHSYSL KSSASFNVIE FPYKNLPIED ITNSTLVTTN VTWGIQPAPM          960
PVPVWVIILA VLAGLLLLAV LVFVMYRMGF FKRVRPPQEE QEREQLQPHE NGEGNSET          1018

SEQ ID NO: 394              moltype = AA   length = 727
FEATURE                     Location/Qualifiers
source                      1..727
                            mol_type = protein
                            organism = Homo sapiens
SEQUENCE: 394
EDNRCASSNA ASCARCLALG PECGWCVQED FISGGSRSER CDIVSNLISK GCSVDSIEYP           60
SVHVIIPTEN EINTQVTPGE VSIQLRPGAE ANFMLKVHPL KKYPVDLYYL VDVSASMHNN          120
IEKLNSVGND LSRKMAFFSR DFRLGFGSYV DKTVSPYISI HPERIHNQCS DYNLDCMPPH          180
GYIHVLSLTE NITEFEKAVH RQKISGNIDT PEGGFDAMLQ AAVCESHIGW RKEAKRLLLV          240
MTDQTSHLAL DSKLAGIVVP NDGNCHLKNN VYVKSTTMEH PSLGQLSEKL IDNNINVIFA          300
VQGKQFHWYK DLLPLLPGTI AGEIESKAAN LNNLVVEAYQ KLISEVKVQV ENQVQGIYFN          360
ITAICPDGSR KPGMEGCRNV TSNDEVLFNV TVTMKKCDVT GGKNYAIIKP IGFNETAKIH          420
IHRNCSCQCE DNRGPKGKCV DETFLDSKCF QCDENKCHFD EDQFSSESCK SHKDQPVCSG          480
RGVCVCGKCS CHKIKLGKVY GKYCEKDDFS CPYHHGNLCA GHGECEAGRC QCFSGWEGDR          540
CQCPSAAAQH CVNSKGQVCS GRGTCVCGRC ECTDPRSIGR FCEHCPTCYT ACKENWNCMQ          600
CLHPHNLSQA ILDQCKTSCA LMEQQHYVDQ TSECFSSPSY LRIFFIIFIV TFLIGLLKVL          660
IIRQVILQWN SNKIKSSSDY RVSASKKDKL ILQSVCTRAV TYRREKPEEI KMDISKLNAH          720
ETFRCNF                                                                    727

SEQ ID NO: 395              moltype = AA   length = 116
FEATURE                     Location/Qualifiers
REGION                      1..116
                            note = Human (Homo sapiens), chimeric or humanized antibody
                             peptide sequence
source                      1..116
```

-continued

```
                                mol_type = protein
                                organism = unidentified
SEQUENCE: 395
QIQLVQSGAE VKKPGASVKI SCKASGYTFT DYSMHWVRQA PGQGLEWVAR INTETGEPTF         60
ADDFRGRFTV TLDTSTSTAY LEIRSLRSDD TAVYFCAIFY YGRDSWGQGT TLTVSS            116

SEQ ID NO: 396          moltype = AA   length = 30
FEATURE                 Location/Qualifiers
REGION                  1..30
                        note = Human (Homo sapiens), chimeric or humanized antibody
                         peptide sequence
source                  1..30
                        mol_type = protein
                        organism = unidentified
SEQUENCE: 396
QIQLVQSGAE VKKPGASVKI SCKASGYTFT                                          30

SEQ ID NO: 397          moltype = AA   length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 397
DYSMH                                                                      5

SEQ ID NO: 398          moltype = AA   length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 398
WVRQAPGQGL EWVA                                                           14

SEQ ID NO: 399          moltype = AA   length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 399
RINTETGEPT FADDFRG                                                        17

SEQ ID NO: 400          moltype = AA   length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 400
RFTVTLDTST STAYLEIRSL RSDDTAVYFC AI                                       32

SEQ ID NO: 401          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 401
FYYGRDS                                                                    7

SEQ ID NO: 402          moltype = AA   length = 11
FEATURE                 Location/Qualifiers
REGION                  1..11
                        note = Human (Homo sapiens), chimeric or humanized antibody
                         peptide sequence
source                  1..11
                        mol_type = protein
```

```
                                    organism = unidentified
SEQUENCE: 402
WGQGTTLTVS S                                                                    11

SEQ ID NO: 403          moltype = AA   length = 116
FEATURE                 Location/Qualifiers
REGION                  1..116
                        note = Human (Homo sapiens), chimeric or humanized antibody
                          peptide sequence
source                  1..116
                        mol_type = protein
                        organism = unidentified
SEQUENCE: 403
QIQLVQSGAE VKKPGASVKI SCKASGYTFT DYSMHWVRQA PGQGLEWVAR INTETGEPTF    60
ADDFRGRFTV TLDTSTSTAY LEIRSLRSDD TAVYFCAIFY YGRDSWGQGT TLTVSS        116

SEQ ID NO: 404          moltype = AA   length = 30
FEATURE                 Location/Qualifiers
REGION                  1..30
                        note = Human (Homo sapiens), chimeric or humanized antibody
                          peptide sequence
source                  1..30
                        mol_type = protein
                        organism = unidentified
SEQUENCE: 404
QIQLVQSGAE VKKPGASVKI SCKASGYTFT                                                30

SEQ ID NO: 405          moltype = AA   length = 5
FEATURE                 Location/Qualifiers
REGION                  1..5
                        note = Human (Homo sapiens), chimeric or humanized antibody
                          peptide sequence
source                  1..5
                        mol_type = protein
                        organism = unidentified
SEQUENCE: 405
DYSMH                                                                            5

SEQ ID NO: 406          moltype = AA   length = 14
FEATURE                 Location/Qualifiers
REGION                  1..14
                        note = Human (Homo sapiens), chimeric or humanized antibody
                          peptide sequence
source                  1..14
                        mol_type = protein
                        organism = unidentified
SEQUENCE: 406
WVRQAPGQGL EWVA                                                                 14

SEQ ID NO: 407          moltype = AA   length = 17
FEATURE                 Location/Qualifiers
REGION                  1..17
                        note = Human (Homo sapiens), chimeric or humanized antibody
                          peptide sequence
source                  1..17
                        mol_type = protein
                        organism = unidentified
SEQUENCE: 407
RINTETGEPT FADDFRG                                                              17

SEQ ID NO: 408          moltype = AA   length = 32
FEATURE                 Location/Qualifiers
REGION                  1..32
                        note = Human (Homo sapiens), chimeric or humanized antibody
                          peptide sequence
source                  1..32
                        mol_type = protein
                        organism = unidentified
SEQUENCE: 408
RFTVTLDTST STAYLEIRSL RSDDTAVYFC AI                                              32

SEQ ID NO: 409          moltype = AA   length = 7
FEATURE                 Location/Qualifiers
REGION                  1..7
                        note = Human (Homo sapiens), chimeric or humanized antibody
                          peptide sequence
source                  1..7
                        mol_type = protein
                        organism = unidentified
```

```
SEQUENCE: 409
FYYGRDS                                                                  7

SEQ ID NO: 410         moltype = AA  length = 11
FEATURE                Location/Qualifiers
REGION                 1..11
                       note = Human (Homo sapiens), chimeric or humanized antibody
                         peptide sequence
source                 1..11
                       mol_type = protein
                       organism = unidentified
SEQUENCE: 410
WGQGTTLTVS S                                                            11

SEQ ID NO: 411         moltype = AA  length = 116
FEATURE                Location/Qualifiers
REGION                 1..116
                       note = Human (Homo sapiens), chimeric or humanized antibody
                         peptide sequence
source                 1..116
                       mol_type = protein
                       organism = unidentified
SEQUENCE: 411
QIQLVQSGAK VKKPGASVKI SCKASGYTFT DYSMHWVRQA PGQGLEWVAR INTETGEPTF        60
ADDFRGRFSV TLDTSTSTAY LEITSLRSDD TAVYFCAIFY YGRDTWGQGT ALTVSS           116

SEQ ID NO: 412         moltype = AA  length = 30
FEATURE                Location/Qualifiers
REGION                 1..30
                       note = Human (Homo sapiens), chimeric or humanized antibody
                         peptide sequence
source                 1..30
                       mol_type = protein
                       organism = unidentified
SEQUENCE: 412
QIQLVQSGAK VKKPGASVKI SCKASGYTFT                                        30

SEQ ID NO: 413         moltype = AA  length = 5
FEATURE                Location/Qualifiers
REGION                 1..5
                       note = Human (Homo sapiens), chimeric or humanized antibody
                         peptide sequence
source                 1..5
                       mol_type = protein
                       organism = unidentified
SEQUENCE: 413
DYSMH                                                                    5

SEQ ID NO: 414         moltype = AA  length = 14
FEATURE                Location/Qualifiers
REGION                 1..14
                       note = Human (Homo sapiens), chimeric or humanized antibody
                         peptide sequence
source                 1..14
                       mol_type = protein
                       organism = unidentified
SEQUENCE: 414
WVRQAPGQGL EWVA                                                         14

SEQ ID NO: 415         moltype = AA  length = 17
FEATURE                Location/Qualifiers
REGION                 1..17
                       note = Human (Homo sapiens), chimeric or humanized antibody
                         peptide sequence
source                 1..17
                       mol_type = protein
                       organism = unidentified
SEQUENCE: 415
RINTETGEPT FADDFRG                                                      17

SEQ ID NO: 416         moltype = AA  length = 32
FEATURE                Location/Qualifiers
REGION                 1..32
                       note = Human (Homo sapiens), chimeric or humanized antibody
                         peptide sequence
source                 1..32
                       mol_type = protein
                       organism = unidentified
SEQUENCE: 416
```

```
RFSVTLDTST STAYLEITSL RSDDTAVYFC AI                                       32

SEQ ID NO: 417          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 417
FYYGRDT                                                                    7

SEQ ID NO: 418          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 418
WGQGTALTVS S                                                              11

SEQ ID NO: 419          moltype = AA  length = 116
FEATURE                 Location/Qualifiers
REGION                  1..116
                        note = Human (Homo sapiens), chimeric or humanized antibody
                         peptide sequence
source                  1..116
                        mol_type = protein
                        organism = unidentified
SEQUENCE: 419
QIQLVQSGAE VKKPGASVKI SCKASGYTFT DYSMHWVRQA PGQGLEWVAR INTETGEPTF          60
ADDFRGRFTV TLDTSTSTAY LEIRSLRSDD TAVYFCAIFY YGRDTWGQGT TLTVSS             116

SEQ ID NO: 420          moltype = AA  length = 30
FEATURE                 Location/Qualifiers
REGION                  1..30
                        note = Human (Homo sapiens), chimeric or humanized antibody
                         peptide sequence
source                  1..30
                        mol_type = protein
                        organism = unidentified
SEQUENCE: 420
QIQLVQSGAE VKKPGASVKI SCKASGYTFT                                          30

SEQ ID NO: 421          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 421
DYSMH                                                                      5

SEQ ID NO: 422          moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 422
WVRQAPGQGL EWVA                                                           14

SEQ ID NO: 423          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 423
RINTETGEPT FADDFRG                                                        17
```

```
SEQ ID NO: 424          moltype = AA   length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 424
RFTVTLDTST STAYLEIRSL RSDDTAVYFC AI                                         32

SEQ ID NO: 425          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 425
FYYGRDT                                                                      7

SEQ ID NO: 426          moltype = AA   length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 426
WGQGTTLTVS S                                                                11

SEQ ID NO: 427          moltype = AA   length = 116
FEATURE                 Location/Qualifiers
REGION                  1..116
                        note = Human (Homo sapiens), chimeric or humanized antibody
                         peptide sequence
source                  1..116
                        mol_type = protein
                        organism = unidentified
SEQUENCE: 427
QIQLVQSGAE VKKPGASVKI SCKASGYTFT DYSMHWVRQA PGQGLEWVAR INTETGEPTF           60
ADDFRGRFTV TLDTSTSTAY LEIRSLRSDD TAVYFCAIFY YGRDTWGQGT TLTVSS              116

SEQ ID NO: 428          moltype = AA   length = 30
FEATURE                 Location/Qualifiers
REGION                  1..30
                        note = Human (Homo sapiens), chimeric or humanized antibody
                         peptide sequence
source                  1..30
                        mol_type = protein
                        organism = unidentified
SEQUENCE: 428
QIQLVQSGAE VKKPGASVKI SCKASGYTFT                                            30

SEQ ID NO: 429          moltype = AA   length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 429
DYSMH                                                                        5

SEQ ID NO: 430          moltype = AA   length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 430
WVRQAPGQGL EWVA                                                             14
```

-continued

```
SEQ ID NO: 431            moltype = AA   length = 17
FEATURE                   Location/Qualifiers
REGION                    1..17
                          note = Human (Homo sapiens), chimeric or humanized antibody
                           peptide sequence
source                    1..17
                          mol_type = protein
                          organism = unidentified
SEQUENCE: 431
RINTETGEPT FADDFRG                                                          17

SEQ ID NO: 432            moltype = AA   length = 32
FEATURE                   Location/Qualifiers
REGION                    1..32
                          note = Human (Homo sapiens), chimeric or humanized antibody
                           peptide sequence
source                    1..32
                          mol_type = protein
                          organism = unidentified
SEQUENCE: 432
RFTVTLDTST STAYLEIRSL RSDDTAVYFC AI                                         32

SEQ ID NO: 433            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 433
FYYGRDT                                                                      7

SEQ ID NO: 434            moltype = AA   length = 11
FEATURE                   Location/Qualifiers
REGION                    1..11
                          note = Human (Homo sapiens), chimeric or humanized antibody
                           peptide sequence
source                    1..11
                          mol_type = protein
                          organism = unidentified
SEQUENCE: 434
WGQGTTLTVS S                                                                11

SEQ ID NO: 435            moltype = AA   length = 116
FEATURE                   Location/Qualifiers
REGION                    1..116
                          note = Human (Homo sapiens), chimeric or humanized antibody
                           peptide sequence
source                    1..116
                          mol_type = protein
                          organism = unidentified
SEQUENCE: 435
QIQLLQSGPE LKKPGETVKI SCKASGYTFT DYSMHWVKQA PGKGLKWVAR INTETGEPTF           60
ADDFRGRFAV SLETSASTAY LQINNLKNED TATYFCAIFY YGRDSWGQGT TLTVSS              116

SEQ ID NO: 436            moltype = AA   length = 30
FEATURE                   Location/Qualifiers
REGION                    1..30
                          note = Human (Homo sapiens), chimeric or humanized antibody
                           peptide sequence
source                    1..30
                          mol_type = protein
                          organism = unidentified
SEQUENCE: 436
QIQLLQSGPE LKKPGETVKI SCKASGYTFT                                            30

SEQ ID NO: 437            moltype = AA   length = 5
FEATURE                   Location/Qualifiers
REGION                    1..5
                          note = Human (Homo sapiens), chimeric or humanized antibody
                           peptide sequence
source                    1..5
                          mol_type = protein
                          organism = unidentified
SEQUENCE: 437
DYSMH                                                                        5

SEQ ID NO: 438            moltype = AA   length = 14
```

```
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 438
WVKQAPGKGL KWVA                                                           14

SEQ ID NO: 439          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 439
RINTETGEPT FADDFRG                                                        17

SEQ ID NO: 440          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 440
RFAVSLETSA STAYLQINNL KNEDTATYFC AI                                       32

SEQ ID NO: 441          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 441
FYYGRDS                                                                    7

SEQ ID NO: 442          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 442
WGQGTTLTVS S                                                              11

SEQ ID NO: 443          moltype = AA  length = 116
FEATURE                 Location/Qualifiers
REGION                  1..116
                        note = Human (Homo sapiens), chimeric or humanized antibody
                         peptide sequence
source                  1..116
                        mol_type = protein
                        organism = unidentified
SEQUENCE: 443
QIQLVQSGAE VKKPGASVKI SCKASGYTFT DYSMHWVRQA PGQGLEWVAR INTETGEPTF          60
ADDFRGRFTV TLDTSTSTAY LEIRSLRSDD TAVYFCAIFY YGRDTWGQGT TLTVSS             116

SEQ ID NO: 444          moltype = AA  length = 30
FEATURE                 Location/Qualifiers
REGION                  1..30
                        note = Human (Homo sapiens), chimeric or humanized antibody
                         peptide sequence
source                  1..30
                        mol_type = protein
                        organism = unidentified
SEQUENCE: 444
QIQLVQSGAE VKKPGASVKI SCKASGYTFT                                          30

SEQ ID NO: 445          moltype = AA  length = 5
FEATURE                 Location/Qualifiers
```

```
REGION                       1..5
                             note = Human (Homo sapiens), chimeric or humanized antibody
                                peptide sequence
source                       1..5
                             mol_type = protein
                             organism = unidentified
SEQUENCE: 445
DYSMH                                                                             5

SEQ ID NO: 446               moltype = AA   length = 14
FEATURE                      Location/Qualifiers
REGION                       1..14
                             note = Human (Homo sapiens), chimeric or humanized antibody
                                peptide sequence
source                       1..14
                             mol_type = protein
                             organism = unidentified
SEQUENCE: 446
WVRQAPGQGL EWVA                                                                  14

SEQ ID NO: 447               moltype = AA   length = 17
FEATURE                      Location/Qualifiers
REGION                       1..17
                             note = Human (Homo sapiens), chimeric or humanized antibody
                                peptide sequence
source                       1..17
                             mol_type = protein
                             organism = unidentified
SEQUENCE: 447
RINTETGEPT FADDFRG                                                               17

SEQ ID NO: 448               moltype = AA   length = 32
FEATURE                      Location/Qualifiers
REGION                       1..32
                             note = Human (Homo sapiens), chimeric or humanized antibody
                                peptide sequence
source                       1..32
                             mol_type = protein
                             organism = unidentified
SEQUENCE: 448
RFTVTLDTST STAYLEIRSL RSDDTAVYFC AI                                              32

SEQ ID NO: 449               moltype = AA   length = 7
FEATURE                      Location/Qualifiers
REGION                       1..7
                             note = Human (Homo sapiens), chimeric or humanized antibody
                                peptide sequence
source                       1..7
                             mol_type = protein
                             organism = unidentified
SEQUENCE: 449
FYYGRDT                                                                           7

SEQ ID NO: 450               moltype = AA   length = 11
FEATURE                      Location/Qualifiers
REGION                       1..11
                             note = Human (Homo sapiens), chimeric or humanized antibody
                                peptide sequence
source                       1..11
                             mol_type = protein
                             organism = unidentified
SEQUENCE: 450
WGQGTTLTVS S                                                                     11

SEQ ID NO: 451               moltype = AA   length = 113
FEATURE                      Location/Qualifiers
REGION                       1..113
                             note = Human (Homo sapiens), chimeric or humanized antibody
                                peptide sequence
source                       1..113
                             mol_type = protein
                             organism = unidentified
SEQUENCE: 451
EIVMTQSPAT LSVSPGERVT MSCKSSQSLL NSRTRKNYLA WYQQKPGQAP RLLIYWASTR                 60
ESGVPARFSG SGSGTEFTLT ISSVQSEDFA VYYCKQSYNL LSFGQGTVLE IKR                       113

SEQ ID NO: 452               moltype = AA   length = 23
FEATURE                      Location/Qualifiers
REGION                       1..23
```

```
                              note = Human (Homo sapiens), chimeric or humanized antibody
                                peptide sequence
source                        1..23
                              mol_type = protein
                              organism = unidentified
SEQUENCE: 452
EIVMTQSPAT LSVSPGERVT MSC                                                          23

SEQ ID NO: 453                moltype = AA   length = 17
FEATURE                       Location/Qualifiers
REGION                        1..17
                              note = Human (Homo sapiens), chimeric or humanized antibody
                                peptide sequence
source                        1..17
                              mol_type = protein
                              organism = unidentified
SEQUENCE: 453
KSSQSLLNSR TRKNYLA                                                                 17

SEQ ID NO: 454                moltype = AA   length = 15
FEATURE                       Location/Qualifiers
REGION                        1..15
                              note = Human (Homo sapiens), chimeric or humanized antibody
                                peptide sequence
source                        1..15
                              mol_type = protein
                              organism = unidentified
SEQUENCE: 454
WYQQKPGQAP RLLIY                                                                   15

SEQ ID NO: 455                moltype = AA   length = 7
FEATURE                       Location/Qualifiers
REGION                        1..7
                              note = Human (Homo sapiens), chimeric or humanized antibody
                                peptide sequence
source                        1..7
                              mol_type = protein
                              organism = unidentified
SEQUENCE: 455
WASTRES                                                                             7

SEQ ID NO: 456                moltype = AA   length = 32
FEATURE                       Location/Qualifiers
REGION                        1..32
                              note = Human (Homo sapiens), chimeric or humanized antibody
                                peptide sequence
source                        1..32
                              mol_type = protein
                              organism = unidentified
SEQUENCE: 456
GVPARFSGSG SGTEFTLTIS SVQSEDFAVY YC                                                 32

SEQ ID NO: 457                moltype = AA   length = 8
FEATURE                       Location/Qualifiers
REGION                        1..8
                              note = Human (Homo sapiens), chimeric or humanized antibody
                                peptide sequence
source                        1..8
                              mol_type = protein
                              organism = unidentified
SEQUENCE: 457
KQSYNLLS                                                                            8

SEQ ID NO: 458                moltype = AA   length = 11
FEATURE                       Location/Qualifiers
REGION                        1..11
                              note = Human (Homo sapiens), chimeric or humanized antibody
                                peptide sequence
source                        1..11
                              mol_type = protein
                              organism = unidentified
SEQUENCE: 458
FGQGTVLEIK R                                                                       11

SEQ ID NO: 459                moltype = AA   length = 113
FEATURE                       Location/Qualifiers
REGION                        1..113
                              note = Human (Homo sapiens), chimeric or humanized antibody
                                peptide sequence
```

```
source              1..113
                    mol_type = protein
                    organism = unidentified
SEQUENCE: 459
EIVMTQSPAT LSVSPGEIVT MSCKSSQSLL NSRSRKNYLA WYQQKPGQAP RLLIYWASTR    60
ESGVPARFSG SGSGTEFTLT ISSVQSEDFA VYYCKQSYNL ISFGQGTVLE IKR           113

SEQ ID NO: 460      moltype = AA  length = 23
FEATURE             Location/Qualifiers
REGION              1..23
                    note = Human (Homo sapiens), chimeric or humanized antibody
                     peptide sequence
source              1..23
                    mol_type = protein
                    organism = unidentified
SEQUENCE: 460
EIVMTQSPAT LSVSPGEIVT MSC                                            23

SEQ ID NO: 461      moltype = AA  length = 17
FEATURE             Location/Qualifiers
REGION              1..17
                    note = Human (Homo sapiens), chimeric or humanized antibody
                     peptide sequence
source              1..17
                    mol_type = protein
                    organism = unidentified
SEQUENCE: 461
KSSQSLLNSR SRKNYLA                                                   17

SEQ ID NO: 462      moltype = AA  length = 15
FEATURE             Location/Qualifiers
REGION              1..15
                    note = Human (Homo sapiens), chimeric or humanized antibody
                     peptide sequence
source              1..15
                    mol_type = protein
                    organism = unidentified
SEQUENCE: 462
WYQQKPGQAP RLLIY                                                     15

SEQ ID NO: 463      moltype = AA  length = 7
FEATURE             Location/Qualifiers
REGION              1..7
                    note = Human (Homo sapiens), chimeric or humanized antibody
                     peptide sequence
source              1..7
                    mol_type = protein
                    organism = unidentified
SEQUENCE: 463
WASTRES                                                              7

SEQ ID NO: 464      moltype = AA  length = 32
FEATURE             Location/Qualifiers
REGION              1..32
                    note = Human (Homo sapiens), chimeric or humanized antibody
                     peptide sequence
source              1..32
                    mol_type = protein
                    organism = unidentified
SEQUENCE: 464
GVPARFSGSG SGTEFTLTIS SVQSEDFAVY YC                                  32

SEQ ID NO: 465      moltype = AA  length = 8
FEATURE             Location/Qualifiers
REGION              1..8
                    note = Human (Homo sapiens), chimeric or humanized antibody
                     peptide sequence
source              1..8
                    mol_type = protein
                    organism = unidentified
SEQUENCE: 465
KQSYNLIS                                                             8

SEQ ID NO: 466      moltype = AA  length = 11
FEATURE             Location/Qualifiers
REGION              1..11
                    note = Human (Homo sapiens), chimeric or humanized antibody
                     peptide sequence
source              1..11
```

```
                            mol_type = protein
                            organism = unidentified
SEQUENCE: 466
FGQGTVLEIK R                                                                   11

SEQ ID NO: 467          moltype = AA  length = 113
FEATURE                 Location/Qualifiers
REGION                  1..113
                        note = Human (Homo sapiens), chimeric or humanized antibody
                         peptide sequence
source                  1..113
                        mol_type = protein
                        organism = unidentified
SEQUENCE: 467
EIVMTQTPVT LSVSPGERVT MSCKSSQSLL NSRTRKNYLA WYQQKPGQAP RLLIYWASTR     60
ESDVPARFSG SGSGTEFTLT ISSVQSEDFA VYYCKQSSNL ISFGQGTVLE IKR            113

SEQ ID NO: 468          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 468
EIVMTQTPVT LSVSPGERVT MSC                                                      23

SEQ ID NO: 469          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 469
KSSQSLLNSR TRKNYLA                                                             17

SEQ ID NO: 470          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 470
WYQQKPGQAP RLLIY                                                               15

SEQ ID NO: 471          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 471
WASTRES                                                                        7

SEQ ID NO: 472          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 472
DVPARFSGSG SGTEFTLTIS SVQSEDFAVY YC                                            32

SEQ ID NO: 473          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
```

```
                                organism = unidentified
SEQUENCE: 473
KQSSNLIS                                                                  8

SEQ ID NO: 474          moltype = AA  length = 11
FEATURE                 Location/Qualifiers
REGION                  1..11
                        note = Human (Homo sapiens), chimeric or humanized antibody
                          peptide sequence
source                  1..11
                        mol_type = protein
                        organism = unidentified
SEQUENCE: 474
FGQGTVLEIK R                                                             11

SEQ ID NO: 475          moltype = AA  length = 113
FEATURE                 Location/Qualifiers
REGION                  1..113
                        note = Human (Homo sapiens), chimeric or humanized antibody
                          peptide sequence
source                  1..113
                        mol_type = protein
                        organism = unidentified
SEQUENCE: 475
EIVMTQSPAT LSVSPGERVT MSCKSSQSLL NSRSRKNYLA WYQQKPGQAP RLLIYWASTR    60
ESGVPARFSG SGSGTEFTLT ISSVQSEDFA VYYCKQSYNL LSFGQGTVLE IKR          113

SEQ ID NO: 476          moltype = AA  length = 23
FEATURE                 Location/Qualifiers
REGION                  1..23
                        note = Human (Homo sapiens), chimeric or humanized antibody
                          peptide sequence
source                  1..23
                        mol_type = protein
                        organism = unidentified
SEQUENCE: 476
EIVMTQSPAT LSVSPGERVT MSC                                                23

SEQ ID NO: 477          moltype = AA  length = 5
FEATURE                 Location/Qualifiers
REGION                  1..5
                        note = Human (Homo sapiens), chimeric or humanized antibody
                          peptide sequence
source                  1..5
                        mol_type = protein
                        organism = unidentified
SEQUENCE: 477
AVHRQ                                                                     5

SEQ ID NO: 478          moltype = AA  length = 17
FEATURE                 Location/Qualifiers
REGION                  1..17
                        note = Human (Homo sapiens), chimeric or humanized antibody
                          peptide sequence
source                  1..17
                        mol_type = protein
                        organism = unidentified
SEQUENCE: 478
KSSQSLLNSR SRKNYLA                                                       17

SEQ ID NO: 479          moltype = AA  length = 15
FEATURE                 Location/Qualifiers
REGION                  1..15
                        note = Human (Homo sapiens), chimeric or humanized antibody
                          peptide sequence
source                  1..15
                        mol_type = protein
                        organism = unidentified
SEQUENCE: 479
WYQQKPGQAP RLLIY                                                         15

SEQ ID NO: 480          moltype = AA  length = 7
FEATURE                 Location/Qualifiers
REGION                  1..7
                        note = Human (Homo sapiens), chimeric or humanized antibody
                          peptide sequence
source                  1..7
                        mol_type = protein
                        organism = unidentified
```

```
SEQUENCE: 480
WASTRES                                                                     7

SEQ ID NO: 481          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 481
GVPARFSGSG SGTEFTLTIS SVQSEDFAVY YC                                         32

SEQ ID NO: 482          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 482
KQSYNLLS                                                                    8

SEQ ID NO: 483          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 483
FGQGTVLEIK R                                                                11

SEQ ID NO: 484          moltype = AA  length = 113
FEATURE                 Location/Qualifiers
REGION                  1..113
                        note = Human (Homo sapiens), chimeric or humanized antibody
                         peptide sequence
source                  1..113
                        mol_type = protein
                        organism = unidentified
SEQUENCE: 484
EIVMTQSPAT LSVSPGERVT MSCKSSQSLL NSRSRKNYLA WYQQKPGQAP RLLIYWASTR           60
ESGVPARFSG SGSGTEFTLT ISSVQSEDFA VYYCKQSYNL LSFGQGTVLE IKR                  113

SEQ ID NO: 485          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 485
EIVMTQSPAT LSVSPGERVT MSC                                                   23

SEQ ID NO: 486          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 486
KSSQSLLNSR SRKNYLA                                                          17

SEQ ID NO: 487          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 487
```

```
WYQQKPGQAP RLLIY                                                             15

SEQ ID NO: 488          moltype = AA   length = 7
FEATURE                 Location/Qualifiers
REGION                  1..7
                        note = Human (Homo sapiens), chimeric or humanized antibody
                          peptide sequence
source                  1..7
                        mol_type = protein
                        organism = unidentified
SEQUENCE: 488
WASTRES                                                                       7

SEQ ID NO: 489          moltype = AA   length = 32
FEATURE                 Location/Qualifiers
REGION                  1..32
                        note = Human (Homo sapiens), chimeric or humanized antibody
                          peptide sequence
source                  1..32
                        mol_type = protein
                        organism = unidentified
SEQUENCE: 489
GVPARFSGSG SGTEFTLTIS SVQSEDFAVY YC                                           32

SEQ ID NO: 490          moltype = AA   length = 8
FEATURE                 Location/Qualifiers
REGION                  1..8
                        note = Human (Homo sapiens), chimeric or humanized antibody
                          peptide sequence
source                  1..8
                        mol_type = protein
                        organism = unidentified
SEQUENCE: 490
KQSYNLLS                                                                      8

SEQ ID NO: 491          moltype = AA   length = 11
FEATURE                 Location/Qualifiers
REGION                  1..11
                        note = Human (Homo sapiens), chimeric or humanized antibody
                          peptide sequence
source                  1..11
                        mol_type = protein
                        organism = unidentified
SEQUENCE: 491
FGQGTVLEIK R                                                                 11

SEQ ID NO: 492          moltype = AA   length = 117
FEATURE                 Location/Qualifiers
REGION                  1..117
                        note = Human (Homo sapiens), chimeric or humanized antibody
                          peptide sequence
source                  1..117
                        mol_type = protein
                        organism = unidentified
SEQUENCE: 492
DIVMTQSPSS LAVSAGEKVT MSCKSSQSLL GRGDLGRLKK NALAWYQQKP GQSPRLLIYW   60
ASTRESGVPD RFTGSGSGTD FTLTISSVQA EDLAVYYCKQ SYNLLSFGAG TKLELKR     117

SEQ ID NO: 493          moltype = AA   length = 23
FEATURE                 Location/Qualifiers
REGION                  1..23
                        note = Human (Homo sapiens), chimeric or humanized antibody
                          peptide sequence
source                  1..23
                        mol_type = protein
                        organism = unidentified
SEQUENCE: 493
DIVMTQSPSS LAVSAGEKVT MSC                                                    23

SEQ ID NO: 494          moltype = AA   length = 21
FEATURE                 Location/Qualifiers
REGION                  1..21
                        note = Human (Homo sapiens), chimeric or humanized antibody
                          peptide sequence
source                  1..21
                        mol_type = protein
                        organism = unidentified
SEQUENCE: 494
KSSQSLLGRG DLGRLKKNAL A                                                      21
```

```
SEQ ID NO: 495         moltype = AA  length = 15
FEATURE                Location/Qualifiers
REGION                 1..15
                       note = Human (Homo sapiens), chimeric or humanized antibody
                        peptide sequence
source                 1..15
                       mol_type = protein
                       organism = unidentified
SEQUENCE: 495
WYQQKPGQSP RLLIY                                                       15

SEQ ID NO: 496         moltype = AA  length = 7
FEATURE                Location/Qualifiers
REGION                 1..7
                       note = Human (Homo sapiens), chimeric or humanized antibody
                        peptide sequence
source                 1..7
                       mol_type = protein
                       organism = unidentified
SEQUENCE: 496
WASTRES                                                                7

SEQ ID NO: 497         moltype = AA  length = 32
FEATURE                Location/Qualifiers
REGION                 1..32
                       note = Human (Homo sapiens), chimeric or humanized antibody
                        peptide sequence
source                 1..32
                       mol_type = protein
                       organism = unidentified
SEQUENCE: 497
GVPDRFTGSG SGTDFTLTIS SVQAEDLAVY YC                                    32

SEQ ID NO: 498         moltype = AA  length = 8
FEATURE                Location/Qualifiers
REGION                 1..8
                       note = Human (Homo sapiens), chimeric or humanized antibody
                        peptide sequence
source                 1..8
                       mol_type = protein
                       organism = unidentified
SEQUENCE: 498
KQSYNLLS                                                               8

SEQ ID NO: 499         moltype = AA  length = 11
FEATURE                Location/Qualifiers
REGION                 1..11
                       note = Human (Homo sapiens), chimeric or humanized antibody
                        peptide sequence
source                 1..11
                       mol_type = protein
                       organism = unidentified
SEQUENCE: 499
FGAGTKLELK R                                                           11

SEQ ID NO: 500         moltype = AA  length = 117
FEATURE                Location/Qualifiers
REGION                 1..117
                       note = Human (Homo sapiens), chimeric or humanized antibody
                        peptide sequence
source                 1..117
                       mol_type = protein
                       organism = unidentified
SEQUENCE: 500
EIVMTQSPAT LSVSPGERVT MSCKSSQSLL GRGDLGRLKK NALAWYQQKP GQAPRLLIYW       60
ASTRESGVPA RFSGSGSGTE FTLTISSVQS EDFAVYYCKQ SYNLLSFGQG TVLEIKR         117

SEQ ID NO: 501         moltype = AA  length = 23
FEATURE                Location/Qualifiers
REGION                 1..23
                       note = Human (Homo sapiens), chimeric or humanized antibody
                        peptide sequence
source                 1..23
                       mol_type = protein
                       organism = unidentified
SEQUENCE: 501
EIVMTQSPAT LSVSPGERVT MSC                                              23
```

```
SEQ ID NO: 502          moltype = AA  length = 21
FEATURE                 Location/Qualifiers
REGION                  1..21
                        note = Human (Homo sapiens), chimeric or humanized antibody
                         peptide sequence
source                  1..21
                        mol_type = protein
                        organism = unidentified
SEQUENCE: 502
KSSQSLLGRG DLGRLKKNAL A                                                     21

SEQ ID NO: 503          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 503
WYQQKPGQAP RLLIY                                                            15

SEQ ID NO: 504          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 504
WASTRES                                                                      7

SEQ ID NO: 505          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 505
GVPARFSGSG SGTEFTLTIS SVQSEDFAVY YC                                          32

SEQ ID NO: 506          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 506
KQSYNLLS                                                                     8

SEQ ID NO: 507          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 507
FGQGTVLEIK R                                                                11

SEQ ID NO: 508          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 508
DYSMH                                                                        5

SEQ ID NO: 509          moltype = AA  length = 17
FEATURE                 Location/Qualifiers
```

```
REGION                    1..17
                          note = Human (Homo sapiens), chimeric or humanized antibody
                           peptide sequence
source                    1..17
                          mol_type = protein
                          organism = unidentified
SEQUENCE: 509
RINTETGEPT FADDFRG                                                              17

SEQ ID NO: 510            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 510
FYYGRDS                                                                          7

SEQ ID NO: 511            moltype = AA   length = 5
FEATURE                   Location/Qualifiers
REGION                    1..5
                          note = Human (Homo sapiens), chimeric or humanized antibody
                           peptide sequence
source                    1..5
                          mol_type = protein
                          organism = unidentified
SEQUENCE: 511
DYSMH                                                                            5

SEQ ID NO: 512            moltype = AA   length = 17
FEATURE                   Location/Qualifiers
REGION                    1..17
                          note = Human (Homo sapiens), chimeric or humanized antibody
                           peptide sequence
source                    1..17
                          mol_type = protein
                          organism = unidentified
SEQUENCE: 512
RINTETGEPT FADDFRG                                                              17

SEQ ID NO: 513            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 513
FYYGRDS                                                                          7

SEQ ID NO: 514            moltype = AA   length = 5
FEATURE                   Location/Qualifiers
REGION                    1..5
                          note = Human (Homo sapiens), chimeric or humanized antibody
                           peptide sequence
source                    1..5
                          mol_type = protein
                          organism = unidentified
SEQUENCE: 514
DYSMH                                                                            5

SEQ ID NO: 515            moltype = AA   length = 17
FEATURE                   Location/Qualifiers
REGION                    1..17
                          note = Human (Homo sapiens), chimeric or humanized antibody
                           peptide sequence
source                    1..17
                          mol_type = protein
                          organism = unidentified
SEQUENCE: 515
RINTETGEPT FADDFRG                                                              17

SEQ ID NO: 516            moltype = AA   length = 7
FEATURE                   Location/Qualifiers
REGION                    1..7
                          note = Human (Homo sapiens), chimeric or humanized antibody
```

```
                              peptide sequence
source                        1..7
                              mol_type = protein
                              organism = unidentified
SEQUENCE: 516
FYYGRDT                                                                          7

SEQ ID NO: 517                moltype = AA  length = 5
FEATURE                       Location/Qualifiers
REGION                        1..5
                              note = Human (Homo sapiens), chimeric or humanized antibody
                              peptide sequence
source                        1..5
                              mol_type = protein
                              organism = unidentified
SEQUENCE: 517
DYSMH                                                                            5

SEQ ID NO: 518                moltype = AA  length = 17
FEATURE                       Location/Qualifiers
REGION                        1..17
                              note = Human (Homo sapiens), chimeric or humanized antibody
                              peptide sequence
source                        1..17
                              mol_type = protein
                              organism = unidentified
SEQUENCE: 518
RINTETGEPT FADDFRG                                                              17

SEQ ID NO: 519                moltype = AA  length = 7
FEATURE                       Location/Qualifiers
REGION                        1..7
                              note = Human (Homo sapiens), chimeric or humanized antibody
                              peptide sequence
source                        1..7
                              mol_type = protein
                              organism = unidentified
SEQUENCE: 519
FYYGRDT                                                                          7

SEQ ID NO: 520                moltype = AA  length = 5
FEATURE                       Location/Qualifiers
REGION                        1..5
                              note = Human (Homo sapiens), chimeric or humanized antibody
                              peptide sequence
source                        1..5
                              mol_type = protein
                              organism = unidentified
SEQUENCE: 520
DYSMH                                                                            5

SEQ ID NO: 521                moltype = AA  length = 17
FEATURE                       Location/Qualifiers
REGION                        1..17
                              note = Human (Homo sapiens), chimeric or humanized antibody
                              peptide sequence
source                        1..17
                              mol_type = protein
                              organism = unidentified
SEQUENCE: 521
RINTETGEPT FADDFRG                                                              17

SEQ ID NO: 522                moltype = AA  length = 7
FEATURE                       Location/Qualifiers
REGION                        1..7
                              note = Human (Homo sapiens), chimeric or humanized antibody
                              peptide sequence
source                        1..7
                              mol_type = protein
                              organism = unidentified
SEQUENCE: 522
FYYGRDT                                                                          7

SEQ ID NO: 523                moltype = AA  length = 5
FEATURE                       Location/Qualifiers
REGION                        1..5
                              note = Human (Homo sapiens), chimeric or humanized antibody
                              peptide sequence
source                        1..5
```

```
                                  SEQUENCE: 523
DYSMH                                                                             5

SEQ ID NO: 524           moltype = AA  length = 17
FEATURE                  Location/Qualifiers
REGION                   1..17
                         note = Human (Homo sapiens), chimeric or humanized antibody
                          peptide sequence
source                   1..17
                         mol_type = protein
                         organism = unidentified
SEQUENCE: 524
RINTETGEPT FADDFRG                                                               17

SEQ ID NO: 525           moltype = AA  length = 7
FEATURE                  Location/Qualifiers
REGION                   1..7
                         note = Human (Homo sapiens), chimeric or humanized antibody
                          peptide sequence
source                   1..7
                         mol_type = protein
                         organism = unidentified
SEQUENCE: 525
FYYGRDS                                                                           7

SEQ ID NO: 526           moltype = AA  length = 5
FEATURE                  Location/Qualifiers
REGION                   1..5
                         note = Human (Homo sapiens), chimeric or humanized antibody
                          peptide sequence
source                   1..5
                         mol_type = protein
                         organism = unidentified
SEQUENCE: 526
DYSMH                                                                             5

SEQ ID NO: 527           moltype = AA  length = 17
FEATURE                  Location/Qualifiers
REGION                   1..17
                         note = Human (Homo sapiens), chimeric or humanized antibody
                          peptide sequence
source                   1..17
                         mol_type = protein
                         organism = unidentified
SEQUENCE: 527
RINTETGEPT FADDFRG                                                               17

SEQ ID NO: 528           moltype = AA  length = 7
FEATURE                  Location/Qualifiers
REGION                   1..7
                         note = Human (Homo sapiens), chimeric or humanized antibody
                          peptide sequence
source                   1..7
                         mol_type = protein
                         organism = unidentified
SEQUENCE: 528
FYYGRDT                                                                           7

SEQ ID NO: 529           moltype = AA  length = 17
FEATURE                  Location/Qualifiers
REGION                   1..17
                         note = Human (Homo sapiens), chimeric or humanized antibody
                          peptide sequence
source                   1..17
                         mol_type = protein
                         organism = unidentified
SEQUENCE: 529
KSSQSLLNSR TRKNYLA                                                               17

SEQ ID NO: 530           moltype = AA  length = 7
FEATURE                  Location/Qualifiers
REGION                   1..7
                         note = Human (Homo sapiens), chimeric or humanized antibody
                          peptide sequence
source                   1..7
                         mol_type = protein
                         organism = unidentified
```

```
SEQUENCE: 530
WASTRES                                                                                     7

SEQ ID NO: 531          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 531
KQSYNLLS                                                                                    8

SEQ ID NO: 532          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 532
KSSQSLLNSR SRKNYLA                                                                         17

SEQ ID NO: 533          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 533
WASTRES                                                                                     7

SEQ ID NO: 534          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 534
KQSYNLIS                                                                                    8

SEQ ID NO: 535          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 535
KSSQSLLNSR TRKNYLA                                                                         17

SEQ ID NO: 536          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 536
WASTRES                                                                                     7

SEQ ID NO: 537          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 537
KQSSNLIS                                                                                    8
```

```
SEQ ID NO: 538            moltype = AA   length = 17
FEATURE                   Location/Qualifiers
REGION                    1..17
                          note = Human (Homo sapiens), chimeric or humanized antibody
                           peptide sequence
source                    1..17
                          mol_type = protein
                          organism = unidentified
SEQUENCE: 538
KSSQSLLNSR SRKNYLA                                                         17

SEQ ID NO: 539            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 539
WASTRES                                                                     7

SEQ ID NO: 540            moltype = AA   length = 8
FEATURE                   Location/Qualifiers
REGION                    1..8
                          note = Human (Homo sapiens), chimeric or humanized antibody
                           peptide sequence
source                    1..8
                          mol_type = protein
                          organism = unidentified
SEQUENCE: 540
KQSYNLLS                                                                    8

SEQ ID NO: 541            moltype = AA   length = 17
FEATURE                   Location/Qualifiers
REGION                    1..17
                          note = Human (Homo sapiens), chimeric or humanized antibody
                           peptide sequence
source                    1..17
                          mol_type = protein
                          organism = unidentified
SEQUENCE: 541
KSSQSLLNSR SRKNYLA                                                         17

SEQ ID NO: 542            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 542
WASTRES                                                                     7

SEQ ID NO: 543            moltype = AA   length = 8
FEATURE                   Location/Qualifiers
REGION                    1..8
                          note = Human (Homo sapiens), chimeric or humanized antibody
                           peptide sequence
source                    1..8
                          mol_type = protein
                          organism = unidentified
SEQUENCE: 543
KQSYNLLS                                                                    8

SEQ ID NO: 544            moltype = AA   length = 21
FEATURE                   Location/Qualifiers
REGION                    1..21
                          note = Human (Homo sapiens), chimeric or humanized antibody
                           peptide sequence
source                    1..21
                          mol_type = protein
                          organism = unidentified
SEQUENCE: 544
KSSQSLLGRG DLGRLKKNAL A                                                    21

SEQ ID NO: 545            moltype = AA   length = 7
```

```
FEATURE              Location/Qualifiers
REGION               1..7
                     note = Human (Homo sapiens), chimeric or humanized antibody
                      peptide sequence
source               1..7
                     mol_type = protein
                     organism = unidentified
SEQUENCE: 545
WASTRES                                                                           7

SEQ ID NO: 546       moltype = AA  length = 8
FEATURE              Location/Qualifiers
REGION               1..8
                     note = Human (Homo sapiens), chimeric or humanized antibody
                      peptide sequence
source               1..8
                     mol_type = protein
                     organism = unidentified
SEQUENCE: 546
KQSYNLLS                                                                          8

SEQ ID NO: 547       moltype = AA  length = 21
FEATURE              Location/Qualifiers
REGION               1..21
                     note = Human (Homo sapiens), chimeric or humanized antibody
                      peptide sequence
source               1..21
                     mol_type = protein
                     organism = unidentified
SEQUENCE: 547
KSSQSLLGRG DLGRLKKNAL A                                                          21

SEQ ID NO: 548       moltype = AA  length = 7
FEATURE              Location/Qualifiers
REGION               1..7
                     note = Human (Homo sapiens), chimeric or humanized antibody
                      peptide sequence
source               1..7
                     mol_type = protein
                     organism = unidentified
SEQUENCE: 548
WASTRES                                                                           7

SEQ ID NO: 549       moltype = AA  length = 8
FEATURE              Location/Qualifiers
REGION               1..8
                     note = Human (Homo sapiens), chimeric or humanized antibody
                      peptide sequence
source               1..8
                     mol_type = protein
                     organism = unidentified
SEQUENCE: 549
KQSYNLLS                                                                          8

SEQ ID NO: 550       moltype = AA  length = 30
FEATURE              Location/Qualifiers
REGION               1..30
                     note = Human (Homo sapiens), chimeric or humanized antibody
                      peptide sequence
VARIANT              9
                     note = MISC_FEATURE - Xaa is Pro or Ala
VARIANT              10
                     note = MISC_FEATURE - Xaa is Glu or Lys
VARIANT              11
                     note = MISC_FEATURE - Xaa is Lys or Val
VARIANT              16
                     note = MISC_FEATURE - Xaa is Glu or Ala
VARIANT              17
                     note = MISC_FEATURE - Xaa is Thr or Ser
source               1..30
                     mol_type = protein
                     organism = unidentified
SEQUENCE: 550
QIQLVQSGXX XKKPGXXVKI SCKASGYTFT                                                  30

SEQ ID NO: 551       moltype = AA  length = 14
FEATURE              Location/Qualifiers
REGION               1..14
                     note = Human (Homo sapiens), chimeric or humanized antibody
```

```
                        peptide sequence
VARIANT                 3
                        note = MISC_FEATURE - Xaa is Lys or Arg
VARIANT                 8
                        note = MISC_FEATURE - Xaa is Lys or Gln
VARIANT                 11
                        note = MISC_FEATURE - Xaa is Lys or Glu
source                  1..14
                        mol_type = protein
                        organism = unidentified
SEQUENCE: 551
WVXQAPGXGL XWVA                                                              14

SEQ ID NO: 552          moltype = AA  length = 32
FEATURE                 Location/Qualifiers
REGION                  1..32
                        note = Human (Homo sapiens), chimeric or humanized antibody
                         peptide sequence
VARIANT                 3
                        note = MISC_FEATURE - Xaa is Ala, Thr or Ser
VARIANT                 5
                        note = MISC_FEATURE - Xaa is Ser or Thr
VARIANT                 7
                        note = MISC_FEATURE - Xaa is Glu or Asp
VARIANT                 10
                        note = MISC_FEATURE - Xaa is Ala or Thr
VARIANT                 18
                        note = MISC_FEATURE - Xaa is Asn , Arg or Thr
VARIANT                 19
                        note = MISC_FEATURE - Xaa is Asn or Ser
VARIANT                 21
                        note = MISC_FEATURE - Xaa is Lys or Arg
VARIANT                 22
                        note = MISC_FEATURE - Xaa is Asn or Ser
VARIANT                 23
                        note = MISC_FEATURE - Xaa is Glu or Asp
VARIANT                 27
                        note = MISC_FEATURE - Xaa is Thr or Val
source                  1..32
                        mol_type = protein
                        organism = unidentified
SEQUENCE: 552
RFXVXLXTSX STAYLZIXXL XXXDTAXYFC AI                                          32

SEQ ID NO: 553          moltype = AA  length = 11
FEATURE                 Location/Qualifiers
REGION                  1..11
                        note = Human (Homo sapiens), chimeric or humanized antibody
                         peptide sequence
VARIANT                 6
                        note = MISC_FEATURE - Xaa is Ala or Thr
source                  1..11
                        mol_type = protein
                        organism = unidentified
SEQUENCE: 553
WGQGTXLTVS S                                                                 11

SEQ ID NO: 554          moltype = AA  length = 23
FEATURE                 Location/Qualifiers
REGION                  1..23
                        note = Human (Homo sapiens), chimeric or humanized antibody
                         peptide sequence
VARIANT                 1
                        note = MISC_FEATURE - Xaa is Asp or Glu
VARIANT                 7
                        note = MISC_FEATURE - Xaa is Ser or Thr
VARIANT                 9
                        note = MISC_FEATURE - Xaa is Ser , Ala or Val
VARIANT                 10
                        note = MISC_FEATURE - Xaa is Ser or Thr
VARIANT                 12
                        note = MISC_FEATURE - Xaa is Ala or Ser
VARIANT                 15
                        note = MISC_FEATURE - Xaa is Ala or Pro
VARIANT                 18
                        note = MISC_FEATURE - Xaa is Lys , Arg or Ile
source                  1..23
                        mol_type = protein
                        organism = unidentified
```

```
SEQUENCE: 554
XIVMTQXPXX LXVSXGEXVT MSC                                              23

SEQ ID NO: 555              moltype = AA  length = 15
FEATURE                     Location/Qualifiers
REGION                      1..15
                            note = Human (Homo sapiens), chimeric or humanized antibody
                             peptide sequence
VARIANT                     9
                            note = MISC_FEATURE - Xaa is Ser or Ala
source                      1..15
                            mol_type = protein
                            organism = unidentified
SEQUENCE: 555
WYQQKPGQXP RLLIY                                                       15

SEQ ID NO: 556              moltype = AA  length = 32
FEATURE                     Location/Qualifiers
REGION                      1..32
                            note = Human (Homo sapiens), chimeric or humanized antibody
                             peptide sequence
VARIANT                     1
                            note = MISC_FEATURE - Xaa is Glu or Asp
VARIANT                     4
                            note = MISC_FEATURE - Xaa is Asp or Ala
VARIANT                     7
                            note = MISC_FEATURE - Xaa is Thr or Ser
VARIANT                     14
                            note = MISC_FEATURE - Xaa is Asp or Glu
VARIANT                     24
                            note = MISC_FEATURE - Xaa is Ala or Ser
VARIANT                     27
                            note = MISC_FEATURE - Xaa is Leu or Phe
source                      1..32
                            mol_type = protein
                            organism = unidentified
SEQUENCE: 556
XVPXRFXGSG SGTXFTLTIS SVQXEDXAVY YC                                    32

SEQ ID NO: 557              moltype = AA  length = 11
FEATURE                     Location/Qualifiers
REGION                      1..11
                            note = Human (Homo sapiens), chimeric or humanized antibody
                             peptide sequence
VARIANT                     3
                            note = MISC_FEATURE - Xaa is Ala or Gln
VARIANT                     6
                            note = MISC_FEATURE - Xaa is Lys or Val
VARIANT                     9
                            note = MISC_FEATURE - Xaa is Leu or Ile
source                      1..11
                            mol_type = protein
                            organism = unidentified
SEQUENCE: 557
FGXGTXLEXK R                                                           11

SEQ ID NO: 558              moltype = AA  length = 30
FEATURE                     Location/Qualifiers
REGION                      1..30
                            note = Human (Homo sapiens), chimeric or humanized antibody
                             peptide sequence
VARIANT                     5
                            note = misc_feature - Xaa can be any naturally occurring
                             amino acid
VARIANT                     9..11
                            note = misc_feature - Xaa can be any naturally occurring
                             amino acid
VARIANT                     16..17
                            note = misc_feature - Xaa can be any naturally occurring
                             amino acid
source                      1..30
                            mol_type = protein
                            organism = unidentified
SEQUENCE: 558
QIQLXQSGXX XKKPGXXVKI SCKASGYTFT                                       30

SEQ ID NO: 559              moltype = AA  length = 14
FEATURE                     Location/Qualifiers
REGION                      1..14
```

```
                        note = Human (Homo sapiens), chimeric or humanized antibody
                         peptide sequence
VARIANT                 3
                        note = MISC_FEATURE - Xaa is Arg or Lys
VARIANT                 8
                        note = MISC_FEATURE - Xaa is Gln or Lys
VARIANT                 11
                        note = MISC_FEATURE - Xaa is Gly or Lys
VARIANT                 13
                        note = MISC_FEATURE - Xaa is Val or Met
VARIANT                 14
                        note = MISC_FEATURE - Xaa is Ala or Gly
source                  1..14
                        mol_type = protein
                        organism = unidentified
SEQUENCE: 559
WVXQAPGXGL XWXX                                                              14

SEQ ID NO: 560          moltype = AA  length = 32
FEATURE                 Location/Qualifiers
REGION                  1..32
                        note = Human (Homo sapiens), chimeric or humanized antibody
                         peptide sequence
VARIANT                 3
                        note = MISC_FEATURE - Xaa is Thr , Ala or Ser
VARIANT                 4
                        note = MISC_FEATURE - Xaa is Val or Phe
VARIANT                 5
                        note = MISC_FEATURE - Xaa is Thr or Ser
VARIANT                 7
                        note = MISC_FEATURE - Xaa is Asp or Glu
VARIANT                 10
                        note = MISC_FEATURE - Xaa is Ala or Thr
VARIANT                 11
                        note = MISC_FEATURE - Xaa is Ser or Thr
VARIANT                 14
                        note = MISC_FEATURE - Xaa is Tyr or Asn
VARIANT                 16
                        note = misc_feature - Xaa can be any naturally occurring
                         amino acid
VARIANT                 18
                        note = MISC_FEATURE - Xaa is Arg, Asn, Ile or Thr
VARIANT                 19
                        note = misc_feature - Xaa can be any naturally occurring
                         amino acid
VARIANT                 20
                        note = MISC_FEATURE - Xaa is Arg or Lys
VARIANT                 21
                        note = MISC_FEATURE - Xaa is Ser or Asn
VARIANT                 22
                        note = MISC_FEATURE - Xaa is Asp or Glu
VARIANT                 22..23
                        note = misc_feature - Xaa can be any naturally occurring
                         amino acid
VARIANT                 26
                        note = MISC_FEATURE - Xaa is Val, Thr or Lys
VARIANT                 27
                        note = misc_feature - Xaa can be any naturally occurring
                         amino acid
source                  1..32
                        mol_type = protein
                        organism = unidentified
SEQUENCE: 560
RFXXXLXTSX XTAXLXIXXL XXXDTAXYFC AI                                          32

SEQ ID NO: 561          moltype = AA  length = 12
FEATURE                 Location/Qualifiers
REGION                  1..12
                        note = Human (Homo sapiens), chimeric or humanized antibody
                         peptide sequence
VARIANT                 6
                        note = misc_feature - Xaa can be any naturally occurring
                         amino acid
VARIANT                 9
                        note = MISC_FEATURE - Xaa is Thr or Ala
source                  1..12
                        mol_type = protein
                        organism = unidentified
SEQUENCE: 561
```

```
WGQGTXLVTV SS                                                                   12

SEQ ID NO: 562           moltype = AA  length = 5
FEATURE                  Location/Qualifiers
REGION                   1..5
                         note = Human (Homo sapiens), chimeric or humanized antibody
                          peptide sequence
source                   1..5
                         mol_type = protein
                         organism = unidentified
SEQUENCE: 562
DYSMH                                                                            5

SEQ ID NO: 563           moltype = AA  length = 17
FEATURE                  Location/Qualifiers
REGION                   1..17
                         note = Human (Homo sapiens), chimeric or humanized antibody
                          peptide sequence
VARIANT                  1
                         note = MISC_FEATURE - Xaa is Arg or Trp
VARIANT                  3
                         note = MISC_FEATURE - Xaa is Asn or Lys
VARIANT                  7
                         note = MISC_FEATURE - Xaa is Gly or Asp
VARIANT                  11
                         note = MISC_FEATURE - Xaa is Phe or Tyr
VARIANT                  16
                         note = MISC_FEATURE - Xaa is Arg, Asn, Lys or Gly
VARIANT                  17
                         note = MISC_FEATURE - Xaa is Gly or Glu
source                   1..17
                         mol_type = protein
                         organism = unidentified
SEQUENCE: 563
XIXTETXEPT XADDFXX                                                              17

SEQ ID NO: 564           moltype = AA  length = 7
FEATURE                  Location/Qualifiers
REGION                   1..7
                         note = Human (Homo sapiens), chimeric or humanized antibody
                          peptide sequence
VARIANT                  1
                         note = MISC_FEATURE - Xaa is Phe or Tyr
VARIANT                  7
                         note = MISC_FEATURE - Xaa is Ser or Thr
source                   1..7
                         mol_type = protein
                         organism = unidentified
SEQUENCE: 564
XYYGRDX                                                                          7

SEQ ID NO: 565           moltype = AA  length = 23
FEATURE                  Location/Qualifiers
REGION                   1..23
                         note = Human (Homo sapiens), chimeric or humanized antibody
                          peptide sequence
VARIANT                  1
                         note = MISC_FEATURE - Xaa is Glu or Asp
VARIANT                  5
                         note = MISC_FEATURE - Xaa is Thr or Ser
VARIANT                  7
                         note = MISC_FEATURE - Xaa is Ser or Thr
VARIANT                  9
                         note = MISC_FEATURE - Xaa is Ala, Ser or Val
VARIANT                  10
                         note = MISC_FEATURE - Xaa is Thr or Ser
VARIANT                  12
                         note = MISC_FEATURE - Xaa is Ser or Ala
VARIANT                  15
                         note = MISC_FEATURE - Xaa is Pro or Ala
VARIANT                  18
                         note = MISC_FEATURE - Xaa is Arg, Lys or Ile
source                   1..23
                         mol_type = protein
                         organism = unidentified
SEQUENCE: 565
XIVMXQXPXX LXVSXGEXVT MSC                                                       23

SEQ ID NO: 566           moltype = AA  length = 15
```

```
FEATURE                 Location/Qualifiers
REGION                  1..15
                        note = Human (Homo sapiens), chimeric or humanized antibody
                         peptide sequence
VARIANT                 9
                        note = MISC_FEATURE - Xaa is Ala or Ser
source                  1..15
                        mol_type = protein
                        organism = unidentified
SEQUENCE: 566
WYQQKPGQXP RLLIY                                                          15

SEQ ID NO: 567          moltype = AA  length = 32
FEATURE                 Location/Qualifiers
REGION                  1..32
                        note = Human (Homo sapiens), chimeric or humanized antibody
                         peptide sequence
VARIANT                 1
                        note = MISC_FEATURE - Xaa is Glu or Asp
VARIANT                 4
                        note = MISC_FEATURE - Xaa is Ala or Asp
VARIANT                 7
                        note = MISC_FEATURE - Xaa is Ser or Thr
VARIANT                 14
                        note = MISC_FEATURE - Xaa is Glu or Asp
VARIANT                 24
                        note = MISC_FEATURE - Xaa is Ser, Asp or Ala
VARIANT                 27
                        note = MISC_FEATURE - Xaa is Phe or Leu
source                  1..32
                        mol_type = protein
                        organism = unidentified
SEQUENCE: 567
XVPXRFXGSG SGTXFTLTIS SVQXEDXAVY YC                                        32

SEQ ID NO: 568          moltype = AA  length = 11
FEATURE                 Location/Qualifiers
REGION                  1..11
                        note = Human (Homo sapiens), chimeric or humanized antibody
                         peptide sequence
VARIANT                 3
                        note = MISC_FEATURE - Xaa is Gln or Ala
VARIANT                 6
                        note = MISC_FEATURE - Xaa is Val or Lys
VARIANT                 9
                        note = MISC_FEATURE - Xaa is Ile or Leu
source                  1..11
                        mol_type = protein
                        organism = unidentified
SEQUENCE: 568
FGXGTXLEXK R                                                              11

SEQ ID NO: 569          moltype = AA  length = 17
FEATURE                 Location/Qualifiers
REGION                  1..17
                        note = Human (Homo sapiens), chimeric or humanized antibody
                         peptide sequence
VARIANT                 11
                        note = MISC_FEATURE - Xaa is Ser or Thr
source                  1..17
                        mol_type = protein
                        organism = unidentified
SEQUENCE: 569
KSSQSLLNSR XRKNYLA                                                        17

SEQ ID NO: 570          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 570
WASTRES                                                                   7

SEQ ID NO: 571          moltype = AA  length = 8
FEATURE                 Location/Qualifiers
REGION                  1..8
```

```
                              note = Human (Homo sapiens), chimeric or humanized antibody
                                 peptide sequence
source                        1..8
                              mol_type = protein
                              organism = unidentified
SEQUENCE: 571
KQSYNLLS                                                                         8

SEQ ID NO: 572           moltype = AA  length = 17
FEATURE                  Location/Qualifiers
REGION                   1..17
                         note = Human (Homo sapiens), chimeric or humanized antibody
                            peptide sequence
source                   1..17
                         mol_type = protein
                         organism = unidentified
SEQUENCE: 572
KSSQSLLNSR SRKNYLA                                                              17

SEQ ID NO: 573           moltype = AA  length = 17
FEATURE                  Location/Qualifiers
REGION                   1..17
                         note = Human (Homo sapiens), chimeric or humanized antibody
                            peptide sequence
source                   1..17
                         mol_type = protein
                         organism = unidentified
SEQUENCE: 573
KSSQSLLGRG DLGNALA                                                              17

SEQ ID NO: 574           moltype = AA  length = 19
FEATURE                  Location/Qualifiers
REGION                   1..19
                         note = Human (Homo sapiens), chimeric or humanized antibody
                            peptide sequence
source                   1..19
                         mol_type = protein
                         organism = unidentified
SEQUENCE: 574
KSSQSLLNSG RGDLGNALA                                                            19

SEQ ID NO: 575           moltype = AA  length = 21
FEATURE                  Location/Qualifiers
REGION                   1..21
                         note = Human (Homo sapiens), chimeric or humanized antibody
                            peptide sequence
source                   1..21
                         mol_type = protein
                         organism = unidentified
SEQUENCE: 575
KSSQSLLGRG DLGRLKKNAL A                                                         21

SEQ ID NO: 576           moltype = AA  length = 25
FEATURE                  Location/Qualifiers
REGION                   1..25
                         note = Human (Homo sapiens), chimeric or humanized antibody
                            peptide sequence
source                   1..25
                         mol_type = protein
                         organism = unidentified
SEQUENCE: 576
KSSQSLLGRG DLGRLKKQKD HNALA                                                     25

SEQ ID NO: 577           moltype = AA  length = 24
FEATURE                  Location/Qualifiers
REGION                   1..24
                         note = Human (Homo sapiens), chimeric or humanized antibody
                            peptide sequence
source                   1..24
                         mol_type = protein
                         organism = unidentified
SEQUENCE: 577
KSSQSLLGRG DLGRLKKQKD NALA                                                      24

SEQ ID NO: 578           moltype = AA  length = 23
FEATURE                  Location/Qualifiers
REGION                   1..23
                         note = Human (Homo sapiens), chimeric or humanized antibody
                            peptide sequence
```

|   |   |   |
|---|---|---|
| source | 1..23<br>mol_type = protein<br>organism = unidentified | |
| SEQUENCE: 578<br>KSSQSLLGRG DLGRLKKQKN ALA | | 23 |
| SEQ ID NO: 579<br>FEATURE<br>REGION | moltype = AA  length = 22<br>Location/Qualifiers<br>1..22<br>note = Human (Homo sapiens), chimeric or humanized antibody<br> peptide sequence | |
| source | 1..22<br>mol_type = protein<br>organism = unidentified | |
| SEQUENCE: 579<br>KSSQSLLGRG DLGRLKKQNA LA | | 22 |
| SEQ ID NO: 580<br>FEATURE<br>REGION | moltype = AA  length = 20<br>Location/Qualifiers<br>1..20<br>note = Human (Homo sapiens), chimeric or humanized antibody<br> peptide sequence | |
| source | 1..20<br>mol_type = protein<br>organism = unidentified | |
| SEQUENCE: 580<br>KSSQSLLGRG DLGRLKNALA | | 20 |
| SEQ ID NO: 581<br>FEATURE<br>REGION | moltype = AA  length = 19<br>Location/Qualifiers<br>1..19<br>note = Human (Homo sapiens), chimeric or humanized antibody<br> peptide sequence | |
| source | 1..19<br>mol_type = protein<br>organism = unidentified | |
| SEQUENCE: 581<br>KSSQSLLGRG DLGRLNALA | | 19 |
| SEQ ID NO: 582<br>FEATURE<br>REGION | moltype = AA  length = 18<br>Location/Qualifiers<br>1..18<br>note = Human (Homo sapiens), chimeric or humanized antibody<br> peptide sequence | |
| source | 1..18<br>mol_type = protein<br>organism = unidentified | |
| SEQUENCE: 582<br>KSSQSLLGRG DLGRNALA | | 18 |
| SEQ ID NO: 583<br>FEATURE<br>REGION | moltype = AA  length = 22<br>Location/Qualifiers<br>1..22<br>note = Human (Homo sapiens), chimeric or humanized antibody<br> peptide sequence | |
| source | 1..22<br>mol_type = protein<br>organism = unidentified | |
| SEQUENCE: 583<br>KSSQSLLGRG DLGRLKKQKD HH | | 22 |
| SEQ ID NO: 584<br>FEATURE<br>REGION | moltype = AA  length = 21<br>Location/Qualifiers<br>1..21<br>note = Human (Homo sapiens), chimeric or humanized antibody<br> peptide sequence | |
| source | 1..21<br>mol_type = protein<br>organism = unidentified | |
| SEQUENCE: 584<br>KSSQSLLGRG DLGRLKKQKD H | | 21 |
| SEQ ID NO: 585<br>FEATURE<br>REGION | moltype = AA  length = 20<br>Location/Qualifiers<br>1..20<br>note = Human (Homo sapiens), chimeric or humanized antibody<br> peptide sequence | |
| source | 1..20<br>mol_type = protein | |

```
                                  organism  = unidentified
SEQUENCE: 585
KSSQSLLGRG DLGRLKKQKD                                                     20

SEQ ID NO: 586            moltype = AA  length = 19
FEATURE                   Location/Qualifiers
REGION                    1..19
                          note = Human (Homo sapiens), chimeric or humanized antibody
                           peptide sequence
source                    1..19
                          mol_type = protein
                          organism  = unidentified
SEQUENCE: 586
KSSQSLLGRG DLGRLKKQK                                                      19

SEQ ID NO: 587            moltype = AA  length = 18
FEATURE                   Location/Qualifiers
REGION                    1..18
                          note = Human (Homo sapiens), chimeric or humanized antibody
                           peptide sequence
source                    1..18
                          mol_type = protein
                          organism  = unidentified
SEQUENCE: 587
KSSQSLLGRG DLGRLKKQ                                                       18

SEQ ID NO: 588            moltype = AA  length = 17
FEATURE                   Location/Qualifiers
REGION                    1..17
                          note = Human (Homo sapiens), chimeric or humanized antibody
                           peptide sequence
source                    1..17
                          mol_type = protein
                          organism  = unidentified
SEQUENCE: 588
KSSQSLLGRG DLGRLKK                                                        17

SEQ ID NO: 589            moltype = AA  length = 16
FEATURE                   Location/Qualifiers
REGION                    1..16
                          note = Human (Homo sapiens), chimeric or humanized antibody
                           peptide sequence
source                    1..16
                          mol_type = protein
                          organism  = unidentified
SEQUENCE: 589
KSSQSLLGRG DLGRLK                                                         16

SEQ ID NO: 590            moltype = AA  length = 15
FEATURE                   Location/Qualifiers
REGION                    1..15
                          note = Human (Homo sapiens), chimeric or humanized antibody
                           peptide sequence
source                    1..15
                          mol_type = protein
                          organism  = unidentified
SEQUENCE: 590
KSSQSLLGRG DLGRL                                                          15

SEQ ID NO: 591            moltype = AA  length = 54
FEATURE                   Location/Qualifiers
source                    1..54
                          mol_type = protein
                          organism  = Homo sapiens
SEQUENCE: 591
FLQDGTKTVE YAPCRSQDID ADGQGFCQGG FSIDFTKADR VLLGGPGSFY WQGQ               54

SEQ ID NO: 592            moltype = AA  length = 54
FEATURE                   Location/Qualifiers
source                    1..54
                          mol_type = protein
                          organism  = Pan troglodytes
SEQUENCE: 592
FLQDGTKTVE YAPCRSQDID ADGQGFCQGG FSIDFTKADR VLLGGPGSFY WQGQ               54

SEQ ID NO: 593            moltype = AA  length = 54
FEATURE                   Location/Qualifiers
source                    1..54
                          mol_type = protein
```

```
                       organism = Macaca mulatta
SEQUENCE: 593
FLQDGTKTVE YAPCRSQDID ADGQGFCQGG FSIDFTKADR VLLGGPGSFY WQGQ         54

SEQ ID NO: 594          moltype = AA   length = 54
FEATURE                 Location/Qualifiers
source                  1..54
                        mol_type = protein
                        organism = Macaca fascicularis
SEQUENCE: 594
FLQDGTKTVE YAPCRSQDID ADGQGFCQGG FSIDFTKADR VLLGGPGSFY WQGQ         54

SEQ ID NO: 595          moltype = AA   length = 54
FEATURE                 Location/Qualifiers
source                  1..54
                        mol_type = protein
                        organism = Bos taurus
SEQUENCE: 595
FLQDGTKTVE YAPCRSKNID ADGQGFCQGG FSIDFTKADR VLLGGPGSFY WQGQ         54

SEQ ID NO: 596          moltype = AA   length = 54
FEATURE                 Location/Qualifiers
REGION                  1..54
                        note = Sus sp.
source                  1..54
                        mol_type = protein
                        organism = unidentified
SEQUENCE: 596
FLQDGTKTVE YAPCRSKNID ADGQGFCQGG FSIDFTKADR VLLGGPGSFY WQGQ         54

SEQ ID NO: 597          moltype = AA   length = 54
FEATURE                 Location/Qualifiers
source                  1..54
                        mol_type = protein
                        organism = Equus ferus
SEQUENCE: 597
FLQDGAKTVE YAPCRSKNID ADGQGFCQGG FSIDFTKADR VLLGGPGSFY WQGQ         54

SEQ ID NO: 598          moltype = AA   length = 54
FEATURE                 Location/Qualifiers
source                  1..54
                        mol_type = protein
                        organism = Mus musculus
SEQUENCE: 598
FLQDGTKTVE YAPCRSKNID ADGQGFCQGG FSIDFTKADR VLLGGPGSFY WQGQ         54

SEQ ID NO: 599          moltype = AA   length = 54
FEATURE                 Location/Qualifiers
REGION                  1..54
                        note = Rattus sp.
source                  1..54
                        mol_type = protein
                        organism = unidentified
SEQUENCE: 599
FLQDGTKTVE YAPCRSKNID ADGQGFCQGG FSIDFTKADR VLLGGPGSFY WQGQ         54

SEQ ID NO: 600          moltype = AA   length = 54
FEATURE                 Location/Qualifiers
REGION                  1..54
                        note = Dasypus sp.
source                  1..54
                        mol_type = protein
                        organism = unidentified
SEQUENCE: 600
FLQDGTKTVE YAPCRSKNID ADGQGFCQGG FSIDFTKADR VLLGGPGSFY WQGQ         54

SEQ ID NO: 601          moltype = AA   length = 54
FEATURE                 Location/Qualifiers
source                  1..54
                        mol_type = protein
                        organism = Ornithorhynchus anatinus
SEQUENCE: 601
FLQDGTKTVE YAPCRSRSID ADGQGFCQGG FSIDFTKADR VLLGGPGSFY WQGQ         54

SEQ ID NO: 602          moltype = AA   length = 92
FEATURE                 Location/Qualifiers
source                  1..92
                        mol_type = protein
                        organism = Homo sapiens
```

```
SEQUENCE: 602
SASMHNNIEK LNSVGNDLSR KMAFFSRDFR LGFGSYVDKT VSPYISIHPE RIHNQCSDYN    60
LDCMPPHGYI HVLSLTENIT EFEKAVHRQK IS                                 92

SEQ ID NO: 603          moltype = AA   length = 92
FEATURE                 Location/Qualifiers
source                  1..92
                        mol_type = protein
                        organism = Pan troglodytes
SEQUENCE: 603
SASMHNNIEK LNSVGNDLSR KMAFFSRDFR LGFGSYVDKT VSPYISIHPE RIHNQCSDYN    60
LDCMPPHGYI HVLSLTENIT EFERAVHRQK IS                                 92

SEQ ID NO: 604          moltype = AA   length = 92
FEATURE                 Location/Qualifiers
source                  1..92
                        mol_type = protein
                        organism = Macaca mulatta
SEQUENCE: 604
SASMHNNIEK LNSVGNDLSR KMAFFSRDFR LGFGSYVDKT VSPYISIHPE RIHNQCSDYN    60
LDCMPPHGYI HVLSLTENIT EFEKAVHRQK IS                                 92

SEQ ID NO: 605          moltype = AA   length = 92
FEATURE                 Location/Qualifiers
source                  1..92
                        mol_type = protein
                        organism = Macaca fascicularis
SEQUENCE: 605
SASMHNNIEK LNSVGNDLSR KMAFFSRDFR LGFGSYVDKT VSPYISIHPE RIHNQCSDYN    60
LDCMPPHGYI HVLSLTENIT EFEKAVHRQK IS                                 92

SEQ ID NO: 606          moltype = AA   length = 92
FEATURE                 Location/Qualifiers
source                  1..92
                        mol_type = protein
                        organism = Bos taurus
SEQUENCE: 606
SASMHNNIEK LNSVGNDLSR KMAFFSRDFR LGFGSYVDKT VSPYISIHPE RIHNQCSDYN    60
LDCMPPHGYI HVLSLTENIT EFEKAVHRQK IS                                 92

SEQ ID NO: 607          moltype = AA   length = 92
FEATURE                 Location/Qualifiers
REGION                  1..92
                        note = Sus sp.
source                  1..92
                        mol_type = protein
                        organism = unidentified
SEQUENCE: 607
SASMHNNIEK LNTVGNDLSR KMAFFSRDFR LGFGSYVDKT VSPYISIHPE RIHNQCSDYN    60
LDCMPPHGYI HVLSLTENIT EFEKAVHRQK IS                                 92

SEQ ID NO: 608          moltype = AA   length = 92
FEATURE                 Location/Qualifiers
source                  1..92
                        mol_type = protein
                        organism = Equus ferus
SEQUENCE: 608
SASMHNNIEK LNSVGNDLSR KMAFFSRDFR LGFGSYVDKT VSPYISIHPE RIHNQCSDYN    60
LDCMPPHGYI HVLSLTENIT EFEKAVHRQK IS                                 92

SEQ ID NO: 609          moltype = AA   length = 92
FEATURE                 Location/Qualifiers
source                  1..92
                        mol_type = protein
                        organism = Mus musculus
SEQUENCE: 609
SASMHNNIEK LNSVGNDLSK KMALYSRDFR LGFGSYVDKT VSPYISIHPE RIHNQCSDYN    60
LDCMPPHGYI HVLSLTENIT EFEKAVHRQK IS                                 92

SEQ ID NO: 610          moltype = AA   length = 92
FEATURE                 Location/Qualifiers
REGION                  1..92
                        note = Rattus sp.
source                  1..92
                        mol_type = protein
                        organism = unidentified
SEQUENCE: 610
SASMHNNIEK LNSVGNDLSK KMALFSHDFR LGFGSYVDKT VSPYISIHPE RIHNQCSDYN    60
LDCMPPHGYI HVLSLTENIT EFEKAVHRQK IS                                 92
```

```
SEQ ID NO: 611          moltype = AA   length = 92
FEATURE                 Location/Qualifiers
REGION                  1..92
                        note = Dasypus sp.
source                  1..92
                        mol_type = protein
                        organism = unidentified
SEQUENCE: 611
SASMHNNIEK LNSVGNDLSR KMAFFSLDFR LGFGSYVDKT VSPYISIHPE RIHNQCSDYN   60
LDCMPPHGYI HVLSLTENIT EFAKAVHRQK IS                                92

SEQ ID NO: 612          moltype = AA   length = 92
FEATURE                 Location/Qualifiers
source                  1..92
                        mol_type = protein
                        organism = Ornithorhynchus anatinus
SEQUENCE: 612
SASMHNNIEK LNSVGNDLSQ KMADFTRDFR LGFGSYVDKT VSPYISIHPG RIRNQCSQYD   60
LDCMPPHGYI HVLPLTENVT EFEKAVNKQK IS                                92

SEQ ID NO: 613          moltype = AA   length = 9
FEATURE                 Location/Qualifiers
REGION                  1..9
                        note = Human (Homo sapiens), chimeric or humanized antibody
                         peptide sequence
source                  1..9
                        mol_type = protein
                        organism = unidentified
SEQUENCE: 613
YTFTDYSMH                                                           9

SEQ ID NO: 614          moltype = AA   length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 614
RINTETGEPT FADDFRG                                                 17

SEQ ID NO: 615          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 615
FYYGRDS                                                             7

SEQ ID NO: 616          moltype = AA   length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 616
KSSQSLLNSR TRKNYLA                                                 17

SEQ ID NO: 617          moltype = AA   length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 617
YWASTRES                                                            8

SEQ ID NO: 618          moltype = AA   length = 8
FEATURE                 Location/Qualifiers
REGION                  1..8
```

```
                            note = Human (Homo sapiens), chimeric or humanized antibody
                              peptide sequence
source                      1..8
                            mol_type = protein
                            organism = unidentified
SEQUENCE: 618
KQSYNLLS                                                                         8

SEQ ID NO: 619              moltype = AA  length = 26
FEATURE                     Location/Qualifiers
REGION                      1..26
                            note = Human (Homo sapiens), chimeric or humanized antibody
                              peptide sequence
source                      1..26
                            mol_type = protein
                            organism = unidentified
SEQUENCE: 619
SASMHNNIEK LNSVGNDLSR KMAFFS                                                    26

SEQ ID NO: 620              moltype = AA  length = 28
FEATURE                     Location/Qualifiers
REGION                      1..28
                            note = Human (Homo sapiens), chimeric or humanized antibody
                              peptide sequence
source                      1..28
                            mol_type = protein
                            organism = unidentified
SEQUENCE: 620
TVSPYISIHP ERIHNQCSDY NLDCMPPH                                                  28

SEQ ID NO: 621              moltype = AA  length = 11
FEATURE                     Location/Qualifiers
REGION                      1..11
                            note = Human (Homo sapiens), chimeric or humanized antibody
                              peptide sequence
source                      1..11
                            mol_type = protein
                            organism = unidentified
SEQUENCE: 621
NITEFEKAVH R                                                                    11

SEQ ID NO: 622              moltype = AA  length = 118
FEATURE                     Location/Qualifiers
REGION                      1..118
                            note = Human (Homo sapiens), chimeric or humanized antibody
                              peptide sequence
source                      1..118
                            mol_type = protein
                            organism = unidentified
SEQUENCE: 622
KQDKILACAP LYHWRTEMKQ EREPVGTCFL QDGTKTVEYA PCRSQDIDAD GQGFCQGGFS               60
IDFTKADRVL LGGPGSFYWQ GQLISDQVAE IVSKYDPNVY SIKYNNQLAT RTAQAIFD                118

SEQ ID NO: 623              moltype = AA  length = 439
FEATURE                     Location/Qualifiers
source                      1..439
                            mol_type = protein
                            organism = Homo sapiens
SEQUENCE: 623
FNLDVDSPAE YSGPEGSYFG FAVDFFVPSA SSRMFLLVGA PKANTTQPGI VEGGQVLKCD               60
WSSTRRCQPI EFDATGNRDY AKDDPLEFKS HQWFGASVRS KQDKILACAP LYHWRTEMKQ              120
EREPVGTCFL QDGTKTVEYA PCRSQDIDAD GQGFCQGGFS IDFTKADRVL LGGPGSFYWQ              180
GQLISDQVAE IVSKYDPNVY SIKYNNQLAT RTAQAIFDDS YLGYSVAVGD FNGDGIDDFV              240
SGVPRAARTL GMVYIYDGKN MSSLYNFTGE QMAAYFGFSV AATDINGDDY ADVFIGAPLF              300
MDRGSDGKLQ EVGQVSVSLQ RASGDFQTTK LNGFEVFARF GSAIAPLGDL DQDGFNDIAI              360
AAPYGGEDKK GIVYIFNGRS TGLNAVPSQI LEGQWAARSM PPSFGYSMKG ATDIDKNGYP              420
DLIVGAFGVD RAILYRARP                                                          439

SEQ ID NO: 624              moltype = AA  length = 122
FEATURE                     Location/Qualifiers
REGION                      1..122
                            note = Human (Homo sapiens), chimeric or humanized antibody
                              peptide sequence
source                      1..122
                            mol_type = protein
                            organism = unidentified
SEQUENCE: 624
QVQLQQSGAE LVRPGTSVKV SCKASGYAFT NYLIEWVKQR PGQGLEWIGV INPGTGGTNY               60
NKKFKVKATL TADKSSSTAY MQLGGLTFDD SAVYFCAREG NARTYYYAMD YWGQGTSVTV              120
```

```
SS                                                                              122

SEQ ID NO: 625            moltype = AA  length = 27
FEATURE                   Location/Qualifiers
REGION                    1..27
                          note = Human (Homo sapiens), chimeric or humanized antibody
                            peptide sequence
source                    1..27
                          mol_type = protein
                          organism = unidentified
SEQUENCE: 625
QVQLQQSGAE LVRPGTSVKV SCKASGY                                                    27

SEQ ID NO: 626            moltype = AA  length = 27
FEATURE                   Location/Qualifiers
REGION                    1..27
                          note = Human (Homo sapiens), chimeric or humanized antibody
                            peptide sequence
source                    1..27
                          mol_type = protein
                          organism = unidentified
SEQUENCE: 626
QVQLQQSGAE LVRPGASVKV SCKASGY                                                    27

SEQ ID NO: 627            moltype = AA  length = 27
FEATURE                   Location/Qualifiers
REGION                    1..27
                          note = Human (Homo sapiens), chimeric or humanized antibody
                            peptide sequence
source                    1..27
                          mol_type = protein
                          organism = unidentified
SEQUENCE: 627
QVQLQQSGAE LVRPGTSVKV PCKASGY                                                    27

SEQ ID NO: 628            moltype = AA  length = 8
FEATURE                   Location/Qualifiers
REGION                    1..8
                          note = Human (Homo sapiens), chimeric or humanized antibody
                            peptide sequence
source                    1..8
                          mol_type = protein
                          organism = unidentified
SEQUENCE: 628
AFTNYLIE                                                                          8

SEQ ID NO: 629            moltype = AA  length = 8
FEATURE                   Location/Qualifiers
REGION                    1..8
                          note = Human (Homo sapiens), chimeric or humanized antibody
                            peptide sequence
source                    1..8
                          mol_type = protein
                          organism = unidentified
SEQUENCE: 629
AFTDYLIE                                                                          8

SEQ ID NO: 630            moltype = AA  length = 8
FEATURE                   Location/Qualifiers
REGION                    1..8
                          note = Human (Homo sapiens), chimeric or humanized antibody
                            peptide sequence
source                    1..8
                          mol_type = protein
                          organism = unidentified
SEQUENCE: 630
AFTDNLIE                                                                          8

SEQ ID NO: 631            moltype = AA  length = 8
FEATURE                   Location/Qualifiers
REGION                    1..8
                          note = Human (Homo sapiens), chimeric or humanized antibody
                            peptide sequence
source                    1..8
                          mol_type = protein
                          organism = unidentified
SEQUENCE: 631
AFTDYLIQ                                                                          8
```

| | |
|---|---|
| SEQ ID NO: 632 | moltype = AA length = 14 |
| FEATURE | Location/Qualifiers |
| REGION | 1..14 |
| | note = Human (Homo sapiens), chimeric or humanized antibody peptide sequence |
| source | 1..14 |
| | mol_type = protein |
| | organism = unidentified |
| SEQUENCE: 632 | |
| WVKQRPGQGL EWIG | 14 |

| | |
|---|---|
| SEQ ID NO: 633 | moltype = AA length = 14 |
| FEATURE | Location/Qualifiers |
| REGION | 1..14 |
| | note = Human (Homo sapiens), chimeric or humanized antibody peptide sequence |
| source | 1..14 |
| | mol_type = protein |
| | organism = unidentified |
| SEQUENCE: 633 | |
| WVRQRPGQGL EWIG | 14 |

| | |
|---|---|
| SEQ ID NO: 634 | moltype = AA length = 17 |
| FEATURE | Location/Qualifiers |
| REGION | 1..17 |
| | note = Human (Homo sapiens), chimeric or humanized antibody peptide sequence |
| source | 1..17 |
| | mol_type = protein |
| | organism = unidentified |
| SEQUENCE: 634 | |
| VINPGTGGTN YNKKFKV | 17 |

| | |
|---|---|
| SEQ ID NO: 635 | moltype = AA length = 17 |
| FEATURE | Location/Qualifiers |
| REGION | 1..17 |
| | note = Human (Homo sapiens), chimeric or humanized antibody peptide sequence |
| source | 1..17 |
| | mol_type = protein |
| | organism = unidentified |
| SEQUENCE: 635 | |
| VINPETGGTN YNAKFKG | 17 |

| | |
|---|---|
| SEQ ID NO: 636 | moltype = AA length = 17 |
| FEATURE | Location/Qualifiers |
| REGION | 1..17 |
| | note = Human (Homo sapiens), chimeric or humanized antibody peptide sequence |
| source | 1..17 |
| | mol_type = protein |
| | organism = unidentified |
| SEQUENCE: 636 | |
| VINPETGGTN YNAKFRG | 17 |

| | |
|---|---|
| SEQ ID NO: 637 | moltype = AA length = 32 |
| FEATURE | Location/Qualifiers |
| REGION | 1..32 |
| | note = Human (Homo sapiens), chimeric or humanized antibody peptide sequence |
| source | 1..32 |
| | mol_type = protein |
| | organism = unidentified |
| SEQUENCE: 637 | |
| KATLTADKSS STAYMQLGGL TFDDSAVYFC AR | 32 |

| | |
|---|---|
| SEQ ID NO: 638 | moltype = AA length = 32 |
| FEATURE | Location/Qualifiers |
| REGION | 1..32 |
| | note = Human (Homo sapiens), chimeric or humanized antibody peptide sequence |
| source | 1..32 |
| | mol_type = protein |
| | organism = unidentified |
| SEQUENCE: 638 | |
| KATLTADKSS SSAYMQLSSL TSGDSAVYFC AR | 32 |

| | |
|---|---|
| SEQ ID NO: 639 | moltype = AA length = 32 |
| FEATURE | Location/Qualifiers |

```
REGION                   1..32
                         note = Human (Homo sapiens), chimeric or humanized antibody
                          peptide sequence
source                   1..32
                         mol_type = protein
                         organism = unidentified
SEQUENCE: 639
KATLTADKSS SSVYMQLSSL TSGDSAVYFC AR                                          32

SEQ ID NO: 640           moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 640
KATLTADKSS STAYMQLSSL TSGDSAVYFC AR                                          32

SEQ ID NO: 641           moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 641
KATLTADKSS SSAYMQLSGL TSGDSAVYFC AR                                          32

SEQ ID NO: 642           moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 642
KATLTADKSS SSAYMQLSSL SSGDSAVYFC AR                                          32

SEQ ID NO: 643           moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 643
KATLTADKSS SSAYMQLSGL TSGDSAVYFC AR                                          32

SEQ ID NO: 644           moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 644
RATLTADKSS SSAYMQLSSL TSGDSAVYFC AR                                          32

SEQ ID NO: 645           moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 645
KATLTADKSS SSAYMQLSSL TSDDSAVYFC AR                                          32

SEQ ID NO: 646           moltype = AA  length = 32
FEATURE                  Location/Qualifiers
REGION                   1..32
                         note = Human (Homo sapiens), chimeric or humanized antibody
```

```
                              peptide sequence
source                        1..32
                              mol_type = protein
                              organism = unidentified
SEQUENCE: 646
KVTLTADKTS SSAYMQLSSL TSGDSAVYFC AR                                    32

SEQ ID NO: 647                moltype = AA  length = 32
FEATURE                       Location/Qualifiers
REGION                        1..32
                              note = Human (Homo sapiens), chimeric or humanized antibody
                              peptide sequence
source                        1..32
                              mol_type = protein
                              organism = unidentified
SEQUENCE: 647
KVTLTADKSS SSAYMQLNSL TSGDSAVYFC AR                                    32

SEQ ID NO: 648                moltype = AA  length = 32
FEATURE                       Location/Qualifiers
REGION                        1..32
                              note = Human (Homo sapiens), chimeric or humanized antibody
                              peptide sequence
source                        1..32
                              mol_type = protein
                              organism = unidentified
SEQUENCE: 648
KATLTANKSS SSAYMQLSSL TSGDSAVYFC AR                                    32

SEQ ID NO: 649                moltype = AA  length = 32
FEATURE                       Location/Qualifiers
REGION                        1..32
                              note = Human (Homo sapiens), chimeric or humanized antibody
                              peptide sequence
source                        1..32
                              mol_type = protein
                              organism = unidentified
SEQUENCE: 649
KATLTADKSS SSAYLQLSSL TSGDSAVYFC AR                                    32

SEQ ID NO: 650                moltype = AA  length = 32
FEATURE                       Location/Qualifiers
REGION                        1..32
                              note = Human (Homo sapiens), chimeric or humanized antibody
                              peptide sequence
source                        1..32
                              mol_type = protein
                              organism = unidentified
SEQUENCE: 650
RATLTADKSS SSAYMQLSSL TSGDSAVYFC AR                                    32

SEQ ID NO: 651                moltype = AA  length = 13
FEATURE                       Location/Qualifiers
REGION                        1..13
                              note = Human (Homo sapiens), chimeric or humanized antibody
                              peptide sequence
source                        1..13
                              mol_type = protein
                              organism = unidentified
SEQUENCE: 651
EGNARTYYYA MDY                                                         13

SEQ ID NO: 652                moltype = AA  length = 11
FEATURE                       Location/Qualifiers
REGION                        1..11
                              note = Human (Homo sapiens), chimeric or humanized antibody
                              peptide sequence
source                        1..11
                              mol_type = protein
                              organism = unidentified
SEQUENCE: 652
EAGNYIYAMD Y                                                           11

SEQ ID NO: 653                moltype = AA  length = 10
FEATURE                       Location/Qualifiers
REGION                        1..10
                              note = Human (Homo sapiens), chimeric or humanized antibody
                              peptide sequence
source                        1..10
```

```
                         mol_type = protein
                         organism = unidentified
SEQUENCE: 653
AGNYIYAMDY                                                                 10

SEQ ID NO: 654           moltype = AA   length = 11
FEATURE                  Location/Qualifiers
REGION                   1..11
                         note = Human (Homo sapiens), chimeric or humanized antibody
                          peptide sequence
source                   1..11
                         mol_type = protein
                         organism = unidentified
SEQUENCE: 654
EAGNYIYAMD Y                                                               11

SEQ ID NO: 655           moltype = AA   length = 11
FEATURE                  Location/Qualifiers
REGION                   1..11
                         note = Human (Homo sapiens), chimeric or humanized antibody
                          peptide sequence
source                   1..11
                         mol_type = protein
                         organism = unidentified
SEQUENCE: 655
WGQGTSVTVS S                                                               11

SEQ ID NO: 656           moltype = AA   length = 120
FEATURE                  Location/Qualifiers
REGION                   1..120
                         note = Human (Homo sapiens), chimeric or humanized antibody
                          peptide sequence
source                   1..120
                         mol_type = protein
                         organism = unidentified
SEQUENCE: 656
QVQLQQSGAE LVRPGTSVKV SCKASGYAFT DYLIEWVKQR PGQGLEWIGV INPETGGTNY          60
NAKFKGKATL TADKSSSSAY MQLSSLTSGD SAVYFCAREA GNYIYAMDYW GQGTSVTVSS         120

SEQ ID NO: 657           moltype = AA   length = 119
FEATURE                  Location/Qualifiers
REGION                   1..119
                         note = Human (Homo sapiens), chimeric or humanized antibody
                          peptide sequence
source                   1..119
                         mol_type = protein
                         organism = unidentified
SEQUENCE: 657
QVQLQQSGAE LVRPGTSVKV SCKASGYAFT DYLIEWVKQR PGQGLEWIGV INPETGGTNY          60
NAKFRGKATL TADKSSSSAY MQLSSLTSGD SAVYFCARAG NYIYAMDYWG QGTSVTVSS          119

SEQ ID NO: 658           moltype = AA   length = 120
FEATURE                  Location/Qualifiers
REGION                   1..120
                         note = Human (Homo sapiens), chimeric or humanized antibody
                          peptide sequence
source                   1..120
                         mol_type = protein
                         organism = unidentified
SEQUENCE: 658
QVQLQQSGAE LVRPGASVKV SCKASGYAFT DYLIEWVRQR PGQGLEWIGV INPETGGTNY          60
NAKFRGKATL TADKSSSSVY MQLSSLTSGD SAVYFCAREA GNYIYAMDYW GQGTSVTVSS         120

SEQ ID NO: 659           moltype = AA   length = 120
FEATURE                  Location/Qualifiers
REGION                   1..120
                         note = Human (Homo sapiens), chimeric or humanized antibody
                          peptide sequence
source                   1..120
                         mol_type = protein
                         organism = unidentified
SEQUENCE: 659
QVQLQQSGAE LVRPGTSVKV SCKASGYAFT DYLIEWVRQR PGQGLEWIGV INPETGGTNY          60
NAKFRGKATL TADKSSSTAY MQLSSLTSGD SAVYFCAREA GNYIYAMDYW GQGTSVTVSS         120

SEQ ID NO: 660           moltype = AA   length = 120
FEATURE                  Location/Qualifiers
REGION                   1..120
                         note = Human (Homo sapiens), chimeric or humanized antibody
```

-continued

```
                           peptide sequence
source                     1..120
                           mol_type = protein
                           organism = unidentified
SEQUENCE: 660
QVQLQQSGAE LVRPGTSVKV SCKASGYAFT DYLIEWVRQR PGQGLEWIGV INPETGGTNY   60
NAKFRGKATL TADKSSSSAY MQLSGLTSGD SAVYFCAREA GNYIYAMDYW GQGTSVTVSS  120

SEQ ID NO: 661             moltype = AA  length = 120
FEATURE                    Location/Qualifiers
REGION                     1..120
                           note = Human (Homo sapiens), chimeric or humanized antibody
                            peptide sequence
source                     1..120
                           mol_type = protein
                           organism = unidentified
SEQUENCE: 661
QVQLQQSGAE LVRPGTSVKV SCKASGYAFT DNLIEWVRQR PGQGLEWIGV INPETGGTNY   60
NAKFRGKATL TADKSSSSAY MQLSSLTSGD SAVYFCAREA GNYIYAMDYW GQGTSVTVSS  120

SEQ ID NO: 662             moltype = AA  length = 120
FEATURE                    Location/Qualifiers
REGION                     1..120
                           note = Human (Homo sapiens), chimeric or humanized antibody
                            peptide sequence
source                     1..120
                           mol_type = protein
                           organism = unidentified
SEQUENCE: 662
QVQLQQSGAE LVRPGTSVKV SCKASGYAFT DYLIEWVKQR PGQGLEWIGV INPETGGTNY   60
NAKFRGKATL TADKSSSSAY MQLSSLSSGD SAVYFCAREA GNYIYAMDYW GQGTSVTVSS  120

SEQ ID NO: 663             moltype = AA  length = 120
FEATURE                    Location/Qualifiers
REGION                     1..120
                           note = Human (Homo sapiens), chimeric or humanized antibody
                            peptide sequence
source                     1..120
                           mol_type = protein
                           organism = unidentified
SEQUENCE: 663
QVQLQQSGAE LVRPGTSVKV SCKASGYAFT DYLIEWVRQR PGQGLEWIGV INPETGGTNY   60
NAKFRGKATL TADKSSSSAY MQLSGLTSGD SAVYFCAREA GNYIYAMDYW GQGTSVTVSS  120

SEQ ID NO: 664             moltype = AA  length = 120
FEATURE                    Location/Qualifiers
REGION                     1..120
                           note = Human (Homo sapiens), chimeric or humanized antibody
                            peptide sequence
source                     1..120
                           mol_type = protein
                           organism = unidentified
SEQUENCE: 664
QVQLQQSGAE LVRPGTSVKV SCKASGYAFT DYLIEWVRQR PGQGLEWIGV INPETGGTNY   60
NAKFRGRATL TADKSSSSAY MQLSSLTSGD SAVYFCAREA GNYIYAMDYW GQGTSVTVSS  120

SEQ ID NO: 665             moltype = AA  length = 120
FEATURE                    Location/Qualifiers
REGION                     1..120
                           note = Human (Homo sapiens), chimeric or humanized antibody
                            peptide sequence
source                     1..120
                           mol_type = protein
                           organism = unidentified
SEQUENCE: 665
QVQLQQSGAE LVRPGTSVKV SCKASGYAFT DYLIEWVRQR PGQGLEWIGV INPETGGTNY   60
NAKFRGKATL TADKSSGSAY MQLSSLTSGD SAVYFCAREA GNYIYAMDYW GQGTSVTVSS  120

SEQ ID NO: 666             moltype = AA  length = 120
FEATURE                    Location/Qualifiers
REGION                     1..120
                           note = Human (Homo sapiens), chimeric or humanized antibody
                            peptide sequence
source                     1..120
                           mol_type = protein
                           organism = unidentified
SEQUENCE: 666
QVQLQQSGAE LVRPGTSVKV SCKASGYAFT DYLIEWVRQR PGQGLEWIGV INPETGGTNY   60
NAKFRGKATL TADKSSSSAY MQLSSLTSDD SAVYFCAREA GNYIYAMDYW GQGTSVTVSS  120
```

```
SEQ ID NO: 667          moltype = AA   length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 667
QVQLQQSGAE LVRPGTSVKV SCKASGYAFT DYLIEWVRQR PGQGLEWIGV INPETGGTNY   60
NAKFRGKVTL TADKTSSSAY MQLSSLTSGD SAVYFCAREA GNYIYAMDYW GQGTSVTVSS  120

SEQ ID NO: 668          moltype = AA   length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 668
QVQLQQSGAE LVRPGTSVKV SCKASGYAFT DYLIEWVRQR PGQGLEWIGV INPETGGTNY   60
NAKFRGKVTL TADKSSSSAY MQLNSLTSGD SAVYFCAREA GNYIYAMDYW GQGTSVTVSS  120

SEQ ID NO: 669          moltype = AA   length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 669
QVQLQQSGAE LVRPGTSVKV SCKASGYAFT DYLIEWVRQR PGQGLEWIGV INPETGGTNY   60
NAKFRGRATL TADKSSSSAY MQLSSLTSGD SAVYFCAREA GNYIYAMDYW GQGTSVTVSS  120

SEQ ID NO: 670          moltype = AA   length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 670
QVQLQQSGAE LVRPGTSVKV SCKASGYAFT DYLIEWVRQR PGQGLEWIGV INPETGGTNY   60
NAKFRGKVTL TADKTSSSAY MQLSSLTSGD SAVYFCAREA GNYIYAMDYW GQGTSVTVSS  120

SEQ ID NO: 671          moltype = AA   length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 671
QVQLQQSGAE LVRPGTSVKV SCKASGYAFT DYLIEWVKQR PGQGLEWIGV INPETGGTNY   60
NAKFRGRATL TADKSSSSAY MQLSSLTSGD SAVYFCAREA GNYIYAMDYW GQGTSVTVSS  120

SEQ ID NO: 672          moltype = AA   length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 672
QVQLQQSGAE LVRPGTSVKV SCKASGYAFT DYLIQWVKQR PGQGLEWIGV INPETGGTNY   60
NAKFRGKATL TADKSSSSAY MQLSSLTSGD SAVYFCAREA GNYIYAMDYW GQGTSVTVSS  120

SEQ ID NO: 673          moltype = AA   length = 120
FEATURE                 Location/Qualifiers
REGION                  1..120
                        note = Human (Homo sapiens), chimeric or humanized antibody
                         peptide sequence
source                  1..120
```

```
                        mol_type = protein
                        organism = unidentified
SEQUENCE: 673
QVQLQQSGAE LVRPGTSVRV SCKASGYAFT DYLIQWVKQR PGQGLEWIGV INPETGGTNY   60
NAKFRGKATL TANKSSSSAY MQLSSLTSGD SAVYFCAREA GNYIYAMDYW GQGTSVTVSS  120

SEQ ID NO: 674          moltype = AA  length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 674
QVQLQQSGAE LVRPGTSVKV PCKASGYAFT DYLIQWVKQR PGQGLEWIGV INPETGGTNY   60
NAKFRGKATL TADKSSSSAY MQLSSLTSGD SAVYFCAREA GNYIYAMDYW GQGTSVTVSS  120

SEQ ID NO: 675          moltype = AA  length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 675
QVQLQQSGAE LVRPGTSVKV SCKASGYAFT DYLIEWVKQR PGQGLEWIGV INPETGGTNY   60
NAKFRGKATL TADKSSSSAY MQLSSLTSGD SAVYFCAREA GNYIYAMDYW GQGTSVTVSS  120

SEQ ID NO: 676          moltype = AA  length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 676
QVQLQQSGAE LVRPGTSVKV SCKASGYAFT DYLIQWVKQR PGQGLEWIGV INPETGGTNY   60
NAKFRGKATL TADKSSSSAY LQLSSLTSGD SAVYFCAREA GNYIYAMDYW GQGTSVTVSS  120

SEQ ID NO: 677          moltype = AA  length = 120
FEATURE                 Location/Qualifiers
REGION                  1..120
                        note = Human (Homo sapiens), chimeric or humanized antibody
                         peptide sequence
source                  1..120
                        mol_type = protein
                        organism = unidentified
SEQUENCE: 677
QVQLQQSGAE LVRPGTSVKV SCKASGYAFT DYLIQWVKQR PGQGLEWIGV INPETGGTNY   60
NAKFRGKATL TADKSSSSAY MQLSSLTSGD SAVYFCAREA GNYIYAMDYW GQGTSVTVSS  120

SEQ ID NO: 678          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 678
DIQMTQSPAS LSASVGETVT ITCRASVNIY SYLVWYQQKQ GKSPQLLVHN AKTLAEGVPS   60
RFSGSGSGTQ FSLKINSLQP EDFGSYYCQH HHGTPYTFGG GTKLEIKA              108

SEQ ID NO: 679          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 679
DIEMTQTPAS LSASVGETVT ITCRASENIY SYLVWYQQKQ GKSPQVLVYN AKTLAEGVPS   60
RFSGSGSGTQ FSLKINSLQP EDFGSYYCQH HNGTPYTFGG GTKLEIKA              108

SEQ ID NO: 680          moltype = AA  length = 108
```

```
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 680
DIVMTQSPAS LSASVGETVT ITCRASVNIY SYLVWYQQKQ GKSPQLLVHN AKTLAEGVPS    60
RFSGSGSGTQ FSLKINSLQP EDFGSYYCQH HHGTPYTFGG GTKLEIKA                108

SEQ ID NO: 681          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 681
DIVMTQSPAS LSASVGETVT ITCRASVNIY SYLVWYQQKQ GKSPQLLVHN AKTLAEGVPS    60
RFSGSGSGTQ FSLKINSLQP EDFGSYYCQH HHGTPYTFGG GTKLEIKA                108

SEQ ID NO: 682          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 682
DIVMTQSPAS LSASVGETVT ITCRASVNIY SYLVWYQQKQ GKSPQLLVHN AKTLAEGVPS    60
RFSGSGSGTQ FSLKINSVQP EDFGSYYCQH HHGTPYTFGG GTKLEIKA                108

SEQ ID NO: 683          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 683
HIVMTQSPAS LSASVGETVT ITCRASVNIY SYLVWYQQKQ GKSPQLLVHN AKTLAEGVPS    60
RFSGSGSGTQ FSLKINSLQP EDFGSYYCQH HHGTPYTFGG GTKLEIKA                108

SEQ ID NO: 684          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 684
DIVMTQSPAS LSASVGETVT ITCRASVNIY SYLVWYQQKQ GKSPQLLVHN AKTLAEGVPS    60
RFSGSGSGTQ FSLKINSLQP EDVGSYYCQH HHGTPYTFGG GTKLEIKA                108

SEQ ID NO: 685          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 685
DIVMTQSPAS LSASVGETVT ITCRASVNIY SYLVWYQQKQ GKSPQLLVHN AKTLAEGVPS    60
RFSGSGSGTQ FSLKINSLQP EDFGSYYCQH HHGTPYTFGG GTKLEIKA                108

SEQ ID NO: 686          moltype = AA  length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
```

-continued

```
SEQUENCE: 686
DIVMTQSPAS LSASVGETVT ITCRASVNIY SYLVWYQQKQ GKSPQLLVHN AKTLAEGVPS     60
RFSGSGSGTQ FSLKINSLQP EDFGSYYCQH HHGTPYTFGG GTKLEIKA                 108

SEQ ID NO: 687          moltype = AA   length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 687
DIVMTQSPAS LSASVGETVT ITCRASVNIY SYLVWYQQKQ GKSPQLLVHN AKTLAEGVPS     60
RFSGSGSGTQ FSLKINSLQP EDFGSYYCQH HHGTPYTFGG GTKLEIKR                 108

SEQ ID NO: 688          moltype = AA   length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 688
DIEMTQTPAS LSASVGETVT ITCRASVNIY SYLVWYQQKQ GKSPQLLVHN AKTLAEGVPS     60
RFSGSGSGTQ FSLKINSLQP EDFGSYYCQH HHGTPYTFGG GTKLEIKR                 108

SEQ ID NO: 689          moltype = AA   length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 689
DIVMTQSPAS LSASVGETVT ITCRASVNIY SYLVWYQQKQ GKSPQLLVHN AKTLAEGVPS     60
RFSGSGSGTQ FSLKINSLQP EDFGSYYCQH HHGTPYTFGG GTKLEIKA                 108

SEQ ID NO: 690          moltype = AA   length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 690
DIVVTQSPAS LSASVGETVT ITCRASVNIY SYLVWYQQKQ GKSPQLLVHN AKTLAEGVPS     60
RFSGSGSGTQ FSLKINSLQP EDFGSYYCQH HHGTPYTFGG GTKLEIKA                 108

SEQ ID NO: 691          moltype = AA   length = 108
FEATURE                 Location/Qualifiers
REGION                  1..108
                        note = Human (Homo sapiens), chimeric or humanized antibody
                         peptide sequence
source                  1..108
                        mol_type = protein
                        organism = unidentified
SEQUENCE: 691
DIVMTQSPAF LSASVGETVT ITCRASVNIY SYLVWYQQKQ GKSPQLLVHN AKTLAEGVPS     60
RFSGSGSGTQ FSLKINSLQP EDFGSYYCQH HHGTPYTFGG GTKLEIKR                 108

SEQ ID NO: 692          moltype = AA   length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 692
DIQMTQSPAS LSASVGETVT ITC                                             23

SEQ ID NO: 693          moltype = AA   length = 11
FEATURE                 Location/Qualifiers
REGION                  1..11
                        note = Human (Homo sapiens), chimeric or humanized antibody
```

```
                         peptide sequence
source                   1..11
                         mol_type = protein
                         organism = unidentified
SEQUENCE: 693
RASVNIYSYL V                                                           11

SEQ ID NO: 694           moltype = AA  length = 15
FEATURE                  Location/Qualifiers
REGION                   1..15
                         note = Human (Homo sapiens), chimeric or humanized antibody
                          peptide sequence
source                   1..15
                         mol_type = protein
                         organism = unidentified
SEQUENCE: 694
WYQQKQGKSP QLLVH                                                       15

SEQ ID NO: 695           moltype = AA  length = 7
FEATURE                  Location/Qualifiers
REGION                   1..7
                         note = Human (Homo sapiens), chimeric or humanized antibody
                          peptide sequence
source                   1..7
                         mol_type = protein
                         organism = unidentified
SEQUENCE: 695
NAKTLAE                                                                 7

SEQ ID NO: 696           moltype = AA  length = 32
FEATURE                  Location/Qualifiers
REGION                   1..32
                         note = Human (Homo sapiens), chimeric or humanized antibody
                          peptide sequence
source                   1..32
                         mol_type = protein
                         organism = unidentified
SEQUENCE: 696
GVPSRFSGSG SGTQFSLKIN SLQPEDFGSY YC                                    32

SEQ ID NO: 697           moltype = AA  length = 9
FEATURE                  Location/Qualifiers
REGION                   1..9
                         note = Human (Homo sapiens), chimeric or humanized antibody
                          peptide sequence
source                   1..9
                         mol_type = protein
                         organism = unidentified
SEQUENCE: 697
QHHHGTPYT                                                               9

SEQ ID NO: 698           moltype = AA  length = 11
FEATURE                  Location/Qualifiers
REGION                   1..11
                         note = Human (Homo sapiens), chimeric or humanized antibody
                          peptide sequence
source                   1..11
                         mol_type = protein
                         organism = unidentified
SEQUENCE: 698
FGGGTKLEIK A                                                           11

SEQ ID NO: 699           moltype = AA  length = 23
FEATURE                  Location/Qualifiers
REGION                   1..23
                         note = Human (Homo sapiens), chimeric or humanized antibody
                          peptide sequence
source                   1..23
                         mol_type = protein
                         organism = unidentified
SEQUENCE: 699
DIEMTQTPAS LSASVGETVT ITC                                              23

SEQ ID NO: 700           moltype = AA  length = 11
FEATURE                  Location/Qualifiers
REGION                   1..11
                         note = Human (Homo sapiens), chimeric or humanized antibody
                          peptide sequence
source                   1..11
```

```
                        mol_type = protein
                        organism = unidentified
SEQUENCE: 700
RASENIYSYL V                                                            11

SEQ ID NO: 701          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 701
WYQQKQGKSP QVLVY                                                        15

SEQ ID NO: 702          moltype = AA  length = 9
FEATURE                 Location/Qualifiers
REGION                  1..9
                        note = Human (Homo sapiens), chimeric or humanized antibody
                         peptide sequence
source                  1..9
                        mol_type = protein
                        organism = unidentified
SEQUENCE: 702
QHHNGTPYT                                                                9

SEQ ID NO: 703          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 703
DIVMTQSPAS LSASVGETVT ITC                                               23

SEQ ID NO: 704          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 704
HIVMTQSPAS LSASVGETVT ITC                                               23

SEQ ID NO: 705          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 705
DIVVTQSPAS LSASVGETVT ITC                                               23

SEQ ID NO: 706          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 706
FGGGTKLEIK R                                                            11

SEQ ID NO: 707          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
```

```
SEQUENCE: 707
DYSMH                                                                 5

SEQ ID NO: 708         moltype = AA  length = 6
FEATURE                Location/Qualifiers
REGION                 1..6
                       note = Human (Homo sapiens), chimeric or humanized antibody
                        peptide sequence
source                 1..6
                       mol_type = protein
                       organism = unidentified
SEQUENCE: 708
ASTRES                                                                6

SEQ ID NO: 709         moltype = AA  length = 10
FEATURE                Location/Qualifiers
REGION                 1..10
                       note = Human (Homo sapiens), chimeric or humanized antibody
                        peptide sequence
source                 1..10
                       mol_type = protein
                       organism = unidentified
SEQUENCE: 709
GRGDLGRLKK                                                           10

SEQ ID NO: 710         moltype = AA  length = 6
FEATURE                Location/Qualifiers
REGION                 1..6
                       note = Human (Homo sapiens), chimeric or humanized antibody
                        peptide sequence
source                 1..6
                       mol_type = protein
                       organism = unidentified
SEQUENCE: 710
GRGDSP                                                                6

SEQ ID NO: 711         moltype = AA  length = 7
FEATURE                Location/Qualifiers
REGION                 1..7
                       note = Human (Homo sapiens), chimeric or humanized antibody
                        peptide sequence
source                 1..7
                       mol_type = protein
                       organism = unidentified
SEQUENCE: 711
AKQRGDV                                                               7

SEQ ID NO: 712         moltype = AA  length = 9
FEATURE                Location/Qualifiers
REGION                 1..9
                       note = Human (Homo sapiens), chimeric or humanized antibody
                        peptide sequence
source                 1..9
                       mol_type = protein
                       organism = unidentified
SEQUENCE: 712
RGDLGRLKK                                                             9

SEQ ID NO: 713         moltype = AA  length = 12
FEATURE                Location/Qualifiers
REGION                 1..12
                       note = Human (Homo sapiens), chimeric or humanized antibody
                        peptide sequence
source                 1..12
                       mol_type = protein
                       organism = unidentified
SEQUENCE: 713
DDHGRGDLGR LK                                                        12

SEQ ID NO: 714         moltype = AA  length = 390
FEATURE                Location/Qualifiers
REGION                 1..390
                       note = Human (Homo sapiens), chimeric or humanized antibody
                        peptide sequence
source                 1..390
                       mol_type = protein
                       organism = unidentified
SEQUENCE: 714
MPPSGLRLLL LLLPLLWLLV LTPGRPAAGL STCKTIDMEL VKRKRIEAIR GQILSKLRLA    60
```

```
SPPSQGEVPP GPLPEAVLAL YNSTRDRVAG ESAEPEPEPE ADYYAKEVTR VLMVETHNEI    120
YDKFKQSTHS IYMFFNTSEL REAVPEPVLL SRAELRLLRL KLKVEQHVEL YQKYSNNSWR    180
YLSNRLLAPS DSPEWLSFDV TGVVRQWLSR GGEIEGFRLS AHCSCDSRDN TLQVDINGFT    240
TGRRGDLATI HGMNRPFLLL MATPLERAQH LQSSRHRRAL DTNYCFSSTE KNCCVRQLYI    300
DFRKDLGWKW IHEPKGYHAN FCLGPCPYIW SLDTQYSKVL ALYNQHNPGA SAAPCCVPQA    360
LEPLPIVYYV GRKPKVEQLS NMIVRSCKCS                                    390

SEQ ID NO: 715           moltype = AA  length = 338
FEATURE                  Location/Qualifiers
REGION                   1..338
                         note = Human (Homo sapiens), chimeric or humanized antibody
                           peptide sequence
source                   1..338
                         mol_type = protein
                         organism = unidentified
SEQUENCE: 715
MHYCVLSAFL ILHLVTVALS LSTCSTLDMD QFMRKRIEAI RGQILSKLKL TSPPEDYPEP     60
EEVPPEVISI YNSTRDLLQE KASRRAAACE RERSDEEYYA KEVYKIDMPP FFPSENAIPP    120
TFYRPYFRIV RFDVSAMEKN ASNLVKAEFR VFRLQNPKAR VPEQRIELYQ ILKSKDLTSP    180
TQRYIDSKVV KTRAEGEWLS FDVTDAVHEW LPSYRLESQQ TNRRKKRALD AAYCFRVQDN    240
CCLRPLYIDF KRDLGWKWIH EPKGYNANFC AGACPYLWSS DTQHSRVLSL YNTINPEASA    300
SPCCVSQDLE PLTILYYIGK TPKIEQLSNM IVKSCKCS                           338

SEQ ID NO: 716           moltype = AA  length = 411
FEATURE                  Location/Qualifiers
REGION                   1..411
                         note = Human (Homo sapiens), chimeric or humanized antibody
                           peptide sequence
source                   1..411
                         mol_type = protein
                         organism = unidentified
SEQUENCE: 716
MKMHLQRALV VLALLNFATV SLSLSTCTTL DFGHIKKKRV EAIRGQILSK LRLTSPPEPT     60
VTHVPYQVLA LYNSTRELLE EMHGEREEGC TQENTESEYY AKEIHKFDMI QGLAEHNELA    120
VCPKGITSKV FRFNVSSVEK NRTNLFRAEF RVLRVPNPSS KRNEQRIELF QILRPDEHIA    180
KQRYIGGKNL PTRGTAEWLS FDVTDTVREW LRRESNLGL EISIHCPCHT FQPNGDILEN     240
IHEVMEIKFK GVDNEDDHGR GDLGRLKKQK QHHNPHLILM MIPPHRLDNP GQGGQRKKRA    300
LDTNYCFRNL EENCCVRPLY IDFRQDLGWK WVHEPKGYYA NFCSGPCPYL RSADTTHSTV    360
LGLYNTLNPE ASASPCCVPQ DLEPLTILYY VGRTPKVEQL SNMVVKSCKC S             411

SEQ ID NO: 717           moltype = AA  length = 219
FEATURE                  Location/Qualifiers
REGION                   1..219
                         note = Human (Homo sapiens), chimeric or humanized antibody
                           peptide sequence
source                   1..219
                         mol_type = protein
                         organism = unidentified
SEQUENCE: 717
DIVMTQSPSS LAVSAGEKVT MSCKSSQSLL NSRTRKNYLA WYQQKPGQSP RLLIYWASTR     60
ESGVPDRFTG SGSGTDFTLT ISSVQAEDLA VYYCKQSYNL LSFGAGTKLE LKAADAAPTV    120
SIFPPSSEQL TSGGASVVCF LNNFYPKDIN VKWKIDGSER QNGVLNSWTD QDSKDSTYSM    180
SSTLTLTKDE YERHNSYTCE ATHKTSTSPI VKSFNRNEC                          219

SEQ ID NO: 718           moltype = AA  length = 17
FEATURE                  Location/Qualifiers
REGION                   1..17
                         note = Human (Homo sapiens), chimeric or humanized antibody
                           peptide sequence
source                   1..17
                         mol_type = protein
                         organism = unidentified
SEQUENCE: 718
KSSQSLLGRG DLGNALA                                                   17

SEQ ID NO: 719           moltype = AA  length = 19
FEATURE                  Location/Qualifiers
REGION                   1..19
                         note = Human (Homo sapiens), chimeric or humanized antibody
                           peptide sequence
source                   1..19
                         mol_type = protein
                         organism = unidentified
SEQUENCE: 719
KSSQSLLNSG RGDLGNALA                                                 19

SEQ ID NO: 720           moltype = AA  length = 21
FEATURE                  Location/Qualifiers
REGION                   1..21
```

```
                        note = Human (Homo sapiens), chimeric or humanized antibody
                            peptide sequence
source                  1..21
                        mol_type = protein
                        organism = unidentified
SEQUENCE: 720
KSSQSLLGRG DLGRLKKNAL A                                            21

SEQ ID NO: 721          moltype = AA  length = 9
FEATURE                 Location/Qualifiers
REGION                  1..9
                        note = Human (Homo sapiens), chimeric or humanized antibody
                            peptide sequence
source                  1..9
                        mol_type = protein
                        organism = unidentified
SEQUENCE: 721
GRGDLGRLK                                                           9

SEQ ID NO: 722          moltype = AA  length = 116
FEATURE                 Location/Qualifiers
REGION                  1..116
                        note = Human (Homo sapiens), chimeric or humanized antibody
                            peptide sequence
source                  1..116
                        mol_type = protein
                        organism = unidentified
SEQUENCE: 722
QIQLVQSGPE LKKPGETVKI SCKASGYTFT DYSMHWVKQA PGKGLKWVAR INTETGEPTF   60
ADDFRGRFAV SLETSASTAY LQINNLKNED TATYFCAIFY YGRDSWGQGT TLTVSS      116

SEQ ID NO: 723          moltype = AA  length = 116
FEATURE                 Location/Qualifiers
REGION                  1..116
                        note = Human (Homo sapiens), chimeric or humanized antibody
                            peptide sequence
source                  1..116
                        mol_type = protein
                        organism = unidentified
SEQUENCE: 723
QIQLVQSGAE VKKPGASVKI SCKASGYTFT DYSMHWVRQA PGQGLEWVAR INTETGEPTF   60
ADDFRGRFTV TLDTSTSTAY LEIRSLRSDD TAVYFCAIFY YGRDSWGQGT TLTVSS      116

SEQ ID NO: 724          moltype = AA  length = 116
FEATURE                 Location/Qualifiers
REGION                  1..116
                        note = Human (Homo sapiens), chimeric or humanized antibody
                            peptide sequence
source                  1..116
                        mol_type = protein
                        organism = unidentified
SEQUENCE: 724
QIQLVQSGAE VKKPGASVKI SCKASGYTFT DYSMHWVRQA PGQGLEWVAR INTETGEPTF   60
ADDFRGRFTV TLDTSTSTAY LEIRSLRSDD TAVYFCAIFY YGRDSWGQGT TLTVSS      116

SEQ ID NO: 725          moltype = AA  length = 116
FEATURE                 Location/Qualifiers
REGION                  1..116
                        note = Human (Homo sapiens), chimeric or humanized antibody
                            peptide sequence
source                  1..116
                        mol_type = protein
                        organism = unidentified
SEQUENCE: 725
QIQLVQSGAK VKKPGASVKI SCKASGYTFT DYSMHWVRQA PGQGLEWVAR INTETGEPTF   60
ADDFRGRFSV TLDTSTSTAY LEITSLRSDD TAVYFCAIFY YGRDTWGQGT TLTVSS      116

SEQ ID NO: 726          moltype = AA  length = 116
FEATURE                 Location/Qualifiers
REGION                  1..116
                        note = Human (Homo sapiens), chimeric or humanized antibody
                            peptide sequence
source                  1..116
                        mol_type = protein
                        organism = unidentified
SEQUENCE: 726
QIQLVQSGAE VKKPGASVKI SCKASGYTFT DYSMHWVRQA PGQGLEWVAR INTETGEPTF   60
ADDFRGRFTV TLDTSTSTAY LEIRSLRSDD TAVYFCAIFY YGRDTWGQGT TLTVSS      116
```

```
SEQ ID NO: 727            moltype = AA  length = 113
FEATURE                   Location/Qualifiers
REGION                    1..113
                          note = Human (Homo sapiens), chimeric or humanized antibody
                           peptide sequence
source                    1..113
                          mol_type = protein
                          organism = unidentified
SEQUENCE: 727
DIVMTQSPSS LAVSAGEKVT MSCKSSQSLL NSRTRKNYLA WYQQKPGQSP RLLIYWASTR    60
ESGVPDRFTG SGSGTDFTLT ISSVQAEDLA VYYCKQSYNL LSFGAGTKLE LKR          113

SEQ ID NO: 728            moltype = AA  length = 113
FEATURE                   Location/Qualifiers
REGION                    1..113
                          note = Human (Homo sapiens), chimeric or humanized antibody
                           peptide sequence
source                    1..113
                          mol_type = protein
                          organism = unidentified
SEQUENCE: 728
EIVMTQSPAT LSVSPGERVT MSCKSSQSLL NSRTRKNYLA WYQQKPGQAP RLLIYWASTR    60
ESGVPARFSG SGSGTEFTLT ISSVQSEDFA VYYCKQSYNL LSFGQGTVLE IKR          113

SEQ ID NO: 729            moltype = AA  length = 113
FEATURE                   Location/Qualifiers
REGION                    1..113
                          note = Human (Homo sapiens), chimeric or humanized antibody
                           peptide sequence
source                    1..113
                          mol_type = protein
                          organism = unidentified
SEQUENCE: 729
EIVMTQSPAT LSVSPGEIVT MSCKSSQSLL NSRSRKNYLA WYQQKPGQAP RLLIYWASTR    60
ESGVPARFSG SGSGTEFTLT ISSVQSEDFA VYYCKQSYNL LSFGQGTVLE IKR          113

SEQ ID NO: 730            moltype = AA  length = 113
FEATURE                   Location/Qualifiers
REGION                    1..113
                          note = Human (Homo sapiens), chimeric or humanized antibody
                           peptide sequence
source                    1..113
                          mol_type = protein
                          organism = unidentified
SEQUENCE: 730
EIVMTQTPVT LSVSPGERVT MSCKSSQSLL NSRTRKNYLA WYQQKPGQAP RLLIYWASTR    60
ESDVPARFSG SGSGTEFTLT ISSVQSEDFA VYYCKQSSNL LSFGQGTVLE IKR          113

SEQ ID NO: 731            moltype = AA  length = 113
FEATURE                   Location/Qualifiers
REGION                    1..113
                          note = Human (Homo sapiens), chimeric or humanized antibody
                           peptide sequence
source                    1..113
                          mol_type = protein
                          organism = unidentified
SEQUENCE: 731
EIVMTQSPAT LSVSPGERVT MSCKSSQSLL NSRSRKNYLA WYQQKPGQAP RLLIYWASTR    60
ESGVPARFSG SGSGTEFTLT ISSVQSEDFA VYYCKQSYNL LSFGQGTVLE IKR          113

SEQ ID NO: 732            moltype = AA  length = 30
FEATURE                   Location/Qualifiers
REGION                    1..30
                          note = Human (Homo sapiens), chimeric or humanized antibody
                           peptide sequence
source                    1..30
                          mol_type = protein
                          organism = unidentified
SEQUENCE: 732
QIQLVQSGPE LKKPGETVKI SCKASGYTFT                                     30

SEQ ID NO: 733            moltype = AA  length = 5
FEATURE                   Location/Qualifiers
REGION                    1..5
                          note = Human (Homo sapiens), chimeric or humanized antibody
                           peptide sequence
source                    1..5
                          mol_type = protein
                          organism = unidentified
```

```
SEQUENCE: 733
DYSMH                                                                        5

SEQ ID NO: 734          moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 734
WVKQAPGKGL KWVA                                                             14

SEQ ID NO: 735          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 735
RINTETGEPT FADDFRG                                                          17

SEQ ID NO: 736          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 736
RFAVSLETSA STAYLQINNL KNEDTATYFC AI                                         32

SEQ ID NO: 737          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 737
FYYGRDS                                                                      7

SEQ ID NO: 738          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 738
WGQGTTLTVS S                                                                11

SEQ ID NO: 739          moltype = AA  length = 30
FEATURE                 Location/Qualifiers
REGION                  1..30
                        note = Human (Homo sapiens), chimeric or humanized antibody
                         peptide sequence
source                  1..30
                        mol_type = protein
                        organism = unidentified
SEQUENCE: 739
QIQLVQSGAE VKKPGASVKI SCKASGYTFT                                            30

SEQ ID NO: 740          moltype = AA  length = 14
FEATURE                 Location/Qualifiers
REGION                  1..14
                        note = Human (Homo sapiens), chimeric or humanized antibody
                         peptide sequence
source                  1..14
                        mol_type = protein
                        organism = unidentified
SEQUENCE: 740
WVRQAPGQGL EWVA                                                             14
```

```
SEQ ID NO: 741          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 741
RFTVTLDTST STAYLEIRSL RSDDTAVYFC AI                                         32

SEQ ID NO: 742          moltype = AA  length = 30
FEATURE                 Location/Qualifiers
REGION                  1..30
                        note = Human (Homo sapiens), chimeric or humanized antibody
                         peptide sequence
source                  1..30
                        mol_type = protein
                        organism = unidentified
SEQUENCE: 742
QIQLVQSGAK VKKPGASVKI SCKASGYTFT                                            30

SEQ ID NO: 743          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 743
RFSVTLDTST STAYLEITSL RSDDTAVYFC AI                                         32

SEQ ID NO: 744          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 744
FYYGRDT                                                                      7

SEQ ID NO: 745          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 745
DIVMTQSPSS LAVSAGEKVT MSC                                                   23

SEQ ID NO: 746          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 746
KSSQSLLNSR TRKNYLA                                                          17

SEQ ID NO: 747          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 747
WYQQKPGQSP RLLIY                                                            15

SEQ ID NO: 748          moltype = AA  length = 7
```

```
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 748
WASTRES                                                                          7

SEQ ID NO: 749          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 749
GVPDRFTGSG SGTDFTLTIS SVQAEDLAVY YC                                              32

SEQ ID NO: 750          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 750
KQSYNLLS                                                                         8

SEQ ID NO: 751          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 751
FGAGTKLELK R                                                                     11

SEQ ID NO: 752          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 752
EIVMTQSPAT LSVSPGERVT MSC                                                        23

SEQ ID NO: 753          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 753
GVPARFSGSG SGTEFTLTIS SVQSEDFAVY YC                                              32

SEQ ID NO: 754          moltype = AA  length = 11
FEATURE                 Location/Qualifiers
REGION                  1..11
                        note = Human (Homo sapiens), chimeric or humanized antibody
                         peptide sequence
source                  1..11
                        mol_type = protein
                        organism = unidentified
SEQUENCE: 754
FGQGTVLEIK R                                                                     11

SEQ ID NO: 755          moltype = AA  length = 23
FEATURE                 Location/Qualifiers
REGION                  1..23
```

```
                        note = Human (Homo sapiens), chimeric or humanized antibody
                         peptide sequence
source                  1..23
                        mol_type = protein
                        organism = unidentified
SEQUENCE: 755
EIVMTQSPAT LSVSPGEIVT MSC                                              23

SEQ ID NO: 756          moltype = AA  length = 4
FEATURE                 Location/Qualifiers
REGION                  1..4
                        note = Human (Homo sapiens), chimeric or humanized antibody
                         peptide sequence
source                  1..4
                        mol_type = protein
                        organism = unidentified
SEQUENCE: 756
RGDL                                                                   4

SEQ ID NO: 757          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 757
EIVMTQTPVT LSVSPGERVT MSC                                              23

SEQ ID NO: 758          moltype = AA  length = 32
FEATURE                 Location/Qualifiers
REGION                  1..32
                        note = Human (Homo sapiens), chimeric or humanized antibody
                         peptide sequence
source                  1..32
                        mol_type = protein
                        organism = unidentified
SEQUENCE: 758
DVPARFSGSG SGTEFTLTIS SVQSEDFAVY YC                                    32

SEQ ID NO: 759          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 759
FDDSY                                                                  5

SEQ ID NO: 760          moltype = AA  length = 118
FEATURE                 Location/Qualifiers
REGION                  1..118
                        note = Human (Homo sapiens), chimeric or humanized antibody
                         peptide sequence
source                  1..118
                        mol_type = protein
                        organism = unidentified
SEQUENCE: 760
KQDKILACAP LYHWRTEMKQ EREPVGTCFL QDGTKTVEYA PCRSQDIDAD GQGFCQGGFS      60
IDFTKADRVL LGGPGSFYWQ GQLISDQVAE IVSKYDPNVY SIKYNNQLAT RTAQAIFD       118

SEQ ID NO: 761          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 761
NLDCM                                                                  5

SEQ ID NO: 762          moltype = AA  length = 5
FEATURE                 Location/Qualifiers
REGION                  1..5
                        note = Human (Homo sapiens), chimeric or humanized antibody
```

```
                            peptide sequence
source                      1..5
                            mol_type = protein
                            organism = unidentified
SEQUENCE: 762
YNLDC                                                                   5

SEQ ID NO: 763              moltype = AA  length = 7
FEATURE                     Location/Qualifiers
REGION                      1..7
                            note = Human (Homo sapiens), chimeric or humanized antibody
                            peptide sequence
source                      1..7
                            mol_type = protein
                            organism = unidentified
SEQUENCE: 763
QCSDYNL                                                                 7

SEQ ID NO: 764              moltype = AA  length = 5
FEATURE                     Location/Qualifiers
REGION                      1..5
                            note = Human (Homo sapiens), chimeric or humanized antibody
                            peptide sequence
source                      1..5
                            mol_type = protein
                            organism = unidentified
SEQUENCE: 764
SMHNN                                                                   5

SEQ ID NO: 765              moltype = AA  length = 17
FEATURE                     Location/Qualifiers
REGION                      1..17
                            note = Human (Homo sapiens), chimeric or humanized antibody
                            peptide sequence
source                      1..17
                            mol_type = protein
                            organism = unidentified
SEQUENCE: 765
KSSQSLLGRG DLGRLKK                                                     17

SEQ ID NO: 766              moltype = AA  length = 8
FEATURE                     Location/Qualifiers
REGION                      1..8
                            note = Human (Homo sapiens), chimeric or humanized antibody
                            peptide sequence
source                      1..8
                            mol_type = protein
                            organism = unidentified
SEQUENCE: 766
TFTDYSMH                                                                8

SEQ ID NO: 767              moltype = AA  length = 17
FEATURE                     Location/Qualifiers
REGION                      1..17
                            note = Human (Homo sapiens), chimeric or humanized antibody
                            peptide sequence
source                      1..17
                            mol_type = protein
                            organism = unidentified
SEQUENCE: 767
RINTETGEPT FADDFRG                                                     17

SEQ ID NO: 768              moltype = AA  length = 7
FEATURE                     Location/Qualifiers
REGION                      1..7
                            note = Human (Homo sapiens), chimeric or humanized antibody
                            peptide sequence
source                      1..7
                            mol_type = protein
                            organism = unidentified
SEQUENCE: 768
FYYGRDS                                                                 7

SEQ ID NO: 769              moltype = AA  length = 5
FEATURE                     Location/Qualifiers
REGION                      1..5
                            note = Human (Homo sapiens), chimeric or humanized antibody
                            peptide sequence
source                      1..5
```

```
SEQUENCE: 769
DYSMH                                                                            5

SEQ ID NO: 770         moltype = AA   length = 17
FEATURE                Location/Qualifiers
REGION                 1..17
                       note = Human (Homo sapiens), chimeric or humanized antibody
                        peptide sequence
source                 1..17
                       mol_type = protein
                       organism = unidentified
SEQUENCE: 770
RINTETGEPT FADDFRG                                                              17

SEQ ID NO: 771         moltype = AA   length = 7
FEATURE                Location/Qualifiers
REGION                 1..7
                       note = Human (Homo sapiens), chimeric or humanized antibody
                        peptide sequence
source                 1..7
                       mol_type = protein
                       organism = unidentified
SEQUENCE: 771
FYYGRDS                                                                          7

SEQ ID NO: 772         moltype = AA   length = 19
FEATURE                Location/Qualifiers
REGION                 1..19
                       note = Human (Homo sapiens), chimeric or humanized antibody
                        peptide sequence
source                 1..19
                       mol_type = protein
                       organism = unidentified
SEQUENCE: 772
KSSQSLLNSG RGDLGNALA                                                            19

SEQ ID NO: 773         moltype = AA   length = 7
FEATURE                Location/Qualifiers
REGION                 1..7
                       note = Human (Homo sapiens), chimeric or humanized antibody
                        peptide sequence
source                 1..7
                       mol_type = protein
                       organism = unidentified
SEQUENCE: 773
WASTRES                                                                          7

SEQ ID NO: 774         moltype = AA   length = 8
FEATURE                Location/Qualifiers
REGION                 1..8
                       note = Human (Homo sapiens), chimeric or humanized antibody
                        peptide sequence
source                 1..8
                       mol_type = protein
                       organism = unidentified
SEQUENCE: 774
KQSYNLIS                                                                         8

SEQ ID NO: 775         moltype = AA   length = 5
FEATURE                Location/Qualifiers
REGION                 1..5
                       note = Human (Homo sapiens), chimeric or humanized antibody
                        peptide sequence
source                 1..5
                       mol_type = protein
                       organism = unidentified
SEQUENCE: 775
DYSMH                                                                            5

SEQ ID NO: 776         moltype = AA   length = 17
FEATURE                Location/Qualifiers
REGION                 1..17
                       note = Human (Homo sapiens), chimeric or humanized antibody
                        peptide sequence
source                 1..17
                       mol_type = protein
                       organism = unidentified
```

```
SEQUENCE: 776
RINTETGEPT FADDFRG                                                                   17

SEQ ID NO: 777          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 777
FYYGRDT                                                                               7

SEQ ID NO: 778          moltype = AA  length = 25
FEATURE                 Location/Qualifiers
REGION                  1..25
                        note = Human (Homo sapiens), chimeric or humanized antibody
                         peptide sequence
source                  1..25
                        mol_type = protein
                        organism = unidentified
SEQUENCE: 778
KSSQSLLGRG DLGRLKKQKD HNALA                                                          25

SEQ ID NO: 779          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 779
WASTRES                                                                               7

SEQ ID NO: 780          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 780
KQSSNLIS                                                                              8

SEQ ID NO: 781          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 781
DYSMH                                                                                 5

SEQ ID NO: 782          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 782
RINTETGEPT FADDFRG                                                                   17

SEQ ID NO: 783          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 783
FYYGRDY                                                                               7
```

```
SEQ ID NO: 784          moltype = AA  length = 24
FEATURE                 Location/Qualifiers
REGION                  1..24
                        note = Human (Homo sapiens), chimeric or humanized antibody
                         peptide sequence
source                  1..24
                        mol_type = protein
                        organism = unidentified
SEQUENCE: 784
KSSQSLLGRG DLGRLKKQKD NALA                                                  24

SEQ ID NO: 785          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 785
WASTRES                                                                      7

SEQ ID NO: 786          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 786
KQSYNLLS                                                                     8

SEQ ID NO: 787          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 787
DYSMH                                                                        5

SEQ ID NO: 788          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 788
RINTETGEPT FADDFRG                                                          17

SEQ ID NO: 789          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 789
FYYGRDT                                                                      7

SEQ ID NO: 790          moltype = AA  length = 23
FEATURE                 Location/Qualifiers
REGION                  1..23
                        note = Human (Homo sapiens), chimeric or humanized antibody
                         peptide sequence
source                  1..23
                        mol_type = protein
                        organism = unidentified
SEQUENCE: 790
KSSQSLLGRG DLGRLKKQKN ALA                                                   23

SEQ ID NO: 791          moltype = AA  length = 7
```

```
FEATURE            Location/Qualifiers
REGION             1..7
                   note = Human (Homo sapiens), chimeric or humanized antibody
                    peptide sequence
source             1..7
                   mol_type = protein
                   organism = unidentified
SEQUENCE: 791
WASTRES                                                                    7

SEQ ID NO: 792     moltype = AA  length = 8
FEATURE            Location/Qualifiers
REGION             1..8
                   note = Human (Homo sapiens), chimeric or humanized antibody
                    peptide sequence
source             1..8
                   mol_type = protein
                   organism = unidentified
SEQUENCE: 792
KQSYNLLS                                                                   8

SEQ ID NO: 793     moltype = AA  length = 5
FEATURE            Location/Qualifiers
REGION             1..5
                   note = Human (Homo sapiens), chimeric or humanized antibody
                    peptide sequence
source             1..5
                   mol_type = protein
                   organism = unidentified
SEQUENCE: 793
DYSMH                                                                      5

SEQ ID NO: 794     moltype = AA  length = 17
FEATURE            Location/Qualifiers
REGION             1..17
                   note = Human (Homo sapiens), chimeric or humanized antibody
                    peptide sequence
source             1..17
                   mol_type = protein
                   organism = unidentified
SEQUENCE: 794
RINTETGEPT FADDFRG                                                         17

SEQ ID NO: 795     moltype = AA  length = 7
FEATURE            Location/Qualifiers
REGION             1..7
                   note = Human (Homo sapiens), chimeric or humanized antibody
                    peptide sequence
source             1..7
                   mol_type = protein
                   organism = unidentified
SEQUENCE: 795
FYYGRDS                                                                    7

SEQ ID NO: 796     moltype = AA  length = 22
FEATURE            Location/Qualifiers
REGION             1..22
                   note = Human (Homo sapiens), chimeric or humanized antibody
                    peptide sequence
source             1..22
                   mol_type = protein
                   organism = unidentified
SEQUENCE: 796
KSSQSLLGRG DLGRLKKQNA LA                                                   22

SEQ ID NO: 797     moltype = AA  length = 7
FEATURE            Location/Qualifiers
REGION             1..7
                   note = Human (Homo sapiens), chimeric or humanized antibody
                    peptide sequence
source             1..7
                   mol_type = protein
                   organism = unidentified
SEQUENCE: 797
WASTRES                                                                    7

SEQ ID NO: 798     moltype = AA  length = 8
FEATURE            Location/Qualifiers
REGION             1..8
```

```
                              -continued note = Human (Homo sapiens), chimeric or humanized antibody
                         peptide sequence
source                  1..8
                        mol_type = protein
                        organism = unidentified
SEQUENCE: 798
KQSYNLLS                                                                        8

SEQ ID NO: 799          moltype = AA   length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 799
DYSMH                                                                           5

SEQ ID NO: 800          moltype = AA   length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 800
RINTETGEPT FADDFRG                                                             17

SEQ ID NO: 801          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 801
FYYGRDT                                                                         7

SEQ ID NO: 802          moltype = AA   length = 21
FEATURE                 Location/Qualifiers
REGION                  1..21
                        note = Human (Homo sapiens), chimeric or humanized antibody
                         peptide sequence
source                  1..21
                        mol_type = protein
                        organism = unidentified
SEQUENCE: 802
KSSQSLLGRG DLGRLKKNAL A                                                        21

SEQ ID NO: 803          moltype = AA   length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 803
WASTRES                                                                         7

SEQ ID NO: 804          moltype = AA   length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 804
KQSYNLLS                                                                        8

SEQ ID NO: 805          moltype = AA   length = 5
FEATURE                 Location/Qualifiers
REGION                  1..5
                        note = Human (Homo sapiens), chimeric or humanized antibody
                         peptide sequence
```

| | | |
|---|---|---|
| source | 1..5<br>mol_type = protein<br>organism = unidentified | |
| SEQUENCE: 805<br>DYSMH | | 5 |
| SEQ ID NO: 806<br>FEATURE<br>REGION | moltype = AA length = 17<br>Location/Qualifiers<br>1..17<br>note = Human (Homo sapiens), chimeric or humanized antibody<br>  peptide sequence | |
| source | 1..17<br>mol_type = protein<br>organism = unidentified | |
| SEQUENCE: 806<br>RINTETGEPT FADDFRG | | 17 |
| SEQ ID NO: 807<br>FEATURE<br>REGION | moltype = AA length = 7<br>Location/Qualifiers<br>1..7<br>note = Human (Homo sapiens), chimeric or humanized antibody<br>  peptide sequence | |
| source | 1..7<br>mol_type = protein<br>organism = unidentified | |
| SEQUENCE: 807<br>FYYGRDS | | 7 |
| SEQ ID NO: 808<br>FEATURE<br>REGION | moltype = AA length = 20<br>Location/Qualifiers<br>1..20<br>note = Human (Homo sapiens), chimeric or humanized antibody<br>  peptide sequence | |
| source | 1..20<br>mol_type = protein<br>organism = unidentified | |
| SEQUENCE: 808<br>KSSQSLLGRG DLGRLKNALA | | 20 |
| SEQ ID NO: 809<br>FEATURE<br>REGION | moltype = AA length = 7<br>Location/Qualifiers<br>1..7<br>note = Human (Homo sapiens), chimeric or humanized antibody<br>  peptide sequence | |
| source | 1..7<br>mol_type = protein<br>organism = unidentified | |
| SEQUENCE: 809<br>WASTRES | | 7 |
| SEQ ID NO: 810<br>FEATURE<br>REGION | moltype = AA length = 8<br>Location/Qualifiers<br>1..8<br>note = Human (Homo sapiens), chimeric or humanized antibody<br>  peptide sequence | |
| source | 1..8<br>mol_type = protein<br>organism = unidentified | |
| SEQUENCE: 810<br>KQSYNLLS | | 8 |
| SEQ ID NO: 811<br>FEATURE<br>REGION | moltype = AA length = 5<br>Location/Qualifiers<br>1..5<br>note = Human (Homo sapiens), chimeric or humanized antibody<br>  peptide sequence | |
| source | 1..5<br>mol_type = protein<br>organism = unidentified | |
| SEQUENCE: 811<br>DYSMH | | 5 |
| SEQ ID NO: 812<br>FEATURE<br>REGION | moltype = AA length = 17<br>Location/Qualifiers<br>1..17<br>note = Human (Homo sapiens), chimeric or humanized antibody<br>  peptide sequence | |
| source | 1..17<br>mol_type = protein | |

```
                            organism = unidentified
SEQUENCE: 812
RINTETGEPT FADDFRG                                                      17

SEQ ID NO: 813          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 813
FYYGRDS                                                                  7

SEQ ID NO: 814          moltype = AA  length = 19
FEATURE                 Location/Qualifiers
REGION                  1..19
                        note = Human (Homo sapiens), chimeric or humanized antibody
                         peptide sequence
source                  1..19
                        mol_type = protein
                        organism = unidentified
SEQUENCE: 814
KSSQSLLGRG DLGRLNALA                                                    19

SEQ ID NO: 815          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 815
WASTRES                                                                  7

SEQ ID NO: 816          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 816
KQSYNLIS                                                                 8

SEQ ID NO: 817          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 817
DYSMH                                                                    5

SEQ ID NO: 818          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 818
RINTETGEPT FADDFRG                                                      17

SEQ ID NO: 819          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 819
```

```
FYYGRDT                                                                         7

SEQ ID NO: 820          moltype = AA  length = 18
FEATURE                 Location/Qualifiers
REGION                  1..18
                        note = Human (Homo sapiens), chimeric or humanized antibody
                         peptide sequence
source                  1..18
                        mol_type = protein
                        organism = unidentified
SEQUENCE: 820
KSSQSLLGRG DLGRNALA                                                            18

SEQ ID NO: 821          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 821
WASTRES                                                                         7

SEQ ID NO: 822          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 822
KQSSNLIS                                                                        8

SEQ ID NO: 823          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 823
DYSMH                                                                           5

SEQ ID NO: 824          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 824
RINTETGEPT FADDFRG                                                             17

SEQ ID NO: 825          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 825
FYYGRDY                                                                         7

SEQ ID NO: 826          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 826
KSSQSLLGRG DLGNALA                                                             17
```

```
SEQ ID NO: 827        moltype = AA  length = 7
FEATURE               Location/Qualifiers
REGION                1..7
                      note = Human (Homo sapiens), chimeric or humanized antibody
                       peptide sequence
source                1..7
                      mol_type = protein
                      organism = unidentified
SEQUENCE: 827
WASTRES                                                                    7

SEQ ID NO: 828        moltype = AA  length = 8
FEATURE               Location/Qualifiers
REGION                1..8
                      note = Human (Homo sapiens), chimeric or humanized antibody
                       peptide sequence
source                1..8
                      mol_type = protein
                      organism = unidentified
SEQUENCE: 828
KQSYNLLS                                                                   8

SEQ ID NO: 829        moltype = AA  length = 5
FEATURE               Location/Qualifiers
REGION                1..5
                      note = Human (Homo sapiens), chimeric or humanized antibody
                       peptide sequence
source                1..5
                      mol_type = protein
                      organism = unidentified
SEQUENCE: 829
DYSMH                                                                      5

SEQ ID NO: 830        moltype = AA  length = 17
FEATURE               Location/Qualifiers
REGION                1..17
                      note = Human (Homo sapiens), chimeric or humanized antibody
                       peptide sequence
source                1..17
                      mol_type = protein
                      organism = unidentified
SEQUENCE: 830
RINTETGEPT FADDFRG                                                        17

SEQ ID NO: 831        moltype = AA  length = 7
FEATURE               Location/Qualifiers
REGION                1..7
                      note = Human (Homo sapiens), chimeric or humanized antibody
                       peptide sequence
source                1..7
                      mol_type = protein
                      organism = unidentified
SEQUENCE: 831
FYYGRDT                                                                    7

SEQ ID NO: 832        moltype = AA  length = 22
FEATURE               Location/Qualifiers
REGION                1..22
                      note = Human (Homo sapiens), chimeric or humanized antibody
                       peptide sequence
source                1..22
                      mol_type = protein
                      organism = unidentified
SEQUENCE: 832
KSSQSLLGRG DLGRLKKQKD HH                                                  22

SEQ ID NO: 833        moltype = AA  length = 7
FEATURE               Location/Qualifiers
REGION                1..7
                      note = Human (Homo sapiens), chimeric or humanized antibody
                       peptide sequence
source                1..7
                      mol_type = protein
                      organism = unidentified
SEQUENCE: 833
WASTRES                                                                    7

SEQ ID NO: 834        moltype = AA  length = 8
FEATURE               Location/Qualifiers
```

```
REGION                  1..8
                        note = Human (Homo sapiens), chimeric or humanized antibody
                         peptide sequence
source                  1..8
                        mol_type = protein
                        organism = unidentified
SEQUENCE: 834
KQSYNLLS                                                                        8

SEQ ID NO: 835          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 835
DYSMH                                                                           5

SEQ ID NO: 836          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 836
RINTETGEPT FADDFRG                                                              17

SEQ ID NO: 837          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 837
FYYGRDS                                                                         7

SEQ ID NO: 838          moltype = AA  length = 21
FEATURE                 Location/Qualifiers
REGION                  1..21
                        note = Human (Homo sapiens), chimeric or humanized antibody
                         peptide sequence
source                  1..21
                        mol_type = protein
                        organism = unidentified
SEQUENCE: 838
KSSQSLLGRG DLGRLKKQKD H                                                         21

SEQ ID NO: 839          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 839
WASTRES                                                                         7

SEQ ID NO: 840          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 840
KQSYNLLS                                                                        8

SEQ ID NO: 841          moltype = AA  length = 5
FEATURE                 Location/Qualifiers
REGION                  1..5
                        note = Human (Homo sapiens), chimeric or humanized antibody
```

```
                        peptide sequence
source                  1..5
                        mol_type = protein
                        organism = unidentified
SEQUENCE: 841
DYSMH                                                                    5

SEQ ID NO: 842          moltype = AA  length = 17
FEATURE                 Location/Qualifiers
REGION                  1..17
                        note = Human (Homo sapiens), chimeric or humanized antibody
                        peptide sequence
source                  1..17
                        mol_type = protein
                        organism = unidentified
SEQUENCE: 842
RINTETGEPT FADDFRG                                                      17

SEQ ID NO: 843          moltype = AA  length = 7
FEATURE                 Location/Qualifiers
REGION                  1..7
                        note = Human (Homo sapiens), chimeric or humanized antibody
                        peptide sequence
source                  1..7
                        mol_type = protein
                        organism = unidentified
SEQUENCE: 843
FYYGRDT                                                                  7

SEQ ID NO: 844          moltype = AA  length = 20
FEATURE                 Location/Qualifiers
REGION                  1..20
                        note = Human (Homo sapiens), chimeric or humanized antibody
                        peptide sequence
source                  1..20
                        mol_type = protein
                        organism = unidentified
SEQUENCE: 844
KSSQSLLGRG DLGRLKKQKD                                                   20

SEQ ID NO: 845          moltype = AA  length = 7
FEATURE                 Location/Qualifiers
REGION                  1..7
                        note = Human (Homo sapiens), chimeric or humanized antibody
                        peptide sequence
source                  1..7
                        mol_type = protein
                        organism = unidentified
SEQUENCE: 845
WASTRES                                                                  7

SEQ ID NO: 846          moltype = AA  length = 8
FEATURE                 Location/Qualifiers
REGION                  1..8
                        note = Human (Homo sapiens), chimeric or humanized antibody
                        peptide sequence
source                  1..8
                        mol_type = protein
                        organism = unidentified
SEQUENCE: 846
KQSYNLLS                                                                 8

SEQ ID NO: 847          moltype = AA  length = 5
FEATURE                 Location/Qualifiers
REGION                  1..5
                        note = Human (Homo sapiens), chimeric or humanized antibody
                        peptide sequence
source                  1..5
                        mol_type = protein
                        organism = unidentified
SEQUENCE: 847
DYSMH                                                                    5

SEQ ID NO: 848          moltype = AA  length = 17
FEATURE                 Location/Qualifiers
REGION                  1..17
                        note = Human (Homo sapiens), chimeric or humanized antibody
                        peptide sequence
source                  1..17
```

```
                          mol_type = protein
                          organism = unidentified
SEQUENCE: 848
RINTETGEPT FADDFRG                                                        17

SEQ ID NO: 849            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 849
FYYGRDT                                                                    7

SEQ ID NO: 850            moltype = AA   length = 19
FEATURE                   Location/Qualifiers
REGION                    1..19
                          note = Human (Homo sapiens), chimeric or humanized antibody
                           peptide sequence
source                    1..19
                          mol_type = protein
                          organism = unidentified
SEQUENCE: 850
KSSQSLLGRG DLGRLKKQK                                                      19

SEQ ID NO: 851            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
SEQUENCE: 851
WASTRES                                                                    7

SEQ ID NO: 852            moltype = AA   length = 8
FEATURE                   Location/Qualifiers
REGION                    1..8
                          note = Human (Homo sapiens), chimeric or humanized antibody
                           peptide sequence
source                    1..8
                          mol_type = protein
                          organism = unidentified
SEQUENCE: 852
KQSSNLIS                                                                   8

SEQ ID NO: 853            moltype = AA   length = 5
FEATURE                   Location/Qualifiers
REGION                    1..5
                          note = Human (Homo sapiens), chimeric or humanized antibody
                           peptide sequence
source                    1..5
                          mol_type = protein
                          organism = unidentified
SEQUENCE: 853
DYSMH                                                                      5

SEQ ID NO: 854            moltype = AA   length = 17
FEATURE                   Location/Qualifiers
REGION                    1..17
                          note = Human (Homo sapiens), chimeric or humanized antibody
                           peptide sequence
source                    1..17
                          mol_type = protein
                          organism = unidentified
SEQUENCE: 854
RINTETGEPT FADDFRG                                                        17

SEQ ID NO: 855            moltype = AA   length = 7
FEATURE                   Location/Qualifiers
REGION                    1..7
                          note = Human (Homo sapiens), chimeric or humanized antibody
                           peptide sequence
source                    1..7
                          mol_type = protein
                          organism = unidentified
```

```
SEQUENCE: 855
FYYGRDY                                                                  7

SEQ ID NO: 856         moltype = AA  length = 18
FEATURE                Location/Qualifiers
REGION                 1..18
                       note = Human (Homo sapiens), chimeric or humanized antibody
                        peptide sequence
source                 1..18
                       mol_type = protein
                       organism = unidentified
SEQUENCE: 856
KSSQSLLGRG DLGRLKKQ                                                     18

SEQ ID NO: 857         moltype = AA  length = 7
FEATURE                Location/Qualifiers
REGION                 1..7
                       note = Human (Homo sapiens), chimeric or humanized antibody
                        peptide sequence
source                 1..7
                       mol_type = protein
                       organism = unidentified
SEQUENCE: 857
WASTRES                                                                  7

SEQ ID NO: 858         moltype = AA  length = 8
FEATURE                Location/Qualifiers
REGION                 1..8
                       note = Human (Homo sapiens), chimeric or humanized antibody
                        peptide sequence
source                 1..8
                       mol_type = protein
                       organism = unidentified
SEQUENCE: 858
KQSYNLLS                                                                 8

SEQ ID NO: 859         moltype = AA  length = 5
FEATURE                Location/Qualifiers
REGION                 1..5
                       note = Human (Homo sapiens), chimeric or humanized antibody
                        peptide sequence
source                 1..5
                       mol_type = protein
                       organism = unidentified
SEQUENCE: 859
DYSMH                                                                    5

SEQ ID NO: 860         moltype = AA  length = 17
FEATURE                Location/Qualifiers
REGION                 1..17
                       note = Human (Homo sapiens), chimeric or humanized antibody
                        peptide sequence
source                 1..17
                       mol_type = protein
                       organism = unidentified
SEQUENCE: 860
RINTETGEPT FADDFRG                                                      17

SEQ ID NO: 861         moltype = AA  length = 7
FEATURE                Location/Qualifiers
REGION                 1..7
                       note = Human (Homo sapiens), chimeric or humanized antibody
                        peptide sequence
source                 1..7
                       mol_type = protein
                       organism = unidentified
SEQUENCE: 861
FYYGRDT                                                                  7

SEQ ID NO: 862         moltype = AA  length = 17
FEATURE                Location/Qualifiers
REGION                 1..17
                       note = Human (Homo sapiens), chimeric or humanized antibody
                        peptide sequence
source                 1..17
                       mol_type = protein
                       organism = unidentified
SEQUENCE: 862
KSSQSLLGRG DLGRLKK                                                      17
```

```
SEQ ID NO: 863          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 863
WASTRES                                                                    7

SEQ ID NO: 864          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 864
KQSYNLLS                                                                   8

SEQ ID NO: 865          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 865
DYSMH                                                                      5

SEQ ID NO: 866          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 866
RINTETGEPT FADDFRG                                                        17

SEQ ID NO: 867          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 867
FYYGRDS                                                                    7

SEQ ID NO: 868          moltype = AA  length = 16
FEATURE                 Location/Qualifiers
REGION                  1..16
                        note = Human (Homo sapiens), chimeric or humanized antibody
                         peptide sequence
source                  1..16
                        mol_type = protein
                        organism = unidentified
SEQUENCE: 868
KSSQSLLGRG DLGRLK                                                         16

SEQ ID NO: 869          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 869
WASTRES                                                                    7

SEQ ID NO: 870          moltype = AA  length = 8
```

```
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 870
KQSYNLLS                                                                         8

SEQ ID NO: 871          moltype = AA  length = 5
FEATURE                 Location/Qualifiers
REGION                  1..5
                        note = Human (Homo sapiens), chimeric or humanized antibody
                         peptide sequence
source                  1..5
                        mol_type = protein
                        organism = unidentified
SEQUENCE: 871
DYSMH                                                                            5

SEQ ID NO: 872          moltype = AA  length = 17
FEATURE                 Location/Qualifiers
REGION                  1..17
                        note = Human (Homo sapiens), chimeric or humanized antibody
                         peptide sequence
source                  1..17
                        mol_type = protein
                        organism = unidentified
SEQUENCE: 872
RINTETGEPT FADDFRG                                                              17

SEQ ID NO: 873          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 873
FYYGRDT                                                                          7

SEQ ID NO: 874          moltype = AA  length = 15
FEATURE                 Location/Qualifiers
REGION                  1..15
                        note = Human (Homo sapiens), chimeric or humanized antibody
                         peptide sequence
source                  1..15
                        mol_type = protein
                        organism = unidentified
SEQUENCE: 874
KSSQSLLGRG DLGRL                                                                15

SEQ ID NO: 875          moltype = AA  length = 7
FEATURE                 Location/Qualifiers
REGION                  1..7
                        note = Human (Homo sapiens), chimeric or humanized antibody
                         peptide sequence
source                  1..7
                        mol_type = protein
                        organism = unidentified
SEQUENCE: 875
WASTRES                                                                          7

SEQ ID NO: 876          moltype = AA  length = 8
FEATURE                 Location/Qualifiers
REGION                  1..8
                        note = Human (Homo sapiens), chimeric or humanized antibody
                         peptide sequence
source                  1..8
                        mol_type = protein
                        organism = unidentified
SEQUENCE: 876
KQSYNLLS                                                                         8

SEQ ID NO: 877          moltype = AA  length = 14
FEATURE                 Location/Qualifiers
REGION                  1..14
```

```
                        note = Human (Homo sapiens), chimeric or humanized antibody
                         peptide sequence
VARIANT                 3
                        note = MISC_FEATURE - Xaa is Lys or Arg
VARIANT                 8
                        note = MISC_FEATURE - Xaa is Lys or Gln
VARIANT                 11
                        note = MISC_FEATURE - Xaa is Lys or Glu
VARIANT                 13
                        note = MISC_FEATURE - Xaa is Val or Met
VARIANT                 14
                        note = MISC_FEATURE - Xaa is Ala or Gly
source                  1..14
                        mol_type = protein
                        organism = unidentified
SEQUENCE: 877
WVXQAPGXGL XWXX                                                              14

SEQ ID NO: 878          moltype = AA  length = 32
FEATURE                 Location/Qualifiers
REGION                  1..32
                        note = Human (Homo sapiens), chimeric or humanized antibody
                         peptide sequence
VARIANT                 3
                        note = MISC_FEATURE - Xaa is Ala, Thr or Ser
VARIANT                 4
                        note = MISC_FEATURE - Xaa is Val or Phe
VARIANT                 5
                        note = MISC_FEATURE - Xaa is Ser or Thr
VARIANT                 7
                        note = MISC_FEATURE - Xaa is Glu or Asp
VARIANT                 10
                        note = MISC_FEATURE - Xaa is Ala or Thr
VARIANT                 11
                        note = MISC_FEATURE - Xaa is Ser or Thr
VARIANT                 14
                        note = misc_feature - Xaa can be any naturally occurring
                         amino acid
VARIANT                 15
                        note = MISC_FEATURE - Xaa is Tyr or Asn
VARIANT                 18
                        note = misc_feature - Xaa can be any naturally occurring
                         amino acid
VARIANT                 19
                        note = MISC_FEATURE - Xaa is Asn, Arg, Ile or Thr
VARIANT                 20
                        note = MISC_FEATURE - Xaa is Asn or Ser
VARIANT                 21
                        note = misc_feature - Xaa can be any naturally occurring
                         amino acid
VARIANT                 22
                        note = MISC_FEATURE - Xaa is Lys or Arg
VARIANT                 23
                        note = MISC_FEATURE - Xaa is Asn or Ser
VARIANT                 24
                        note = MISC_FEATURE - Xaa is Glu or Asp
VARIANT                 27
                        note = MISC_FEATURE - Xaa is Thr, Val or Lys
source                  1..32
                        mol_type = protein
                        organism = unidentified
SEQUENCE: 878
RFXXXLXTSX XTAXLZIXXL XXXDTAXYFC AI                                          32

SEQ ID NO: 879          moltype = AA  length = 11
FEATURE                 Location/Qualifiers
REGION                  1..11
                        note = Human (Homo sapiens), chimeric or humanized antibody
                         peptide sequence
VARIANT                 6
                        note = MISC_FEATURE - Xaa is Thr or Ala
source                  1..11
                        mol_type = protein
                        organism = unidentified
SEQUENCE: 879
WGQGTXLTVS S                                                                 11

SEQ ID NO: 880          moltype = AA  length = 23
FEATURE                 Location/Qualifiers
```

| | | |
|---|---|---|
| REGION | 1..23 | |
| | note = Human (Homo sapiens), chimeric or humanized antibody peptide sequence | |
| VARIANT | 1 | |
| | note = MISC_FEATURE - Xaa is Asp or Glu | |
| VARIANT | 5 | |
| | note = MISC_FEATURE - Xaa is Thr or Ser | |
| VARIANT | 7 | |
| | note = MISC_FEATURE - Xaa is Ser or Thr | |
| VARIANT | 9 | |
| | note = MISC_FEATURE - Xaa is Ser, Ala or Val | |
| VARIANT | 10 | |
| | note = MISC_FEATURE - Xaa is Ser or Thr | |
| VARIANT | 12 | |
| | note = MISC_FEATURE - Xaa is Ala or Ser | |
| VARIANT | 15 | |
| | note = MISC_FEATURE - Xaa is Ala or Pro | |
| VARIANT | 18 | |
| | note = MISC_FEATURE - Xaa is Lys, Arg or Ile | |
| source | 1..23 | |
| | mol_type = protein | |
| | organism = unidentified | |
| SEQUENCE: 880 | | |
| XIVMXQXPXX LXVSXGEXVT MSC | | 23 |
| | | |
| SEQ ID NO: 881 | moltype = AA  length = 15 | |
| FEATURE | Location/Qualifiers | |
| REGION | 1..15 | |
| | note = Human (Homo sapiens), chimeric or humanized antibody peptide sequence | |
| VARIANT | 9 | |
| | note = MISC_FEATURE - Xaa is Ser or Ala | |
| source | 1..15 | |
| | mol_type = protein | |
| | organism = unidentified | |
| SEQUENCE: 881 | | |
| WYQQKPGQXP RLLIY | | 15 |
| | | |
| SEQ ID NO: 882 | moltype = AA  length = 32 | |
| FEATURE | Location/Qualifiers | |
| REGION | 1..32 | |
| | note = Human (Homo sapiens), chimeric or humanized antibody peptide sequence | |
| VARIANT | 1 | |
| | note = MISC_FEATURE - Xaa is Gly or Asp | |
| VARIANT | 4 | |
| | note = MISC_FEATURE - Xaa is Asp or Ala | |
| VARIANT | 7 | |
| | note = MISC_FEATURE - Xaa is Thr or Ser | |
| VARIANT | 14 | |
| | note = MISC_FEATURE - Xaa is Asp or Glu | |
| VARIANT | 24 | |
| | note = MISC_FEATURE - Xaa is Ala, Ser or Asp | |
| VARIANT | 27 | |
| | note = MISC_FEATURE - Xaa is Leu or Phe | |
| source | 1..32 | |
| | mol_type = protein | |
| | organism = unidentified | |
| SEQUENCE: 882 | | |
| XVPXRFXGSG SGTXFTLTIS SVQXEDXAVY YC | | 32 |
| | | |
| SEQ ID NO: 883 | moltype = AA  length = 11 | |
| FEATURE | Location/Qualifiers | |
| REGION | 1..11 | |
| | note = Human (Homo sapiens), chimeric or humanized antibody peptide sequence | |
| VARIANT | 3 | |
| | note = MISC_FEATURE - Xaa is Ala or Gln | |
| VARIANT | 6 | |
| | note = MISC_FEATURE - Xaa is Lys or Val | |
| VARIANT | 9 | |
| | note = MISC_FEATURE - Xaa is Leu or Ile | |
| source | 1..11 | |
| | mol_type = protein | |
| | organism = unidentified | |
| SEQUENCE: 883 | | |
| FGXGTXLEXK R | | 11 |
| | | |
| SEQ ID NO: 884 | moltype = AA  length = 32 | |

```
FEATURE              Location/Qualifiers
REGION               1..32
                     note = Human (Homo sapiens), chimeric or humanized antibody
                      peptide sequence
source               1..32
                     mol_type = protein
                     organism = unidentified
SEQUENCE: 884
GVPSRFSGSG SGTRFSLKIN SLQPEDFGSY YC                                           32

SEQ ID NO: 885       moltype = AA  length = 17
FEATURE              Location/Qualifiers
REGION               1..17
                     note = Human (Homo sapiens), chimeric or humanized antibody
                      peptide sequence
source               1..17
                     mol_type = protein
                     organism = unidentified
SEQUENCE: 885
KSSQSLLNSR SRKNYLA                                                            17

SEQ ID NO: 886       moltype = AA  length = 5
FEATURE              Location/Qualifiers
REGION               1..5
                     note = Human (Homo sapiens), chimeric or humanized antibody
                      peptide sequence
source               1..5
                     mol_type = protein
                     organism = unidentified
SEQUENCE: 886
DADGQ                                                                          5

SEQ ID NO: 887       moltype = AA  length = 5
FEATURE              Location/Qualifiers
REGION               1..5
                     note = Human (Homo sapiens), chimeric or humanized antibody
                      peptide sequence
source               1..5
                     mol_type = protein
                     organism = unidentified
SEQUENCE: 887
SFYWQ                                                                          5
```

What is claimed is:

1. An antibody that specifically binds to human αvβ8 and that comprises heavy chain complementarity determining regions (CDRs) SEQ ID NO:299, SEQ ID NO:301, and SEQ ID NO:303; and light chain CDRs SEQ ID NO:307, SEQ ID NO:309, and SEQ ID NO:311.

2. The antibody of claim 1, wherein the antibody comprises a heavy chain variable region comprising SEQ ID NO: 297.

3. The antibody of claim 1, wherein the antibody comprises a light chain variable region comprising SEQ ID NO: 305.

4. The antibody of claim 1, wherein the antibody comprises a heavy chain variable region comprising SEQ ID NO: 297 and a light chain variable region comprising SEQ ID NO: 305.

5. The antibody of claim 1, wherein the antibody is a single-chain variable fragment (scFv).

6. The antibody of claim 1, wherein the antibody is an IgG.

7. The antibody of claim 1, wherein the antibody is linked to a detectable label.

8. A method of detecting the presence, absence, or quantity of human αvβ8 in a sample, the method comprising, contacting the antibody of claim 1 to the sample, and detecting or quantifying binding of the antibody to the sample.

9. The method of claim 8, wherein the sample is a formalin-fixed sample.

10. The method of claim 9, wherein the sample is a formalin-fixed paraffin-embedded (FFPE) sample.

11. The method of claim 9, wherein the sample comprises fibroblasts, stellate cells, chondrocytes, activated macrophages, T cells, or B cells.

12. The method of claim 9, wherein the sample is a tumor.

* * * * *